United States Patent
Guo et al.

(10) Patent No.: US 11,518,766 B2
(45) Date of Patent: Dec. 6, 2022

(54) TRICYCLIC COMPOUND, PREPARATION METHOD THEREFOR AND USE THEREOF

(71) Applicants: SHANGHAI JEMINCARE PHARMACEUTICALS CO., LTD., Shanghai (CN); JIANGXI JEMINCARE GROUP CO., LTD., Nanchang (CN)

(72) Inventors: Shuchun Guo, Shanghai (CN); Jiangwei Wang, Shanghai (CN); Shan Yao, Shanghai (CN); Yong Zhang, Shanghai (CN); Zhangping Kang, Shanghai (CN); Qiong Zhang, Shanghai (CN); Yan Ye, Shanghai (CN); Jianbiao Peng, Shanghai (CN); Haibing Guo, Shanghai (CN)

(73) Assignees: SHANGHAI JEMINCARE PHARMACEUTICALS CO., LTD., Shanghai (CN); JIANGXI JEMINCARE GROUP CO., LTD., Jiangxi (CN)

( * ) Notice: Subject to any disclaimer, the term of this patent is extended or adjusted under 35 U.S.C. 154(b) by 50 days.

(21) Appl. No.: 17/621,901

(22) PCT Filed: Jun. 28, 2020

(86) PCT No.: PCT/CN2020/098412
§ 371 (c)(1),
(2) Date: Dec. 22, 2021

(87) PCT Pub. No.: WO2020/259668
PCT Pub. Date: Dec. 30, 2020

(65) Prior Publication Data
US 2022/0251095 A1    Aug. 11, 2022

(30) Foreign Application Priority Data

Jun. 28, 2019  (CN) .......................... 201910578620.6
Feb. 28, 2020  (CN) .......................... 202010129623.4
Jun. 18, 2020  (CN) .......................... 202010561350.0

(51) Int. Cl.
*C07D 487/04*    (2006.01)
*C07D 471/04*    (2006.01)

(52) U.S. Cl.
CPC ......... *C07D 487/04* (2013.01); *C07D 471/04* (2013.01)

(58) Field of Classification Search
CPC ........................... C07D 471/04; C07D 487/04
USPC ........................................................ 514/267
See application file for complete search history.

(56) References Cited

U.S. PATENT DOCUMENTS

| 9,732,085 B2 * | 8/2017 | Courtney .................. A61P 7/02 |
| 9,809,545 B2 | 11/2017 | Ogawa et al. |
| 2016/0145263 A1 | 5/2016 | Pinto et al. |
| 2017/0349580 A1 | 12/2017 | Tanaka et al. |

FOREIGN PATENT DOCUMENTS

| CN | 105228996 A | 1/2016 |
| JP | 2017218449 A | 12/2017 |
| WO | 2013093484 A1 | 6/2013 |
| WO | 2013118805 A | 8/2013 |
| WO | 2014160592 A2 | 10/2014 |

OTHER PUBLICATIONS

Sep. 28, 2020 International Search Report issued in International Patent Application No. PCT/CN2020/098412.
Sep. 28, 2020 Written Opinion of the International Searching Authority issued in International Patent Application No. PCT/CN2020/098412.
Avery, C.A. et al. "(±)cis-bisamido epoxides: A novel series of potent FXIII-A inhibitors." European Journal of Medicinal Chemistry, May 16, 2015, vol. 98, 49-53.
Al-Horani, R.A. et al. "Factor XIa inhibitors: A review of the patent literature." Expert Opinion on Therapeutic Patents, Feb. 25, 2016, Issue 3, vol. 26, 1-47.
Mar. 22, 2022 First Office Action issued in Indian Patent Application No. 202247004634.
May 10, 2022 First Office Action issued in Canadian Patent Application No. 3,145,111.
Mar. 21, 2022 First Office Action issued in Singaporean Patent Application No. 11202114435R.

* cited by examiner

*Primary Examiner* — Niloofar Rahmani
(74) *Attorney, Agent, or Firm* — SZDC Law P.C.

(57) ABSTRACT

A compound represented by formula (I), an optical isomer thereof and a pharmaceutically acceptable salt thereof, as well as an application of said compound as an FXIa inhibitor.

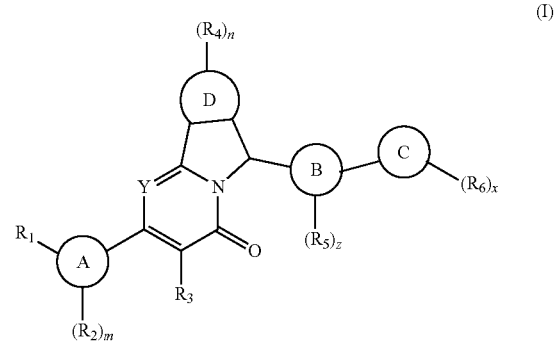

23 Claims, No Drawings

TRICYCLIC COMPOUND, PREPARATION METHOD THEREFOR AND USE THEREOF

The present application is the national stage of application of PCT/CN2020/098412, filed on Jun. 28, 2020, which claims the following priorities:
CN201910578620.6, filed on Jun. 28, 2019;
CN202010129623.4, filed on Feb. 28, 2020;
CN202010561350.0, filed on Jun. 18, 2020.

FIELD OF THE INVENTION

The present disclosure relates to a compound represented by formula (I), an optical isomer thereof and a pharmaceutically acceptable salt thereof, and a use of the compound as an FXIa inhibitor.

BACKGROUND

Thromboembolism is a disease caused by abnormal blood clots formed in blood vessels during the survival of human and animals. There are three reasons for thrombosis: blood vessel damage, blood change and blood stasis; thrombosis is a group of complications caused by many different diseases and different reasons. Due to the differences of various basic diseases and the different sites of thromboembolism, thrombosis may be clinically manifested as myocardial infarction, stroke, deep vein thrombosis (DVT), pulmonary embolism, atrial fibrillation and cerebral infarction and the like; especially, heart attack, cerebral infarction and pulmonary infarction, for which embolism and infarction are the main causes, ranking first among all kinds of death causes, claiming nearly 12 million lives every year in the world, which is close to a quarter of the world's total deaths.

Human blood coagulation process is composed of intrinsic pathway, extrinsic pathway and common pathway, which is a coagulation cascade reaction in which a series of coagulation factors are activated one after another and then amplified, and finally fibrin is formed. Intrinsic pathway (also known as contact activation pathway) and extrinsic pathway (also known as tissue factor pathway) start to produce coagulation Factor Xa (Factor Xa, FXa), and then produce thrombin IIa (Factor IIa, FIIa) through common pathway, and finally fibrin is formed. Procoagulation (hemostasis) and anticoagulation (antithrombotic) are opposed to each other and maintain relative balance in human blood system. When the function of anticoagulant and fibrinolytic system in vivo decreases, and the coagulation and anticoagulation functions in blood are out of balance, coagulation occurs, resulting in thrombosis or embolism.

With the elucidation of the mechanism of thrombosis, three major classes of antithrombotic drugs have been researched and developed: anticoagulants (such as warfarin and heparin and the like), antiplatelet aggregation drugs (such as aspirin and clopidogrel and the like) and thrombolytic drugs (such as urokinase and reteplase and the like). The domestic anticoagulant drug market is growing rapidly, wherein traditional varieties such as heparin drugs still occupy a major share, but the market scale gradually tends to be stable. However, new therapeutic drugs, direct thrombin (FIIA) inhibitors (such as dabigatran ester and the like) and activated coagulation factor Xa (FXa) inhibitors (such as rivaroxaban and apixaban and the like), show strong market vitality and are strong competitors of heparin drugs. The use of activated coagulation factor (FXa) inhibitors is increasing rapidly because of their good performance in efficacy and safety in the prevention and treatment of thromboembolic disorders such as stroke, pulmonary embolism and venous thromboembolism (VTE) and the like. However, this is accompanied by an increase in bleeding-related hospital admissions and mortality, which are major complications of anticoagulation therapy. In 2016, there were approximately 117,000 inpatient deaths due to FXa inhibitor-related bleeding in the United States alone, which equates to nearly 2,000 bleeding-related deaths per month. Therefore, it is important to develop anticoagulant drugs with little bleeding tendency.

Coagulation factor XI (FXI), a plasma serine proteasome necessary for the maintenance of the endogenous pathway, is activated to produce activated coagulation factor XIa (FXIa), FXIa plays a key role in the amplification of the coagulation cascade. In the coagulation cascade reaction, thrombin can activate FXI by feedback, and the activated FXI promotes the production of thrombin in large quantities, thus amplifying the coagulation cascade reaction. Therefore, drugs targeting FXI targets can block intrinsic pathways and inhibit the amplification of coagulation cascade reaction, thus having an antithrombotic effect. In recent years, the clinical data related to the occurrence of thrombotic diseases with human coagulation factor XI (FXI) deficiency or elevated FXI level, and the antithrombotic experimental studies with animal FXI deficiency or knockout or inhibition show that compared with direct FXa inhibitors, inhibition of FXI may have less bleeding risk, which is a new target for antithrombotic prevention and treatment.

Human FXI deficiency, also known as hemophilia C, the bleeding phenotype is mild and spontaneous bleeding is rare, joint bleeding and intramuscular bleeding are rare, thus indicating a lower risk of bleeding when FXI is inhibited. Secondly, in patients with FXI deficiency, the incidence of ischemic stroke and deep vein thrombosis is significantly reduced, indicating that inhibition of FXI is beneficial to reduce the risk of ischemic stroke and deep vein thrombosis. Thirdly, in a study on the tendency to thrombosis with 474 patients and controls each, the risk of DVT was 2.2 times higher in people with high FXI levels than in the rest of the population, indicating that high levels of FXI are a risk factor for the development of DVT and that FXI levels are positively associated with the development of DVT. Other studies have shown that the increase of FXI level can significantly increase the risk of stroke and venous thrombosis, and the inhibition of FXI may reduce thrombotic diseases.

FXI knockout mice can survive healthily, and have the same fecundity and hemostatic function as wild mice, they also show prolonged activated partial thromboplastin time (APTT) and normal prothrombin time (T) as FXI deficient patients. Knocking out FXI gene in mouse can inhibit arterial and venous thrombosis, compared with several clinically used antithrombotic drugs, the antithrombotic effect is equal to or even more effective than high-dose heparin, and more effective than other drugs such as aspirin, clopidogrel or argatroban; moreover, these antithrombotic drugs may cause a small amount of bleeding, and the tail bleeding time of FXI-knocked mice shows no different from that of wild-type mice. This indicates that FXI may be an antithrombotic prevention and treatment target with little side effects of bleeding. The reported FXI inhibitors mainly include monoclonal antibodies, antisense oligonucleotides, small chemical molecules, polypeptides or proteins, and polypeptide mimics and the like. At present, Novartis's FXIa monoclonal antibody MAA-868 and Bayer's monoclonal antibody BAY1213790 have entered clinical phase II research, and FXIa antisense oligonucleic acid ISIS416858/

BAY2306001/IONIX-FXIRx developed by Ionis and Bayer is currently in clinical phase II research. BMS-986177, a small molecule oral FXIa inhibitor developed by BMS and Johnson & Johnson, has completed several Phase I clinical studies and entered Phase II clinical trials; ONO-7684, a small molecule oral FXIa inhibitor developed by Ono Corporation of Japan, has entered clinical phase II research. Phase I clinical trial of BMS-962122, a small molecule FXIa inhibitor injected intravenously into BMS, has been completed. Monoclonal antibodies and antisense oligonucleotides need to be administered by injection, and have the disadvantages of being expensive, slow-acting and potentially uncontrollable and the like, while chemical small molecules have the advantages of relatively better oral bioavailability and better patient compliance and the like. Therefore, the research and development of safe, effective, specific and active FXIa small molecule inhibitors may make up for the shortage of bleeding complications in clinical anticoagulant and antithrombotic drugs and meet the unmet clinical needs.

Plasma kallikrein (PK) is a trypsin-like serine proteasome present in plasma and is similar to the coagulation factor XIa gene with 58% amino acid sequence similarity. In the blood, most of the plasma kallikrein exists in the form of complex with high molecular weight kininogen (HMWK). Plasma kininase is involved in blood coagulation, fibrinolysis and kinin production, and plays a role in blood coagulation and many inflammatory diseases. Activated factor XII (Factor XIIa, FXIIa) shears prekallikrein to form kallikrein (PK), and PK promotes HWMK shearing to form Bradykinin, thus promoting blood coagulation. Plasma kallikrein inhibitors may be used to treat hereditary angioedema (HAE) and advanced diabetic macular edema (HDM) and the like. Ecallantide (Kalbitor), a plasma kininase inhibitor, has been approved by FDA to treat HAE, but there is no small molecule plasma kininase inhibitor approved for marketing at present, and the development of a new, safe and effective small molecule inhibitor of Kallikrein may also meet the unmet clinical need.

CONTENT OF THE PRESENT INVENTION

In one aspect of the present disclosure, the present disclosure provides a compound represented by formula (I), an optical isomer thereof and a pharmaceutically acceptable salt thereof

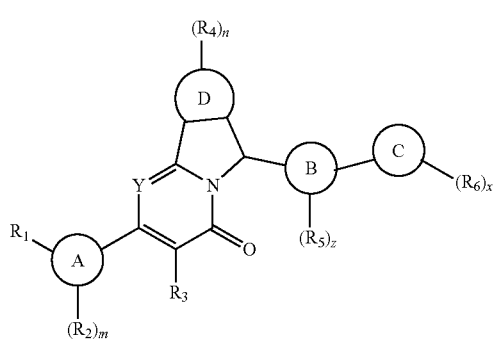

wherein,
ring A is selected from phenyl and 5-6 membered heteroaryl;
ring B is selected from 5-6 membered heteroaryl;
ring C is selected from phenyl, 5-10 membered heteroaryl, benzo 5-9 membered heterocycloalkyl, pyrido 5-9 membered heterocycloalkyl and benzo 5-9 membered heterocycloalkenyl;
ring D is selected from $C_{3-5}$ cycloalkyl and 3-5 membered heterocycloalkyl;
$R_1$ is selected from H, $C_{1-6}$ alkyl, $C_{1-6}$ heteroalkyl and 5-6 membered heteroaryl, and the $C_{1-6}$ alkyl, $C_{1-6}$ heteroalkyl or 5-6 membered heteroaryl is optionally substituted by 1, 2 or 3 R;
$R_2$ is independently selected from H, halogen, OH, $NH_2$, CN, $C_{1-6}$ alkyl and $C_{1-6}$ heteroalkyl, and the $C_{1-6}$ alkyl or $C_{1-6}$ heteroalkyl is optionally substituted by 1, 2 or 3 R;
$R_3$ is selected from H, F, Cl, Br, I, OH, $NH_2$, CN and Me;
$R_4$ is selected from H, F, Cl, Br, I, OH, $NH_2$, CN, COOH, $CH_2OH$ and $C_{1-6}$ alkyl;
$R_5$ is independently selected from H, halogen, OH, $NH_2$, CN,

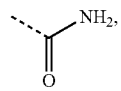

$C_{1-6}$ alkyl and $C_{1-6}$ heteroalkyl, and the $C_{1-6}$ alkyl or $C_{1-6}$ heteroalkyl is optionally substituted by 1, 2 or 3 R;
$R_6$ is independently selected from H, halogen, OH, $NH_2$, CN, COOH

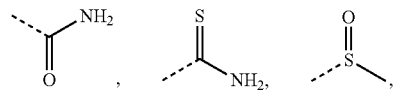

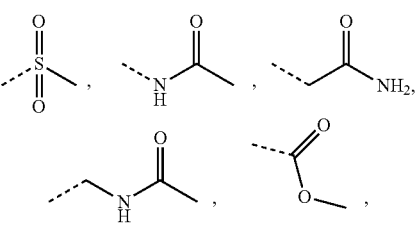

$C_{1-6}$ alkyl and $C_{1-6}$ heteroalkyl, and the $C_{1-6}$ alkyl, $C_1$-6 heteroalkyl or

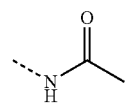

is optionally substituted by 1, 2 or 3 R;
Y is selected from N and C($R_7$);
$R_7$ is selected from H, F, Cl, Br, I, OH, $NH_2$, CN, $C_{1-6}$ alkyl and $C_{1-6}$ heteroalkyl, and the $C_{1-6}$ alkyl or $C_{1-6}$ heteroalkyl is optionally substituted by 1, 2 or 3 R;
m is selected from 0, 1, 2 and 3;
n is selected from 0, 1, 2 and 3;
x is selected from 0, 1, 2 and 3;
z is selected from 0, 1 and 2;
R is independently selected from H, halogen, OH, $NH_2$, CN,

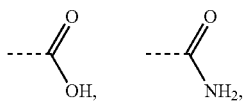

$C_{1-6}$ alkyl, $C_{1-6}$ alkoxy, $C_{1-6}$ alkylthio, $C_{1-6}$ alkylamino, $C_{3-6}$ cycloalkyl, and the $C_{1-6}$ alkyl, $C_{1-6}$ alkoxy, $C_{1-6}$ alkylthio, $C_{1-6}$ alkylamino, or $C_{3-6}$ cycloalkyl is optionally substituted by 1, 2, or 3 R';

R' is selected from H, F, Cl, Br, I, OH, $NH_2$ and $CH_3$;

the 3-5 membered heterocycloalkyl, 5-6 membered heterocycloalkyl, 5-9 membered heterocycloalkenyl, 5-9 membered heterocycloalkyl, 5-6 membered heteroaryl, 5-10 membered heteroaryl, $C_{1-6}$ heteroalkyl or $C_{1-6}$ heterocycloalkyl contains 1, 2 or 3 heteroatoms or heteroatom groups independently selected from —O—, —NH—, —S—, —C(=O)—, —C(=O)O—, —S(=O)—, —S(=O)$_2$— and N.

In some embodiments of the present disclosure, the R is selected from H, F, Cl, Br, I, OH, $NH_2$, COOH, $CF_3$, $CF_2H$, CN, $CH_3O$, $CH_3CH_2O$,

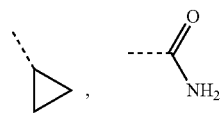

and Me, and the other variables are as defined herein.

In some embodiments of the present disclosure, the $R_1$ is selected from H, $C_{1-3}$ alkyl, $C_{1-3}$ heteroalkyl, tetrazolyl and 1,2,3-triazolyl, and the tetrazolyl or 1,2,3-triazolyl is optionally substituted by R, the $C_{1-3}$ alkyl or $C_{1-3}$ heteroalkyl is optionally substituted by 1, 2 or 3 R, and the other variables are as defined herein.

In some embodiments of the present disclosure, the $R_1$ is selected from H, $C_{1-3}$ alkyl, $C_{1-3}$ alkoxy,

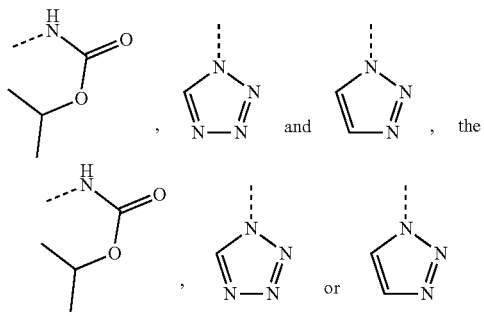

is optionally substituted by R, the $C_{1-3}$ alkyl or $C_{1-3}$ alkoxy is optionally substituted by 1, 2 or 3 R, and the other variables are as defined herein.

In some embodiments of the present disclosure, the $R_1$ is selected from H, —$CHF_2$, —$OCF_3$,

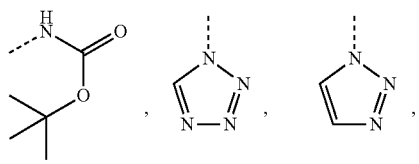

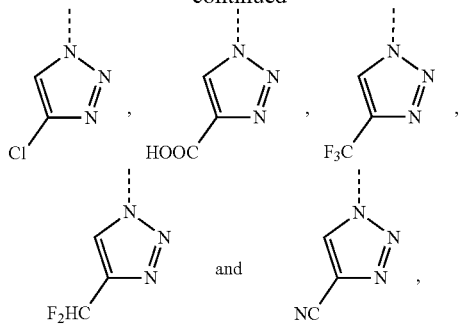

and the other variables are as defined herein.

In some embodiments of the present disclosure, the $R_2$ is independently selected from H, halogen, OH, $NH_2$, CN, $C_{1-3}$ alkyl and $C_{1-3}$ alkoxy, and the $C_{1-3}$ alkyl or $C_{1-3}$ alkoxy is optionally substituted by 1, 2 or 3 R, and the other variables are as defined herein.

In some embodiments of the present disclosure, the $R_2$ is independently selected from H, F, Cl, Br, I, OH, $NH_2$, CN, Me and

and the other variables are as defined herein.

In some embodiments of the present disclosure, the structural moiety

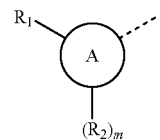

is selected from

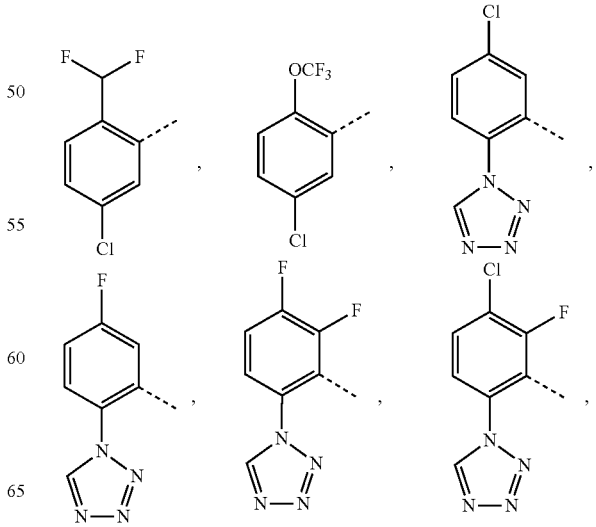

-continued

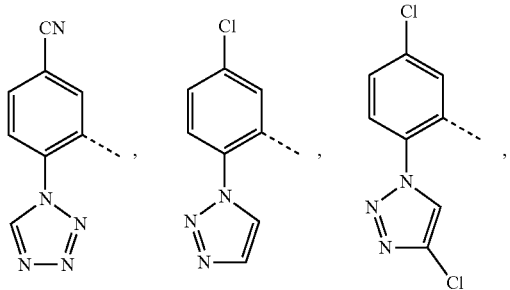

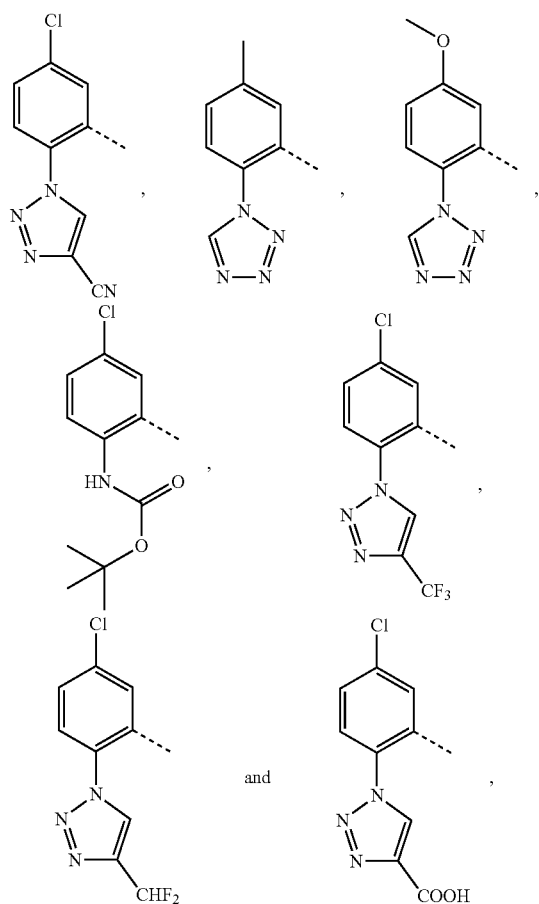

and the other variables are as defined herein.

In some embodiments of the present disclosure, the ring B is selected from pyrrolyl, imidazolyl, 1,2,4-triazolyl and pyridyl, and the other variables are as defined herein.

In some embodiments of the present disclosure, the $R_5$ is independently selected from H, F, Cl, Br, OH, $NH_2$, Me, CN and

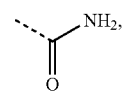

and the other variables are as defined herein.

In some embodiments of the present disclosure, the structural moiety

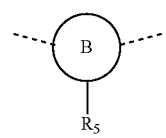

is selected from

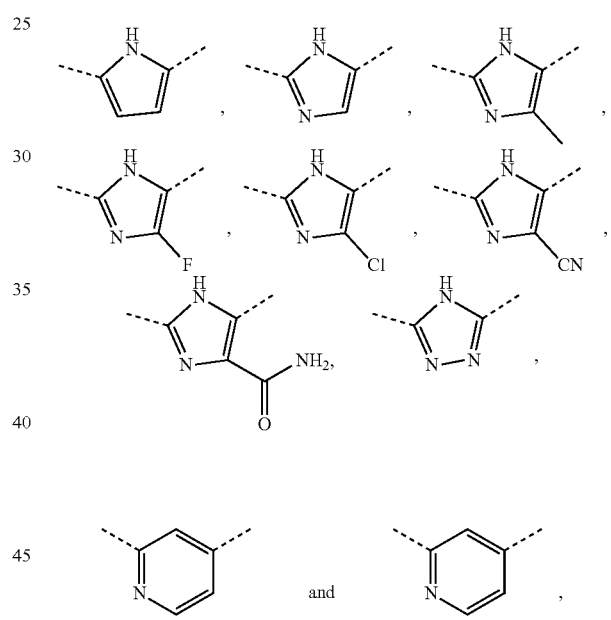

and the other variables are as defined herein.

In some embodiments of the present disclosure, the ring C is selected from thienyl, phenyl, pyridyl, pyrimidinyl, pyridazinyl, pyrazinyl, indazolyl, isoindolin-1-one, quinolinyl, isoquinolinyl, 1,2,3,4-tetrahydroquinolinyl, quinolin-2(1H)-one, benzoisoxazolyl, 1H-benzo[d]imidazolyl, dihydroindol-2-one, dihydroindol-1-one, 3,4-dihydroquinolin-2(1H)-one, quinolin-2(1H)-one, 1H-pyrido[2,3-b][1,4]oxazin-2(3H)-one, 3,4-dihydro-2H-benzo[b][1,4]oxazinyl, 3,4-dihydro-2H-benzo[b][1,4]thiazinyl-2H-benzo[b][1,4]oxazin-3(4H)-one, 3,4-dihydro-1,8-naphthyridin-2(1H)-one, quinoxalin-2(1H)-one, spiro[benzo[b][1,4]oxazin-2,1'-cyclopropane]-3(4H)-one, 1,4-dihydro-2H-benzo[d][1,3]oxazin-2-one, 2H-benzo[b][1,4]thiazin-3(4H)-one, 3,4-dihydro-2H-benzo[b][1,4]thiazin-1,1-dioxide, 1,4-dihydrochromeno[4,3-c]pyrazolyl and 4,5-dihydro-1H-benzo[g]indazolyl, and the other variables are as defined herein.

In some embodiments of the present disclosure, the $R_6$ is independently selected from H, halogen, OH, $NH_2$, CN, COOH,

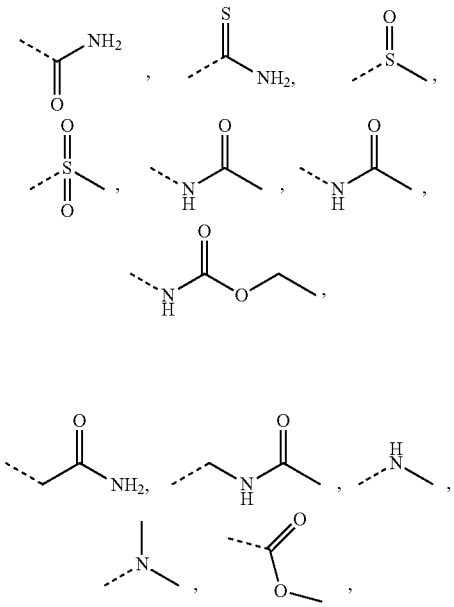

$C_{1-3}$ alkyl, $C_{1-3}$ heteroalkyl and $C_{3-6}$ cycloalkyl, and the $C_{1-3}$ alkyl, $C_{1-3}$ heteroalkyl or $C_{3-6}$ cycloalkyl is optionally substituted by 1, 2 or 3 R, and the other variables are as defined herein.

In some embodiments of the present disclosure, the $R_6$ is independently selected from H, F, Cl, Br, I, OH, $NH_2$, CN, Me,

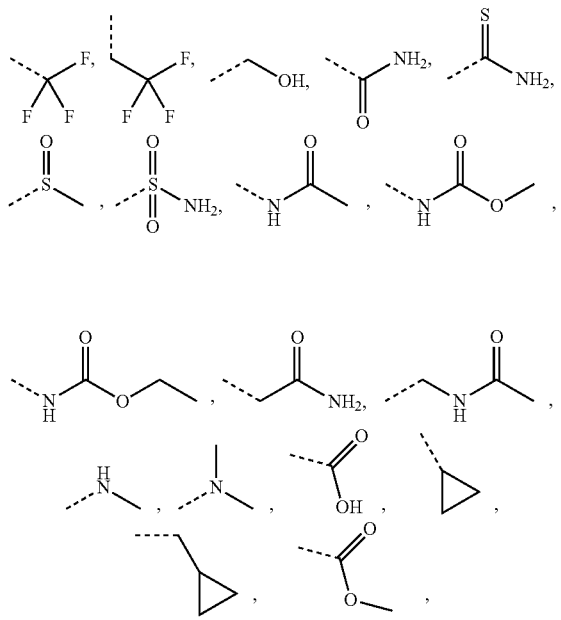

and the other variables are as defined herein.

In some embodiments of the present disclosure, the structural moiety

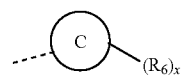

is selected from

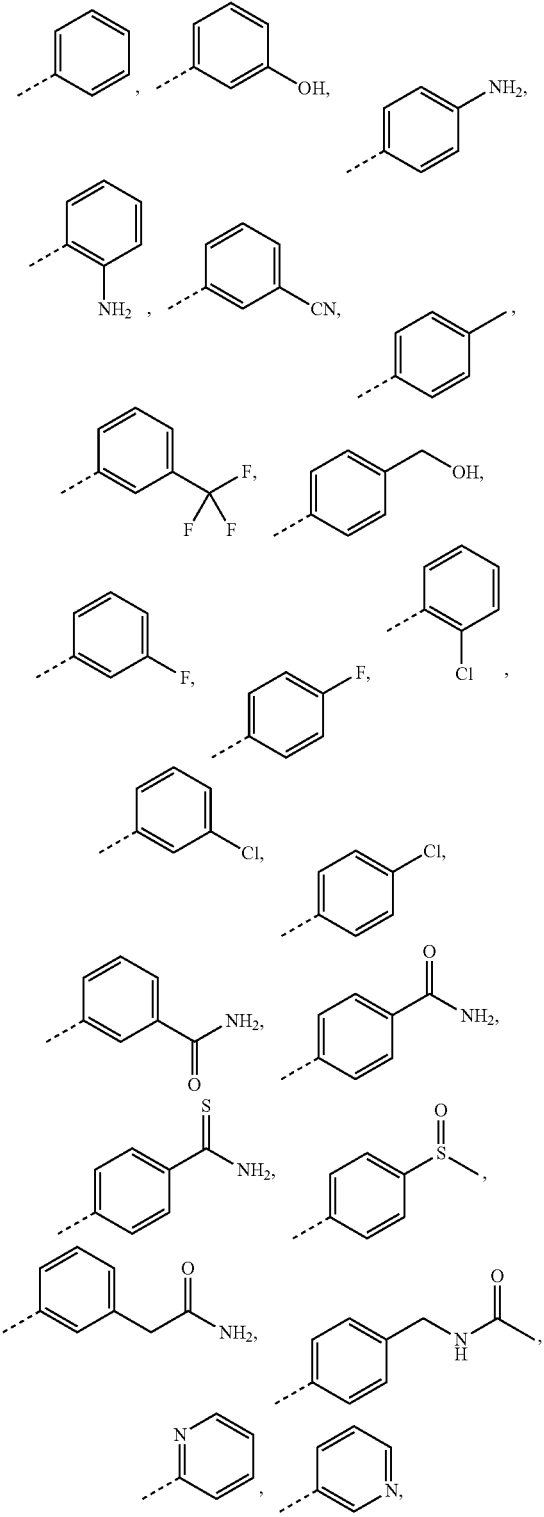

-continued
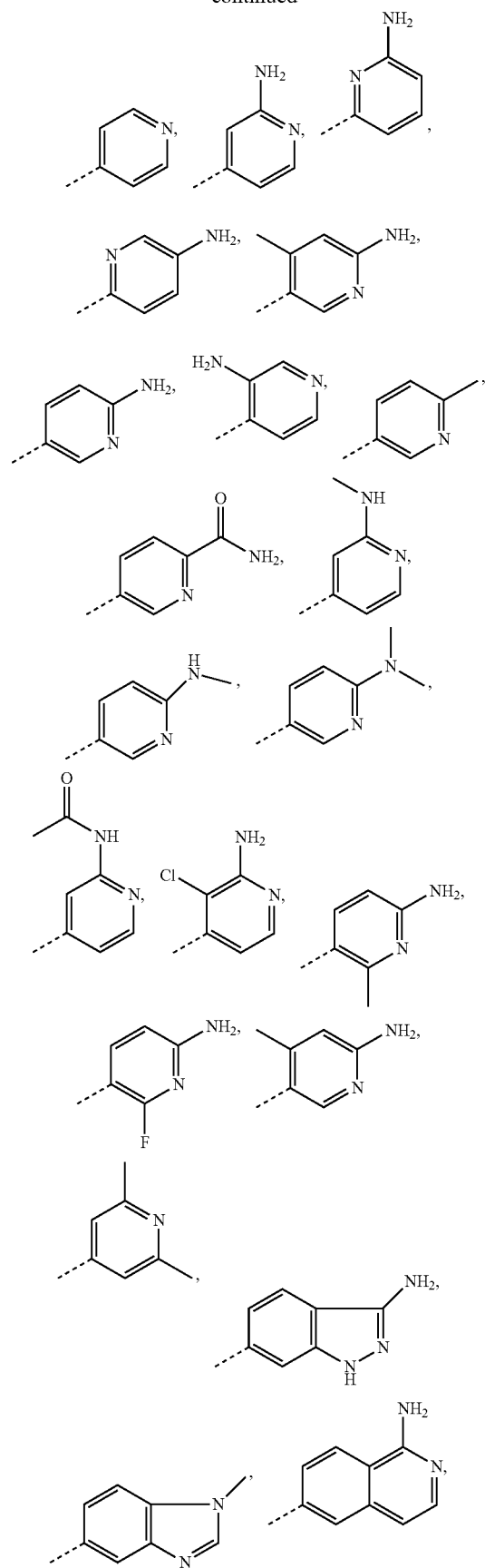
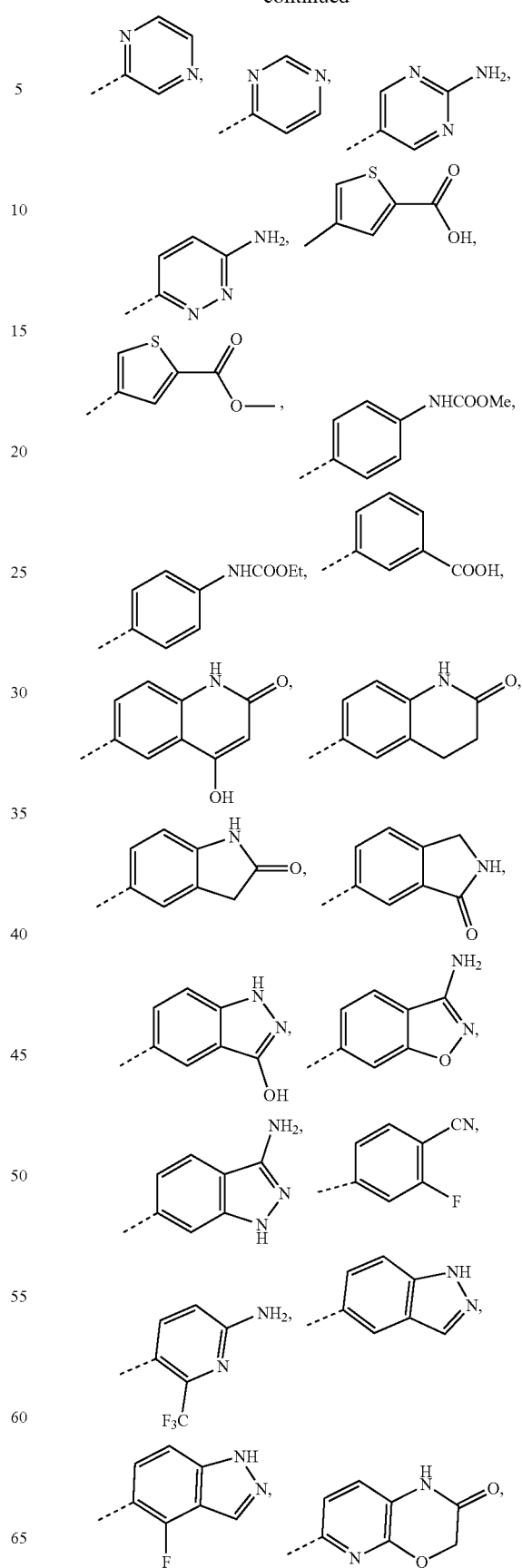

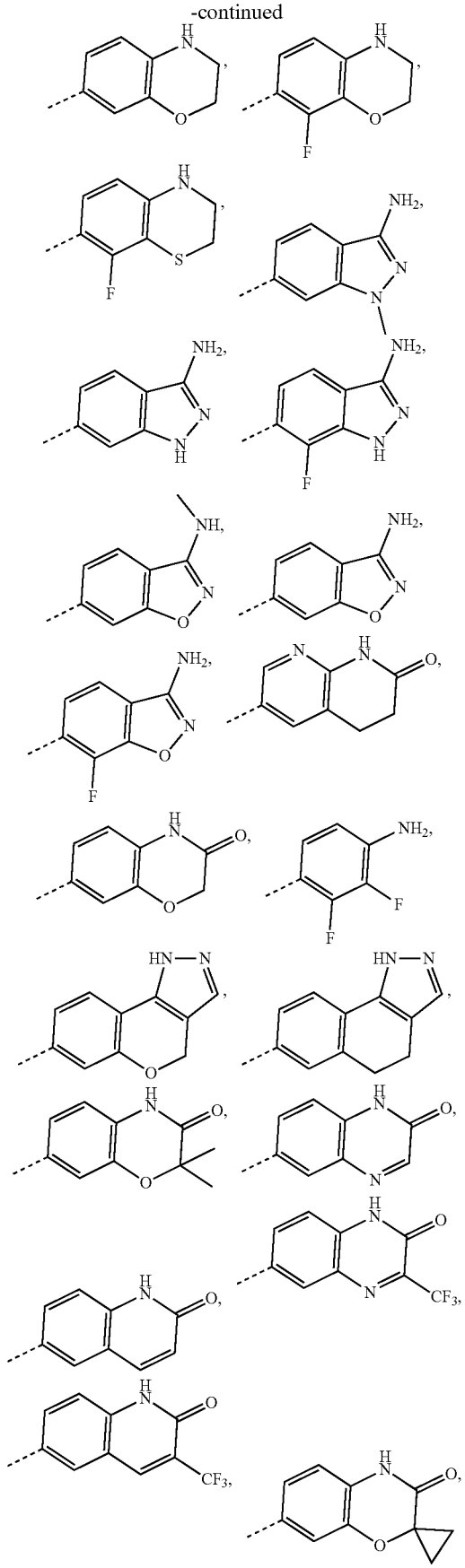
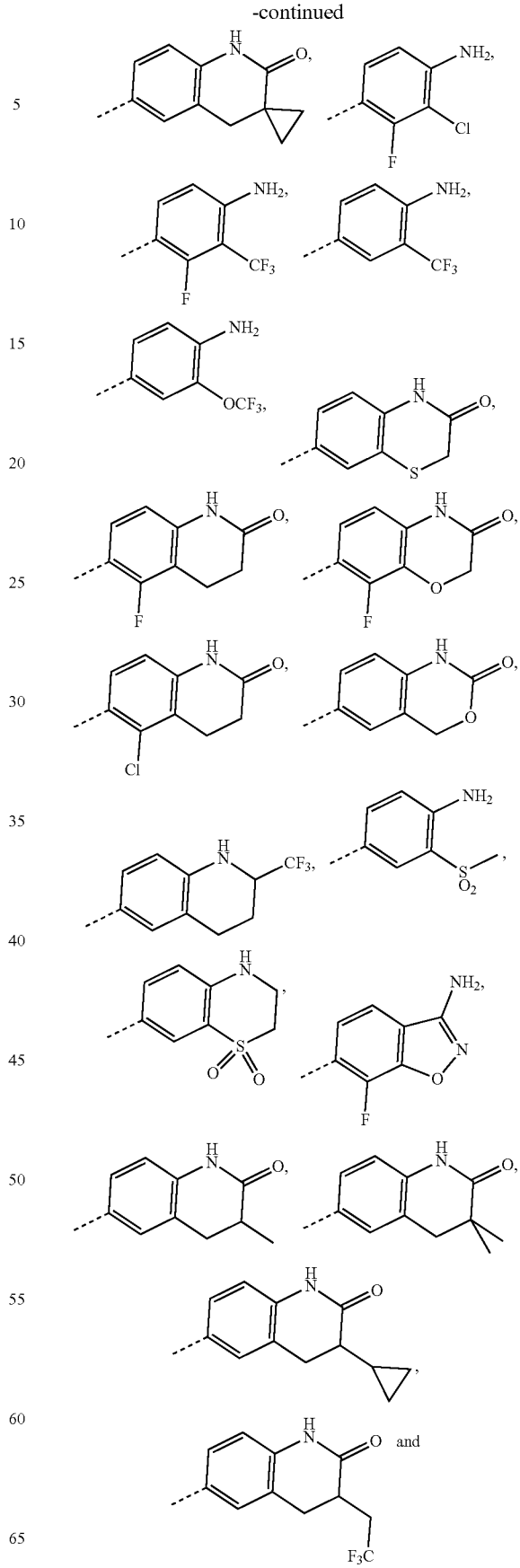

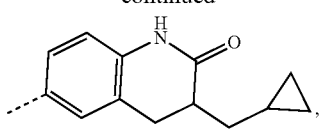
and the other variables are as defined herein.
In some embodiments of the present disclosure, the structural moiety
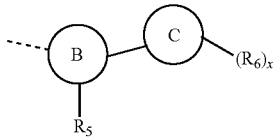
selected from
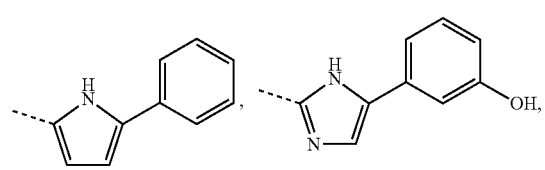
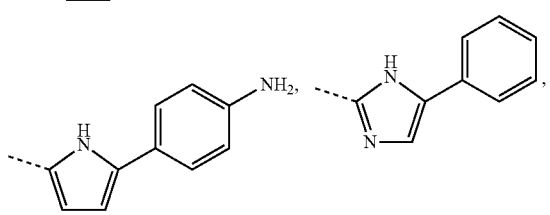
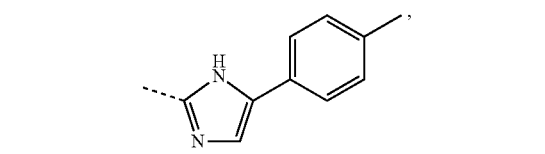
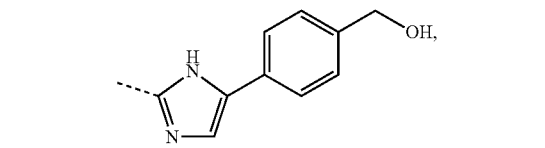
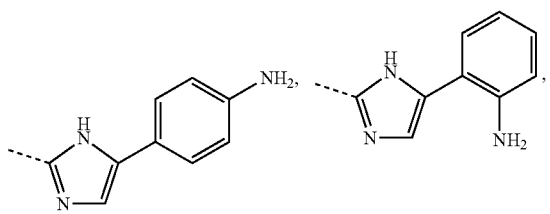
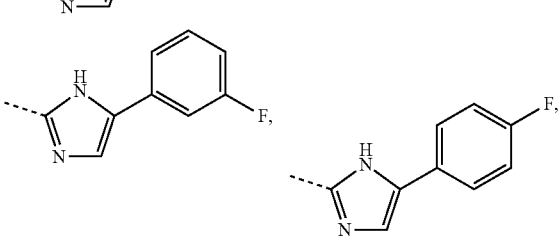
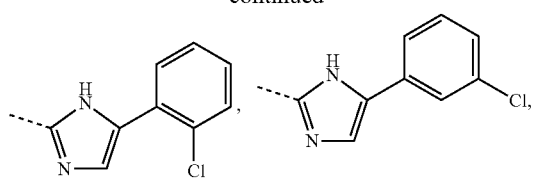
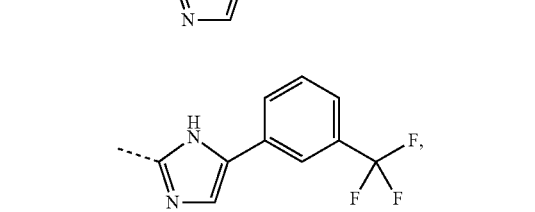
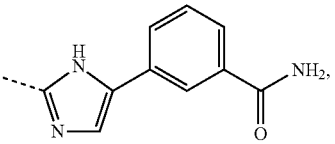
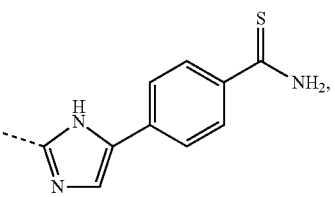
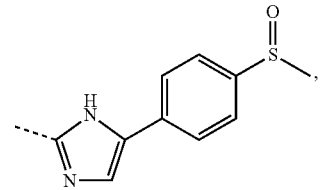
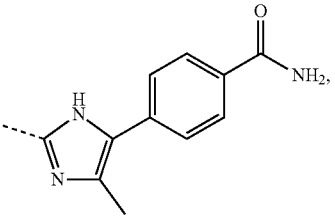
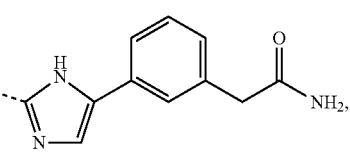
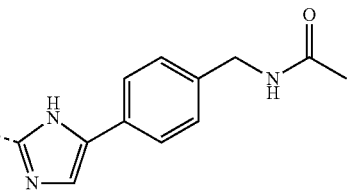

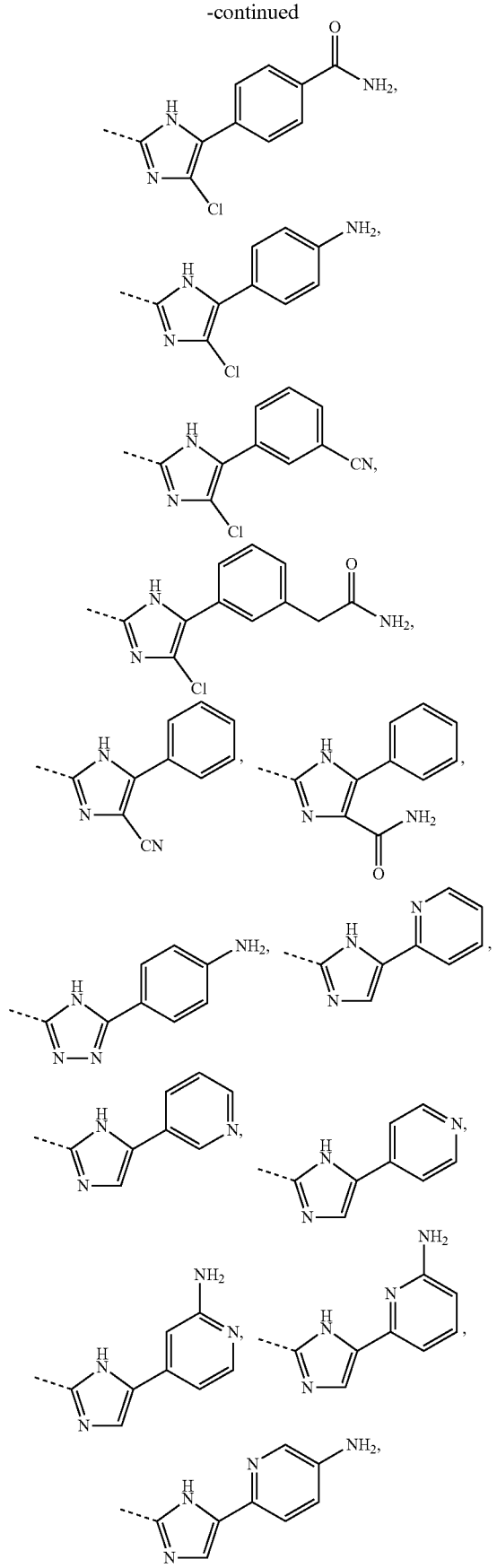
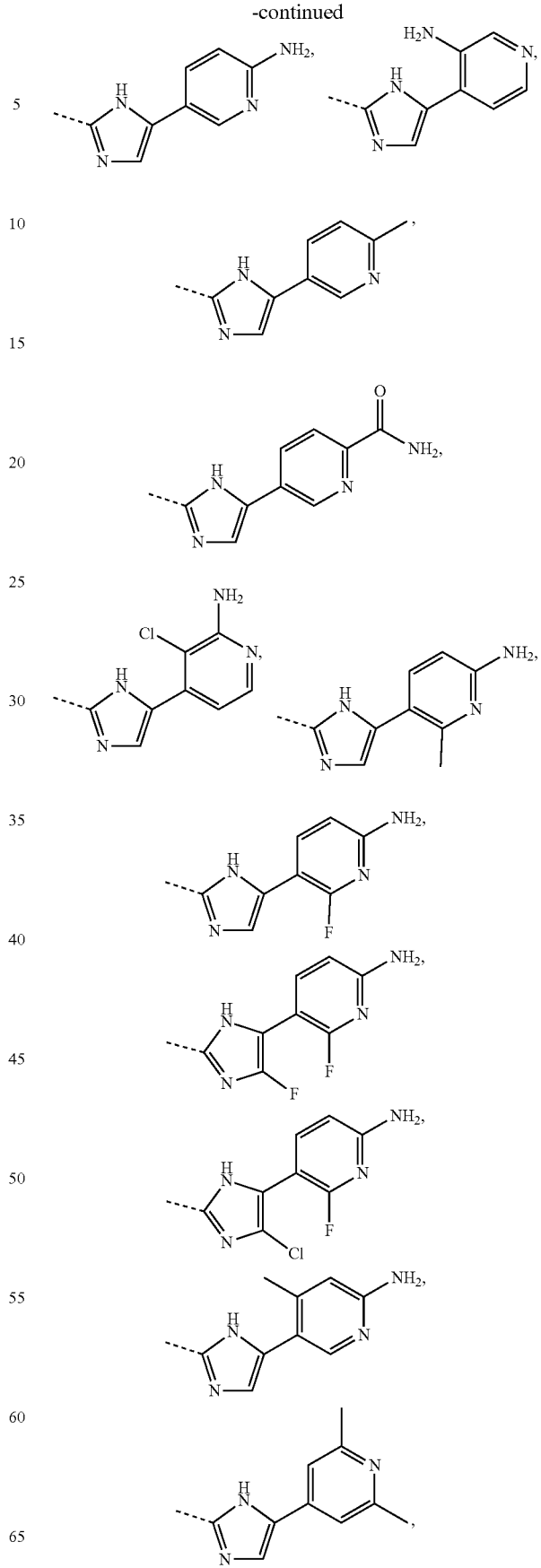

-continued
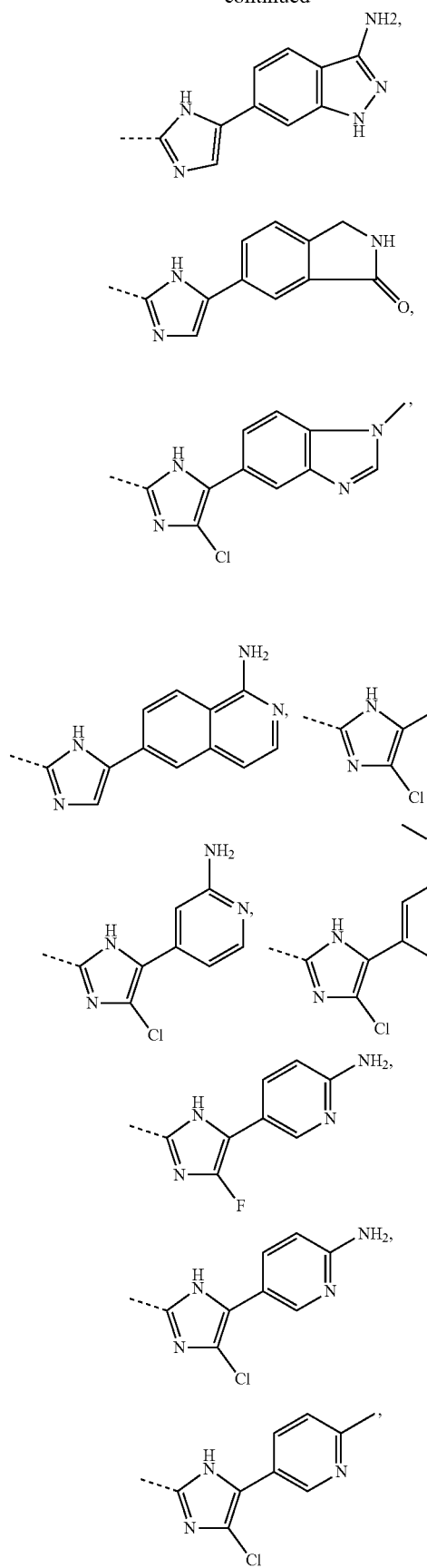
-continued
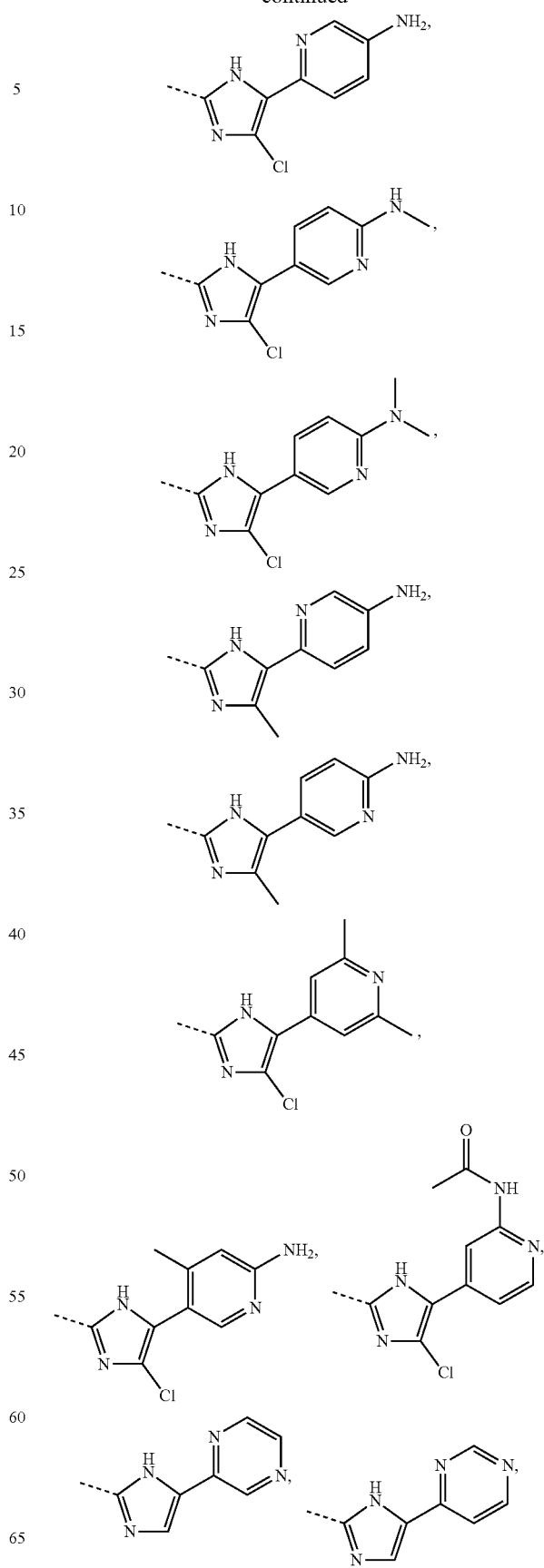

-continued
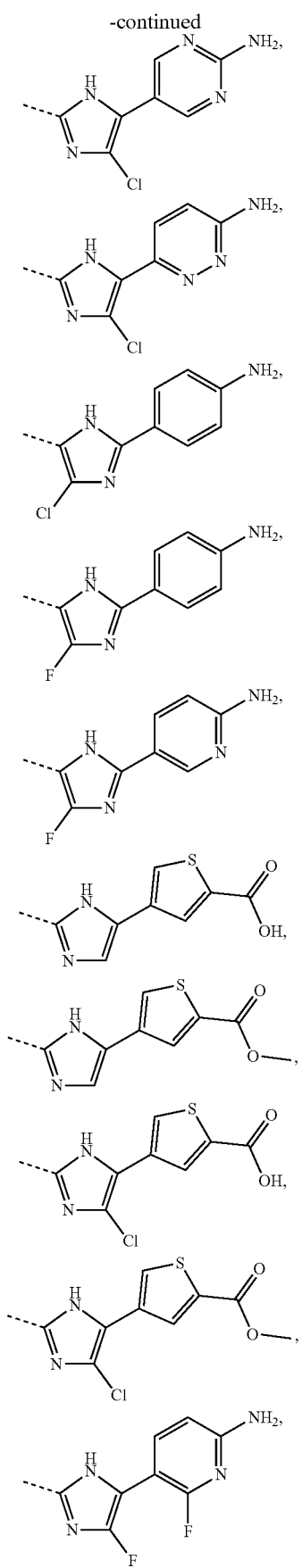
-continued
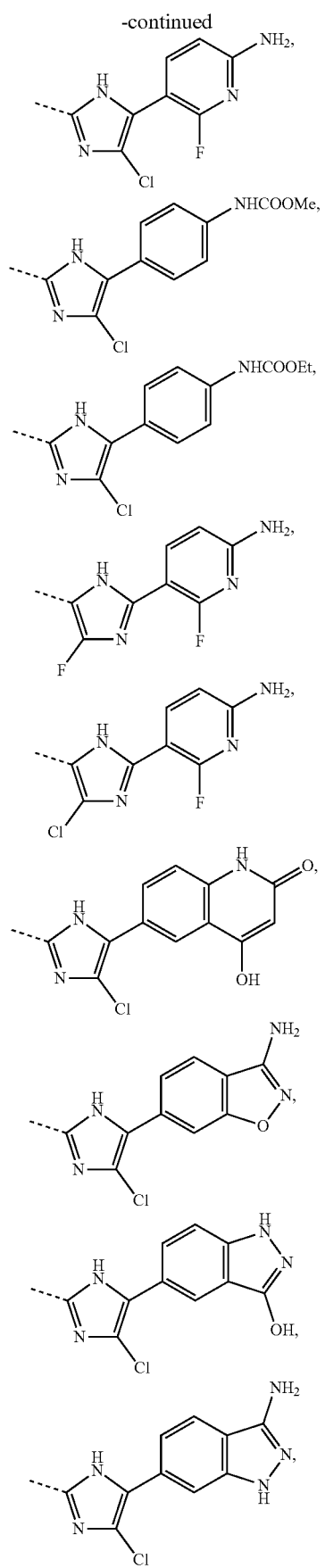

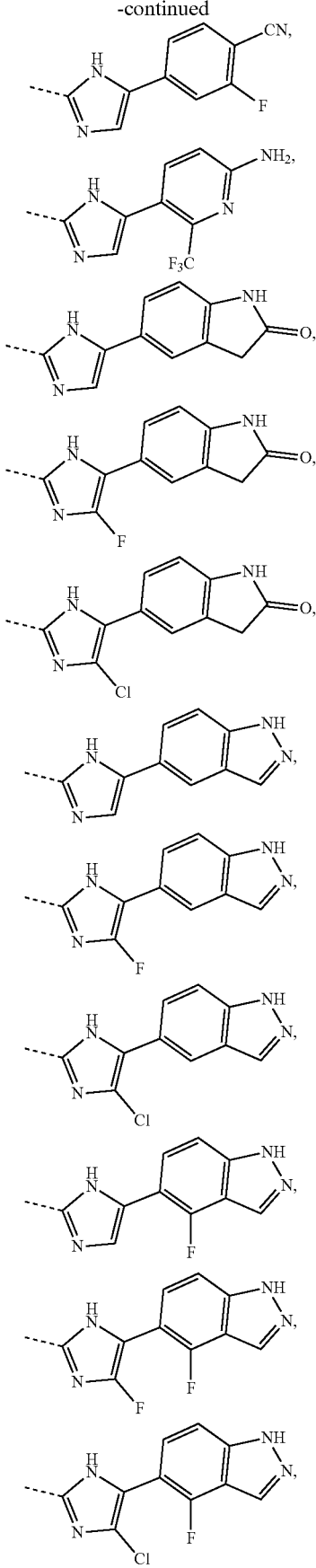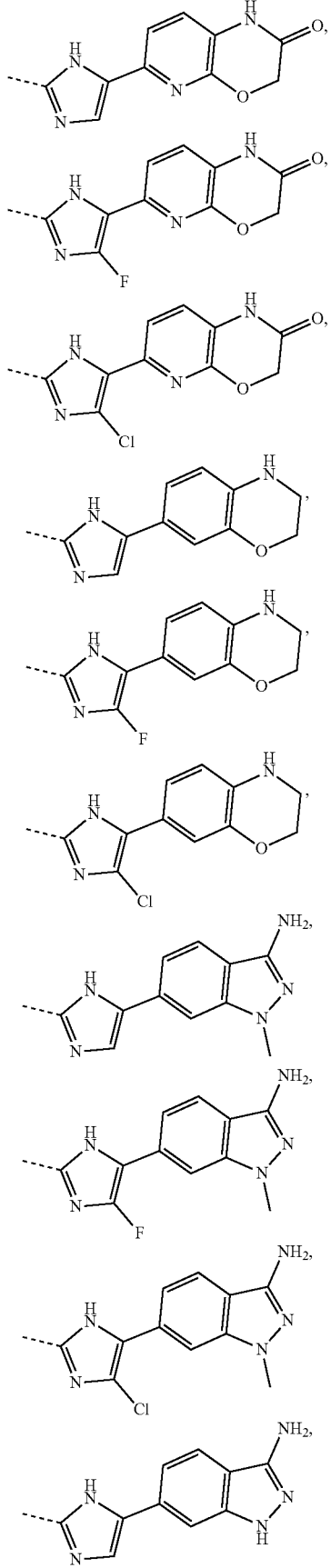

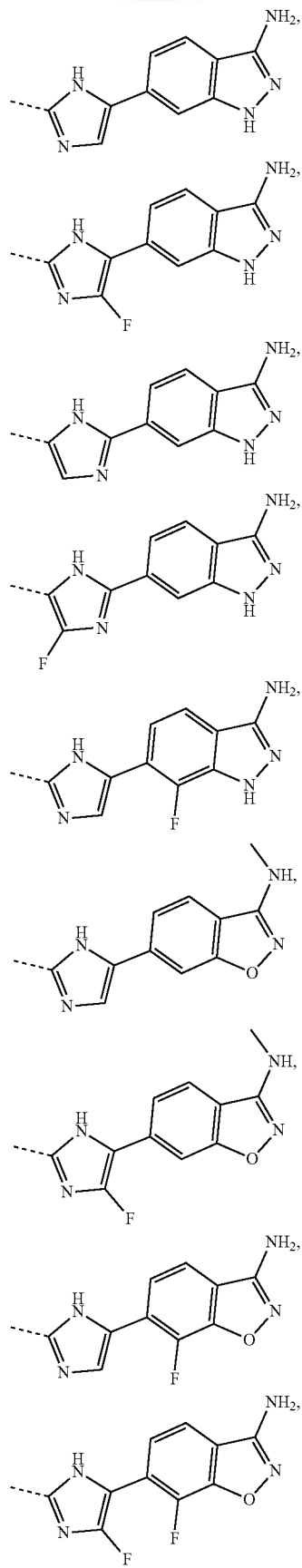
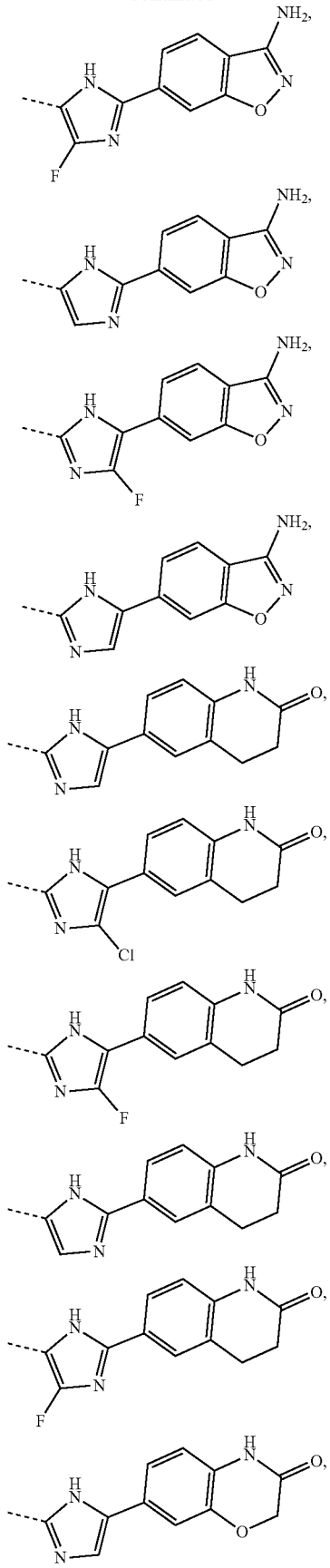

-continued
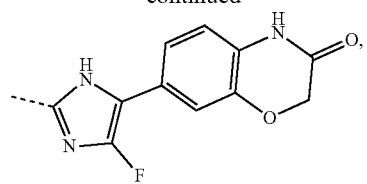
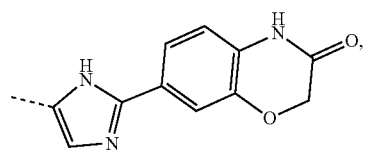
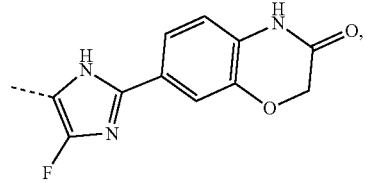
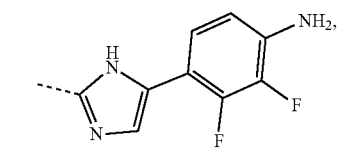
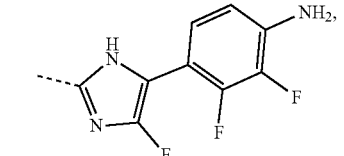
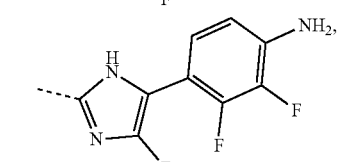
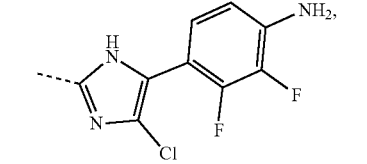
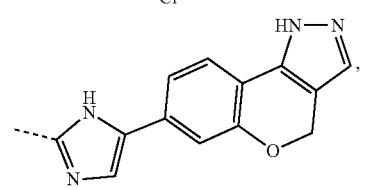
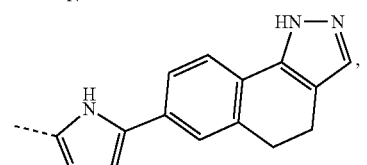
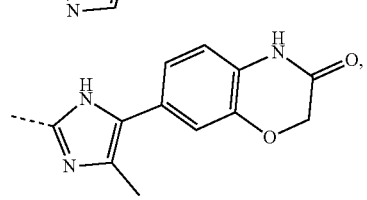
-continued
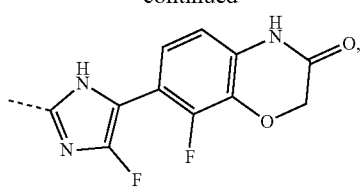
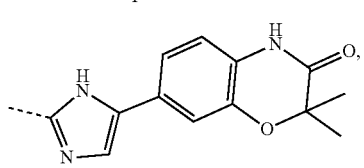
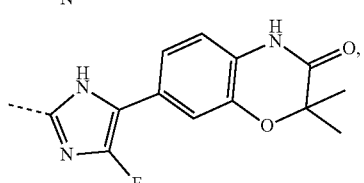
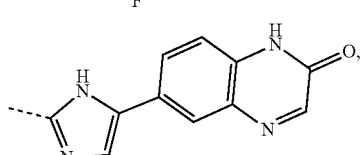
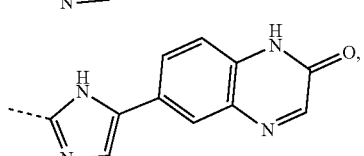
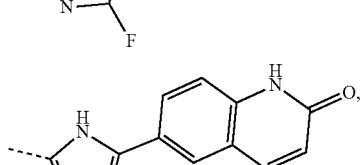
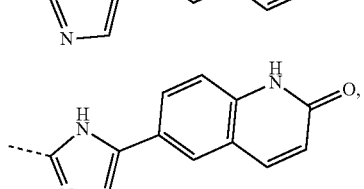
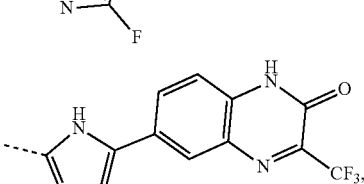
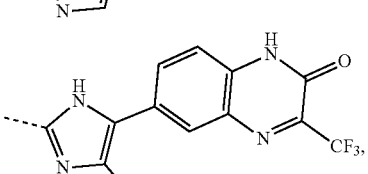
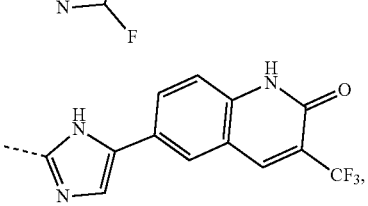

-continued
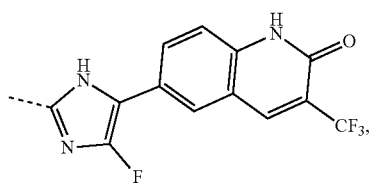
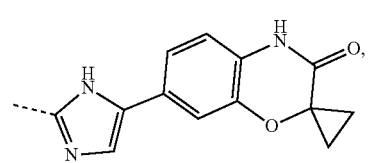
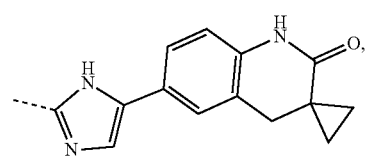
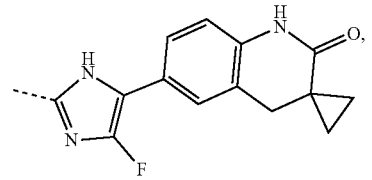
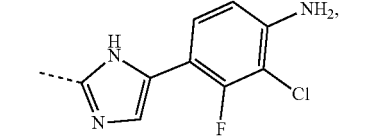
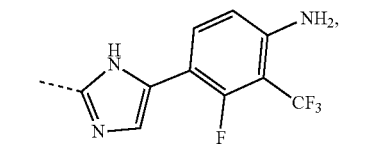
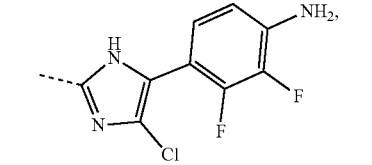
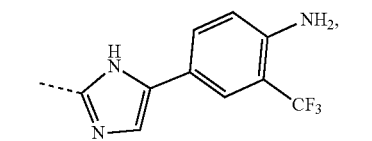
-continued
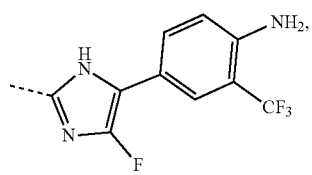
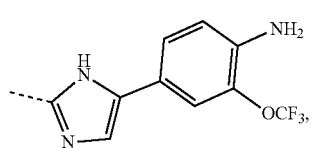
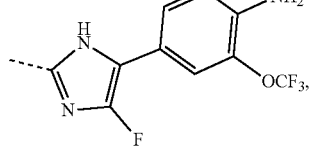
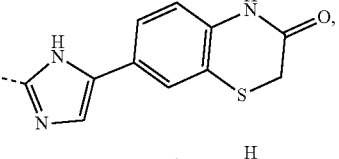
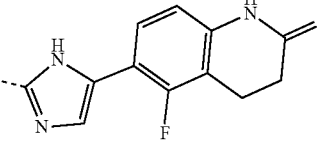
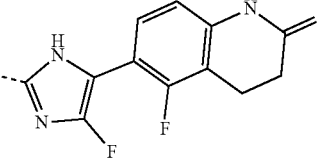
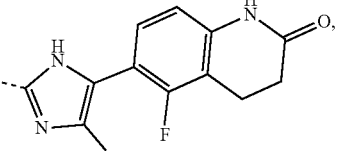
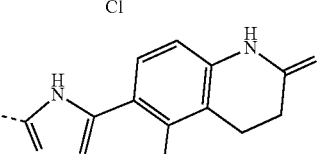
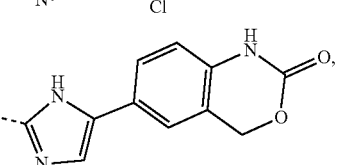

-continued
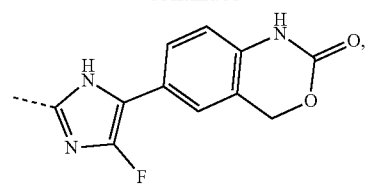
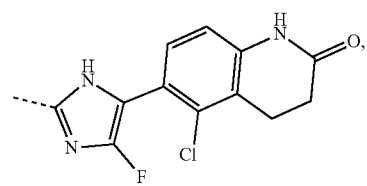
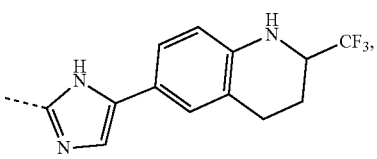
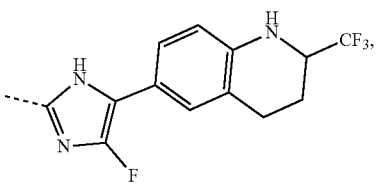
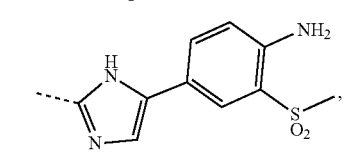
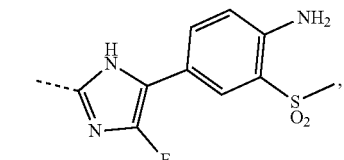
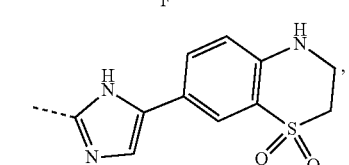
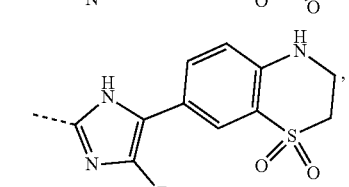
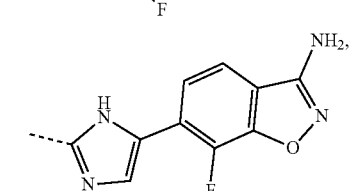
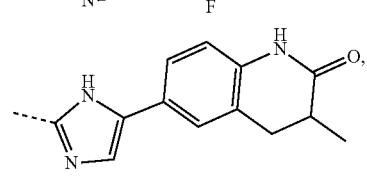
-continued
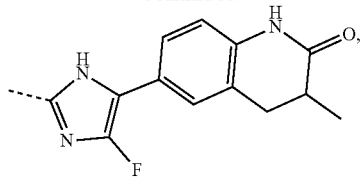
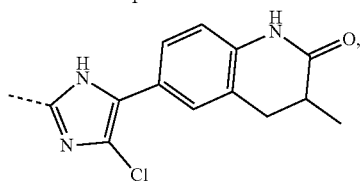
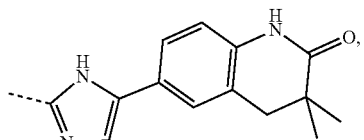
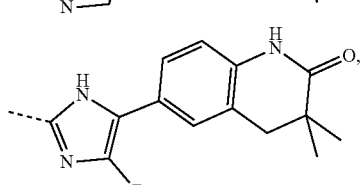
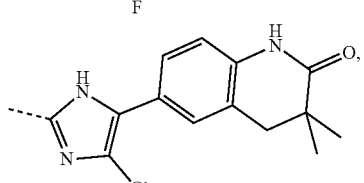
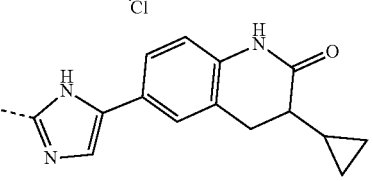
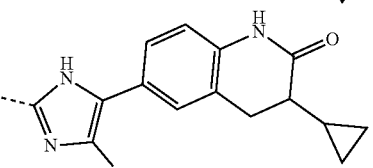
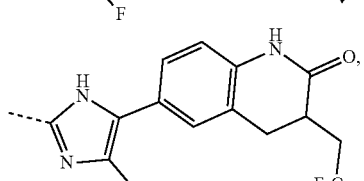
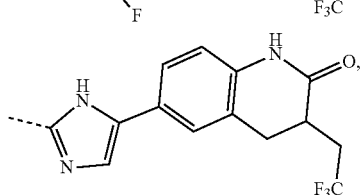
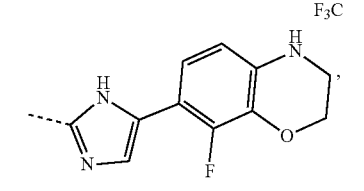

-continued

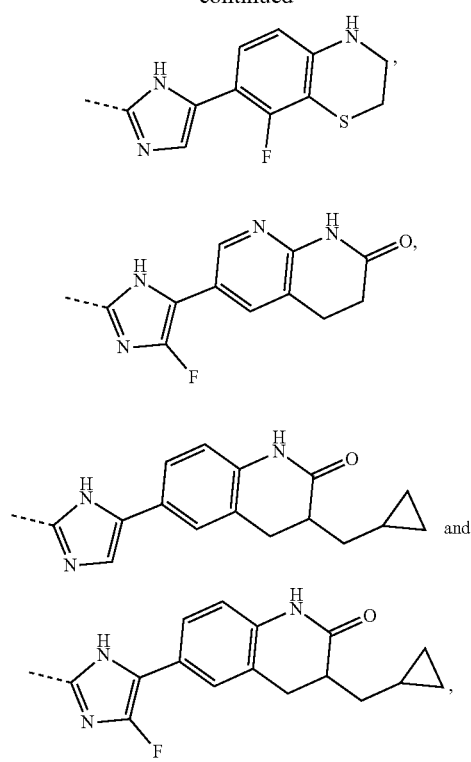

and the other variables are as defined herein.

In some embodiments of the present disclosure, the ring D is selected from cyclopropyl, cyclobutyl, azetidinyl, oxetanyl and pyrrolidinyl, and the other variables are as defined herein.

In some embodiments of the present disclosure, the structural moiety

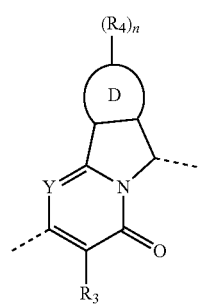

is selected from

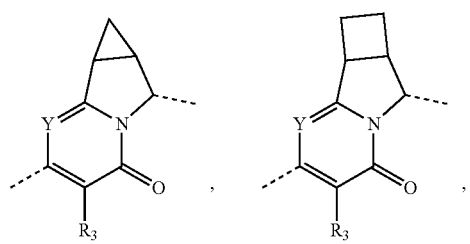

-continued

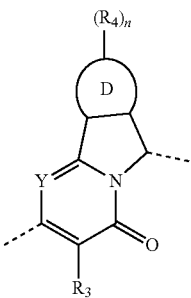

and the other variables are as defined herein.

In some embodiments of the present disclosure, the structural moiety is selected from

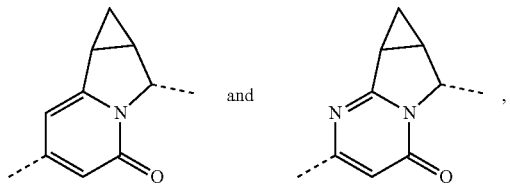

and the other variables are as defined herein.

In one aspect of the present disclosure, the compound represented by formula (I), the optical isomer thereof and the pharmaceutically acceptable salt thereof, selected from

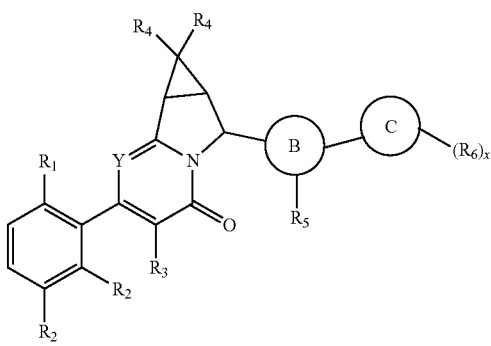
(I-1)

wherein,
$R_1$ is as defined above;
$R_2$ is as defined above;
$R_3$ is as defined above;
$R_4$ is as defined above;
$R_5$ is as defined above;
$R_6$ is as defined above;
x, Y are as defined above;
ring B is as defined above;
ring C is as defined above;

In one aspect of the present disclosure, the compound, the optical isomer thereof and the pharmaceutically acceptable salt thereof, selected from

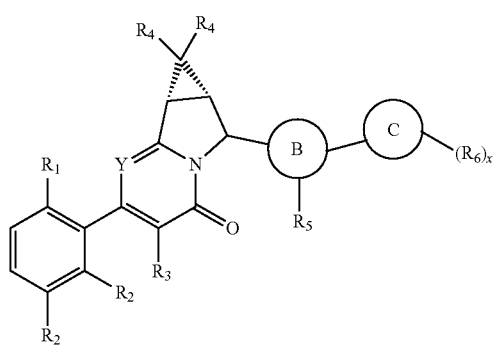
(I-1a)

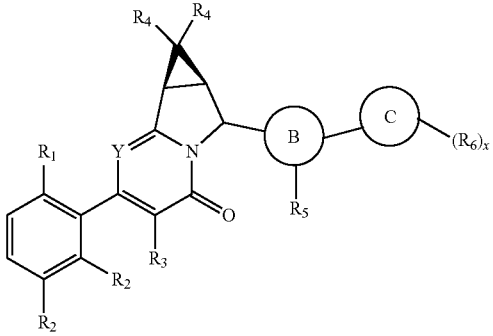
(I-1b).

wherein,
$R_1$, $R_2$, $R_3$, $R_4$, $R_5$, $R_6$, x, Y, ring B, ring C are as defined above.

In one aspect of the present disclosure, the compound, the optical isomer thereof and the pharmaceutically acceptable salt thereof, selected from

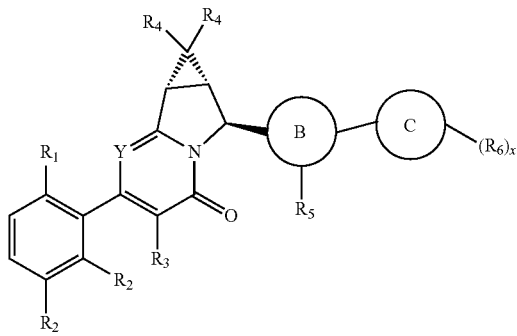
(I-1a1)

(I-1a2)

(I-1b1)

-continued
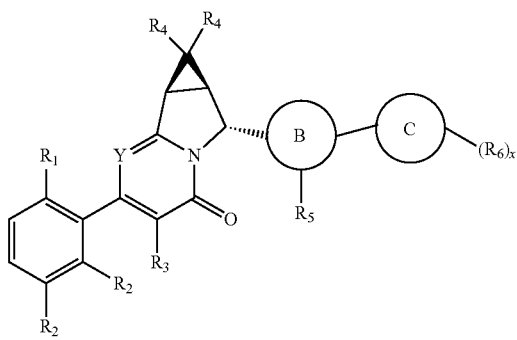
(I-1b2)
wherein,
R₁, R₂, R₃, R₄, R₅, R₆, x, Y, ring B, ring C are as defined above.
In another aspect of the present disclosure, the present disclosure also presents a compound of the following formula, an optical isomer thereof and a pharmaceutically acceptable salts thereof, selected from
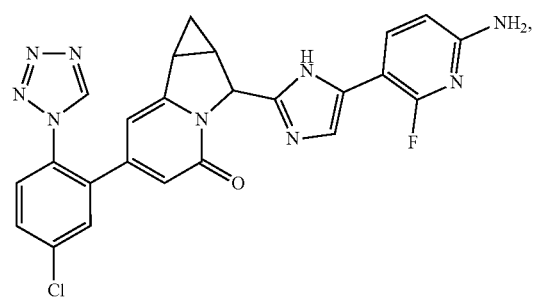
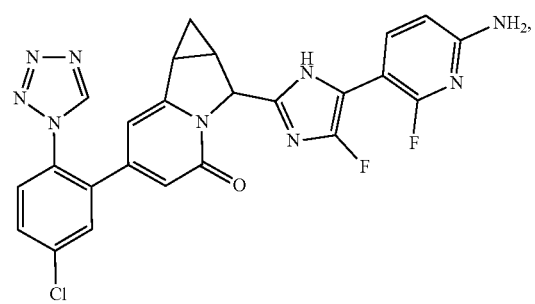
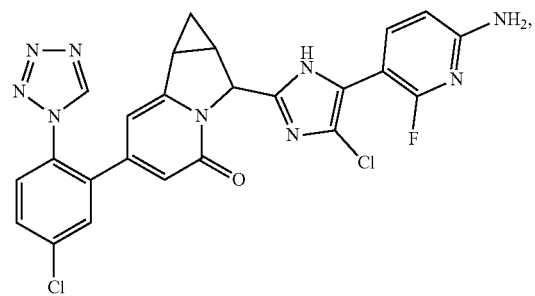
-continued
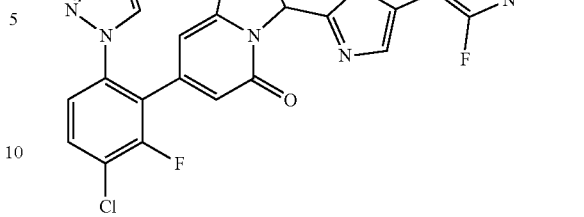
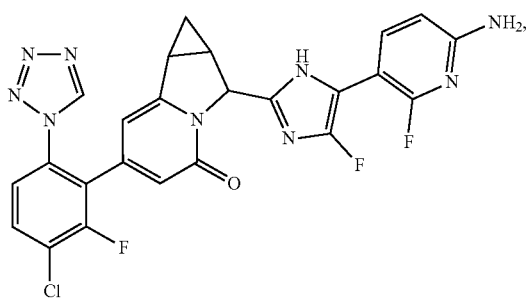
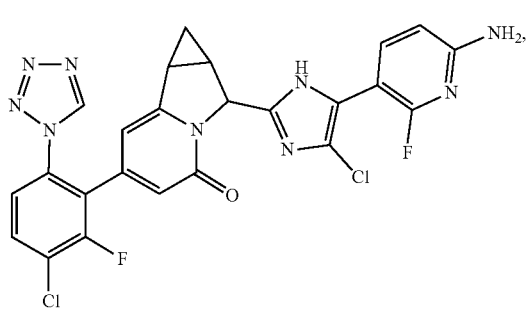
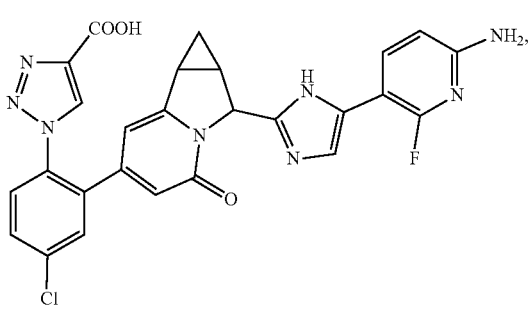
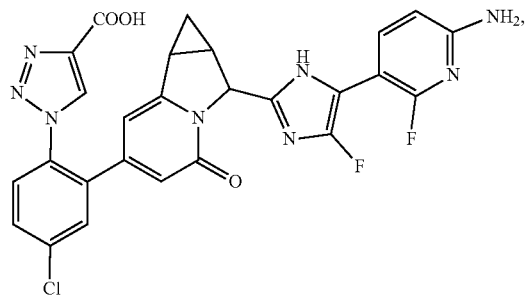

39
-continued

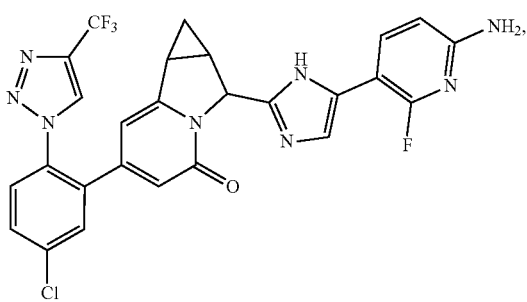
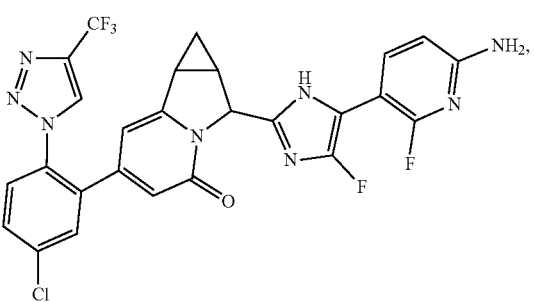
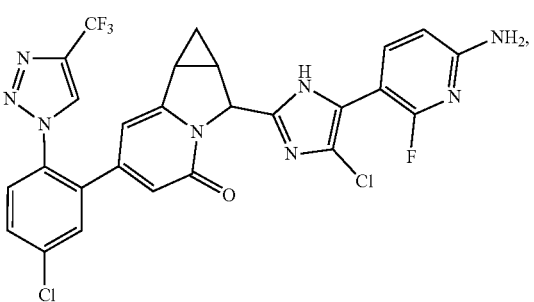
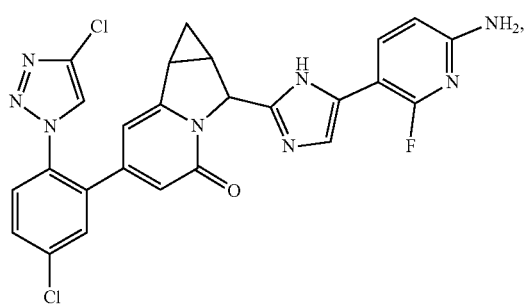
40
-continued
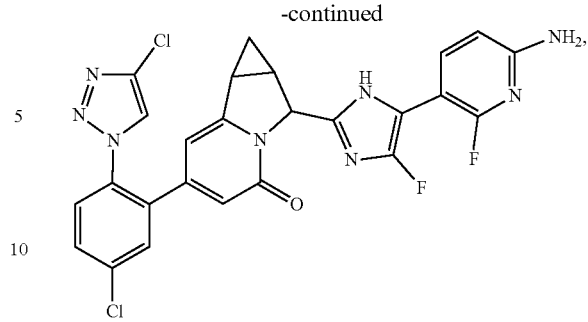
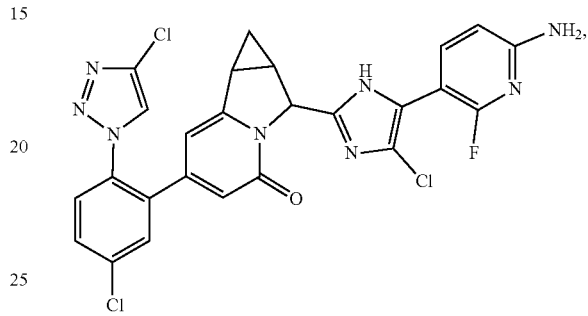
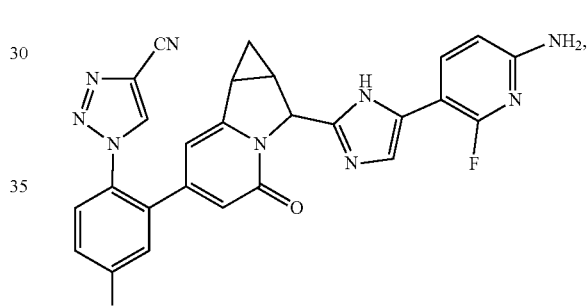
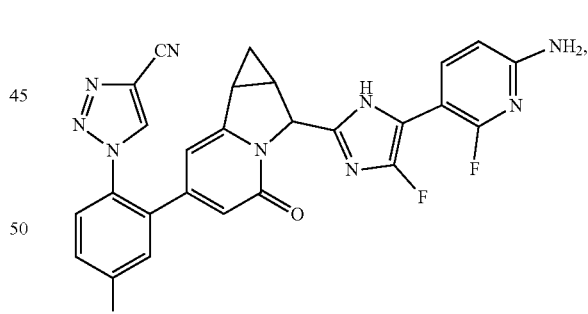
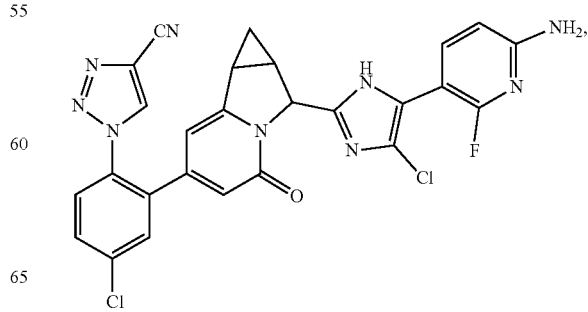

41
-continued
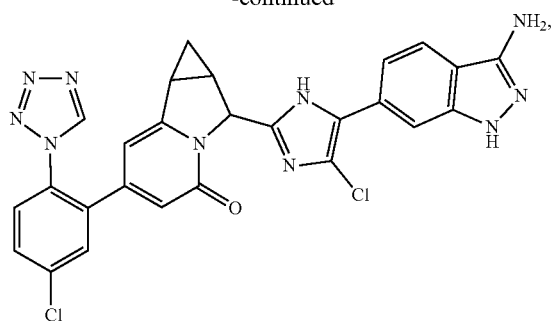
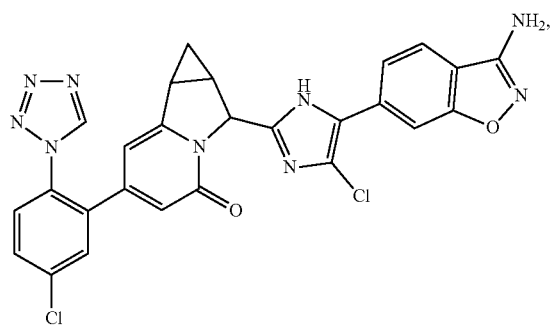
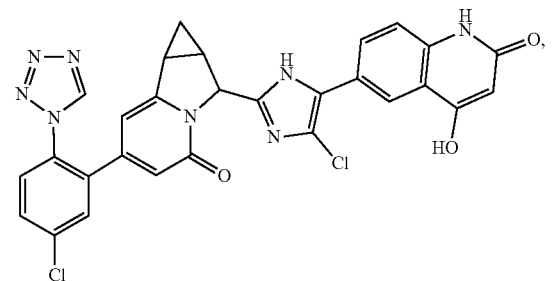
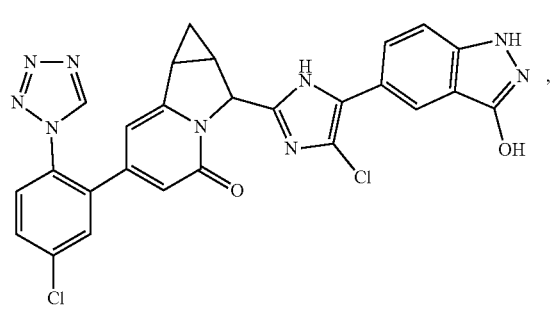
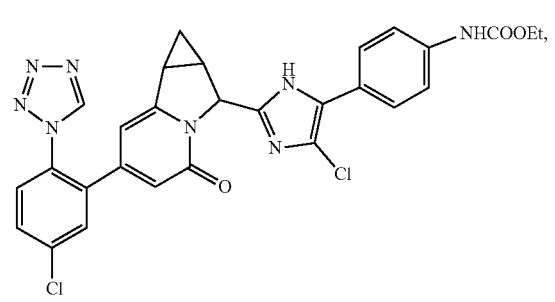
42
-continued
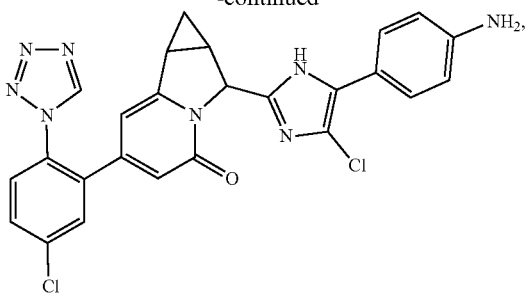
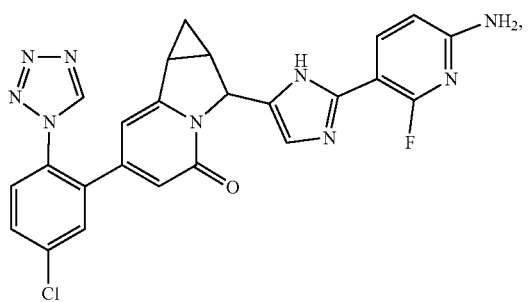
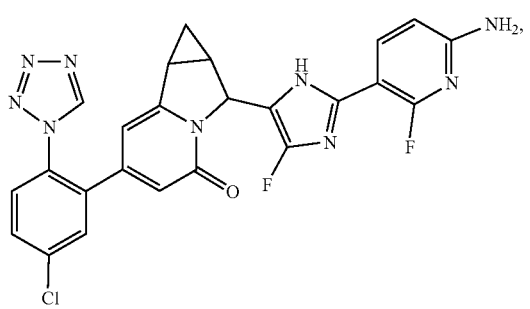
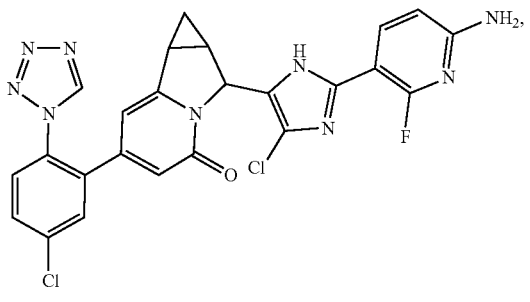
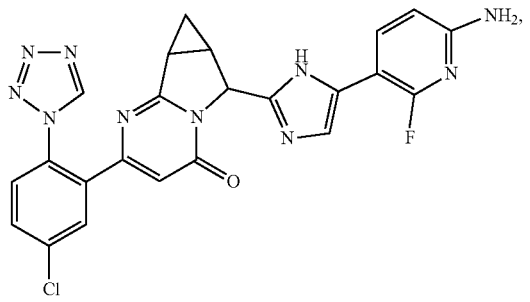

43
-continued
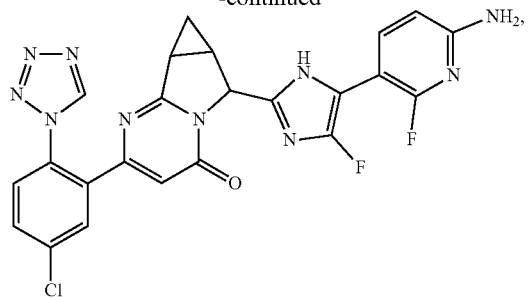
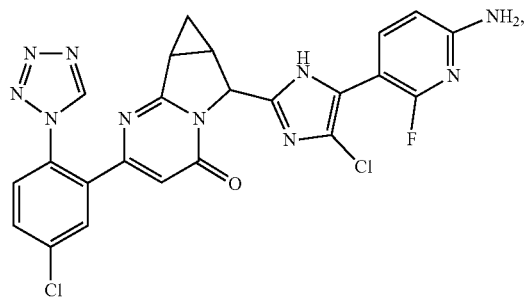
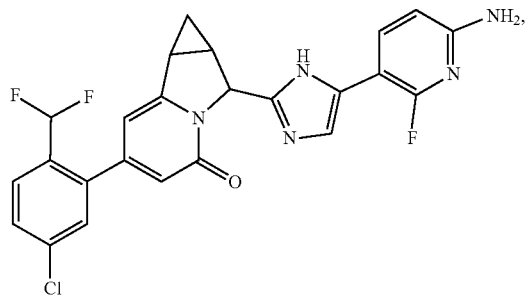
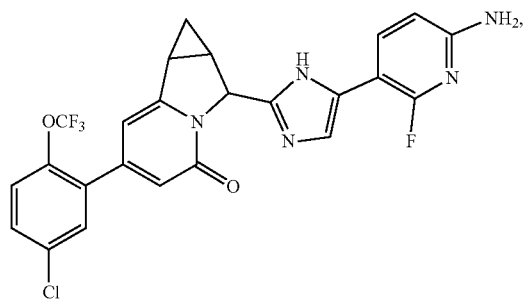
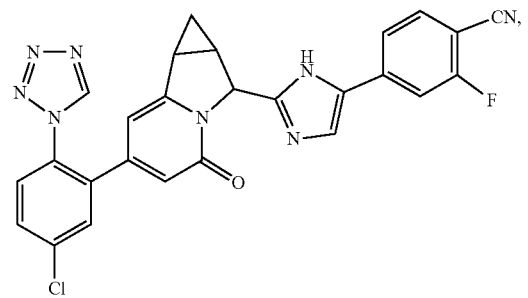
44
-continued
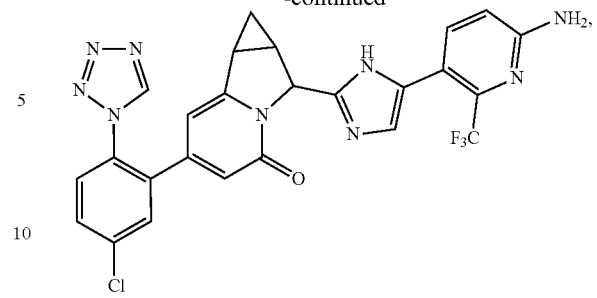
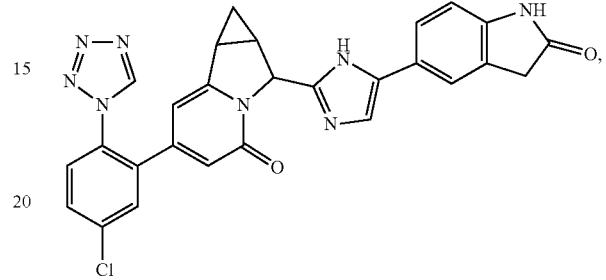
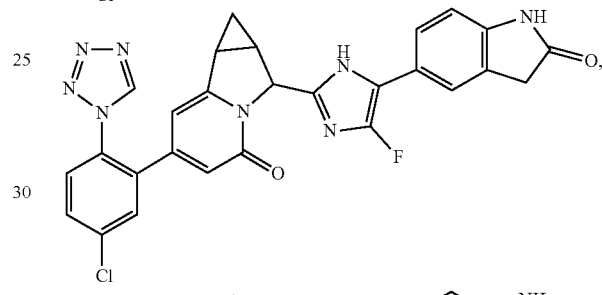
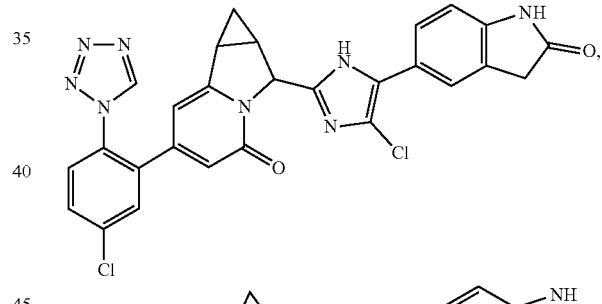
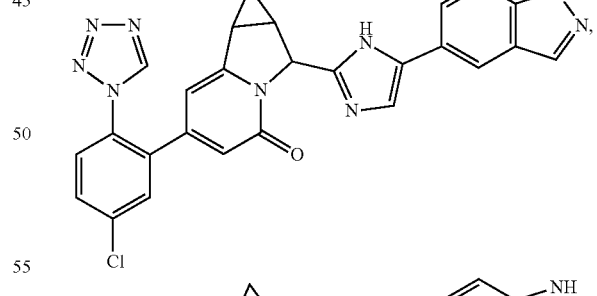
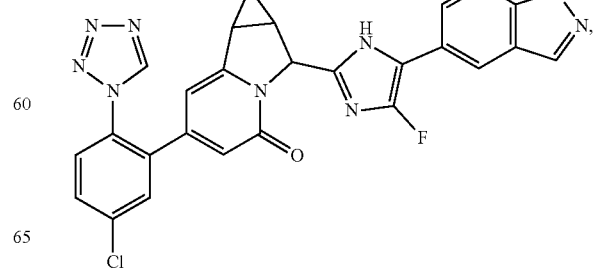

45
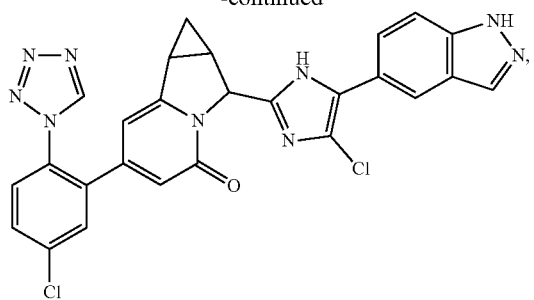
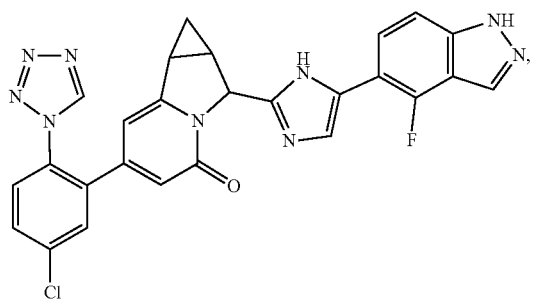
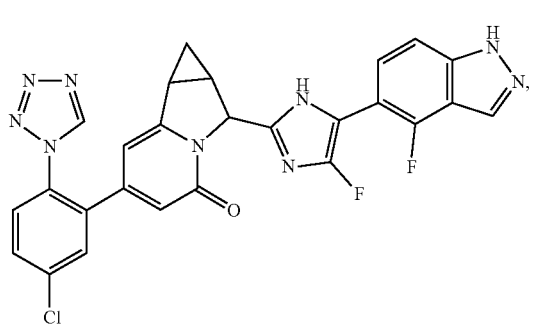
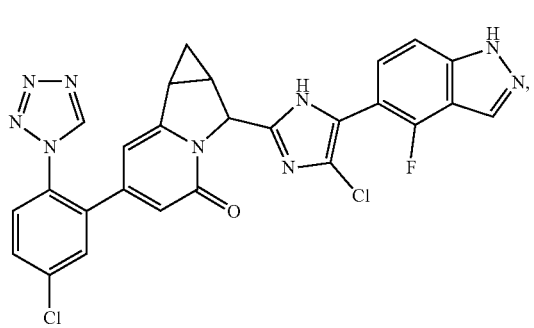
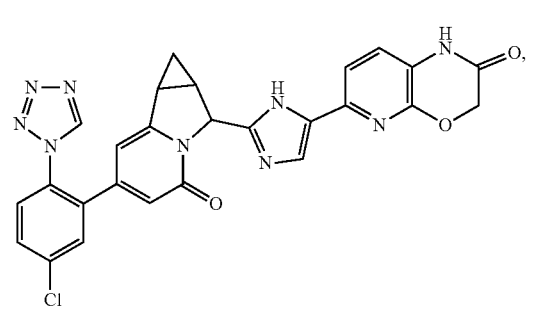
46
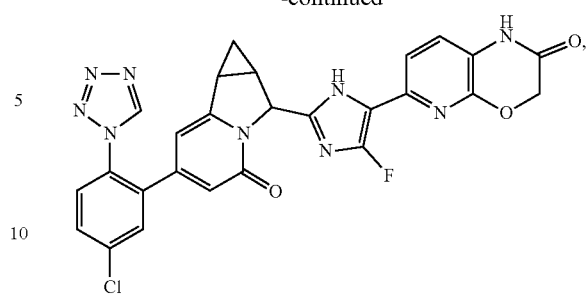
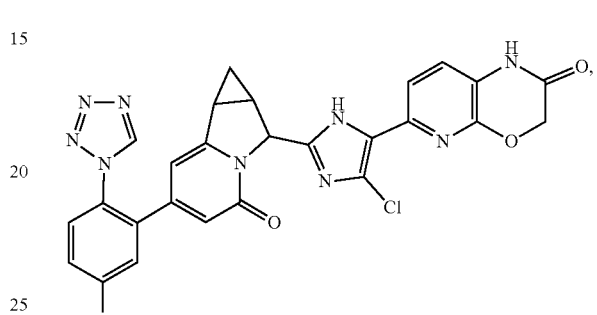
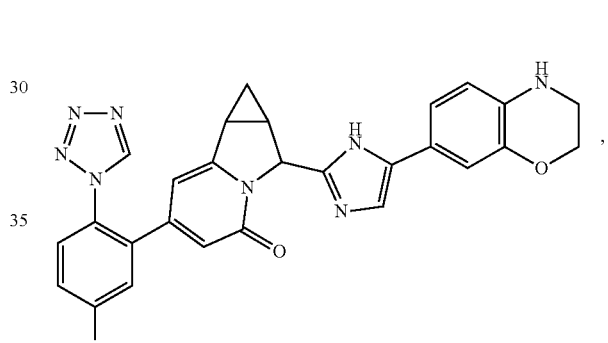
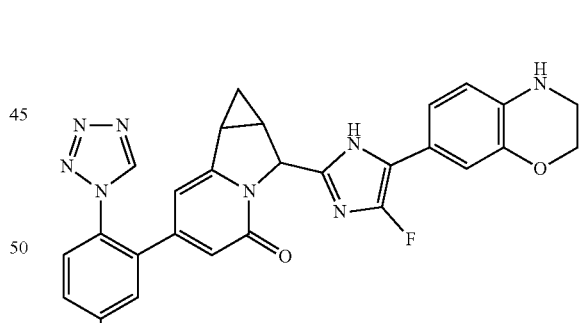
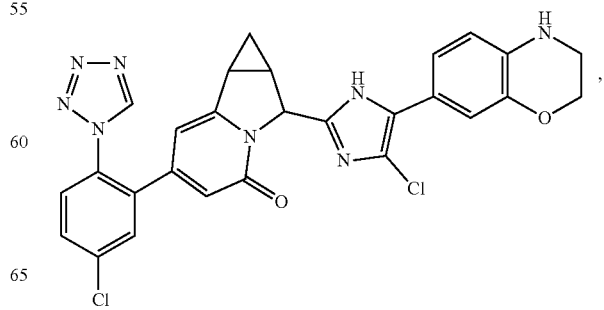

47
-continued
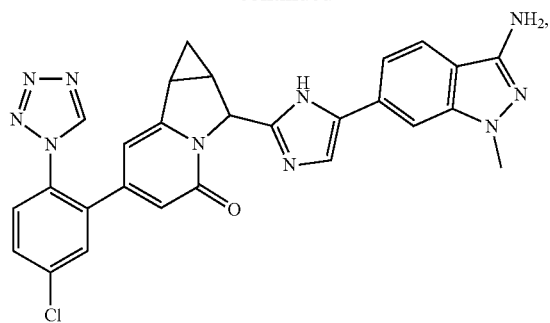
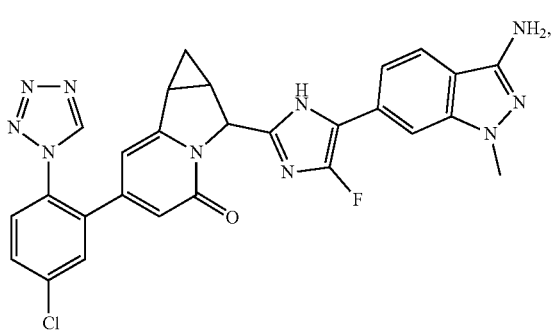
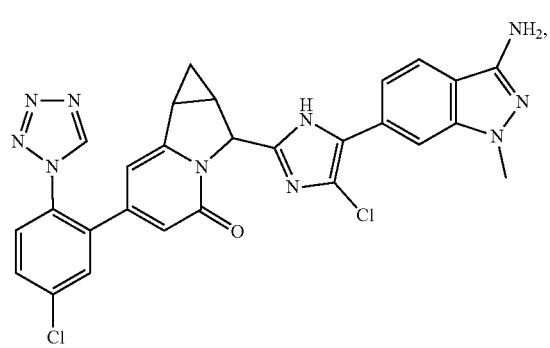
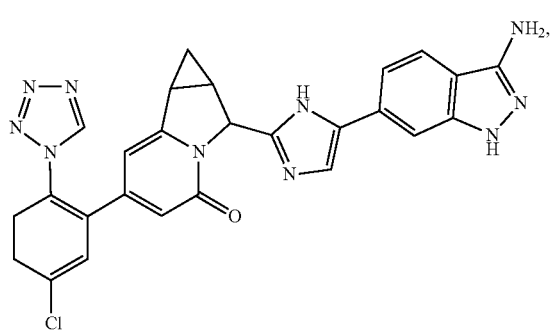
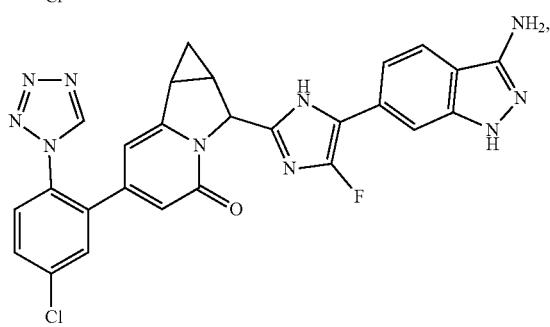
48
-continued
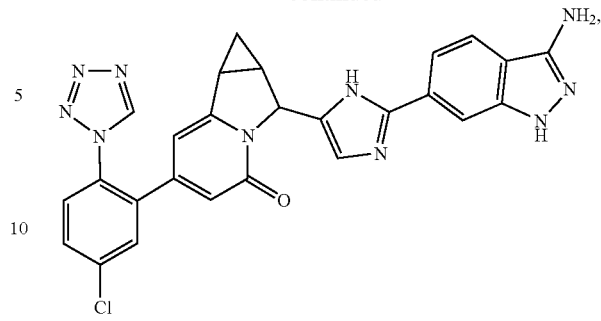
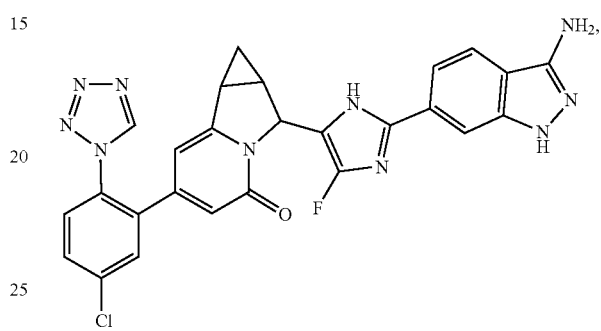
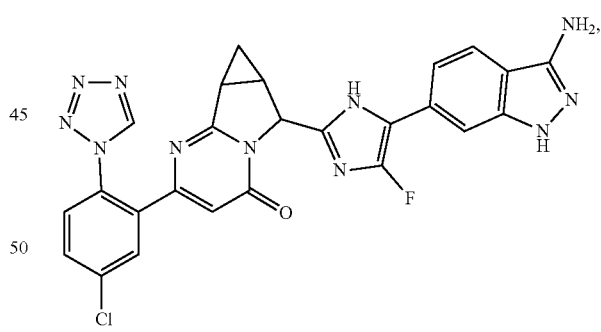
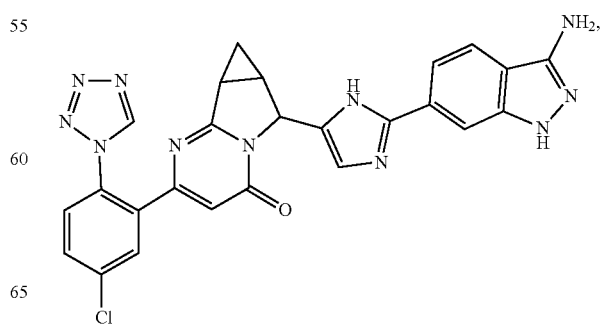

49
-continued
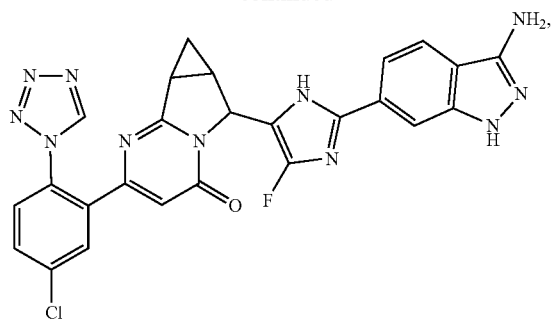
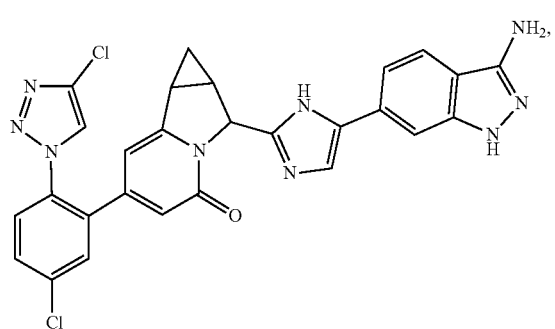
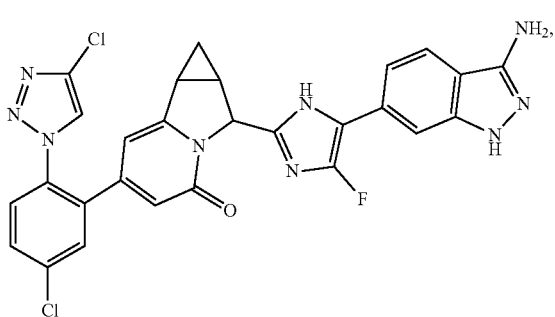
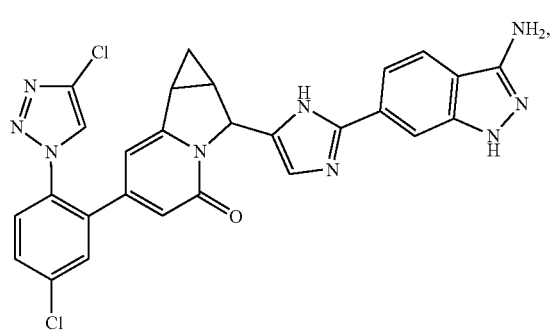
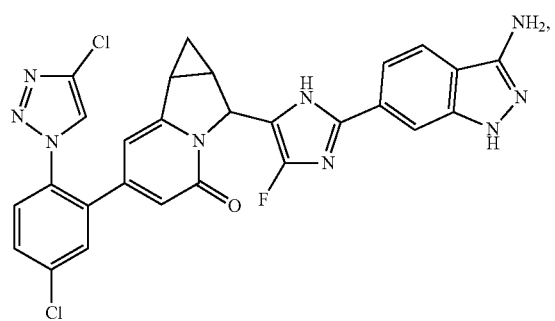
50
-continued
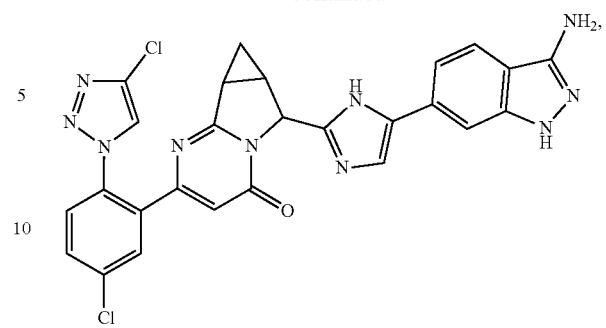
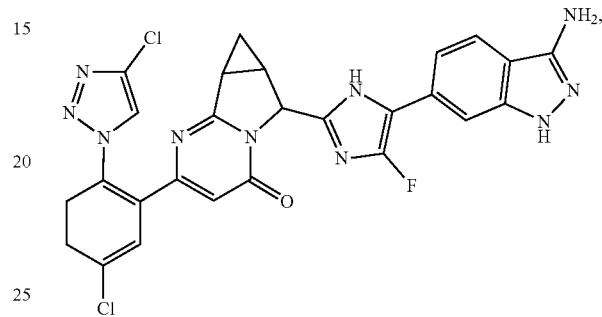
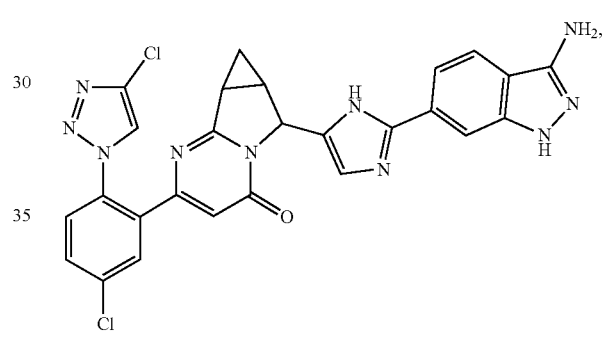
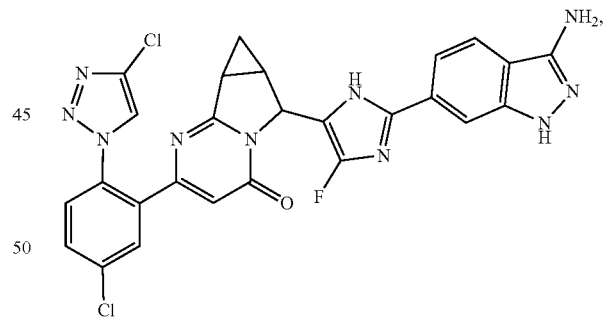
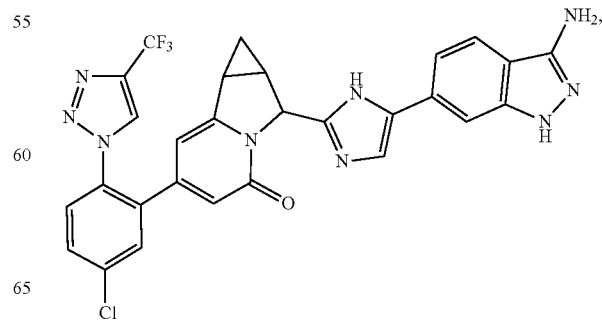

51
-continued
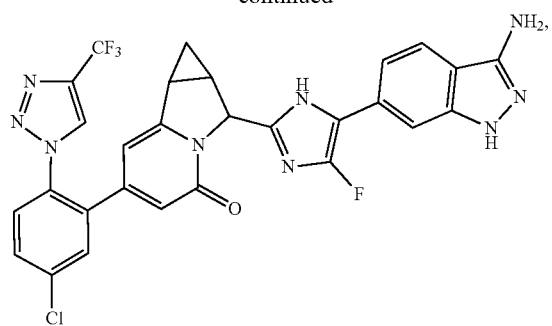
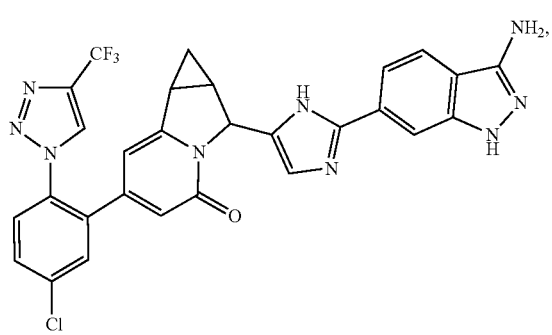
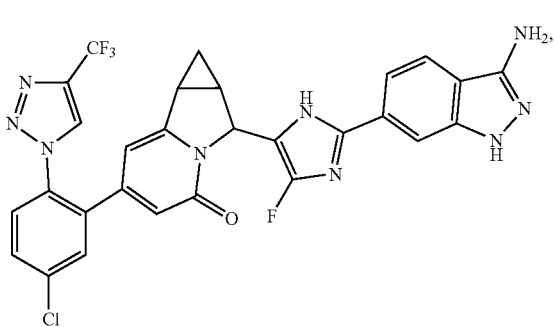
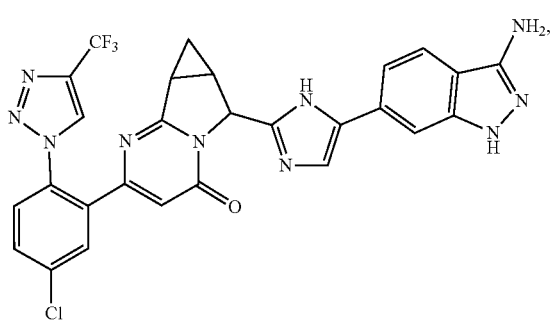
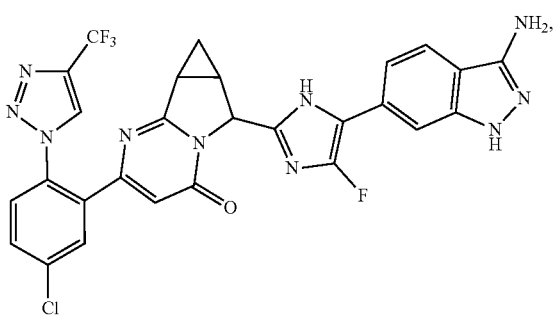
52
-continued
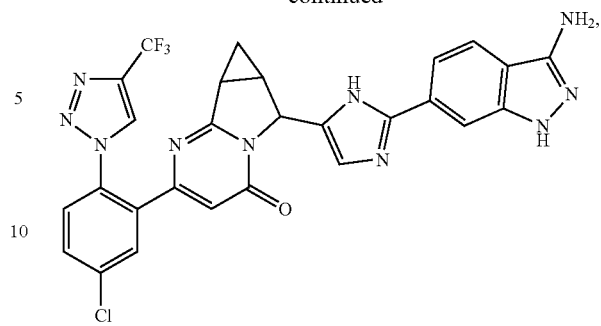
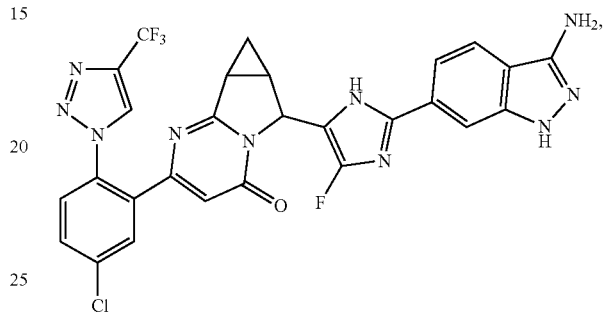
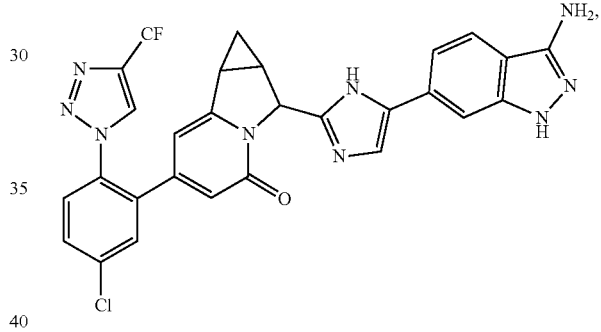
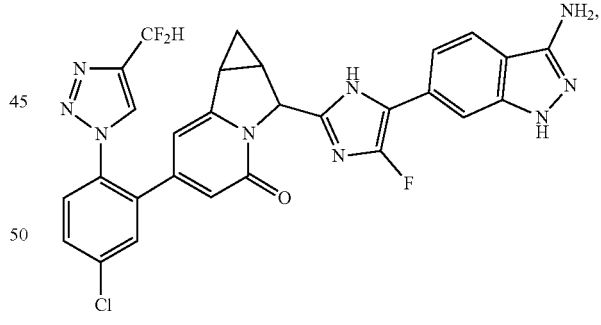
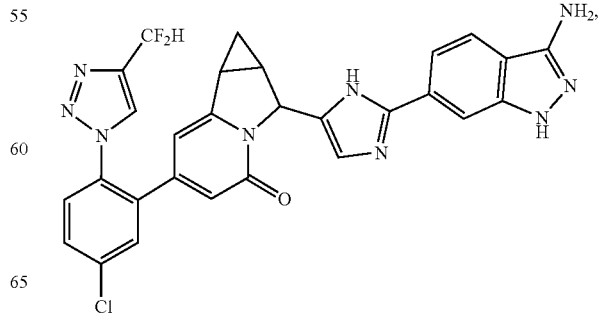

53
-continued
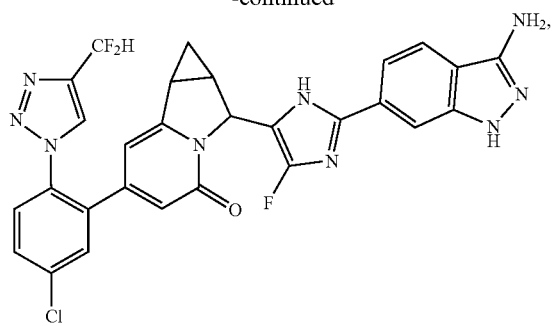
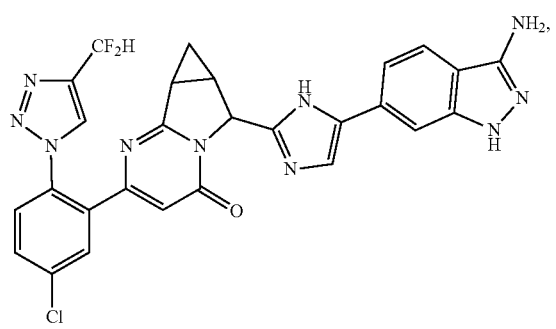
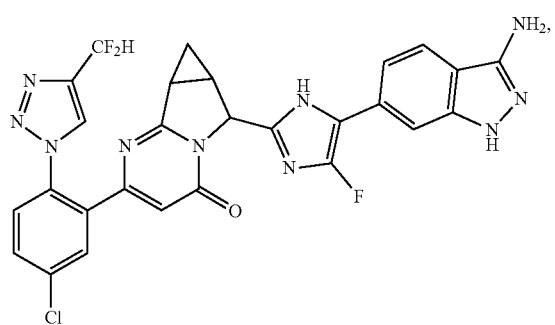
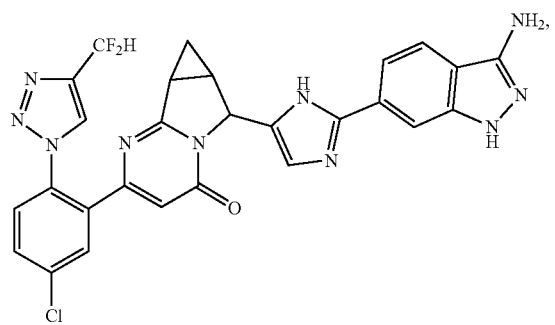
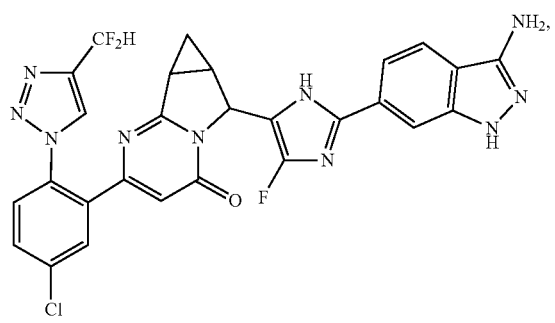
54
-continued
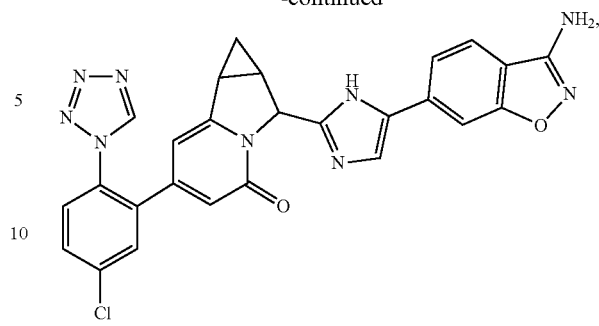
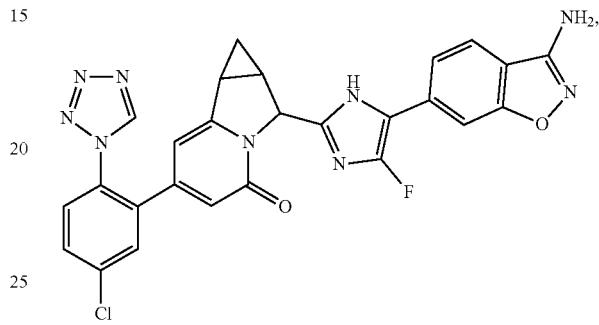
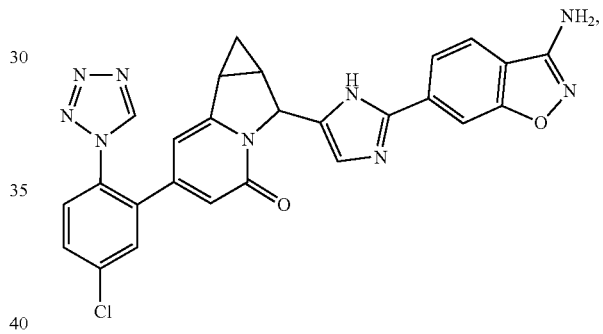
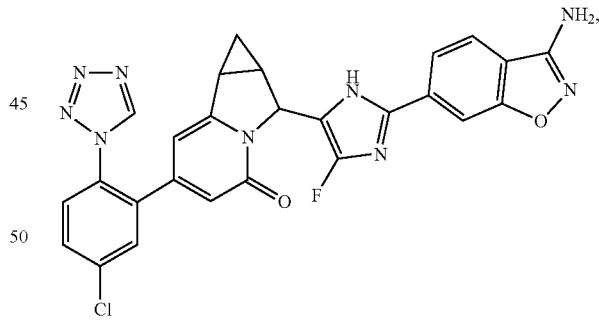
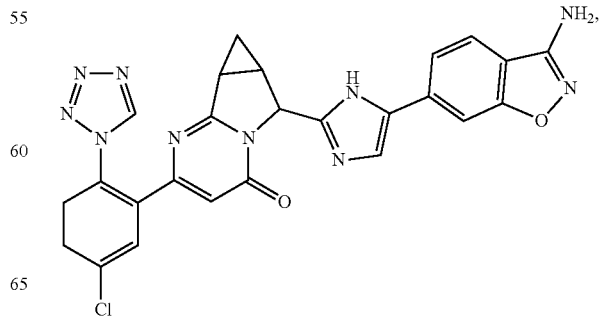

55
-continued
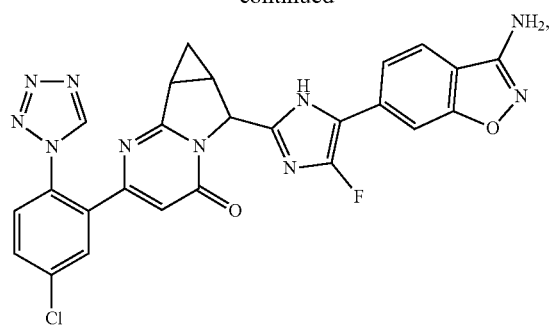
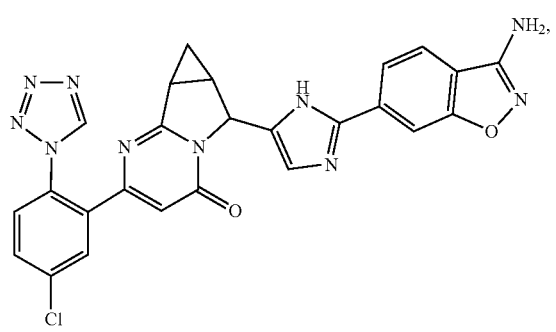
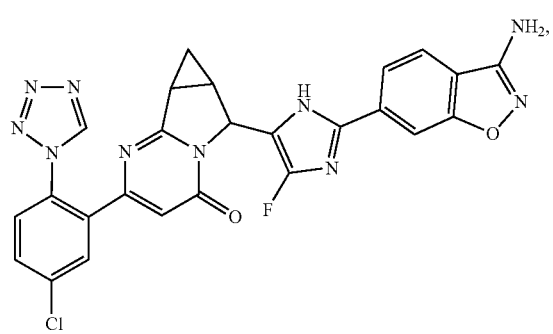
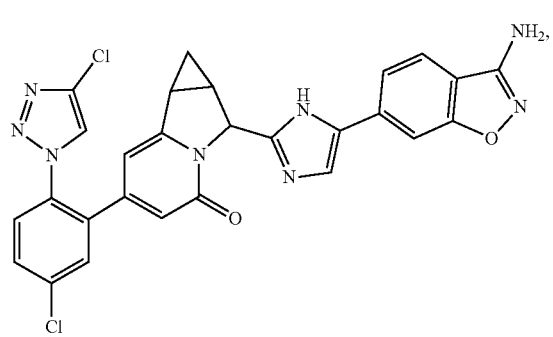
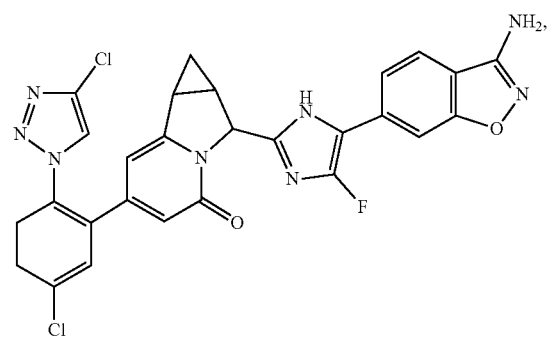
56
-continued
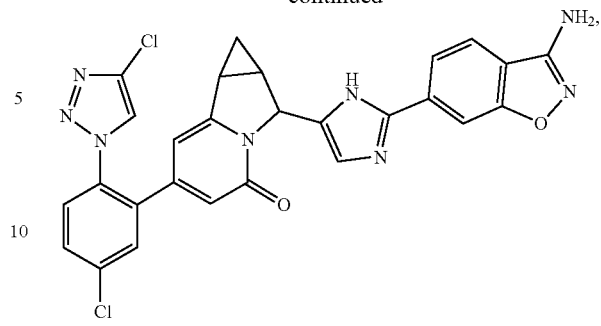

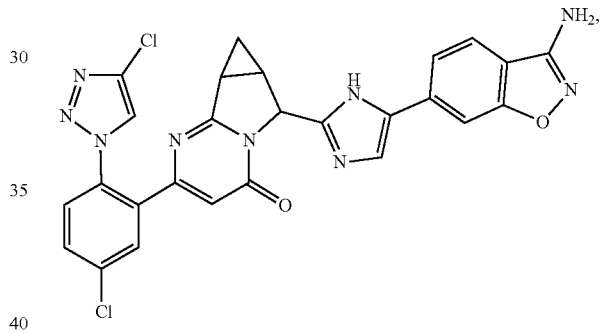
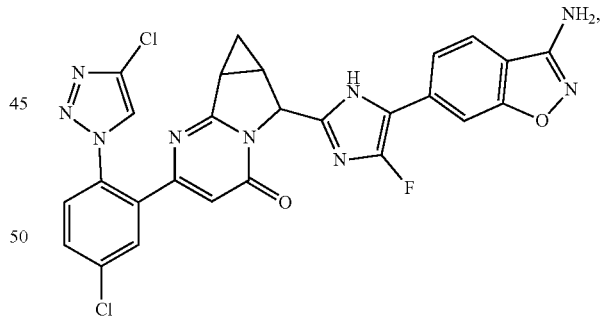
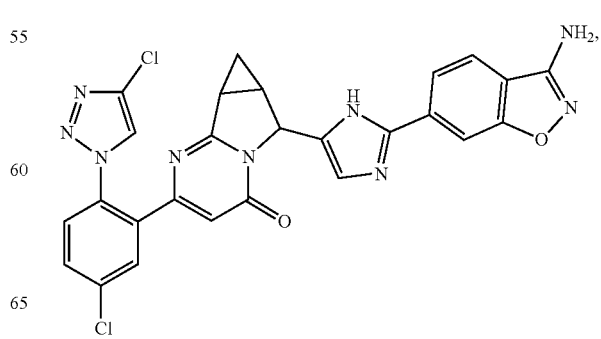

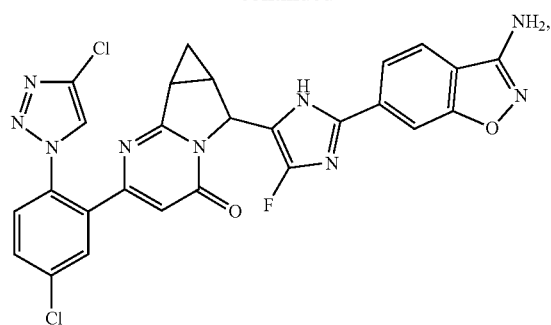
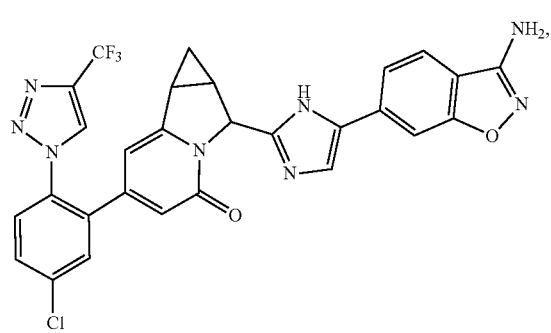
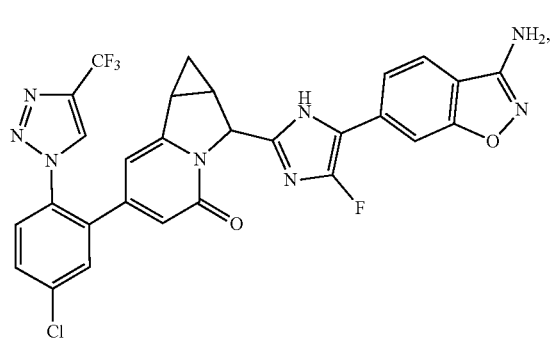
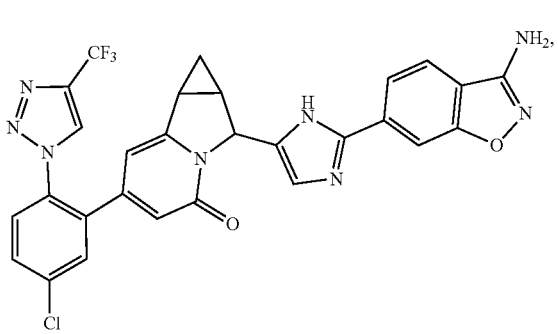
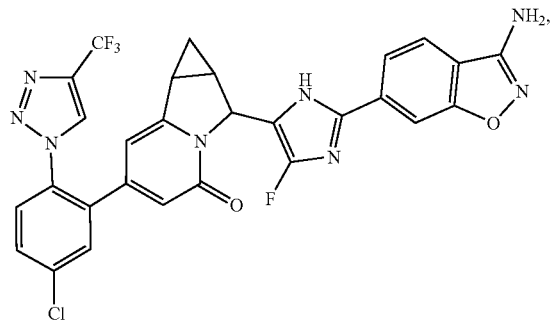
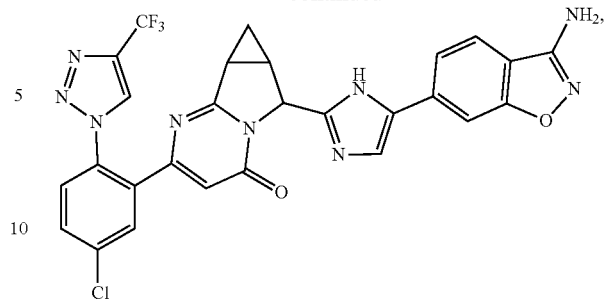
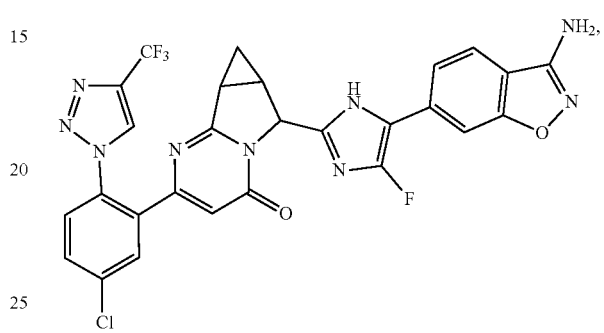
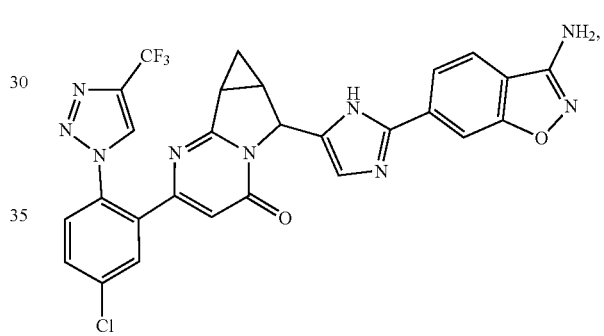
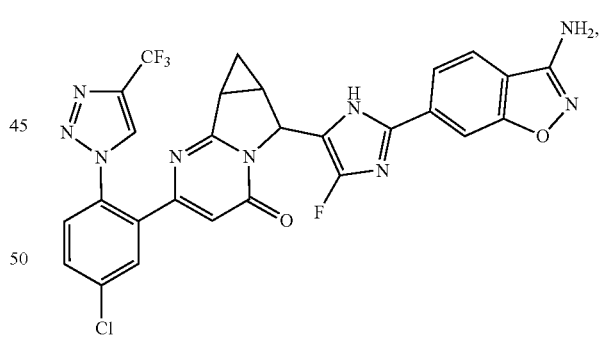
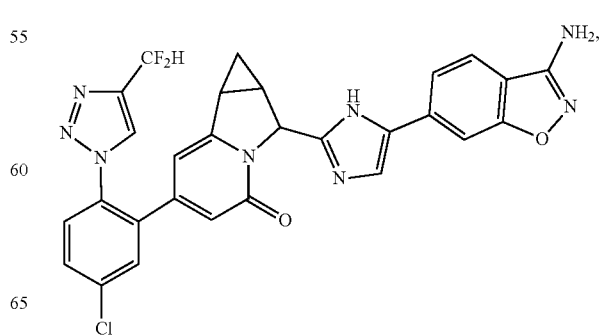

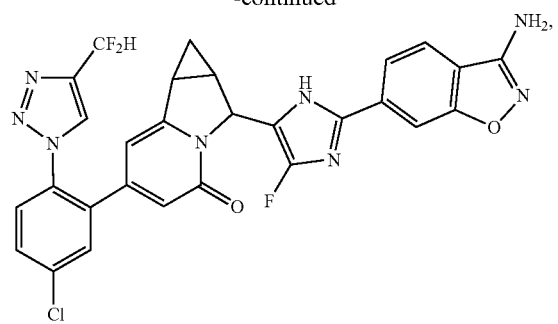
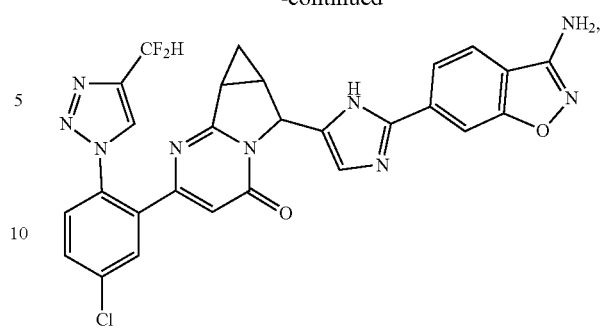
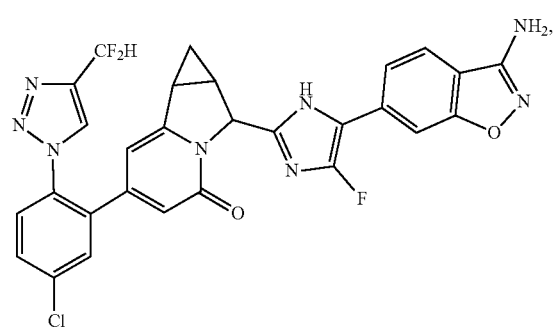
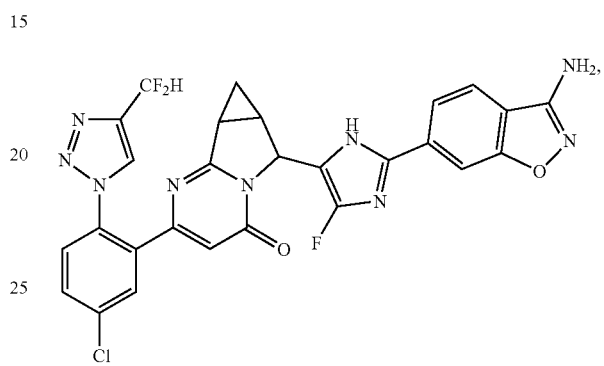
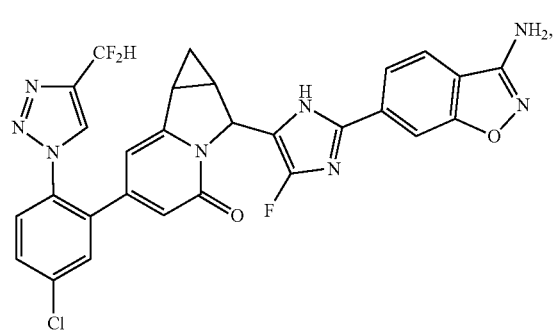
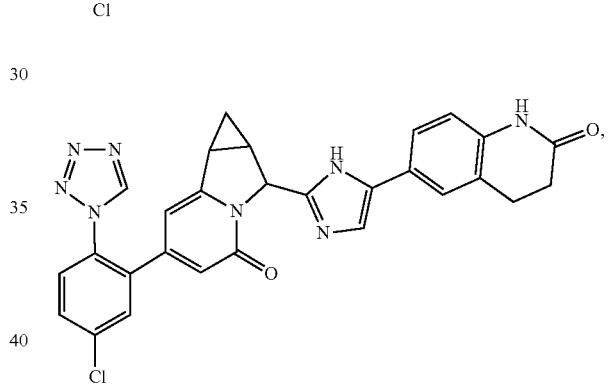
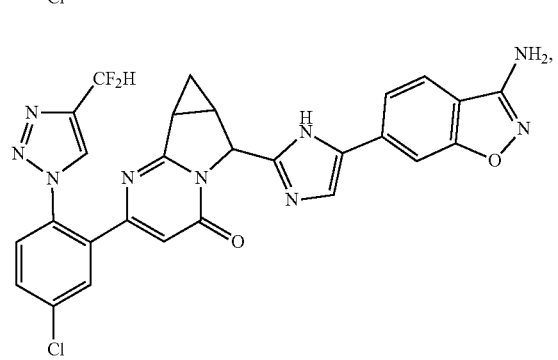
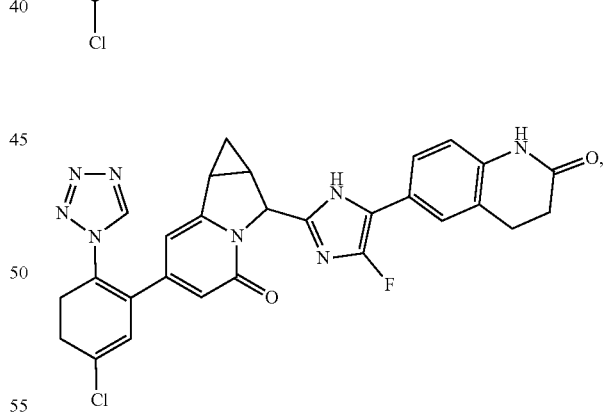
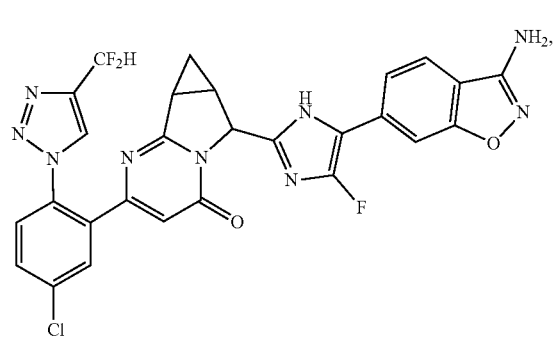
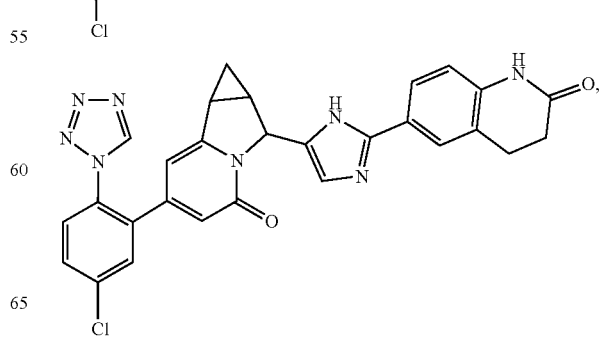

61
-continued
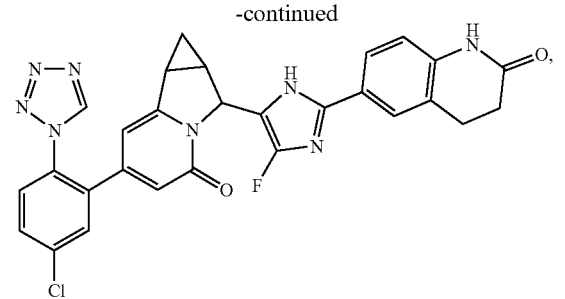
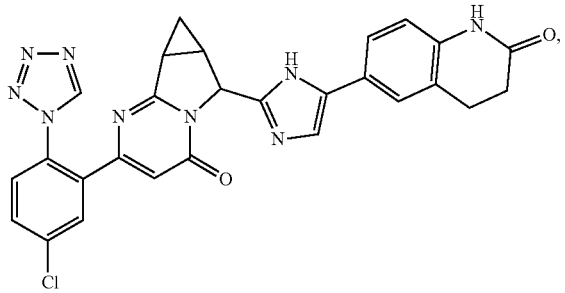
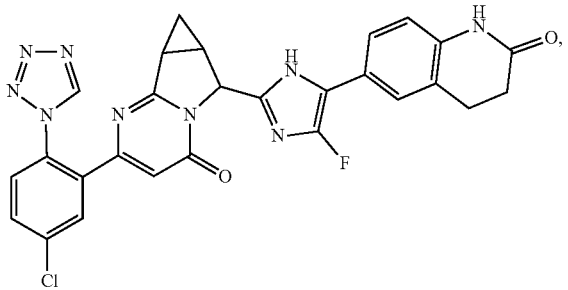
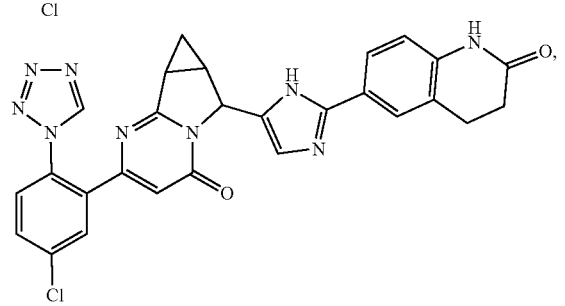
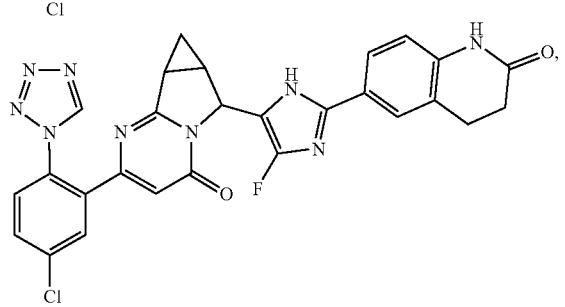
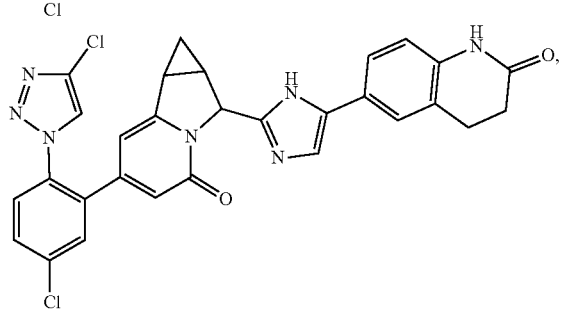
62
-continued
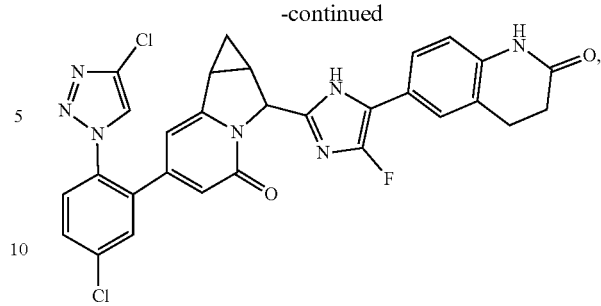
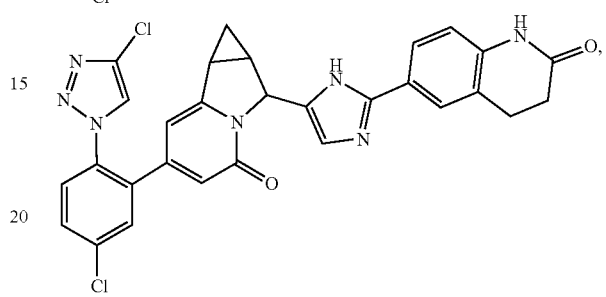
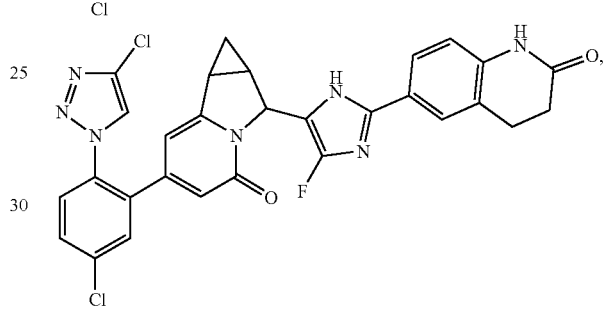
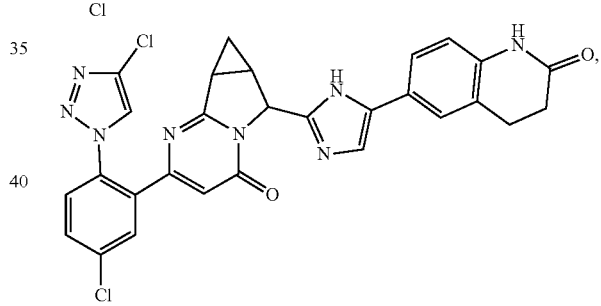
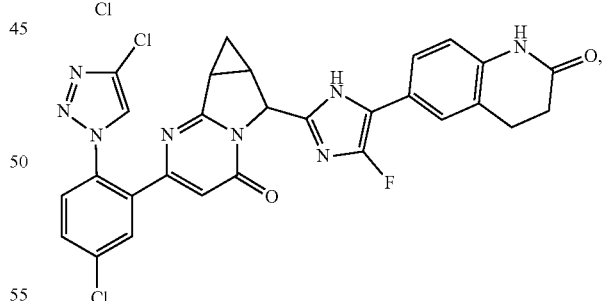
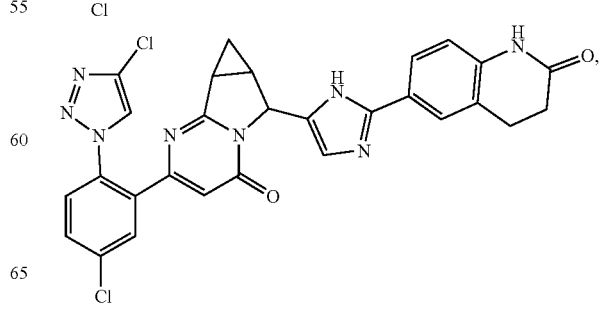

63
-continued
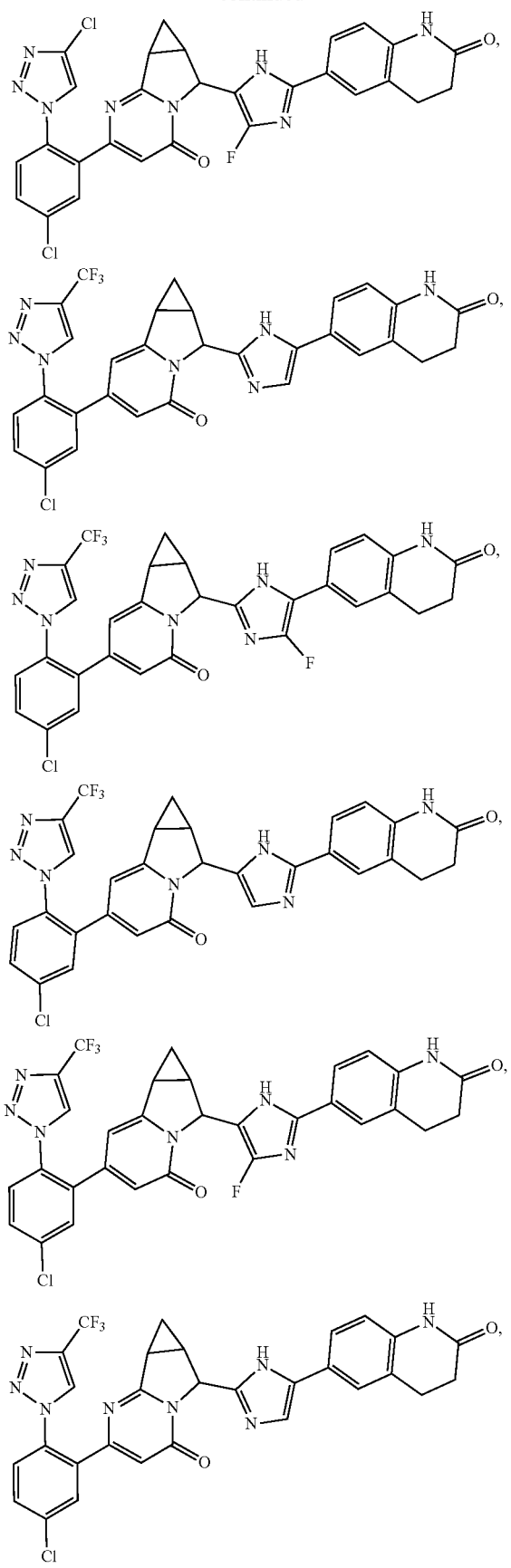
64
-continued
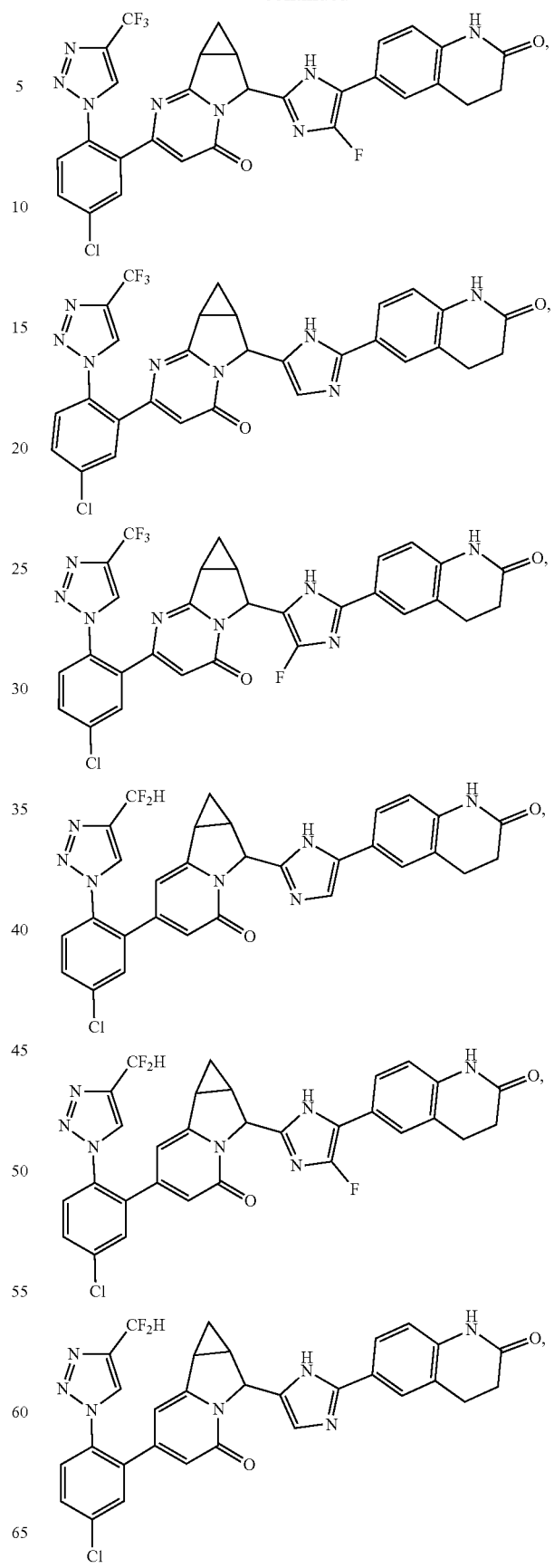

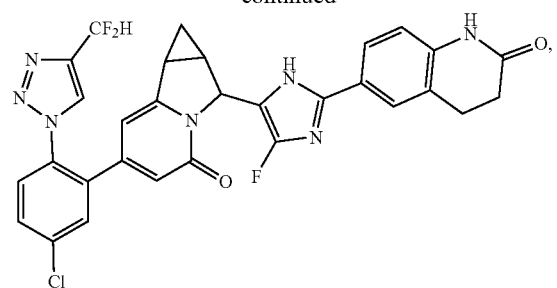
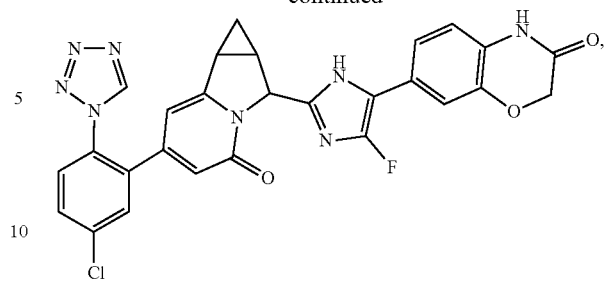
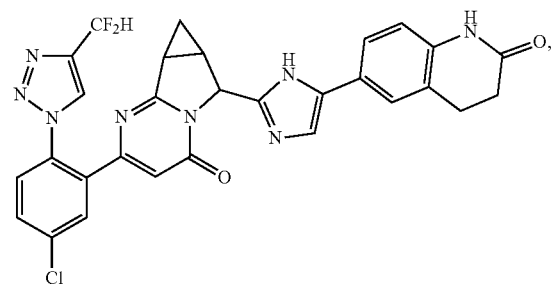
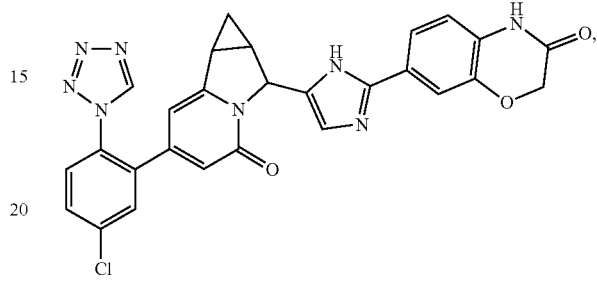
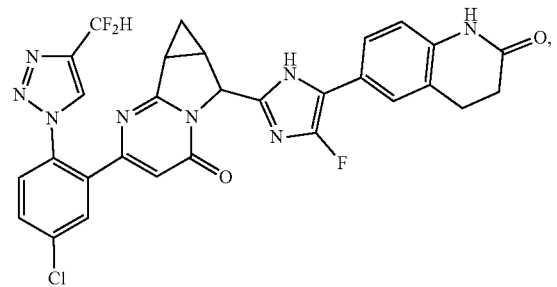
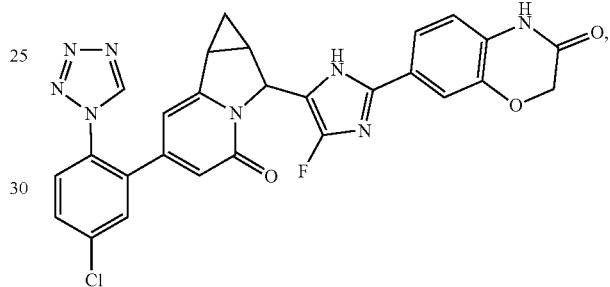
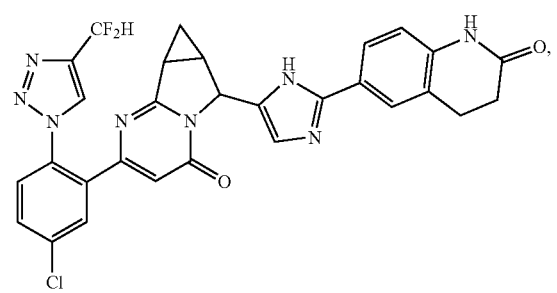
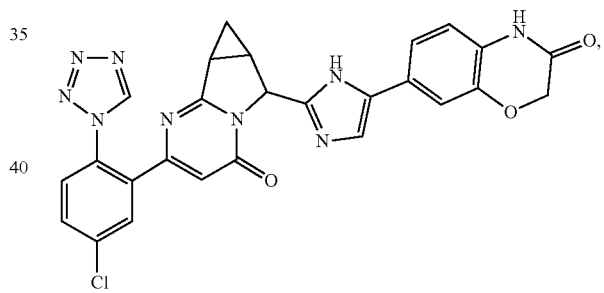
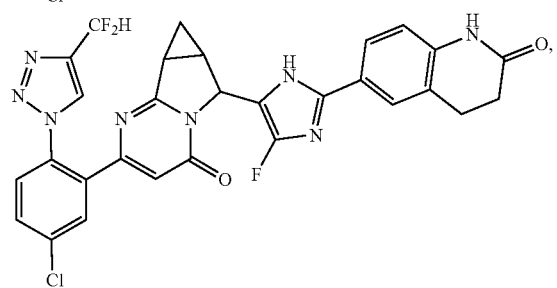
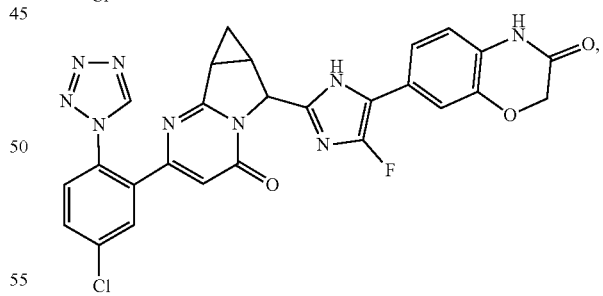
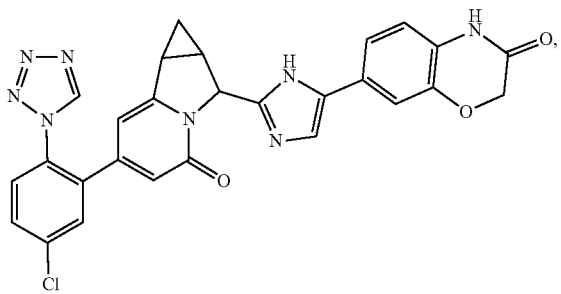
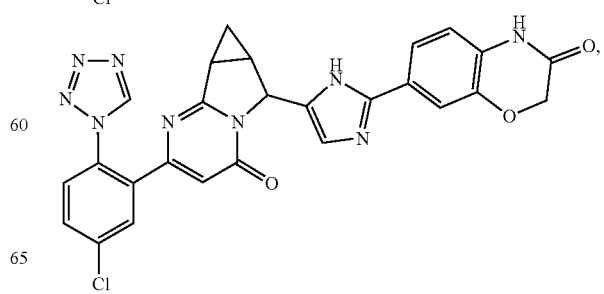

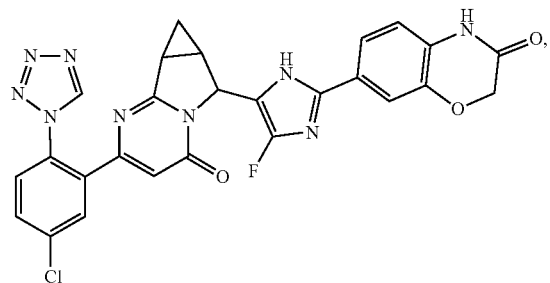
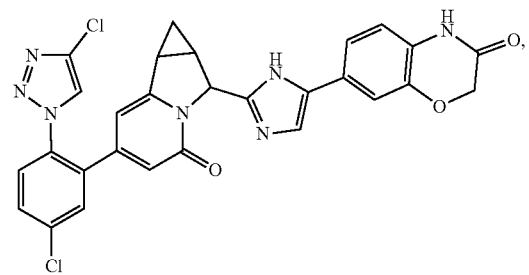
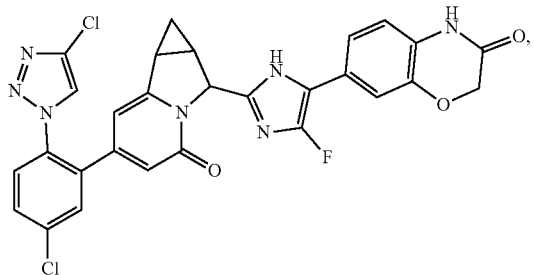
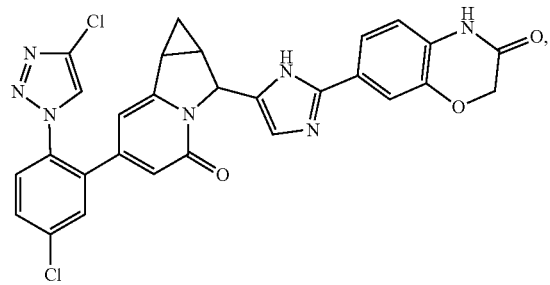
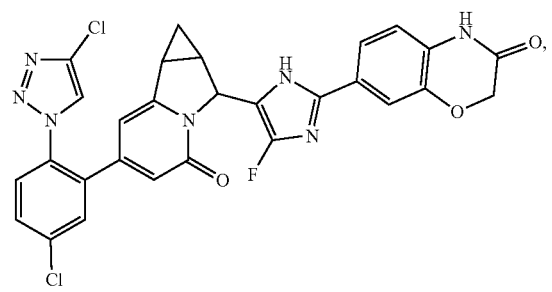
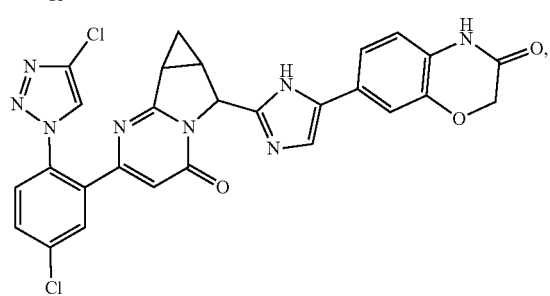
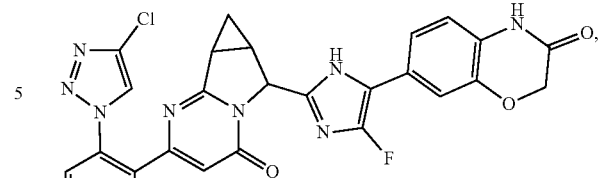
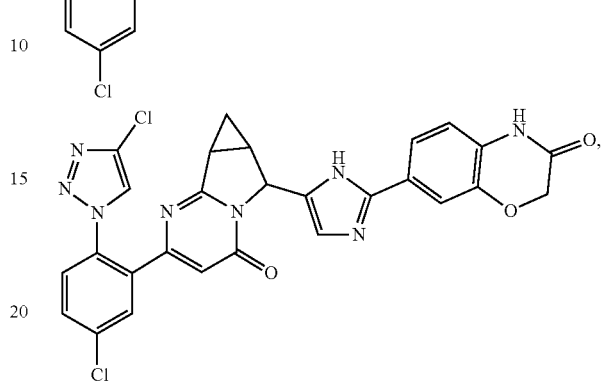
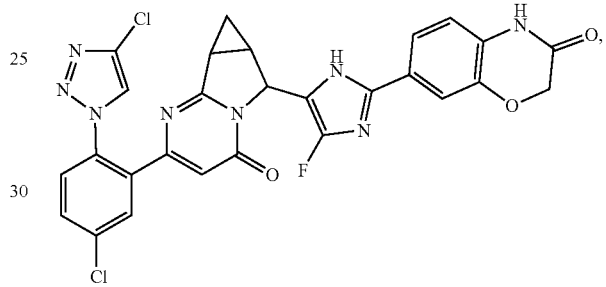
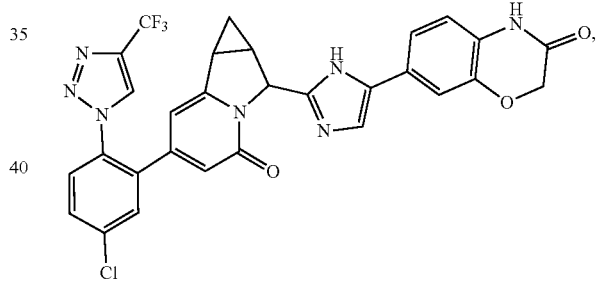
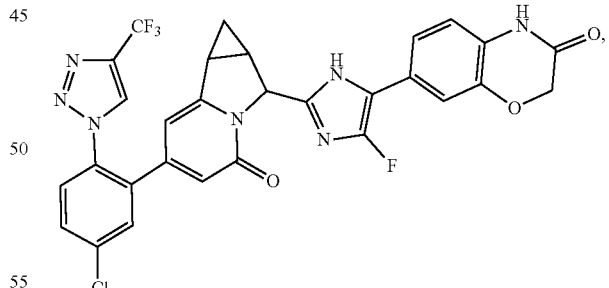
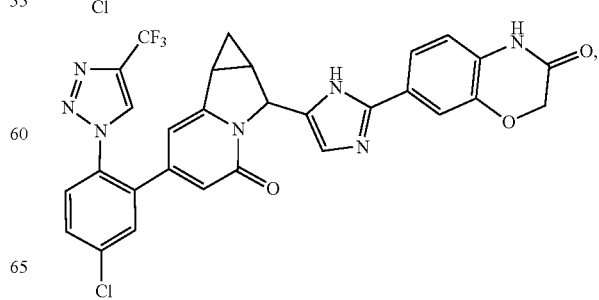

69
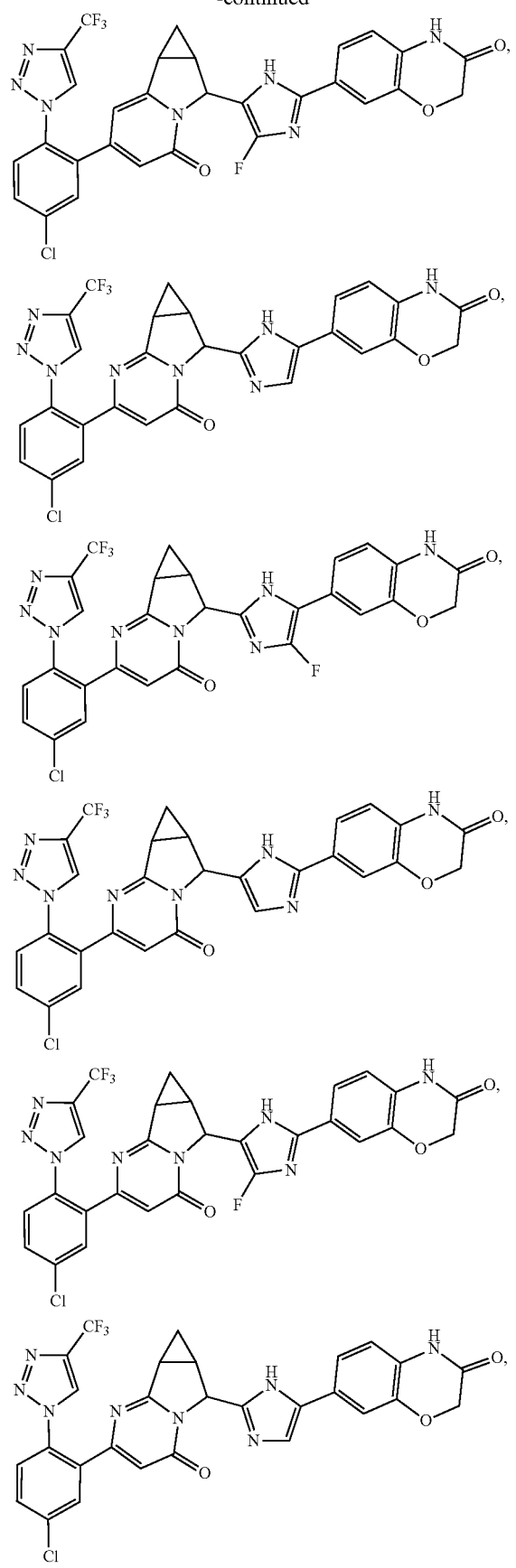
70
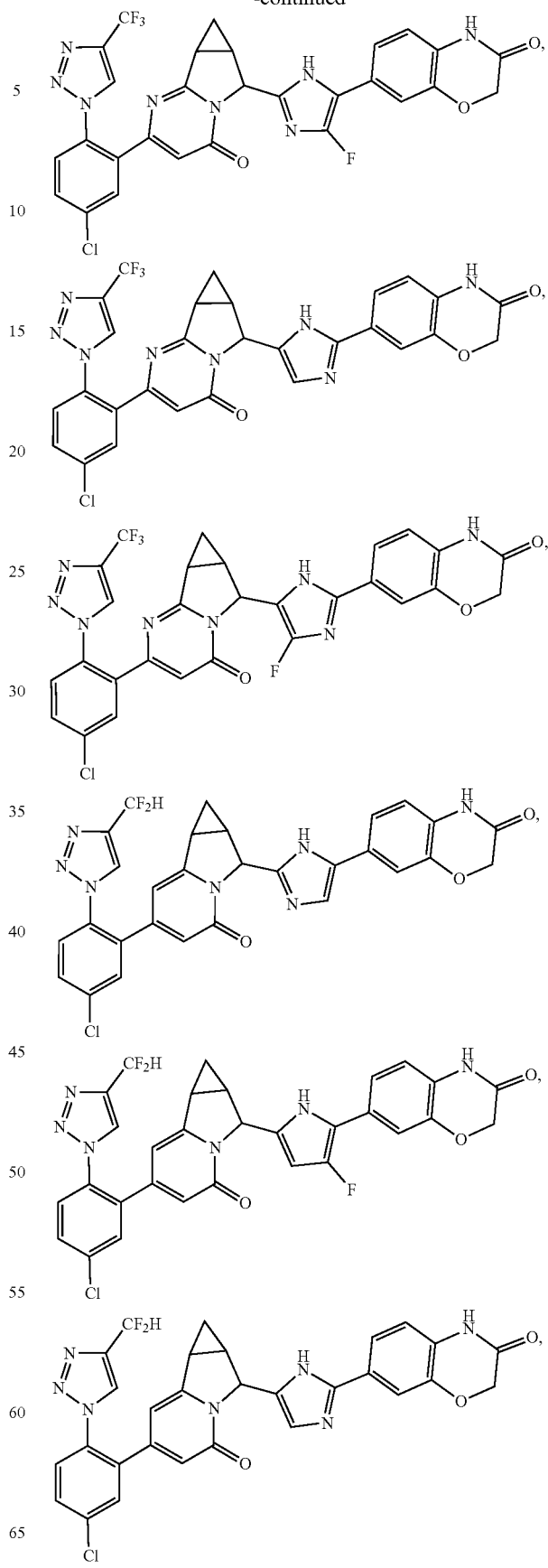

71
-continued
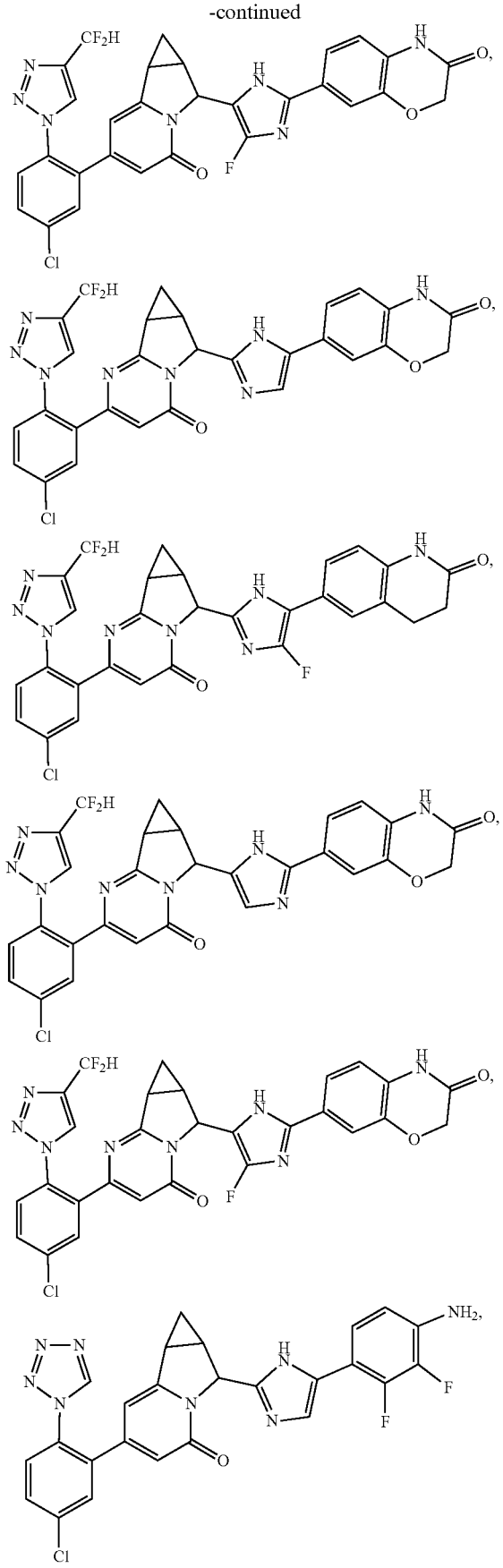
72
-continued
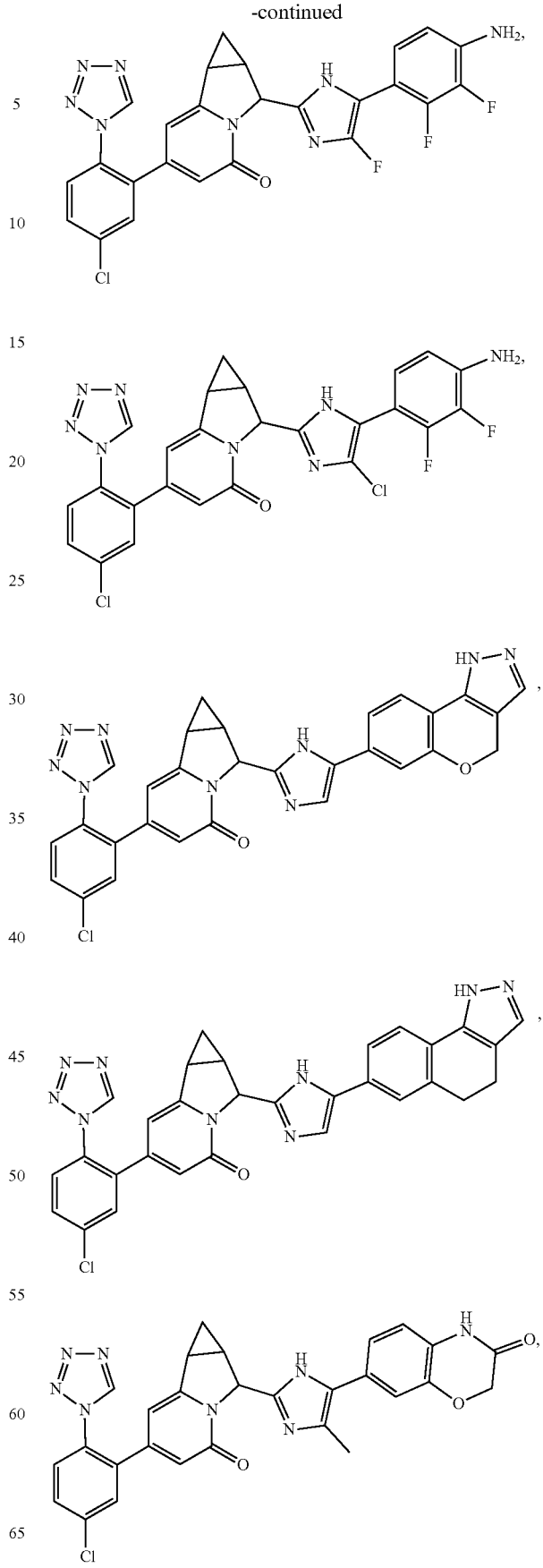

73
-continued
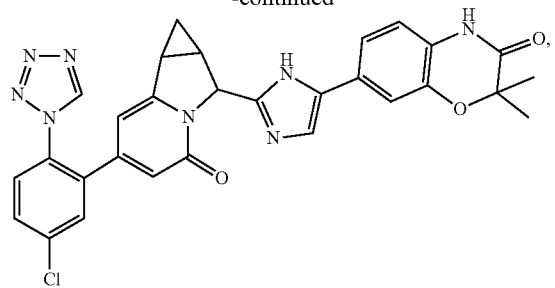
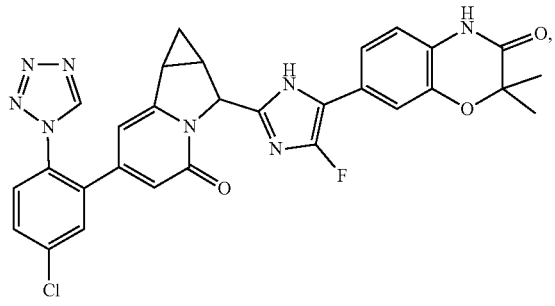
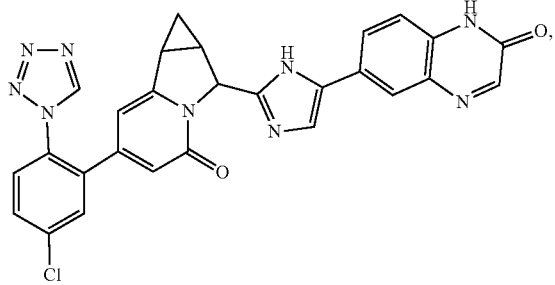
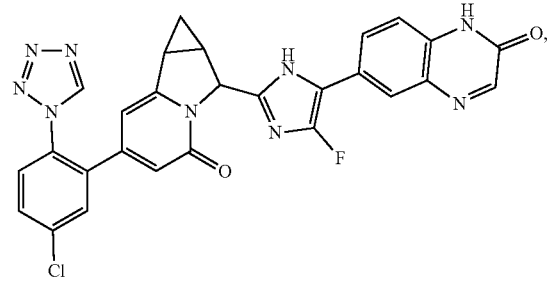
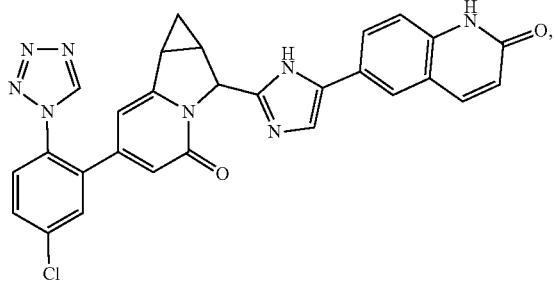
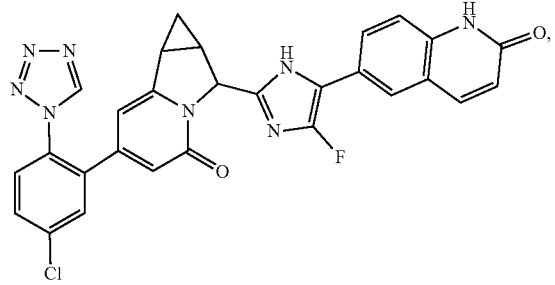
74
-continued
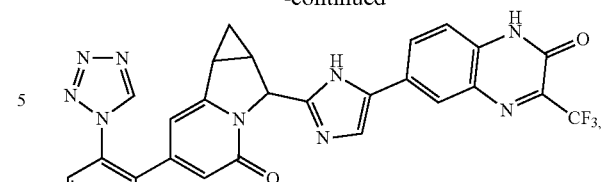
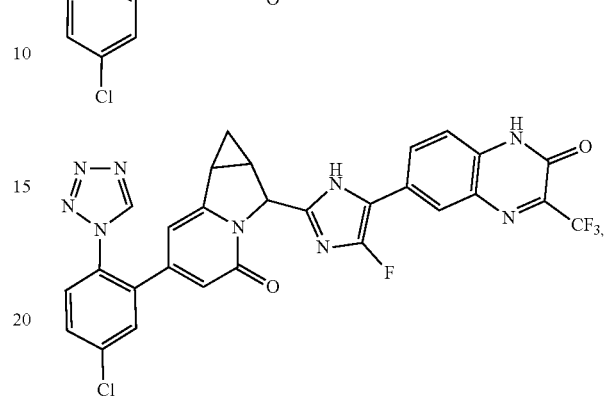
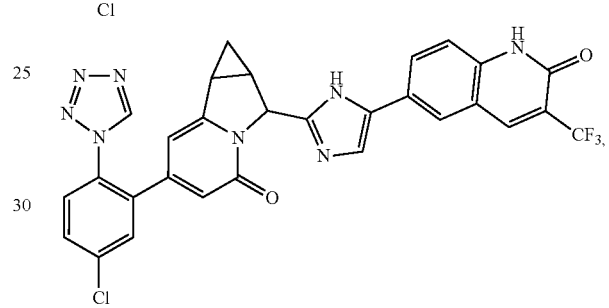
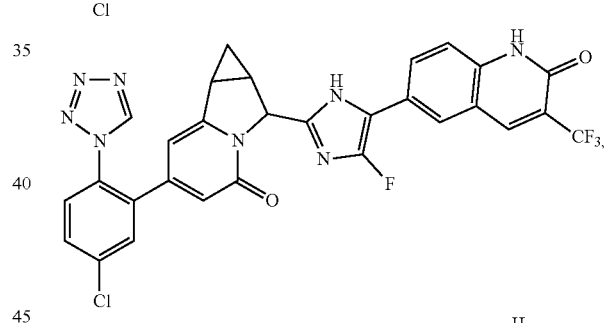
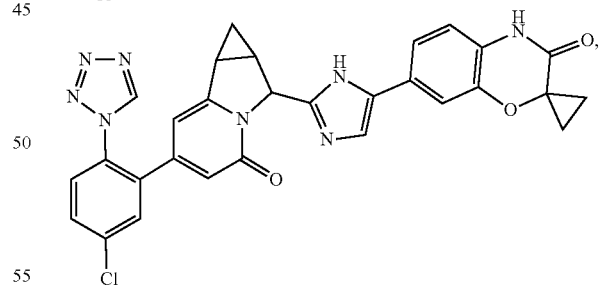
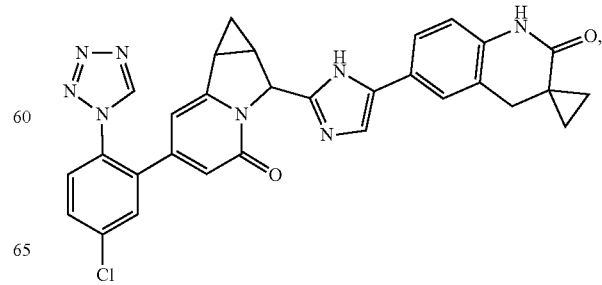

75
-continued
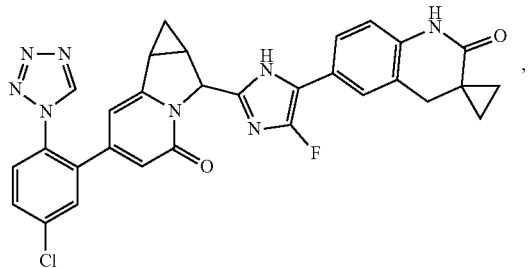
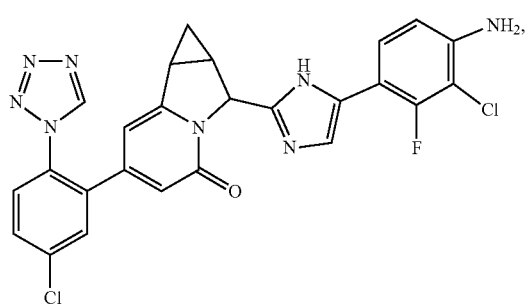
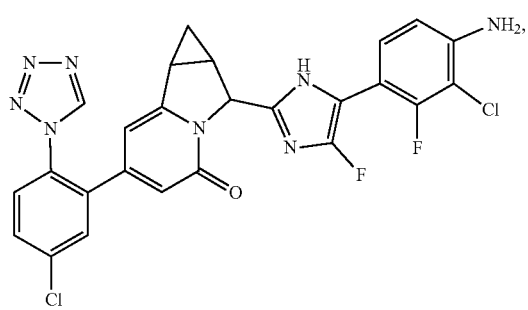
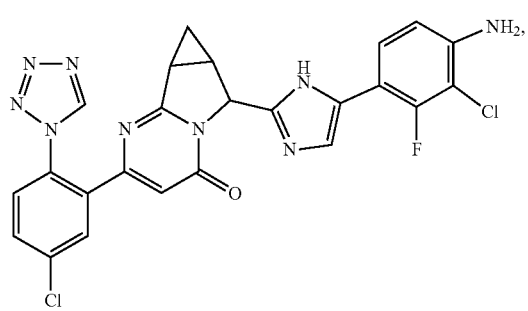
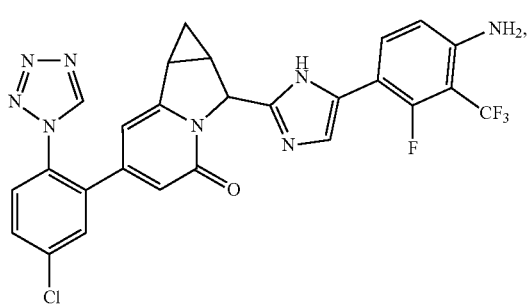
76
-continued
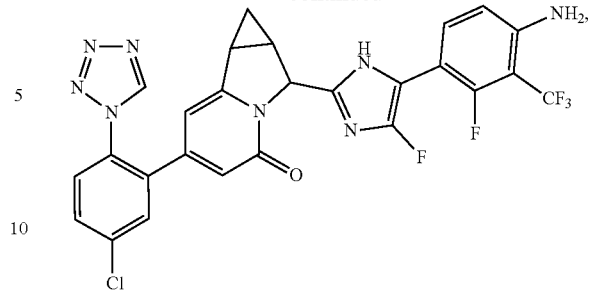
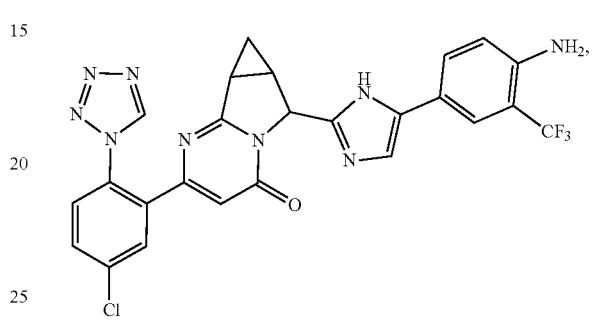
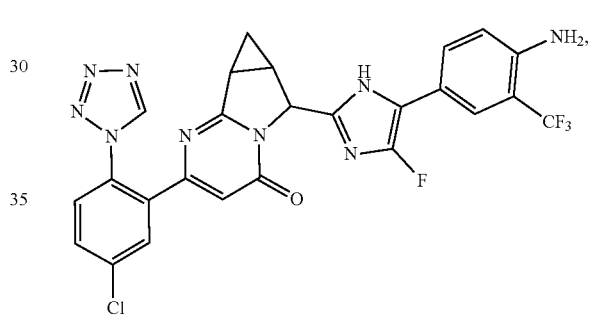
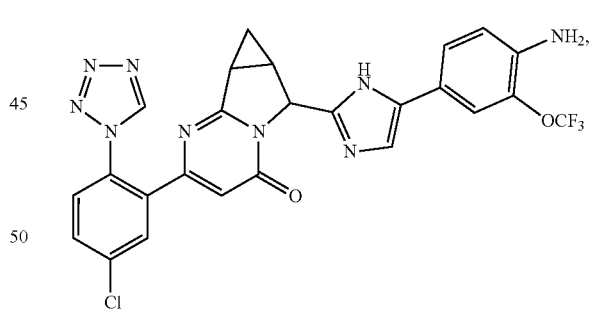
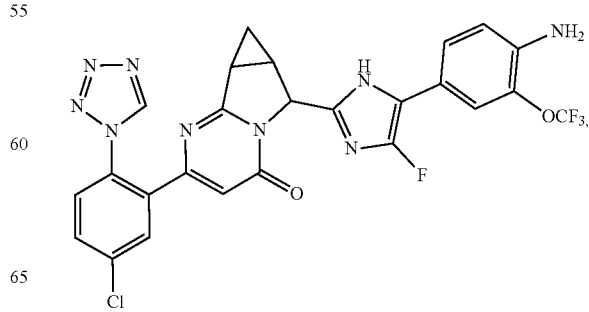

77
-continued
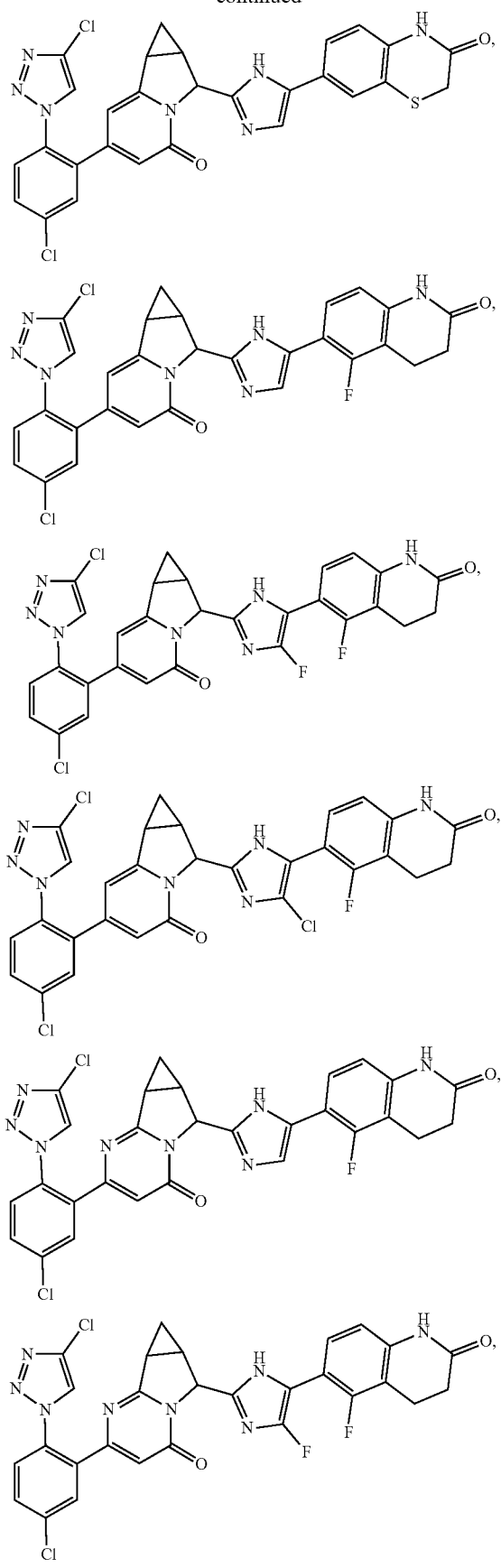
78
-continued
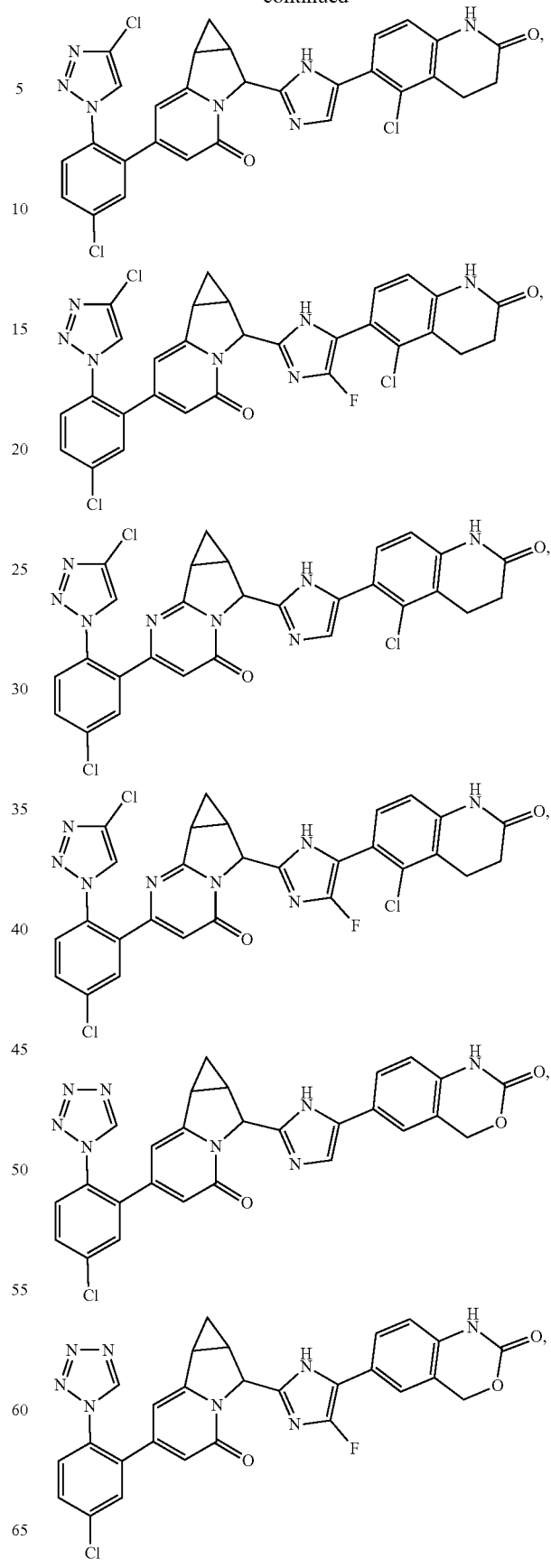

79
-continued
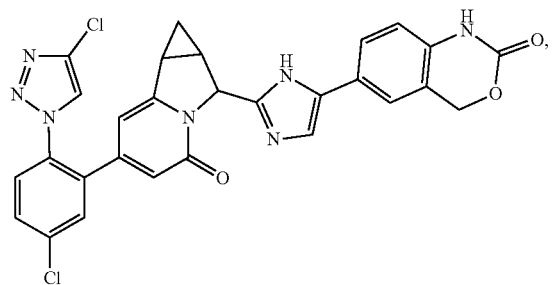
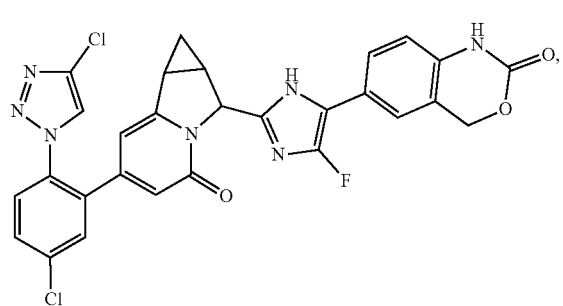
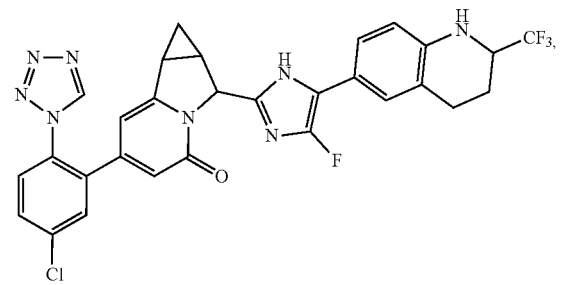
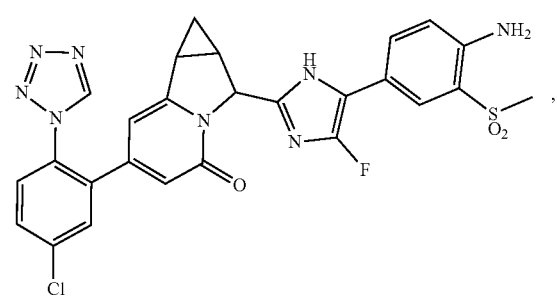
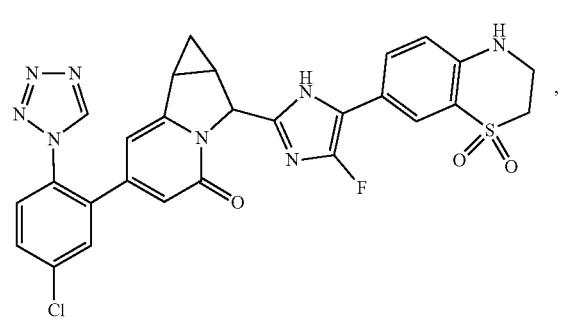
80
-continued
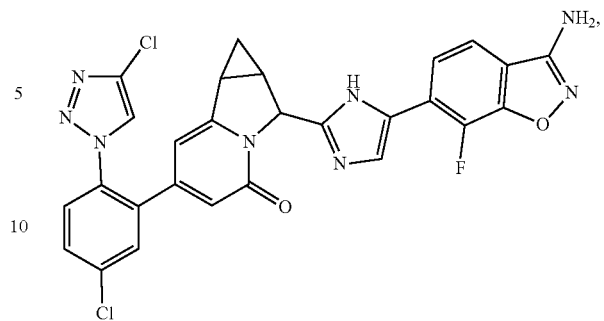
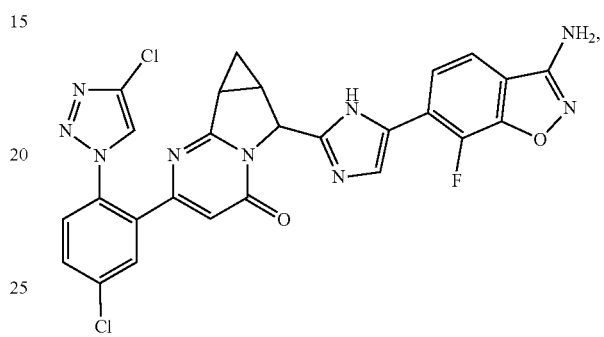
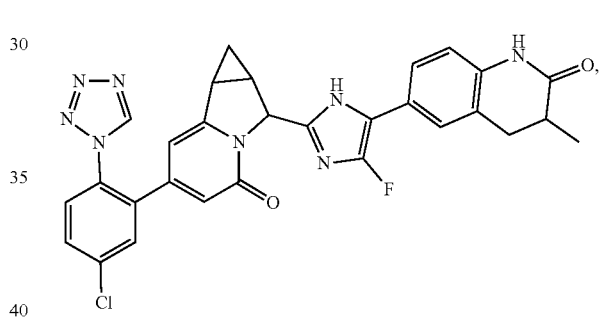
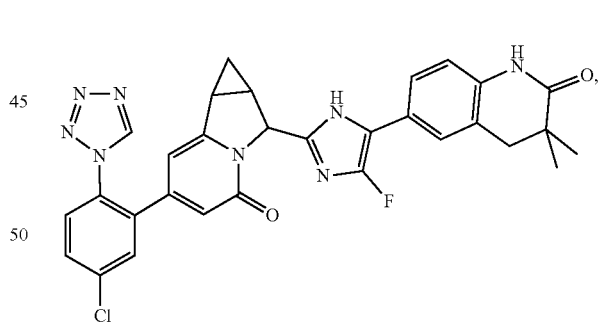
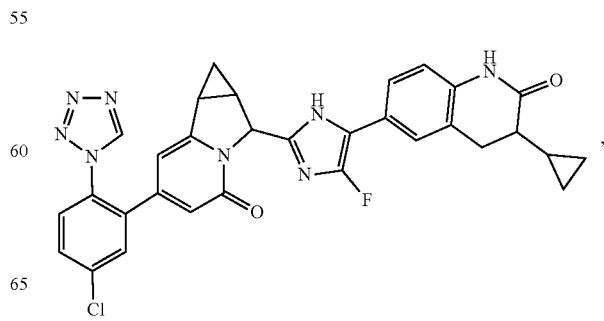

81
-continued
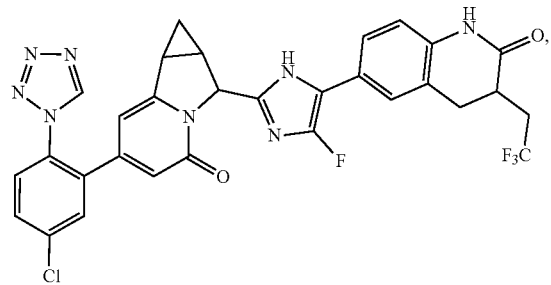
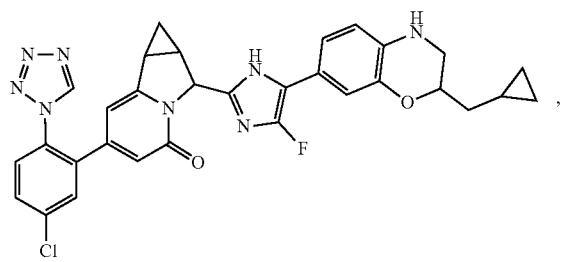
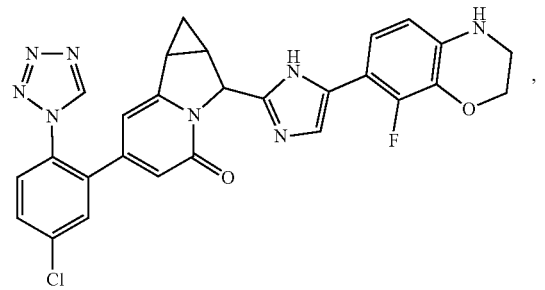
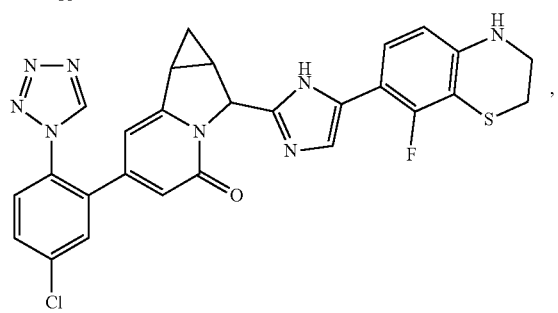
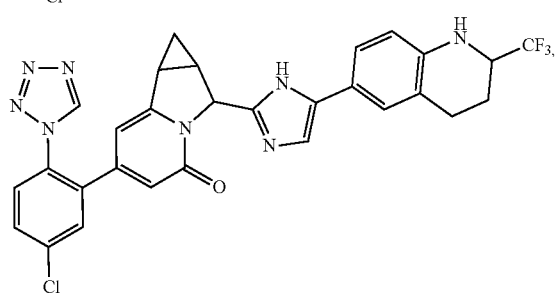
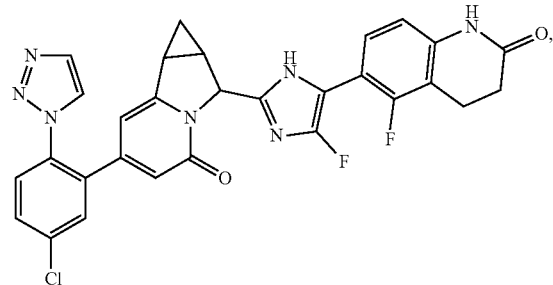
82
-continued
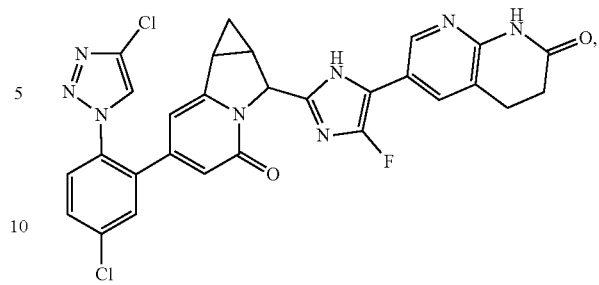
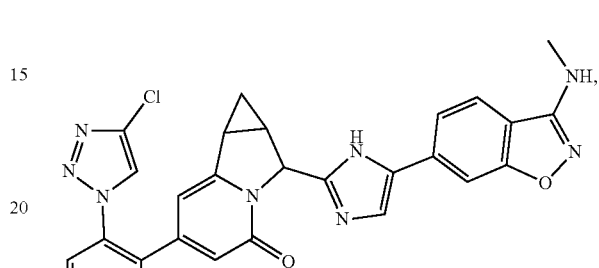
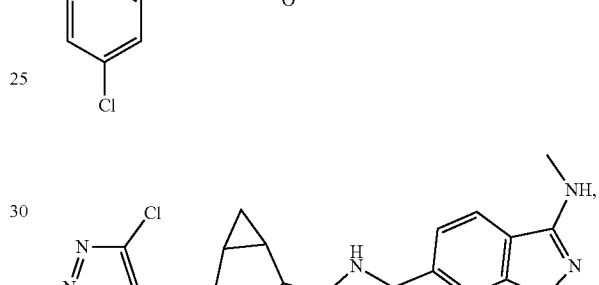
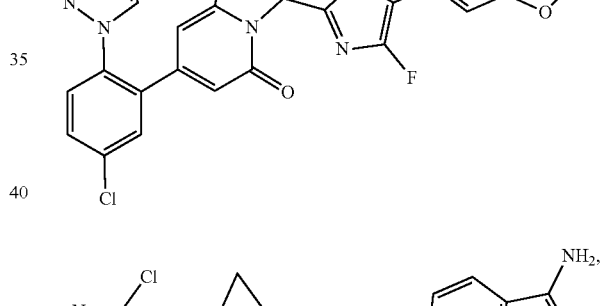
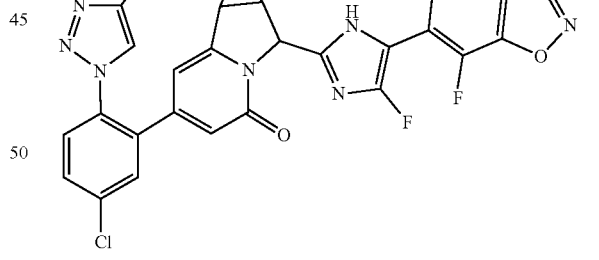
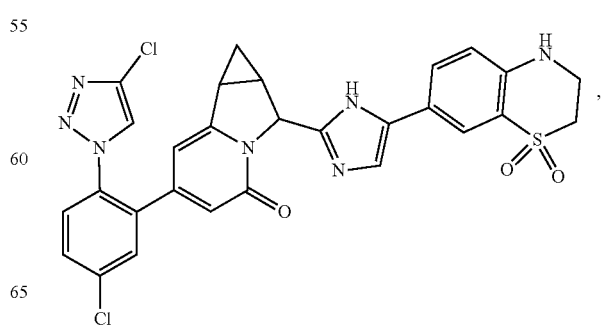

83
-continued
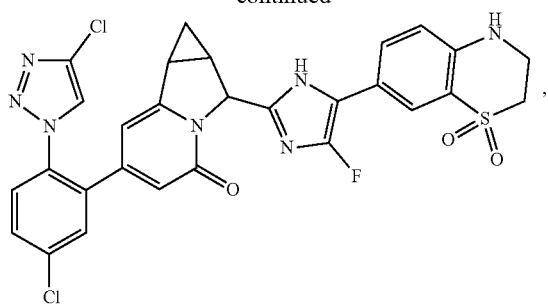
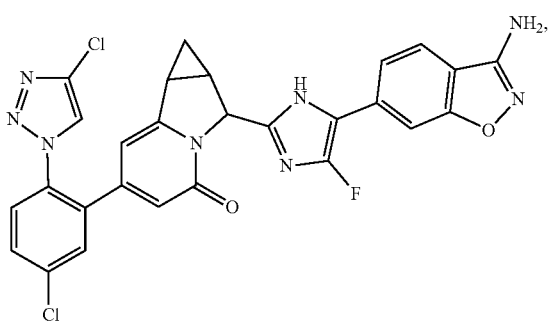
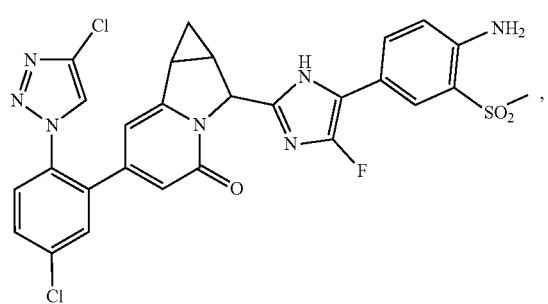
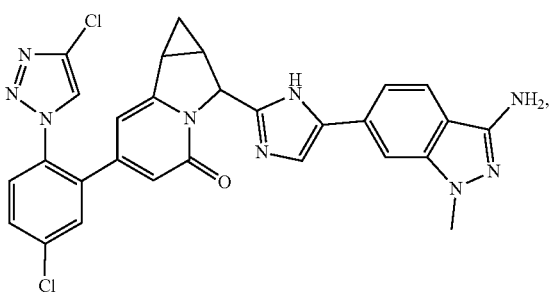
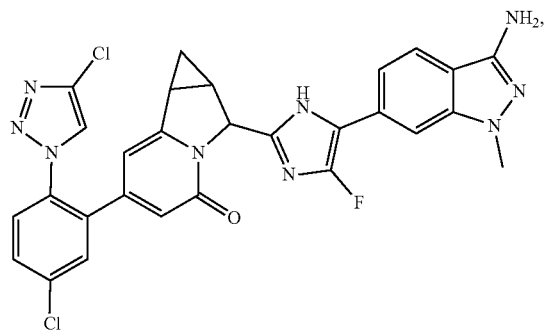
84
-continued
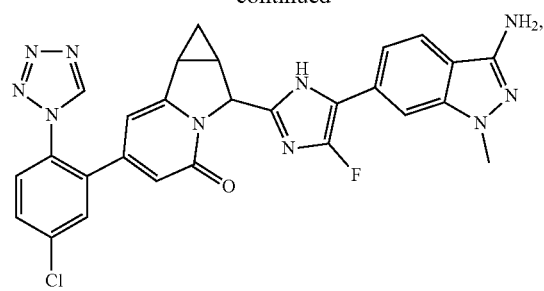
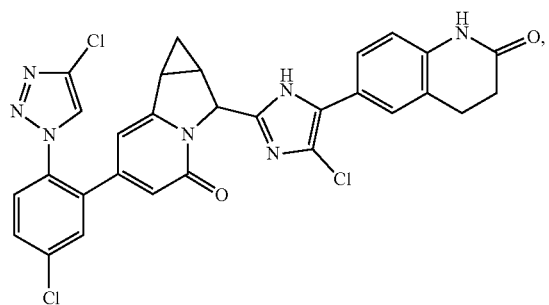
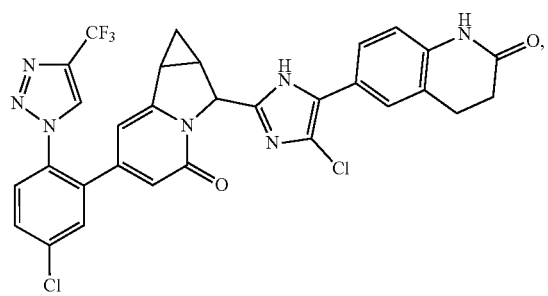
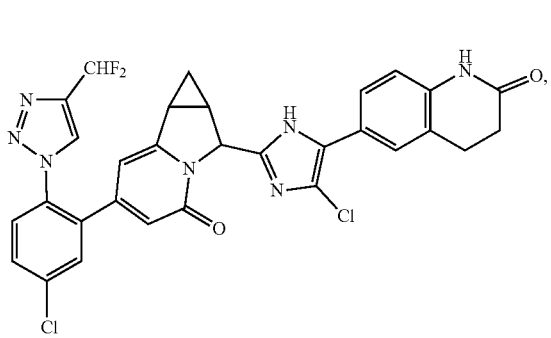
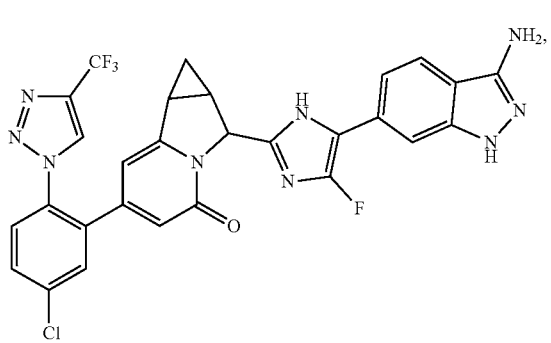

-continued

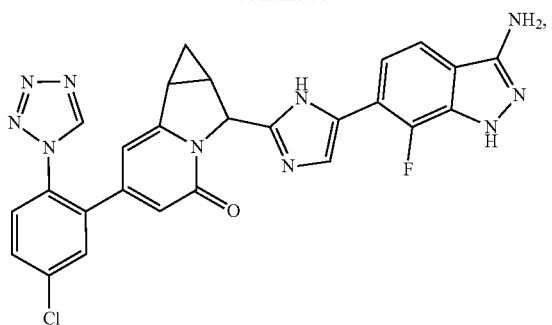

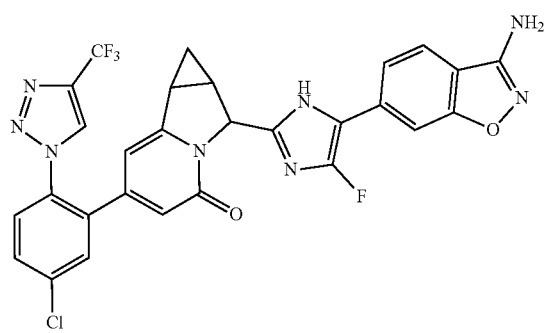

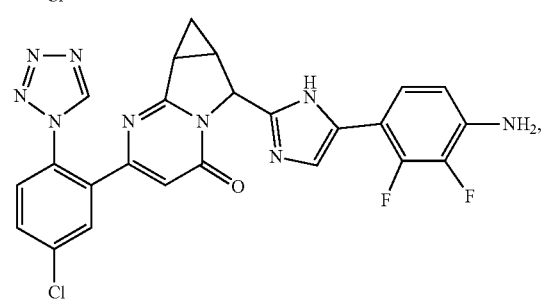

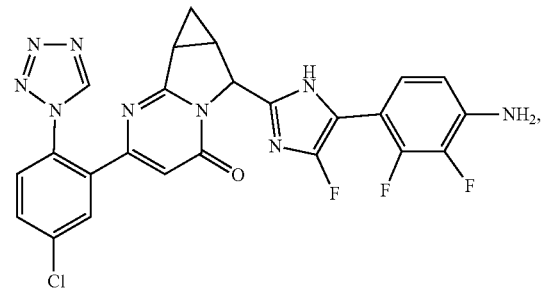

and

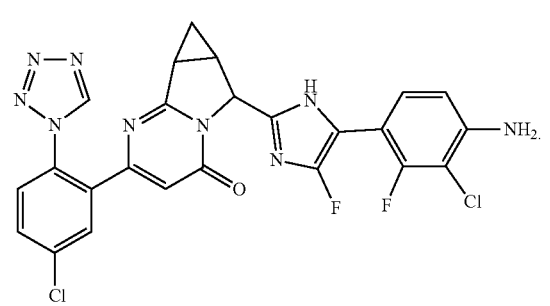

In another aspect of the present disclosure, the present disclosure also provides a pharmaceutical composition, the pharmaceutical composition comprises the compound or the pharmaceutically available salt thereof.

In some aspects of the present disclosure, the pharmaceutical composition further comprises one or more pharmaceutically acceptable carriers, diluents, or excipients.

In a further aspect of the present disclosure, the present disclosure also provides a use of the compound or the pharmaceutically acceptable salt thereof or the pharmaceutical composition in the preparation of an FXIa inhibitor.

In a further aspect of the present disclosure, the present disclosure also provides a use of the compound or the pharmaceutically acceptable salt thereof or the pharmaceutical composition in the preparation of a medicament for the prevention and/or treatment of FXIa factor-mediated diseases.

In some aspects of the present disclosure, the FXIa factor-mediated diseases are selected from cardiovascular and cerebrovascular diseases.

In some embodiments of the present disclosure, the cardiovascular and cerebrovascular diseases are selected from thromboembolic diseases.

In some embodiments of the present disclosure, the thromboembolic diseases are selected from hereditary angioneurotic edema, advanced diabetic macular edema, myocardial infarction, angina pectoris, reobstruction and restenosis after angioplasty or aortocoronary bypass, diffuse intravascular coagulation, stroke, transient local ischemic attack, peripheral arterial occlusive disease, pulmonary embolism, or deep venous thrombosis.

In a further aspect of the present disclosure, the present disclosure also provides a method for treating FXIa factor-mediated disease, the method comprises administering a therapeutically effective amount of the compound or the pharmaceutically available salt thereof or a therapeutically effective amount of the pharmaceutical composition to a patient suffering from an FXIa factor-mediated disease.

Definition

Unless otherwise specified, the following terms and phrases when used herein have the following meanings. A specific term or phrase should not be considered indefinite or unclear in the absence of a particular definition, but should be understood in the ordinary sense. When a trade name appears herein, it is intended to refer to its corresponding commodity or active ingredient thereof.

The term "pharmaceutically acceptable" is used herein in terms of those compounds, materials, compositions, and/or dosage forms, which are suitable for use in contact with human and animal tissues within the scope of reliable medical judgment, with no excessive toxicity, irritation, an allergic reaction or other problems or complications, commensurate with a reasonable benefit/risk ratio.

The term "pharmaceutically acceptable salt" refers to a salt of the compound of the present disclosure that is prepared by reacting the compound having a specific substituent of the present disclosure with a relatively non-toxic acid or base. When the compound of the present disclosure contains a relatively acidic functional group, a base addition salt can be obtained by bringing the neutral form of the compound into contact with a sufficient amount of base in a pure solution or a suitable inert solvent. The pharmaceutically acceptable base addition salt includes a salt of sodium, potassium, calcium, ammonium, organic amine or magnesium, or similar salts. When the compound of the present disclosure contains a relatively basic functional group, an acid addition salt can be obtained by bringing the neutral form of the compound into contact with a sufficient amount of acid in a pure solution or a suitable inert solvent.

Examples of the pharmaceutically acceptable acid addition salt include an inorganic acid salt, wherein the inorganic acid includes, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid, phosphorous acid, and the like; and an organic acid salt, wherein the organic acid includes, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, and methanesulfonic acid, and the like; and salts of amino acid (such as arginine and the like), and a salt of an organic acid such as glucuronic acid and the like. Certain specific compounds of the present disclosure contain both basic and acidic functional groups, thus can be converted to any base or acid addition salt.

The pharmaceutically acceptable salt of the present disclosure can be prepared from the parent compound that contains an acidic or basic moiety by conventional chemical method. Generally, such salt can be prepared by reacting the free acid or base form of the compound with a stoichiometric amount of an appropriate base or acid in water or an organic solvent or a mixture thereof.

The compounds of the present disclosure may exist in specific geometric or stereoisomeric forms. The present disclosure contemplates all such compounds, including cis and trans isomers, (−)-and (+)-enantiomers, (R)-and (S)-enantiomers, diastereomers isomers, (D)-isomers, (L)-isomers, and racemic and other mixtures thereof, such as enantiomers or diastereomeric enriched mixtures, all of which are within the scope of the present disclosure. Additional asymmetric carbon atoms may be present in substituents such as alkyl. All these isomers and their mixtures are included within the scope of the present disclosure.

Unless otherwise specified, the term "enantiomer" or "optical isomer" refers to stereoisomers that are mirror images of each other.

Unless otherwise specified, the term "cis-trans isomer" or "geometric isomer" is caused by the inability to rotate freely of double bonds or single bonds of ring-forming carbon atoms.

Unless otherwise specified, the term "diastereomer" refers to a stereoisomer in which a molecule has two or more chiral centers and the relationship between the molecules is not mirror images.

Unless otherwise specified, "(D)" or "(+)" refers to dextrorotation, "(L)" or "(−)" refers to levorotation, and "(DL)" or "(±)" refers to racemic.

Unless otherwise specified, the absolute configuration of a stereogenic center is represented by a wedged solid bond (◢) and a wedged dashed bond (⋰), and the relative configuration of a stereogenic center is represented by a straight solid bond (◢) and a straight dashed bond (⋰), a wave line (~) is used to represent a wedged dashed bond (◢) or a wedged dashed bond (⋰), or the wave line (~) is used to represent a straight solid bond (◢) and a straight dashed bond (⋰).

The compounds of the present disclosure may exist in specific. Unless otherwise specified, the term "tautomer" or "tautomeric form" means that at room temperature, the isomers of different functional groups are in dynamic equilibrium and can be transformed into each other quickly. If tautomers possibly exist (such as in solution), the chemical equilibrium of tautomers can be reached. For example, proton tautomer (also called prototropic tautomer) includes interconversion through proton migration, such as keto-enol isomerization and imine-enamine isomerization. Valence tautomer includes some recombination of bonding electrons for mutual transformation. A specific example of keto-enol tautomerization is the tautomerism between two tautomers of pentane-2,4-dione and 4-hydroxypent-3-en-2-one.

The compound of the present disclosure may contain an unnatural proportion of atomic isotope at one or more than one atom(s) that constitute the compound. For example, the compound can be radiolabeled with a radioactive isotope, such as tritium ($^{3}H$), iodine-125 ($^{125}I$) or C-14 ($^{14}C$). For another example, deuterated drugs can be formed by replacing hydrogen with heavy hydrogen, the bond formed by deuterium and carbon is stronger than that of ordinary hydrogen and carbon, compared with non-deuterated drugs, deuterated drugs have the advantages of reduced toxic and side effects, increased drug stability, enhanced efficacy, extended biological half-life of drugs and the like. All isotopic variations of the compound of the present disclosure, whether radioactive or not, are encompassed within the scope of the present disclosure. The term "optional" or "optionally" means that the subsequent event or condition may occur but not requisite, that the term includes the instance in which the event or condition occurs and the instance in which the event or condition does not occur.

The term "substituted" means one or more than one hydrogen atom(s) on a specific atom are substituted with the substituent, including deuterium and hydrogen variables, as long as the valence of the specific atom is normal and the substituted compound is stable. When the substituent is an oxygen (i.e., =O), it means two hydrogen atoms are substituted. Positions on an aromatic ring cannot be substituted with a ketone. The term "optionally substituted" means an atom can be substituted with a substituent or not, unless otherwise specified, the type and number of the substituent may be arbitrary as long as being chemically achievable.

When any variable (such as R) occurs in the constitution or structure of the compound more than once, the definition of the variable at each occurrence is independent. Thus, for example, if a group is substituted with 0-2 R, the group can be optionally substituted with up to two R, wherein the definition of R at each occurrence is independent. Moreover, a combination of the substituent and/or the variant thereof is allowed only when the combination results in a stable compound.

When the number of a linking group is 0, such as —(CRR)$_0$—, it means that the linking group is a single bond.

When one of the variables is selected from a single bond, it means that the two groups linked by the single bond are connected directly. For example, when L in A-L-Z represents a single bond, the structure of A-L-Z is actually A-Z.

When the enumerative linking group does not indicate the direction for linking the direction for linking is arbitrary, for example, the linking group L contained in

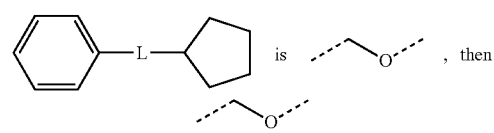

can link phenyl and cyclopentyl to form

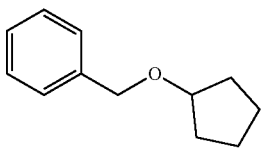 [SMILES: c1ccc(COC2CCCC2)cc1]

in the direction same as left-to-right reading order, and can link phenyl and cyclopentyl to form

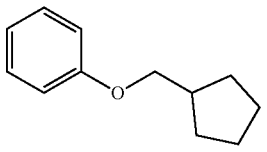 [SMILES: c1ccc(OCC2CCCC2)cc1]

in the direction contrary to left-to-right reading order. A combination of the linking groups, substituents and/or variables thereof is allowed only when such combination can result in a stable compound.

Unless otherwise specified, the number of atoms on a ring is usually defined as the number of membered ring, such as a "5-7 membered ring" is a "ring" with 5-7 atoms arranged around it.

Unless otherwise specified, the term "$C_{1-6}$ alkyl" refers to a linear or branched saturated hydrocarbon group consisting of 1 to 6 carbon atoms. The $C_{1-6}$ alkyl includes $C_{1-5}$, $C_{1-4}$, $C_{1-3}$, $C_{1-2}$, $C_{2-6}$, $C_{2-4}$, $C_6$ and $C_5$ alkyl and the like, the alkyl may be monovalent (such as methyl), divalent (such as methylene) or multivalent (such as methine). Examples of $C_{1-6}$ alkyl include but are not limited to methyl (Me), ethyl (Et), propyl (including n-propyl and isopropyl), butyl (including n-butyl, isobutyl, s-butyl, and t-butyl), pentyl (including n-pentyl, iso-pentyl and neopentyl), hexyl and the like.

Unless otherwise specified, the term "$C_{1-6}$ alkyl" refers to a linear or branched saturated hydrocarbon group consisting of 1 to 5 carbon atoms. The $C_{1-5}$ alkyl includes $C_{1-4}$, $C_{1-3}$, $C_{1-2}$, $C_{2-5}$, $C_{2-4}$ and $C_5$ alkyl and the like, the alkyl may be monovalent (such as methyl), divalent (such as methylene) or multivalent (such as methine). Examples of $C_{1-5}$ alkyl include but are not limited to methyl (Me), ethyl (Et), propyl (including n-propyl and isopropyl), butyl (including n-butyl, isobutyl, s-butyl, and t-butyl), pentyl (including n-pentyl, iso-pentyl and neopentyl) and the like.

Unless otherwise specified, the term "$C_{1-4}$ alkyl" refers to a linear or branched saturated hydrocarbon group consisting of 1 to 4 carbon atoms. The $C_{1-4}$ alkyl includes $C_{1-2}$, $C_{1-3}$ and $C_{2-3}$ alkyl and the like, the alkyl may be monovalent (such as methyl), divalent (such as methylene) or multivalent (such as methine). Examples of $C_{1-4}$ alkyl include but are not limited to methyl (Me), ethyl (Et), propyl (including n-propyl and isopropyl), butyl (including n-butyl, isobutyl, s-butyl, and t-butyl) and the like.

Unless otherwise specified, the term "$C_{1-3}$ alkyl" refers to a linear or branched saturated hydrocarbon group consisting of 1 to 3 carbon atoms. The $C_{1-3}$ alkyl includes $C_{1-2}$ and $C_{2-3}$ alkyl and the like; the alkyl may be monovalent (such as methyl), divalent (such as methylene) or multivalent (such as methine). Examples of $C_{1-3}$ alkyl include but are not limited to methyl (Me), ethyl (Et), propyl (including n-propyl and isopropyl) and the like. Unless otherwise specified, "$C_{2-8}$ alkenyl" refers to hydrocarbon groups consisting of 2 to 8 carbon atoms containing at least one carbon-carbon double bond with linear or branched chains, and the carbon-carbon double bond may be located at any position of the group. The $C_{2-8}$ alkenyl includes $C_{2-6}$, $C_{2-4}$, $C_{2-3}$, $C_4$, $C_3$ and $C_2$ alkenyl and the like; the alkenyl may be monovalent, divalent or multivalent. Examples of $C_{2-8}$ alkenyl include, but are not limited to, vinyl, propenyl, butenyl, pentenyl, hexenyl, butadienyl, pentadienyl, hexadienyl and the like.

The term "heteroalkyl" by itself or in combination with another term, refers to a stable straight-chain or branched-chain alkyl consisting of a certain number of carbon atoms and at least one heteroatom or heteroatom group. In some embodiments, the heteroatoms are selected from B, O, N, and S, wherein nitrogen and sulfur atoms are optionally oxidized, and nitrogen heteroatoms are optionally quaternized. In other embodiments, the heteroatom group is selected from —C(=O)O—, —C(=O)—, —C(=S)—, —S(=O), —S(=O)$_2$—, —C(=O)N(H)—, —N(H)—, —C(=NH)—, —S(=O)$_2$N(H)— and —S(=O)N(H)—. In some embodiments, the heteroalkyl is $C_{1-6}$ heteroalkyl; in other embodiments, the heteroalkyl is $C_{1-3}$ heteroalkyl. The heteroatoms or heteroatom groups may be located at any internal position of a heteroalkyl, including the position where the alkyl is attached to the rest of the molecule, but the terms "alkoxy", "alkylamino" and "alkylthio" (or thioalkoxy) are customary expressions referring to those alkyl that are attached to the rest of the molecule by an oxygen, amino or sulfur atom, respectively. Examples of heteroalkyl include but are not limited to —OCH$_3$, —OCH$_2$CH$_3$, —OCH$_2$CH$_2$CH$_3$, —OCH$_2$(CH$_3$)$_2$, —CH$_2$—CH$_2$—O—CH$_3$, —NHCH$_3$, —N(CH$_3$)$_2$, —NHCH$_2$CH$_3$, —N(CH$_3$)(CH$_2$CH$_3$), —CH$_2$—CH$_2$—NH—CH$_3$, —CH$_2$—CH$_2$—N(CH$_3$)—CH$_3$, —SCH$_3$, —SCH$_2$CH$_3$, —SCH$_2$CH$_2$CH$_3$, —SCH$_2$(CH$_3$)$_2$, —CH$_2$—S—CH$_2$—CH$_3$, —CH$_2$—CH$_2$, —S(=O)—CH$_3$ and —CH$_2$—CH$_2$—S(=O)$_2$—CH$_3$. At most two heteroatoms may be continuous, such as —CH$_2$—NH—OCH$_3$.

Unless otherwise specified, the term "$C_{1-6}$ alkoxy" refers to an alkyl containing 1 to 6 carbon atoms that are connected to the rest of the molecule through an oxygen atom. The $C_{1-6}$ alkoxy includes $C_{1-4}$, $C_{1-3}$, $C_{1-2}$, $C_{2-6}$, $C_{2-4}$, $C_6$, $C_5$, $C_4$ and $C_3$ alkoxy and the like. Examples of $C_{1-6}$ alkoxy include, but are not limited to, methoxy, ethoxy, propoxy (including n-propoxy and isopropoxy), butoxy (including n-butoxy, isobutoxy, s-butoxy and t-butoxy), pentoxy (including n-pentoxy, isopentyloxy and neopentyloxy), hexyloxy and the like.

Unless otherwise specified, the term "$C_{1-4}$ alkoxy" refers to an alkyl containing 1 to 4 carbon atoms that are connected to the rest of the molecule through an oxygen atom. The $C_{1-4}$ alkoxy includes C1-3, C1-2, C2-4, C4 and C3 alkoxy and the like. Examples of C1-4 alkoxy include, but are not limited to, methoxy, ethoxy, propoxy (including n-propoxy and isopropoxy), butoxy (including n-butoxy, isobutoxy, s-butoxy and t-butoxy), and the like.

Unless otherwise specified, the term "$C_{1-3}$ alkoxy" refers to an alkyl containing 1 to 3 carbon atoms that are connected to the rest of the molecule through an oxygen atom. The $C_{1-3}$ alkoxy includes $C_{1-2}$, $C_{2-3}$, $C_3$ and $C_2$ alkoxy and the like. Examples of $C_{1-3}$ alkoxy include, but are not limited to, methoxy, ethoxy, propoxy (including n-propoxy and isopropoxy) and the like.

Unless otherwise specified, the term "$C_{1-6}$ alkylamino" refers to an alkyl containing 1 to 6 carbon atoms that are connected to the rest of the molecule through an amino group. The $C_{1-6}$ alkylamino includes $C_{1-4}$, $C_{1-3}$, $C_{1-2}$, $C_{2-6}$, $C_{2-4}$, $C_6$, $C_5$, $C_4$, $C_3$ and $C_2$ alkylamino and the like. Examples of $C_{1-6}$ alkylamino include but are not limited to —NHCH₃, —N(CH₃)₂, —NHCH₂CH₃, —N(CH₃) CH₂CH₃, —N(CH₂CH₃)(CH₂CH₃), —NHCH₂CH₂CH₃, —NHCH₂(CH₃)₂, —NHCH₂CH₂CH₂CH₃ and the like.

Unless otherwise specified, the term "C₁₋₄ alkylamino" refers to an alkyl containing 1 to 4 carbon atoms that are connected to the rest of the molecule through an amino group. The C₁₋₄ alkylamino includes C₁₋₃, C₁₋₂, C₂₋₄, C₄, C₃ and C₂ alkylamino and the like. Examples of C₁₋₄ alkylamino include but are not limited to —NHCH₃, —N(CH₃)₂, —NHCH₂CH₃, —N(CH₃)CH₂CH₃, —N(CH₂CH₃)(CH₂CH₃), —NHCH₂CH₂CH₃, —NHCH₂(CH₃)₂, —NHCH₂CH₂CH₂CH₃ and the like.

Unless otherwise specified, the term "C₁₋₃ alkylamino" refers to an alkyl containing 1 to 3 carbon atoms that are connected to the rest of the molecule through an amino group. The C₁₋₃ alkylamino includes C₁₋₂, C₃ and C₂ alkylamino and the like. Examples of C₁₋₃ alkylamino include, but are not limited to, —NHCH₃, —N(CH₃)₂, —NHCH₂CH₃, —N(CH₃)CH₂CH₃, —NHCH₂CH₂CH₃, —NHCH₂(CH₃)₂ and the like.

Unless otherwise specified, "C₃₋₆ cycloalkyl" refers to a saturated cyclic hydrocarbon group consisting of 3 to 6 carbon atoms in monocyclic and bicyclic systems, the C₃₋₆ cycloalkyl includes C₃₋₅, C₄₋₅ and C₅₋₆ cycloalkyl and the like; the cycloalkyl may be monovalent, divalent or polyvalent. Examples of C₃₋₆ cycloalkyl include, but are not limited to cyclopropyl, cyclobutyl, cyclopentyl, cyclohexyl and the like.

Unless otherwise specified, "C₃₋₅ cycloalkyl" refers to a saturated cyclic hydrocarbon group consisting of 3 to 5 carbon atoms in monocyclic system, the C₃₋₅ cycloalkyl includes C₃₋₄ and C₄₋₅ cycloalkyl and the like; the cycloalkyl may be monovalent, divalent or polyvalent. Examples of C₃₋₅ cycloalkyl include, but are not limited to cyclopropyl, cyclobutyl, cyclopentyl and the like.

Unless otherwise specified, the term "5-9 membered heterocycloalkyl" by itself or in combination with other terms refers to a saturated cyclic group consisting of 5 to 9 ring atoms, respectively, wherein 1, 2, 3 or 4 ring atoms are heteroatoms independently selected from O, S and N and the rest are carbon atoms, wherein the nitrogen atoms are optionally quaternized and the nitrogen and sulfur heteroatoms may optionally oxidized (i.e., NO and S(O)ₚ, p is 1 or 2). The heterocycloalkyl includes monocyclic and bicyclic ring systems, wherein the bicyclic ring system includes spiro rings, fused rings and bridged rings. In addition, in the case of the "5-9-membered heterocycloalkyl", the heteroatom may occupy the position where the heterocycloalkyl is attached to the rest of the molecule. The 5-9 membered heterocycloalkyl includes 5 membered, 6 membered, 7 membered, 8 membered, 9 membered heterocycloalkyl and the like. Examples of 5-9 membered heterocycloalkyl include, but are not limited to, pyrrolidinyl, pyrazolidinyl, imidazolidinyl, tetrahydrothiophenyl (including tetrahydrothiophen-2-yl and tetrahydrothiophen-3-yl and the like), tetrahydrofuranyl (including tetrahydrofuran-2-yl and the like), tetrahydropyranyl, piperidinyl (including 1-piperidinyl, 2-piperidinyl and 3-piperidinyl and the like), piperazinyl (including 1-piperazinyl and 2-piperazinyl and the like), morpholinyl (including 3-morpholinyl and 4-morpholinyl and the like), dioxolyl, dithianyl, isoxazolidinyl, isothiazolidinyl, 1,2-oxazinyl, 1,2-thiazinyl, hexahydropyridazinyl, homopiperazinyl or homopiperidinyl and the like. When the term "5-9 membered heterocycloalkyl" is combined with other terms, such as the term "benzo 5-9 membered heterocycloalkyl" as used herein, examples include, but are not limited to

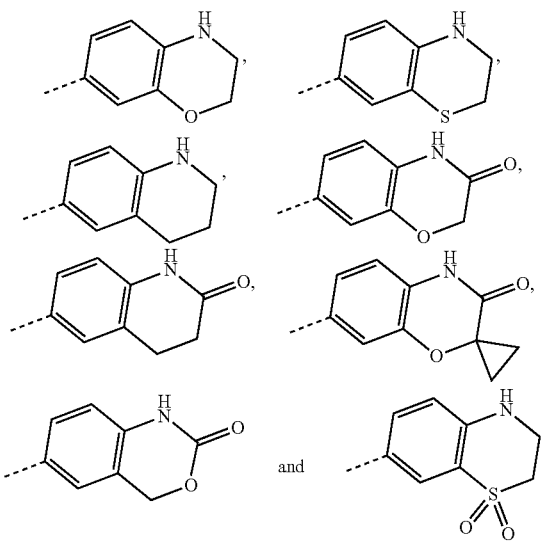

and the like, as used herein, examples of the term "pyrido 5-9 membered heterocycloalkyl" include, but are not limited to

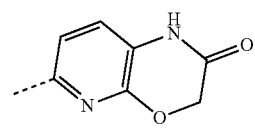

or

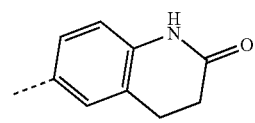

and the like.

Unless otherwise specified, the term "3-5-membered heterocycloalkyl" by itself or in combination with other terms refers to a saturated monocyclic group consisting of 3 to 5 ring atoms, respectively, wherein 1, 2, 3 or 4 ring atoms are heteroatoms independently selected from O, S and N and the rest are carbon atoms, wherein the nitrogen atoms are optionally quaternized and the nitrogen and sulfur heteroatoms may optionally oxidized (i.e., NO and S(O)ₚ, p is 1 or 2). In addition, in the case of the "3-5 membered heterocycloalkyl", the heteroatom may occupy the position where the heterocycloalkyl is attached to the rest of the molecule. The 3-5 membered heterocycloalkyl includes 4-5 membered, 4 membered and 5 membered heterocycloalkyl and the like. Examples of 3-5 membered heterocycloalkyl include, but are not limited to, azetidinyl, oxetanyl, thietidinyl, pyrrolidinyl, pyrazolidinyl, imidazolidinyl, tetrahydrothiophenyl (including tetrahydrothiophen-2-yl and tetrahydrothiophen-3-yl and the like), tetrahydrofuranyl (including tetrahydrofuran-2-yl and the like).

Unless otherwise specified, the term "4-5 membered heterocycloalkyl" by itself or in combination with other terms refers to a saturated monocyclic group consisting of 4 to 5 ring atoms, respectively, wherein 1, 2, 3 or 4 ring atoms are heteroatoms independently selected from O, S and N and the rest are carbon atoms, wherein the nitrogen atoms are optionally quaternized and the nitrogen and sulfur heteroatoms may optionally oxidized (i.e., NO and S(O)$_p$, p is 1 or 2). In addition, in the case of the "4-5-membered heterocycloalkyl", the heteroatom may occupy the position where the heterocycloalkyl is attached to the rest of the molecule. The 4-5 membered heterocycloalkyl includes 4 membered and 5 membered heterocycloalkyl and the like. Examples of 4-5 membered heterocycloalkyl include, but are not limited to, azetidinyl, oxetanyl, thietidinyl, pyrrolidinyl, pyrazolidinyl, imidazolidinyl, tetrahydrothiophenyl (including tetrahydrothiophen-2-yl and tetrahydrothiophen-3-yl and the like), tetrahydrofuranyl (including tetrahydrofuran-2-yl and the like).

Unless otherwise specified, the term "3-4 membered heterocycloalkyl" by itself or in combination with other terms refers to a saturated monocyclic group consisting of 3 to 4 ring atoms, respectively, wherein 1, 2, 3 or 4 ring atoms are heteroatoms independently selected from O, S and N and the rest are carbon atoms, wherein the nitrogen atoms are optionally quaternized and the nitrogen and sulfur heteroatoms may optionally oxidized (i.e., NO and S(O)$_p$, p is 1 or 2). In addition, in the case of the "3-4 membered heterocycloalkyl", the heteroatom may occupy the position where the heterocycloalkyl is attached to the rest of the molecule. The 3-4 membered heterocycloalkyl includes 3 membered and 4 membered heterocycloalkyl and the like. Examples of 3-4 membered heterocycloalkyl include, but are not limited to, azetidinyl, oxetanyl, thietidinyl and the like. Unless otherwise specified, the term "3-12 membered heterocycloalkenyl" by itself or in combination with other terms refers to a partially unsaturated cyclic group comprising at least one carbon-carbon double bond consisting of 3 to 12 ring atoms, respectively, wherein 1, 2, 3 or 4 ring atoms are heteroatoms independently selected from O, S and N and the rest are carbon atoms, wherein the nitrogen atoms are optionally quaternized and the nitrogen and sulfur heteroatoms may optionally oxidized (i.e., NO and S(O)$_p$, p is 1 or 2). The heterocycloalkenyl includes monocyclic, bicyclic and tricyclic systems, wherein bicyclic and tricyclic systems include spiro, fused and bridge rings, and any ring in this system is non-aromatic. In addition, in the case of the "3-12-membered heterocycloalkenyl", the heteroatom may occupy the position where the heterocycloalkenyl is attached to the rest of the molecule. The 3-12 membered heterocycloalkenyl includes 3-10 membered, 3-8 membered, 3-6 membered, 3-5 membered, 4-6 membered, 4-5 membered, 5-6 membered, 4 membered, 5 membered and 6-membered heterocycloalkenyl and the like. Examples of 3-12-membered heterocycloalkenyl include, but are not limited to

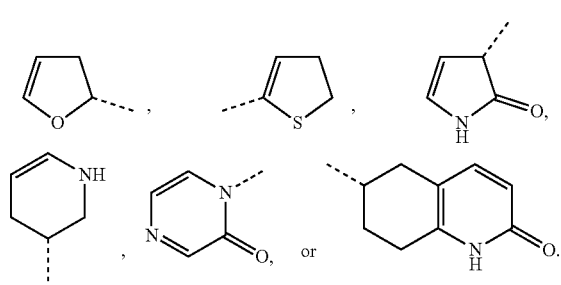

Unless otherwise specified, the term "5-9 membered heterocycloalkenyl" by itself or in combination with other terms refers to a partially unsaturated cyclic group comprising at least one carbon-carbon double bond consisting of 5 to 9 ring atoms, respectively, wherein 1, 2, 3 or 4 ring atoms are heteroatoms independently selected from O, S and N and the rest are carbon atoms, wherein the nitrogen atoms are optionally quaternized and the nitrogen and sulfur heteroatoms may optionally oxidized (i.e., NO and S(O)$_p$, p is 1 or 2). The heterocycloalkenyl includes monocyclic and tricyclic systems, wherein bicyclic system includes spiro, fused and bridge rings, and any ring in this system is non-aromatic. In addition, in the case of the "5-9 membered heterocycloalkenyl", the heteroatom may occupy the position where the heterocycloalkenyl is attached to the rest of the molecule. The 5-9 membered heterocycloalkenyl includes 5 membered, 6 membered, 7 membered, 8 membered, 9 membered heterocycloalkenyl and the like. Examples of 5-9-membered heterocycloalkenyl include, but are not limited to

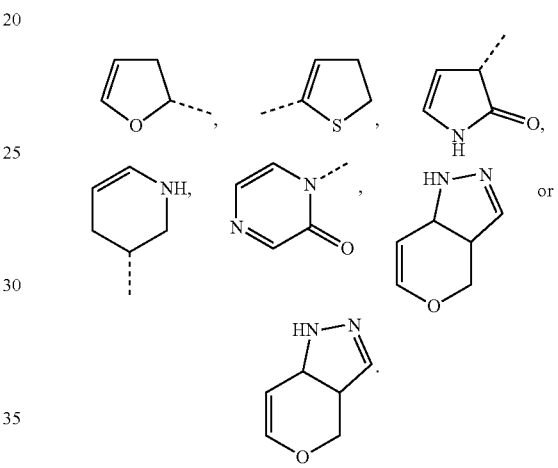

When the term "5-9 heterocycloalkenyl" is used in combination with other terms, for example, examples of "benzo 5-9 heterocycloalkenyl" in the present disclosure include, but are not limited to

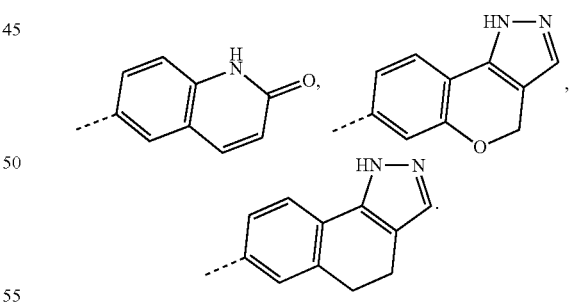

Unless otherwise specified, the terms "5-12 membered heteroaromatic ring" and "5-12 membered heteroaryl" in the present disclosure may be used interchangeably, and the term "5-12 membered heteroaryl" refers to a cyclic group consisting of 5 to 12 ring atoms with conjugated π electronic system, of which 1, 2, 3 or 4 ring atoms are heteroatoms independently selected from O, S and N, and the rest are carbon atoms. The heteroaryl may be a monocyclic, fused bicyclic or fused tricyclic system, wherein each ring is aromatic. Wherein the nitrogen atom is optionally quaternized, and the nitrogen and sulfur heteroatoms are optionally oxidized (i.e., NO and $S(O)_p$, p is 1 or 2). The 5-12 membered heteroaryl may be attached to the rest of the molecule through a heteroatom or a carbon atom. The 5-12 membered heteroaryl includes 5-10 membered, 5-8 membered, 5-7 membered, 5-6 membered, 5 membered and 6 membered heteroaryl and the like. Examples of the 5-12 membered heteroaryl include, but are not limited to, pyrrolyl (including N-pyrrolyl, 2-pyrrolyl and 3-pyrrolyl and the like), pyrazolyl (including 2-pyrazolyl and 3-pyrazolyl and the like), imidazolyl (including N-imidazolyl, 2-imidazolyl, 4-imidazolyl and 5-imidazolyl and the like), oxazolyl (including 2-oxazolyl, 4-oxazolyl and 5-oxazolyl and the like), triazolyl (1H-1,2,3-triazolyl, 2H-1,2,3-triazolyl, 1H-1,2,4-triazolyl and 4H-1,2,4-triazolyl and the like), tetrazolyl, isoxazolyl (3-isoxazolyl, 4-isoxazolyl and 5-isoxazolyl and the like), thiazolyl (including 2-thiazolyl, 4-thiazolyl and 5-thiazolyl and the like), furanyl (including 2-furanyl and 3-furanyl and the like), and thienyl (including 2-thienyl and 3-thienyl and the like), pyridinyl (including 2-pyridyl, 3-pyridyl and 4-pyridyl and the like), pyrazinyl, pyrimidinyl (including 2-pyrimidinyl and 4-pyrimidinyl and the like), benzothiazolyl (including 5-benzothiazolyl and the like), purinyl, benzimidazolyl (including 2-benzimidazolyl and the like), benzoxazolyl, indolyl (including 5-indolyl and the like), isoquinolinyl (including 1-isoquinolinyl and 5-isoquinolinyl and the like), quinoxalinyl (including 2-quinoxalinyl and 5-quinoxalinyl and the like) or quinolinyl (including 3-quinolinyl and 6-quinolinyl and the like).

Unless otherwise specified, the terms "5-10 membered heteroaromatic ring" and "5-10 membered heteroaryl" in the present disclosure may be used interchangeably, and the term "5-10 membered heteroaryl" refers to a cyclic group consisting of 5 to 10 ring atoms with conjugated π electronic system, of which 1, 2, 3 or 4 ring atoms are heteroatoms independently selected from O, S and N, and the rest are carbon atoms. The heteroaryl may be a monocyclic, fused bicyclic or fused tricyclic system, wherein each ring is aromatic. Wherein the nitrogen atom is optionally quaternized, and the nitrogen and sulfur heteroatoms are optionally oxidized (i.e., NO and $S(O)_p$, p is 1 or 2). The 5-10 membered heteroaryl may be attached to the rest of the molecule through a heteroatom or a carbon atom. The 5-10 membered heteroaryl includes 5-8 membered, 5-7 membered, 5-6 membered, 5 membered and 6 membered heteroaryl and the like. Examples of the 5-10 membered heteroaryl include, but are not limited to, pyrrolyl (including N-pyrrolyl, 2-pyrrolyl and 3-pyrrolyl and the like), pyrazolyl (including 2-pyrazolyl and 3-pyrazolyl and the like), imidazolyl (including N-imidazolyl, 2-imidazolyl, 4-imidazolyl and 5-imidazolyl and the like), oxazolyl (including 2-oxazolyl, 4-oxazolyl and 5-oxazolyl and the like), triazolyl (1H-1,2,3-triazolyl, 2H-1,2,3-triazolyl, 1H-1,2,4-triazolyl and 4H-1,2,4-triazolyl and the like), tetrazolyl, isoxazolyl (3-isoxazolyl, 4-isoxazolyl and 5-isoxazolyl and the like), thiazolyl (including 2-thiazolyl, 4-thiazolyl and 5-thiazolyl and the like), furanyl (including 2-furanyl and 3-furanyl and the like), and thienyl (including 2-thienyl and 3-thienyl and the like), pyridinyl (including 2-pyridyl, 3-pyridyl and 4-pyridyl and the like), pyrazinyl, pyrimidinyl (including 2-pyrimidinyl and 4-pyrimidinyl and the like), benzothiazolyl (including 5-benzothiazolyl and the like), purinyl, benzimidazolyl (including 2-benzimidazolyl and the like), benzoxazolyl, indolyl (including 5-indolyl and the like), and isoquinolinyl (including 1-isoquinolinyl and 5-isoquinolinyl and the like), quinoxalinyl (including 2-quinoxalinyl and 5-quinoxalinyl and the like) or quinolinyl (including 3-quinolinyl and 6-quinolinyl and the like).

Unless otherwise specified, the terms "5-6 membered heteroaromatic ring" and "5-6 membered heteroaryl" in the present disclosure may be used interchangeably, and the term "5-6 membered heteroaryl" refers to a monocyclic group consisting of 5 to 6 ring atoms with conjugated π electronic system, of which 1, 2, 3 or 4 ring atoms are heteroatoms independently selected from O, S and N, and the rest are carbon atoms. Wherein the nitrogen atom is optionally quaternized, and the nitrogen and sulfur heteroatoms are optionally oxidized (i.e., NO and $S(O)_p$, p is 1 or 2). The 5-6 membered heteroaryl may be attached to the rest of the molecule through a heteroatom or a carbon atom. The 5-6 membered heteroaryl includes 5 membered and 6 membered heteroaryl. Examples of the 5-6 membered heteroaryl include, but are not limited to, pyrrolyl (including N-pyrrolyl, 2-pyrrolyl and 3-pyrrolyl and the like), pyrazolyl (including 2-pyrazolyl and 3-pyrazolyl and the like), imidazolyl (including N-imidazolyl, 2-imidazolyl, 4-imidazolyl and 5-imidazolyl and the like), oxazolyl (including 2-oxazolyl, 4-oxazolyl and 5-oxazolyl and the like), triazolyl (1H-1,2,3-triazolyl, 2H-1,2,3-triazolyl, 1H-1,2,4-triazolyl and 4H-1,2,4-triazolyl and the like), tetrazolyl, isoxazolyl (3-isoxazolyl, 4-isoxazolyl and 5-isoxazolyl and the like), thiazolyl (including 2-thiazolyl, 4-thiazolyl and 5-thiazolyl and the like), furanyl (including 2-furanyl and 3-furanyl and the like), and thienyl (including 2-thienyl and 3-thienyl and the like), pyridinyl (including 2-pyridyl, 3-pyridyl and 4-pyridyl and the like), pyrazinyl or pyrimidinyl (including 2-pyrimidinyl and 4-pyrimidinyl and the like)

Unless otherwise specified, $C_{n-n+m}$ or $C_{n-Cn+m}$ includes any specific case of n to n+m carbons, for example, $C_{1-12}$ includes $C_1$, $C_2$, $C_3$, $C_4$, $C_5$, $C_6$, $C_7$, $C_8$, $C_9$, $C_{10}$, $C_{11}$, and $C_{12}$, and any range from n to n+m is also included, for example $C_{1-12}$ includes $C_{1-3}$, $C_{1-6}$, $C_{1-9}$, $C_{3-6}$, $C_{3-9}$, $C_{3-12}$, $C_{6-9}$, $C_{6-12}$, and $C_{9-12}$ and the like; similarly, n membered to n+m membered means that the number of atoms on the ring is from n to n+m, for example, 3-12 membered ring includes 3 membered ring, 4 membered ring, 5 membered ring, 6 membered ring, 7 membered ring, 8 membered ring, 9 membered ring, 10 membered ring, 11 membered ring, and 12 membered ring, and any range from n to n+m is also included, for example, 3-12 membered ring includes 3-6 membered ring, 3-9 membered ring, 5-6 membered ring, 5-7 membered ring, 6-7 membered ring, 6-8 membered ring, and 6-10 membered ring and the like.

The term "leaving group" refers to a functional group or atom that can be replaced by another functional group or atom by a substitution reaction (such as an affinity substitution reaction). For example, representative leaving groups include triflate; chlorine, bromine, and iodine; sulfonate group, such as mesylate, tosylate, p-bromobenzenesulfonate, p-toluenesulfonates and the like; acyloxy, such as acetoxy, trifluoroacetoxy and the like.

The term "protecting group" includes, but is not limited to "amino protecting group", "hydroxy protecting group" or "thio protecting group". The term "amino protecting group" refers to a protecting group suitable for blocking the side reaction on the nitrogen of an amino. Representative amino protecting groups include, but are not limited to: formyl; acyl, such as alkanoyl (such as acetyl, trichloroacetyl or trifluoroacetyl); alkoxycarbonyl, such as tert-butoxycarbonyl (Boc); arylmethoxycarbonyl such as benzyloxycarbonyl (Cbz) and 9-fluorenylmethoxycarbonyl (Fmoc); arylmethyl, such as benzyl (Bn), trityl (Tr), 1,1-bis-(4'-methoxyphenyl) methyl; silyl, such as trimethylsilyl (TMS) and tert-butyldimethylsilyl (TBS) and the like. The term "hydroxy protecting group" refers to a protecting group suitable for blocking the side reaction on hydroxy. Representative hydroxy protecting groups include, but are not limited to: alkyl, such as methyl, ethyl, and tert-butyl; acyl, such as alkanoyl (such as acetyl); arylmethyl, such as benzyl (Bn), p-methoxybenzyl (PMB), 9-fluorenylmethyl (Fm), and diphenylmethyl (benzhydryl, DPM); silyl, such as trimethylsilyl (TMS) and tert-butyl dimethyl silyl (TBS) and the like.

The term "treatment" as used herein refers to the administration of one or more pharmaceutical substances, in particular compounds of formula (I) and/or pharmaceutically acceptable salts thereof, to an individual suffering from a disease or having symptoms of the disease, for the purpose of curing, alleviating, mitigating, modifying, healing, improving, ameliorating or affecting the disease or symptoms of the disease. As used herein, the term "prevention" refers to the administration of one or more pharmaceutical substances, especially the compound of formula (I) described herein and/or pharmaceutically acceptable salts thereof, to an individual with a constitution susceptible to the disease, to prevent the individual from suffering from the disease. When referring to chemical reactions, the terms "treating", "contacting" and "reacting" refer to adding or mixing two or more reagents under appropriate conditions to produce the indicated and/or desired products. It should be understood that the reaction to produce the indicated and/or desired products may not necessarily come directly from the combination of the two reagents initially added, i.e. there may be one or more intermediates generated in the mixture, which eventually lead to the formation of the indicated and/or desired products.

As used herein, the term "effective amount" refers to an amount generally sufficient to produce a beneficial effect on an individual. The effective amount of a compound of the present disclosure can be determined by conventional methods (such as modeling, dose-escalation studies, or clinical trials) in combination with conventional influencing factors (such as mode of administration, pharmacokinetics of the compound, severity and duration of the disease, medical history of the individual, health status of the individual, degree of response of the individual to the drug and the like).

The compounds of the present disclosure can be prepared by a variety of synthetic methods known to those skilled in the art, including the specific embodiments listed below, the embodiments formed by their combination with other chemical synthesis methods, and equivalent alternatives known to those skilled in the art, preferred implementations include but are not limited to the embodiments of the present disclosure.

The technical and scientific terms used herein that are not specifically defined have the meanings commonly understood by those skilled in the art to which the present disclosure belongs.

The solvent used in the present disclosure is commercially available. The following abbreviations are used in the present disclosure: NaHMDS refers to sodium bis(trimethylsilyl)amide, LiHMDS refers to lithium bis(trimethylsilyl)amide, DMPU refers to 1,3-dimethyl-3,4,5,6-tetrahydro-2-pyrimidinone, h refers to hour, and min refers to minute.

HPLC analysis conditions used in the present disclosure: chromatographic column: waters XSelect CSH C18 4.6*100 mm, 3.5 um; mobile phase: [water (0.01% trifluoroacetic acid)-acetonitrile (0.01% trifluoroacetic acid)], B %: 5%-95%; flow rate: 1.2 mL/min, column temperature: 40° C.

The compounds of the present disclosure are named according to the conventional naming principles in the art or by ChemDraw® software, and the commercially available compounds use the supplier catalog names.

DETAILED DESCRIPTION OF THE INVENTION

The present application is described in detail by the embodiments below, but it does not mean that there are any adverse restrictions on the present application. The present application has been described in detail herein, wherein specific embodiments thereof are also disclosed, and it will be apparent to those skilled in the art that various variations and improvements can be made to specific embodiments of the present application without departing from the spirit and scope of the present application.

The experimental materials and reagents used in the following embodiments can be obtained from commercially available sources unless otherwise specified.

Preparation of Intermediates:

1) Preparation of Intermediate Int-A

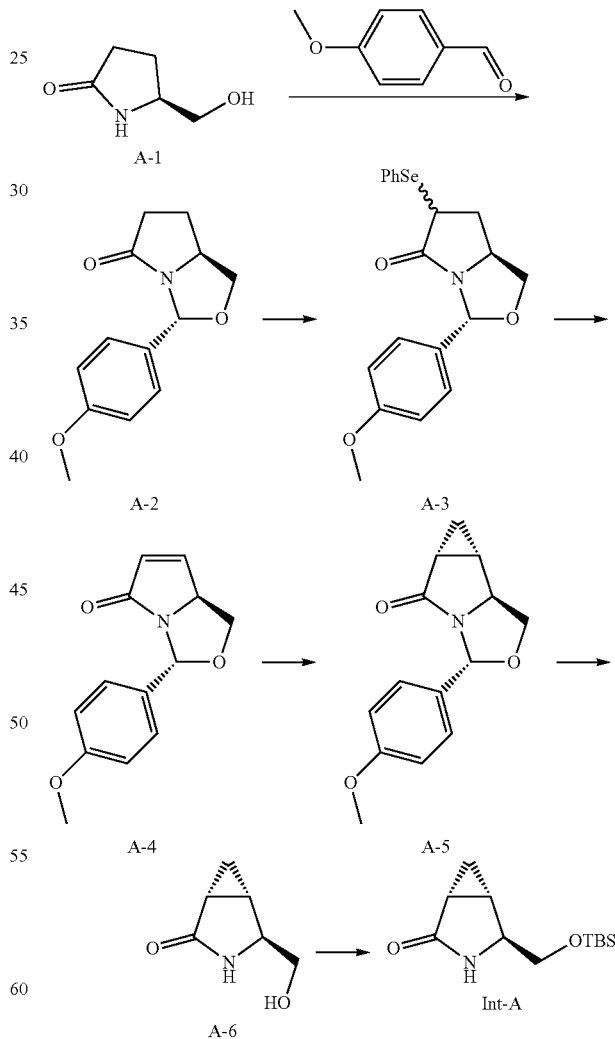

Step 1. Synthesis of Compound A-2

Compound A-1 (50.0 g, 0.43 mol) was dissolved in toluene (500 mL) at room temperature. P-toluenesulfonic acid monohydrate (1.24 g, 6.5 mmol) and p-methoxybenzaldehyde (88.7 g, 0.65 mol) were added sequentially, the reaction was heated to reflux, the mixture was stirred and refluxed with water separation for 15 hours, and the disappearance of raw materials was detected by TLC. The solvent was removed under reduced pressure, and the crude product was purified by silica gel column chromatography (petroleum ether/ethyl acetate (v/v)=90:10) to obtain compound A-2.

MS (ESI) m/z (M+H)$^+$=234.2.

Step 2. Synthesis of Compound A-3

At 0° C., compound A-2 (57.1 g, 0.24 mol), DMPU (87.9 g, 0.69 mol) were dissolved in tetrahydrofuran (500 mL), NaHMDS (2.0 M tetrahydrofuran solution, 294 mL, 0.59 mol) was added dropwise, the mixture was stirred for 20 min at this temperature, then cooled to −78° C.; and a solution of phenyl selenium chloride (47.9 g, 0.25 mol) in tetrahydrofuran (200 mL) was added dropwise thereto, and the mixture was stirred for 2 hours; the completion of the reaction was detected by LCMS, saturated ammonium chloride solution (300 mL) was added to quench the reaction, the mixture was slowly warmed to room temperature, the phases were separated, the aqueous phase was extracted with ethyl acetate (300 mL×2), the organic phases were combined and washed with water (300 mL×2), saturated saline (300 mL) sequentially, dried over anhydrous sodium sulfate, filtered, and the filtrate was concentrated under reduced pressure to obtain crude product A-3, which was directly used for the next step without further purification.

Step 3. Synthesis of Compound A-4

At 0° C., compound A-3 obtained in the previous step was dissolved in a mixed solvent of ethyl acetate (300 mL) and tetrahydrofuran (200 mL), then sodium bicarbonate (25.2 g, 0.3 mol) was added, and hydrogen peroxide aqueous solution (100 mL) was added dropwise; after the addition was completed, the mixture was stirred and the reaction was carried out for 1 hour, and the disappearance of raw materials was detected by TLC, water (200 mL) was added, and the phases were separated, the aqueous phase was extracted with ethyl acetate (200 mL×2), the organic phases were combined, washed with water (300 mL×2) and saturated saline (300 mL) sequentially, dried over anhydrous sodium sulfate, filtered, and the filtrate was concentrated to dryness under reduced pressure, the crude product was purified by silica gel column chromatography (petroleum ether/ethyl acetate (v/v)=90:10) to obtain compound A-4.

MS (ESI) m/z (M+H)$^+$=232.2.

Step 4. Synthesis of Compound A-5

Under the protection of nitrogen, trimethyl sulfoxide iodide (96.0 g, 436.0 mmol) was dissolved in dimethyl sulfoxide (600 mL), sodium hydride (15.0 g, 374.0 mmol) was slowly added, and after the addition was completed, the mixture was stirred at room temperature for 10 min, and the reaction temperature was heated to 55° C. and the mixture was stirred for 1 hour; at this temperature, a solution of compound A-4 (36.0 g, 155.8 mmol) in dimethyl sulfoxide (100 mL) was added dropwise, and the mixture was stirred for 1.5 hours; the completion of the reaction was detected by LCMS, and the reaction mixture was cooled to room temperature, quenched by adding water (400 mL), and ethyl acetate (500 mL) was added thereto, the mixture was stirred and then the phases were separated, and the aqueous phase was extracted with ethyl acetate (300 mL×2); the organic phases were combined, washed with water (500 mL×2) and saturated saline (500 mL) sequentially, dried over anhydrous sodium sulfate, filtered, and the filtrate was concentrated to dryness under reduced pressure; then the crude product was purified by silica gel column chromatography (petroleum ether/ethyl acetate (v/v)=90:10) to obtain compound A-5.

$^1$H NMR (400 MHz, DMSO-d$_6$) δ 7.30-7.26 (m, 1H), 6.88-6.84 (m, 1H), 6.27 (s, 1H), 4.21-4.17 (m, 1H), 3.92-3.88 (m, 1H), 3.79 (s, 3H), 3.46-3.41 (m, 1H), 2.15-2.09 (m, 1H), 2.05-2.03 (m, 1H), 1.34-1.26 (m, 1H), 1.15-1.12 (m, 1H).

Step 5. Synthesis of Compound A-6

Compound A-5 (25.0 g, 102.0 mmol) was dissolved in dichloromethane (300 mL), and the mixture was cooled to 0° C., trifluoroacetic acid (93.1 g, 816.3 mmol) was added dropwise and after the addition was completed, the mixture was stirred at room temperature for 1 hour; the completion of the reaction was detected by LCMS and the solvent was removed by concentration under reduced pressure, and the crude product was purified by silica gel column chromatography (petroleum ether/ethyl acetate (v/v)=20:80) to obtain compound A-6.

$^1$H NMR (400 MHz, DMSO-d$_6$) δ 7.14 (s, 1H), 4.87-4.81 (t, J=6.0 Hz, 1H), 3.41-3.22 (m, 2H), 1.85-1.81 (m, 1H), 1.61-1.57 (m, 1H), 1.02-1.00 (m, 1H), 1.00-0.42 (m, 1H).

Step 6. Synthesis of Compound Int-A

Compound A-6 (3 g, 23.6 mmol) was dissolved in N,N-dimethylformamide (20 mL), and imidazole (1.9 g, 28.3 mmol) and tert-butyldimethylchlorosilane (4.2 g, 28.3 mmol) were added sequentially, and the mixture was stirred at room temperature for 12 hours. The reaction was quenched by adding water (20 mL), extracted with ethyl acetate (50 mL×2); the organic phases were combined, washed with saturated saline (50 mL), dried over anhydrous sodium sulfate, filtered, and the filtrate was concentrated to dryness under reduced pressure, and the crude product was purified by silica gel column chromatography (petroleum ether:ethyl acetate=60:40→40:60) to obtain compound Int-A.

MS (ESI) m/z (M+H)$^+$=242.2.

2) Preparation of Intermediate Int-B

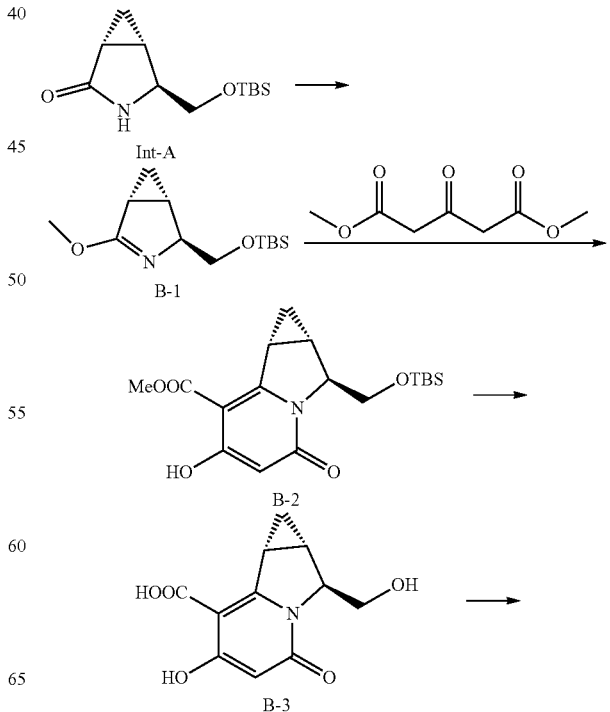

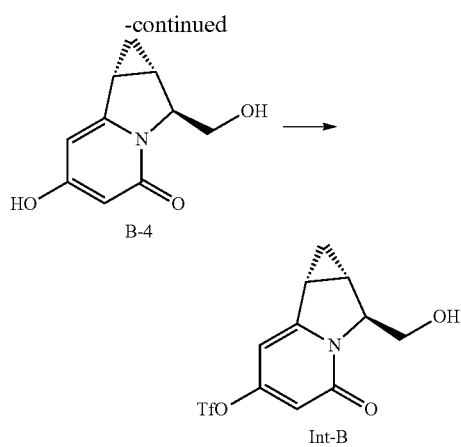

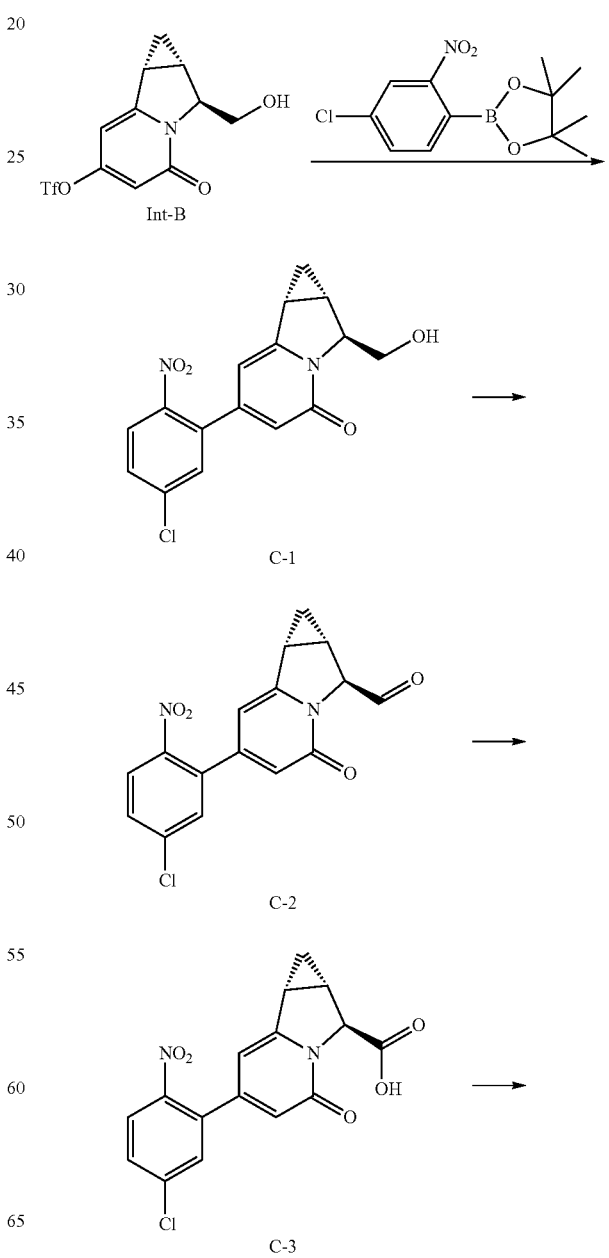

Step 5. Synthesis of Compound Int-B

Compound B-4 (0.64 g, 3.2 mmol) was dissolved in N,N-dimethylformamide (5 mL), triethylamine (0.65 mL, 4.9 mmol) and N-phenylbis(trifluoromethanesulfonyl)imide (1.76 g, 4.9 mmol) were added sequentially, and the mixture was stirred at room temperature for 12 hours. The reaction was quenched by adding water (20 mL), extracted with ethyl acetate (20 mL×3); the organic phases were combined, washed with saturated saline (20 mL), dried over anhydrous sodium sulfate, filtered, and the filtrate was concentrated to dryness under reduced pressure, and the crude product was purified by silica gel column chromatography (petroleum ether:ethyl acetate=80: 20-100:0) to obtain compound Int-B.

3) Preparation of Intermediate Int-C (Method 1)

Step 1. Synthesis of Compound B-1

Compound Int-A (3.4 g, 14 mmol) was dissolved in dichloromethane (20 mL), and trimethyloxonium tetrafluoroborate (2.5 g, 17 mmol) was added, and the mixture was stirred at room temperature for 3 hours. The reaction was cooled to 0° C., and the reaction was quenched by adding saturated sodium bicarbonate aqueous solution (15 mL) and water (5 mL), and the mixture was extracted with dichloromethane (20 mL×3). The organic phases were combined, washed with saturated saline (20 mL), dried over anhydrous sodium sulfate, filtered, and the filtrate was concentrated to dryness under reduced pressure to obtain crude B-1, which was used directly in the next step without further purification.

Step 2. Synthesis of Compound B-2

B-1 (3.16 g, 12.3 mmol), dimethyl 3-oxoglutarate (2.14 g, 14.8 mmol) and triethylamine (0.16 mL) were mixed, and the mixture was stirred at 70° C. for 72 hours. Then the mixture was cooled to room temperature. The crude product was purified by silica gel column chromatography (petroleum ether:ethyl acetate=60: 40-80:20) to obtain compound B-2.

MS (ESI) m/z $(M+H)^+$=366.2.

Step 3. Synthesis of Compound B-3

Compound B-2 (1.2 g, 3.2 mmol) was dissolved in methanol (2 mL), and 2.0 M sodium hydroxide aqueous solution (0.66 g, 16.4 mmol) was added, and the mixture was stirred at room temperature for 16 hours. 6 M hydrochloric acid aqueous solution was added to quench the reaction, the pH of the solution was adjusted to 4.0, the mixture was filtered and the solid was collected, then the solid was washed with water (15 mL) and dichloromethane (15 mL) sequentially, and dried under vacuum to obtain compound B-3, which was directly used in the next step without further purification.

MS (ESI) m/z $(M+H)^+$=238.1.

Step 4. Synthesis of Compound B-4

Compound B-3 (0.78 g, 3.2 mmol) was dissolved in 6.0 M hydrochloric acid aqueous solution (3 mL) and 12.0 M hydrochloric acid aqueous solution (1 mL), and the system was stirred in a sealed tube at 140° C. for 3 hours. The mixture was cooled to room temperature and concentrated under reduced pressure. The crude product was purified by silica gel column chromatography (petroleum ether:ethyl acetate=60: 40-80:20) to obtain compound B-4.

MS (ESI) m/z $(M+H)^+$=194.2.

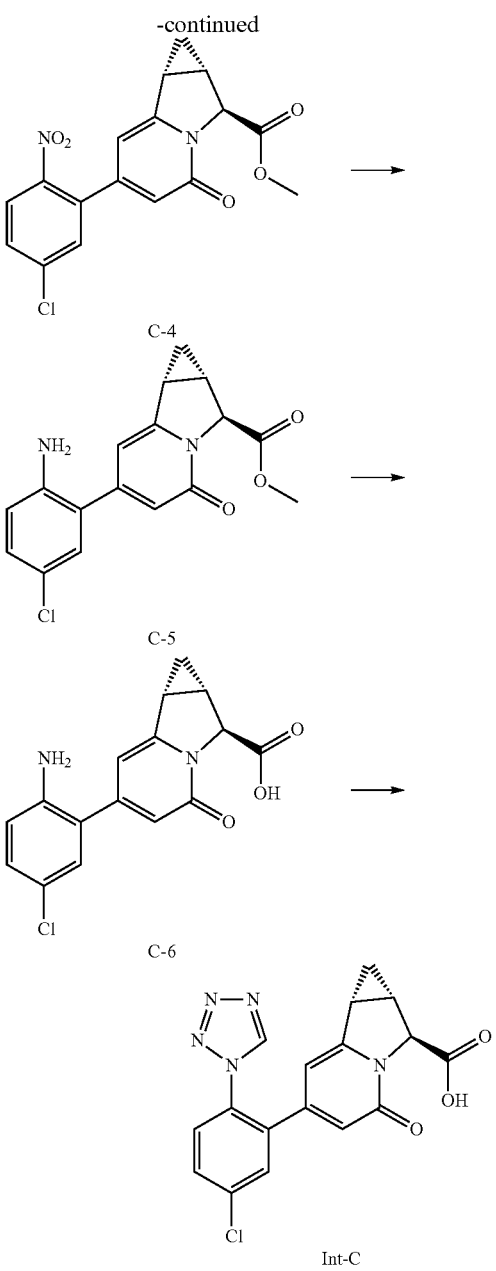

Step 1. Synthesis of Compound C-1

Under the protection of nitrogen, compound Int-B (0.75 g, 2.3 mmol) was dissolved in 1, 4-dioxane (15 mL); 5-chloro-2-nitrophenylboronic acid pinacol ester (0.65 g, 2.3 mmol), cesium fluoride (1.05 g, 6.9 mmol) and tetrakis(triphenylphosphine)palladium (80 mg, 0.07 mmol) were added, and the reaction system was stirred at 105° C. for 30 min. The reaction was quenched by adding water (10 mL), extracted with ethyl acetate (10 mL×3); the organic phases were combined, dried over anhydrous sodium sulfate, filtered, and the filtrate was concentrated to dryness under reduced pressure, and the crude product was purified by silica gel column chromatography (dichloromethane:methanol=100:0→90:10) to obtain compound C-1.

MS (ESI) m/z (M+H)$^+$=333.2.

Step 2. Synthesis of Compound C-2

Compound C-1 (0.8 g, 2.4 mmol) was dissolved in dichloromethane (10 mL), and Dess-Martin oxidant (1.5 g, 3.6 mmol) was added. The mixture was stirred at room temperature for 3 hours, quenched by adding water (1 mL), and filtered to remove the solid, the solvent was removed under reduced pressure, and the crude product was purified by silica gel column chromatography (dichloromethane:methanol=100:0→90:10) to obtain compound C-2.

MS (ESI) m/z (M+H)$^+$=331.1.

Step 3. Synthesis of Compound C-3

Compound C-2 (1.14 g, 3.4 mmol) was dissolved in acetonitrile (10 mL) at 10° C., and water (4 mL), sodium dihydrogen phosphate (0.12 g, 1.0 mmol), 30% hydrogen peroxide aqueous solution (0.4 mL, 3.4 mmol) and sodium chlorite (0.43 g, 4.7 mmol) aqueous solution (4 mL) were added sequentially. The reaction mixture was warmed to room temperature, stirred and the reaction was carried out for 12 hours, and the reaction was quenched by adding saturated sodium sulfite aqueous solution (1 mL), the solvent was removed under reduced pressure, water (10 mL) and ethyl acetate (10 mL) were added, the organic phase was separated, the aqueous phase was extracted with ethyl acetate (10 mL×3), then the organic phases were combined, dried over anhydrous sodium sulfate, filtered, and the filtrate was concentrated to dryness under reduced pressure to obtain crude product C-3, which was directly used for the next step without further purification.

MS (ESI) m/z (M+H)$^+$=347.1.

Step 4. Synthesis of Compound C-4

Compound C-3 (1.0 g, 2.8 mmol) was dissolved in methanol (20 mL) at 0° C., and a solution of trimethylsilylated diazomethane (2.0 M) (14 mL, 28 mmol) in hexane was added. The mixture was warmed to room temperature, stirred for 12 hours, and the reaction was quenched by adding saturated sodium bicarbonate aqueous solution (1 mL), the solvent was removed under reduced pressure, water (10 mL) and ethyl acetate (10 mL) were added, the organic phase was separated, the aqueous phase was extracted with ethyl acetate (10 mL×3), then the organic phases were combined, dried over anhydrous sodium sulfate, filtered, and the filtrate was concentrated to dryness under reduced pressure, the crude product was purified by silica gel column chromatography (petroleum ether:ethyl acetate=50:50→0:100) to obtain compound C-4.

MS (ESI) m/z (M+H)$^+$=361.1.

Step 5. Synthesis of Compound C-5

Compound C-4 (260 mg, 0.72 mmol) was dissolved in ethanol (20 mL), and ammonium chloride (404 mg, 7.2 mmol) and iron powder (386 mg, 7.2 mmol) were added sequentially. The mixture was heated to 70° C. and stirred for 4 hours, the solvent was removed under reduced pressure, water (10 mL) and ethyl acetate (10 mL) were added, the organic phase was separated, the aqueous phase was extracted with ethyl acetate (10 mL×3), then the organic phases were combined, dried over anhydrous sodium sulfate, filtered, and the filtrate was concentrated to dryness under reduced pressure, the crude product was purified by silica gel column chromatography (petroleum ether. ethyl acetate=50:50→0:100) to obtain compound C-5.

MS (ESI) m/z (M+H)$^+$=331.1.

Step 6. Synthesis of Compound C-6

Compound C-5 (220 mg, 0.67 mmol) was dissolved in methanol (10 mL), and sodium hydroxide (80 mg, 2 mmol) was added, and the mixture was stirred at room temperature for 12 hours. Methanol was removed under reduced pressure, and the pH of the solution was adjusted to 4.0 by adding 2.0 M hydrochloric acid aqueous solution. The mixture was extracted with ethyl acetate (10 mL×3), the organic phases were combined, dried over anhydrous sodium sulfate, filtered, and the filtrate was concentrated to dryness to obtain crude product C-6.

MS (ESI) m/z (M+H)$^+$=317.2.

$^1$H NMR (400 MHz, DMSO-d$_6$) 7.12 (dd, J=8.7, 2.6 Hz, 1H), 7.04 (d, J=2.6 Hz, 1H), 6.77 (d, J=8.7 Hz, 1H), 6.37 (d, J=1.5 Hz, 1H), 6.18 (d, J=1.5 Hz, 1H), 5.19 (s, 2H), 4.79 (s, 1H), 2.75 (s, 1H), 2.24 (dt, J=7.6, 4.5 Hz, 1H), 1.33 (dt, J=8.2, 4.1 Hz, 1H), 0.62 (q, J=4.3 Hz, 1H).

Step 7. Synthesis of Compound Int-C

Compound C-6 (140 mg, 0.44 mmol) was dissolved in acetic acid (2 mL), trimethyl orthoformate (188 mg, 1.77 mmol) and sodium azide (115 mg, 1.77 mmol) were added sequentially, respectively. The reaction system was heated to 40° C. and stirred for 16 hours. The solid was filtered off, and the filtrate was purified by reverse phase column chromatography [water (0.05% trifluoroacetic acid solution): acetonitrile=100:0→5:95] to obtain compound Int-C.

MS (ESI) m/z (M+H)$^+$=370.1.

4) Preparation of Intermediate Int-C (Method 2)

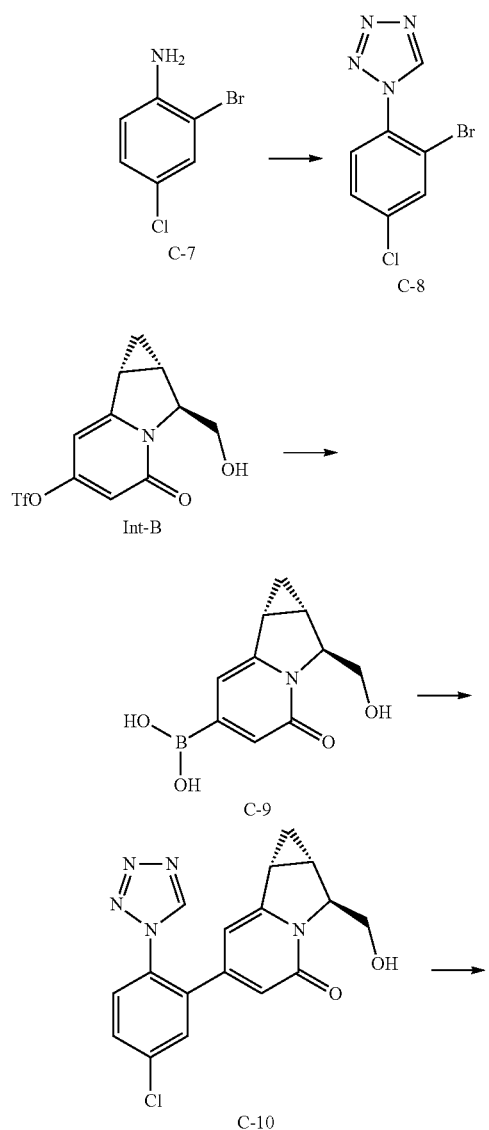

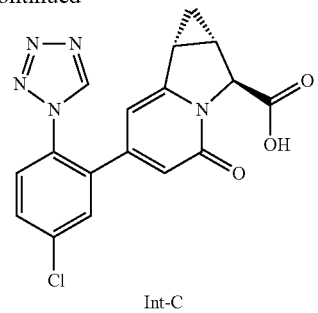

Step 1. Synthesis of Compound C-8

Compound C-7 (10 g, 48.4 mmol) and trimethyl orthoformate (15.4 g, 145.3 mmol) were dissolved in acetic acid (200 mL), sodium azide (9.5 g, 145.3 mmol) was added in batches, and the reaction was stirred at room temperature for 18 hours. The reaction mixture was slowly added dropwise to water (400 mL), filtered after the solid was completely precipitated, the filter cake was rinsed with a small amount of water, and then dried under vacuum to obtain crude product C-8, which was directly used for the next step without further purification.

MS (ESI) m/z (M+H)$^+$=261.0.

Step 2. Synthesis of Compound C-9

Under the protection of nitrogen, potassium acetate (6.8 g, 69.2 mmol) and bis(pinacolato)diboron (17.6 g, 69.2 mmol) were dissolved in dioxane (100 mL), the reaction was heated to 100° C. and stirred for 30 min, Int-B (7.5 g, 23.1 mmol) and [1,1'-bis(diphenylphosphino)ferrocene]dichloropalladium (1.7 g, 2.31 mmol) were added, and the mixture was stirred at this temperature for 2 hours, the reaction mixture was cooled to room temperature and used directly for the next step.

MS (ESI) m/z (M+H)$^+$=222.2.

Step 3. Synthesis of Compound C-10

Under the protection of nitrogen, C-8 (6.59 g, 25.38 mmol), [1,1'-bis(diphenylphosphino)ferrocene]dichloropalladium (543 mg, 1.17 mmol), potassium carbonate (4.78 g, 34.61 mmol), dioxane (100 mL) and water (10 mL) were added sequentially to the reaction mixture of C-9, and the reaction was heated to 100° C. and stirred for 2 hours. The reaction mixture was cooled to room temperature, water (100 mL) and ethyl acetate (100 mL) were added, the organic phase was separated, the aqueous phase was extracted with ethyl acetate (100 mL×3), then the organic phases were combined, washed with saturated saline (100 mL), dried over anhydrous sodium sulfate, filtered, and the filtrate was concentrated to dryness under reduced pressure, the crude product was purified by silica gel column chromatography (petroleum ether. ethyl acetate=50:50) to obtain compound C-10.

MS (ESI) m/z (M+H)$^+$=356.2.

Step 4. Synthesis of Compound Int-C

Compound C-10 (3.5 g, 9.8 mmol) was dissolved in dichloromethane (100 mL), and Dess-Martin oxidant (14.6 g, 34.4 mmol) was added, and the mixture was stirred at room temperature for 18 hours. The reaction mixture was diluted with dichloromethane (100 mL), filtered, and the filtrate was concentrated. The crude product was purified by C18 reverse phase column chromatography (acetonitrile: 0.5% ammonium bicarbonate aqueous solution=5:95→95:5), and compound Int-C was obtained.

MS (ESI) m/z (M+H)$^+$=370.2.

5) Preparation of Intermediate Int-D

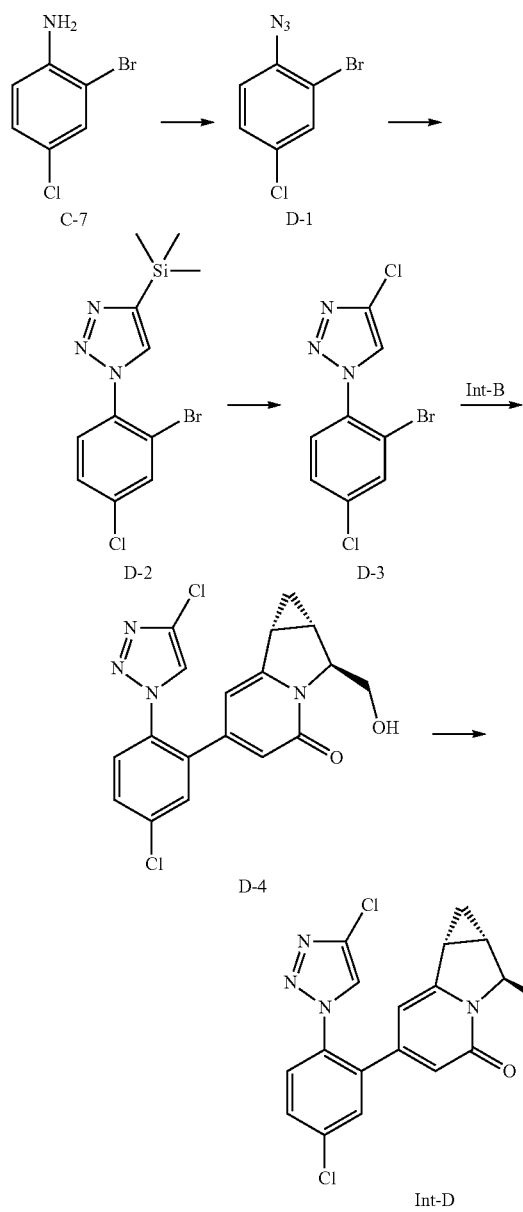

Step 1. Synthesis of Compound D-1

At 0° C., under the protection of nitrogen, compound C-7 (5 g, 24.2 mmol) and azido trimethylsilane (3.35 g, 29.1 mmol) were dissolved in acetonitrile (120 mL), then tert-butyl nitrite (129.2 mg, 0.32 mmol) was slowly added, and the reaction was warmed to room temperature and stirred for 72 hours. The reaction mixture was concentrated under reduced pressure, the crude product was purified by silica gel column chromatography (petroleum ether:ethyl acetate=100:0→80:20) to obtain compound D-1.

Step 2. Synthesis of Compound D-2

Compound D-1 (1 g, 4.3 mmol) was dissolved in toluene (10 mL) and trimethylsilylacetylene (1.2 g, 12.9 mmol) was added, and the mixture was stirred for 12 hours at 100° C. The reaction mixture was concentrated under reduced pressure, the crude product was purified by silica gel column chromatography (petroleum ether:ethyl acetate=100:0→90:10) to obtain compound D-2.

MS (ESI) m/z (M+H)$^+$=332.

Step 3. Synthesis of Compound D-3

Compound D-2 (1.4 g, 4.2 mmol) was dissolved in acetonitrile (30 mL), N-chlorosuccinimide (5.6 g, 42.0 mmol) and potassium fluoride (1.5 g, 25.2 mmol) were added sequentially, and the reaction was heated to 90° C. and stirred for 40 hours. The reaction mixture was cooled to room temperature, filtered, and the filtrate was concentrated under reduced pressure, the crude product was purified by silica gel column chromatography (petroleum ether:ethyl acetate=100:0→90:10) to obtain compound D-3.

MS (ESI) m/z (M+H)$^+$=293.9.

$^1$H NMR (400 MHz, DMSO-$d_6$) δ 8.90 (s, 1H), 8.15 (d, J=2.0 Hz, 1H), 7.78-7.74 (m, 2H).

Step 4-5. Synthesis of Compound Int-D

According to the synthesis method of Int-B→Int-C described in the preparation of intermediate Int-C (method 2), compound Int-B and D-3 were treated to obtain compound Int-D.

MS (ESI) m/z (M+H)$^+$=403.2.

6) Preparation of Intermediate Int-E

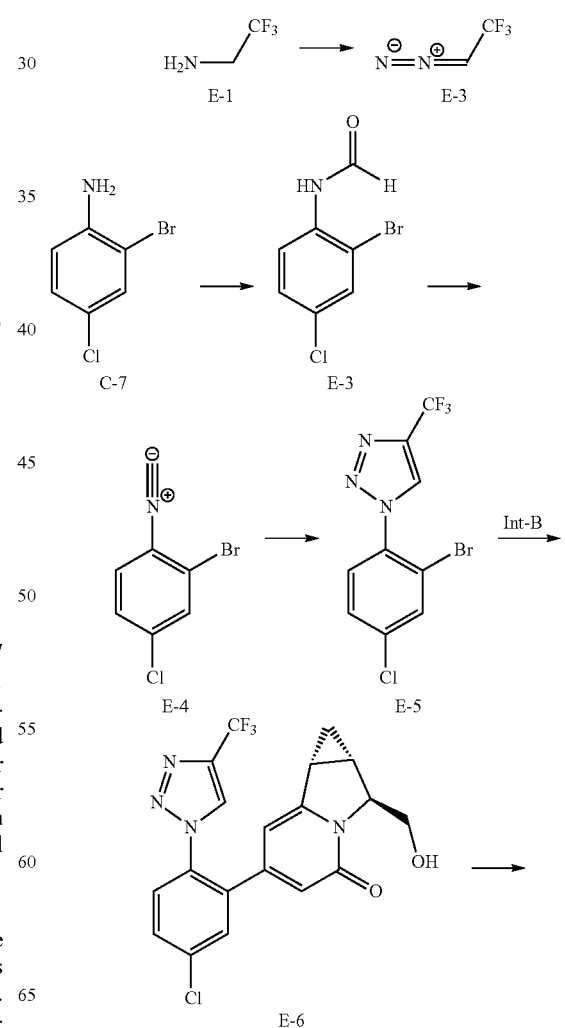

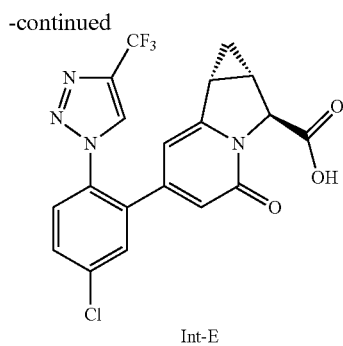

Int-E

Step 1. Synthesis of Compound E-2

At 0° C., under the protection of argon, 2, 2, 2-trifluoroethylamine hydrochloride (4050 mg, 30.0 mmol) was dissolved in toluene (60 mL), sodium nitrite (2277 mg, 33 mmol) was added, and the reaction was stirred for 30 min, water (6 mL) was added, the mixture was stirred for 2 hours, heated to 10° C., and stirred for 30 min. The reaction mixture was left to stand for 16 hours at −18° C. The organic phase was separated, and dried over anhydrous potassium carbonate (3000 mg) for 1 hour to obtain a solution of compound E-2 (60 mL, about 0.3-0.4 M) in toluene. The solution was directly used for subsequent reaction.

Step 2. Synthesis of Compound E-3

2-Bromo-4-chloroaniline (2500 mg, 12.2 mmol) was dissolved in formic acid (2245 mg, 48.8 mmol), and sodium formate (415 mg, 6.1 mmol) was added, then the mixture was stirred for 16 hours at room temperature. The reaction mixture was diluted with ethyl acetate (50 mL), washed with water (50 mL×3) and saturated sodium bicarbonate aqueous solution (50 mL) sequentially, dried over anhydrous sodium sulfate, filtered, and the filtrate was concentrated under reduced pressure to obtain crude product E-3, which was directly used in the next step without further purification.

$^1$H NMR (400 MHz, DMSO-d6) δ 9.82 (s, 1H), 8.36 (d, J=1.3 Hz, 1H), 8.05 (d, J=8.8 Hz, 1H), 7.80 (d, J=2.4 Hz, 1H), 7.46 (dd, J=8.6, 2.4 Hz, 1H).

Step 3. Synthesis of Compound E-4

At 0° C., under the protection of nitrogen, compound E-3 (2600 mg, 11.2 mmol) and triethylamine (3393 mg, 33.6 mmol) were dissolved in tetrahydrofuran (30 mL), then a solution of phosphorus oxychloride (2050 mg, 13.4 mmol) in tetrahydrofuran (10 mL) was added, and the reaction was stirred at this temperature for 1 hour. The reaction mixture was poured into saturated potassium carbonate aqueous solution (60 mL), extracted by methyl tert-butyl ether (50 mL×2), the organic phase was dried over anhydrous sodium sulfate, filtered, and the filtrate was concentrated under reduced pressure. The crude product was purified by silica gel column chromatography (petroleum ether:dichloromethane=100:0→70:30) to obtain compound E-4.

$^1$H NMR (400 MHz, CDCl$_3$) δ 7.68 (d, J=2.1 Hz, 1H), 7.39 (d, J=8.5 Hz, 1H), 7.34 (dd, J=8.5, 2.1 Hz, 1H).

Step 4. Synthesis of Compound E-5

Compound E-4 (1650 mg, 7.6 mmol), E-2 (30 mL, 0.3-0.4 M in toluene solution), silver carbonate (416 mg, 1.52 mmol) and 4 A molecular sieve (900 mg) were dissolved in N, N-dimethylformamide (10 mL), and the reaction was heated to 40° C. and stirred for 16 hours. The reaction mixture was filtered, concentrated to dryness under reduced pressure, the residue was dissolved in water (50 mL) and ethyl acetate (50 mL), the phases were separated, the aqueous phase was extracted with ethyl acetate (50 mL×2); the organic phases were combined, washed with saturated saline (200 mL), dried over anhydrous sodium sulfate, filtered, the filtrate was concentrated under reduced pressure, the crude product was purified by silica gel column chromatography (petroleum ether:dichloromethane=100:0→50:50) to obtain compound E-5.

MS (ESI) m/z (M+H)$^+$=328.0.

Step 5-6. Synthesis of Compound Int-E

According to the synthesis method of Int-B→Int-C described in the preparation of intermediate Int-C (method 2), compound Int-B and E-5 were treated to obtain compound Int-E.

MS (ESI) m/z (M+H)$^+$=437.0.

7) Preparation of Intermediate Int-F

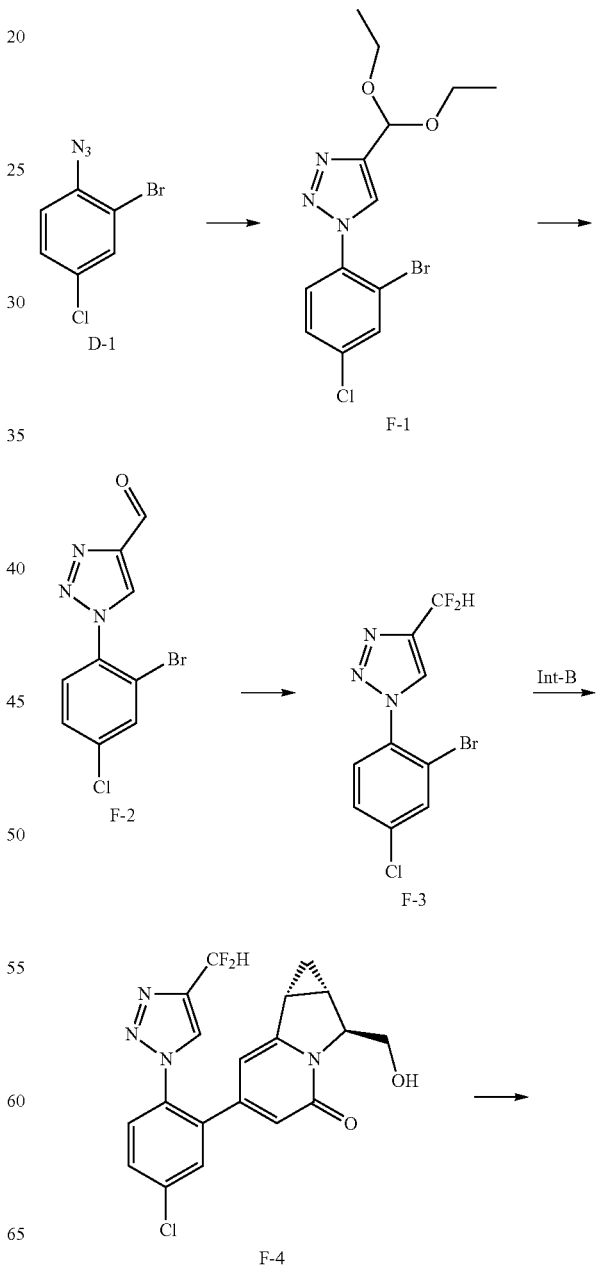

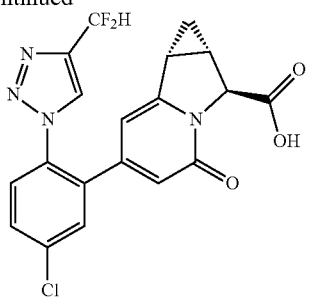

Int-F

Step 1. Synthesis of Compound F-1

Compound D-1 (1150 mg, 4.98 mmol) was dissolved in toluene (10 mL), and 3,3-diethoxyprop-1-yne (956 mg, 7.47 mmol) was added, and the reaction was warmed to 110° C. and stirred for 16 hours. The reaction mixture was concentrated under reduced pressure, the crude product was purified by silica gel column chromatography (petroleum ether: ethyl acetate=100:0→50:50) to obtain compound F-1.

MS (ESI) m/z (M+H)$^+$=362.0.

Step 2. Synthesis of Compound F-2

Compound F-1 (1200 mg, 3.34 mmol) was dissolved in dioxane (20 mL), concentrated hydrochloric acid (20 mL) was added, the reaction was heated to 30° C. and stirred for 16 hours. The reaction mixture was diluted with water (40 mL) and extracted with ethyl acetate (200 mL). The organic phase was washed with water (100 mL×2) and saturated saline (100 mL×2) sequentially, dried over anhydrous sodium sulfate, filtered, and the filtrate was concentrated under reduced pressure to obtain crude product F-2, which was directly used in the next step without further purification.

MS (ESI) m/z (M+H)$^+$=288.0.

Step 3. Synthesis of Compound F-3

Compound F-2 (950 mg, 3.33 mmol) was dissolved in dichloromethane (20 mL), and diethylaminosulfur trifluoride (1072 mg, 6.66 mmol) was added, and the mixture was stirred at room temperature for 2 hours. The reaction mixture was poured into saturated sodium bicarbonate aqueous solution (60 mL) at 0° C., extracted with dichloromethane (60 mL×2), and the organic phases were combined and washed with water (100 mL) and saturated saline (100 mL) sequentially, dried over anhydrous sodium sulfate, filtered, and the filtrate was concentrated under reduced pressure. The crude product was purified by silica gel column chromatography (petroleum ether:ethyl acetate=100:0→85:15) to obtain compound F-3.

MS (ESI) m/z (M+H)$^+$=310.0.

Step 4-5. Synthesis of Compound Int-F

According to the synthesis method of Int-B→Int-C described in the preparation of intermediate Int-C (method 2), compound Int-B and F-3 were treated to obtain compound Int-F.

MS (ESI) m/z (M+H)$^+$=419.0.

8) Preparation of Intermediate Int-G

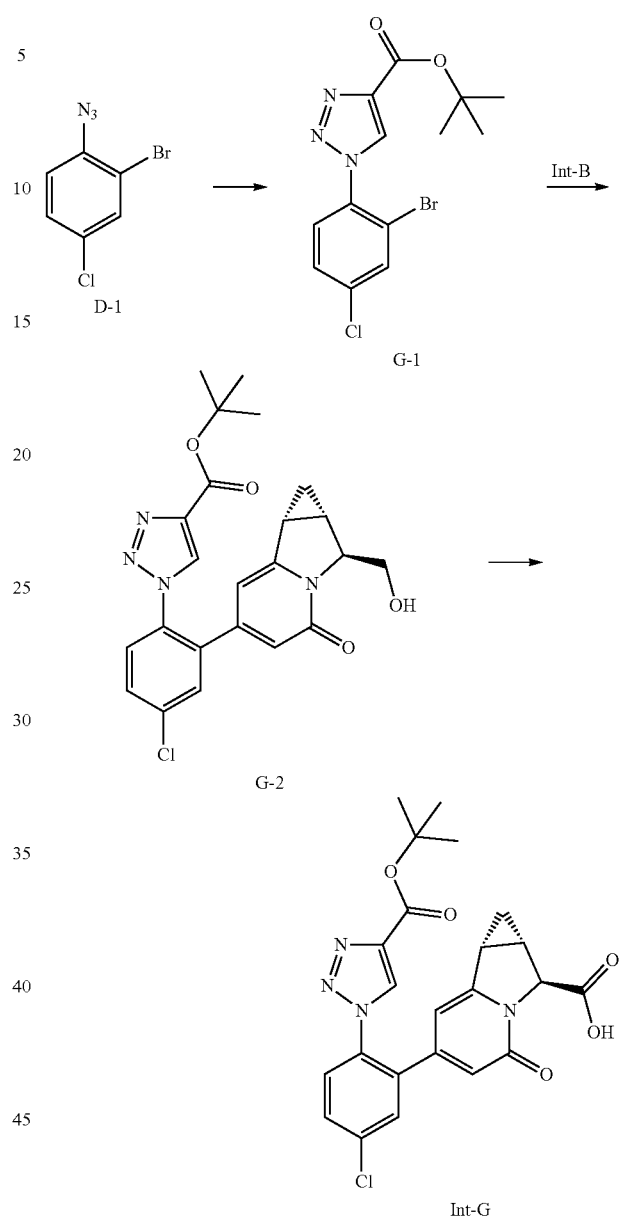

Step 1. Synthesis of Compound G-1

Compound D-1 (1 g, 4.3 mmol) was dissolved in toluene (10 mL), and tert-butyl propiolate (1.08 g, 12.9 mmol) was added, and the reaction was heated to 100° C. and stirred for 16 hours. The reaction mixture was concentrated under reduced pressure. The crude product was purified by silica gel column chromatography (petroleum ether:ethyl acetate=100:0→90:10) to obtain compound G-1.

MS (ESI) m/z (M+H)$^+$=360.

$^1$H NMR (400 MHz, DMSO-d$_6$) δ 9.14 (s, 1H), 8.14 (d, J=1.9 Hz, 1H), 7.76-7.75 (m, 2H), 1.56 (s, 9H).

Step 2-3. Synthesis of Compound Int-G

According to the synthesis method of Int-B→Int-C described in the preparation of intermediate Int-C (method 2), compound Int-B and G-1 were treated to obtain compound Int-G.

MS (ESI) m/z (M+H)$^+$=469.2.

9) Preparation of Intermediate Int-H

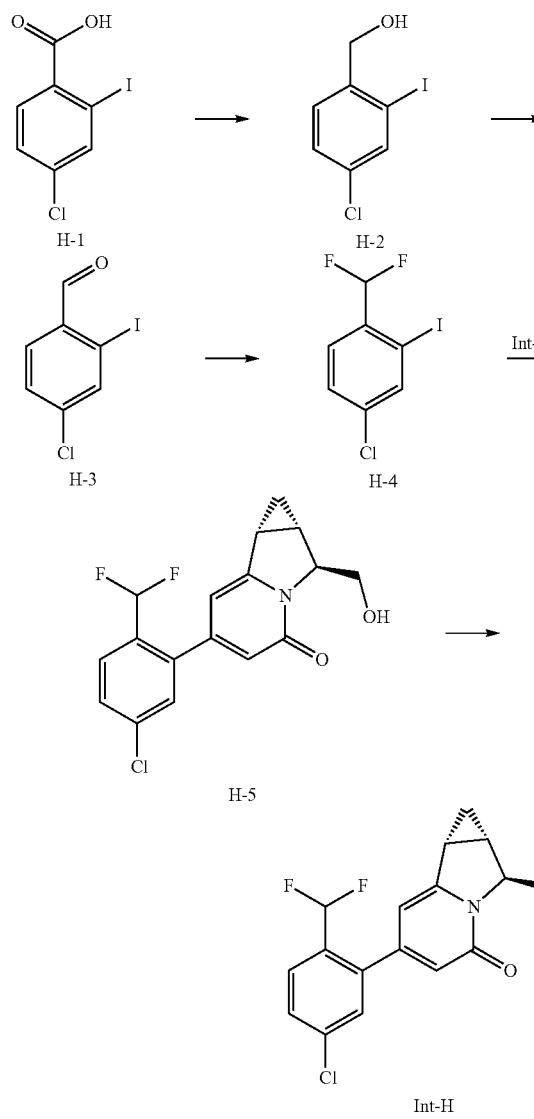

Step 1. Synthesis of Compound H-2

At 0° C., under the protection of nitrogen, compound H-1 (1 g, 3.5 mmol) was dissolved in tetrahydrofuran (10 mL), borane tetrahydrofuran complex (129.2 mg, 0.32 mmol) was added, the reaction was warmed to room temperature and stirred for 60 hours. The reaction mixture was quenched by adding 1.0 M hydrochloric acid (8 mL), the mixture was stirred for 1 hour, diluted with water (40 mL) and extracted with ethyl acetate (20 mL×2). The organic phases were combined, and washed with 1.0 M sodium hydroxide solution (20 mL) and saturated saline (20 mL) sequentially, dried over anhydrous sodium sulfate, filtered, and the filtrate was concentrated under reduced pressure, and the crude product was purified by silica gel column chromatography (petroleum ether:ethyl acetate=100:0→80:20) to obtain compound H-2.

MS (ESI) m/z (M+H)$^+$=534.9.

Step 2. Synthesis of Compound H-3

At 0° C., compound H-2 (910 mg, 3.37 mmol) was dissolved in dichloromethane (5 mL), and silicon dioxide (1 g) and pyridinium chlorochromate (1.45 g, 6.74 mmol) were added sequentially, and the reaction was warmed to room temperature and stirred for 2 hours. The reaction mixture was filtered, the filtrate was concentrated under reduced pressure. The crude product was purified by silica gel column chromatography (petroleum ether:ethyl acetate=100:0→80:20) to obtain compound H-3.

Step 3. Synthesis of Compound H-4

At 0° C., compound H-3 (0.9 g, 3.38 mmol) was dissolved in dichloromethane (10 mL), and diethylaminosulfur trifluoride (817 mg, 5.07 mmol) was added, and the mixture was stirred at this temperature for 2 hours. The reaction mixture was concentrated under reduced pressure, the crude product was purified by silica gel column chromatography (petroleum ether:ethyl acetate=100:0→90:10) to obtain compound H-4.

$^1$H NMR (400 MHz, DMSO-d$_6$) δ 8.16-8.03 (m, 1H), 7.65-7.57 (m, 2H), 6.99 (t, J=54.3 Hz, 1H).

Step 4-5. Synthesis of Compound Int-H

According to the synthesis method of Int-B→Int-C described in the preparation of intermediate Int-C (method 2), compound Int-B and H-4 were treated to obtain compound Int-H.

MS (ESI) m/z (M+H)$^+$=352.0.

10) Preparation of Intermediate Int-I

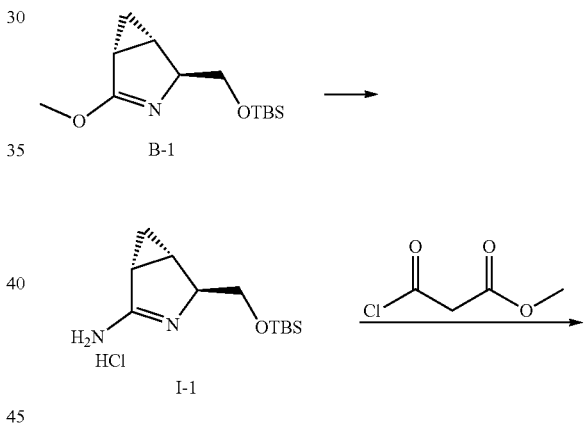

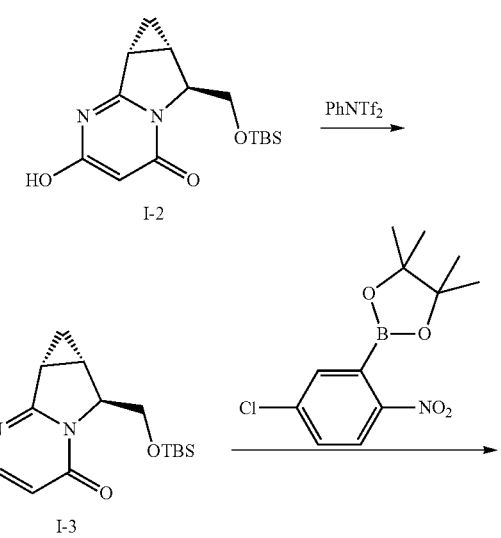

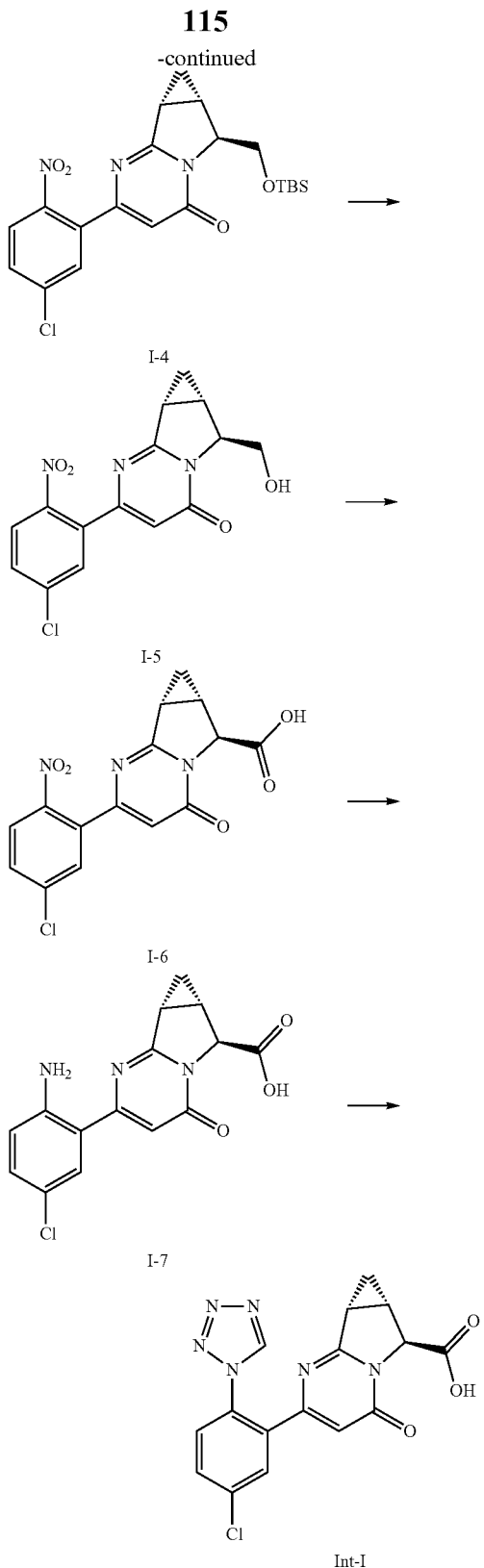

Step 1. Synthesis of Compound I-1

Compound B-1 (1 g, 3.9 mmol) was dissolved in methanol (20 mL), ammonium chloride (230 mg, 4.3 mmol) was added, and the reaction was heated to 75° C. and stirred for 15 hours, the reaction mixture was concentrated to dryness under reduced pressure. Crude product I-1 was obtained.

Step 2. Synthesis of Compound I-2

At 0° C., compound I-1 (1 g, 4.2 mmol) was dissolved in dioxane (25 mL), triethylamine (1.26 g, 12.5 mmol) and methyl 3-chloro-3-oxopropionate (624 mg, 4.6 mmol) were added sequentially, and the reaction was heated to 80° C. and stirred for 18 hours, the reaction mixture was diluted with ethyl acetate (25 mL), water (25 mL) was added for phase separation, and the aqueous phase was extracted with ethyl acetate (20 mL×3). The organic phases were combined, washed with water (25 mL) and saturated saline (25 mL) sequentially, dried over anhydrous sodium sulfate, filtered, and the filtrate was concentrated under reduced pressure. The crude product was purified by C-18 reverse phase column chromatography (acetonitrile: 0.5% ammonium bicarbonate aqueous solution=5: 95-95:5), and compound I-2 was obtained.

MS (ESI) m/z (M+H)$^+$=309.3.

Step 3. Synthesis of Compound I-3

Compound I-2 (220 mg, 0.71 mmol) was dissolved in N, N-dimethylformamide (10 mL), 1, 1, 1-trifluoro-N-phenyl-N-((trifluoromethyl)sulfonyl)methanesulfonamide (510 mg, 1.43 mmol) and triethylamine (217 mg, 2.14 mmol) were added sequentially, the mixture was stirred for 16 hours at room temperature. The reaction mixture was diluted with ethyl acetate (10 mL), water (10 mL) was added for phase separation, and the aqueous phase was extracted with ethyl acetate (10 mL×3). The organic phases were combined, washed with saturated saline (25 mL), dried over anhydrous sodium sulfate, filtered, and the filtrate was concentrated under reduced pressure. The crude product was purified by silica gel column chromatography (ethyl acetate:petroleum ether=40:60→100:0) to obtain compound I-3.

MS (ESI) m/z (M+H)$^+$=441.2.

Step 4. Synthesis of Compound I-4

Under the protection of nitrogen, compound I-3 (200 mg, 0.46 mmol) and 2-(5-chloro-2-nitrophenyl)-4, 4, 5, 5-tetramethyl-1, 3, 2-dioxaborolane (129 mg, 0.46 mmol) were dissolved in dioxaborolane (10 mL), cesium fluoride (173 mg, 1.14 mmol) and tetrakis(triphenylphosphine)palladium (53 mg, 0.046 mmol) were added sequentially, and the reaction was stirred at 105° C. for 4 hours. The reaction mixture was cooled to room temperature, diluted with ethyl acetate (10 mL), water (10 mL) was added for phase separation, and the aqueous phase was extracted with ethyl acetate (10 mL×3). The organic phases were combined, washed with saturated saline (25 mL), dried over anhydrous sodium sulfate, filtered, and the filtrate was concentrated under reduced pressure. The crude product was purified by silica gel column chromatography (ethyl acetate:petroleum ether=50:50) to obtain compound I-4.

MS (ESI) m/z (M+H)$^+$=448.2.

Step 5. Synthesis of Compound I-5

Compound I-4 (165 mg, 0.37 mmol) was dissolved in methanol (5 mL), 1.0 M hydrochloric acid aqueous solution (0.5 mL) was added, the mixture was stirred at room temperature for 3 hours, and the reaction mixture was concentrated to dryness under reduced pressure. The crude product was purified by C18 reverse phase column chromatography (acetonitrile: 0.5% ammonium bicarbonate aqueous solution=5:95→95:5), and compound I-5 was obtained.

MS (ESI) m/z (M+H)$^+$=334.1.

Step 6. Synthesis of Compound I-6

Compound I-5 (40 mg, 0.12 mmol) was dissolved in dichloromethane (4 mL), and Dess-Martin oxidant (762.6 mg, 1.8 mmol) was added, the mixture was stirred at room temperature for 18 hours, diluted with dichloromethane (10 mL) and filtered, the filtrate was concentrated to dryness.

The crude product was purified by C18 reverse phase column chromatography (acetonitrile: 0.5% ammonium bicarbonate aqueous solution=5:95→95:5), and compound I-6 was obtained.

MS (ESI) m/z (M+H)$^+$=348.1.

Step 7. Synthesis of Compound I-7

Compound I-6 (65 mg, 0.19 mmol) was dissolved in acetone (5 mL) and water (0.5 mL), zinc powder (122 mg, 1.87 mmol) and ammonium chloride (100 mg, 1.87 mmol) were added sequentially, then the mixture was stirred at room temperature for 18 hours. The reaction mixture was diluted with acetone (5 mL), the solid was filtered off, and the filtrate was concentrated to dryness. The crude product was purified by C18 reverse phase column (acetonitrile: 0.5% ammonium bicarbonate aqueous solution=5:95→95:5), and compound I-7 was obtained.

MS (ESI) m/z (M+H)$^+$=318.1.

Step 8. Synthesis of Compound Int-I

Compound I-7 (18 mg, 0.057 mmol) was dissolved in acetic acid (1 mL), trimethyl orthoformate (60.1 mg, 0.057 mmol) and azido trimethylsilane (13.1 mg, 0.11 mmol) were added sequentially, and the reaction was stirred at 85° C. for 18 hours in a sealed tube. The reaction mixture was cooled to room temperature, diluted with ethyl acetate (5 mL), water (5 mL) was added for phase separation, and the aqueous phase was extracted with ethyl acetate (5 mL×3). The organic phases were combined, washed with saturated saline (10 mL), dried over anhydrous sodium sulfate, filtered, and the filtrate was concentrated under reduced pressure. The crude product was purified by silica gel column chromatography (ethyl acetate:petroleum ether=80:20→100:0) to obtain compound Int-I.

MS (ESI) m/z (M+H)$^+$=371.1.

11) Preparation of Intermediate Int-J

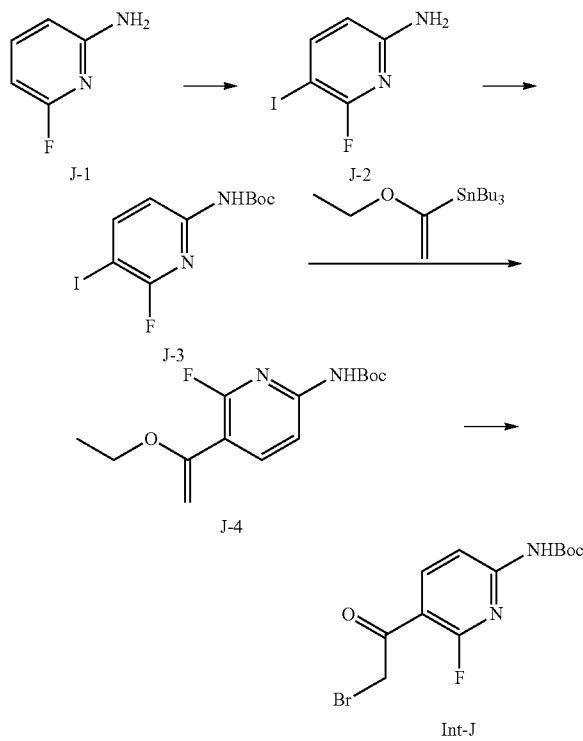

Step 1. Synthesis of Compound J-2

At 0° C., compound J-1 (20.4 g, 182 mmol) was dissolved in N, N-dimethylformamide (160 mL), N-iodosuccinimide (45.0 g, 200 mmol) was added in batches, and the mixture was warmed to room temperature and stirred for 3 hours. The reaction was quenched by adding water (500 mL), extracted with a mixed solvent of petroleum ether and ethyl acetate (800 mL×3, v/v=1:1), the organic phases were combined, washed with saturated sodium carbonate aqueous solution (1500 mL) and saturated saline (1500 mL) sequentially, dried over anhydrous sodium sulfate, filtered, and the filtrate was concentrated to dryness under reduced pressure, the crude product was slurried by a mixed solvent of petroleum ether and ethyl acetate (petroleum ether:ethyl acetate=75:25), and then purified by silica gel column chromatography (petroleum ether:dichloromethane=50:50→0:100) to obtain compound J-2.

MS (ESI) m/z (M+H)$^+$=239.1.

Step 2. Synthesis of Compound J-3

Compound J-2 (22.2 g, 93.28 mmol) was dissolved in acetonitrile (444 mL), and di-tert-butyl dicarbonate (22.4 g, 102.61 mmol) and 4-dimethylaminopyridine (1.14 g, 9.33 mmol) were added sequentially, and the reaction was stirred for 4 hours. The solids were removed by filtration, the filtrate was concentrated under reduced pressure, the crude product was purified by silica gel column chromatography (petroleum ether:ethyl acetate=100:0→95:5) to obtain compound J-3.

MS (ESI) m/z (M−56+H)$^+$=282.9.

Step 3. Synthesis of Compound J-4

Under the protection of argon, compound J-3 (15.2 g, 44.95 mmol), tributyl(1-ethoxyvinyl)tin (18.9 g, 52.33 mmol), and tetrakis(triphenylphosphine)palladium (1.22 g, 1.06 mmol) were dissolved in N, N-dimethylformamide (75 mL). The mixture was heated to 120° C., stirred and the reaction was carried out for 16 hours. The reaction mixture was quenched by adding ethyl acetate (300 mL) and 1.0 M potassium fluoride aqueous solution (600 mL), the mixture was stirred for 30 min, and the solid was filtered off. The filtrate was extracted with ethyl acetate (200 mL×2), the organic phases were combined, dried over anhydrous sodium sulfate. The mixture was filtered, the filtrate was concentrated to dryness under reduced pressure, the crude product was purified by silica gel column chromatography (petroleum ether:ethyl acetate=100:0→95:5) to obtain compound J-4.

MS (ESI) m/z (M−56+H)$^+$=227.2.

Step 4. Synthesis of Compound Int-J

At 0° C., compound J-4 (5.0 g, 17.7 mmol) was dissolved in a mixed solvent of tetrahydrofuran (60 mL) and water (20 mL), and N-bromosuccinimide (3.14 g, 17.7 mmol) was added in batches. After the addition was completed, the reaction was stirred for 30 min at this temperature. Ethyl acetate (100 mL×3) was added for extraction, and the organic phases were combined. The organic phase was washed with saturated sodium bicarbonate aqueous solution (100 mL×3), dried over anhydrous sodium sulfate, filtered, the filtrate was concentrated to dryness under reduced pressure, and the crude product was purified by silica gel column chromatography (petroleum ether:ethyl acetate=100:0→80:20) to obtain compound Int-J.

MS (ESI) m/z (M−56+H)$^+$=276.9.

12) Preparation of Intermediate Int-K

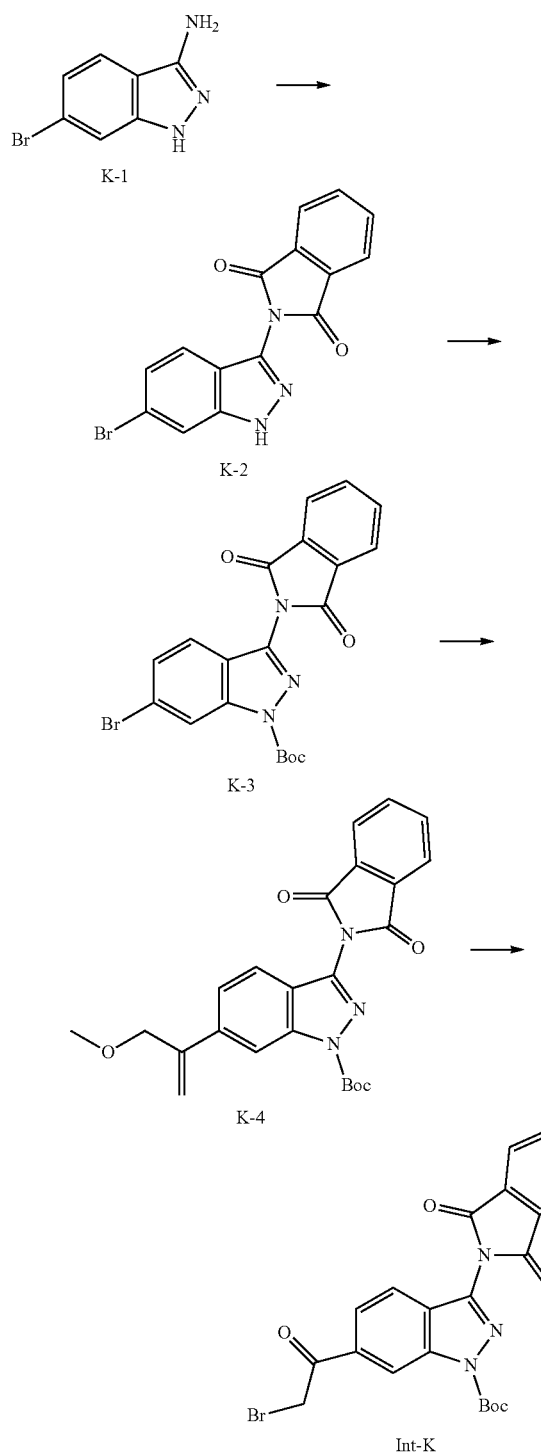

Step 1. Synthesis of Compound K-2

A mixture of compound K-1 (2 g, 9.43 mmol) and phthalic anhydride (1.40 g, 9.43 mmol) was heated to 170° C., and the mixture was stirred for 3 hours for reaction. The reaction system was cooled to room temperature, and a mixed solution of methanol/dichloromethane (1:1, 50 mL) was used for slurrying to obtain compound K-2, which was directly used for the next step without further purification.

MS (ESI) m/z (M+H)$^+$=289.0.

Step 2. Synthesis of Compound K-3

Under the protection of nitrogen, compound K-2 (2.46 g, 7.19 mmol) was dissolved in dichloromethane (50 mL), and 4-dimethylaminopyridine (264 mg, 2.16 mmol) and di-tert-butyl dicarbonate (1.88 g, 8.63 mmol, 1.98 mL) were added sequentially, and the reaction was stirred at room temperature for 16 hours. The reaction mixture was diluted with ethyl acetate (800 mL), washed with saturated saline (200 mL×3), dried over anhydrous sodium sulfate, filtered, and the filtrate was concentrated under reduced pressure, the crude product was purified by silica gel column chromatography (petroleum ether:ethyl acetate=100:0→50:50) to obtain compound K-3.

MS (ESI) m/z (M+H)$^+$=387.7.

$^1$HNMR (400 MHz, CDCl$_3$) δ 8.50 (s, 1H), 8.03 (dd, J=4.8, 3.2 Hz, 2H), 7.87 (dd, J=6.0, 3.2 Hz, 2H), 7.53-7.37 (m, 2H), 1.74 (s, 9H).

Step 3-4. Synthesis of Compound Int-K

According to the synthesis method of J-3→Int-J described in the preparation of intermediate Int-J, compound K-3 was treated to obtain compound Int-K.

MS (ESI) m/z (M+H)$^+$=429.8.

$^1$H NMR (400 MHz, CDCl$_3$) δ 8.92 (s, 1H), 8.04 (dd, J=6.0, 3.2 Hz, 2H), 7.98 (dd, J=8.0, 1.2 Hz, 1H), 7.88 (dd, J=6.0, 3.2 Hz, 2H), 7.72 (d, J=8.0 Hz, 1H), 4.58 (s, 2H), 1.77 (s, 9H).

13) Preparation of Intermediate Int-L

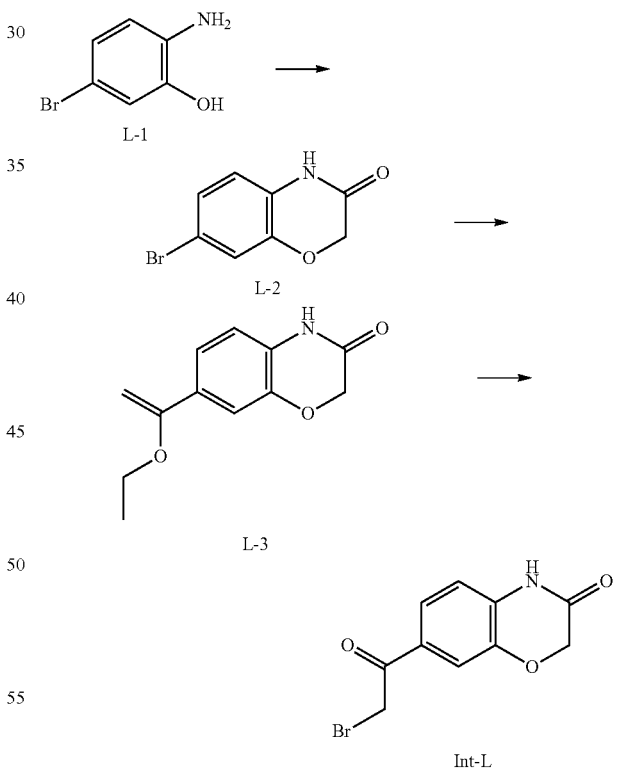

Step 1. Synthesis of Compound L-2

2-Amino-5-bromophenol (12 g, 63.82 mmol) was dissolved in acetonitrile (500 mL), chloroacetyl chloride (5.58 mL, 70.20 mmol) and cesium carbonate (62.38 g, 191.46 mmol) were slowly added sequentially, and the reaction was stirred at room temperature for 16 hours. The reaction mixture was concentrated under reduced pressure, the residue was diluted with water (800 mL) and extracted with ethyl acetate (500 mL×2). The organic phases were combined, washed with saturated saline (300 mL), dried over anhydrous sodium sulfate, and filtered. The filtrate was concentrated to obtain crude product L-2, which was directly used in the next step without further purification.

MS (ESI) m/z (M+H+41)⁺=269.1.

Step 2-3. Synthesis of Compound Int-L

According to the synthesis method of J-3→Int-J described in the preparation of intermediate Int-J, compound L-2 was treated to obtain compound Int-L.

$^1$H NMR (400 MHz, DMSO-$d_6$) δ 11.11 (s, 1H), 7.65 (dd, J=8.3, 1.7 Hz, 1H), 7.55 (d, J=1.4 Hz, 1H), 7.00 (d, J=8.2 Hz, 1H), 4.83 (s, 2H), 4.67 (s, 2H).

14) Preparation of Intermediate Int-M

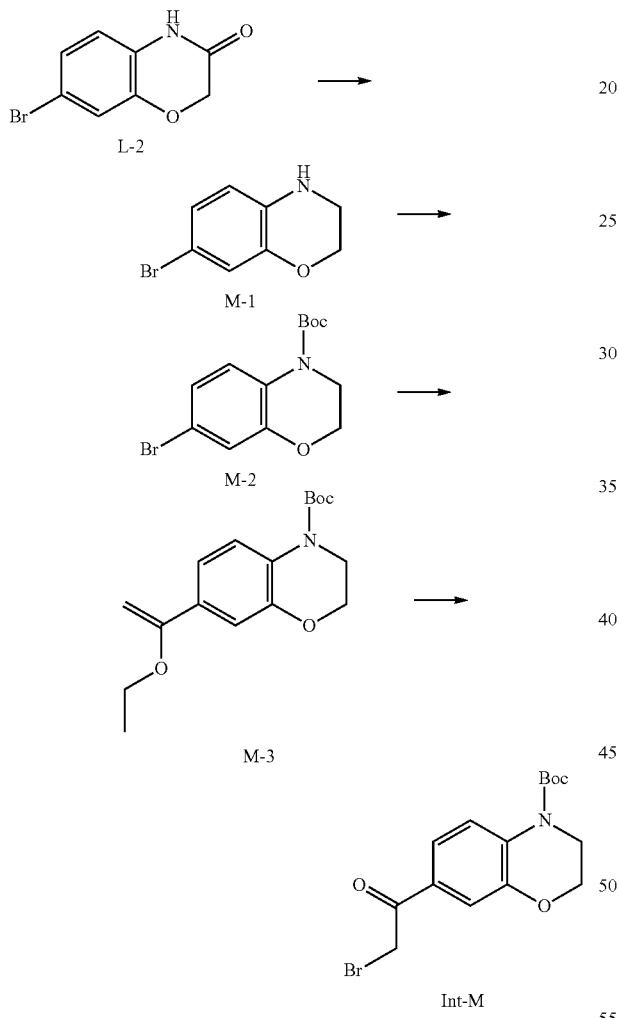

Step 1. Synthesis of Compound M-1

Compound L-1 (6.00 g, 26.31 mmol) was dissolved in tetrahydrofuran (30.0 mL), and a solution of boric acid in tetrahydrofuran (78.93 mL, 78.93 mmol, 1.0 M tetrahydrofuran solution) was slowly added dropwise, and the reaction was heated to 70° C. and stirred for 1 hour. The reaction mixture was slowly poured into ice water (200 mL) and extracted with ethyl acetate (500 mL×2). The organic phases were combined, washed with saturated saline (300 mL), dried over anhydrous sodium sulfate, and filtered. The filtrate mixture was concentrated under reduced pressure, the crude product was purified by silica gel column chromatography (petroleum ether:ethyl acetate=90:10→80:20) to obtain compound M-1.

MS (ESI) m/z (M+H)⁺=214.1.

Step 2. Synthesis of Compound M-2

Compound M-1 (3.00 g, 14.01 mmol) was dissolved in dichloromethane (30.0 mL), and di-tert-butyl dicarbonate (6.12 g, 28.03 mmol), triethylamine (4.25 g, 42.04 mmol) and 4-dimethylaminopyridine (1.71 g, 14.01 mmol) were added sequentially, and the reaction was stirred at room temperature for 16 hours. The reaction mixture was diluted with water (100 mL) and extracted with dichloromethane (150 mL×2). The organic phases were combined, washed with saturated saline (100 mL), dried over anhydrous sodium sulfate, and filtered. The filtrate mixture was concentrated under reduced pressure, the crude product was purified by silica gel column chromatography (petroleum ether:ethyl acetate=90:10) to obtain compound M-2.

$^1$H NMR (400 MHz, CD$_3$OD) δ 7.68 (d, J=8.2 Hz, 1H), 7.01-6.93 (m, 2H), 4.20 (t, J=4.0 Hz, 2H), 3.81 (t, J=4.0 Hz, 2H), 1.52 (s, 9H).

Step 3-4. Synthesis of Compound Int-M

According to the synthesis method of J-3→Int-J described in the preparation of intermediate Int-J, compound M-2 was treated to obtain compound Int-M.

MS (ESI) m/z (M+H)⁺=356.0, 358.0.

$^1$H NMR (400 MHz, CDCl$_3$) δ 8.02 (d, J=8.0, 1H), 7.53-7.51 (m, 2H), 4.39 (s, 2H), 4.27 (t, J=4.0, 2H), 3.90 (t, J=4.0, 2H), 1.56 (s, 9H).

15) Preparation of Intermediate Int-N

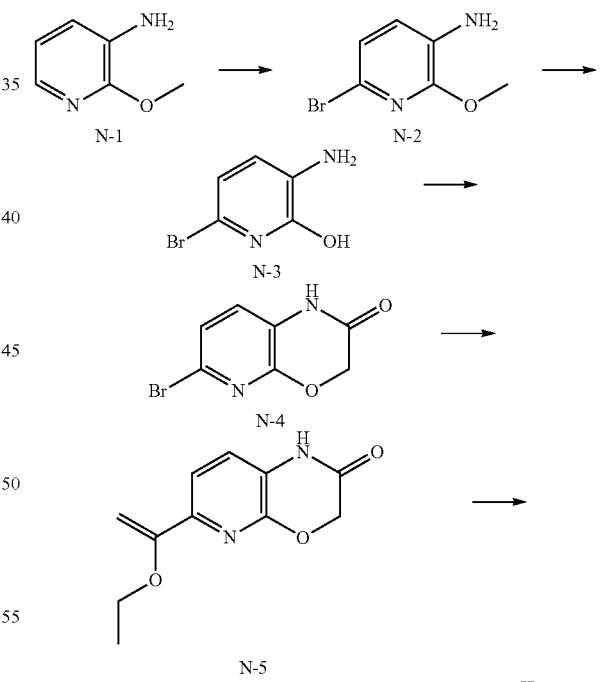

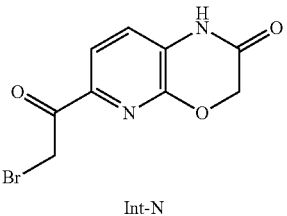

Step 1. Synthesis of Compound N-2

At 0° C., under the protection of argon, compound N-1 (19.0 g, 153 mmol) was dissolved in N, N-dimethylformamide (200 mL). N-bromosuccinimide (30.4 g, 171 mmol) was added. The reaction was stirred at this temperature for 1 hour. The reaction mixture was quenched by adding saturated ammonium chloride aqueous solution (10 mL), diluted with water (200 mL), and extracted with ethyl acetate (200 mL×2). The organic phases were combined, the solvent was removed by concentration under reduced pressure, and the crude product was purified by silica gel column chromatography (petroleum ether:ethyl acetate=80:20) to obtain compound N-2.

MS (ESI) m/z (M+H+CH$_3$CN)$^+$=244.1.

Step 2. Synthesis of Compound N-3

Under the protection of argon, compound N-2 (20.0 g, 98.5 mmol) was dissolved in a mixed solvent (200 mL, 1/1) of acetic acid and hydrobromic acid (40%, w/w). The reaction was heated to 120° C. and stirred for 1 hour. The reaction mixture was cooled to room temperature, concentrated under reduced pressure, and the residue was diluted with water (50 mL), and the pH was adjusted to 12.0 with sodium hydroxide aqueous solution (30% w/w). The obtained aqueous phase was extracted with ethyl acetate (200 mL×2) and dichloromethane/methanol (10/1, 200 mL×2). The organic phases were combined, concentrated under reduced pressure to obtain crude product N-3, which was directly used in the next step without further purification.

MS (ESI) m/z (M+H)$^+$=188.9, 190.9.

Step 3. Synthesis of Compound N-4

Compound N-3 (15.2 g, 80.4 mmol) was dissolved in acetonitrile (200 mL), and cesium carbonate (78.5 g, 241 mmol) and chloroacetyl chloride (9.98 g, 88.4 mmol) were added sequentially, and the reaction mixture was stirred at 25° C. for 16 hours. The reaction mixture was quenched by adding saturated saline (500 mL), extracted with dichloromethane (200 mL×2), the organic phases were combined, and concentrated under reduced pressure, and the crude product was purified by silica gel column chromatography (petroleum ether:ethyl acetate=70:30) to obtain compound N-4.

MS (ESI) m/z (M+H)$^+$=228.9, 230.9.

Step 4-5. Synthesis of Compound Int-N

According to the synthesis method of J-3→Int-J described in the preparation of intermediate Int-J, compound N-4 was treated to obtain compound Int-N.

MS (ESI) m/z (M+H)$^+$=270.9, 272.9.

$^1$H NMR (400 MHz, DMSO-d$_6$) δ 11.26 (s, 1H), 7.66 (d, J=8.0 Hz, 1H), 7.37 (d, J=7.6 Hz, 1H), 4.88 (s, 2H), 4.79 (s, 2H).

16) Preparation of Intermediate Int-0

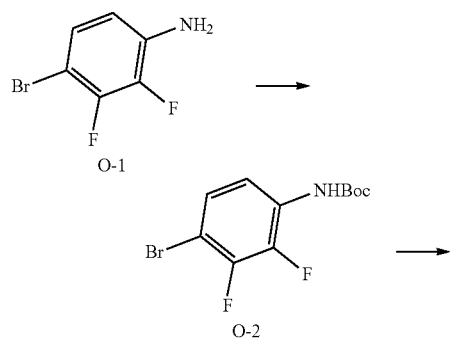

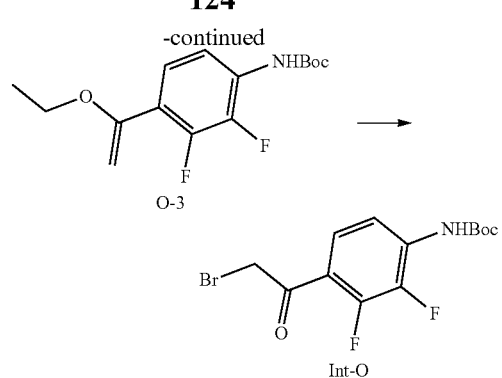

Step 1. Synthesis of Compound O-2

At 0° C., compound O-1 (1.5 g, 7.21 mmol) was dissolved in tetrahydrofuran (30 mL), LiHMDS (14.42 mL, 1.0 M in tetrahydrofuran solution) was added and the reaction was warmed to 20° C., a solution of di-tert-butyl dicarbonate (1.89 g, 8.65 mmol) in tetrahydrofuran (15 mL) was added, and the reaction was stirred at this temperature for 15 min. The reaction mixture was cooled to 0° C., quenched by adding water (20 mL), extracted with ethyl acetate (100 mL), the organic phase was washed with saturated saline (30 mL×2), dried over anhydrous sodium sulfate, filtered, the filtrate was concentrated under reduced pressure, and the crude product was purified by silica gel column chromatography (petroleum ether:ethyl acetate=100:0→70:30) to obtain compound O-2.

$^1$H NMR (400 MHz, CDCl$_3$) δ 7.77-7.73 (m, 1H), 7.20-7.16 (m, 1H), 6.62 (br s, 1H), 1.45 (s, 9H),

Step 2-3. Synthesis of Compound Int-0

According to the synthesis method of J-3→Int-J described in the preparation of intermediate Int-J, compound O-2 was treated to obtain compound Int-0.

MS (ESI) m/z (M+H)$^+$=352.0, 354.0.

$^1$H NMR (400 MHz, CDCl$_3$) δ 8.09-8.07 (m, 1H), 7.75-7.71 (m, 1H), 6.94 (s, 1H), 1.57-1.55 (m, 9H).

17) Preparation of Intermediate Int-P

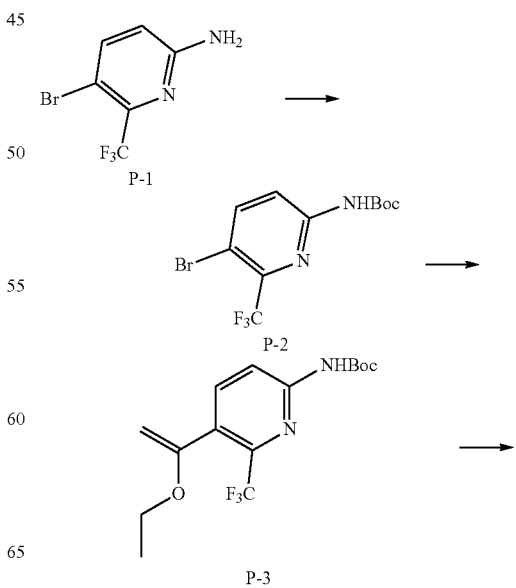

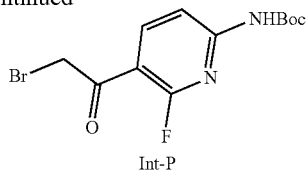

According to the synthesis method of O-1→Int-0 described in the preparation of intermediate Int-0, compound P-1 was treated to obtain compound Int-P.

MS (ESI) m/z (M+H)=382.7, 384.7.

¹H NMR (400 MHz, CDCl₃) δ 8.23 (d, J=8.8 Hz, 1H), 7.86 (d, J=8.8 Hz, 1H), 7.55 (br s, 1H), 4.32 (s, 2H), 1.54 (s, 9H).

18) Preparation of Intermediate Int-Q

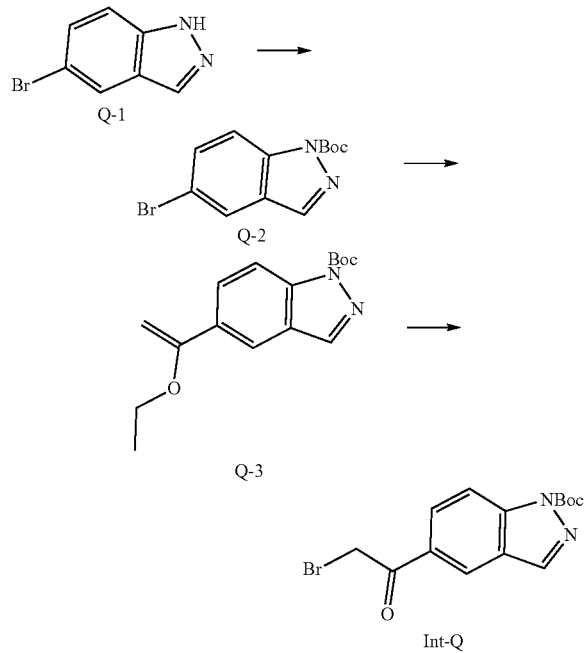

According to the synthesis method of O-1→Int-0 described in the preparation of intermediate Int-0, compound Q-1 was treated to obtain compound Int-Q.

MS (ESI) m/z (M+H-100)⁺=284.8.

¹H NMR (400 MHz, DMSO-d₆) δ 8.65-8.56 (m, 2H), 8.27-8.14 (m, 2H), 5.01 (s, 2H), 1.66 (s, 9H).

19) Preparation of Intermediate Int-R

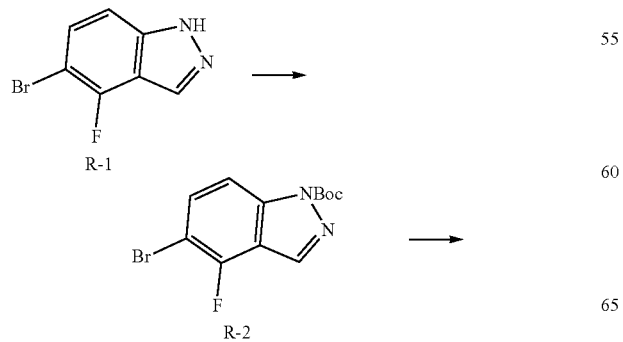

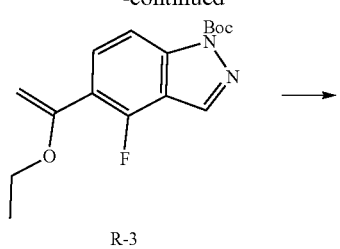

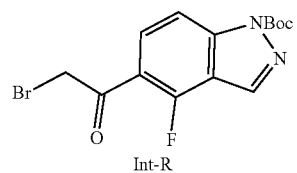

According to the synthesis method of O-1→Int-0 described in the preparation of intermediate Int-0, compound R-1 was treated to obtain compound Int-R.

MS (ESI) m/z (M+H-100)⁺=300.8.

¹H NMR (400 MHz, DMSO-d₆) δ 8.72 (d, J=16.0 Hz, 1H), 8.18-7.92 (m, 2H), 4.91 (d, J=2.3 Hz, 2H), 1.66 (d, J=1.2 Hz, 9H).

20) Preparation of Intermediate Int-S

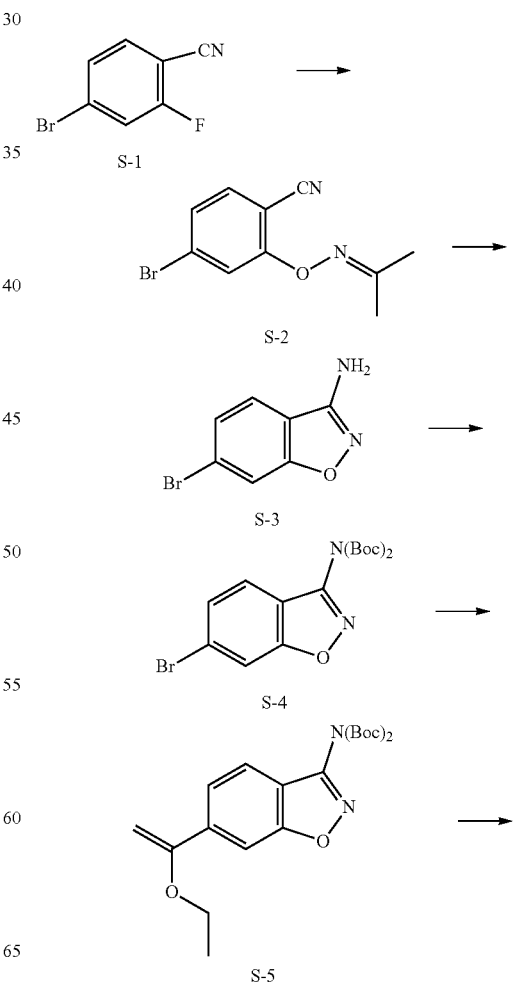

-continued

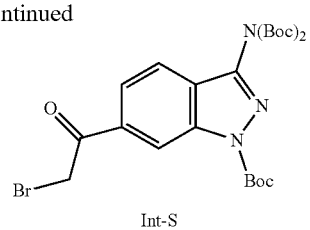

Int-S

Step 1. Synthesis of Compound S-2

Acetone oxime (6 g, 30.0 mmol) was dissolved in N,N-dimethylformamide (60 mL), potassium tert-butoxide (3.7 g, 33.0 mmol) was added, and the mixture was stirred for 30 min at room temperature, S-1 (2.4 g, 33.0 mmol) was added, and the reaction was continued to stir at room temperature for 1 hour. The reaction mixture was quenched by adding saturated ammonium chloride solution (100 mL), diluted by adding methyl tert-butyl ether (100 mL) and water (50 mL), the phases were separated, the aqueous phase was extracted by methyl tert-butyl ether (50 mL×2), the organic phases were combined, washed with saturated saline (50 mL), dried over anhydrous sodium sulfate, filtered, and the filtrate was concentrated to obtain crude product S-2, which was directly used for the next step without further purification.

MS (ESI) m/z $(M+H)^+=255.0$.

Step 2. Synthesis of Compound S-3

Compound S-2 (8 g, 31.61 mmol) was dissolved in ethanol (100 mL), concentrated hydrochloric acid (20 mL) was added, the reaction was heated to 110° C. and stirred for 5 hours. The reaction mixture was concentrated under reduced pressure. The crude product was purified by silica gel column chromatography (ethyl acetate:petroleum ether=0:100→90:10) to obtain compound S-3.

MS (ESI) m/z $(M+H)^+=213.0$.

Step 3. Synthesis of Compound S-4

Compound S-3 (2 g, 9.4 mmol) was dissolved in dichloromethane (30 mL), and di-tert-butyl dicarbonate (2.4 g, 11.3 mmol) and triethylamine (2.8 g, 28.2 mmol) were added sequentially, and the reaction was stirred at room temperature for 6 hours. The reaction mixture was concentrated under reduced pressure, the crude product was purified by silica gel column chromatography (ethyl acetate: petroleum ether=0:100→10:90) to obtain compound S-4.

Step 4-5. Synthesis of Compound Int-S

According to the synthesis method of J-3→Int-J described in the preparation of intermediate Int-J, compound S-4 was treated to obtain compound Int-S.

MS (ESI) m/z $(M+H)^+=301.0$.

21) Preparation of Intermediate Int-T

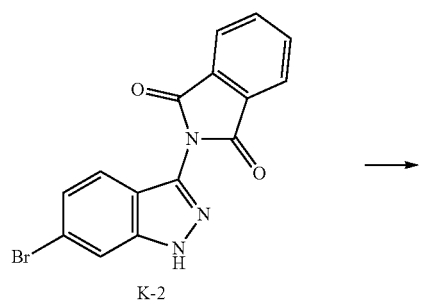

K-2

-continued

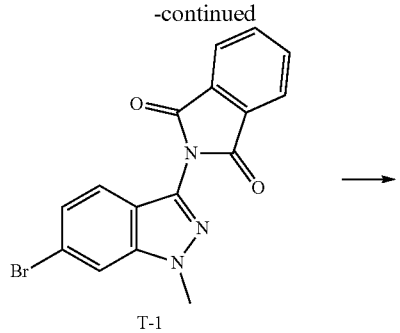

T-1

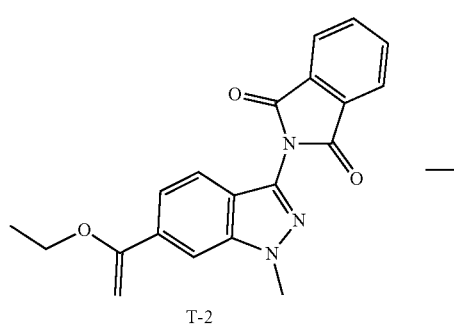

T-2

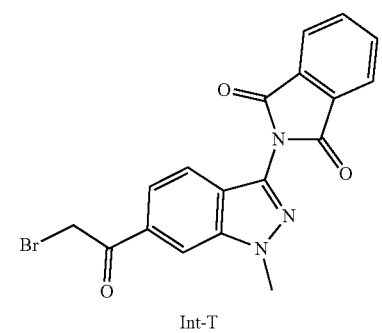

Int-T

Step 1. Synthesis of Compound T-1

Compound K-2 (1 g, 2.92 mmol) was dissolved in N,N-dimethylformamide (10 mL), and potassium carbonate (808 mg, 5.85 mmol) and iodomethane (498 mg, 3.51 mmol) were added sequentially, and the reaction was stirred at 20° C. for 4 hours. The reaction mixture was quenched by pouring into water (150 mL), the mixture was filtered, and the filter cake was dried under vacuum to obtain crude product T-1, which was directly used in the next step without further purification.

MS (ESI) m/z $(M+H)^+=357.7$.

$^1$H NMR (400 MHz, DMSO-$d_6$) δ 8.13 (s, 1H), 8.04-8.02 (m, 2H), 7.97-7.95 (m, 2H), 7.72-7.70 (m, 1H), 7.34-7.32 (m, 1H), 4.11 (s, 3H).

Step 2-3. Synthesis of Compound Int-T

According to the synthesis method of J-3→Int-J described in the preparation of intermediate Int-J, compound T-1 was treated to obtain compound Int-T.

MS (ESI) m/z $(M+H)^+=397.9$.

$^1$H NMR (400 MHz, DMSO-$d_6$) δ 8.50 (s, 1H), 8.02-7.95 (m, 2H), 7.94-7.87 (m, 2H), 7.82 (br d, J=8.8 Hz, 1H), 7.69 (br d, J=8.6 Hz, 1H), 5.03 (s, 2H), 4.24 (s, 3H).

22) Preparation of Intermediate Int-U

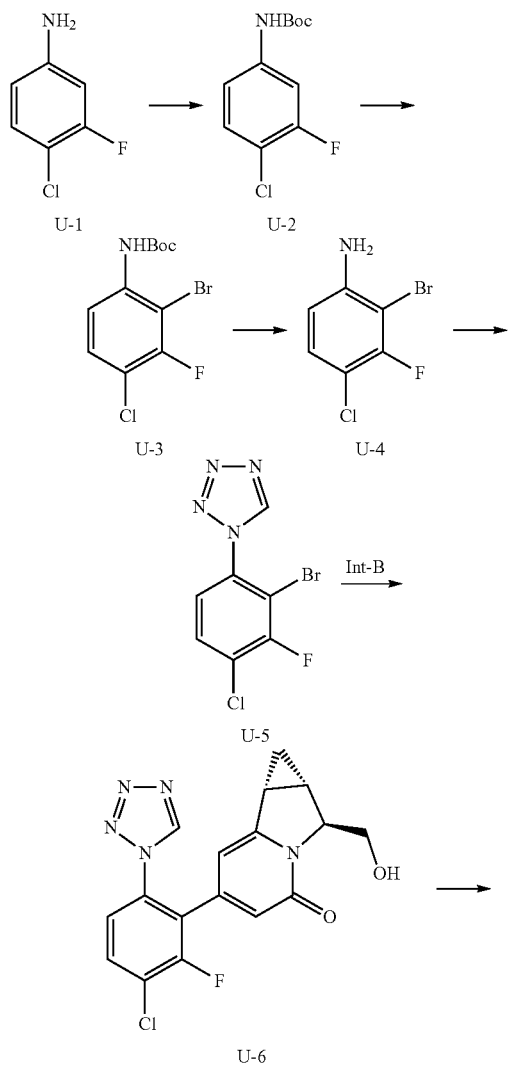

Step 1. Synthesis of Compound U-2

Compound U-1 (10.2 g, 70.1 mmol) was dissolved in water (100 mL), and di-tert-butyl dicarbonate (16.8 g, 77.1 mmol) was added, and the reaction was stirred at 25° C. for 18 hours. The reaction mixture was filtered and the filter cake was dried under vacuum to obtain crude product U-2.

$^1$H NMR (400 MHz, CDCl$_3$) δ 7.43 (d, J=6.6 Hz, 1H), 7.26 (d, J=8.4 Hz, 1H), 6.94 (d, J=6.2 Hz, 1H), 6.51 (br, 1H), 1.53 (s, 9H).

Step 2. Synthesis of Compound U-3

At −78° C., compound U-2 (1.00 g, 4.07 mmol) was dissolved in tetrahydrofuran (30 mL), isobutyllithium (10.18 mL, 10.18 mmol) was added dropwise, and the reaction was stirred at this temperature for 2 hours, 1,2-dibromoethane (1.30 g, 6.92 mmol) was added dropwise, and the reaction was slowly warmed to 25° C. and stirred for 16 hours. The reaction mixture was quenched by adding water (30 mL), extracted with ethyl acetate (20 mL×3), the organic phases were combined, dried over anhydrous sodium sulfate, filtered, and the filtrate was concentrated under reduced pressure, and the crude product was purified by reverse phase C18 column chromatography (acetonitrile: 0.1% aqueous trifluoroacetic acid=5:95→95:5) to obtain compound U-3.

$^1$H NMR (400 MHz, CD$_3$OD) δ 7.63 (dd, J=9.0, 1.8 Hz, 1H), 7.41 (m, 1H), 1.51 (s, 9H).

Step 3. Synthesis of Compound U-4

Compound U-3 (800 mg, 2.46 mmol) was dissolved in dichloromethane (10.0 mL), and trifluoroacetic acid (3.0 mL) was added, and the reaction was stirred at 25° C. for 2 hours. The reaction mixture was concentrated under reduced pressure to remove the organic solvent to obtain crude product U-4, which was directly used in the next step without further purification.

MS (ESI) m/z (M+H)$^+$=224.1.

Step 4. Synthesis of Compound U-5

Compound U-4 (500 mg, 2.23 mmol) was dissolved in acetic acid (10.0 mL), triethyl orthoformate (1.32 g, 8.91 mmol) and sodium azide (579.27 mg, 8.91 mmol) were added sequentially, and the reaction was stirred at 25° C. for 2 hours. The reaction mixture was directly purified by reverse phase C18 column chromatography (acetonitrile: 0.1% trifluoroacetic acid aqueous solution=5:95→95:5) to obtain compound U-5.

MS (ESI) m/z: (M+H)$^+$=277.1.

Step 5-6. Synthesis of Compound Int-U

According to the synthesis method of Int-B→Int-C described in the preparation of intermediate Int-C (method 2), compound Int-B and U-5 were treated to obtain compound Int-U.

MS (ESI) m/z (M+H)$^+$=388.1.

23) Preparation of Intermediate Int-V

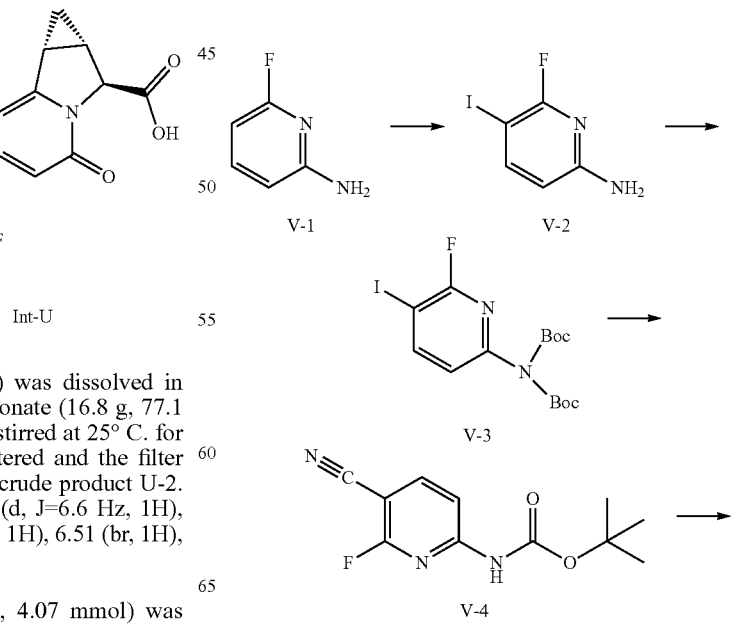

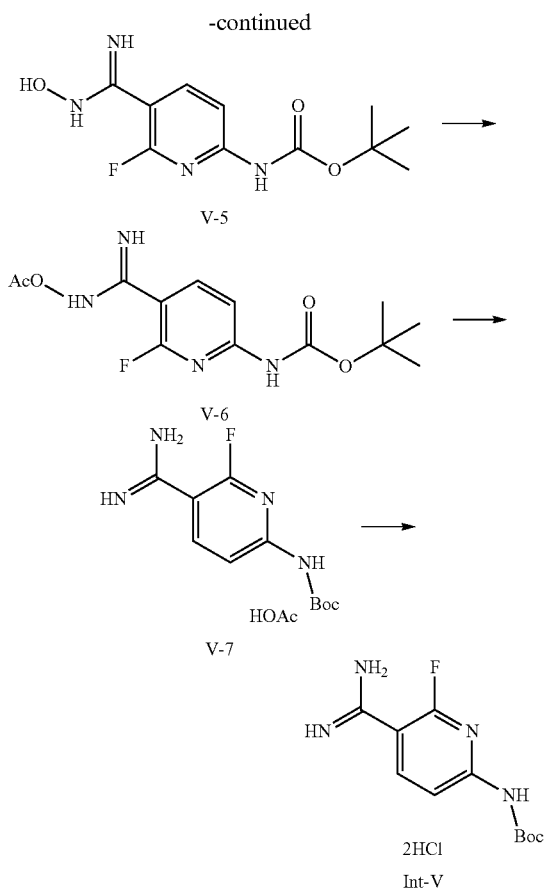

Step 1. Synthesis of Compound V-2

At 0° C., compound V-1 (469.8 g, 4.19 mol) was dissolved in N, N-dimethylformamide (3.760 L), iodosuccinimide (1037 g, 4.61 mol) was added in batches, and the mixture was warmed to room temperature and stirred for 18 hours. The reaction system was quenched by adding water (12 L), extracted with ethyl acetate (4.0 L×3), the organic phases were combined, washed with saturated saline (3.0 L×2), dried over anhydrous sodium sulfate, filtered, and the filtrate was concentrated under reduced pressure to obtain crude product V-2, which was directly used for the next step without further purification.

$^1$H NMR (400 MHz, CDCl$_3$) δ 7.74 (t, J=8.4 Hz, 1H), 6.18 (dd, J=8.2, 1.8 Hz, 1H), 4.57 (s, 2H).

Step 2. Synthesis of Compound V-3

Compound V-2 (540.0 g, 2.27 mol) was dissolved in acetonitrile (5.67 L), and di-tert-butyl dicarbonate (1090.2 g, 4.99 mol) and dimethylaminopyridine (13.87 g, 0.11 mol) were added sequentially, and the reaction was stirred at room temperature for 3 hours. The reaction system was concentrated under reduced pressure to remove the solvent, the crude product was purified by silica gel column chromatography (ethyl acetate:petroleum ether=0:100→90:10) to obtain compound V-3.

$^1$H NMR (400 MHz, CDCl$_3$) δ 8.14 (t, J=8.2 Hz, 1H), 7.02 (d, J=7.9 Hz, 1H), 1.47 (s, 18H).

Step 3. Synthesis of Compound V-4

Under the protection of nitrogen, compound V-3 (669.6 g, 1.53 mol) was dissolved in N-methylpyrrolidone (4.70 L), and zinc cyanide (269.1 g, 2.29 mol) and tetrakis(triphenylphosphine)palladium (176.6 g, 152.8 mmol) were added sequentially, and the reaction was stirred at 105° C. for 6 hours. The reaction system was cooled to room temperature, quenched by adding water (10 L), extracted with ethyl acetate (5.0 L×3), the organic phases were combined, washed with saturated saline (10.0 L×2), dried over anhydrous sodium sulfate, filtered, the filtrate was concentrated under reduced pressure, and the crude product was purified by silica gel column chromatography (ethyl acetate:petroleum ether=0:100→90 10) to obtain compound V-4.

$^1$H NMR (400 MHz, CDCl$_3$) δ 8.02-7.90 (m, 2H), 7.40 (s, 1H), 1.53 (s, 9H).

Step 4. Synthesis of Compound V-5

Compound V-4 (234.8 g, 0.99 mol) was dissolved in ethanol (1.78 L), and hydroxylamine hydrochloride (137.7 g, 1.98 mol) and diisopropylethylamine (307.3 g, 2.38 mol) were added sequentially, and the reaction was heated to 60° C. and stirred for 1 hour. The reaction system was concentrated under reduced pressure to remove the solvent, and the crude product was purified by slurrying with water (1.8 L) and ethanol (0.9 L) to obtain V-5, which was directly used in the next step without further purification.

$^1$H NMR (400 MHz, DMSO) δ 10.15 (s, 1H), 9.66 (s, 1H), 7.94 (t, J=9.0 Hz, 1H), 7.69 (d, J=8.0 Hz, 1H), 5.81 (s, 2H), 1.46 (s, 9H).

Step 5. Synthesis of Compound V-6

Compound V-5 (182.0 g, 674.6 mmol) was dissolved in acetic acid (192.0 mL), acetic anhydride (960.0 mL) was added, and the reaction was stirred at room temperature for 30 min. The reaction system was concentrated under reduced pressure to remove the solvent, and the crude product was purified by slurrying with n-heptane (0.3 L) to obtain V-6.

$^1$H NMR (400 MHz, DMSO-d$_6$) δ 10.30 (s, 1H), 7.97 (dd, J=9.5, 8.4 Hz, 1H), 7.75 (dd, J=8.3, 1.5 Hz, 1H), 6.91 (s, 2H), 2.10 (s, 3H), 1.47 (s, 9H).

Step 6. Synthesis of Compound V-7

Compound V-6 (200.0 g, 0.64 mol) was dissolved in acetic acid (1.00 L), and palladium hydroxide/carbon (40 g, 20%) was added, and the reaction was stirred for 18 hours under hydrogen atmosphere. The reaction system was filtered to remove the catalyst, the filtrate was concentrated to obtain crude product V-7, which was directly used in the next step without further purification.

$^1$H NMR (400 MHz, CD$_3$OD) δ 8.13 (t, J=9.0 Hz, 1H), 7.98 (dd, J=8.5, 1.4 Hz, 1H), 1.53 (s, 9H).

Step 7. Synthesis of Compound Int-V

Compound V-7 (396.0 g, 1.26 mol) was dissolved in a solution of hydrogen chloride in methanol (660.0 mL, 4.0 M), and the reaction was stirred at room temperature for 30 min. The reaction system was filtered, and the solid was dried under vacuum to obtain Int-V.

$^1$H NMR (400 MHz, DMSO-d$_6$) δ 10.62 (s, 1H), 9.42 (s, 1H), 9.34 (s, 1H) (d, J=36.6 Hz, 4H), 8.24-8.11 (m, 1H), 7.83 (dd, J=8.5, 1.2 Hz, 1H), 1.48 (s, 9H).

24) Preparation of Intermediate Int-W

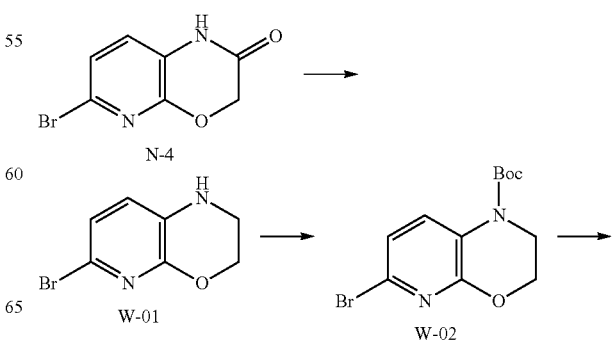

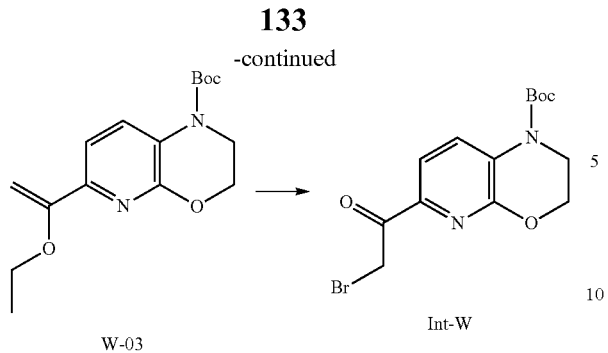

According to the synthesis method of L-2→Int-M described in the preparation of intermediate Int-M, compound N-4 was treated to obtain compound Int-W.

MS (ESI) m/z (M+H)$^+$=357.0, 359.0.

$^1$H NMR (400 MHz, CDCl$_3$) δ 8.47 (d, J=7.2 Hz, 1H), 7.78 (d, J=7.2 Hz, 1H), 4.76 (s, 2H), 4.44 (t, J=3.6 Hz, 2H), 3.95 (t, J=3.6 Hz, 2H), 1.57 (s, 9H).

25) Preparation of Intermediate Int-X

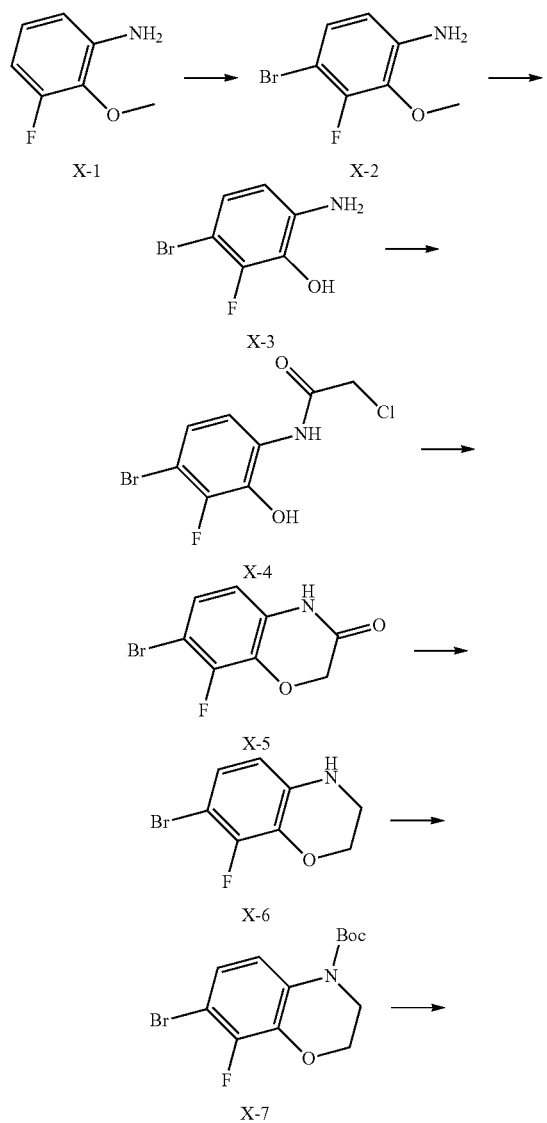

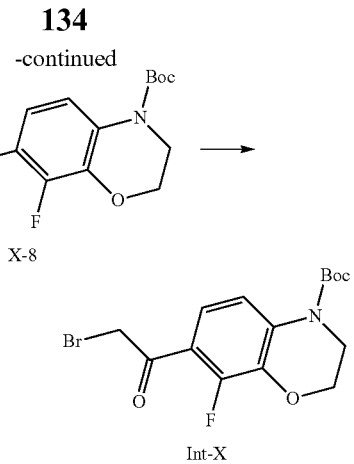

Step 1. Synthesis of Compound X-2

Compound X-1 (2.82 g, 20.0 mmol) was dissolved in acetic acid (10 mL), and a solution of liquid bromine (0.82 mL, 16.0 mmol) in acetic acid (10 mL) was slowly added dropwise, and the mixture was stirred at room temperature for 1 hour. The system was filtered, the pH of the filter cake was adjusted to 12 with 3.0 M sodium hydroxide aqueous solution, the mixture was extracted with ethyl acetate (40 mL×2), the organic phases were combined, washed with water (40 mL) and saturated saline (40 mL) sequentially, dried over anhydrous sodium sulfate, filtered, the filtrate was concentrated under reduced pressure, and the crude product was purified by silica gel column chromatography (ethyl acetate:petroleum ether=0:100→30:70) to obtain compound X-2.

MS(ESI) m/z (M+H)$^+$=220.0, 222.0.

$^1$H NMR (400 MHz, DMSO-d$_6$) δ 7.02 (dd, J=8.8, 7.4 Hz, 1H), 6.47 (dd, J=8.8, 1.7 Hz, 1H), 5.41 (s, 2H), 3.74 (d, J=0.9 Hz, 3H).

Step 2. Synthesis of Compound X-3

Under the protection of nitrogen, compound X-2 (2.2 g, 10.0 mmol) was dissolved in hydrobromic acid (40 mL, 44% aqueous solution), and the reaction was heated to 100° C. and stirred for 16 hours. The system was concentrated under reduced pressure to remove the solvent to obtain crude product X-3, which was directly used in the next step without further purification.

MS(ESI) m/z (M+H)$^+$=206.0, 208.0

Step 3. Synthesis of Compound X-4

At 0° C., under the protection of nitrogen, compound X-3 (2.0 g, 10.0 mmol) and triethylamine (2.1 mL, 15.0 mmol) were dissolved in tetrahydrofuran (40 mL), and chloroacetyl chloride (0.87 mL, 11.0 mmol) was added dropwise, and the reaction was stirred at this temperature for 2 hours. The system was quenched by adding saturated sodium bicarbonate solution (40 mL), extracted with ethyl acetate (30 mL×2), the organic phases were combined, washed with saturated saline (40 mL), dried over anhydrous sodium sulfate, filtered, the filtrate was concentrated under reduced pressure, and the crude product was purified by silica gel column chromatography (ethyl acetate:petroleum ether=0: 100→50:10) to obtain compound X-4.

MS(ESI) m/z (M+H)$^+$=282.0, 284.0

Step 4. Synthesis of Compound X-5

Under the protection of nitrogen, compound X-4 (1.55 g, 5.45 mmol) was dissolved in N, N-dimethylformamide (20 mL), and potassium carbonate (904 mg, 6.54 mmol) was added, and the reaction was stirred at room temperature for 3 hours. Water (40 mL) and ethyl acetate (40 mL) were added into the system, the phases were separated, and the organic phase was washed with water (60 mL×2) and saturated saline (60 mL) sequentially, dried over anhydrous sodium sulfate, filtered, the filtrate was concentrated under reduced pressure, and the crude product was purified by silica gel column chromatography (ethyl acetate:petroleum ether=0:100→60:40) to obtain compound X-5.

MS(ESI) m/z (M+H)$^+$=246.0, 248.0

Step 5-8. Synthesis of Compound Int-X

According to the synthesis method of L-2→Int-M described in the preparation of intermediate Int-M, compound X-5 was treated to obtain compound Int-X.

MS(ESI) m/z (M+H)$^+$=374.2, 376.2

26) Preparation of Intermediate Int-Y

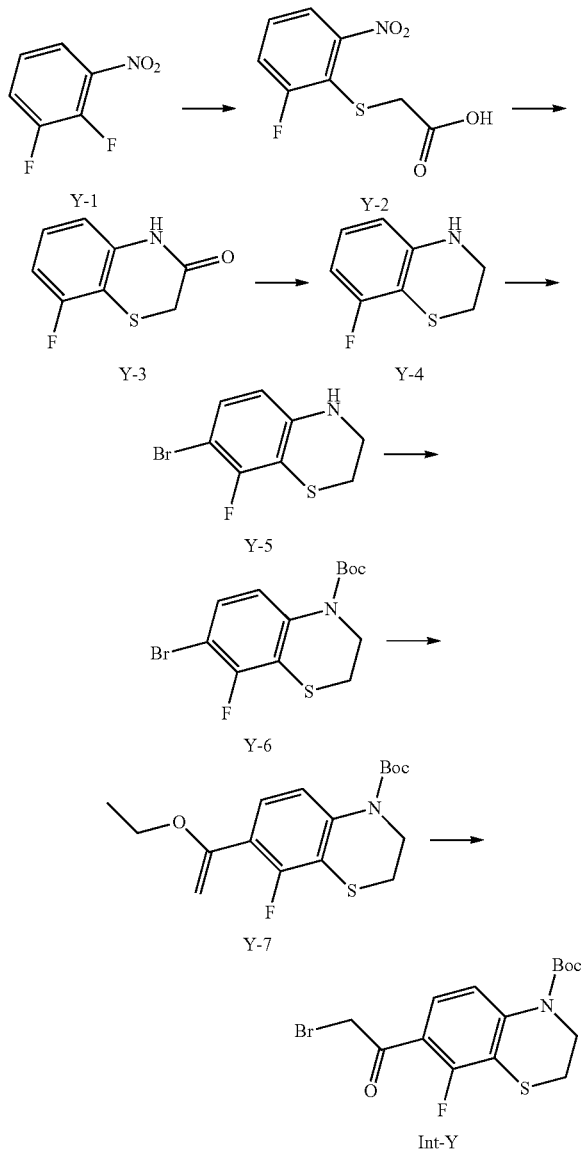

Step 1. Synthesis of Compound Y-2

Under the protection of nitrogen, compound Y-1 (2.50 g, 15.7 mmol) and triethylamine (22 mL, 157.1 mmol) were dissolved in acetonitrile (10 mL) and water (5 mL), then mercaptoacetic acid (1.41 mL, 20.4 mmol) was added dropwise, and the reaction was heated to 70° C. and stirred for 16 hours. Dichloromethane (30 mL) was added into the system for dilution, the mixture was washed with water (30 mL×3), the pH of the aqueous phase was adjusted to 4.0 with 2.0 M hydrochloric acid, extracted with dichloromethane (30 mL×2), the organic phases were combined, washed with saturated saline (30 mL), dried over anhydrous sodium sulfate, filtered, and the filtrate was concentrated under reduced pressure to obtain crude product Y-2, which was directly used in the next reaction without further purification.

MS(ESI) m/z (M+H)$^+$=254.0

$^1$H NMR (400 MHz, DMSO-d$_6$) δ 7.86-7.76 (m, 1H), 7.65-7.57 (m, 2H), 3.72-3.69 (m, 2H).

Step 2. Synthesis of Compound Y-3

Under the protection of nitrogen, compound Y-2 (3.16 g, 13.67 mmol) and potassium carbonate (17.4 g, 125.6 mmol) were dissolved in water (60 mL), then a solution of sodium hydrosulfite (16.4 g, 94.2 mmol) in water (40 mL) was slowly added dropwise, and the reaction was stirred at 30° C. for 16 hours. The pH of the system was adjusted to 3.0 by adding concentrated hydrochloric acid, the mixture was continued to stir for 1 hour, cooled to 0° C., and filtered to obtain crude product Y-3.

MS(ESI) m/z (M+H)$^+$=184.0

$^1$H NMR (400 MHz, DMSO-d$_6$) δ 10.80 (s, 1H), 7.21 (td, J=8.1, 6.1 Hz, 1H), 6.92 (t, J=8.8 Hz, 1H), 6.83 (d, J=8.1 Hz, 1H), 3.52 (s, 2H).

Step 3. Synthesis of Compound Y-4

At 0° C., under the protection of nitrogen, a solution of compound Y-3 (1.83 g, 10.0 mmol) in tetrahydrofuran (30 mL) was added dropwise to a suspension (10.0 mL, 10.0 mmol, 1.0 M) of lithium aluminum hydride in tetrahydrofuran, and the reaction was heated to 80° C. and stirred for 2 hours. The system was cooled to 0° C., quenched by adding ice water (0.4 mL), 15% sodium hydroxide aqueous solution (0.4 mL) and water (50 mL) sequentially, then the mixture was extracted with ethyl acetate (30 mL×2), the organic phases were combined, washed with saturated saline (30 mL), dried over anhydrous sodium sulfate, filtered, and the filtrate was concentrated under reduced pressure to obtain crude product Y-4.

MS(ESI) m/z (M+H)$^+$=170.0

$^1$H NMR (400 MHz, CDCl$_3$) δ 6.82 (td, J=8.1, 6.3 Hz, 1H), 6.40 (ddd, J=9.3, 8.1, 1.1 Hz, 1H), 6.26 (dt, J=8.2, 1.0 Hz, 1H), 4.19-4.04 (m, 1H), 3.65-3.61 (m, 2H), 3.06-3.02 (m, 2H).

Step 4. Synthesis of Compound Y-5

At 0° C., under the protection of nitrogen, compound Y-4 (1.62 g, 9.57 mmol) was dissolved in a solution of compound Y-4 (1.62 g, 9.57 mmol) in dichloromethane (40 mL), and N-bromosuccinimide (1.45 g, 8.14 mmol) was added, and the reaction was stirred at this temperature for 1 hour. The system was quenched by adding saturated sodium bicarbonate solution (20 mL) and saturated sodium thiosulfate solution (20 mL), the mixture was extracted with dichloromethane (30 mL), the organic phase was washed with saturated saline (30 mL), dried over anhydrous sodium sulfate, filtered, the filtrate was concentrated under reduced pressure, and the crude product was purified by silica gel column chromatography (ethyl acetate:petroleum ether=0:100→40:60) to obtain compound Y-5.

MS(ESI) m/z (M+H)$^+$=248.0, 250.0

$^1$H NMR (400 MHz, CDCl$_3$) δ 6.98 (dd, J=8.7, 7.5 Hz, 1H), 6.17 (dd, J=8.7, 1.4 Hz, 1H), 4.21-4.10 (m, 1H), 3.67-3.57 (m, 2H), 3.06-2.98 (m, 2H).

Step 5. Synthesis of Compound Y-6

Under the protection of nitrogen, compound Y-5 (1.03 g, 4.15 mmol) and 4-dimethylaminopyridine (25 mg, 0.21 mmol) were dissolved in di-tert-butyl dicarbonate (7.6 mL, 33.2 mmol), and the reaction was heated to 50° C. and stirred for 16 hours. The system was cooled to room temperature, and the crude product was purified by silica gel column chromatography (ethyl acetate:petroleum ether=0:100→10:90) to obtain compound Y-6.

MS(ESI) m/z (M–55)$^+$=292.0, 294.0

Step 6-7. Synthesis of Compound Int-Y

According to the synthesis method of M-2→Int-M described in the preparation of intermediate Int-M, compound Y-6 was treated to obtain compound Int-Y.

MS(ESI) m/z (M+H)$^+$=390.0, 392.0

27) Preparation of Intermediate Int-Z

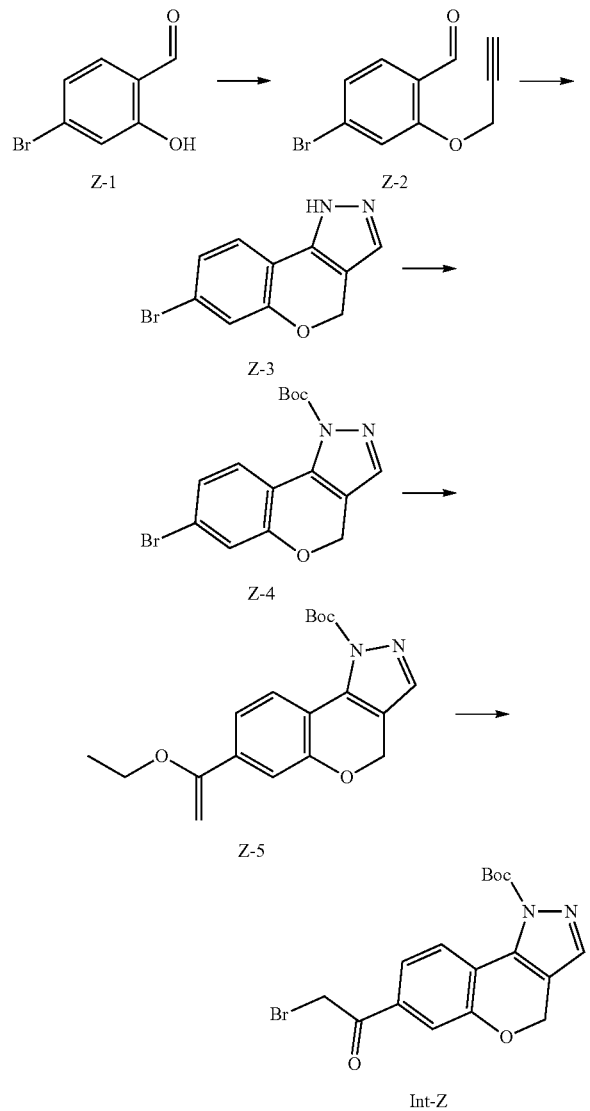

Step 1. Synthesis of Compound Z-2

Compound Z-1 (3.4 g, 16.91 mmol) was dissolved in acetonitrile (30 mL), and potassium carbonate (9.35 g, 67.66 mmol) and propargyl bromide (2.80 g, 23.68 mmol, 2.00 mL) were added sequentially, and the reaction was heated to 80° C. and stirred for 2 hours. The system was filtered, concentrated under reduced pressure to remove the solvent, the crude product was purified by silica gel column chromatography (ethyl acetate:petroleum ether=0:100→30:70) to obtain compound Z-2.

$^1$H NMR (400 MHz, CDCl$_3$) δ 10.39 (s, 1H), 7.80-7.63 (m, 1H), 7.31-7.19 (m, 2H), 4.82 (d, J=2.4 Hz, 2H), 2.61 (t, J=2.4 Hz, 1H).

Step 2. Synthesis of Compound Z-3

Under the protection of nitrogen, compound Z-2 (1.5 g, 6.27 mmol) was dissolved in ethanol (20 mL), and 4-methylbenzenesulfonyl hydrazide (1.17 g, 6.27 mmol) was added, and the reaction was stirred at 20° C. for 3 hours. The system was diluted with ethyl acetate (200 mL), washed with saturated saline (50 mL×3), the organic phase was dried over anhydrous sodium sulfate, filtered, and the filtrate was concentrated under reduced pressure, and the crude product was purified by slurrying with methyl tert-butyl ether (10 mL) to obtain compound Z-3.

MS (ESI) m/z (M+H)$^+$=250.6.

$^1$H NMR (400 MHz, CD$_3$OD) δ 7.56-7.50 (m, 2H), 7.15-7.11 (m, 2H), 5.31 (s, 2H).

Step 3. Synthesis of Compound Z-4

Under the protection of nitrogen, compound Z-3 (1 g, 3.98 mmol) was dissolved in pyridine (10 mL), and 4-dimethylaminopyridine (146 mg, 1.19 mmol) and di-tert-butyl dicarbonate (1.04 g, 4.78 mmol, 1.10 mL) were added sequentially, and the reaction was stirred at 80° C. for 16 hours. The system was diluted with ethyl acetate (300 mL), washed with saturated saline (80 mL×3), the organic phase was dried over anhydrous sodium sulfate, filtered, and the filtrate was concentrated under reduced pressure, and the crude product was purified by silica gel column chromatography (ethyl acetate:petroleum ether=0:100→30:70) to obtain compound Z-4.

MS (ESI) m/z (M+Na)$^+$=372.9.

$^1$H NMR (400 MHz, CDCl$_3$) δ 7.86 (s, 1H), 7.83-7.78 (m, 1H), 7.19-7.16 (m, 2H), 5.27 (d, J=1.1 Hz, 2H), 1.67 (s, 9H).

Step 4-5. Synthesis of Compound Int-Z

According to the synthesis method of M-2→Int-M described in the preparation of intermediate Int-M, compound Z-4 was treated to obtain compound Int-Z.

MS (ESI) m/z (M+H)$^+$=392.8.

$^1$H NMR (400 MHz, CDCl$_3$) δ 8.07-8.03 (m, 1H), 7.91 (s, 1H), 7.67-7.61 (m, 2H), 5.33-5.31 (m, 2H), 4.45 (s, 2H), 1.80-1.50 (m, 9H).

28) Preparation of Intermediate Int-AA

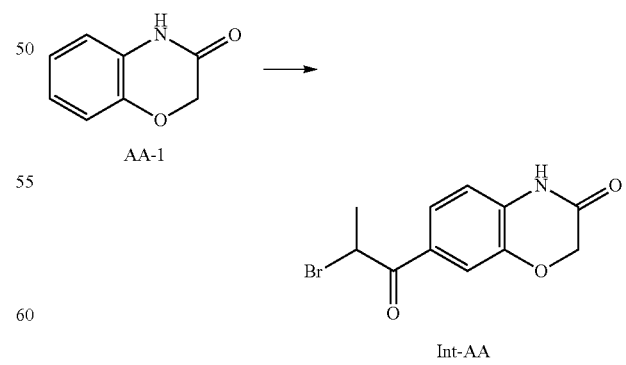

Step 1. Synthesis of Compound Z-2

Compound AA-1 (1.49 g, 10.0 mmol) and 2-bromopropanoyl bromide (4.32 g, 20.0 mmol) were dissolved in dichloromethane (25 mL), and aluminum trichloride (3.47 g, 26.0 mmol) was added, and the reaction was stirred under reflux for 4 hours. The system was cooled to room temperature, poured into ice water, the solid was filtered out and dried under vacuum to obtain compound Int-AA.

$^1$H NMR (400 MHz, DMSO-d$_6$) δ 10.91 (br, 1H), 7.71-7.69 (m, 1H), 7.54 (s, 1H), 7.09-7.06 (m, 1H), 5.70-5.64 (m, 1H), 4.71 (s, 2H), 1.76-1.59 (m, 3H).

29) Preparation of Intermediate Int-AB

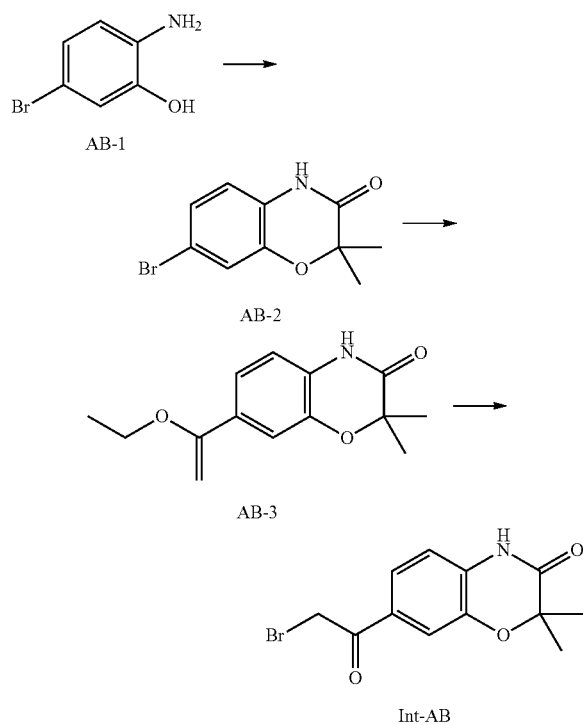

Step 1. Synthesis of Compound AB-2

Compound AB-1 (5.00 g, 26.6 mmol) and ethyl 2-bromo-2-methylpropionate (6.75 g, 34.6 mmol) were dissolved in acetone (100 mL), and potassium carbonate (11.0 g, 79.8 mmol) was added, and the reaction was stirred at 25° C. for 16 hours, heated to reflux and continued to stir for 16 hours. The system was cooled to room temperature, concentrated under reduced pressure to remove the solvent, the crude product was purified by silica gel column chromatography (ethyl acetate:petroleum ether=25:75) to obtain compound AB-2.

MS (ESI) m/z (M+H)$^+$=256.2, 258.2.

Step 2-3. Synthesis of Compound Int-AB

According to the synthesis method of J-3→Int-J described in the preparation of intermediate Int-J, compound AB-2 was treated to obtain compound Int-AB.

$^1$H NMR (400 MHz, DMSO-d$_6$) δ 11.06 (br, 1H), 7.68-7.65 (m, 1H), 7.56 (s, 1H), 7.02-7.00 (m, 1H), 4.84 (s, 2H), 1.43 (s, 6H).

30) Preparation of Intermediate Int-AC

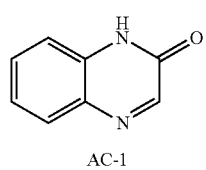

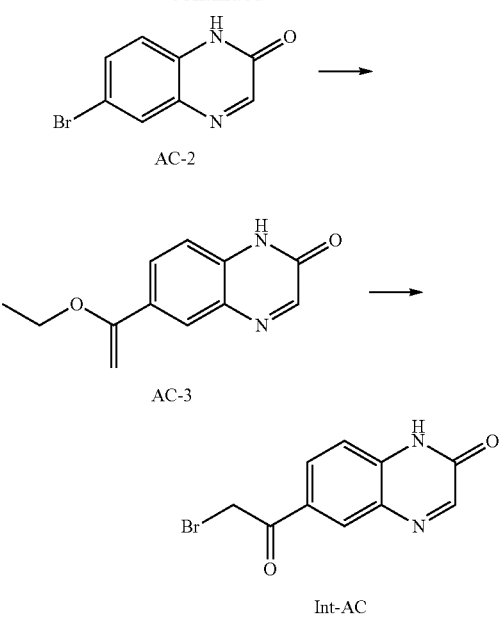

Step 1. Synthesis of Compound AC-2

Compound AC-1 (5.0 g, 34.21 mmol) and silver sulfate (5.33 g, 17.11 mmol) were dissolved in concentrated sulfuric acid (30 mL), and liquid bromine (6.01 g, 37.63 mmol, 1.94 mL) was added, and the reaction was stirred at 20° C. for 16 hours. The system was poured into ice water (100 mL), stirred for 30 min, filtered, dried under vacuum, and purified by slurrying with methanol (30 mL) to obtain compound AC-2.

$^1$H NMR (400 MHz, DMSO-d$_6$) δ 12.54 (br s, 1H), 8.20 (s, 1H), 7.95 (d, J=2.0 Hz, 1H), 7.78-7.69 (m, 1H), 7.25 (d, J=8.8 Hz, 1H).

Step 2-3. Synthesis of Compound Int-AC

According to the synthesis method of J-3→Int-J described in the preparation of intermediate Int-J, compound AC-2 was treated to obtain compound Int-AC.

MS (ESI) m/z (M+H)$^+$=269.0.

$^1$H NMR (400 MHz, DMSO-d$_6$) δ 12.74 (br s, 1H), 8.44 (s, 1H), 8.26 (s, 1H), 8.14-8.08 (m, 1H), 7.38 (d, J=8.8 Hz, 1H), 4.99 (s, 2H).

31) Preparation of Intermediate Int-AD

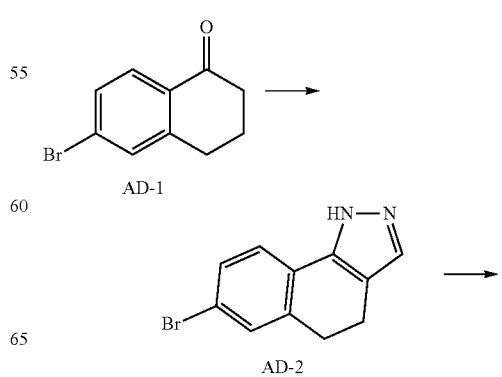

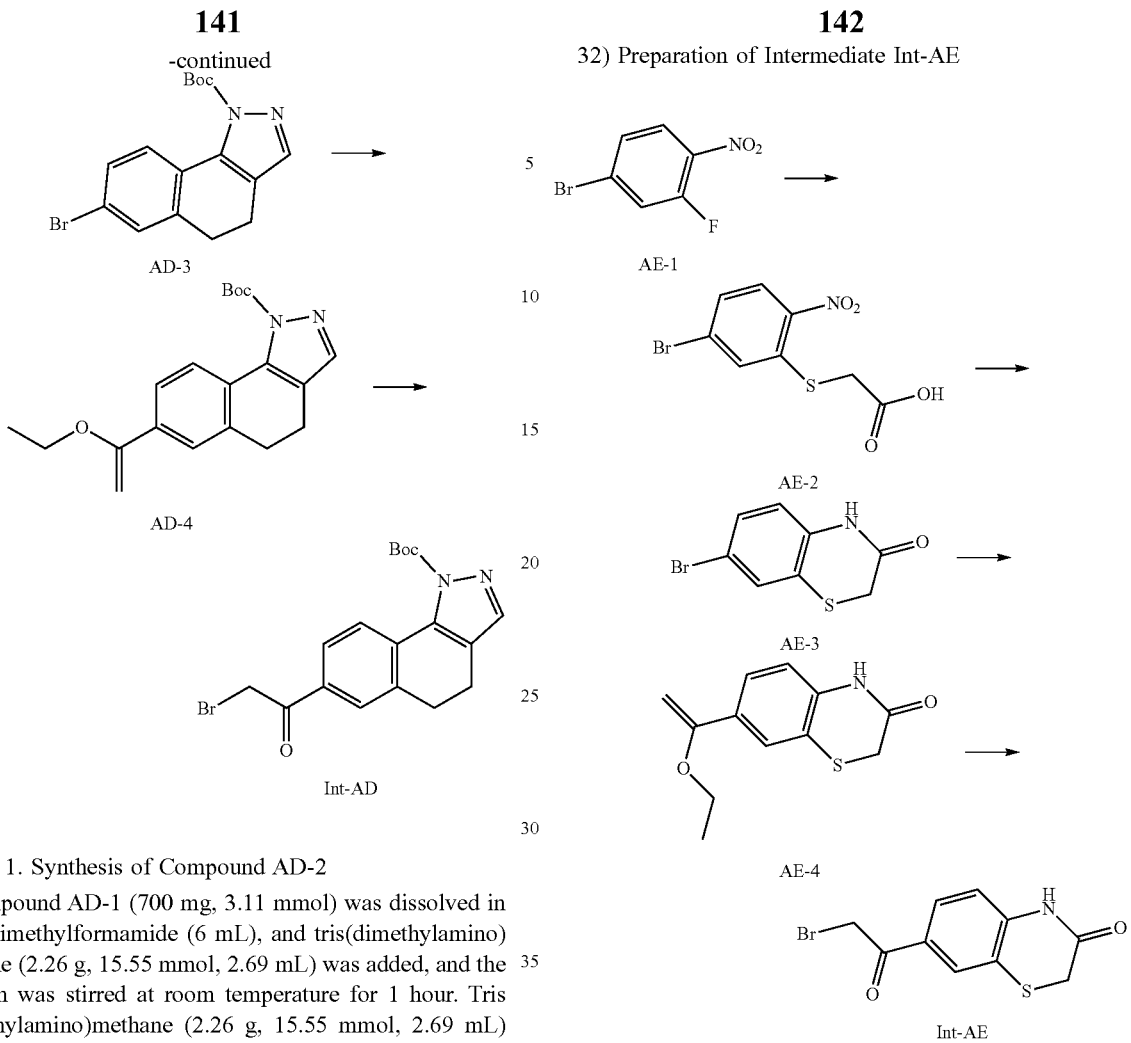

32) Preparation of Intermediate Int-AE

Step 1. Synthesis of Compound AD-2

Compound AD-1 (700 mg, 3.11 mmol) was dissolved in N, N-dimethylformamide (6 mL), and tris(dimethylamino)methane (2.26 g, 15.55 mmol, 2.69 mL) was added, and the reaction was stirred at room temperature for 1 hour. Tris(dimethylamino)methane (2.26 g, 15.55 mmol, 2.69 mL) was continuously added, and the reaction was stirred at 20° C. for 16 hours. The system was concentrated under reduced pressure to remove the solvent, and the crude product was dissolved in acetic acid (6 mL), and hydrazine hydrate (915.80 mg, 15.55 mmol, 889.13 uL, 85% purity) was added, the mixture was stirred at 20° C. for 15 min. The pH of the system was adjusted to 11.0 with concentrated ammonia water, and the mixture was extracted with dichloromethane (100 mL×3), the organic phases were combined, dried over anhydrous sodium sulfate, filtered, the filtrate was concentrated under reduced pressure, and the crude product was purified by silica gel column chromatography (ethyl acetate:petroleum ether=0:100→50:50) to obtain compound AD-2.

MS (ESI) m/z (M+H)$^+$=248.7, 250.7.

$^1$HNMR (400 MHz, CDCl$_3$) δ 7.68-7.66 (m, 1H), 7.42-7.39 (m, 3H), 2.96-2.92 (m, 2H), 2.83-2.79 (m, 2H).

Step 2-4. Synthesis of Compound Int-AD

According to the synthesis method of O-1→Int-O described in the preparation of intermediate Int-O, compound AD-2 was treated to obtain compound Int-AD.

MS (ESI) m/z (M+H)$^+$=336.7.

$^1$HNMR (400 MHz, CDCl$_3$) δ 8.16-8.14 (m, 1H), 7.91-7.88 (m, 3H), 4.48 (s, 2H), 3.05-3.01 (m, 2H), 2.86-2.83 (m, 2H), 1.68 (s, 9H).

Step 1. Synthesis of Compound AE-2

Under the protection of nitrogen, compound AE-1 (2.20 g, 10.0 mmol) and triethylamine (14 mL, 100.0 mmol) were dissolved in acetonitrile (7 mL) and water (3.5 mL), then mercaptoacetic acid (0.9 mL, 13.0 mmol) was added dropwise, and the reaction was heated to 70° C. and stirred for 16 hours. Dichloromethane (20 mL) was added into the system for dilution, the mixture was extracted with water (20 mL×3), the aqueous phases were combined, the pH was adjusted to 4.0 with 2.0 M hydrochloric acid, then the mixture was extracted with dichloromethane (20 mL×3), the organic phases were combined, washed with saturated saline (20 mL), dried over anhydrous sodium sulfate, filtered, and the filtrate was concentrated under reduced pressure to obtain crude product AE-2, which was directly used in the next reaction without further purification.

MS (ESI) m/z (M+NH$_4$)$^+$=309.0, 311.0.

$^1$H NMR (400 MHz, DMSO-d$_6$) δ 8.14 (d, J=8.8 Hz, 1H), 7.75 (d, J=2.0 Hz, 1H), 7.61 (dd, J=8.8, 2.0 Hz, 1H), 4.08 (s, 2H).

Step 2. Synthesis of Compound AE-3

At 30° C., under nitrogen protection, compound AE-2 (2.48 g, 8.49 mmol) and potassium carbonate (9.4 g, 67.92 mmol) were dissolved in water (30 mL), then a solution of sodium hydrosulfite (8.87 g, 50.94 mmol) in water (20 mL) was slowly added dropwise, and the reaction was stirred at this temperature for 16 hours. The pH of the system was adjusted to 3.0 by adding concentrated hydrochloric acid. The mixture was continued to stir for 1 hour. The system was cooled to 0° C., filtered, and the solid was dried under vacuum to obtain crude product AE-3, which was directly used in the next step without further purification.

MS (ESI) m/z (M+H)$^+$=244.0, 246.0.

Step 3-4. Synthesis of Compound Int-AE

According to the synthesis method of J-3→Int-J described in the preparation of intermediate Int-J, compound AE-3 was treated to obtain compound Int-AE.

MS (ESI) m/z (M+H)$^+$=286.0, 288.0.

33) Preparation of Intermediate Int-AF

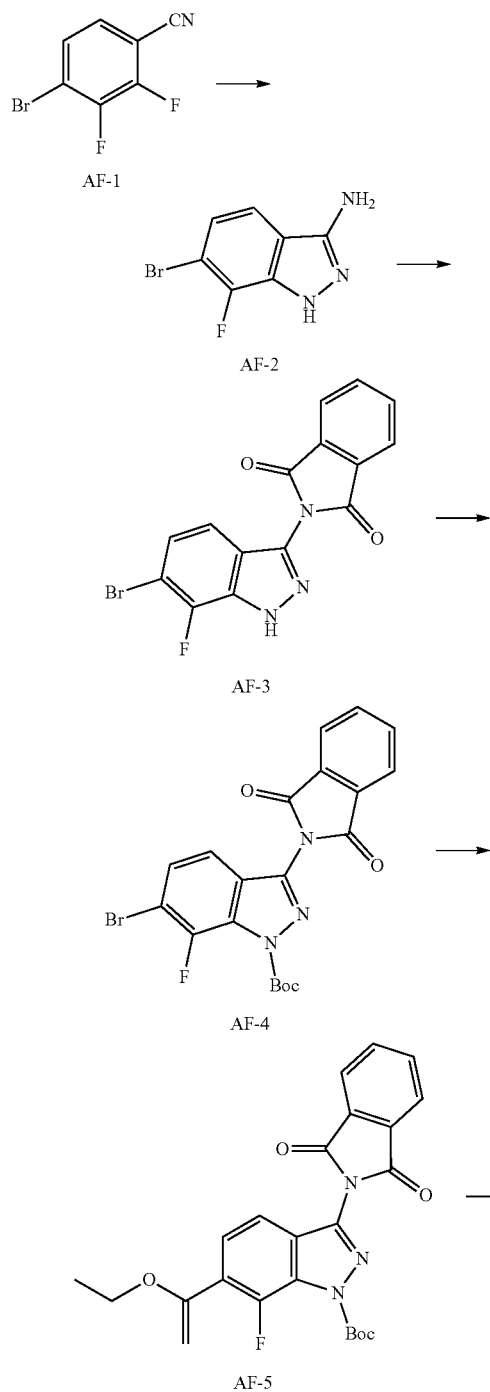

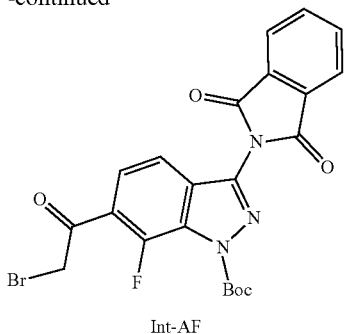

Step 1. Synthesis of Compound AF-2

Under the protection of nitrogen, compound AF-1 (3 g, 13.76 mmol) was dissolved in ethanol (30 mL), hydrazine hydrate (3.24 g, 55.05 mmol, 3.20 mL, 85%) was added dropwise, and the reaction was heated to 90° C. and stirred for 2 hours. The reaction was quenched by adding acetone (50 mL) to the system, extracted with ethyl acetate (300 mL), the organic phase was washed with saturated saline (100 mL×3), dried over anhydrous sodium sulfate, filtered, and the filtrate was concentrated under reduced pressure to obtain crude product AF-2, which was directly used for the next step without further purification.

MS (ESI) m/z (M+H)$^+$=229.9.

$^1$H NMR (400 MHz, DMSO-d$_6$) δ 12.08 (br s, 1H), 7.47 (d, J=8.5 Hz, 1H), 7.07 (dd, J=5.6, 8.4 Hz, 1H), 5.62 (br s, 2H).

Step 2-5. Synthesis of Compound Int-AF

According to the synthesis method of K-1→Int-K described in the preparation of intermediate Int-K, compound AF-2 was treated to obtain compound Int-AF.

MS (ESI) m/z (M+H)$^+$=403.8.

$^1$H NMR (400 MHz, CDCl$_3$) δ 8.04 (dd, J=3.0, 5.4 Hz, 2H), 7.89 (dd, J=3.1, 5.3 Hz, 2H), 7.83 (dd, J=5.3, 8.4 Hz, 1H), 7.46 (d, J=8.4 Hz, 1H), 4.63 (d, J=2.9 Hz, 2H), 1.74 (s, 9H).

34) Preparation of Intermediate Int-AG

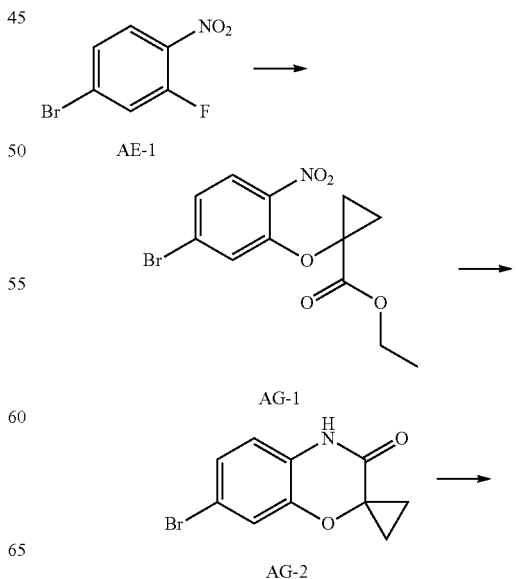

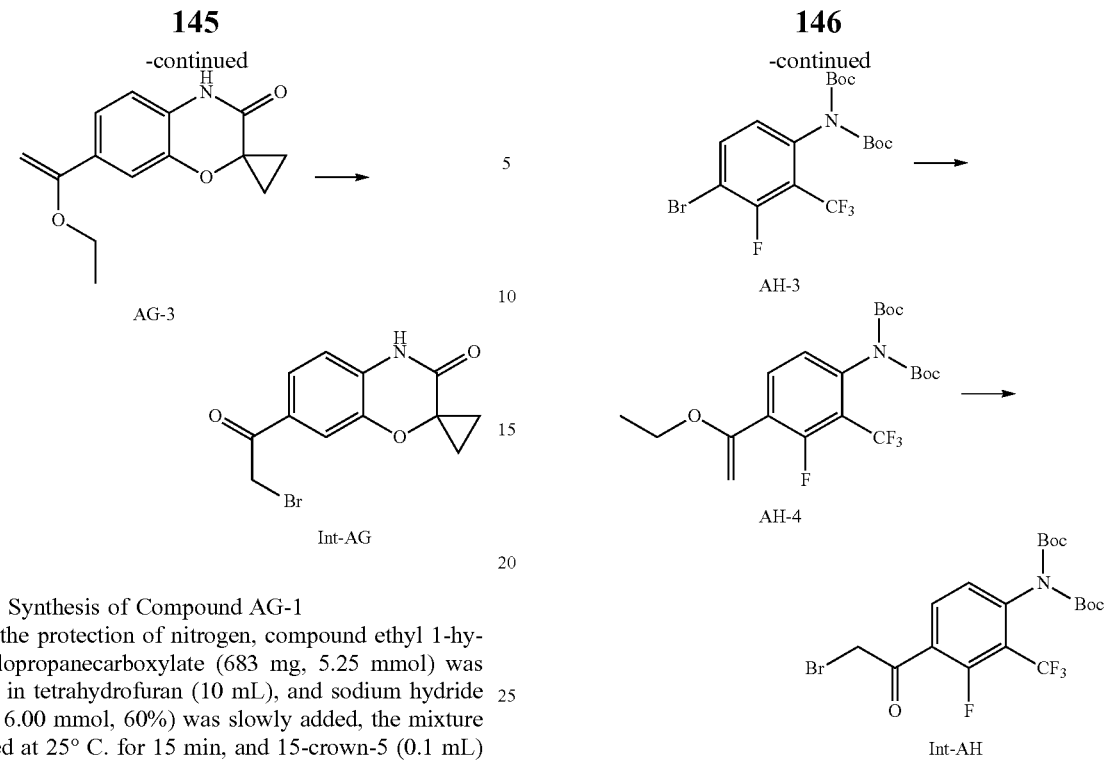

Step 1. Synthesis of Compound AG-1

Under the protection of nitrogen, compound ethyl 1-hydroxycyclopropanecarboxylate (683 mg, 5.25 mmol) was dissolved in tetrahydrofuran (10 mL), and sodium hydride (240 mg, 6.00 mmol, 60%) was slowly added, the mixture was stirred at 25° C. for 15 min, and 15-crown-5 (0.1 mL) and compound AE (1.10 g, 5.00 mmol) were added sequentially, and the reaction was stirred at 25° C. for 16 hours. The reaction mixture was poured into ice water (10 mL), extracted with ethyl acetate (20 mL×3), the organic phases were combined, dried over anhydrous sodium sulfate, filtered, and the filtrate was concentrated under reduced pressure, and the crude product was purified by silica gel column chromatography (ethyl acetate:petroleum ether=25:75) to obtain compound AG-1.

MS (ESI) m/z $(M+H)^+=330.2$.

Step 2. Synthesis of Compound AG-2

Compound AG-1 (1.40 g, 4.24 mmol) was dissolved in acetic acid (20.0 mL), and reduced iron powder (2.37 g, 42.4 mmol) was added, and the reaction was stirred at 60° C. for 3 hours. The system was filtered and the filtrate was concentrated under reduced pressure to remove the solvent, and the crude product was purified by silica gel column chromatography (ethyl acetate:petroleum ether=25:75) to obtain compound AG-2.

MS (ESI) m/z $(M+H)^+=253.9$.

Step 3-4. Synthesis of Compound Int-AG

According to the synthesis method of J-3→Int-J described in the preparation of intermediate Int-J, compound AG-2 was treated to obtain compound Int-AG.

MS (ESI) m/z $(M+H)^+=295.9$.

$^1$H NMR (400 MHz, DMSO-$d_6$) δ 11.19 (br, 1H), 7.71-7.68 (m, 1H), 7.49 (s, 1H), 7.04-7.02 (m, 1H), 4.83 (s, 2H), 1.32-1.28 (m, 2H), 1.25-1.23 (m, 2H).

35) Preparation of Intermediate Int-AH

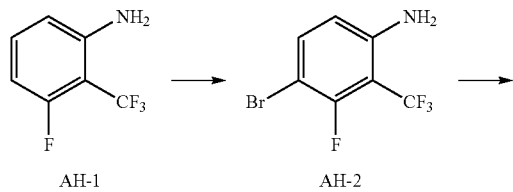

Step 1. Synthesis of Compound AH-2

Under the protection of nitrogen, compound AH-1 (3 g, 16.75 mmol) was dissolved in N, N-dimethylformamide (30 mL), and bromosuccinimide (3.13 g, 17.59 mmol) was added in batches, and the reaction was stirred at room temperature for 1 hour. The reaction was quenched by adding water (200 mL) to the system, extracted with ethyl acetate (100 mL×2), the organic phases were combined, washed by water (80 mL×2), dried over anhydrous sodium sulfate, filtered, and the filtrate was concentrated under reduced pressure, and the crude product was purified by silica gel column chromatography (ethyl acetate:petroleum ether=0:100→20:80) to obtain compound AH-2.

$^1$HNMR (400 MHz, CDCl$_3$) δ 7.39-7.35 (m, 1H), 6.42-6.40 (m, 1H), 4.32 (br s, 2H).

Step 2. Synthesis of Compound AH-3

Compound AH-2 (1.5 g, 5.81 mmol) was dissolved in tetrahydrofuran (30 mL), and di-tert-butyl dicarbonate (3.81 g, 17.44 mmol) and 4-dimethylaminopyridine (71.02 mg, 581.37 μmol) were added sequentially, and the reaction was heated to 80° C. and stirred for 3 hours. The system was concentrated under reduced pressure to remove the solvent, the crude product was purified by silica gel column chromatography (ethyl acetate:petroleum ether=0:100→20:80) to obtain compound AH-3.

MS (ESI) m/z $(M+H)^+=347.9$.

$^1$HNMR (400 MHz, CDCl$_3$) δ 7.77-7.73 (m, 1H), 6.96-6.93 (m, 1H), 1.40 (s, 18H).

Step 3-4. Synthesis of Compound Int-AH

According to the synthesis method of J-3→Int-J described in the preparation of intermediate Int-J, compound AH-3 was treated to obtain compound Int-AH.

MS (ESI) m/z $(M+Na)^+=523.8$.

$^1$H NMR (400 MHz, CDCl$_3$) δ 8.11-8.09 (m, 1H), 7.19-7.17 (m, 1H), 4.53 (s, 2H), 1.40 (s, 18H).

36) Preparation of Intermediate Int-AI

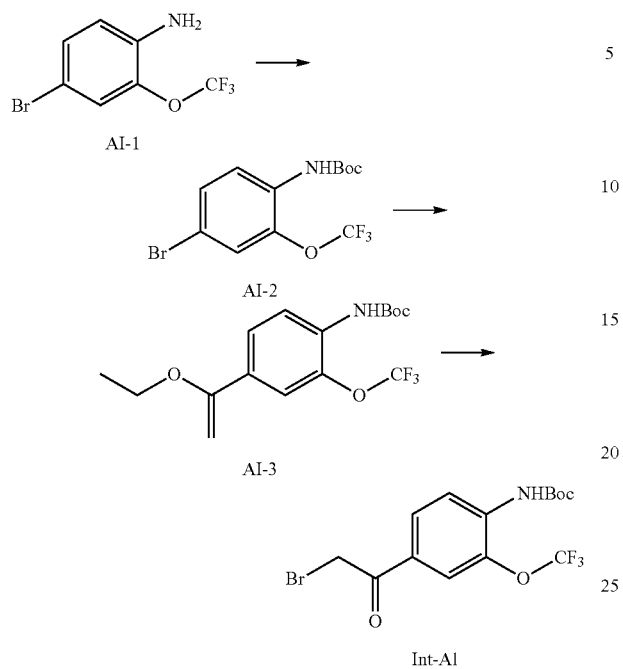

According to the synthesis method of O-1→Int-O described in the preparation of intermediate Int-0, compound AI-1 was treated to obtain compound Int-AI.

MS (ESI) m/z (M+H)$^+$=398.0.

$^1$H NMR (400 MHz, CDCl$_3$) δ 8.40 (d, J=8.6 Hz, 1H), 7.93-7.84 (m, 2H), 7.04 (br s, 1H), 4.39 (s, 2H), 1.55 (s, 9H).

37) Preparation of Intermediate Int-AJ

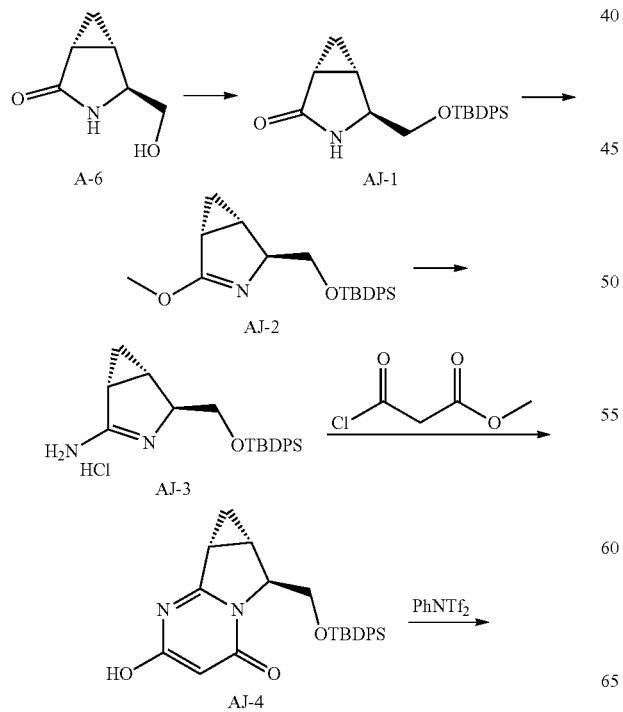

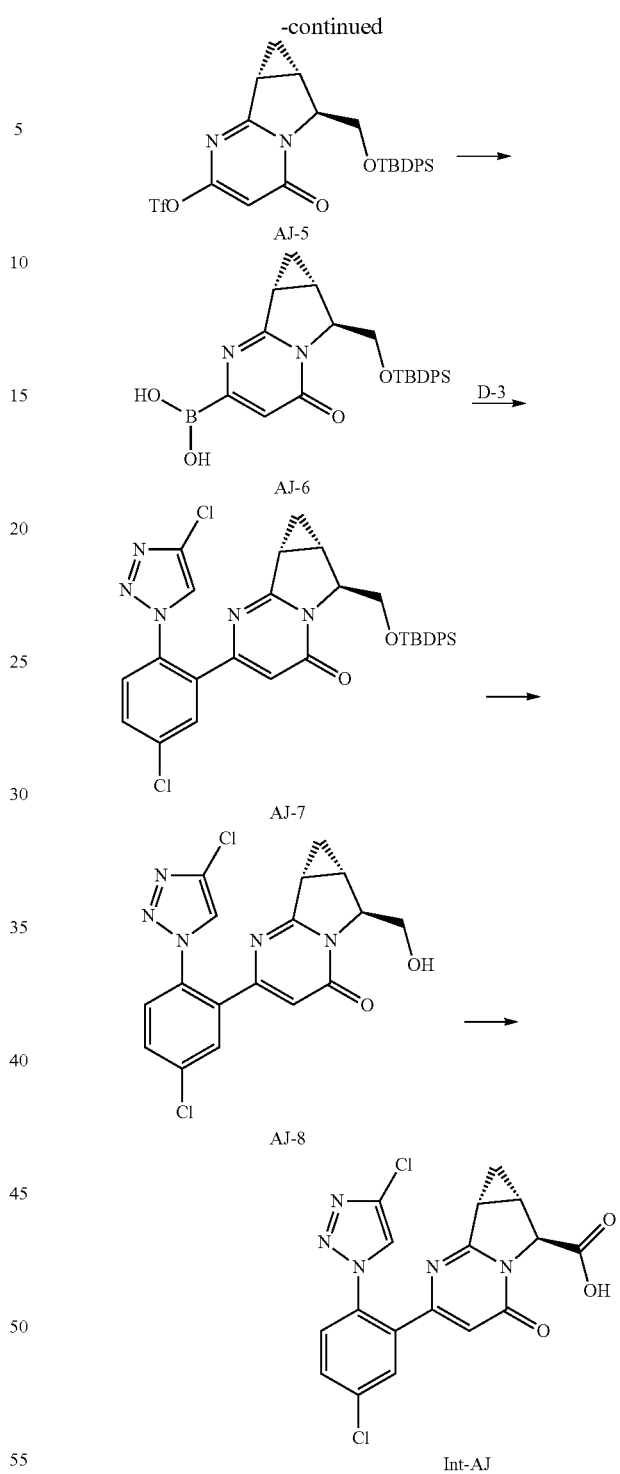

Step 1. Synthesis of Compound AJ-1

Compound A-6 (40 g, 314.6 mmol) was dissolved in dichloromethane (1500 mL), and imidazole (26 g, 377.5 mmol) and tert-butylchlorodiphenylsilane (104 g, 377.5 mmol) were added, and the mixture was stirred at room temperature for 18 hours. The reaction mixture was filtered, the filtrate was concentrated under reduced pressure. The crude product was purified by silica gel column chromatography (ethyl acetate:petroleum ether=0:100→25:75) to obtain compound AJ-1.

MS (ESI) m/z (M+H)$^+$=366.3.

Step 2. Synthesis of Compound AJ-2

Compound AJ-1 (20 g, 54.71 mmol) was dissolved in dichloromethane (400 mL), and trimethyloxonium tetrafluoroborate (11.33 mg, 76.60 mmol) was added, and the mixture was stirred at room temperature for 3 hours. The system was cooled to 0° C., quenched by adding saturated sodium bicarbonate aqueous solution (100 mL), the mixture was stirred for 1 hour, water (400 mL) and dichloromethane (400 mL) were added, the phases were separated, the aqueous layer was extracted with dichloromethane (200 mL×2), the organic phases were combined, dried over anhydrous sodium sulfate, filtered, and the filtrate was concentrated under reduced pressure to obtain crude product AJ-2, which was directly used in the next step without further purification.

Step 3. Synthesis of Compound AJ-3

Compound AJ-2 (20 g, 52.69 mmol) was dissolved in methanol (200 mL), ammonium chloride (4.23 g, 79.04 mmol) was added, and the reaction was heated to 75° C. and stirred for 5 hours. The reaction mixture was concentrated under reduced pressure, the crude product was purified by silica gel column chromatography (methanol:dichloromethane=0:100→10:90) to obtain compound AJ-3.

Step 4. Synthesis of Compound AJ-4

Compound AJ-3 (12 g, 29.92 mmol) and potassium 3-methoxy-3-oxopropanoate (11.7 g, 74.81 mmol) were dissolved in N,N-dimethylformamide (25 mL), and N,N-diisopropylethylamine (19.3 g, 149.62 mmol) and 1-(3-dimethylaminopropyl)-3-ethylcarbodiimide hydrochloride (14.3 g, 74.81 mmol) were added sequentially, and the reaction was heated to 70° C. and stirred for 36 hours. The system was diluted with ethyl acetate (100 mL), water (100 mL) was added, the phases were separated, the aqueous phase was extracted with ethyl acetate (100 mL×2), the organic phases were combined, washed with water (100 mL) and saturated saline (100 mL) sequentially, dried over anhydrous sodium sulfate, filtered, and the filtrate was concentrated under reduced pressure. The crude product was purified by C18 reverse phase column chromatography (acetonitrile: 0.5% ammonium bicarbonate aqueous solution=5:95→95:5), and compound AJ-4 was obtained.

MS (ESI) m/z (M+H)$^+$=433.2.

Step 5. Synthesis of Compound AJ-5

Compound AJ-4 (6 g, 13.87 mmol) was dissolved in N,N-dimethylformamide (10 mL) and 1, 1, 1-trifluoro-N-phenyl-N-((trifluoromethyl)sulfonyl)methanesulfonamide (9.91 g, 27.74 mmol) and triethylamine (4.21 g, 41.61 mmol) were added, the mixture was stirred for 5 hours. The system was diluted with ethyl acetate (50 mL), water (50 mL) was added, the phases were separated, the aqueous phase was extracted with ethyl acetate (50 mL×2), the organic phases were combined, washed with saturated saline (50 mL), dried over anhydrous sodium sulfate, filtered, and the filtrate was concentrated under reduced pressure. The crude product was purified by silica gel column chromatography (ethyl acetate:petroleum ether=40:60→100:0) to obtain compound AJ-5.

MS (ESI) m/z (M+H)$^+$=565.2.

Step 6. Synthesis of Compound AJ-6

Under the protection of nitrogen, potassium acetate (260.72 mg, 2.66 mmol) and bis(pinacolato)diboron (574.59 mg, 2.66 mmol) were dissolved in dioxane (10 mL), the mixture was heated to 100° C. and stirred for 30 min, and AJ-5 (0.5 g, 0.89 mmol) and [1,1'-bis(diphenylphosphino)ferrocene]dichloropalladium (65.88 mg, 0.09 mmol) were added, the reaction was continued to stir at 100° C. for 2 hours, the reaction mixture was cooled to room temperature and directly used for the next step.

Step 7. Synthesis of Compound AJ-7

Under the protection of nitrogen, compound D-3 (337.23 mg, 1.15 mmol), potassium carbonate (4.78 mg, 1.33 mmol), [1,1'-bis(diphenylphosphino)ferrocene]dichloropalladium (36.60 mg, 0.05 mmol), dioxane (10 mL) and water (1 mL) were added to the reaction mixture in step 2, and the reaction was heated to 100° C. and stirred for 2 hours. The reaction mixture was cooled to room temperature, diluted with ethyl acetate (20 mL), water (20 mL) was added, the phases were separated, the aqueous phase was extracted with ethyl acetate (20 mL×2); the organic phases were combined, washed with saturated saline (20 mL), dried over anhydrous sodium sulfate, filtered, the filtrate was concentrated under reduced pressure, and the crude product was purified by silica gel column chromatography (ethyl acetate:petroleum ether=50:50) to obtain compound AJ-7.

MS (ESI) m/z (M+H)$^+$=630.3.

Step 8. Synthesis of Compound AJ-8

Compound AJ-7 (472 mg, 0.75 mmol) was dissolved in tetrahydrofuran (10 mL), and acetic acid (0.085 mL, 1.5 mmol) and tetrabutylammonium fluoride (1.5 mL, 1.5 mmol, 1.0 M in tetrahydrofuran solution) were added sequentially, and the mixture was stirred at room temperature for 18 hours. The reaction mixture was quenched by adding 1.0 M dilute hydrochloric acid (1.5 mL), water (10 mL) and ethyl acetate (10 mL) were added, the phases were separated, and the organic phase was washed with saturated saline (10 mL), dried over anhydrous sodium sulfate, filtered, and the filtrate was concentrated under reduced pressure. The crude product was purified by silica gel column chromatography (ethyl acetate:petroleum ether=50:50) to obtain compound AJ-8.

MS (ESI) m/z (M+H)$^+$=390.2.

Step 9. Synthesis of Compound Int-AJ

Compound AJ-8 (140 mg, 0.36 mmol) was dissolved in dichloromethane (10 mL), and Dess-Martin oxidant (532.59 mg, 1.26 mmol) was added, and the mixture was stirred at room temperature for 18 hours. The reaction mixture was diluted with dichloromethane (10 mL), water (10 mL) was added, the mixture was filtered, and the filtrate was concentrated under reduced pressure, and the crude product was purified by C18 reverse phase column chromatography (acetonitrile: 0.5% ammonium bicarbonate aqueous solution=5:95→95:5) to obtain compound Int-AJ.

MS (ESI) m/z (M+H)$^+$=404.0.

38) Preparation of Intermediate Int-AL

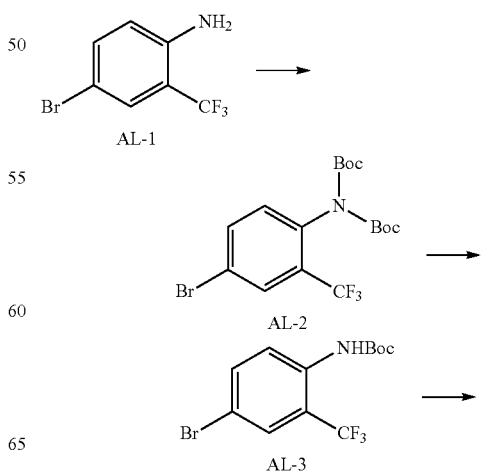

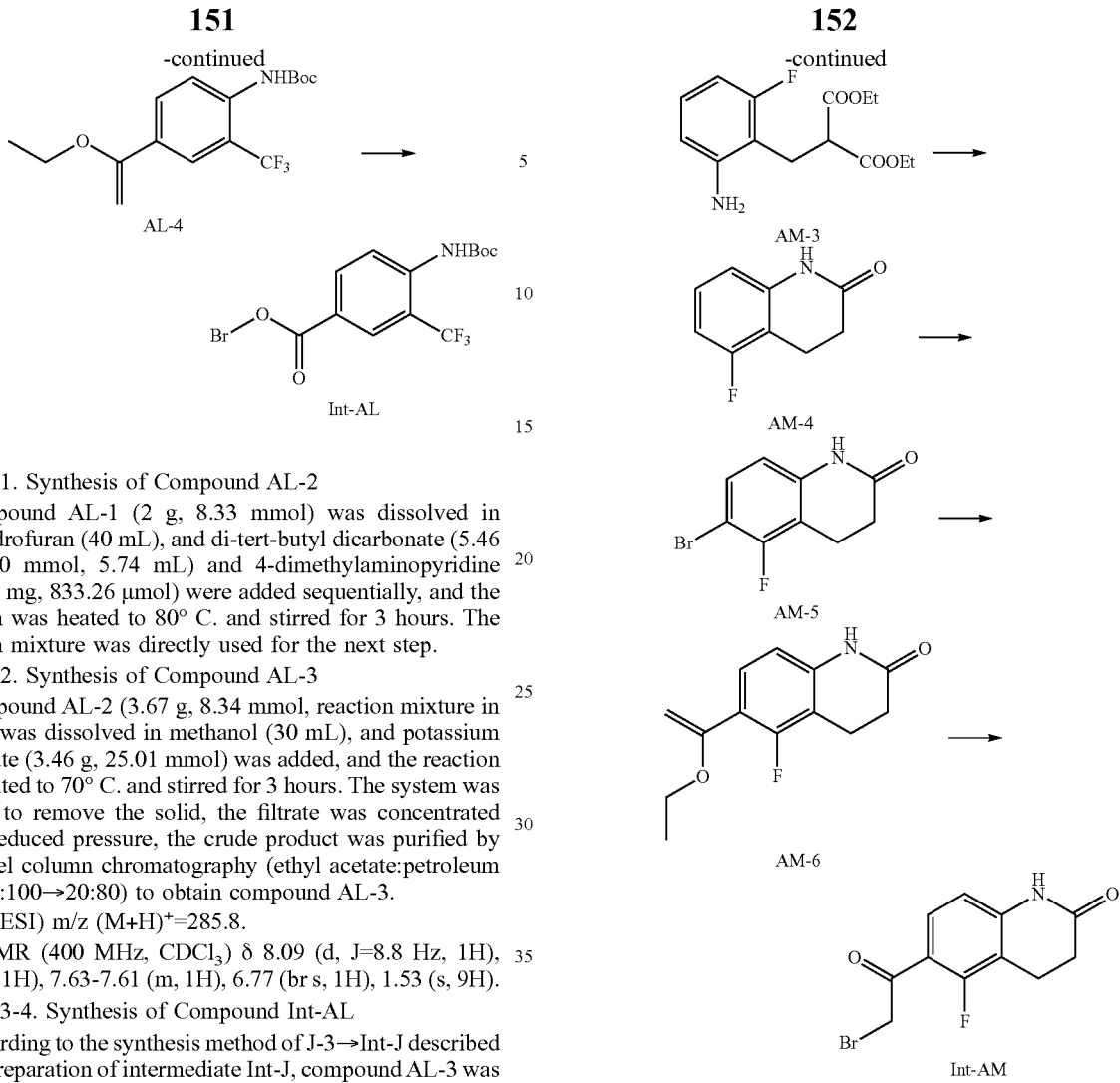

Step 1. Synthesis of Compound AL-2

Compound AL-1 (2 g, 8.33 mmol) was dissolved in tetrahydrofuran (40 mL), and di-tert-butyl dicarbonate (5.46 g, 25.00 mmol, 5.74 mL) and 4-dimethylaminopyridine (101.80 mg, 833.26 μmol) were added sequentially, and the reaction was heated to 80° C. and stirred for 3 hours. The reaction mixture was directly used for the next step.

Step 2. Synthesis of Compound AL-3

Compound AL-2 (3.67 g, 8.34 mmol, reaction mixture in step 1) was dissolved in methanol (30 mL), and potassium carbonate (3.46 g, 25.01 mmol) was added, and the reaction was heated to 70° C. and stirred for 3 hours. The system was filtered to remove the solid, the filtrate was concentrated under reduced pressure, the crude product was purified by silica gel column chromatography (ethyl acetate:petroleum ether=0:100→20:80) to obtain compound AL-3.

MS (ESI) m/z (M+H)$^+$=285.8.

$^1$HNMR (400 MHz, CDCl$_3$) δ 8.09 (d, J=8.8 Hz, 1H), 7.69 (s, 1H), 7.63-7.61 (m, 1H), 6.77 (br s, 1H), 1.53 (s, 9H).

Step 3-4. Synthesis of Compound Int-AL

According to the synthesis method of J-3→Int-J described in the preparation of intermediate Int-J, compound AL-3 was treated to obtain compound Int-AL.

MS (ESI) m/z (M+H)$^+$=328.0.

$^1$HNMR (400 MHz, CDCl$_3$) δ 8.46 (d, J=9.2 Hz, 1H), 8.22 (s, 1H), 8.12-8.10 (m, 1H), 7.08 (br s, 1H), 4.40 (s, 2H), 1.54 (s, 9H).

39) Preparation of Intermediate Int-AM

Step 1. Synthesis of Compound AM-2

At 0° C., sodium hydride (666.6 mg, 16.7 mmol) was dissolved in N, N-dimethylformamide (13 mL), diethyl malonate (2.5 g, 15.4 mmol) was added dropwise, and the mixture was stirred for 10 min at this temperature. A solution of compound AM-1 (3.0 g, 12.8 mmol) in N, N-dimethylformamide (12 mL) was added dropwise, and the reaction was stirred at 0° C. for 1 hour. The system was quenched by saturated ammonium chloride solution (30 mL), water (60 mL) was added, the mixture was extracted by ethyl acetate (50 mL×3), the organic phases were combined, washed with saturated saline (80 mL), dried over anhydrous sodium sulfate, filtered, and the filtrate was concentrated under reduced pressure to obtain compound AM-2, which was used directly in the next step without further purification.

MS (ESI) m/z (M+H)$^+$=314.0.

Step 2. Synthesis of Compound AM-3

Compound AM-2 (4.0 g, 12.8 mmol) was dissolved in ethanol (30 mL), and palladium hydroxide/carbon (180 mg, 1.3 mmol, 5% wet) was added, and the system was stirred for 16 hours at room temperature under hydrogen atmosphere. The system was filtered to remove the catalyst, the filtrate was concentrated to obtain crude product AM-3, which was directly used in the next step without further purification.

MS (ESI) m/z (M+H)$^+$=284.0.

Step 3. Synthesis of Compound AM-4

Compound AM-3 (3.1 g, 10.9 mmol) was dissolved in acetic acid (8 mL), concentrated hydrochloric acid (1.0 mL) was slowly added, the reaction was heated to 90° C. and stirred for 1 hour. The system was cooled to room temperature, the pH was adjusted to 7.0 by adding saturated sodium bicarbonate solution, the mixture was diluted with water (30 mL), extracted with ethyl acetate (25 mL×3), the organic phases were combined, washed with saturated saline (30 mL), dried over anhydrous sodium sulfate, filtered, and the filtrate was concentrated under reduced pressure to obtain compound AM-4, which was directly used in the next step without further purification.

MS (ESI) m/z (M+H)$^+$=166.0.

Step 4. Synthesis of Compound AM-5

Compound AM-4 (1.0 g, 6.1 mmol) was dissolved in N,N-dimethylformamide (20 mL), and bromosuccinimide (1.1 g, 6.2 mmol) was added in batches, and the reaction was stirred at room temperature for 16 hours. The system was quenched by adding water (20 mL), extracted with ethyl acetate (25 mL×3), the organic phases were combined, washed with saturated saline (30 mL), dried over anhydrous sodium sulfate, filtered, the filtrate was concentrated under reduced pressure, and the crude product was purified by silica gel column chromatography (ethyl acetate:petroleum ether=0:100→35:65) to obtain compound AM-5.

MS (ESI) m/z (M+H)$^+$=243.8.

Step 5-6. Synthesis of Compound Int-AM

According to the synthesis method of J-3→Int-J described in the preparation of intermediate Int-J, compound AM-5 was treated to obtain compound Int-AM.

MS (ESI) m/z (M+H)$^+$=288.0.

40) Preparation of Intermediate Int-AN

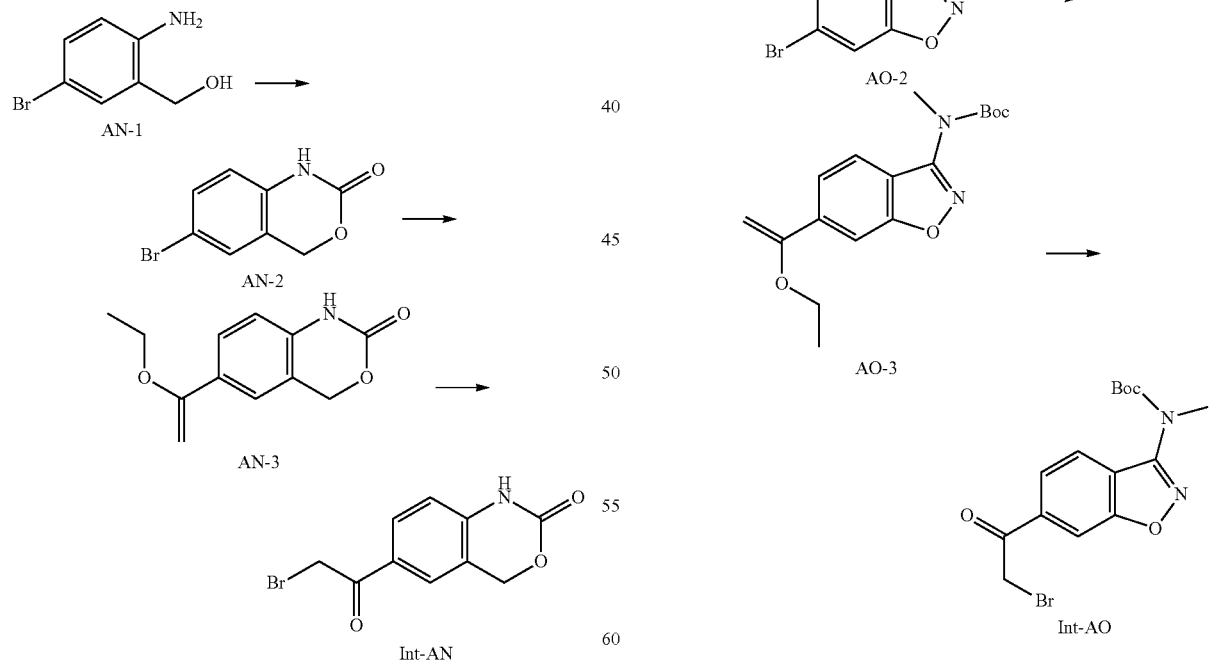

Step 1. Synthesis of Compound AM-2

Under the protection of nitrogen, compound AN-1 (1.57 g, 7.77 mmol) was dissolved in tetrahydrofuran (30 mL), and triphosgene (2.31 g, 7.77 mmol) was added, and the reaction was stirred at room temperature for 1 hour. The system was quenched by adding water (30 mL), the mixture was extracted by ethyl acetate (20 mL×3), the organic phases were combined, washed with saturated saline (50 mL), dried over anhydrous sodium sulfate, filtered, and the filtrate was concentrated under reduced pressure to obtain compound AN-2, which was used directly in the next step without further purification.

MS (ESI) m/z (M+H)$^+$=228.0, 210.0.

$^1$H NMR (400 MHz, DMSO-d$_6$) δ 10.28 (s, 1H), 7.48-7.38 (m, 2H), 6.86-6.79 (m, 1H), 5.27 (s, 2H).

Step 2-3. Synthesis of Compound Int-AN

According to the synthesis method of J-3→Int-J described in the preparation of intermediate Int-J, compound AN-2 was treated to obtain compound Int-AN.

MS (ESI) m/z (M+H)$^+$=270.0, 272.0.

41) Preparation of Intermediate Int-AO

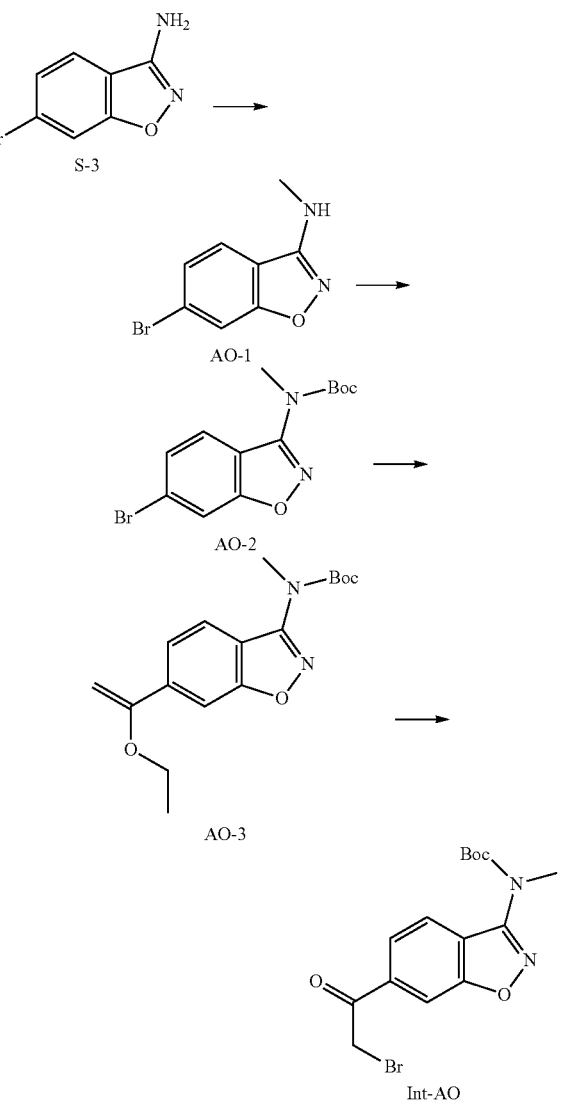

Step 1. Synthesis of Compound AO-1

Compound S-3 (500 mg, 2.00 mmol) and paraformaldehyde (54 mg, 1.80 mmol) were dissolved in dichloromethane (26 mL), and the reaction was stirred at room temperature for 1 h, triethylsilane (233 mg, 2.00 mmol) and trifluoroacetic acid (684 mg, 6.00 mmol) were added, and the mixture was stirred at 55° C. for 16 hours. The system was cooled to room temperature, the pH was adjusted to 8.0 with saturated sodium bicarbonate, the organic phase was separated, the aqueous phase was extracted with dichloromethane (30 mL×4), the organic phases were combined, washed with saturated sodium chloride solution (100 mL), dried over anhydrous sodium sulfate, filtered, the filtrate was concentrated under reduced pressure, the crude product was purified by silica gel column chromatography (ethyl acetate: petroleum ether=0:100→35:65) to obtain compound AO-1.

MS (ESI) m/z (M+H)$^+$=228.9.

Step 2-4. Synthesis of Compound Int-AO

According to the synthesis method of J-2→Int-J described in the preparation of intermediate Int-J, compound AO-1 was treated to obtain compound Int-AO.

MS (ESI) m/z (M−55)$^+$=314.8.

$^1$H NMR (400 MHz, CDCl$_3$) δ 8.12 (s, 1H), 7.96 (d, J=8.5 Hz, 1H), 7.90 (d, J=8.5, 1H), 4.50 (s, 2H), 3.50 (s, 3H), 1.56 (s, 9H).

42) Preparation of Intermediate Int-AP

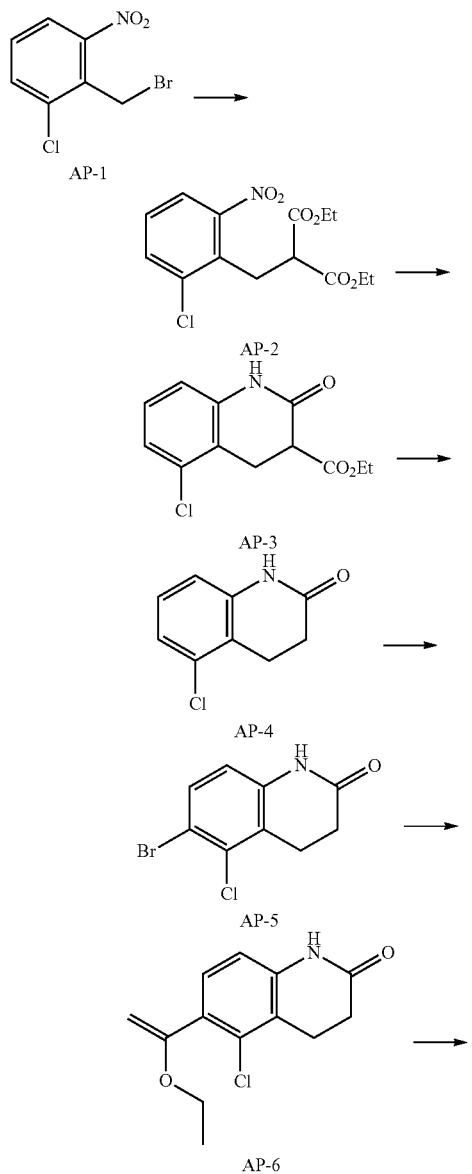

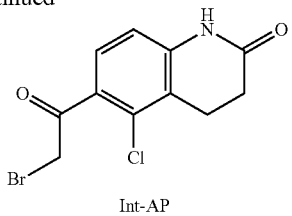

Step 1. Synthesis of Compound AP-2

At 0° C., sodium hydride (3.36 g, 84.0 mmol) was dissolved in N, N-dimethylformamide (160 mL), diethyl malonate (10.8 g, 67.2 mmol) was added dropwise, and the mixture was stirred for 10 min at this temperature. A solution of compound AP-1 (14.0 g, 56.0 mmol) in N, N-dimethylformamide (160 mL) was added dropwise, and the reaction was stirred at 0° C. for 1 hour. The system was quenched by adding saturated ammonium chloride aqueous solution (50 mL), extracted with ethyl acetate (100 mL×2), the organic phases were combined, dried over anhydrous sodium sulfate, filtered, the filtrate was concentrated under reduced pressure, and the crude product was purified by silica gel column chromatography (ethyl acetate:petroleum ether=0: 100→20:80) to obtain compound AP-2.

MS (ESI) m/z (M+H)$^+$=330.0.

Step 2. Synthesis of Compound AP-3

Compound AP-2 (12.0 g, 36.4 mmol) was dissolved in acetonitrile (200 mL), and Raney nickel (1.20 g) was added, and the reaction was stirred for 16 hours at room temperature under hydrogen atmosphere. The catalyst was removed by filtration, the filtrate was concentrated under reduced pressure, the crude product was purified by silica gel column chromatography (ethyl acetate:petroleum ether=0:100→40: 60) to obtain compound AP-3.

MS (ESI) m/z (M+H)$^+$=254.1.

Step 3. Synthesis of Compound AP-4

Compound AP-3 (4.80 g, 18.9 mmol) was dissolved in acetic acid (30.0 mL), concentrated hydrochloric acid (15 mL) was slowly added dropwise, the reaction was heated to 90° C. and stirred for 1 hour. The system was cooled to room temperature, water (50 mL) was added, the mixture was extracted with ethyl acetate (50 mL×2), the organic phases were combined, dried over anhydrous sodium sulfate, filtered, and the filtrate was concentrated under reduced pressure to obtain crude product AP-4, which was directly used in the next step without further purification.

MS (ESI) m/z (M+H)$^+$=182.1.

Step 4-6. Synthesis of Compound Int-AP

According to the synthesis method of AM-4→Int-AM described in the preparation of intermediate Int-AM, compound AP-4 was treated to obtain compound Int-AP.

MS (ESI) m/z (M+H)$^+$=303.9.

$^1$H NMR (400 MHz, DMSO-d$_6$) δ 10.54 (br, 1H), 7.68 (d, J=4.0 Hz, 1H), 6.91 (d, J=4.0 Hz, 1H), 4.80 (s, 2H), 3.04 (t, J=7.6 Hz, 2H), 2.55 (t, J=7.6 Hz, 2H).

43) Preparation of Intermediate Int-AQ

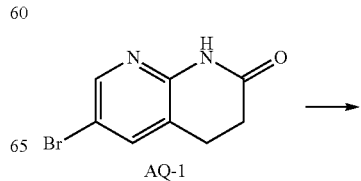

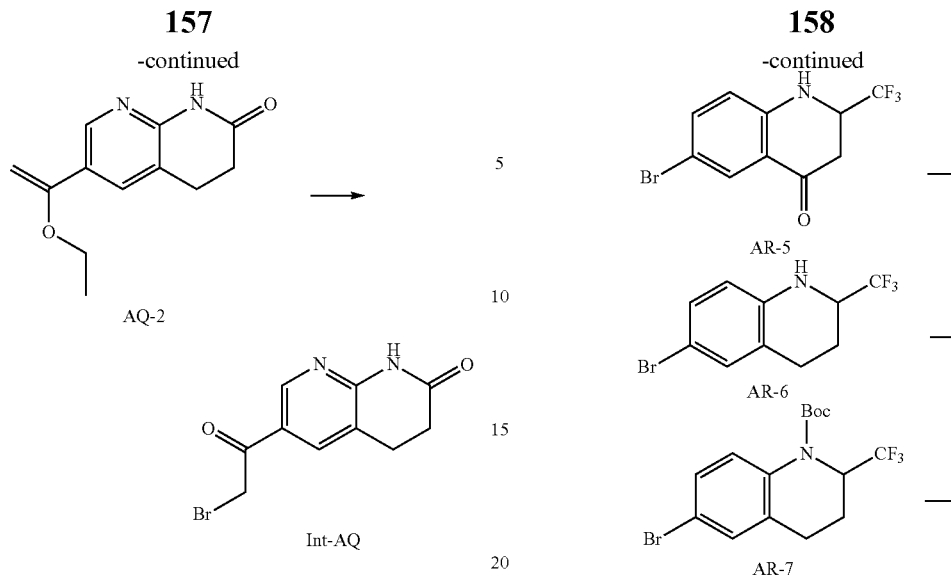

According to the synthesis method of J-3→Int-J described in the preparation of intermediate Int-J, compound AQ-1 was treated to obtain compound Int-AQ.

MS (ESI) m/z (M+H)$^+$=268.8.

$^1$H NMR (400 MHz, DMSO-d$_6$) δ 10.99 (d, J=3.0 Hz, 1H), 8.76 (dd, J=13.5, 2.2 Hz, 1H), 8.14-8.12 (m, 1H), 5.16 (s, 1H), 4.89 (s, 1H), 2.97 (t, J=7.6 Hz, 2H), 2.59-2.54 (m, 2H).

44) Preparation of Intermediate Int-AR

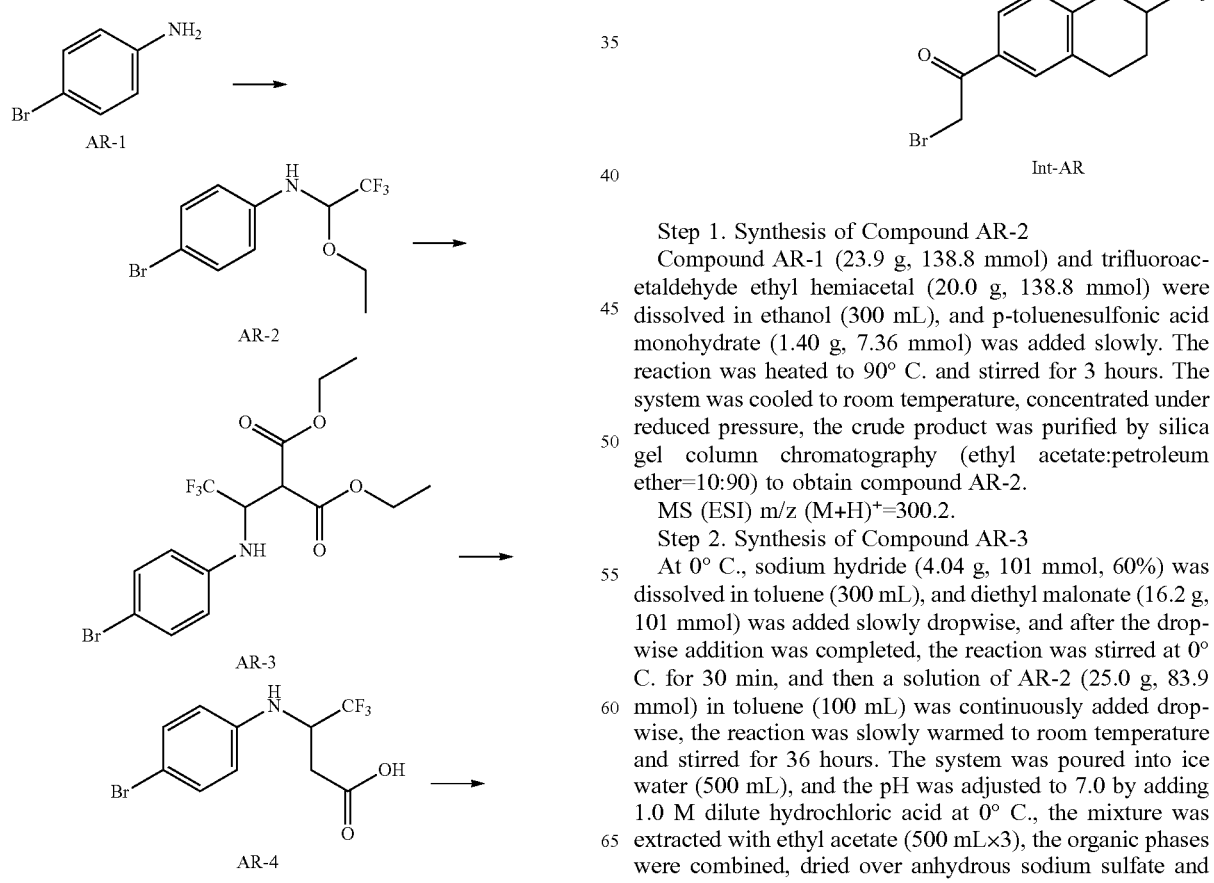

Step 1. Synthesis of Compound AR-2

Compound AR-1 (23.9 g, 138.8 mmol) and trifluoroacetaldehyde ethyl hemiacetal (20.0 g, 138.8 mmol) were dissolved in ethanol (300 mL), and p-toluenesulfonic acid monohydrate (1.40 g, 7.36 mmol) was added slowly. The reaction was heated to 90° C. and stirred for 3 hours. The system was cooled to room temperature, concentrated under reduced pressure, the crude product was purified by silica gel column chromatography (ethyl acetate:petroleum ether=10:90) to obtain compound AR-2.

MS (ESI) m/z (M+H)$^+$=300.2.

Step 2. Synthesis of Compound AR-3

At 0° C., sodium hydride (4.04 g, 101 mmol, 60%) was dissolved in toluene (300 mL), and diethyl malonate (16.2 g, 101 mmol) was added slowly dropwise, and after the dropwise addition was completed, the reaction was stirred at 0° C. for 30 min, and then a solution of AR-2 (25.0 g, 83.9 mmol) in toluene (100 mL) was continuously added dropwise, the reaction was slowly warmed to room temperature and stirred for 36 hours. The system was poured into ice water (500 mL), and the pH was adjusted to 7.0 by adding 1.0 M dilute hydrochloric acid at 0° C., the mixture was extracted with ethyl acetate (500 mL×3), the organic phases were combined, dried over anhydrous sodium sulfate and filtered. The filtrate was concentrated under reduced pressure, the crude product was purified by silica gel column chromatography (ethyl acetate:petroleum ether=10:90) to obtain compound AR-3.

MS (ESI) m/z $(M+H)^+$=412.1.

Step 3. Synthesis of Compound AR-4

At 0° C., compound AR-3 (23.5 g, 57.0 mmol) was dissolved in ethanol (300 mL), and 2.0 M sodium hydroxide aqueous solution (150 mL) was slowly added dropwise, and the reaction was stirred at reflux for 2 hours. The system was cooled to 0° C., the pH was slowly adjusted to 4.0 by adding 1.0 M diluted hydrochloric acid, the mixture was extracted with ethyl acetate (500 mL×3), the organic phases were combined, dried over anhydrous sodium sulfate and filtered. The filtrate was concentrated under reduced pressure, the crude product was purified by silica gel column chromatography (ethyl acetate:petroleum ether=10:90→50:50; Methanol:dichloromethane=10:80) to obtain compound AR-4.

MS (ESI) m/z $(M+H)^+$=311.9.

Step 4. Synthesis of Compound AR-5

Compound AR-4 (8.90 g, 28.5 mmol) was added to polyphosphoric acid (20.0 g), and the reaction was heated to 120° C. and stirred for 0.5 hours. The system was cooled to room temperature, ice water (100 mL) was added, the mixture was extracted with ethyl acetate (100 mL×3), the organic phases were combined, dried over anhydrous sodium sulfate, filtered, and the filtrate was concentrated under reduced pressure, and the crude product was purified by silica gel column chromatography (ethyl acetate:petroleum ether=10:90→20:80) to obtain compound AR-5.

MS (ESI) m/z $(M+H)^+$=296.0.

Step 5. Synthesis of Compound AR-6

Compound AR-5 (2.10 g, 7.14 mmol) was dissolved in ethanol (20 mL), diethylene glycol (20 mL) and 95% hydrazine hydrate (1.13 g, 21.4 mmol) were added, and the reaction was heated to 100° C. and the reaction was carried out for 2 hours. The system was cooled to room temperature, potassium hydroxide (801 mg, 14.3 mmol) was added, and the mixture was stirred at room temperature for 15 min, and the system was concentrated under reduced pressure to remove water and ethanol. The residue was heated to 200° C. and stirred for 1.5 hours. The system was cooled to room temperature, ice water (50 mL) was added, the mixture was extracted with ethyl acetate (100 mL×3), the organic phases were combined, dried over anhydrous sodium sulfate, filtered, and the filtrate was concentrated under reduced pressure, and the crude product was purified by silica gel column chromatography (ethyl acetate:petroleum ether=50:50) to obtain compound AR-6.

MS (ESI) m/z $(M+H)^+$=280.0.

Step 6-8. Synthesis of Compound Int-AR

According to the synthesis method of J-2→Int-J described in the preparation of intermediate Int-J, compound AR-6 was treated to obtain compound Int-AR.

$^1$H NMR (400 MHz, DMSO-$d_6$) δ 7.87-7.85 (m, 2H), 7.57-7.55 (m, 1H), 5.27-5.25 (m, 1H), 4.90 (s, 2H), 2.78-2.56 (m, 2H), 1.78-1.77 (m, 2H), 1.43 (s, 9H).

45) Preparation of Intermediate Int-AS

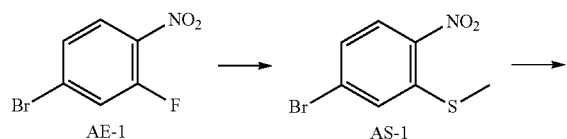

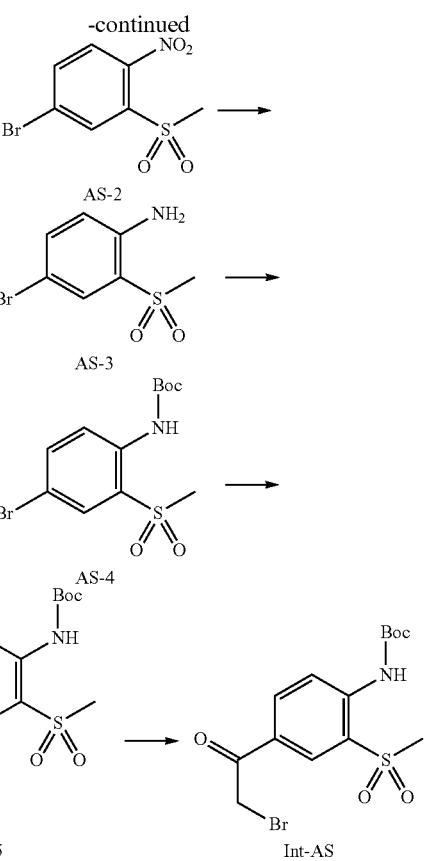

Step 1. Synthesis of Compound AS-1

At 0° C., compound AE-1 (6.60 g, 30.0 mmol) was dissolved in N, N-dimethylformamide (70.0 mL), and sodium thiomethoxide (5.04 g, 72.0 mol) was added, and the reaction was stirred for 2 hours at that temperature. The reaction mixture was poured into ice water (50.0 mL), a yellow solid was precipitated, the mixture was filtered and the solid was dried to obtain crude product AS-1, which was directly used in the next step without further purification.

MS (ESI) m/z $(M+H)^+$=248.0.

Step 2. Synthesis of Compound AS-2

At 0° C., compound AS-1 (3.60 g, 14.5 mmol) was dissolved in a mixed solvent of water/dichloromethane/acetonitrile (15.0 mL/9.00 mL/9.00 mL), sodium periodate (12.4 g, 58.0 mmol) and tetrapropylammonium perruthenate (1.02 g, 2.90 mmol) were slowly added sequentially, and the reaction was stirred at room temperature for 3 hours. The reaction mixture was poured into ice water (50.0 mL), the mixture was stirred for 10 min, extracted with dichloromethane (100 mL×2), the organic phases were combined, dried over anhydrous sodium sulfate, filtered, and the filtrate was concentrated under reduced pressure, and the crude product was purified by silica gel column chromatography (ethyl acetate:petroleum ether=35:65) to obtain compound AS-2.

$^1$H NMR (400 MHz, DMSO-$d_6$) δ 8.26-8.23 (m, 2H), 8.08-8.06 (m, 1H), 3.54 (s, 3H).

Step 3. Synthesis of Compound AS-3

Compound AS-2 (2.40 g, 8.57 mmol) was dissolved in ethanol (50.0 mL), reduced iron powder (4.80 g, 85.7 mmol) and ammonium chloride (2.30 g, 42.9 mmol) were added, and the reaction was heated to 80° C. and stirred for 16 hours. The system was cooled to room temperature, the mixture was filtered, and the filtrate was concentrated under reduced pressure, the crude product was purified by silica gel column chromatography (ethyl acetate:petroleum ether=50:50) to obtain compound AS-3.

MS (ESI) m/z (M+H)$^+$=252.0.

Step 4-6. Synthesis of Compound Int-AS

According to the synthesis method of J-2→Int-J described in the preparation of intermediate Int-J, compound AS-3 was treated to obtain compound Int-AS.

$^1$H NMR (400 MHz, DMSO-d$_6$) δ 9.27 (s, 1H), 8.43-8.37 (m, 2H), 8.30 (dd, J=8.9, 2.0 Hz, 1H), 4.95 (s, 2H), 3.40 (s, 3H), 1.51 (s, 9H).

46) Preparation of Intermediate Int-AT

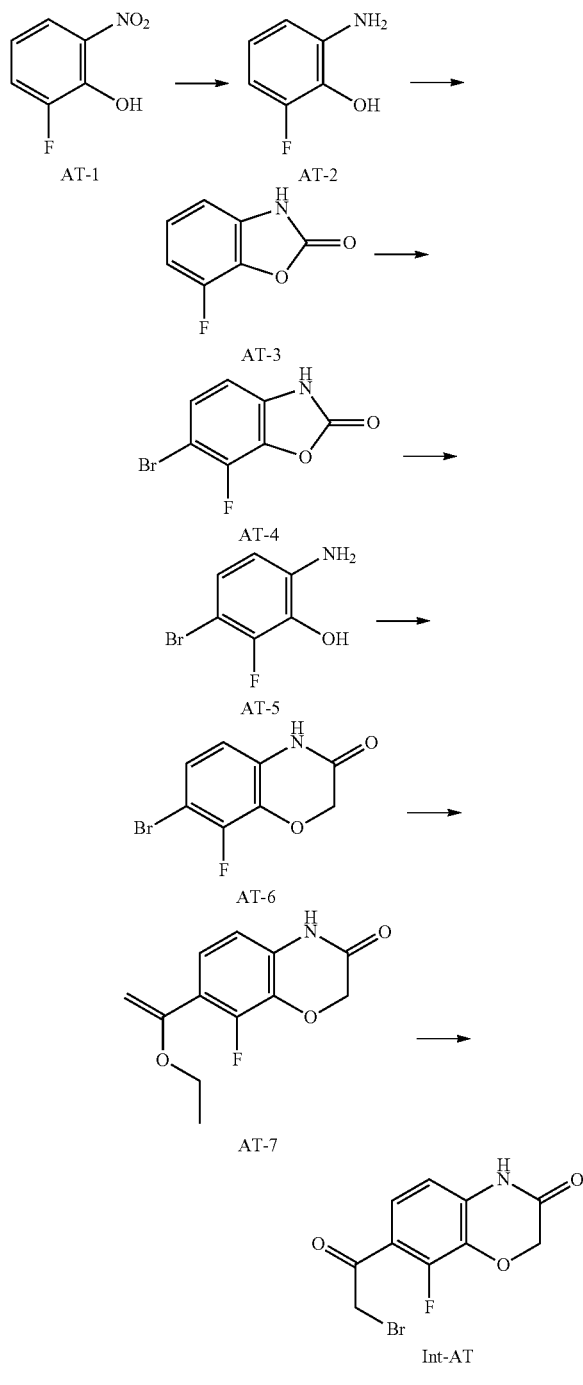

Step 1. Synthesis of Compound AT-2

Compound 2-fluoro-6-nitrophenol (5.00 g, 31.83 mmol) was dissolved in methanol (80.0 mL), and palladium/carbon (500 mg, 10% w/w) was added, and the reaction was stirred at room temperature for 2 hours under hydrogen atmosphere. The reaction mixture was filtered to remove the catalyst, the filtrate was concentrated to obtain crude product AT-2, which was directly used in the next step without further purification.

MS (ESI) m/z (M+H)$^+$=128.1.

Step 2. Synthesis of Compound AT-3

Under the protection of nitrogen, compound AT-2 (3.50 g, 27.53 mmol) was dissolved in tetrahydrofuran (30.0 mL), and N, N'-carbonyl diimidazole (8.04 g, 49.56 mmol) was added, and the reaction was heated to 60° C. and stirred for 2 hours. The system was cooled to room temperature, the pH was adjusted to 5.0 by adding 2.0 M hydrochloric acid, the mixture was extracted with ethyl acetate (200 mL×2), the organic phases were combined, washed with saturated saline (100 mL), dried over anhydrous sodium sulfate, filtered, the filtrate was concentrated under reduced pressure, and the crude product was purified by silica gel column chromatography (ethyl acetate:petroleum ether=15:85→20:80) to obtain compound AT-3.

$^1$H NMR (400 MHz, DMSO-d$_6$) δ 11.95 (s, 1H), 7.19-7.11 (m, 1H), 7.08-7.00 (m, 1H), 6.95 (dd, J=7.8 Hz, 1H)

Step 3. Synthesis of Compound AT-4

Compound AT-3 (2.00 g, 13.06 mmol) was dissolved in N, N-dimethylformamide (10.0 mL), and N-bromosuccinimide (2.32 g, 13.06 mmol) was slowly added, and the reaction was stirred at 25° C. for 3 hours. The crude product was purified by reverse phase C18 column chromatography (acetonitrile: 0.1% trifluoroacetic acid aqueous solution=5:95→95:5) to obtain compound AT-4.

$^1$H NMR (400 MHz, DMSO-d$_6$) δ 12.12 (s, 1H), 7.43 (dd, J=8.4 Hz, 1H), 6.97-6.89 (m, 1H).

Step 4. Synthesis of Compound AT-5

Compound AT-4 (2.50 g, 10.78 mmol) was dissolved in water (60.0 mL), sodium hydroxide (646.48 mg, 16.16 mmol) was added in batches, and the reaction was heated to 100° C. and stirred for 6 hours. The pH of the system was adjusted to 7.0 by adding 6.0 M hydrochloric acid, the mixture was extracted with ethyl acetate (300 mL), the organic phase was concentrated under reduced pressure, and the crude product was purified by reverse phase C18 column chromatography (acetonitrile: 0.1% aqueous trifluoroacetic acid=5:95→95:5) to obtain compound AT-5.

MS (ESI) m/z (M+H)$^+$=246.9.

Step 5-7. Synthesis of Compound Int-AT

According to the synthesis method of L-1→Int-L described in the preparation of intermediate Int-L, compound AT-5 was treated to obtain compound Int-AT.

MS (ESI) m/z (M+H)$^+$=287.9.

$^1$H NMR (400 MHz, DMSO-d$_6$) δ 11.26 (s, 1H), 7.52 (dd, J=8.5 Hz, 1H), 6.82 (dd, J=8.6 Hz, 1H), 4.77 (s, 2H), 4.74 (s, 2H).

47) Preparation of Intermediate Int-AU

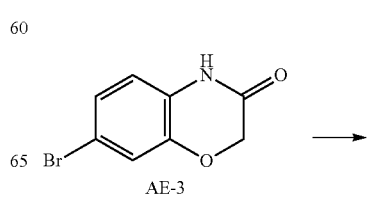

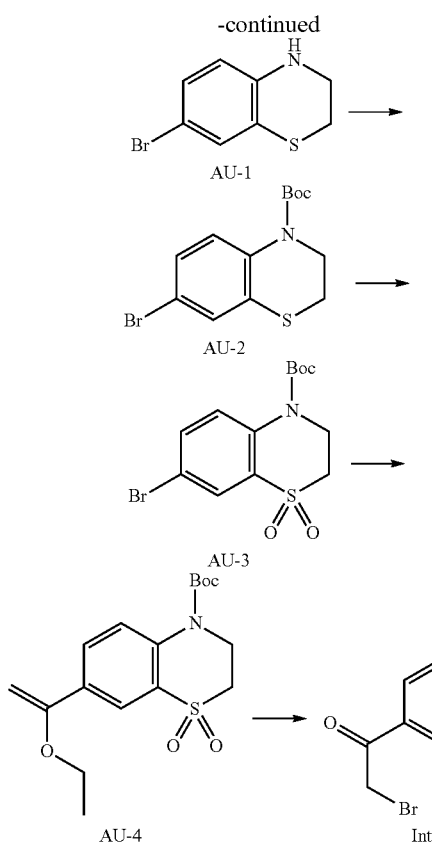

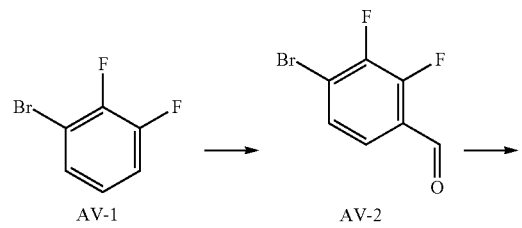

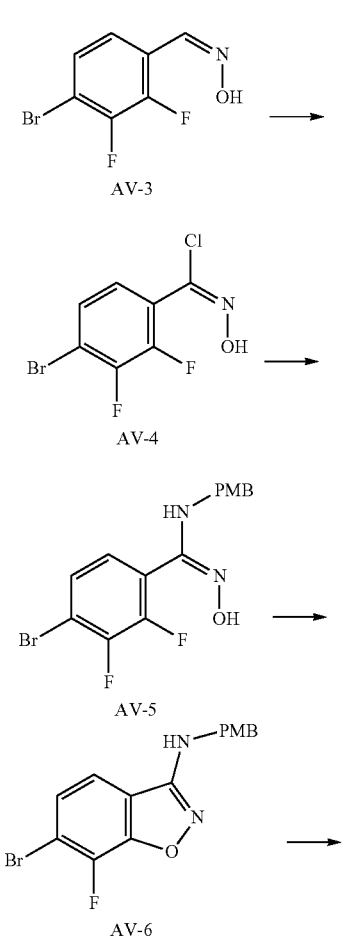

extracted with dichloromethane (50 mL×2), the organic phases were combined, dried over anhydrous sodium sulfate, filtered, and the filtrate was concentrated under reduced pressure, and the crude product was purified by silica gel column chromatography (ethyl acetate:petroleum ether=25:75) to obtain compound AU-3.

$^1$H NMR (400 MHz, DMSO-$d_6$) δ 7.87-7.86 (m, 1H), 7.80-7.77 (m, 1H), 7.70-7.68 (m, 1H), 4.24-4.22 (m, 2H), 3.83-3.80 (m, 2H), 1.49 (s, 9H).

Step 4-5. Synthesis of Compound Int-AU

According to the synthesis method of J-3→Int-J described in the preparation of intermediate Int-J, compound AU-3 was treated to obtain compound Int-AU.

MS (ESI) m/z (M−100+H)$^+$=304.0.

$^1$H NMR (400 MHz, DMSO-$d_6$) δ 8.32 (s, 1H), 8.17-8.14 (m, 1H), 7.94-7.91 (m, 1H), 4.96 (s, 2H), 4.31-4.28 (m, 2H), 3.87-3.84 (m, 2H), 1.50 (s, 9H).

48) Preparation of Intermediate Int-AV

Step 1. Synthesis of Compound AU-1

Compound AE-3 (2.44 g, 10.0 mmol) was dissolved in tetrahydrofuran (30 mL), and a solution of borane (50.0 mL, 50.0 mmol, 1.0 M) in tetrahydrofuran was added, and the reaction was stirred at room temperature for 2 hours. The system was quenched by adding water (50 mL), the mixture was extracted with ethyl acetate (50 mL×2), the organic phases were combined, dried over anhydrous sodium sulfate, filtered, and the filtrate was concentrated under reduced pressure, and the crude product was purified by silica gel column chromatography (ethyl acetate:petroleum ether=50:50) to obtain compound AU-1.

MS (ESI) m/z (M+H)$^+$=229.9.

Step 2. Synthesis of Compound AU-2

Compound AU-1 (2.00 g, 8.70 mmol) was dissolved in dichloromethane (30.0 mL), and di-tert-butyl dicarbonate (3.79 g, 17.4 mmol), triethylamine (1.76 g, 17.4 mmol) and 4-dimethylaminopyridine (212 mg, 1.74 mmol) were slowly added, and the reaction was stirred at 25° C. for 16 hours. The reaction mixture was concentrated under reduced pressure, the crude product was purified by silica gel column chromatography (ethyl acetate:petroleum ether=20:80) to obtain compound AU-2.

MS (ESI) m/z (M−55)$^+$=275.9.

Step 3. Synthesis of Compound AU-3

At 0° C., compound AU-2 (1.20 g, 3.64 mmol) was dissolved in a mixed solvent of water/dichloromethane/acetonitrile (15.0 mL/9.00 mL/9.00 mL), and sodium periodate (3.12 g, 14.6 mmol) and tetrapropylammonium perruthenate (256 mg, 0.728 mmol) were slowly added sequentially, and the reaction was stirred at room temperature for 3 hours. The reaction mixture was poured into ice water (50.0 mL), the mixture was stirred for 10 min,

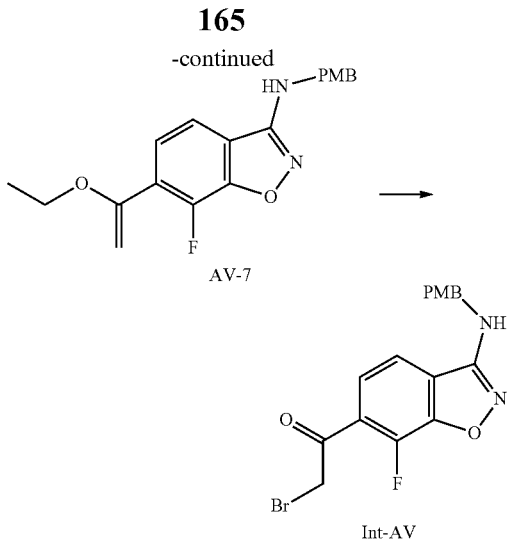

AV-7

Int-AV

Step 1. Synthesis of Compound AV-2

At 0° C., under the protection of nitrogen, compound 2, 2, 6, 6-tetramethylpiperidine (20.1 g, 142.4 mmol) was dissolved in tetrahydrofuran (120 mL), a solution of n-butyllithium (89.0 mL, 142.4 mmol, 1.6 M) in tetrahydrofuran was added dropwise, and the mixture was stirred for 1 hour at that temperature, cooled to −70° C., a solution of compound AV-1 (25 g, 130.2 mmol) in tetrahydrofuran solution (250 mL) was added, and the mixture was stirred at −70° C. for 1 hour for reaction, N, N-dimethylformamide (20 mL) was added dropwise, and the reaction was slowly warmed to room temperature and stirred for 16 hours. The system was quenched by adding saturated ammonium chloride solution (500 mL), extracted with ethyl acetate (800 mL×3), the organic phases were combined, washed with saturated saline (2000 mL), dried over anhydrous sodium sulfate, filtered, the filtrate was concentrated under reduced pressure, and the crude product was purified by silica gel column chromatography (dichloromethane:petroleum ether=0:100→10:90) to obtain compound AV-2.

$^1$H NMR (400 MHz, CDCl$_3$) δ 10.31 (d, J=0.5 Hz, 1H), 7.60-7.43 (m, 2H).

Step 2. Synthesis of Compound AV-3

Compound AV-2 (2 g, 9.1 mmol) was dissolved in ethanol/water (30 mL, v/v=8/1), and hydroxylamine hydrochloride (1.25 g, 18.2 mmol) and sodium acetate (2.24 g, 27.3 mmol) were added sequentially, and the reaction was stirred for 2 hours at room temperature. The system was concentrated under reduced pressure to remove the organic solvent, filtered, and the solid was washed with water (20 mL) and dried under vacuum to obtain crude product AV-3, which was used directly in the next step without further purification.

$^1$H NMR (400 MHz, CDCl$_3$) δ 8.30 (s, 1H), 7.88 (s, 1H), 7.47-7.30 (m, 2H).

Step 3. Synthesis of Compound AV-4

Compound AV-3 (2.1 g, 8.94 mmol) was dissolved in N, N-dimethylformamide (20 mL), and chlorosuccinimide (1.19 g, 8.94 mmol) was added, and the reaction was stirred at room temperature for 1 hour. The system was quenched by adding water (100 mL), the mixture was extracted by ethyl acetate (80 mL×3), the organic phases were combined, washed with saturated saline (250 mL), dried over anhydrous sodium sulfate, filtered, and the filtrate was concentrated under reduced pressure to obtain crude product AV-4, which was used directly in the next step without further purification.

$^1$H NMR (400 MHz, CDCl$_3$) δ 8.60 (s, 1H), 7.44-7.30 (m, 2H).

Step 4. Synthesis of Compound AV-5

Compound AV-4 (1 g, 3.72 mmol) and triethylamine (375 mg, 3.72 mmol) were dissolved in methanol (15 mL), and p-methoxybenzylamine (509 mg, 3.72 mmol) was added, and the reaction was stirred at room temperature for 1 hour. The system was concentrated under reduced pressure, the crude product was purified by silica gel column chromatography (ethyl acetate:petroleum ether=0:100→50:50) to obtain compound AV-5.

MS (ESI) m/z (M+H)$^+$=370.9.

Step 5. Synthesis of Compound AV-6

Compound AV-5 (940 mg, 2.54 mmol) and 1, 8-diazabicycloundec-7-ene (425 mg, 2.79 mmol) were dissolved in tetrahydrofuran (5 mL). The reaction was heated to 110° C. and stirred for 1 hour under microwave conditions. The system was concentrated under reduced pressure, the crude product was purified by silica gel column chromatography (ethyl acetate:petroleum ether=0:100→25:75) to obtain compound AV-6.

MS (ESI) m/z (M+H)$^+$=350.9.

Step 6-7. Synthesis of Compound Int-AV

According to the synthesis method of J-3→Int-J described in the preparation of intermediate Int-J, compound AV-6 was treated to obtain compound Int-AV.

MS (ESI) m/z (M+H)$^+$=394.8.

$^1$H NMR (400 MHz, DMSO) δ 7.90-7.69 (m, 3H), 7.34 (d, J=8.6 Hz, 2H), 6.92 (d, J=8.6 Hz, 2H), 4.93 (d, J=2.0 Hz, 2H), 4.39 (d, J=5.6 Hz, 2H), 3.74 (s, 3H).

49) Preparation of Intermediate Int-AW

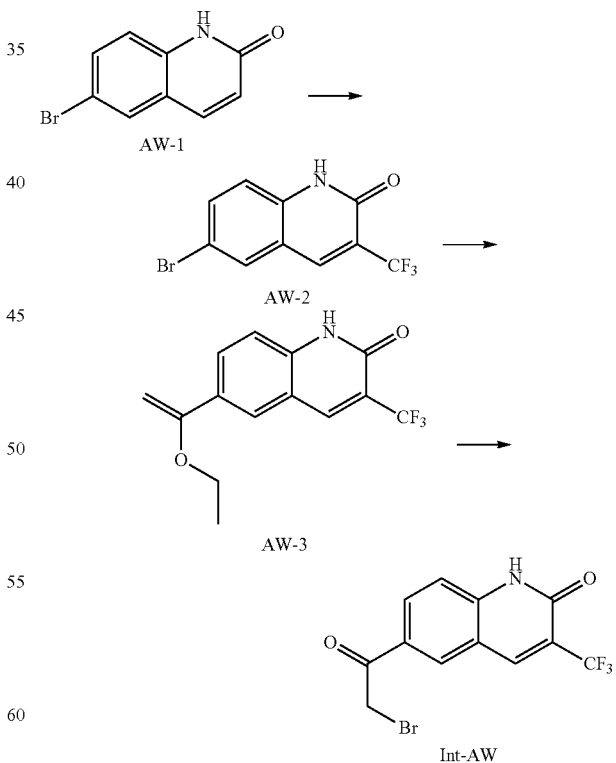

Step 1. Synthesis of Compound AW-2

Compounds 6-bromoquinolin-2-one (3.00 g, 13.39 mmol), manganese triacetate dihydrate (14.36 g, 53.56 mmol) and sodium trifluoromethanesulfinate (6.27 g, 40.17 mmol) were dissolved in glacial acetic acid (100 mL), and the reaction was stirred at 25° C. for 24 hours. Water (350 mL) was added to the system, the mixture was extracted with ethyl acetate (500 mL×2), the organic phases were combined, washed with saturated saline (300 mL), dried over anhydrous sodium sulfate, filtered, the filtrate was concentrated under reduced pressure, and the crude product was purified by silica gel column chromatography (ethyl acetate:petroleum ether=5:95→10:90) to obtain compound AW-2.

MS (ESI) m/z (M+H)$^+$=293.9.

Step 2-3. Synthesis of Compound Int-AW

According to the synthesis method of J-3→Int-J described in the preparation of intermediate Int-J, compound AW-2 was treated to obtain compound Int-AW.

$^1$H NMR (400 MHz, DMSO-d$_6$) δ 12.66 (s, 1H), 8.67-8.64 (m, 2H), 8.23 (dd, J=8.7 Hz, 1H), 7.45 (d, J=8.7 Hz, 1H), 4.90 (s, 2H).

50) Preparation of Intermediate Int-AX

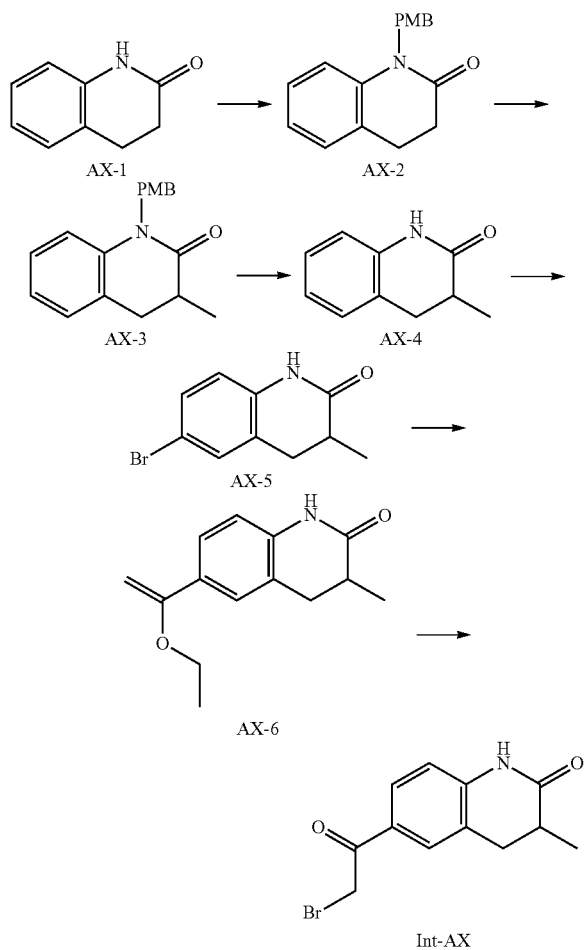

Step 1. Synthesis of Compound AX-2

At 0° C., compound AX-1 (5.89 g, 40.0 mmol) was dissolved in N, N-dimethylformamide (60 mL), sodium hydride (2.08 g, 52.0 mmol, 60%) was added in batches, and the mixture was stirred for 0.5 hours at that temperature, p-methoxybenzyl chloride (8.14 g, 52.0 mmol) was added dropwise, and the reaction was warmed to 25° C. and stirred for 19 hours. The reaction mixture was quenched by adding water (100 mL), the mixture was extracted with ethyl acetate (200 mL×2), the organic phases were combined, dried over anhydrous sodium sulfate, filtered, and the filtrate was concentrated under reduced pressure, and the crude product was purified by silica gel column chromatography (ethyl acetate:petroleum ether=20:80) to obtain compound AX-2.

MS (ESI) m/z (M+H)$^+$=268.1.

Step 2. Synthesis of Compound AX-3

At −78° C., compound AX-2 (2.67 g, 10.0 mmol) was dissolved in tetrahydrofuran (30 mL), and lithium bis(trimethylsilyl)amide (11.4 mL, 11.4 mmol, 1.0 M tetrahydrofuran solution) was slowly added dropwise, and the mixture was stirred at this temperature for 0.5 hours, iodomethane (1.56 g, 11.0 mmol) was slowly added dropwise, after the dropwise addition was completed, the reaction was slowly warmed to room temperature and stirred for 16 hours. The reaction mixture was quenched by adding water (50 mL), the mixture was extracted with ethyl acetate (50 mL×2), the organic phases were combined, dried over anhydrous sodium sulfate, filtered, and the filtrate was concentrated under reduced pressure, and the crude product was purified by silica gel column chromatography (ethyl acetate:petroleum ether=10:90) to obtain compound AX-3.

MS (ESI) m/z (M+H)$^+$=282.1.

Step 3. Synthesis of Compound AX-4

Compound AX-3 (1.94 g, 6.90 mmol) was dissolved in trifluoroacetic acid (7.87 g, 69.0 mmol), anisole (746 mg, 6.90 mmol) was added, and the reaction was heated to 65° C. and stirred for 3 hours. The system was cooled to room temperature, concentrated under reduced pressure, the crude product was purified by silica gel column chromatography (ethyl acetate:petroleum ether=25:75) to obtain compound AX-4.

MS (ESI) m/z (M+H)$^+$=162.1.

Step 4. Synthesis of Compound AX-5

Compound AX-4 (1.02 g, 6.34 mmol) was dissolved in N, N-dimethylformamide (15.0 mL), and N-bromosuccinimide (2.29 g, 6.34 mmol) was added, and the reaction was stirred at 25° C. for 3 hours. Water (50 mL) was added to the system, the mixture was extracted with ethyl acetate (50 mL×2), the organic phases were combined, dried over anhydrous sodium sulfate, filtered, and the filtrate was concentrated under reduced pressure, and the crude product was purified by silica gel column chromatography (ethyl acetate:petroleum ether=20:80) to obtain compound AX-5.

MS (ESI) m/z (M+H)$^+$=239.9.

Step 5-6. Synthesis of Compound Int-AX

According to the synthesis method of J-3→Int-J described in the preparation of intermediate Int-J, compound AX-5 was treated to obtain compound Int-AX.

MS (ESI) m/z (M+H)$^+$=282.0.

$^1$H NMR (400 MHz, DMSO-d$_6$) δ 10.47 (br, 1H), 7.85-7.82 (m, 2H), 6.96-6.94 (m, 1H), 4.81 (s, 2H), 3.02-3.01 (m, 1H), 2.73-2.51 (m, 2H), 1.14 (d, J=3.4 Hz, 3H).

51) Preparation of Intermediate Int-AY

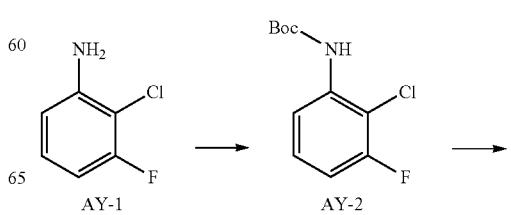

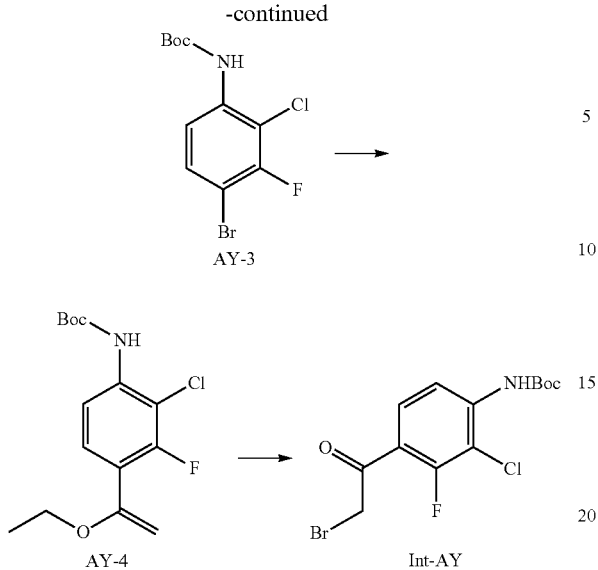

Step 1. Synthesis of Compound AY-2

At 0° C., under the protection of nitrogen, compound AY-1 (1.0 mg, 6.87 mmol) was dissolved in tetrahydrofuran (7 mL), and lithium bis(trimethylsilyl)amide (13.8 mL, 13.8 mmol, 1.0 M tetrahydrofuran solution) was added dropwise, and the mixture was slowly warmed to room temperature, and a solution of di-tert-butyl dicarbonate (1.50 g, 6.87 mmol) in tetrahydrofuran (4 mL) was added dropwise, and the reaction was stirred at room temperature for 1 hour. The system was concentrated under reduced pressure, the crude product was purified by silica gel column chromatography (ethyl acetate:petroleum ether=0:100→10 90) to obtain compound AY-2.

MS (ESI) m/z (M−55)$^+$=190.0.

Step 2. Synthesis of Compound AY-3

At 0° C., compound AY-2 (690 mg, 2.81 mmol) was dissolved in N, N-dimethylformamide (4 mL), and bromosuccinimide (474 mg, 2.67 mmol) was added in batches, and the reaction was stirred at room temperature for 40 hours. The crude product was purified by reverse phase C18 column chromatography (acetonitrile: 0.5% trifluoroacetic acid aqueous solution=5:95→95:5) to obtain compound AY-3.

$^1$H NMR (400 MHz, DMSO-d$_6$) δ 9.00 (s, 1H), 7.64 (dd, J=8.9, 7.7 Hz, 1H), 7.45 (dd, J=9.0, 1.7 Hz, 1H), 1.47 (s, 9H).

Step 3-4. Synthesis of Compound Int-AY

According to the synthesis method of J-3→Int-J described in the preparation of intermediate Int-J, compound AY-3 was treated to obtain compound Int-AY $^1$H NMR (400 MHz, DMSO-d$_6$) δ 9.16 (s, 1H), 7.92-7.80 (dd, J=8.8, 8.0 Hz, 1H), 7.77 (d, J=9.3 Hz, 1H), 4.82 (d, J=2.3 Hz, 2H), 1.49 (s, 9H).

EMBODIMENTS OF SPECIFIC COMPOUND PREPARATION

Embodiment 1: Preparation of Compound 1

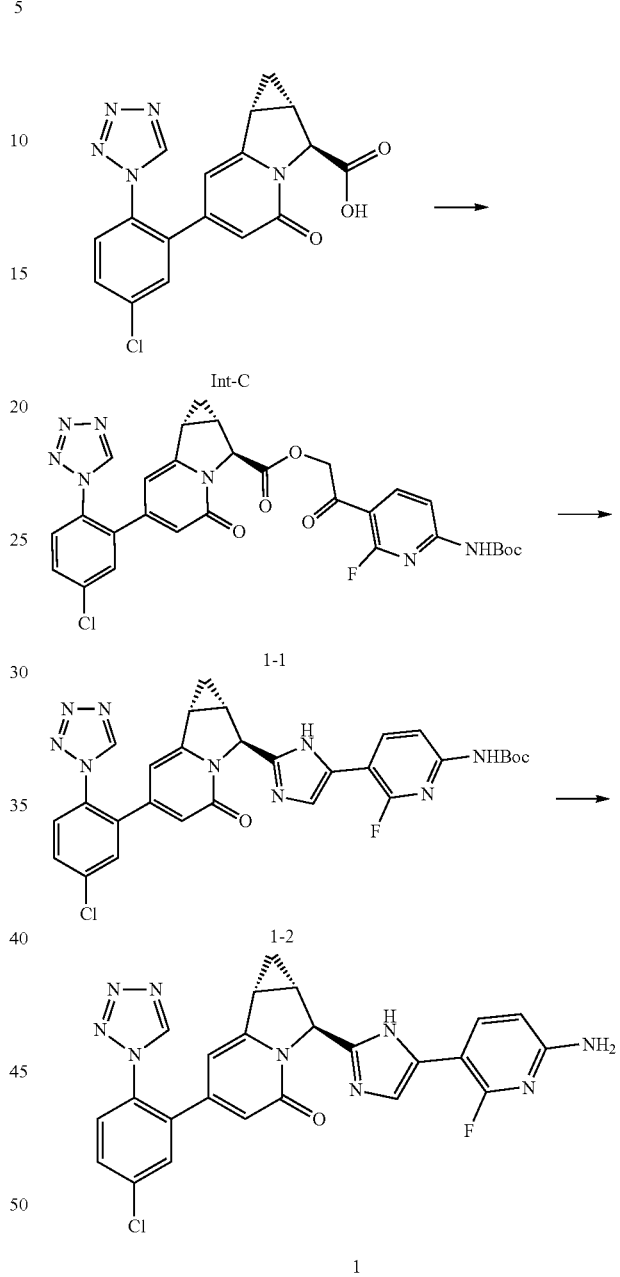

Step 1. Synthesis of Compound 1-1

Compounds Int-C (34.0 mg, 0.11 mmol) and Int-J (40 mg, 0.12 mmol) were dissolved in N, N-dimethylformamide (2 mL), and potassium carbonate (22.4 mg, 0.16 mmol) was added. The mixture was stirred at room temperature for 4 hours, diluted with ethyl acetate (100 mL), and the organic phase was washed with saturated ammonium chloride aqueous solution (30 mL), dried over anhydrous sodium sulfate, filtered, and the filtrate was concentrated to dryness under reduced pressure, and the crude product was purified by silica gel column chromatography (petroleum ether:ethyl acetate=100:0→50:50) to obtain compound 1-1.

MS (ESI) m/z (M+H)$^+$=622.2.

Step 2. Synthesis of Compound 1-2

Compound 1-1 (50 mg, 0.08 mmol) was dissolved in toluene (2 mL) and glacial acetic acid (0.2 mL), ammonium acetate (61.6 mg, 0.8 mmol) was added, the reaction system was heated to 100° C. and stirred for 16 hours in a sealed tube, the reaction system was cooled to room temperature, and the solvent was removed by concentration under reduced pressure, the crude product was purified by silica gel column chromatography (petroleum ether:ethyl acetate=100:0→50:50) to obtain compound 1-2.

MS (ESI) m/z (M+H)$^+$=602.1.

Step 3. Synthesis of Compound 1

Compounds 1-2 (25 mg, 0.041 mmol) were dissolved in dichloromethane (2 mL), trifluoroacetic acid (2 mL) was added, the mixture was stirred for 3 hours at room temperature. The mixture was concentrated under reduced pressure, and the crude product was separated by preparative high performance liquid chromatography (column: Xtimate® C18 10 μm 21.2*250 mm; mobile phase: [water (10 mM ammonium bicarbonate)-acetonitrile]; flow rate: 30 mL/min) to obtain compound 1 (HPLC retention time: 4.290 min).

MS (ESI) m/z (M+H)$^+$=502.1.

$^1$H NMR (400 MHz, DMSO-d$_6$) δ 9.68 (s, 1H), 8.03 (s, 1H), 7.90-7.79 (m, 3H), 7.20 (s, 1H), 6.50 (dd, J=8.3, 2.0 Hz, 1H), 6.13 (d, J=1.6 Hz, 1H), 6.00 (d, J=1.6 Hz, 1H), 5.56 (s, 1H), 2.83 (s, 1H), 2.28 (q, J=6.4 Hz, 1H), 1.42 (td, J=8.1, 5.0 Hz, 1H), 0.61 (d, J=4.0 Hz, 1H).

Embodiment 2: Preparation of Compound 2

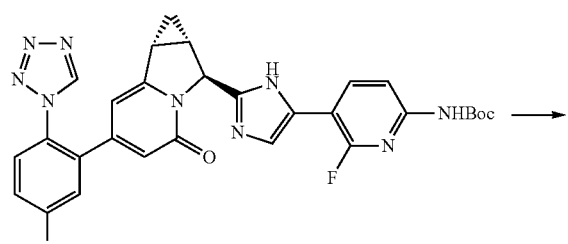

1-2

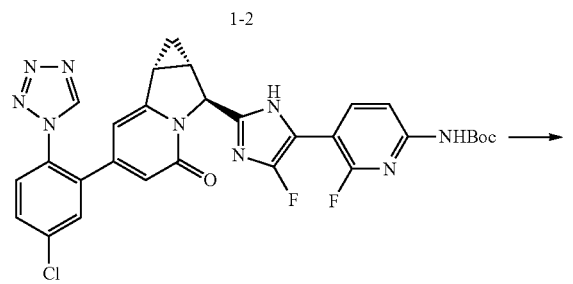

2-1

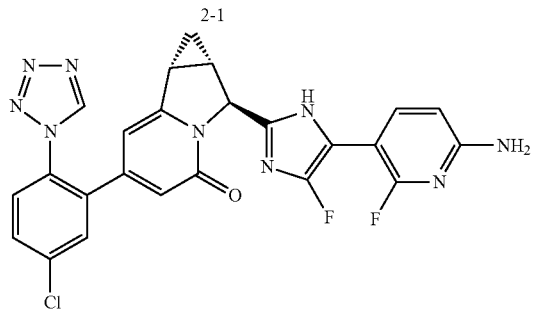

2

Step 1. Synthesis of Compound 2-1

Compound 1-2 (32 mg, 0.053 mmol) and pyridine (0.012 mL, 0.16 mmol) were dissolved in tetrahydrofuran (0.5 mL) and acetonitrile (1.5 mL), and the mixture was cooled to −18° C., and bis(tetrafluoroborate) salt of 1-chloromethyl-4-fluoro-1, 4-diazabicyclo[2. 2. 2]octane (28.2 mg, 0.079 mmol) was added to the reaction system, the mixture was stirred for 2 hours, and ethyl acetate (5 mL), sodium sulfite aqueous solution (5 mL) and water (5 mL) were added sequentially, the organic phase was separated, the aqueous phase was extracted with ethyl acetate (5 mL×3). The organic phases were combined and washed with 1.0 M hydrochloric acid (5 mL), saturated sodium bicarbonate aqueous solution (5 mL), saturated saline (5 mL) sequentially, dried over anhydrous sodium sulfate, filtered, and the filtrate was concentrated to dryness under reduced pressure, and the crude product was purified by silica gel column chromatography (petroleum ether:ethyl acetate=20:80→0:100) to obtain compound 2-1.

MS (ESI) m/z (M+H)$^+$=620.2.

Step 2. Synthesis of Compound 2

Compounds 2-1 (20 mg, 0.032 mmol) were dissolved in dichloromethane (2 mL), and trifluoroacetic acid (2 mL) was added, and the mixture was stirred for 3 hours at room temperature. The solvent was removed by concentration under reduced pressure, and the crude product was separated by preparative high performance liquid chromatography (column: Xtimate® C18 10 μm 21.2*250 mm; mobile phase: [water (10 mM ammonium bicarbonate)-acetonitrile]; flow rate: 30 mL/min) to obtain compound 2 (HPLC retention time: 4.778 min).

MS (ESI) m/z (M+H)$^+$=520.2.

$^1$H NMR (400 MHz, DMSO-d$_6$) δ 12.38 (s, 1H), 9.60 (s, 1H), 7.75-7.73 (m, 3H), 7.51 (dd, J=10.3, 8.2 Hz, 1H), 6.50 (s, 2H), 6.34 (dd, J=8.3, 1.9 Hz, 1H), 5.93 (d, J=1.6 Hz, 1H), 5.85 (d, J=1.7 Hz, 1H), 5.34 (s, 1H), 2.69-2.63 (m, 1H), 2.12 (q, J=6.4 Hz, 1H), 1.23 (td, J=8.0, 4.8 Hz, 1H), 0.50 (q, J=4.4 Hz, 1H).

Embodiment 3: Preparation of Compound 3

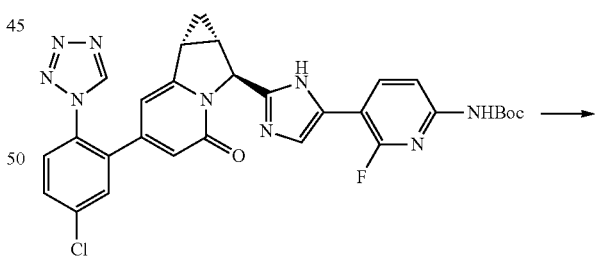

1-2

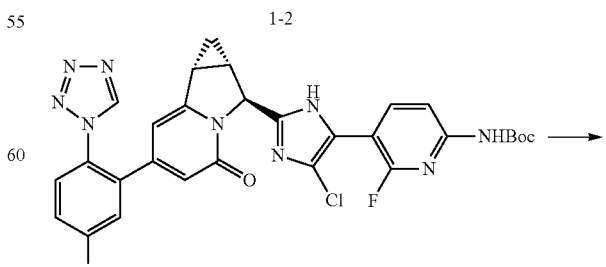

3-1

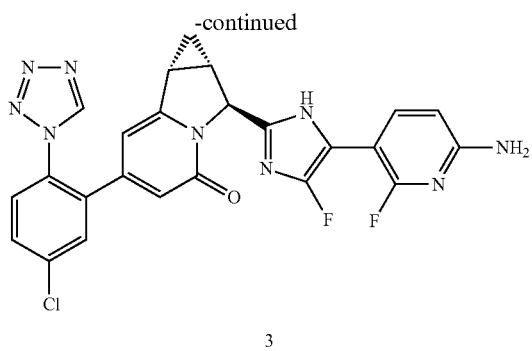

3

Step 1. Synthesis of Compound 3-1

Compound 1-2 (20 mg, 0.033 mmol) was dissolved in tetrahydrofuran (2.0 mL), and N-chlorosuccinimide (4.4 mg, 0.033 mmol) was added, and the reaction was stirred at room temperature for 72 hours. The reaction mixture was concentrated under reduced pressure, the crude product was purified by silica gel column chromatography (petroleum ether:ethyl acetate=20:80) to obtain compound 3-1.

Step 2. Synthesis of Compound 3

Compound 3-1 (10 mg, 0.016 mmol) was dissolved in dichloromethane (2 mL), and trifluoroacetic acid (2 mL) was added, the mixture was stirred for 2 hours at room temperature. The solvent was removed by concentration under reduced pressure, and the crude product was separated by preparative high performance liquid chromatography (column: Xtimate® C18 10 μm 21.2*250 mm; mobile phase: [water (10 mM ammonium bicarbonate)-acetonitrile]; flow rate: 30 mL/min) to obtain compound 2 (HPLC retention time: 4.800 min).

MS (ESI) m/z (M+H)$^+$=536.2.

$^1$H NMR (400 MHz, DMSO-d$_6$) δ 12.71 (s, 1H), 9.67 (s, 1H), 7.81 (s, 3H), 7.61 (dd, J=10.3, 8.2 Hz, 1H), 6.66 (s, 2H), 6.41 (dd, J=8.3, 1.9 Hz, 1H), 6.01 (d, J=1.7 Hz, 1H), 5.91 (d, J=1.7 Hz, 1H), 5.40 (s, 1H), 2.76-2.72 (i, 1H), 2.21-2.17 (i, 1H), 1.32-1.27 (i, 1H), 0.62-0.53 (i, 1H).

Embodiment 4-9

Intermediates Int-D, Int-E, Int-F, Int-G, Int-H, Int-I and Int-U were used as raw materials and the reaction was carried out with intermediate Int-J according to the synthesis method described in the preparation of embodiment 1 to obtain the target compounds, and the data were shown in Table 1 below.

TABLE 1

Structure and analytical data of compounds in embodiments 4-9

| Embodiment | Structural formula | Analytical data |
|---|---|---|
| Embodiment 4 | (structure with Cl-triazole, chlorophenyl, pyridinyl-NH$_2$, F) | MS (ESI) m/z (M + H)$^+$ = 535.1.<br>$^1$H NMR (400 MHz, DMSO-d$_6$) δ 12.16 (s, 1H), 8.64 (s, 1H), 7.95 (t, J = 9.3 Hz, 1H), 7.77-7.73 (m, 3H), 7.11 (d, J = 3.3 Hz, 1H), 6.36 (d, J = 8.4 Hz, 1H), 6.25 (s, 2H), 5.98-5.95 (m, 2H), 5.46 (s, 1H), 2.76 (br s, 1H), 2.26-2.24 (m, 1H), 1.33-1.30 (m, 1H), 0.57-0.54 (m, 1H). |
| Embodiment 5 | (structure with CF$_3$-triazole, chlorophenyl, pyridinyl-NH$_2$, F) | MS (ESI) m/z (M + H)$^+$ = 569.2.<br>$^1$H NMR (400 MHz, DMSO-d$_6$) δ 9.14 (s, 1H), 7.93-7.79 (m, 3H), 7.76 (d, J = 2.1 Hz, 1H), 6.42 (dd, J = 8.3, 2.1 Hz, 1H), 6.07-5.95 (m, 2H), 5.60 (s, 1H), 2.79 (br s, 1H), 2.41-2.36 (m, 1H), 1.42-1.31 (m, 1H), 0.67 (br s, 1H) |
| Embodiment 6 | (structure with CF$_2$H-triazole, chlorophenyl, pyridinyl-NH$_2$, F) | MS (ESI) m/z (M + H)$^+$ = 551.2.<br>$^1$H NMR (400 MHz, DMSO-d$_6$) δ 8.74 (s, 1H), 7.88 (dd, J = 10.5, 8.3 Hz, 1H), 7.79 (d, J = 2.0 Hz, 2H), 7.73 (d, J = 1.7 Hz, 1H), 7.24 (s, 2H), 6.64 (s, 2H), 6.41 (dd, J = 8.3, 2.1 Hz, 1H), 6.02-5.97 (m, 2H), 5.58 (s, 1H), 2.77 (q, J = 4.6, 3.9 Hz, 1H), 2.37 (d, J = 6.0 Hz, 1H), 1.35 (td, J = 8.1, 4.9 Hz, 1H), 0.67 (s, 1H). |

TABLE 1-continued

Structure and analytical data of compounds in embodiments 4-9

| Embodiment | Structural formula | Analytical data |
|---|---|---|
| Embodiment 7 | | MS (ESI) m/z (M + H)$^+$ = 545.2.<br>$^1$H NMR (400 MHz, DMSO-d$_6$) δ 8.94 (s, 1H), 7.87 (dd, J = 10.5, 8.2 Hz, 1H), 7.81-7.75 (m, 2H), 7.72 (d, J = 2.2 Hz, 1H), 7.45 (s, 1H), 6.43 (dd, J = 8.3, 2.0 Hz, 1H), 6.10 (s, 1H), 5.98 (d, J = 1.8 Hz, 1H), 5.60 (s, 1H), 2.83-2.75 (m, 1H), 2.40-2.37 (m, 1H), 1.36 (td, J = 8.2, 4.9 Hz, 1H), 0.75-0.56 (m, 1H). |
| Embodiment 8 | | MS (ESI) m/z: (M + H)$^+$ = 502.2<br>$^1$H NMR (400 MHz, DMSO-d$_6$) δ 12.50-12.42 (s, 1H), 7.79-7.75 (d, J = 8.6 Hz, 1H), 7.70-7.66 (dd, J = 2.2, 8.5 Hz, 1H), 7.63-7.57 (dd, J = 8.2, 10.3 Hz, 1H), 7.55-7.52 (d, J = 2.0 Hz, 1H), 7.26-6.79 (m, 2H), 6.44-6.40 (dd, J = 2.0, 8.2 Hz, 1H), 6.40-6.38 (d, J = 1.7 Hz, 1H), 6.10-6.08 (d, J = 1.7 Hz, 1H), 5.51-5.47 (s, 1H), 2.91-2.84 (ddd, J = 3.3, 7.0, 9.2 Hz, 1H), 2.31-2.24 (m, 1H), 1.41-1.33 (td, J = 4.8, 8.0 Hz, 1H), 0.77-0.72 (q, J = 4.4 Hz, 1H). |
| Embodiment 9 | | MS (ESI) m/z (M + H)$^+$ = 503.1.<br>$^1$H NMR (400 MHz, DMSO-d$_6$) δ 12.29 (s, 1H), 9.77-9.69 (m, 1H), 8.03-7.81 (m, 4H), 7.24-7.09 (m, 1H), 6.45-6.21 (m, 4H), 5.49 (d, J = 1.8 Hz, 1H), 2.23 (td, J = 9.8, 8.5, 4.2 Hz, 1H), 1.34 (td, J = 8.0, 4.8 Hz, 2H), 0.84 (q, J = 4.5 Hz, 1H). |
| Embodiment 10 | | MS (ESI) m/z (M + H)$^+$ = 520.1.<br>$^1$H NMR (400 MHz, CD$_3$OD) δ 9.35 (s, 1 H), 7.94-7.84 (m, 2 H), 7.59-7.56 (m, 1H), 7.33 (s, 1 H), 6.50-6.48 (m, 1 H), 6.32 (s, 1 H), 6.13 (s, 1 H), 5.69 (s, 1 H), 2.92-2.90 (m, 1 H), 2.42-2.41 (m, 1 H), 1.50-1.48 (m, 1 H), 0.75-0.74 (m, 1 H). |

Embodiment 11-14

Intermediates Int-D, Int-E, Int-F, Int-I were used as raw materials and the reaction was carried out with intermediate Int-J respectively according to the synthesis method described in the preparation of embodiment 1→the preparation of embodiment 2 to obtain compounds 11-14, and the data were shown in Table 2 below.

TABLE 2

Structure and analytical data of compounds in embodiments

| Embodiment | Structural formula | Analytical data |
|---|---|---|
| Embodiment 11 | | MS (ESI) m/z (M + H)⁺ = 553.0.<br>$^1$H NMR (400 MHz, DMSO-$d_6$) δ 12.43 (s, 1H), 8.63 (s, 1H), 7.79-7.73 (m, 3H), 7.58 (dd, J = 10.4, 8.2 Hz, 1H), 6.57 (s, 2H), 6.41 (dd, J = 8.2, 1.9 Hz, 1H), 5.97-5.94 (m, 2H), 5.42 (s, 1H), 2.76-2.72 (m, 1H), 2.22-2.17 (m, 1H), 1.32-1.28 (m, 1H), 0.57-0.54 (m, 1H). |
| Embodiment 12 | | MS (ESI) m/z (M + H)⁺ = 587.2.<br>$^1$H NMR (400 MHz, DMSO-$d_6$) δ 12.41 (s, 1H), 9.13 (s, 1H), 7.86-7.77 (m, 3H), 7.57 (dd, J = 10.3, 8.2 Hz, 1H), 6.57 (s, 2H), 6.41 (dd, J = 8.3, 2.0 Hz, 1H), 5.98 (s, 1H), 5.87 (s, 1H), 5.41 (s, 1H), 2.72-2.68 (m, 1H), 2.21-2.16 (m, 1H), 1.31-1.25 (m, 1H), 0.49-0.46 (m, 1H). |
| Embodiment 13 | | MS (ESI) m/z (M + H)⁺ = 569.2.<br>$^1$H NMR (400 MHz, DMSO-$d_6$) δ 12.42 (s, 1H), 8.75-8.72 (m, 1H), 7.77 (s, 3H), 7.57 (dd, J = 10.3, 8.3 Hz, 1H), 7.25 (d, J = 56 Hz,, 1H), 6.57 (s, 2H), 6.41 (dd, J = 8.2, 2.0 Hz, 1H), 5.98 (d, J = 1.8 Hz, 1H), 5.87 (d, J = 1.7 Hz, 1H), 5.41 (s, 1H), 2.72-2.67 (m, 1H), 2.21-2.16 (m, 1H), 1.27 (td, J = 8.0, 4.8 Hz, 1H), 0.50 (q, J = 4.4 Hz, 1H). |
| Embodiment 14 | | MS (ESI) m/z (M + H)⁺ = 521.2.<br>$^1$H NMR (400 MHz, DMSO-$d_6$) δ 12.51 (s, 1H), 9.72 (s, 1H), 7.97 (d, J = 2.3 Hz, 1H), 7.86-7.80 (m, 2H), 7.57 (dd, J = 10.4, 8.2 Hz, 1H), 6.58 (s, 2H), 6.41 (dd, J = 8.3, 2.0 Hz, 1H), 6.30 (s, 1H), 5.43 (s, 1H), 2.48-2.47 (m, 1H), 2.24-2.20 (m, 1H), 1.34-1.31 (m, 1H), 0.86-0.82 (m, 1H). |

Embodiment 15

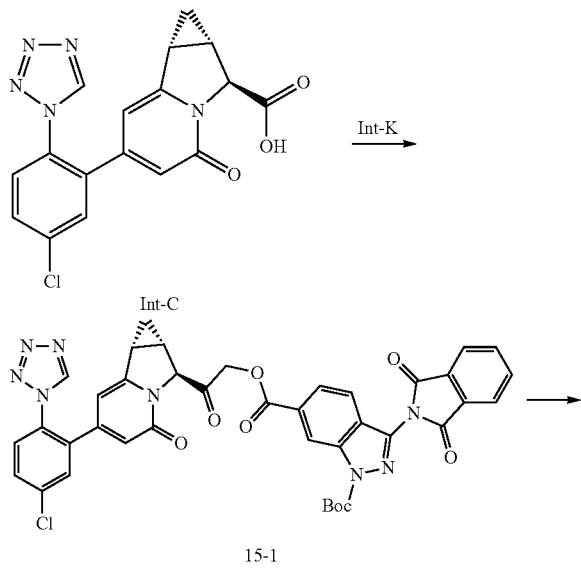

Step 1. Synthesis of Compound 15-1

Compound Int-C (20 mg, 0.054 mmol) was dissolved in N,N-dimethylformamide (1 mL), and diisopropylethylamine (21 mg, 0.162 mmol) and Int-K (39.3 mg, 0.081 mmol) were added sequentially. The reaction was stirred at 25° C. for 16 hours. The reaction mixture was filtered and concentrated under reduced pressure, the crude product was purified by silica gel column chromatography (petroleum ether: ethyl acetate=80:20→100:0) to obtain compound 15-1.

MS (ESI) m/z (M+H)$^+$=773.1.

Step 2. Synthesis of Compound 15-2

Compound 15-1 (15 mg, 0.194 mmol) was dissolved in toluene (2 mL) and acetic acid (0.2 mL), and ammonium acetate (29 mg, 3.8 mmol) was added, and the reaction was heated to 110° C. and stirred for 16 hours. The reaction mixture was concentrated under reduced pressure, the crude product was purified by silica gel column chromatography (ethyl acetate:petroleum ether=80:20→100:0) to obtain compound 15-2.

MS (ESI) m/z (M+H)$^+$=653.2.

Step 3. Synthesis of Compound 15

Compound 15-2 (10 mg, 0.015 mmol) was dissolved in methanol (0.5 mL), hydrazine hydrate (0.5 mL) was added, and the reaction was stirred at room temperature for 3 hours. The reaction mixture was concentrated under reduced pressure, and the crude product was separated by preparative high performance liquid chromatography (column: Xtimate® C18 10 μm 21.2*250 mm; mobile phase: [water (10 mM acetic acid)-acetonitrile]; flow rate: 30 mL/min) to obtain compound 15 (HPLC retention time: 3.192 min).

MS (ESI) m/z (M+H)$^+$=523.2.

$^1$H NMR (400 MHz, Methanol-d$_4$) δ 9.26 (s, 1H), 7.67-7.46 (m, 5H), 7.34-7.19 (m, 2H), 6.08 (d, J=1.6 Hz, 1H), 5.98 (d, J=1.7 Hz, 1H), 5.54 (s, 1H), 4.50 (s, 1H), 2.82-2.69 (m, 1H), 2.31-2.20 (m, 1H), 1.38-1.33 (m, 1H), 0.58 (q, J=4.5 Hz, 1H).

Embodiment 16

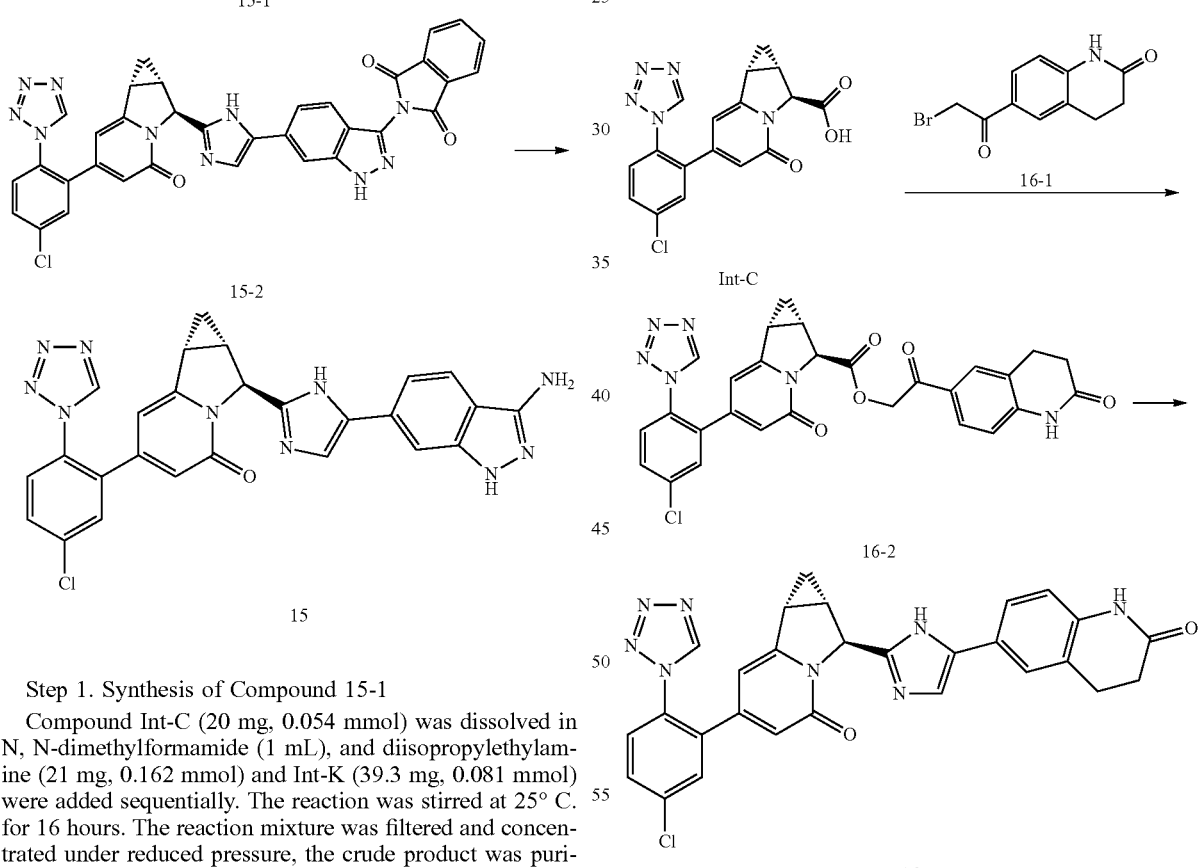

Step 1. Synthesis of Compound 16-2

Compound Int-C (20 mg, 0.054 mmol) was dissolved in N,N-dimethylformamide (2 mL), and potassium carbonate (56 mg, 0.41 mmol), 16-1 (52 mg, 0.19 mmol) were added sequentially. The reaction was stirred at 25° C. for 3 hours. The reaction mixture was diluted with ethyl acetate (10 mL), filtered, and the filtrate was concentrated under reduced pressure to obtain crude product 16-2, which was used directly in the next step without further purification.

MS (ESI) m/z (M+H)$^+$=557.2.

Step 2. Synthesis of Compound 16

Compound 16-2 (109 mg, 0.195 mmol) was dissolved in toluene (5 mL) and acetic acid (0.3 mL), and ammonium acetate (151 mg, 1.96 mmol) was added, and the reaction was carried out in a sealed tube and stirred for 16 hours at 100° C. The reaction mixture was concentrated under reduced pressure, and the crude product was separated by preparative high performance liquid chromatography (separation conditions: chromatographic column: Agilent 10 Prep-C8 250×21.2 mm; mobile phase: [water (0.1% trifluoroacetic acid)-acetonitrile], B %: 30%-50%; flow rate: 30 mL/min) to obtain compound 16 (HPLC retention time: 3.192 min).

MS (ESI) m/z (M+H)$^+$=537.3.

$^1$H NMR (400 MHz, DMSO-d$_6$) δ 12.10 (d, J=2.2 Hz, 1H), 10.04 (s, 1H), 9.66 (d, J=7.1 Hz, 1H), 7.81-7.77 (m, 3H), 7.52-7.39 (m, 3H), 6.80 (d, J=8.2 Hz, 1H), 6.00 (d, J=1.8 Hz, 1H), 5.93 (d, J=1.7 Hz, 1H), 5.44 (d, J=3.9 Hz, 1H), 2.90 (t, J=7.5 Hz, 2H), 2.75-2.73 (m, 1H), 2.29-2.21 (m, 1H), 1.32-1.28 (m, 1H), 0.57 (q, J=4.5 Hz, 1H).

Embodiment 17

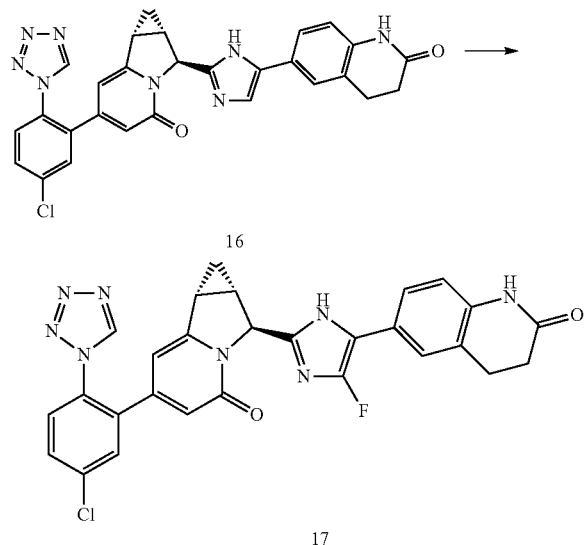

Step 1. Synthesis of Compound 17

At −18° C., compound 16 (27 mg, 0.05 mmol) was dissolved in tetrahydrofuran (1 mL) and acetonitrile (3 mL), and pyridine (12 mg, 0.150 mmol), bis(tetrafluoroborate) salt of 1-chloromethyl-4-fluoro-1,4-diazabicyclo[2.2.2]octane (20 mg, 0.055 mmol) were added sequentially, and the reaction was warmed to −8° C. and stirred for 2 hours. The reaction mixture was diluted with ethyl acetate (10 mL), saturated sodium sulfite aqueous solution (10 mL) was added, the mixture was stirred for 10 min, water (10 mL) was added, the phases were separated, and the aqueous layer was extracted with ethyl acetate (10 mL×3). The organic phases were combined, washed with 1.0 M hydrochloric acid aqueous solution (10 mL), saturated sodium bicarbonate aqueous solution (10 mL) and saturated saline sequentially, dried over anhydrous sodium sulfate, filtered, and the filtrate was concentrated under reduced pressure. The crude product was separated by preparative high performance liquid chromatography (separation conditions: chromatographic column: Agilent 10 Prep-C8 250×21.2 mm; mobile phase: [water (0.1% trifluoroacetic acid)-acetonitrile], B %: 30%-50%; flow rate: 30 mL/min) to obtain compound 17 (HPLC retention time: 4.778 min).

MS (ESI) m/z (M+H)$^+$=555.3.

$^1$H NMR (400 MHz, DMSO-d$_6$) δ 12.78 (s, 1H), 10.18 (s, 1H), 9.67 (s, 1H), 7.81-7.80 (m, 3H), 7.39-7.33 (m, 2H), 6.90 (d, J=8.3 Hz, 1H), 6.01 (d, J=1.7 Hz, 1H), 5.91 (d, J=1.7 Hz, 1H), 5.35 (s, 1H), 2.90 (t, J=7.7 Hz, 2H), 2.76-2.71 (m, 1H), 2.46 (t, J=7.2 Hz, 2H), 2.48-2.45 (m, 1H), 1.32-1.28 (m, 1H), 0.61 (q, J=4.4 Hz, 1H).

Embodiment 18-21

The synthesis of compounds 18 to 21 can be prepared by the synthetic method described in the preparation of compound 16, using commercially available compounds 4-bromoacetyl-2-fluorobenzonitrile, 5-(2-bromoethanoyl)-2-oxindole and intermediates Int-L and Int-N as raw materials, and reacting with intermediate Int-C respectively. The analytical data were shown in Table 3 below.

TABLE 3

Structure and analytical data of compounds in embodiments 18-21

| Embodiment | Structural formula | Analytical data |
|---|---|---|
| Embodiment 18 | 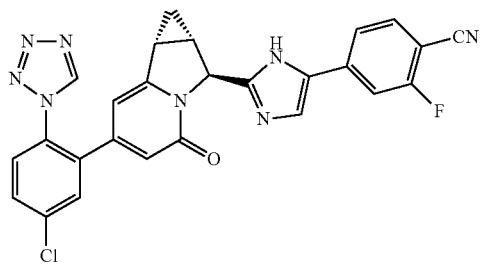 [SMILES: N#Cc1ccc(-c2cnc([C@@H]3[C@H]4C[C@H]4c4cc(-c5cc(Cl)ccc5-n5cnnn5)cc(=O)n43)[nH]2)cc1F] | MS (ESI) m/z (M + H)$^+$ = 511.2.<br>$^1$H NMR (400 MHz, Methanol-d$_4$) δ 9.25 (s, 1H), 7.76-7.39 (m, 7H), 6.08 (d, J = 1.7 Hz, 1H), 5.97 (d, J = 1.6 Hz, 1H), 5.52 (s, 1H), 2.81-2.72 (m, 1H), 2.29-2.25 (m, 1H), 1.37-1.32 (m, 1H), 0.59 (q, J = 4.8 Hz, 1H). |

TABLE 3-continued

Structure and analytical data of compounds in embodiments 18-21

| Embodiment | Structural formula | Analytical data |
|---|---|---|
| Embodiment 19 | | MS (ESI) m/z (M + H)$^+$ = 523.2.<br>$^1$H NMR (400 MHz, DMSO-d$_6$) δ 12.09 (s, 1H), 10.34 (s, 1H), 9.66 (d, J = 5.3 Hz, 1H), 7.81-7.77 (m, 3H), 7.57-7.45 (m, 2H), 7.39 (d, J = 2.0 Hz, 1H), 6.77 (d, J = 8.0 Hz, 1H), 6.01 (d, J = 1.7 Hz, 1H), 5.92 (d, J = 1.7 Hz, 1H), 5.44 (t, J = 2.2 Hz, 1H), 3.48 (s, 2H), 2.76-2.74 (m, 1H), 2.29-2.24 (m, 1H), 1.32-1.28 (m, 1H), 0.57 (q, J = 4.5 Hz, 1H). |
| Embodiment 20 | | MS (ESI) m/z (M + H)$^+$ = 539.2.<br>$^1$H NMR (400 MHz, DMSO-d$_6$) δ 10.67 (s, 1H), 9.65 (s, 1H), 7.80 (d, J = 1.8 Hz, 2H), 7.78-7.76 (m, 1H), 7.46 (s, 1H), 7.27 (s, 1H), 6.86 (d, J = 8.4 Hz, 1H), 6.01 (d, J = 1.7 Hz, 1H), 5.92 (d, J = 1.7 Hz, 1H), 5.44 (s, 1H), 4.56 (s, 2H), 2.75 (br s, 1H), 2.26 (br s, 1H), 1.34-1.28 (m, 1H), 0.57 (br s, 1H). |
| Embodiment 21 | | MS (ESI) m/z (M + H)$^+$ = 540.0.<br>$^1$H NMR (400 MHz, DMSO-d$_6$) δ 12.27 (s, 1H), 10.81 (s, 1H), 9.65 (s, 1H), 7.81 (s, 2H), 7.78 (d, J = 1.6 Hz, 1H), 7.45-7.34 (m, 2H), 7.22 (d, J = 8.0 Hz, 1H), 6.01 (d, J = 1.7 Hz, 1H), 5.94 (d, J = 1.7 Hz, 1H), 5.46 (s, 1H), 4.76 (s, 2H), 2.77-2.72 (m, 1H), 2.29-2.22 (m, 1H), 1.33-1.28 (m, 1H), 0.59-0.54 (m, 1H). |

Embodiment 22

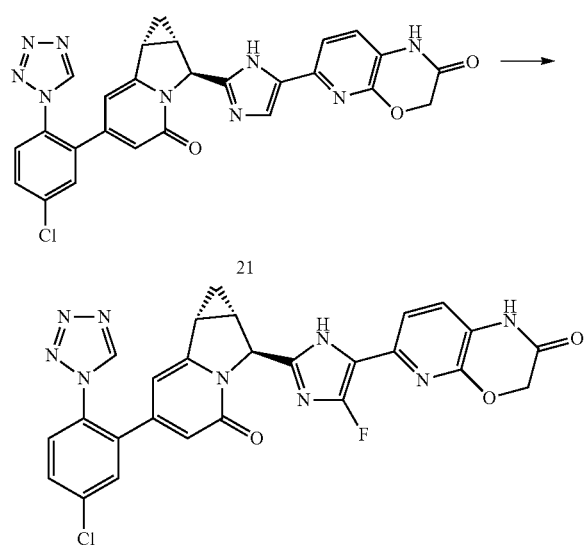

Compound 22 can be synthesized by using compound 21 as raw material through the synthesis method described in the preparation of compound 17, the analytical data were as follows.

MS (ESI) m/z (M+H)$^+$=558.0.

$^1$H NMR (400 MHz, DMSO-d$_6$) δ 12.90 (s, 1H), 10.91 (s, 1H), 9.66 (s, 1H), 7.80 (d, J=2.5 Hz, 2H), 7.62 (t, J=6.1 Hz, 1H), 7.48-7.45 (m, 1H), 7.30 (d, J=8.0 Hz, 1H), 7.18 (d, J=7.8 Hz, 1H), 6.00-5.98 (m, 1H), 5.90 (d, J=1.7 Hz, 1H), 5.47 (s, 1H), 4.83 (s, 2H), 2.74-2.70 (m, 1H), 2.17-2.14 (m, 1H), 1.31-1.27 (m, 1H), 0.56 (q, J=4.4 Hz, 1H).

Embodiment 23-28

The synthesis of compounds 23 to 28 can be prepared by the synthetic method described in the preparation of compound 1, using intermediates Int-M, Int-O, Int-P, Int-Q, Int-R and Int-S as raw materials, and reacting with intermediate Int-C respectively. The analytical data were shown in Table 4 below.

TABLE 4

Structure and analytical data of compounds in embodiments 23-28

| Embodiment | Structural formula | Analytical data |
|---|---|---|
| Embodiment 23 | | MS (ESI) m/z (M + H)⁺ = 525.3.<br>$^1$H NMR (400 MHz, DMSO-$d_6$) δ 11.94 (s, 1H), 9.65 (s, 1H), 7.81-7.78 (m, 3H), 7.24-6.95 (m, 3H), 6.50 (d, J = 8.0 Hz, 1H), 6.00 (d, J = 1.8 Hz, 1H), 5.91 (d, J = 1.8 Hz, 1H), 5.86-5.41 (m, 2H), 4.13-4.09 (m, 2H), 3.34-3.27 (m, 2H), 2.76-2.71 (m, 1H), 2.29-2.25 (m, 1H), 1.33-1.27 (m, 1H), 0.54 (q, J = 4.4 Hz, 1H). |
| Embodiment 24 | | MS (ESI) m/z (M + H)⁺ = 519.2.<br>$^1$H NMR (400 MHz, DMSO-$d_6$) δ 12.11 (s, 1H), 9.58 (s, 1H), 7.74 (s, 2H), 7.71 (s, 1H), 7.31 (t, J = 7.9 Hz, 1H), 7.12 (dd, J = 3.9, 1.8 Hz, 1H), 6.53 (t, J = 8.5 Hz, 1H), 5.94 (d, J = 1.8 Hz, 1H), 5.87 (d, J = 1.7 Hz, 1H), 5.40 (s, 1H), 5.34 (s, 2H), 2.69-2.66 (m, 1H), 2.22-2.17 (m, 1H), 1.26-1.23 (m, 1H), 0.51 (q, J = 4.4 Hz, 1H). |
| Embodiment 25 | | MS (ESI) m/z (M + H)⁺ = 552.2.<br>$^1$H NMR (400 MHz, DMSO-$d_6$) δ 12.11 (s, 1H), 9.59 (s, 1H), 7.74 (s, 2H), 7.70-7.68 (m, 2H), 7.00 (s, 1H), 6.66 (d, J = 8.0 Hz, 1H), 6.60-6.50 (m, 1H), 6.37 (s, 1H), 5.95 (d, J = 1.7 Hz, 1H), 5.86 (d, J = 1.7 Hz, 1H), 5.40 (s, 1H), 2.69-2.64 (m, 1H), 2.24-2.19 (m, 1H), 1.27-1.21 (m, 1H), 0.50-0.48 (m, 1H). |
| Embodiment 26 | | MS (ESI) m/z (M + H)⁺ = 508.0.<br>$^1$H NMR (400 MHz, DMSO-$d_6$) δ 12.97 (s, 1H), 12.15 (s, 1H), 9.68 (s, 1H), 8.05 (s, 1H), 7.82-7.72 (m, 4H), 7.58-7.45 (m, 2H), 6.04 (s, 1H), 5.93 (s, 1H), 5.47 (s, 1H), 2.81-2.76 (m, 1H), 2.34-2.24 (m, 1H), 1.35-1.29 (m, 1H), 0.60-0.57 (m, 1H). |
| Embodiment 27 | | MS (ESI) m/z (M + H)⁺ = 526.0<br>$^1$H NMR (400 MHz, DMSO-$d_6$) δ 13.32 (s, 1H), 12.30 (s, 1H), 9.66 (s, 1H), 8.16 (s, 1H), 7.97 (dd, J = 8.7, 6.8 Hz, 1H), 7.81 (d, J = 1.5 Hz, 2H), 7.79-7.77 (m, 1H), 7.39 (d, J = 8.6 Hz, 2H), 6.03 (d, J = 1.7 Hz, 1H), 5.95 (d, J = 1.7 Hz, 1H), 5.51 (s, 1H), 2.80-2.75 (m, 1H), 2.32-2.28 (m, 1H), 1.35-1.30 (m, 1H), 0.59 (q, J = 4.4 Hz, 1H). |

TABLE 4-continued

Structure and analytical data of compounds in embodiments 23-28

| Embodiment | Structural formula | Analytical data |
|---|---|---|
| Embodiment 28 | 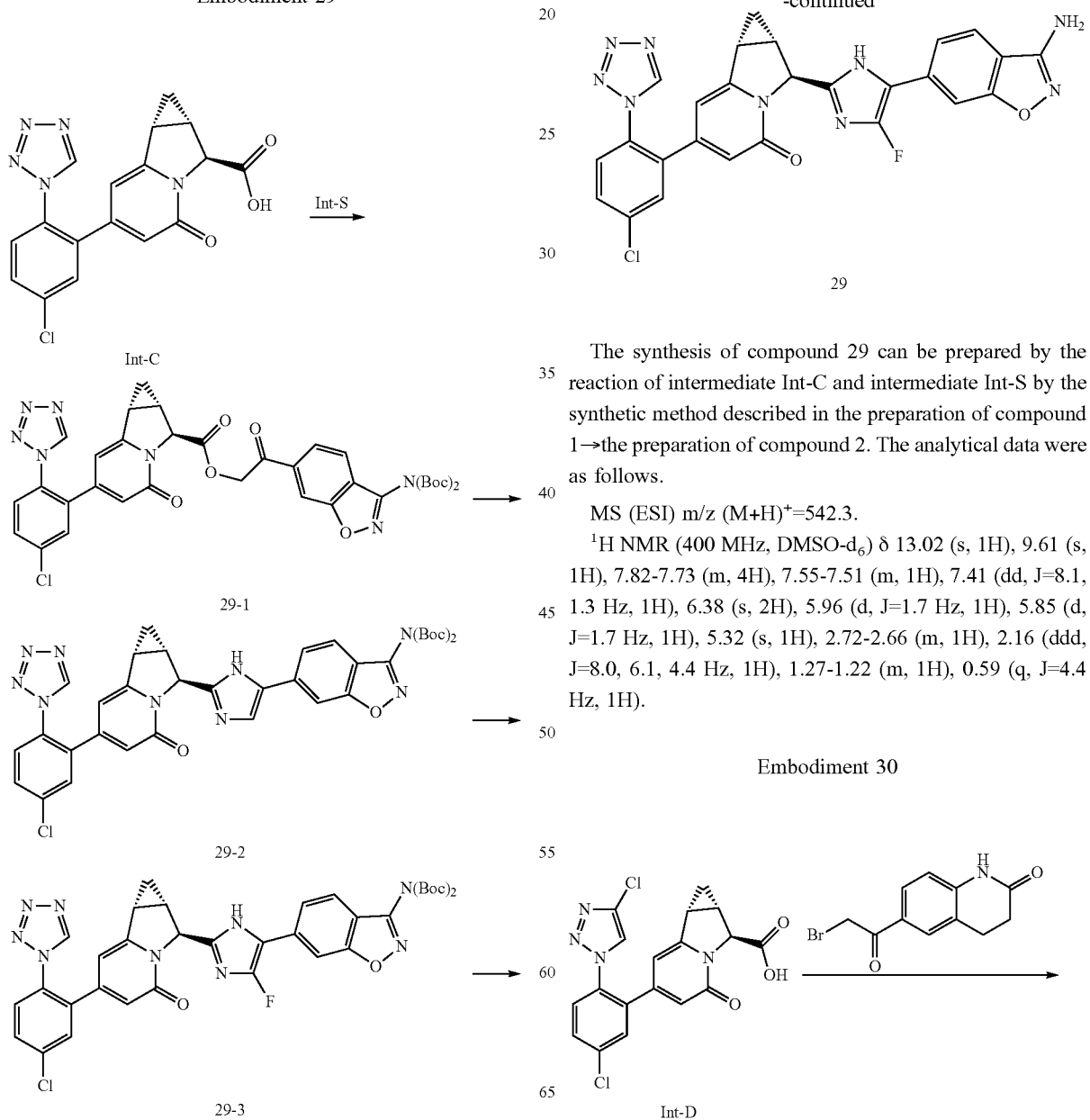 | MS (ESI) m/z (M + H)⁺ = 524.2.<br>¹H NMR (400 MHz, DMSO-d₆) δ 12.24 (s, 1H), 9.58 (s, 1H), 7.74-7.50 (m, 7H), 6.31-6.23 (m, 2H), 5.95 (s, 1H), 5.87 (s, 1H), 5.41 (s, 1H), 2.73-2.69 (m, 1H), 2.25-2.20 (m, 1H), 1.28-1.23 (m, 1H), 0.53 (q, J = 4.4 Hz, 1H). |

Embodiment 29

The synthesis of compound 29 can be prepared by the reaction of intermediate Int-C and intermediate Int-S by the synthetic method described in the preparation of compound 1→the preparation of compound 2. The analytical data were as follows.

MS (ESI) m/z (M+H)⁺=542.3.

¹H NMR (400 MHz, DMSO-d₆) δ 13.02 (s, 1H), 9.61 (s, 1H), 7.82-7.73 (m, 4H), 7.55-7.51 (m, 1H), 7.41 (dd, J=8.1, 1.3 Hz, 1H), 6.38 (s, 2H), 5.96 (d, J=1.7 Hz, 1H), 5.85 (d, J=1.7 Hz, 1H), 5.32 (s, 1H), 2.72-2.66 (m, 1H), 2.16 (ddd, J=8.0, 6.1, 4.4 Hz, 1H), 1.27-1.22 (m, 1H), 0.59 (q, J=4.4 Hz, 1H).

Embodiment 30

-continued

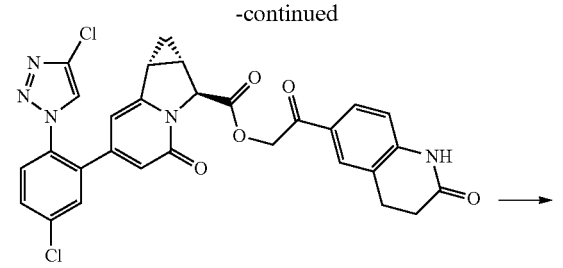

30-1

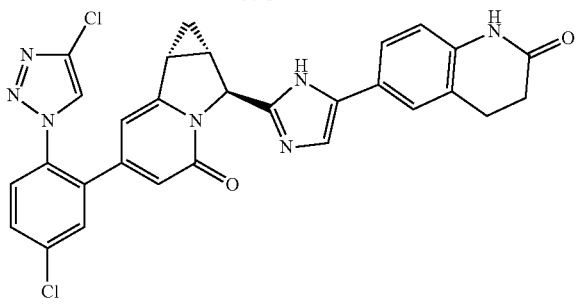

30

The synthesis of compound 30 can be prepared by the synthetic method described in the preparation of compound 16, using Int-D and 16-1 as raw materials, the analytical data were as follows.

MS (ESI) m/z (M+H)$^+$=570.2.

$^1$H NMR (400 MHz, DMSO-d$_6$) δ 12.11 (s, 1H), 10.04 (s, 1H), 8.65 (s, 1H), 7.79-7.73 (m, 3H), 7.51-7.40 (m, 3H), 6.79-6.78 (m, 1H), 5.99-5.93 (m, 2H), 5.45 (s, 1H), 2.88 (t, J=7.7 Hz, 2H), 2.80-2.78 (m, 1H), 2.43 (dd, J=8.5, 6.6 Hz, 2H), 2.31-2.24 (m, 1H), 1.34-1.29 (m, 1H), 0.56 (q, J=4.4 Hz, 1H).

Embodiment 31

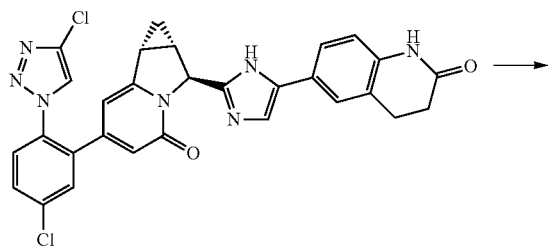

30

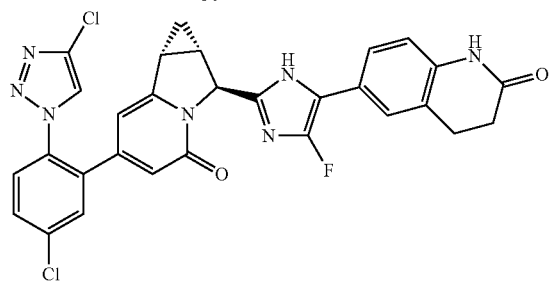

31

The synthesis of compound 31 can be prepared by the synthetic method described in the preparation of compound 17, using compound 30 as raw material, the analytical data were as follows.

MS (ESI) m/z (M+H)$^+$=588.2.

$^1$H NMR (400 MHz, DMSO-d$_6$) δ 12.78 (s, 1H), 10.18 (s, 1H), 8.64 (s, 1H), 7.79-7.73 (m, 2H), 7.48-7.45 (m, 1H), 7.39-7.33 (m, 2H), 6.91 (d, J=8.2 Hz, 1H), 5.98 (d, J=1.7 Hz, 1H), 5.94 (d, J=1.8 Hz, 1H), 5.37 (s, 1H), 2.91 (t, J=7.5 Hz, 2H), 2.77-2.73 (m, 1H), 2.48-2.45 (m, 2H), 2.21-2.16 (m, 1H), 1.33-1.28 (m, 1H), 0.60 (q, J=4.4 Hz, 1H).

Embodiment 32

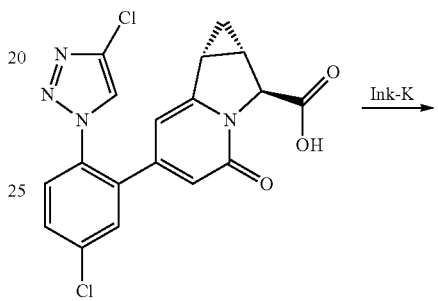

Int-D

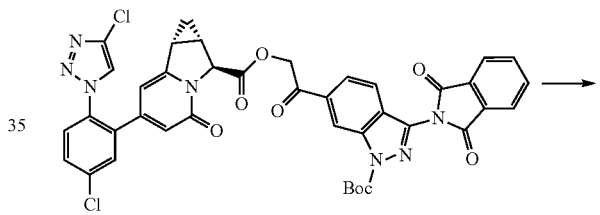

32-1

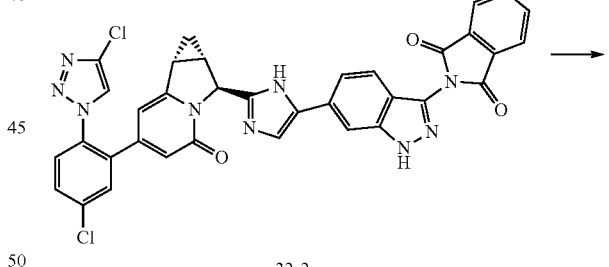

32-2

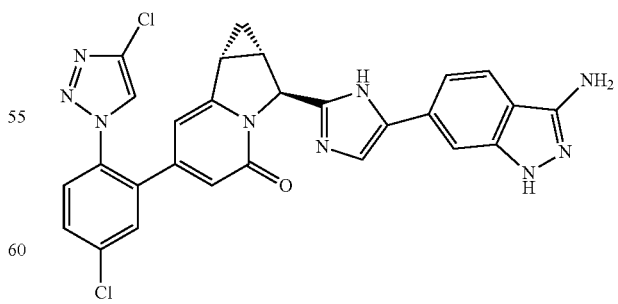

32

The synthesis of compound 32 can be prepared by the synthetic method described in the preparation of compound 15, using Int-D and Int-K as raw materials, the analytical data were as follows.

MS (ESI) m/z (M+H)$^+$=556.2.

$^1$H NMR (400 MHz, DMSO-d$_6$) δ 12.10 (s, 1H), 11.13 (s, 1H), 8.56 (s, 1H), 7.72-7.62 (m, 6H), 7.53-7.40 (m, 1H), 5.91-5.87 (m, 2H), 5.41 (s, 1H), 5.25-5.17 (m, 2H), 2.78-2.73 (m, 1H), 2.25-2.23 (m, 1H), 1.29-1.24 (m, 1H), 0.50 (q, J=4.4 Hz, 1H).

Embodiment 33

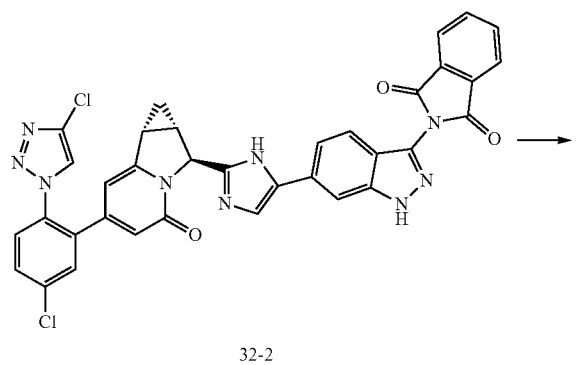

32-2

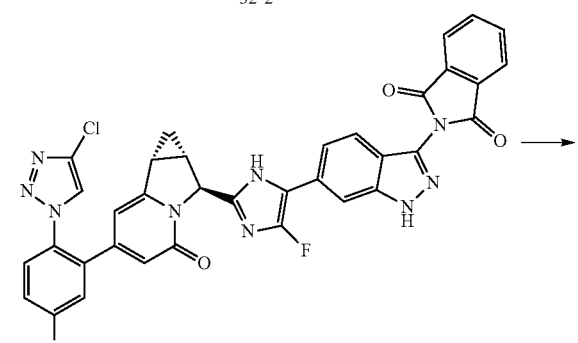

33-1

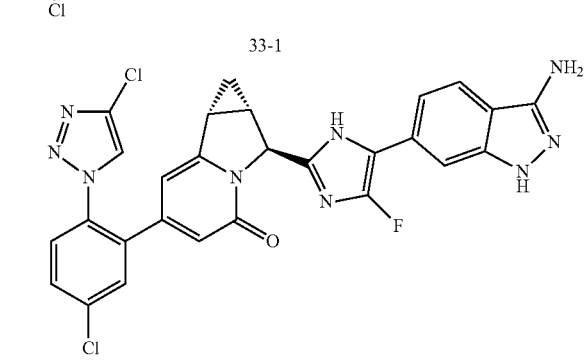

33

Step 1. Synthesis of Compound 33-1

At −18° C., compound 32-2 (74 mg, 0.108 mmol) was dissolved in tetrahydrofuran (1 mL) and acetonitrile (3 mL), and pyridine (26 mg, 0.324 mmol), bis(tetrafluoroborate) salt of 1-chloromethyl-4-fluoro-1,4-diazabicyclo[2.2.2]octane (57 mg, 0.16 mmol) were added sequentially, and the reaction was warmed to −10° C. and stirred for 2 hours. The reaction mixture was diluted with ethyl acetate (10 mL), saturated sodium sulfite aqueous solution (10 mL) was added, the mixture was stirred for 10 min, water (10 mL) was added, the phases were separated, and the aqueous layer was extracted with ethyl acetate (10 mL×3). The organic phases were combined, washed with 1.0 M hydrochloric acid aqueous solution (10 mL), saturated sodium bicarbonate aqueous solution (10 mL) and saturated saline sequentially, dried over anhydrous sodium sulfate, filtered, and the filtrate was concentrated under reduced pressure. The crude product was purified by silica gel column chromatography (dichloromethane:methanol=100:0→0:100) to obtain target compound 33-1.

Step 2. Synthesis of Compound 33

Compound 33-1 (30 mg, 0.053 mmol) was dissolved in methanol (2 mL), hydrazine hydrate (2 mL) was added, and the reaction was stirred at room temperature for 3 hours. The reaction mixture was concentrated under reduced pressure, and the crude product was separated by preparative high performance liquid chromatography (separation conditions: chromatographic column: Agilent 10 Prep-C8 250×21.2 mm; mobile phase: [water (0.1% trifluoroacetic acid)-acetonitrile], B %: 30%-50%; flow rate: 30 mL/min) to obtain compound 33 (HPLC retention time: 4.514 min).

MS (ESI) m/z (M+H)$^+$=574.3.

$^1$H NMR (400 MHz, DMSO-d$_6$) δ 12.88 (s, 1H), 11.44 (s, 1H), 8.59 (s, 1H), 7.74-7.65 (m, 4H), 7.36 (s, 1H), 5.10-7.08 (m, 1H), 6.70 (br s, 1H), 5.93-5.88 (m, 1H), 5.34-5.32 (m, 2H), 2.72-2.70 (m, 1H), 2.18-2.14 (m, 1H), 1.28-1.24 (m, 1H), 0.57-0.54 (m, 1H).

Embodiment 34

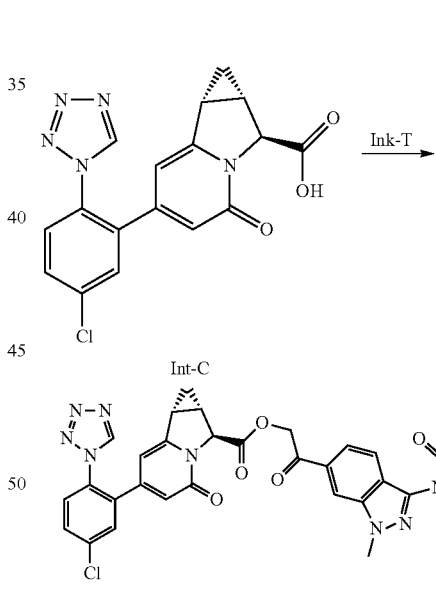

Int-C

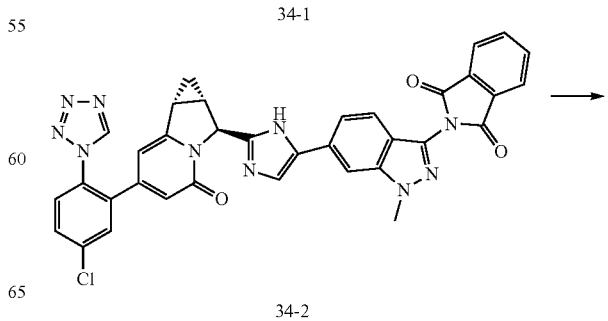

34-1

34-2

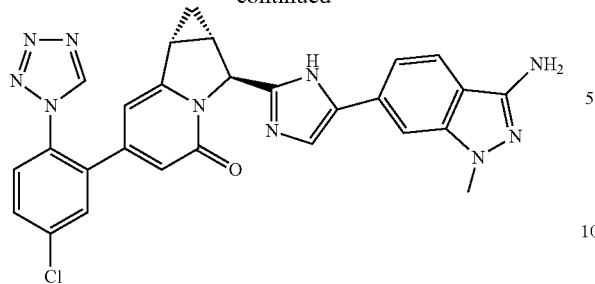

34

The synthesis of compound 34 can be prepared by the synthetic method described in the preparation of compound 15, using Int-C and Int-T as raw materials, the analytical data were as follows.

MS (ESI) m/z (M+H)$^+$=537.2.

$^1$H NMR (400 MHz, DMSO-d$_6$) δ 12.20 (s, 1H), 9.68 (s, 1H), 7.81-7.78 (m, 3H), 7.60-7.58 (m, 3H), 7.31-7.28 (m, 1H), 6.01-5.91 (m, 2H), 5.47-5.33 (m, 3H), 3.75 (s, 3H), 2.80-2.75 (m, 1H), 2.31-2.28 (m, 1H), 1.35-1.29 (m, 1H), 0.61-0.58 (m, 1H).

Embodiment 35

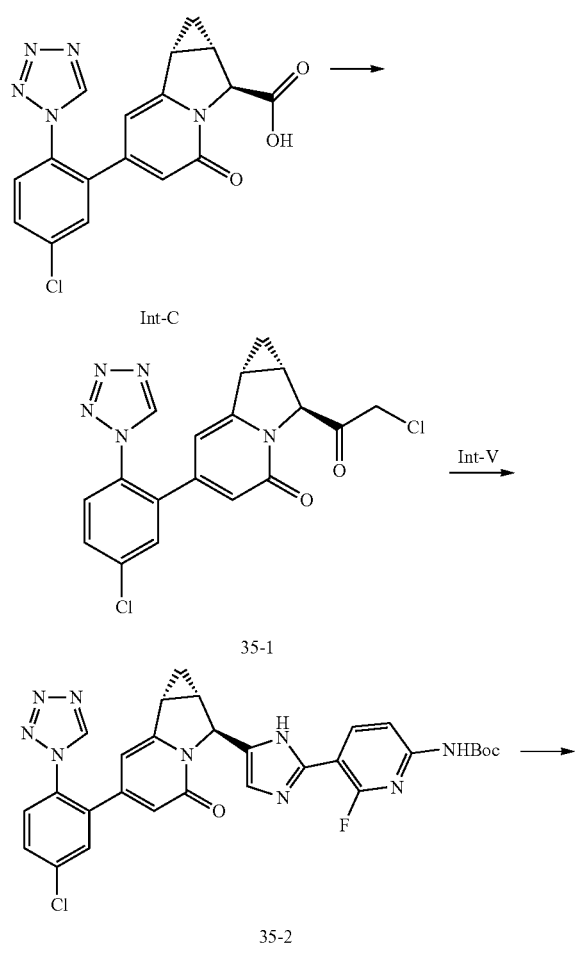

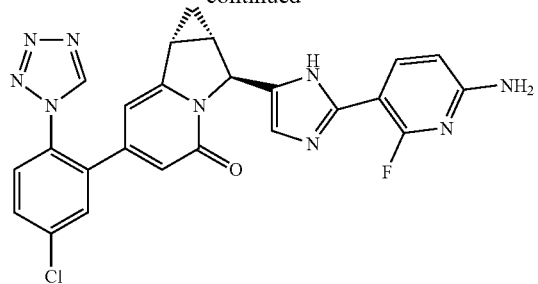

35

Step 1. Synthesis of Compound 35-1

At 0° C., under the protection of nitrogen, compound Int-C (550 mg, 1.49 mmol) was dissolved in dichloromethane (2.5 mL), 1-chloro-N, N, 2-trimethylpropenylamine (399 mg, 2.98 mmol) was added, and after the mixture was stirred for 1 hour at this temperature, trimethylsilylated diazomethane (1.49 mL, 2.0 M hexane solution) was added, the mixture was continued to stir for 2 hours, a solution of hydrogen chloride (1.49 mL, 4.0 M) in dioxane was added dropwise, and the mixture was stirred for 1 hour. The reaction mixture was diluted with dichloromethane (20 mL) and water (10 mL), the phases were separated, the aqueous phase was extracted with dichloromethane (10 mL×3), the organic phases were combined and washed with saturated sodium bicarbonate solution (10 mL) and saturated saline (10 mL) sequentially, dried over anhydrous sodium sulfate, filtered, the filtrate was concentrated under reduced pressure, the crude product was purified by silica gel column chromatography (dichloromethane:methanol=100:0→95:5) to obtain compound 35-1.

MS (ESI) m/z (M+H)$^+$=402.2.

Step 2. Synthesis of Compound 35-2

Compound 35-1 (100 mg, 0.24 mmol) was dissolved in acetonitrile (5 mL), and Int-V (139 mg, 0.48 mmol), potassium carbonate (99 mg, 0.73 mmol) and potassium iodide (55 mg, 0.48 mmol) were added sequentially, and the reaction was heated to 80° C. and stirred for 16 hours, the reaction mixture was cooled to room temperature, filtered, and the filtrate was concentrated to dryness under reduced pressure, the crude product was purified by silica gel column chromatography (petroleum ether:ethyl acetate=20:80→0:100) to obtain compound 35-2.

MS (ESI) m/z (M+H)$^+$=602.2.

Step 3. Synthesis of Compound 35

According to the synthesis method of 1-2→1 described in the preparation of compound 1, compound 35-2 was treated to obtain target compound 35.

MS (ESI) m/z (M+H)$^+$=502.0.

$^1$H NMR (400 MHz, DMSO-d$_6$) δ 11.69 (s, 1H), 9.60 (s, 1H), 7.95-7.82 (m, 1H), 7.79-7.63 (m, 3H), 6.73 (d, J=2.1 Hz, 1H), 6.58 (s, 2H), 6.35 (dd, J=8.3, 2.2 Hz, 1H), 6.00-5.76 (m, 2H), 5.33 (d, J=1.2 Hz, 1H), 2.61-2.51 (m, 1H), 2.14-2.04 (m, 1H), 1.22-1.19 (m, 1H), 0.38 (q, J=4.4 Hz, 1H).

Embodiment 36

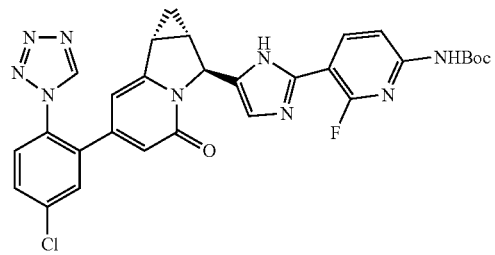

35-2

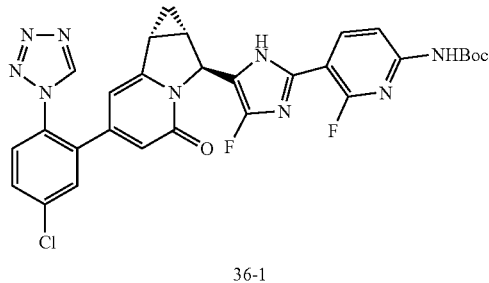

36-1

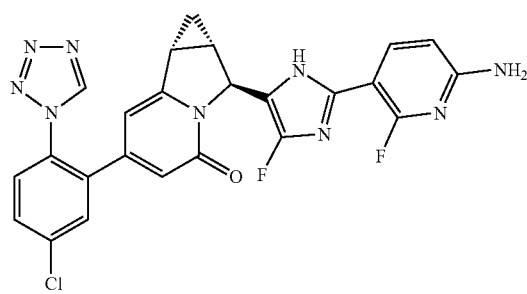

36

The synthesis of compound 36 can be prepared by the synthetic method described in the preparation of compound 2, using 35-2 as raw material, the analytical data were as follows.

MS (ESI) m/z (M+H)$^+$=520.1.

$^1$H NMR (400 MHz, DMSO-d$_6$) δ 11.88 (d, J=1.8 Hz, 1H), 9.55 (s, 1H), 7.80 (dd, J=10.5, 8.3 Hz, 1H), 7.75-7.66 (m, 3H), 6.69 (s, 2H), 6.33 (dd, J=8.4, 2.1 Hz, 1H), 5.89 (s, 2H), 5.45 (d, J=1.3 Hz, 1H), 2.67-2.63 (m, 1H), 2.21-2.08 (m, 1H), 1.28-1.23 (m, 1H), 0.46 (q, J=4.3 Hz, 1H).

Embodiment 37

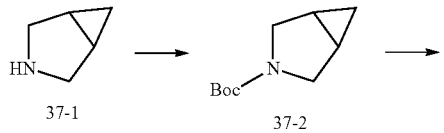

Embodiment 37

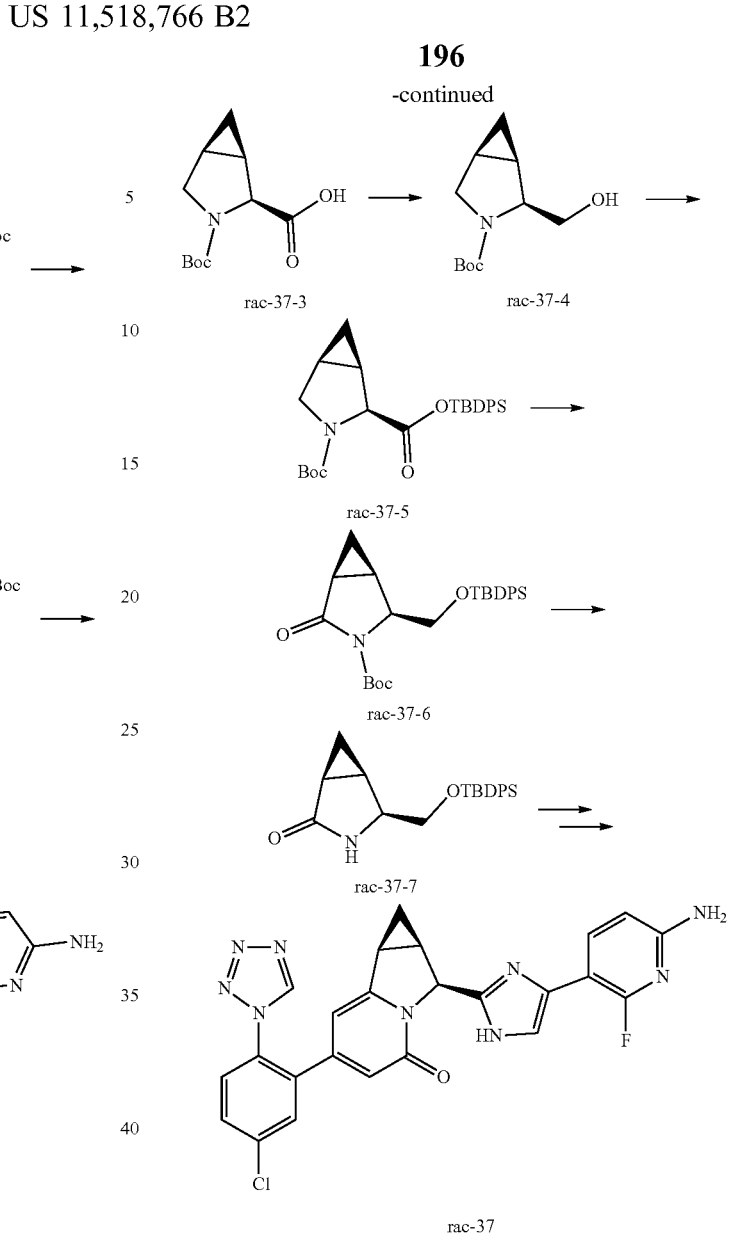

rac-37

Step 1. Synthesis of Compound 37-2

Compound 37-1 (20 g, 167.2 mmol) was dissolved in 1,4-dioxane (100 mL), and 1.0 M sodium hydroxide solution (334 mL) and di-tert-butyl dicarbonate (54.7 g, 250.8 mmol) were added sequentially, and the reaction was stirred at room temperature for 15 hours. The reaction mixture was concentrated under reduced pressure, water (500 mL) was added, the mixture was extracted with petroleum ether (1500 mL), the organic phase was dried over anhydrous sodium sulfate, filtered, the filtrate was concentrated under reduced pressure, and the crude product was purified by silica gel column chromatography (petroleum ether:ethyl acetate=100:0→90:10) to obtain compound 37-2.

$^1$H NMR (400 MHz, DMSO-d$_6$) δ 3.38 (dd, J=10.6, 5.0 Hz, 2H), 3.29-3.19 (m, 2H), 1.48 (ddd, J=7.8, 3.9, 2.5 Hz, 2H), 1.36 (s, 9H), 0.65 (tdt, J=7.8, 4.7, 0.9 Hz, 1H).

Step 2. Synthesis of Compound Rac-37-3

At −60° C., under the protection of nitrogen, compound 37-2 (11 g, 60 mmol) and 3,7-dipropyl-3,7-diazabicyclo[3.3.1]nonane (15.22 g, 72.36 mmol) were dissolved in tetrahydrofuran (300 mL), and a solution of sec-butyllithium (53 mL, 1.3 M) in hexane was slowly added dropwise, the reaction mixture was stirred at this temperature for 5 hours, ground dry ice (15 g) was added, and the reaction was continued to stir for 2 hours. The reaction was quenched by slowly adding water (200 mL) to the reaction mixture, and the reaction was reverse extracted by methyl tert-butyl ether (600 mL), the pH of the aqueous phase was adjusted to 2-3 with 1.0 M diluted hydrochloric acid, the mixture was extracted with methyl tert-butyl ether (600 mL), and the organic phase was dried over anhydrous sodium sulfate, filtered, and the filtrate was concentrated under reduced pressure to obtain crude product rac-37-3, which was directly used in the next step without further purification.

MS (ESI) m/z (M−H)$^-$=226.0.

Step 3. Synthesis of Compound Rac-37-4

At 0° C., compound rac-37-3 (10 g, 44 mmol) was dissolved in tetrahydrofuran (200 mL), and borane tetrahydrofuran complex (55 mL, 1.0 M) was slowly added dropwise, and the reaction was warmed to room temperature and stirred for 16 hours. The reaction mixture was cooled to 0° C., quenched by slow dropwise addition of saturated ammonium chloride solution (200 mL), the mixture was extracted with ethyl acetate (900 mL), the organic phase was washed by saturated saline (200 mL), dried over anhydrous sodium sulfate, filtered, the filtrate was concentrated under reduced pressure, and the crude product was purified by silica gel column chromatography (petroleum ether:ethyl acetate=100:0→85:15) to obtain compound rac-37-4.

MS (ESI) m/z (M+H-100)$^+$=114.2.

Step 4. Synthesis of Compound Rac-37-5

Compound rac-37-4 (8.5 g, 40.1 mmol) was dissolved in N, N-dimethylformamide (100 mL), then tert-butyl diphenyl chlorosilane (22 g, 80.3 mmol) and imidazole (5.47 g, 80.2 mmol) were added sequentially, the reaction was stirred at room temperature for 40 hours. The reaction mixture was quenched by adding water (300 mL), the mixture was extracted with ethyl acetate (900 mL), the organic phase was washed by saturated saline (200 mL), dried over anhydrous sodium sulfate, filtered, the filtrate was concentrated under reduced pressure, and the crude product was purified by silica gel column chromatography (petroleum ether:ethyl acetate=100:0→97:3) to obtain compound rac-37-5.

MS (ESI) m/z (M+H)$^+$=452.2.

Step 5. Synthesis of Compound Rac-37-6

Sodium periodate (15.1 g, 70.8 mmol) and ruthenium oxide (94 mg, 0.71 mmol) were dissolved in water (100 mL), and a solution of compound rac-37-5 (8 g, 7.1 mmol) in ethyl acetate (50 mL) was added, and the reaction was stirred at room temperature for 3 hours. The reaction mixture was quenched by adding saturated sodium sulfite solution (100 mL), filtered, the filtrate was extracted with ethyl acetate (750 mL), the organic phase was dried over anhydrous sodium sulfate, filtered, the filtrate was concentrated under reduced pressure, the crude product was purified by silica gel column chromatography (petroleum ether:ethyl acetate=100:0→85:15) to obtain compound rac-37-6.

MS (ESI) m/z (M+H-100)$^+$=366.2.

Step 6. Synthesis of Compound Rac-37-7

Compound rac-37-6 (7.8 g, 16.75 mmol) was dissolved in dichloromethane (100 mL), trifluoroacetic acid (10 mL) was added, and the reaction was stirred at room temperature for 3 hours, the reaction mixture was quenched by adding saturated sodium bicarbonate solution (150 mL), and the mixture was extracted with dichloromethane (600 mL), the organic phase was dried over anhydrous sodium sulfate, filtered and the filtrate was concentrated under reduced pressure, the crude product was purified by silica gel column chromatography (petroleum ether:ethyl acetate=100:0→60:40) to obtain compound rac-37-7.

MS (ESI) m/z (M+H)$^+$=366.2.

$^1$H NMR (400 MHz, DMSO-d$_6$) δ 7.68-7.61 (m, 4H), 7.49-7.40 (m, 6H), 3.86 (dt, J=7.6, 5.5 Hz, 1H), 3.60 (dd, J=9.8, 5.4 Hz, 1H), 3.47 (dd, J=9.8, 7.6 Hz, 1H), 1.69-1.66 (m, 1H), 0.90-0.78 (m, 1H), 0.56 (q, J=4.0 Hz, 1H).

Step 7. Synthesis of Compound Rac-37

Compound rac-37 was synthesized as described in the preparation of Int-B→Int-C→Compound 1 sequentially, using rac-37-7 as raw material, and the analytical data were as follows.

MS (ESI) m/z (M+H)$^+$=502.2.

$^1$H NMR (400 MHz, Methanol-d$_4$) δ 9.31 (s, 1H), 7.74-7.65 (m, 2H), 7.63-7.59 (m, 2H), 7.48 (d, J=1.7 Hz, 1H), 6.41 (dd, J=8.3, 1.8 Hz, 1H), 6.10 (d, J=1.6 Hz, 1H), 6.06 (d, J=1.6 Hz, 1H), 5.95 (d, J=6.4 Hz, 1H), 2.75 (ddd, J=8.4, 6.3, 3.5 Hz, 1H), 2.57-2.51 (m, 1H), 1.28-1.24 (m, 1H), 0.86-0.82 (m, 1H).

Embodiment 38-47

The synthesis of compounds 38 to 47 can be prepared by the synthetic method described in the preparation of compound 1, using intermediates Int-W, Int-X, Int-Y, Int-Z, Int-AD, Int-AH, Int-AI, Int-AL, Int-AR and Int-AY as raw materials, and reacting with intermediate Int-C respectively. The analytical data were shown in Table 5 below.

TABLE 5

Structure and analytical data of compounds in embodiments 38-47

| Embodiment | Structural formula | Analytical data |
|---|---|---|
| Embodiment 38 | (structure) | MS (ESI) m/z (M + H)$^+$ = 526.20.<br>$^1$H NMR (400 MHz, DMSO-d$_6$) δ 12.07 (s, 1H), 9.67 (s, 1H), 7.81-7.78 (m, 3H), 7.27-7.06 (m, 2H), 6.94-6.84 (m, 1H), 6.14-5.92 (m, 3H), 5.44 (s, 1H), 4.28-4.25 (m, 2H), 3.28-3.26 (m, 2H), 2.74-2.72 (m, 1H), 2.26-2.24 (m, 1H), 1.31-1.27 (m, 1H), 0.56-0.53 (m, 1H). |

TABLE 5-continued

Structure and analytical data of compounds in embodiments 38-47

| Embodiment | Structural formula | Analytical data |
| --- | --- | --- |
| Embodiment 39 | | MS (ESI) m/z (M + H)$^+$ = 543.2.<br>$^1$H NMR (400 MHz, DMSO-d$_6$) δ 12.08 (s, 1H), 9.64 (s, 1H), 7.81-7.76 (m, 3H), 7.20-7.11 (m, 2H), 6.43-6.37 (m, 1H), 6.05-5.94 (m, 2H), 5.92-5.88 (m, 1H), 5.45 (s, 1H), 4.17-4.13 (m, 2H), 2.75-2.71 (m, 1H), 2.28-2.23 (m, 1H), 2.00-1.93 (m, 2H), 1.29-1.27 (m, 1H), 0.54 (q, J = 4.4 Hz, 1H). |
| Embodiment 40 | | MS (ESI) m/z (M + H)$^+$ = 559.2.<br>$^1$H NMR (400 MHz, DMSO-d$_6$) δ 12.08 (s, 1H), 9.64 (s, 1H), 7.80-7.76 (m, 3H), 7.39-7.35 (m, 1H), 7.12 (dd, J = 4.3, 1.9 Hz, 1H), 6.43-6.30 (m, 2H), 5.99 (d, J = 1.8 Hz, 1H), 5.93-5.90 (m, 1H), 5.45 (s, 1H), 3.48-3.44 (m, 2H), 2.99-2.95 (m, 2H), 2.74-2.72 (m, 1H), 2.28-2.23 (m, 1H), 1.30-1.27 (m, 1H), 0.55 (q, J = 4.3 Hz, 1H). |
| Embodiment 41 | | MS (ESI) m/z (M + H)$^+$ = 508.0.<br>$^1$H NMR (400 MHz, DMSO-d$_6$) δ 12.87 (s, 1H), 12.25 (s, 1H), 9.65 (s, 1H), 7.80 (s, 2H), 7.77 (s, 1H), 7.58 (s, 1H), 7.35 (d, J = 7.9 Hz, 1H), 7.27 (s, 1H), 6.02 (s, 1H), 5.92 (d, J = 1.8 Hz, 1H), 5.47 (s, 1H), 5.27 (s, 2H), 2.79-2.74 (m, 1H), 2.31-2.25 (m, 1H), 1.34-1.29 (m, 1H), 0.66-0.55 (m, 1H). |
| Embodiment 42 | | MS (ESI) m/z (M + H)$^+$ = 560.2.<br>$^1$H NMR (400 MHz, DMSO-d$_6$) δ 12.12 (s, 1H), 9.59 (s, 1H), 7.76-7.70 (m, 3H), 7.63-7.34 (m, 5H), 5.94 (d, J = 1.7 Hz, 1H), 5.88 (d, J = 1.8 Hz, 1H), 5.40 (s, 1H), 2.84 (t, J = 7.4 Hz, 2H), 2.71-2.60 (m, 3H), 2.23-2.19 (m, 1H), 1.28-1.22 (m, 1H), 0.52 (q, J = 4.3 Hz, 1H). |
| Embodiment 43 | | MS (ESI) m/z (M + H)$^+$ = 569.0.<br>$^1$H NMR (400 MHz, DMSO-d$_6$) δ 12.13 (s, 1H), 9.58 (s, 1H), 7.76-7.70 (m, 4H), 7.14 (s, 1H), 6.64 (d, J = 8.8 Hz, 1H), 5.94 (d, J = 2.0 Hz, 1H), 5.87 (s, 1H), 5.80 (s, 2H), 5.41 (s, 1H), 2.69-2.65 (m, 1H), 2.20-2.15 (m, 1H), 1.27-1.21 (m, 1H), 0.52-0.49 (m, 1H). |

TABLE 5-continued

Structure and analytical data of compounds in embodiments 38-47

| Embodiment | Structural formula | Analytical data |
|---|---|---|
| Embodiment 44 | | MS (ESI) m/z (M + H)⁺ = 567.0.<br>$^1$H NMR (400 MHz, Methanol-$d_4$) δ 9.25 (s, 1H), 7.69-7.56 (m, 3H), 7.34 (d, J = 1.5 Hz, 1H), 7.28 (dd, J = 8.4, 2.0 Hz, 1H), 7.09 (s, 1H), 6.77 (d, J = 8.3 Hz, 1H), 6.07 (d, J = 1.7 Hz, 1H), 5.96 (d, J = 1.8 Hz, 1H), 5.50 (s, 1H), 2.79-2.71 (m, 1H), 2.27-2.22 (m, 1H), 1.39-1.31 (m, 1H), 0.57-0.54 (m, 1H). |
| Embodiment 45 | | MS (ESI) m/z (M + H)⁺ = 551.0.<br>$^1$H NMR (400 MHz, Methanol-$d_4$) δ 9.24 (s, 1H), 7.67-7.56 (m, 4H), 7.48 (dd, J = 8.5, 2.1 Hz, 1H), 7.12 (s, 1H), 6.76 (d, J = 8.5 Hz, 1H), 6.07 (d, J = 1.7 Hz, 1H), 5.95 (d, J = 1.7 Hz, 1H), 5.50 (s, 1H), 2.80-2.72 (m, 1H), 2.27-2.22 (m, 1H), 1.36-1.31 (m, 1H), 0.57-0.54 (m, 1H). |
| Embodiment 46 | | MS (ESI) m/z (M + H)⁺ = 591.0.<br>$^1$H NMR (400 MHz, DMSO-$d_6$) δ 11.97 (s, 1H), 9.66 (s, 1H), 7.82-7.77 (m, 3H), 7.35-7.15 (m, 3H), 6.68-6.59 (m, 1H), 6.44-6.25 (m, 1H), 6.01-5.88 (m, 2H), 5.42 (s, 1H), 4.06-4.00 (m, 1H), 2.78-2.68 (m, 3H), 2.29-2.20 (m, 1H), 1.99-1.91 (m, 2H), 1.32-1.27 (m, 1H), 0.58-0.52 (m, 1H). |
| Embodiment 47 | | MS (ESI) m/z (M + H)⁺ = 535.2.<br>$^1$H NMR (400 MHz, DMSO-$d_6$) δ 12.17 (s, 1H), 9.65 (s, 1H), 7.81-7.76 (m, 3H), 7.57 (t, J = 8.6 Hz, 1H), 7.20-6.99 (m, 1H), 6.66 (dd, J = 8.7, 1.3 Hz, 1H), 6.01 (d, J = 1.7 Hz, 1H), 5.94 (d, J = 1.7 Hz, 1H), 5.62 (s, 2H), 5.46 (s, 1H), 2.77-2.72 (m, 1H), 2.28-2.23 (m, 1H), 1.33-1.28 (m, 1H), 0.58-0.55 (m, 1H). |

Embodiment 48-52

Compounds 48-52 can be synthesized by the synthesis method described in the preparation of compound 1→the preparation of compound 2, using intermediates Int-O, Int-AI, Int-AL, Int-AH and Int-AR as raw materials and reacting with intermediate Int-C respectively. The analytical data were shown in Table 6 below.

TABLE 6

Structure and analytical data of compounds in embodiments 48-52

| Embodiment | Structural formula | Analytical data |
|---|---|---|
| Embodiment 48 | | MS (ESI) m/z (M + H)⁺ = 537.2.<br>$^1$H NMR (400 MHz, DMSO-d$_6$) δ 12.50 (s, 1H), 9.66 (s, 1H), 7.82-7.78 (m, 3H), 7.01-6.94 (m, 1H), 6.67-6.62 (m, 1H), 5.99 (d, J = 1.7 Hz, 1H), 5.92 (d, J = 1.7 Hz, 1H), 5.69 (s, 2H), 5.41 (s, 1H), 2.75-2.69 (m, 1H), 2.23-2.17 (m, 1H), 1.31-1.28 (m, 1H), 0.60-0.55 (m, 1H). |
| Embodiment 49 | | MS (ESI) m/z (M + H)⁺ = 585.0.<br>$^1$H NMR (400 MHz, Chloroform-d) δ 11.48 (s, 1H), 8.57 (s, 1H), 7.65-7.50 (m, 3H), 7.21 (s, 1H), 7.05 (d, J = 7.9 Hz, 1H), 6.79 (d, J = 7.8 Hz, 1H), 6.29 (s, 1H), 5.88 (s, 1H), 5.63 (s, 1H), 2.87 (s, 1H), 2.71 (s, 1H), 0.57 (s, 1H). |
| Embodiment 50 | | MS (ESI) m/z (M + H)⁺ = 569.2.<br>$^1$H NMR (400 MHz, DMSO-d$_6$) δ 12.70 (s, 1H), 9.60 (s, 1H), 7.76-7.71 (m, 3H), 7.51 (d, J = 2.1 Hz, 1H), 7.42 (dd, J = 8.5, 2.1 Hz, 1H), 6.84 (d, J = 87 Hz, 1H), 5.93 (d, J = 1.7 Hz, 1H), 5.84 (d, J = 1.7 Hz, 1H), 5.68 (s, 2H), 5.26 (s, 1H), 2.72-2.64 (m, 1H), 2.15-2.08 (m, 1H), 1.25-1.20 (m, 1H), 0.54 (q, J = 4.5 Hz, 1H). |
| Embodiment 51 | | MS (ESI) m/z (M + H)⁺ = 587.2.<br>$^1$H NMR (400 MHz, DMSO-d$_6$) δ 12.47 (s, 1H), 9.59 (s, 1H), 7.78-7.67 (m, 3H), 7.29 (t, J = 8.5 Hz, 1H), 6.66 (d, J = 8.8 Hz, 1H), 6.09 (s, 2H), 5.93 (d, J = 1.8 Hz, 1H), 5.85 (d, J = 1.7 Hz, 1H), 5.34 (s, 1H), 2.70-2.63 (m, 1H), 2.14-2.10 (m, 1H), 1.25-1.20 (m, 1H), 0.51 (q, J = 4.4 Hz, 1H). |
| Embodiment 52 | | MS (ESI) m/z (M + H)⁺ = 609.0.<br>$^1$H NMR (400 MHz, DMSO-d$_6$) δ 12.56 (s, 1H), 9.67 (s, 1H), 7.81-7.79 (m, 3H), 7.17-7.15 (m, 2H), 6.71 (d, J = 8.1 Hz, 1H), 6.50 (d, J = 3.7 Hz, 1H), 6.00 (d, J = 1.7 Hz, 1H), 5.90 (d, J = 1.8 Hz, 1H), 5.33 (s, 1H), 4.10-4.03 (m, 1H), 2.77-2.68 (m, 3H), 2.19-2.14 (m, 1H), 2.01-1.92 (m, 2H), 1.31-1.26 (m, 1H), 0.60-0.57 (m, 1H) |

Embodiment 53-57

The synthesis of compounds 53 to 57 can be prepared by the synthetic method described in the preparation of compound 16, using intermediates Int-AA, Int-AB, Int-AC, Int-AG and Int-AN as raw materials, and reacting with intermediate Int-C respectively. The analytical data were shown in Table 7 below.

TABLE 7

Structure and analytical data of compounds in embodiments 53-57

| Embodiment | Structural formula | Analytical data |
|---|---|---|
| Embodiment 53 | | MS (ESI) m/z (M + H)$^+$ = 553.2.<br>$^1$H NMR (400 MHz, DMSO-d$_6$) δ 11.94 (s, 1H), 10.54 (s, 1H), 9.60 (s, 1H), 7.75-7.70 (m, 3H), 7.13-6.84 (m, 2H), 5.94 (d, J = 1.7 Hz, 1H), 5.85 (d, J = 1.7 Hz, 1H), 5.30 (s, 1H), 4.48 (s, 2H), 2.71-2.66 (m, 1H), 2.26 (s, 3H), 2.18-2.16 (m, 1H), 1.24-1.22 (m, 1H), 0.50-0.49 (m, 1H). |
| Embodiment 54 | | MS (ESI) m/z (M + H)$^+$ = 567.2.<br>$^1$H NMR (400 MHz, DMSO-d$_6$) δ 12.12 (s, 1H), 10.55 (s, 1H), 9.62 (s, 1H), 7.78-7.72 (m, 3H), 7.43 (d, J = 2.0 Hz, 1H), 7.29-7.20 (m, 2H), 6.87-6.78 (m, 1H), 6.01-5.93 (m, 1H), 5.91-5.84 (m, 1H), 5.42-5.36 (m, 1H), 2.76-2.69 (m, 1H), 2.28-2.15 (m, 1H), 1.35 (s, 6H), 1.29-1.25 (m, 1H), 0.57-0.50 (m, 1H). |
| Embodiment 55 | | MS (ESI) m/z (M + H)$^+$ = 536.2.<br>$^1$H NMR (400 MHz, DMSO-d$_6$) δ 12.35 (s, 1H), 12.19 (s, 1H), 9.60 (s, 1H), 8.10 (s, 1H), 8.03-7.99 (m, 1H), 7.88-7.86 (m, 1H), 7.75-7.71 (m, 3H), 7.58 (d, J = 2.0 Hz, 1H), 7.26-7.20 (m, 1H), 5.96 (d, J = 1.7 Hz, 1H), 5.87 (d, J = 1.7 Hz, 1H), 5.41 (s, 1H), 2.73-2.70 (m, 1H), 2.25-2.19 (m, 1H), 1.27-1.24 (m, 1H), 0.53 (q, J = 4.3 Hz, 1H). |
| Embodiment 56 | | MS (ESI) m/z (M + H)$^+$ = 565.2.<br>$^1$H NMR (400 MHz, DMSO-d$_6$) δ 12.15 (s, 1H), 10.73 (s, 1H), 9.65 (s, 1H), 7.82-7.77 (m, 3H), 7.46 (d, J = 2.1 Hz, 1H), 7.36-7.26 (m, 1H), 7.22 (d, J = 1.8 Hz, 1H), 6.95-6.85 (m, 1H), 6.02 (d, J = 1.7 Hz, 1H), 5.94-5.89 (m, 1H), 5.44 (s, 1H), 2.77-2.74 (m, 1H), 2.28-2.24 (m, 1H), 1.34-1.28 (m, 1H), 1.27-1.14 (m, 4H), 0.59-0.56 (m, 1H). |
| Embodiment 57 | | MS (ESI) m/z (M + H)$^+$ = 539.2.<br>$^1$H NMR (400 MHz, DMSO-d$_6$) δ 11.98 (s, 1H), 10.05 (s, 1H), 9.59 (s, 1H), 7.78-7.66 (m, 3H), 7.53-7.44 (m, 2H), 7.37 (d, J = 2.1 Hz, 1H), 6.77 (d, J = 8.2 Hz, 1H), 5.95 (d, J = 1.8 Hz, 1H), 5.86 (d, J = 1.7 Hz, 1H), 5.38 (s, 1H), 5.25 (s, 2H), 2.70-2.66 (m, 1H), 2.20-2.16 (m, 1H), 1.26-1.21 (m, 1H), 0.52-0.49 (m, 1H). |

Embodiment 58-59

Compounds 58-59 can be synthesized by the synthesis method described in the preparation of compounds 16 and 17, using intermediates Int-AW and Int-AX as raw materials and reacting with intermediates Int-C respectively. The analytical data were shown in Table 8 below.

TABLE 8

Structure and analytical data of compounds in embodiments 58-59

| Embodiment | Structural formula | Analytical data |
|---|---|---|
| Embodiment 58 | | MS (ESI) m/z (M + H)+ = 621.2.<br>$^1$H NMR (400 MHz, DMSO-$d_6$) δ 13.00 (s, 1H), 12.43 (s, 1H), 9.67 (s, 1H), 8.59 (s, 1H), 8.02 (d, J = 2.0 Hz, 1H), 7.86 (dd, J = 8.7, 2.0 Hz, 1H), 7.82-7.79 (m, 3H), 7.45 (d, J = 8.7 Hz, 1H), 6.03 (d, J = 1.7 Hz, 1H), 5.91 (d, J = 1.7 Hz, 1H), 5.39 (s, 1H), 2.77-2.74 (m, 1H), 2.24-2.20 (m, 1H), 1.33-1.29 (m, 1H), 0.66-0.62 (m, 1H). |
| Embodiment 59 | | MS (ESI) m/z (M + H)+ = 569.0.<br>$^1$H NMR (400 MHz, DMSO-$d_6$) δ 12.70 (s, 1H), 10.09 (s, 1H), 9.60 (s, 1H), 7.74 (m, 3H), 7.32-7.26 (m, 2H), 6.84 (d, J = 8.3 Hz, 1H), 5.94 (d, J = 1.7 Hz, 1H), 5.84 (d, J = 1.7 Hz, 1H), 5.29 (s, 1H), 2.97-2.86 (m, 2H), 2.69-2.67 (m, 1H), 2.63-2.59 (m, 1H), 2.14-2.10 (m, 1H), 1.24-1.22 (m, 1H), 1.06 (d, J = 6.8 Hz, 3H), 0.55-0.54 (m, 1H). |

Embodiment 60-61

The synthesis of compounds 60 to 61 can be prepared by the synthetic method described in the preparation of compound 30, using intermediates Int-L, Int-AE as raw materials, and reacting with intermediate Int-D respectively. The analytical data were shown in Table 9 below.

Embodiment 62-64

The synthesis of compounds 62 to 64 can be prepared by the synthetic method described in the preparation of compound 31, using intermediates Int-L, Int-AM, Int-AN and Int-AQ as raw materials, and reacting with intermediate Int-D respectively. The analytical data were shown in Table 10 below.

TABLE 9

Structure and analytical data of compounds in embodiments 60-61

| Embodiment | Structural formula | Analytical data |
|---|---|---|
| Embodiment 60 | | MS (ESI) m/z (M + H)+ = 572.2.<br>$^1$H NMR (400 MHz, DMSO-$d_6$) δ 10.76 (s, 1H), 8.63 (s, 1H), 7.84-7.67 (m, 4H), 7.32 (s, 2H), 6.89 (brs, 1H), 6.03 (s, 1H), 5.96 (d, J = 1.6 Hz, 1H), 5.51 (s, 1H), 4.58 (s, 2H), 2.82-2.78 (m, 1H), 2.31-2.27 (m, 1H), 1.36-1.32 (m, 1H), 0.68-0.62 (m, 1H). |
| Embodiment 61 | | MS (ESI) m/z (M + H)+ = 588.2.<br>H NMR (400 MHz, DMSO-$d_6$) δ 12.18 (s, 1H), 10.51 (s, 1H), 8.63 (s, 1H), 7.79-7.73 (m, 3H), 7.64 (d, J = 1.9 Hz, 1H), 7.57-7.39 (m, 2H), 6.93 (d, J = 8.3 Hz, 1H), 5.99-5.92 (m, 2H), 5.45 (s, 1H), 3.46 (s, 2H), 2.82-2.74 (m, 1H), 2.34-2.20 (m, 1H), 1.35-1.28 (m, 1H), 0.60-0.53 (m, 1H). |

TABLE 10

Structure and analytical data of compounds in embodiments 62-64

| Embodiment | Structural formula | Analytical data |
|---|---|---|
| Embodiment 62 | 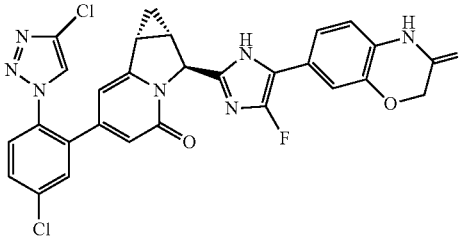 | MS (ESI) m/z (M + H)$^+$ = 590.2.<br>$^1$H NMR (400 MHz, DMSO-d$_6$) δ 12.83 (s, 1H), 10.81 (s, 1H), 8.64 (s, 1H), 7.79-7.73 (m, 3H), 7.19-7.14 (m, 2H), 6.95 (d, J = 8.7 Hz, 1H), 5.98 (d, J = 1.7 Hz, 1H), 5.94 (d, J = 1.7 Hz, 1H), 5.36 (s, 1H), 4.61 (s, 2H), 2.78-2.73 (m, 1H), 2.21-2.17 (m, 1H), 1.33-1.28 (m, 1H), 0.62-0.59 (m, 1H). |
| Embodiment 63 | 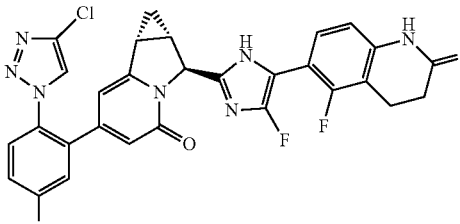 | MS (ESI) m/z (M + H)$^+$= 606.2.<br>$^1$H NMR (400 MHz, DMSO-d$_6$) δ 12.58 (s, 1H), 10.37 (s, 1H), 8.63 (s, 1H), 7.79-7.73 (m, 3H), 7.29 (t, J = 8.1 Hz, 1H), 6.78 (d, J = 8.3 Hz, 1H), 5.98 (d, J = 1.7 Hz, 1H), 5.95 (d, J = 1.7 Hz, 1H), 5.46 (s, 1H), 2.95 (t, J = 7.6 Hz, 2H), 2.77-2.73 (m, 1H), 2.54-2.52 (m, 2H), 2.24-2.19 (m, 1H), 1.34-1.29 (m, 1H), 0.59-0.56 (m, 1H). |
| Embodiment 64 | 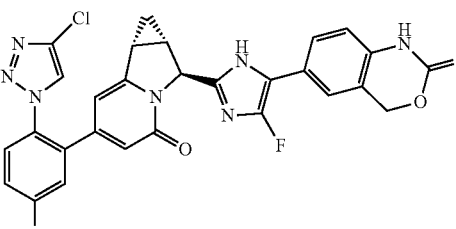 | MS (ESI) m/z (M + H)$^+$ = 590.0.<br>$^1$H NMR (400 MHz, DMSO-d$_6$) δ 12.78 (s, 1H), 10.22 (s, 1H), 8.58 (s, 1H), 7.73-7.67 (m, 3H), 7.42-7.31 (m, 2H), 6.88 (d, J = 8.3 Hz, 1H), 5.92 (d, J = 1.7 Hz, 1H), 5.88 (d, J = 1.7 Hz, 1H), 5.31 (s, 1H), 5.27 (s, 2H), 2.71-2.67 (m, 1H), 2.15-2.11 (m, 1H), 1.30-1.23 (m, 1H), 0.56-0.53 (m, 1H). |
| Embodiment 65 | 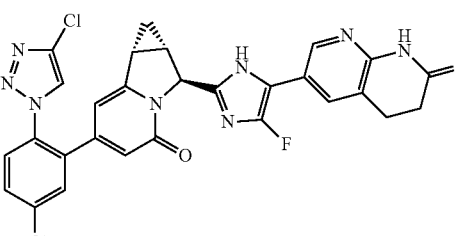 | MS (ESI) m/z (M + H)$^+$ = 588.8.<br>$^1$H NMR (400 MHz, DMSO-d$_6$) δ 12.97 (s, 1H), 10.59 (s, 1H), 8.65 (s, 1H), 8.33 (d, J = 2.2 Hz, 1H), 7.77-7.70 (m, 4H), 5.99 (d, J = 1.8 Hz, 1H), 5.95 (d, J = 1.7 Hz, 1H), 5.38 (s, 1H), 2.94 (t, J = 7.6 Hz, 2H), 2.79-2.74 (m, 1H), 2.57-2.51 (m, 2H), 2.23-2.18 (m, 1H), 1.34-1.28 (m, 1H), 0.64-0.60 (m, 1H). |

Embodiment 66-68

The synthesis of compounds 66 to 68 can be prepared by the synthetic method described in the preparation of compound 1, using intermediates Int-AO, Int-AU, Int-AV as raw materials, and reacting with intermediate Int-D respectively. The analytical data were shown in Table 11 below.

TABLE 11

Structure and analytical data of compounds in embodiments 66-68

| Embodiment | Structural formula | Analytical data |
|---|---|---|
| Embodiment 66 | | MS (ESI) m/z (M + H)+ = 571.2.<br>$^1$H NMR (400 MHz, DMSO-d$_6$) δ 12.37 (s, 1H), 8.57 (s, 1H), 7.74-7.63 (m, 6H), 7.56 (d, J = 9.0 Hz, 1H), 6.86 (d, J = 5.5 Hz, 1H), 5.94 (d, J = 1.7 Hz, 2H), 5.90 (d, J = 1.7 Hz, 2H), 5.43 (s, 1H), 2.79 (d, J = 4.6 Hz, 3H), 2.76-2.71 (m, 1H), 2.24-2.20 (m, 1H), 1.29-1.24 (m, 1H), 0.55-0.54 (m, 1H). |
| Embodiment 67 | | MS (ESI) m/z (M + H)+ = 606.1.<br>$^1$H NMR (400 MHz, DMSO-d$_6$) δ 8.63 (s, 1H), 7.97-7.94 (m, 1H), 7.81-7.72 (m, 4H), 7.65 (dd, J = 8.8, 2.2 Hz, 1H), 7.34 (br s, 1H), 6.85 (d, J = 8.8 Hz, 1H), 6.09 (s, 1H), 5.99 (d, J = 1.7 Hz, 1H), 5.59 (s, 1H), 3.78-3.75 (m, 2H), 3.46-3.44 (m, 2H), 2.87-2.83 (m, 1H), 2.56-2.53 (m, 1H), 1.41-1.36 (m, 1H), 0.80-0.75 (m, 1H). |
| Embodiment 68 | | MS (ESI) m/z (M + H)+ = 575.2.<br>$^1$H NMR (400 MHz, DMSO-d$_6$) δ 12.48 (s, 1H), 8.58 (s, 1H), 7.76-7.68 (m, 4H), 7.55 (d, J = 8.3 Hz, 1H), 7.50-7.49 (m, 1H), 6.47 (s, 2H), 5.93-5.92 (m, 2H), 5.46 (s, 1H), 2.75-2.71 (m, 1H), 2.25-2.20 (m, 1H), 1.29-1.26 (m, 1H), 0.55-0.52 (m, 1H). |

Embodiment 69-73

The synthesis of compounds 69 to 73 can be prepared by the synthetic method described in the preparation of compound 1→preparation of compound 2, using intermediates Int-S, Int-AO, Int-AS, Int-AU and Int-AV as raw materials, and reacting with intermediate Int-C respectively. The analytical data were shown in Table 12 below.

TABLE 12

Structure and analytical data of compounds in embodiments 69-73

| Embodiment | Structural formula | Analytical data |
|---|---|---|
| Embodiment 69 | | MS (ESI) m/z (M + H)+ = 575.2.<br>$^1$H NMR (400 MHz, DMSO-d$_6$) δ 13.06 (s, 1H), 8.64 (s, 1H), 7.87 (d, J = 8.2 Hz, 1H), 7.80-7.73 (m, 3H), 7.60 (s, 1H), 7.48 (dd, J = 8.2, 1.4 Hz, 1H), 6.43 (s, 2H), 6.00 (d, J = 1.8 Hz, 1H), 5.95 (d, J = 1.8 Hz, 1H), 5.41 (s, 1H), 2.80-2.75 (m, 1H), 2.25-2.21 (m, 1H), 1.35-1.30 (m, 1H), 0.66-0.63 (m, 1H). |

TABLE 12-continued

Structure and analytical data of compounds in embodiments 69-73

| Embodiment | Structural formula | Analytical data |
|---|---|---|
| Embodiment 70 | | MS (ESI) m/z (M + H)⁺ = 589.0.<br>$^1$H NMR (400 MHz, DMSO-d$_6$) δ 13.01 (s, 1H), 8.58 (s, 1H), 7.78-7.67 (m, 4H), 7.54-7.49 (m, 1H), 7.41 (dd, J = 8.1, 1.4 Hz, 1H), 6.96-6.94 (m, 1H), 5.94 (d, J = 1.7 Hz, 1H), 5.88 (d, J = 1.7 Hz, 1H), 5.34 (s, 1H), 2.80 (d, J = 4.8 Hz, 3H), 2.73-2.70 (m, 1H), 2.19-2.15 (m, 1H), 1.27-1.24 (m, 1H), 0.58-0.56 (m, 1H). |
| Embodiment 71 | | MS (ESI) m/z (M + H)⁺ = 611.8.<br>$^1$H NMR (400 MHz, DMSO-d$_6$) δ 12.86 (s, 1H), 8.59 (s, 1H), 7.75-7.68 (m, 4H), 7.51 (dd, J = 8.6, 2.3 Hz, 1H), 6.92 (d, J = 87 Hz, 1H), 6.13 (s, 2H), 5.93 (d, J = 1.7 Hz, 1H), 5.88 (d, J = 1.9 Hz, 1H), 5.31 (s, 1H), 3.10 (s, 3H), 2.72-2.68 (m, 1H), 2.16-2.11 (m, 1H), 1.28-1.22 (m, 1H), 0.56-0.53 (m, 1H). |
| Embodiment 72 | | MS (ESI) m/z (M + H)⁺ = 624.2.<br>$^1$H NMR (400 MHz, DMSO-d$_6$) δ 12.91 (s, 1H), 8.63 (s, 1H), 7.79-7.72 (m, 4H), 7.49 (dd, J = 8.7, 2.2 Hz, 1H), 7.21-7.19 (m, 1H), 6.85 (d, J = 8.8 Hz, 1H), 5.97 (d, J = 1.7 Hz, 1H), 5.94 (d, J = 1.7 Hz, 1H), 5.35 (s, 1H), 3.77-3.73 (m, 2H), 3.44-3.42 (m, 2H), 2.78-2.73 (m, 1H), 2.22-2.17 (m, 1H), 1.33-1.28 (m, 1H), 0.61-0.57 (m, 1H). |
| Embodiment 73 | | MS (ESI) m/z (M + H)⁺ = 593.1.<br>$^1$H NMR (400 MHz, DMSO-d$_6$) δ 12.89 (s, 1H), 8.64 (s, 1H), 7.80-7.75 (m, 3H), 7.71 (d, J = 8.3Hz, 1H), 7.39 (dd, J = 8.2, 5.7 Hz, 1H), 6.64 (s, 2H), 6.00 (d, J = 1.8 Hz, 1H), 5.96 (d, J = 1.7 Hz, 1H), 5.50 (s, 1H), 2.79-2.74 (m, 1H), 2.26-2.22 (m, 1H), 1.35-1.30 (m, 1H), 0.63-0.59 (m, 1H). |

Embodiment 74

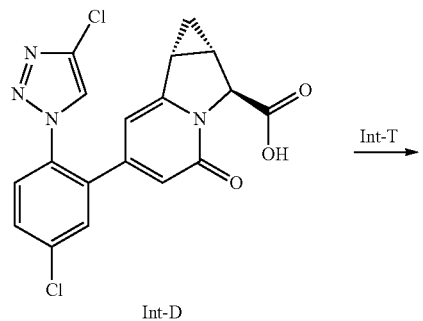

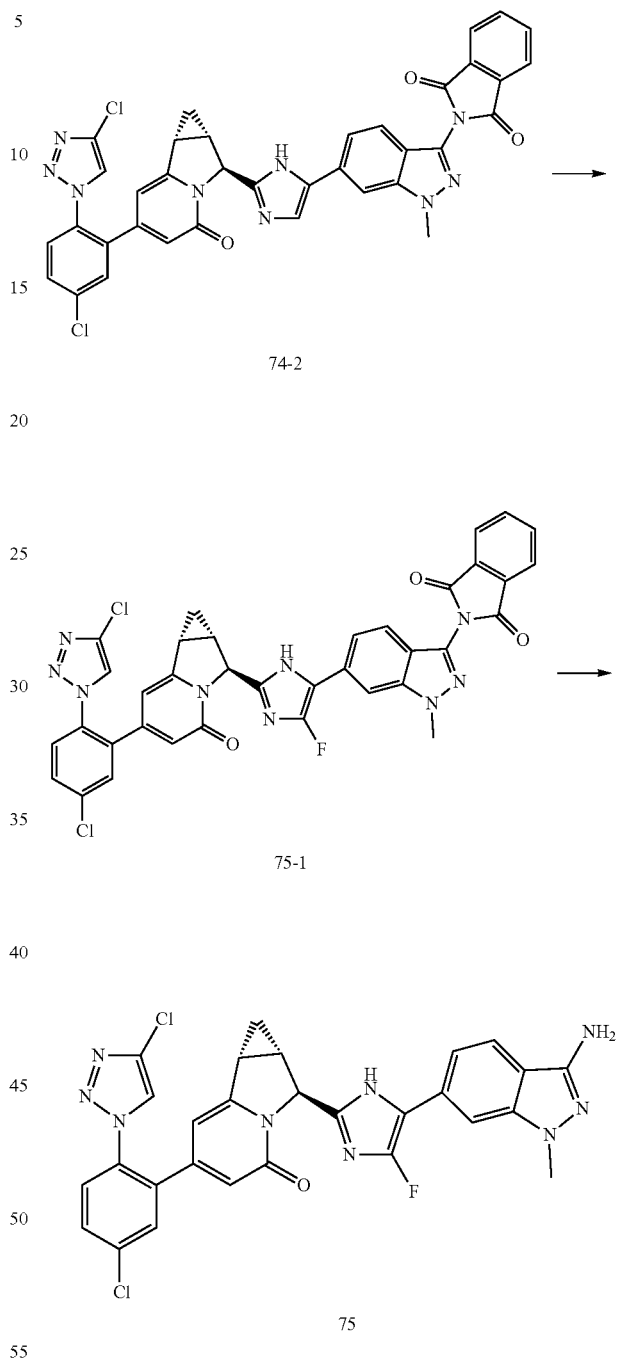

The synthesis of compound 74 can be prepared by the synthetic method described in the preparation of compound 15, using Int-D and Int-T as raw materials, the analytical data were as follows.

MS (ESI) m/z (M+H)$^+$=570.2.

$^1$H NMR (400 MHz, DMSO-d$_6$) δ 12.20 (s, 1H), 8.66 (s, 1H), 7.81-7.61 (m, 4H), 7.59 (d, J=2.6 Hz, 1H), 7.58 (s, 1H), 7.30 (dd, J=8.2, 1.4 Hz, 1H), 6.00-5.93 (m, 2H), 5.49-5.33 (m, 3H), 3.73 (s, 3H), 2.83-2.79 (m, 1H), 2.34-2.29 (m, 1H), 1.36-1.31 (m, 1H), 0.60-0.57 (m, 1H).

Embodiment 75

The synthesis of compound 75 can be prepared by the synthetic method described in the preparation of compound 33, using 74-2 as raw material, the analytical data were as follows.

MS (ESI) m/z (M+H)$^+$=588.2.

$^1$H NMR (400 MHz, DMSO-d$_6$) δ 12.88 (s, 1H), 8.65 (s, 1H), 7.79-7.71 (m, 4H), 7.46 (s, 1H), 7.15 (d, J=8.4 Hz, 1H), 5.99 (d, J=1.7 Hz, 1H), 5.95 (d, J=1.7 Hz, 1H), 5.46 (s, 2H), 5.41 (s, 1H), 3.73 (s, 3H), 2.80-2.75 (m, 1H), 2.25-2.20 (m, 1H), 1.35-1.29 (m, 1H), 0.65-0.61 (m, 1H).

Embodiment 76

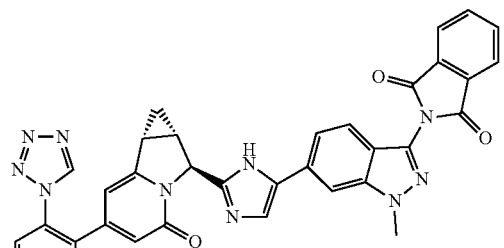

34-2

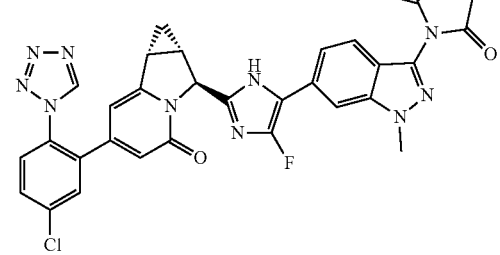

76-1

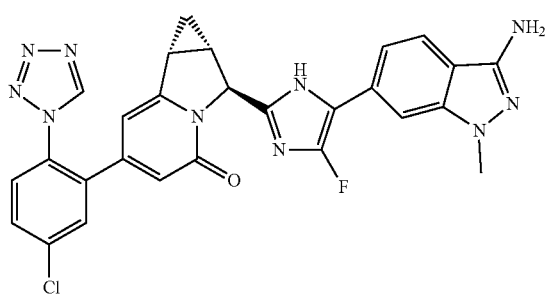

76

The synthesis of compound 76 can be prepared by the synthetic method described in the preparation of compound 33, using 34-2 as raw material, the analytical data were as follows.

MS (ESI) m/z (M+H)$^+$=555.2.

$^1$H NMR (400 MHz, DMSO-d$_6$) δ 12.84 (s, 1H), 9.68 (s, 1H), 7.81 (s, 3H), 7.72 (d, J=8.5 Hz, 1H), 7.46 (s, 1H), 7.17-7.13 (m, 1H), 6.02 (d, J=1.6 Hz, 1H), 5.92 (d, J=1.7 Hz, 1H), 5.46 (s, 2H), 5.39 (s, 1H), 3.74 (s, 3H), 2.78-2.75 (m, 1H), 2.24-2.19 (m, 1H), 1.34-1.29 (m, 1H), 0.66-0.63 (m, 1H).

Embodiment 77

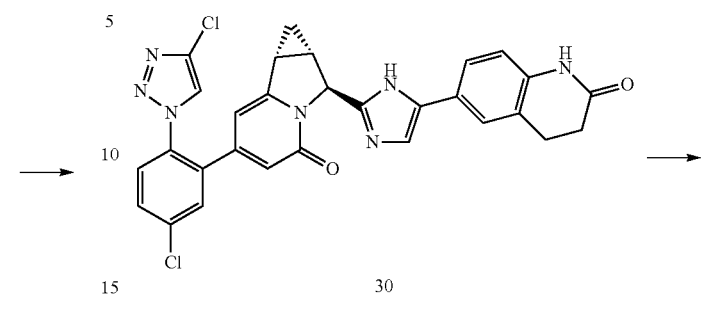

30

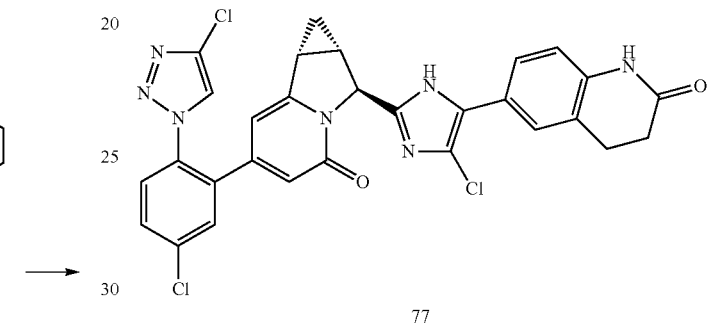

77

Step 1. Synthesis of Compound 77

Compound 30 (900 mg, 1.58 mmol) was dissolved in tetrahydrofuran (20 mL), N-chlorosuccinimide (210.7 mg, 1.58 mmol) was added, the reaction was heated to 55° C. and stirred for 36 hours, the system was cooled to room temperature, diluted with ethyl acetate (20 mL), water (20 mL) was added, and the mixture was stirred for 20 min, the phases were separated, the aqueous phase was extracted with ethyl acetate (20 mL×2), the organic phase was combined, washed with saturated saline (20 mL), dried over anhydrous sodium sulfate, filtered, and the filtrate was concentrated under reduced pressure, the crude product was purified by silica gel column chromatography (methanol:dichloromethane=0:100→10:90) to obtain compound 77. Then the crude product was separated by preparative high performance liquid chromatography (separation conditions: chromatographic column: Agilent 10 Prep-C8 250×21.2 mm; mobile phase: [water (0.1% trifluoroacetic acid)-acetonitrile], B %: 30%-50%; flow rate: 30 mL/min) to obtain compound 77 (HPLC retention time: 5.295 min).

MS (ESI) m/z (M+H)$^+$=604.2.

$^1$H NMR (400 MHz, DMSO-d$_6$) δ 12.91 (s, 1H), 10.20 (s, 1H), 8.64 (s, 1H), 7.80-7.73 (m, 3H), 7.52-7.46 (m, 2H), 6.94 (d, J=8.2 Hz, 1H), 5.99 (d, J=1.7 Hz, 1H), 5.94 (d, J=1.7 Hz, 1H), 5.41 (s, 1H), 2.93 (t, J=7.5 Hz, 2H), 2.80-2.75 (m, 1H), 2.49-2.47 (m, 2H), 2.23-2.18 (m, 1H), 1.34-1.29 (m, 1H), 0.61-0.58 (m, 1H).

Embodiment 78
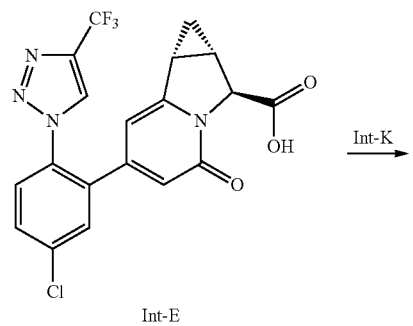
Int-E
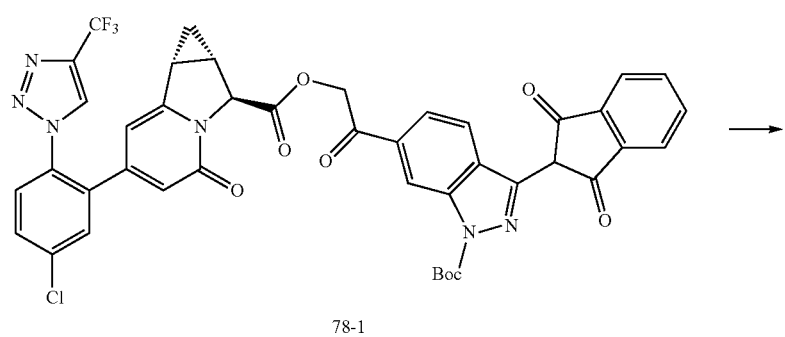
78-1
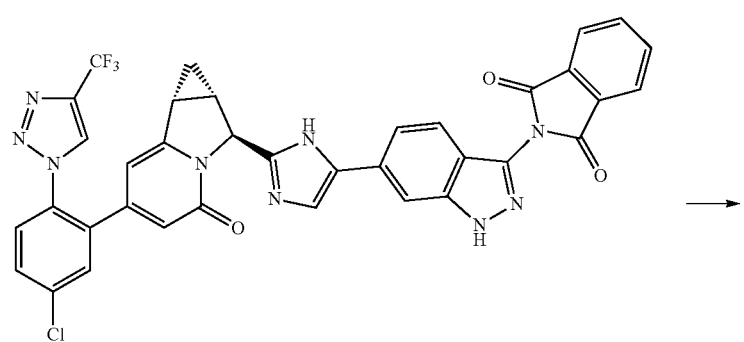
78-2
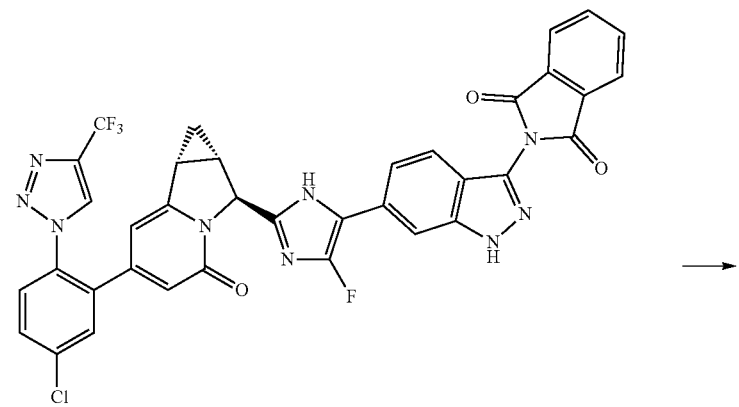
78-3

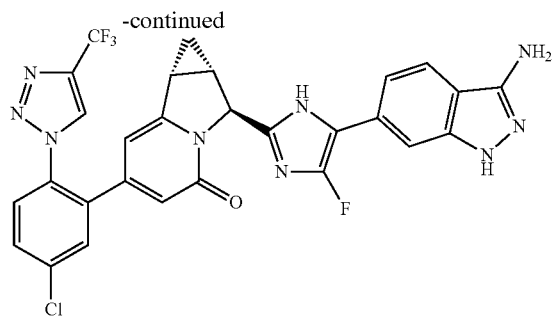
78
The synthesis of compound 78 can be prepared by the synthetic method described in the preparation of compound 32 and 33, using Int-E and Int-K as raw materials, the analytical data were as follows.
MS (ESI) m/z (M+H)$^+$=608.2.
$^1$H NMR (400 MHz, DMSO-d$_6$) δ 12.85 (s, 1H), 11.42 (s, 1H), 9.07 (s, 1H), 7.78-7.72 (m, 3H), 7.66 (d, J=8.4 Hz, 1H), 7.36 (d, J=1.1 Hz, 1H), 7.09 (dd, J=8.3, 1.4 Hz, 1H), 5.92 (d, J=1.7 Hz, 1H), 5.83 (d, J=1.8 Hz, 1H), 5.33-5.29 (m, 3H), 2.69-2.64 (m, 1H), 2.18-2.13 (m, 1H), 1.26-1.21 (m, 1H), 0.48-0.45 (m, 1H).
Embodiment 79
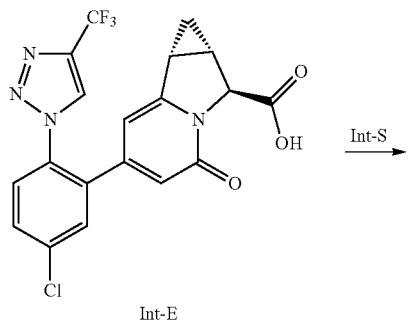
Int-E
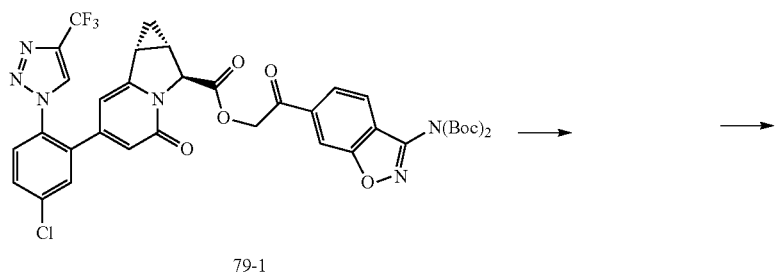
79-1
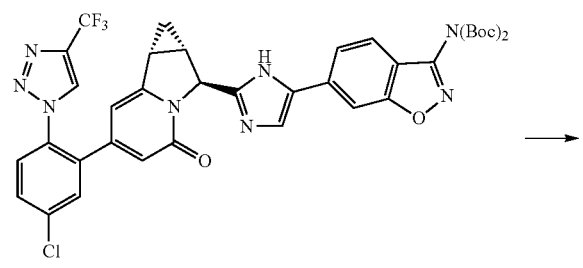
79-2

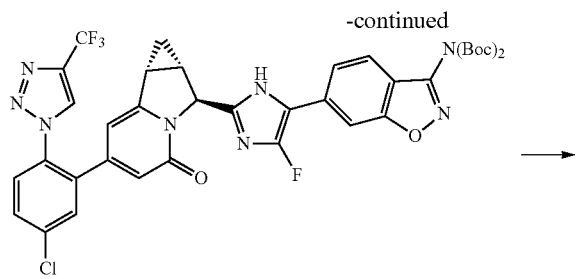

79-3

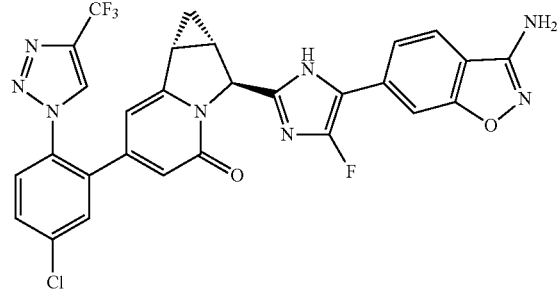

79

The synthesis of compound 79 can be prepared by the synthetic method described in the preparation of compound 29, using Int-E and Int-S as raw materials, the analytical data were as follows.

MS (ESI) m/z (M+H)$^+$=609.2.

$^1$H NMR (400 MHz, DMSO-d$_6$) δ 13.00 (s, 1H), 9.07 (d, J=1.0 Hz, 1H), 7.83-7.72 (m, 4H), 7.57-7.50 (m, 1H), 7.41 (dd, J=8.1, 1.4 Hz, 1H), 6.37 (s, 2H), 5.92 (d, J=1.7 Hz, 1H), 5.84 (d, J=1.7 Hz, 1H), 5.33 (s, 1H), 2.70-2.64 (m, 1H), 2.18-2.13 (m, 1H), 1.26-1.22 (m, 1H), 0.51-0.48 (m, 1H).

Embodiment 80

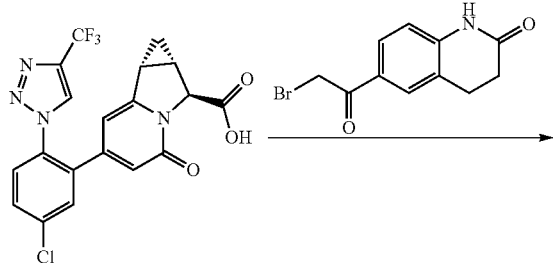

Int-E

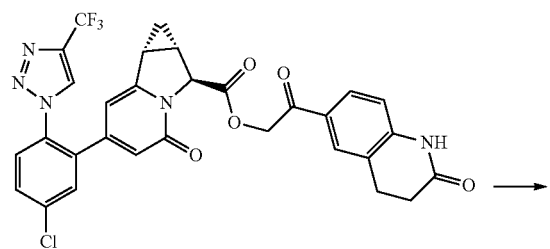

80-1

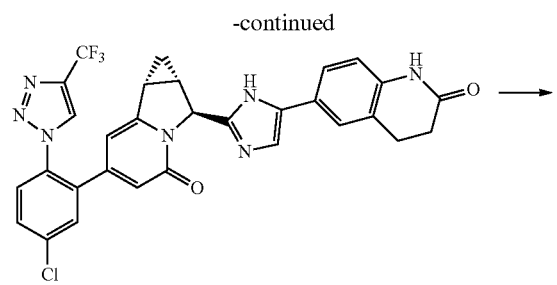

80-2

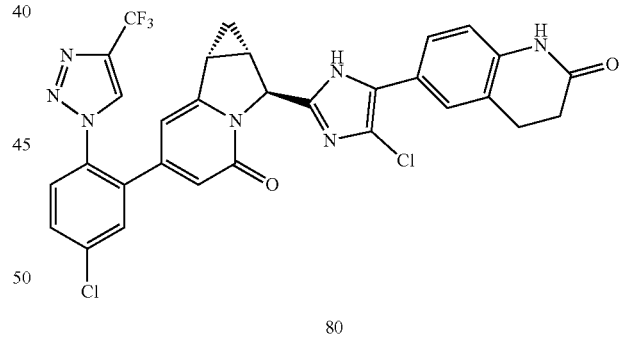

80

The synthesis of compound 80 can be prepared by the synthetic method described in the preparation of compound 30 and 77, using Int-E and 16-1 as raw materials, the analytical data were as follows.

MS (ESI) m/z (M+H)$^+$=638.2.

$^1$H NMR (400 MHz, DMSO-d$_6$) δ 12.86 (s, 1H), 10.15 (s, 1H), 9.09 (d, J=1.0 Hz, 1H), 7.78-7.73 (m, 3H), 7.46-7.39 (m, 2H), 6.87 (d, J=8.2 Hz, 1H), 5.92 (d, J=1.7 Hz, 1H), 5.82 (d, J=1.7 Hz, 1H), 5.33 (d, J=1.3 Hz, 1H), 2.86 (t, J=6.6 Hz, 2H), 2.70-2.65 (m, 1H), 2.41 (t, J=6.7 Hz, 2H), 2.13 (ddd, J=8.1, 6.2, 4.5 Hz, 1H), 1.24-1.21 (m, 1H), 0.46-0.43 (m, 1H).

Embodiment 81

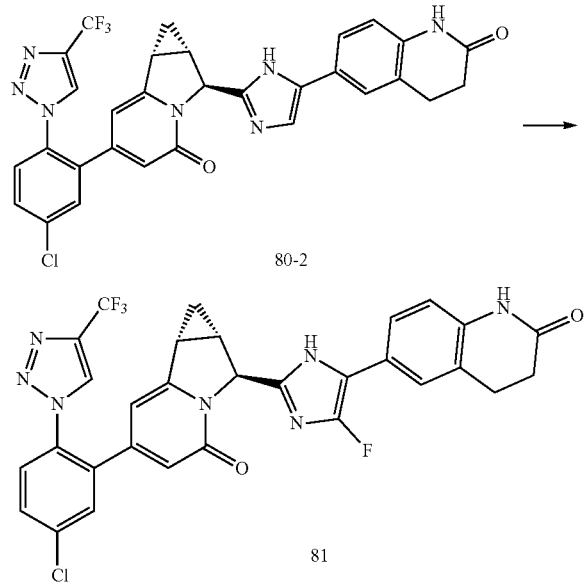

The synthesis of compound 81 can be prepared by the synthetic method described in the preparation of compound 17, using compound 80-2 as raw material, the analytical data were as follows.

MS (ESI) m/z (M+H)$^+$=622.2.

$^1$H NMR (400 MHz, DMSO-d$_6$) δ 12.78 (s, 1H), 10.19 (s, 1H), 9.15 (d, J=1.0 Hz, 1H), 7.85-7.81 (m, 3H), 7.41-7.32 (m, 2H), 6.92 (d, J=8.3 Hz, 1H), 5.99 (d, J=1.7 Hz, 1H), 5.90 (d, J=1.8 Hz, 1H), 5.38 (s, 1H), 2.93 (t, J=7.6 Hz, 2H), 2.76-2.71 (m, 1H), 2.50-2.47 (m, 2H), 2.22-2.17 (m, 1H), 1.33-1.28 (m, 1H), 0.55-0.52 (m, 1H).

Embodiment 82

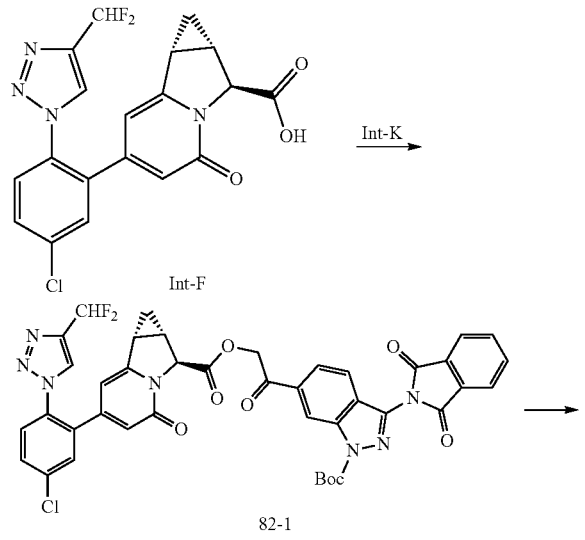

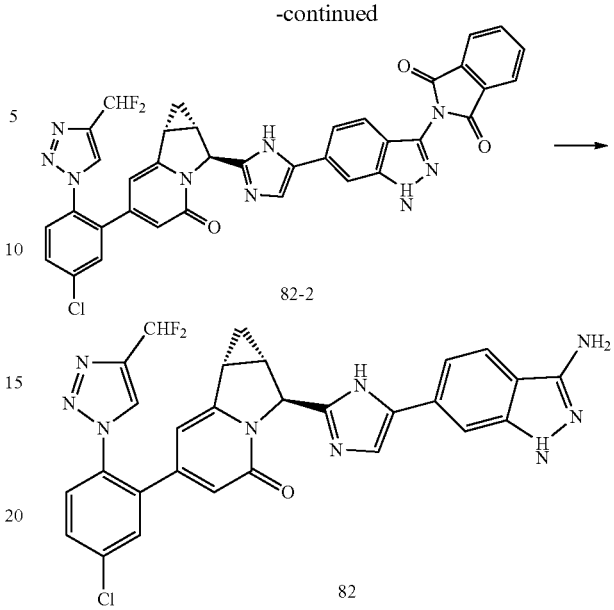

The synthesis of compound 82 can be prepared by the synthetic method described in the preparation of compound 32, using Int-F and Int-K as raw materials, the analytical data were as follows.

MS (ESI) m/z (M+H)$^+$=572.2.

$^1$H NMR (400 MHz, DMSO-d$_6$) δ 12.16 (s, 1H), 11.20 (s, 1H), 8.74 (s, 1H), 7.78-7.77 (m, 3H), 7.60-7.24 (m, 4H), 6.00 (d, J=1.7 Hz, 1H), 5.90 (d, J=1.7 Hz, 1H), 5.47-5.24 (m, 3H), 2.79-2.77 (m, 1H), 2.33-2.31 (m, 1H), 1.36-1.31 (m, 1H), 0.51-0.50 (m, 1H).

Embodiment 83

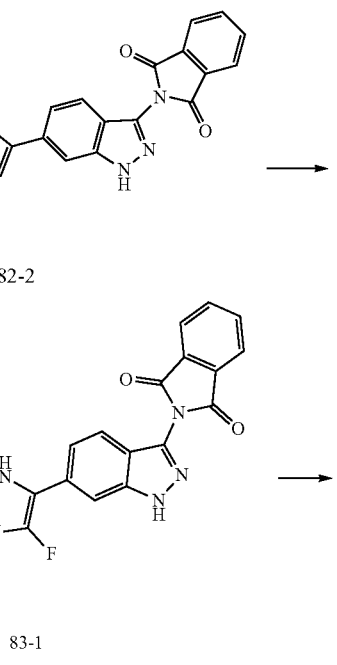

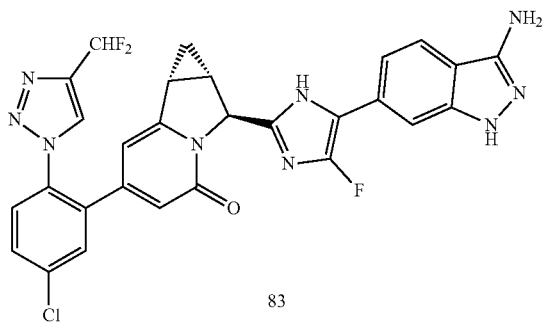

83

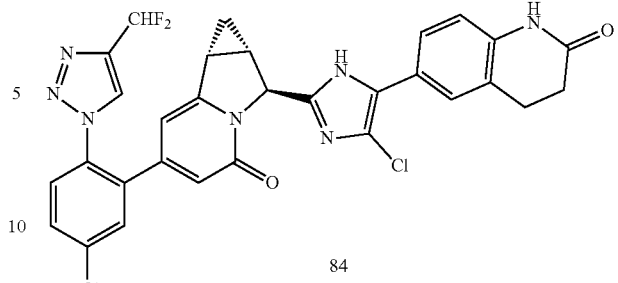

84

The synthesis of compound 83 can be prepared by the synthetic method described in the preparation of compound 33, using 82-2 as raw material, the analytical data were as follows.

MS (ESI) m/z (M+H)$^+$=590.0.

$^1$H NMR (400 MHz, DMSO-d$_6$) δ 12.84 (s, 1H), 11.42 (s, 1H), 8.68 (s, 1H), 7.72-7.65 (m, 4H), 7.36-7.33 (m, 1H), 7.19-7.06 (m, 2H), 5.92 (d, J=1.7 Hz, 1H), 5.83 (d, J=1.8 Hz, 1H), 5.32 (s, 1H), 5.29 (s, 2H), 2.67-2.64 (m, 1H), 2.16-2.13 (m, 1H), 1.24-1.21 (m, 1H), 0.49-0.47 (m, 1H).

The synthesis of compound 84 can be prepared by the synthetic method described in the preparation of compound 30 and 77, using Int-F as raw material, the analytical data were as follows.

MS (ESI) m/z (M+H)$^+$=620.2.

$^1$H NMR (400 MHz, DMSO-d$_6$) δ 12.83 (s, 1H), 10.13 (s, 1H), 8.67 (d, J=1.6 Hz, 1H), 7.72-7.69 (m, 3H), 7.45-7.38 (m, 2H), 7.18 (t, J=52.0 Hz, 1H), 6.87 (d, J=8.2 Hz, 1H), 5.91 (d, J=1.8 Hz, 1H), 5.82 (d, J=1.7 Hz, 1H), 5.32 (s, 1H), 2.86 (t, J=7.5 Hz, 2H), 2.70-2.63 (m, 1H), 2.41-2.39 (m, 2H), 2.15-2.11 (m, 1H), 1.25-1.19 (m, 1H), 0.48-0.45 (m, 1H).

Embodiment 84

Embodiment 85

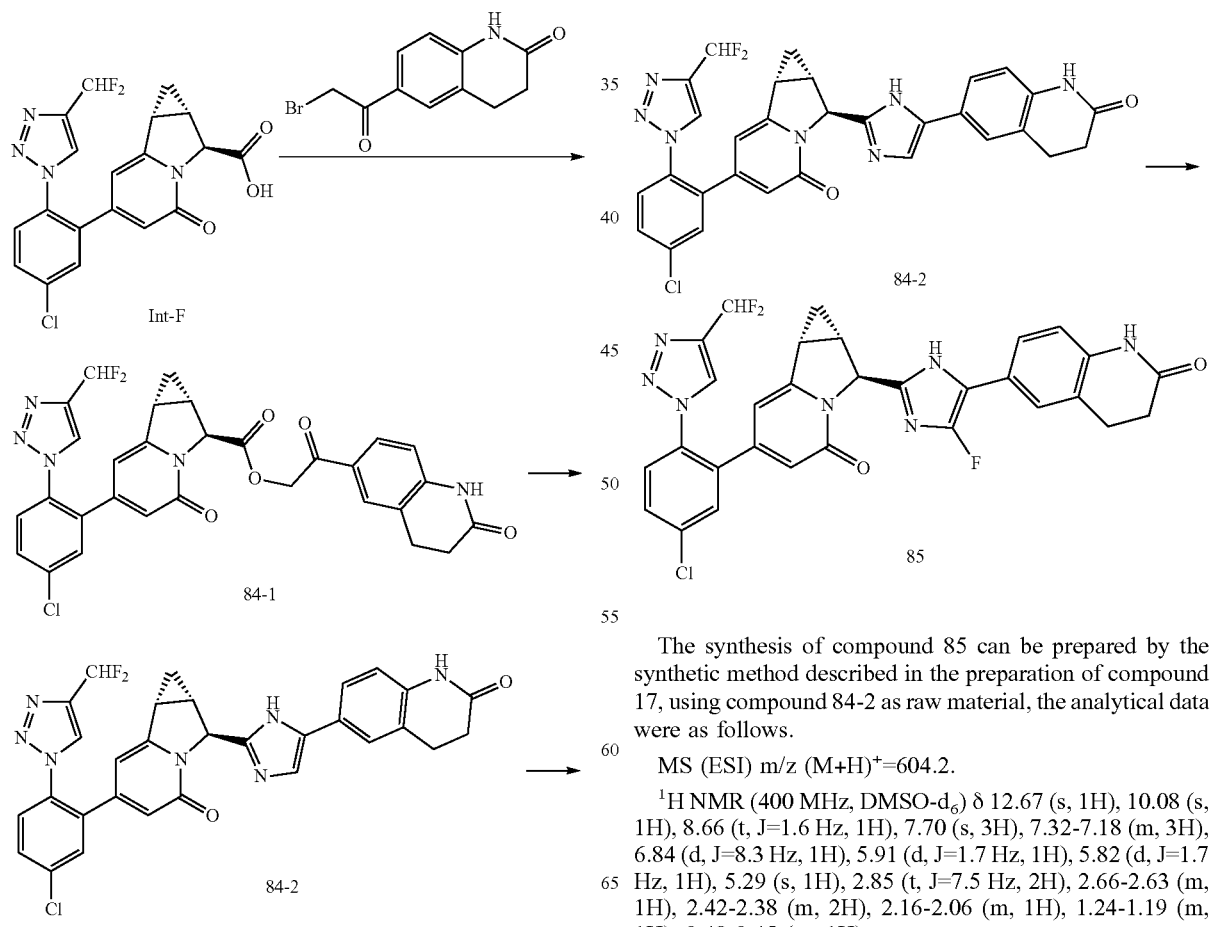

The synthesis of compound 85 can be prepared by the synthetic method described in the preparation of compound 17, using compound 84-2 as raw material, the analytical data were as follows.

MS (ESI) m/z (M+H)$^+$=604.2.

$^1$H NMR (400 MHz, DMSO-d$_6$) δ 12.67 (s, 1H), 10.08 (s, 1H), 8.66 (t, J=1.6 Hz, 1H), 7.70 (s, 3H), 7.32-7.18 (m, 3H), 6.84 (d, J=8.3 Hz, 1H), 5.91 (d, J=1.7 Hz, 1H), 5.82 (d, J=1.7 Hz, 1H), 5.29 (s, 1H), 2.85 (t, J=7.5 Hz, 2H), 2.66-2.63 (m, 1H), 2.42-2.38 (m, 2H), 2.16-2.06 (m, 1H), 1.24-1.19 (m, 1H), 0.48-0.45 (m, 1H).

Embodiment 86

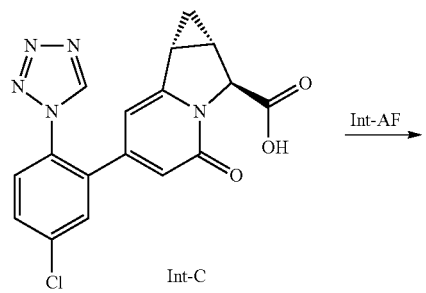

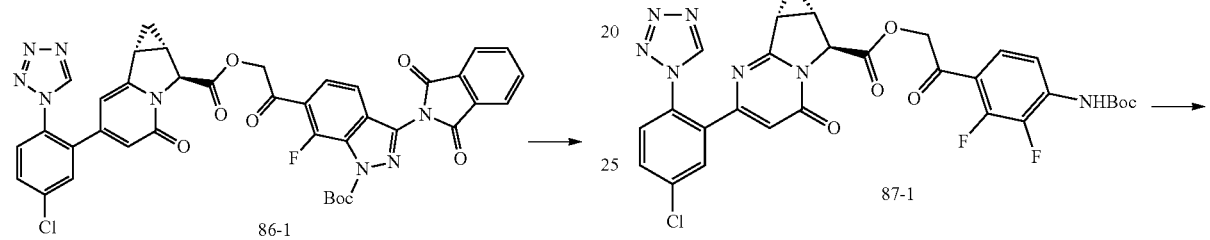

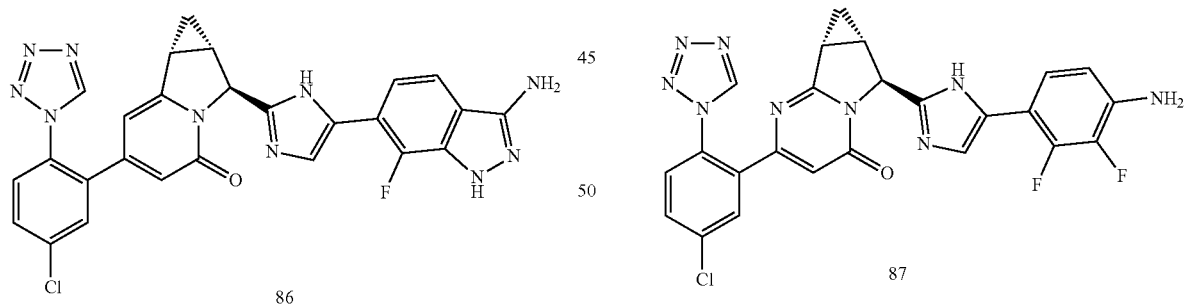

The synthesis of compound 86 can be prepared by the synthetic method described in the preparation of compound 32, using Int-C and Int-AF as raw materials, the analytical data were as follows.

MS (ESI) m/z (M+H)$^+$=541.2.

$^1$H NMR (400 MHz, DMSO-d$_6$) δ 12.27 (s, 1H), 11.69 (s, 1H), 9.59 (s, 1H), 7.75-7.71 (m, 3H), 7.50-7.33 (m, 3H), 5.95 (d, J=1.8 Hz, 1H), 5.89 (d, J=1.8 Hz, 1H), 5.44 (s, 1H), 5.35 (s, 2H), 2.73-2.69 (m, 1H), 2.27-2.22 (m, 1H), 1.29-1.23 (m, 1H), 0.55-0.51 (m, 1H).

Embodiment 87

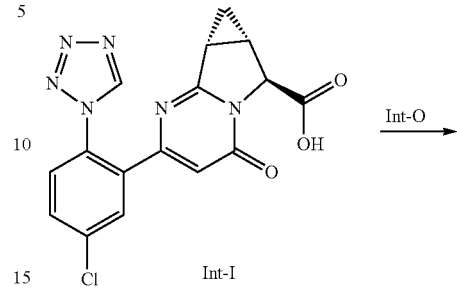

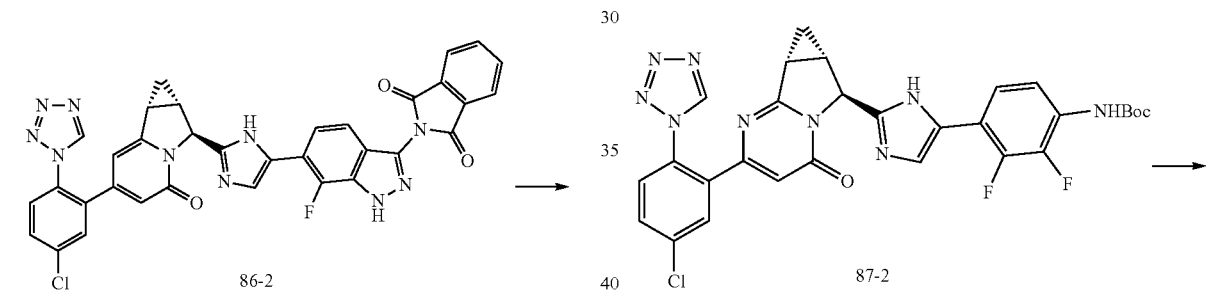

The synthesis of compound 87 can be prepared by the synthetic method described in the preparation of compound 1, using Int-I and Int-O as raw materials, the analytical data were as follows.

MS (ESI) m/z (M+H)$^+$=520.0.

$^1$H NMR (400 MHz, DMSO-d$_6$) δ 12.40 (br s, 1H), 9.72 (s, 1H), 7.95 (d, J=2.2 Hz, 1H), 7.87-7.82 (m, 2H), 7.36-7.28 (m, 2H), 6.61 (t, J=8.4 Hz, 1H), 6.32 (s, 1H), 5.53 (br s, 3H), 3.30-3.24 (m, 1H), 2.30-2.26 (m, 1H), 1.38-1.33 (m, 1H), 0.91-0.87 (m, 1H).

Embodiment 88

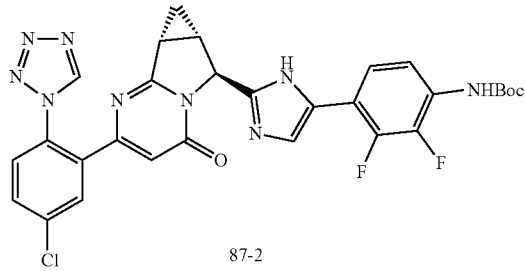

87-2

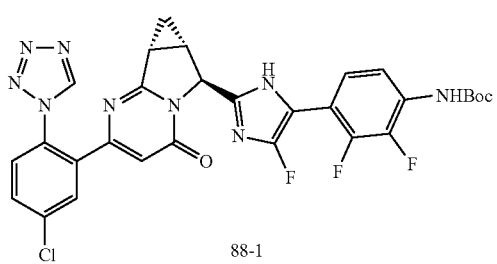

88-1

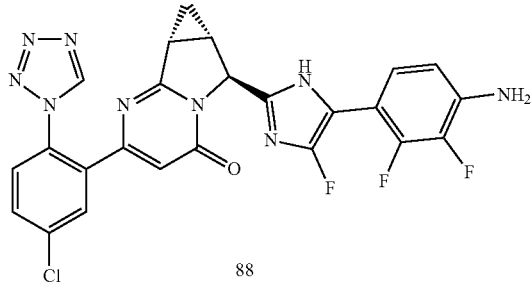

88

The synthesis of compound 88 can be prepared by the synthetic method described in the preparation of compound 2, using 87-2 as raw material, the analytical data were as follows.

MS (ESI) m/z (M+H)$^+$=538.2.
$^1$H NMR (400 MHz, DMSO-d$_6$) δ 12.60 (s, 1H), 9.73 (s, 1H), 7.97 (d, J=2.3 Hz, 1H), 7.86-7.81 (m, 2H), 6.99-6.94 (m, 1H), 6.67-6.62 (m, 1H), 6.31 (s, 1H), 5.72 (br s, 2H), 5.42 (s, 1H), 3.30-3.27 (m, 1H), 2.25-2.21 (m, 1H), 1.36-1.30 (m, 1H), 0.87-0.83 (m, 1H).

Embodiment 89-91

The synthesis of compounds 89 to 91 can be prepared by the synthetic method described in the preparation of compound 30, using 16-1 and intermediates Int-AM, Int-AP as raw materials, and reacting with intermediate Int-AJ respectively. The analytical data were shown in Table 13 below.

TABLE 13

Structure and analytical data of compounds in embodiments 89-91

| Embodiment | Structural formula | Analytical data |
|---|---|---|
| Embodiment 89 | (structure) | MS (ESI) m/z (M + H)$^+$ = 571.2.<br>$^1$H NMR (400 MHz, DMSO-d$_6$) δ 12.24 (s, 1H), 10.04 (s, 1H), 8.71 (s, 1H), 7.92 (d, J = 6.3 Hz, 1H), 7.81 (d, J = 8.5 Hz, 1H), 7.76 (d, J = 8.5 Hz, 1H), 7.55-7.38 (m, 3H), 6.79 (d, J = 1.7 Hz, 1H), 6.15 (s, 1H), 5.48 (s, 1H), 2.88 (t, J = 7.6 Hz, 2H), 2.63-2.59 m, 1H), 2.45-2.41 (m, 2H), 2.28-2.23 (m, 1H), 1.39-1.33 (m, 1H), 0.87-0.84 (m, 1H). |
| Embodiment 90 | (structure) | MS (ESI) m/z (M + H)$^+$ = 589.2.<br>$^1$H NMR (400 MHz, DMSO-d$_6$) δ 12.37 (s, 1H), 10.25 (s, 1H), 8.71 (s, 1H), 7.92 (d, J = 2.4 Hz, 1H), 7.82 (dd, J = 8.5, 2.3 Hz, 1H), 7.78-7.71 (m, 2H), 7.34 (dd, J = 4.3, 2.1 Hz, 1H), 6.71 (d, J = 1.7 Hz, 1H), 6.16 (s, 1H), 5.52 (d, J = 1.5 Hz, 1H), 2.92 (t, J = 7.7 Hz, 2H), 2.63-2.58 (m, 1H), 2.48-2.46 (m, 2H), 2.29-2.24 (m, 1H), 1.39-1.34 (m, 1H), 0.89-0.86 (m, 1H). |

TABLE 13-continued

Structure and analytical data of compounds in embodiments 89-91

| Embodiment | Structural formula | Analytical data |
|---|---|---|
| Embodiment 91 | | MS (ESI) m/z (M + H)⁺ = 605.0.<br>$^1$H NMR (400 MHz, DMSO-d$_6$) δ 12.41 (s, 1H), 10.24 (s, 1H), 8.72 (s, 1H), 7.92 (d, J = 2.4 Hz, 1H), 7.85-7.73 (m, 3H), 7.62 (d, J = 1.7 Hz, 1H), 6.87 (d, J = 8.5 Hz, 1H), 6.17 (s, 1H), 5.52 (d, J = 1.4 Hz, 1H), 3.03 (t, J = 7.7 Hz, 2H), 2.63-2.57 (m, 1H), 2.31-2.27 (m, 1H), 1.39-1.35 (m, 1H), 0.89-0.85 (m, 1H). |

Embodiment 92-94

The synthesis of compounds 92 to 94 can be prepared by the synthetic method described in the preparation of compound 31, using 16-1 and intermediates Int-AP, Int-AT as raw materials, and reacting with intermediate Int-AJ respectively. The analytical data were shown in Table 14 below.

TABLE 14

Structure and analytical data of compounds in embodiments 92-94

| Embodiment | Structural formula | Analytical data |
|---|---|---|
| Embodiment 92 | | MS (ESI) m/z (M + H)⁺ = 589.2.<br>$^1$H NMR (400 MHz, DMSO-d$_6$) δ 12.75 (s, 1H), 10.12 (s, 1H), 8.65 (s, 1H), 7.88 (d, J = 2.4 Hz, 1H), 7.76 (dd, J = 8.5, 2.4 Hz, 1H), 7.70 (d, J = 8.5 Hz, 1H), 7.32-7.26 (m, 2H), 6.84 (d, J = 8.3 Hz, 1H), 6.10 (s, 1H), 5.34 (s, 1H), 2.85 (t, J = 7.5 Hz, 2H), 2.55-2.51 (m, 1H), 2.41-2.39 (m, 2H), 2.21-2.17 (m, 1H), 1.32-1.26 (m, 1H), 0.86-0.83 (m, 1H). |
| Embodiment 93 | | MS (ESI) m/z (M + H)⁺ = 623.0.<br>$^1$H NMR (400 MHz, DMSO-d$_6$) δ 12.63 (s, 1H), 10.32 (s, 1H), 8.64 (s, 1H), 7.88 (d, J = 2.3 Hz, 1H), 7.76 (dd, J = 8.5, 2.3 Hz, 1H), 7.70 (d, J = 8.5 Hz, 1H), 7.18 (d, J = 8.3 Hz, 1H), 6.84 (d, J = 8.3 Hz, 1H), 6.11 (s, 1H), 5.36 (s, 1H), 2.97 (dd, J = 8.4, 6.9 Hz, 2H), 2.54-2.50 (m, 1H), 2.49-2.45 (m, 2H), 2.21-2.16 (m, 1H), 1.32-1.27 (m, 1H), 0.83-0.80 (m, 1H). |
| Embodiment 94 | | MS (ESI) m/z (M + H)⁺ = 609.1.<br>$^1$H NMR (400 MHz, DMSO-d$_6$) δ 12.69 (s, 1H), 10.95 (s, 1H), 8.64 (s, 1H), 7.88 (d, J = 2.3 Hz, 1H), 7.76 (dd, J = 8.5, 2.3 Hz, 1H), 7.70 (d, J = 8.5 Hz, 1H), 6.99 (dd, J = 8.4, 7.1 Hz, 1H), 6.74 (dd, J = 8.5, 1.4 Hz, 1H), 6.10 (s, 1H), 5.41 (s, 1H), 4.65 (s, 2H), 2.53-2.50 (m, 1H), 2.22-2.17 (m, 1H), 1.32-1.27 (m, 1H), 0.84-0.80 (m, 1H) |

Embodiment 95

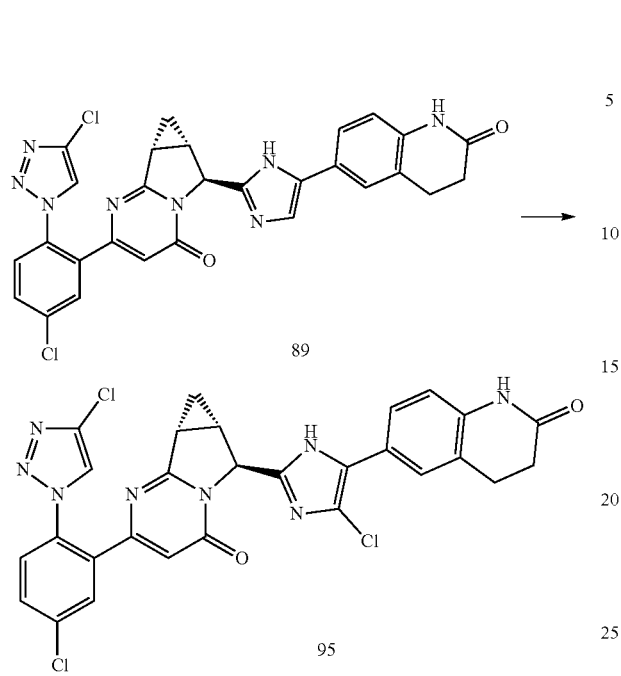

The synthesis of compound 95 can be prepared by the synthetic method described in the preparation of compound 77, using compound 89 as raw material, the analytical data were as follows.

MS (ESI) m/z (M+H)$^+$=605.2.

$^1$H NMR (400 MHz, DMSO-d$_6$) δ 12.99 (s, 1H), 10.23 (s, 1H), 8.71 (s, 1H), 7.96 (d, J=2.4 Hz, 1H), 7.82 (dd, J=8.5, 2.3 Hz, 1H), 7.77 (d, J=8.5 Hz, 1H), 7.50-7.45 (m, 2H), 6.94 (d, J=8.1 Hz, 1H), 6.16 (s, 1H), 5.43 (d, J=1.5 Hz, 1H), 2.93 (t, J=7.5 Hz, 2H), 2.64-2.59 (m, 1H), 2.48-2.47 (m, 2H), 2.29-2.24 (m, 1H), 1.39-1.33 (m 1H), 0.92-0.89 (m, 1H).

Embodiment 96

The synthesis of compound 96 can be prepared by the synthetic method described in the preparation of compound 1, using intermediates Int-AJ and Int-S as raw materials, the analytical data were as follows.

MS (ESI) m/z (M+H)$^+$=558.2.

$^1$H NMR (400 MHz, DMSO-d$_6$) δ 12.59 (s, 1H), 8.65 (s, 1H), 7.87 (d, J=7.9 Hz, 1H), 7.76 (d, J=8.5 Hz, 1H), 7.73-7.66 (m, 4H), 7.61 (dd, J=8.3, 1.2 Hz, 1H), 6.26 (s, 2H), 6.12 (s, 1H), 5.47 (s, 1H), 2.60-2.55 (m, 1H), 2.26-2.21 (m, 1H), 1.35-1.30 (m, 1H), 0.85-0.82 (m, 1H).

Embodiment 97

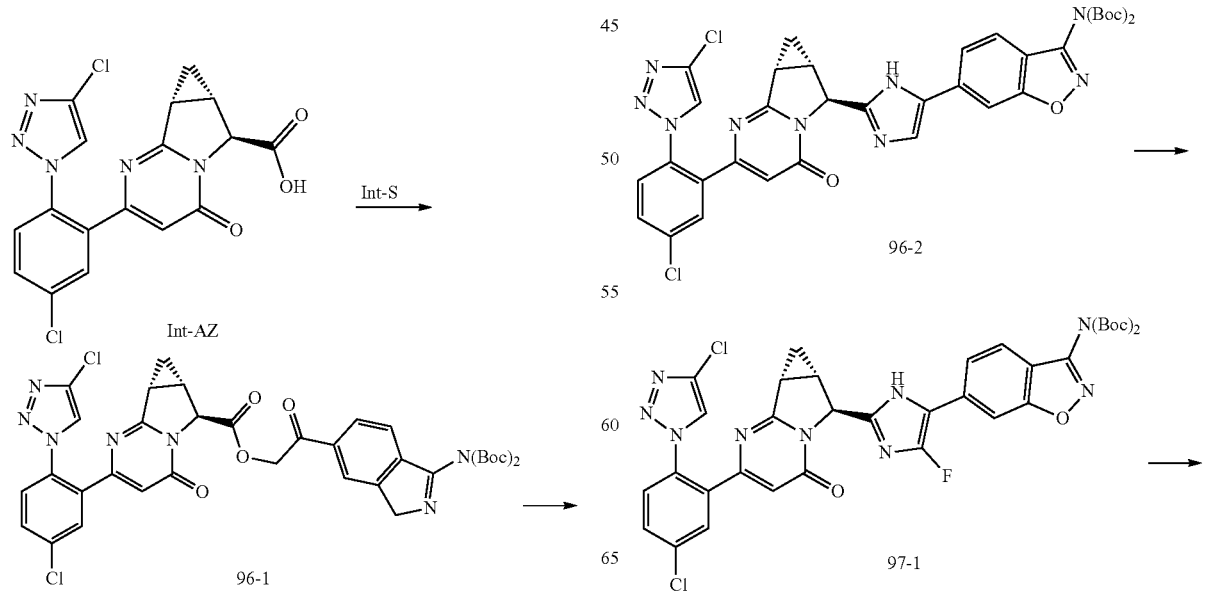

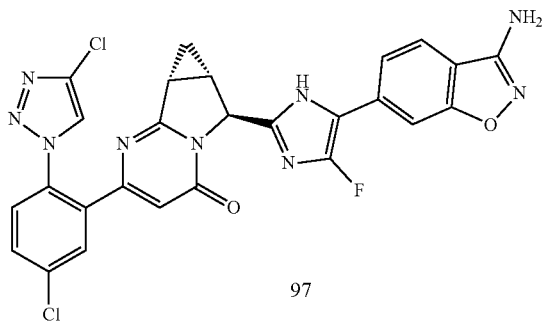

97

The synthesis of compound 97 can be prepared by the synthetic method described in the preparation of compound 2, using compound 96-2 as raw material, the analytical data were as follows.

MS (ESI) m/z (M+H)$^+$=576.2.

$^1$H NMR (400 MHz, DMSO-d$_6$) δ 13.08 (s, 1H), 8.70 (s, 1H), 7.95 (d, J=2.4 Hz, 1H), 7.87 (d, J=8.3 Hz, 1H), 7.83 (dd, J=8.5, 2.3 Hz, 1H), 7.77 (d, J=8.5 Hz, 1H), 7.59 (d, J=1.3 Hz, 1H), 7.48 (dd, J=8.2, 1.4 Hz, 1H), 6.43 (s, 2H), 6.18 (s, 1H), 5.44 (s, 1H), 2.64-2.59 (m, 1H), 2.32-2.28 (m, 1H), 1.40-1.35 (m, 1H), 0.96-0.93 (m, 1H).

Embodiment 98

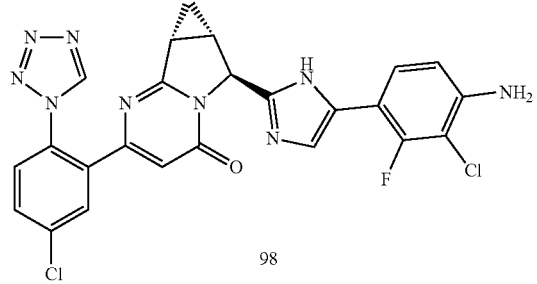

98

The synthesis of compound 98 can be prepared by the synthetic method described in the preparation of compound 1, using Int-I and Int-AY as raw materials, the analytical data were as follows.

MS (ESI) m/z (M+H)$^+$=536.1.

$^1$H NMR (400 MHz, DMSO-d$_6$) δ 12.24 (s, 1H), 9.65 (s, 1H), 7.88 (d, J=2.0 Hz, 1H), 7.80-7.74 (m, 2H), 7.53 (t, J=8.5 Hz, 1H), 7.16 (dd, J=4.1, 1.8 Hz, 1H), 6.58 (d, J=8.7 Hz, 1H), 6.23 (s, 1H), 5.57 (s, 2H), 5.43 (s, 1H), 2.48-2.46 (m, 1H), 2.20-2.15 (m, 1H), 1.30-1.25 (m, 1H), 0.79-0.75 (m, 1H).

Embodiment 99

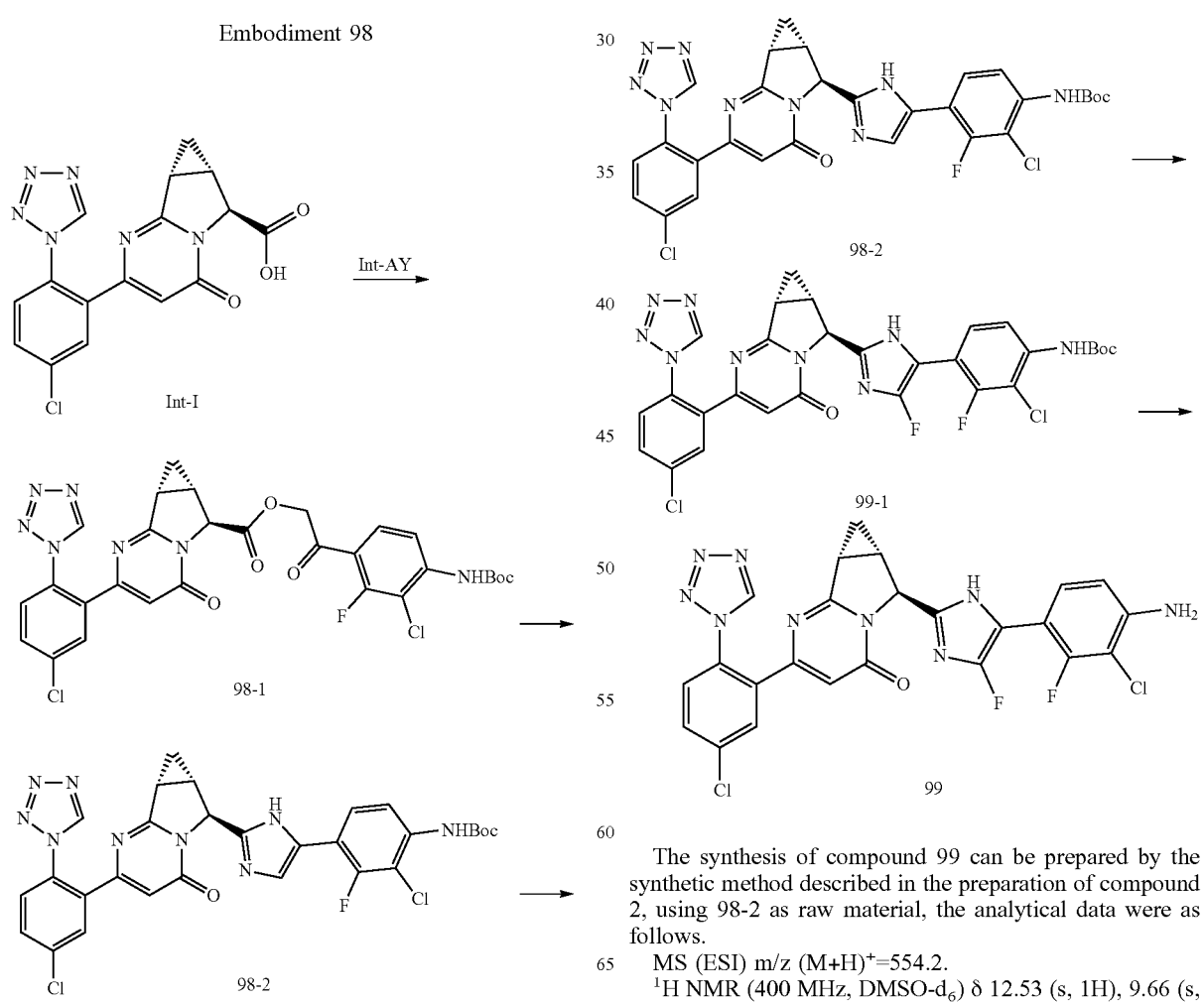

The synthesis of compound 99 can be prepared by the synthetic method described in the preparation of compound 2, using 98-2 as raw material, the analytical data were as follows.

MS (ESI) m/z (M+H)$^+$=554.2.

$^1$H NMR (400 MHz, DMSO-d$_6$) δ 12.53 (s, 1H), 9.66 (s, 1H), 7.90 (d, J=2.2 Hz, 1H), 7.80-7.74 (m, 2H), 7.07 (t,

J=8.4 Hz, 1H), 6.62 (dd, J=8.7, 1.3 Hz, 1H), 6.24 (s, 1H), 5.86 (s, 2H), 5.36 (s, 1H), 2.41-2.39 (m, 1H), 2.19-2.14 (m, 1H), 1.29-1.24 (m, 1H), 0.80-0.76 (m, 1H).

Embodiment 100

Embodiment 101

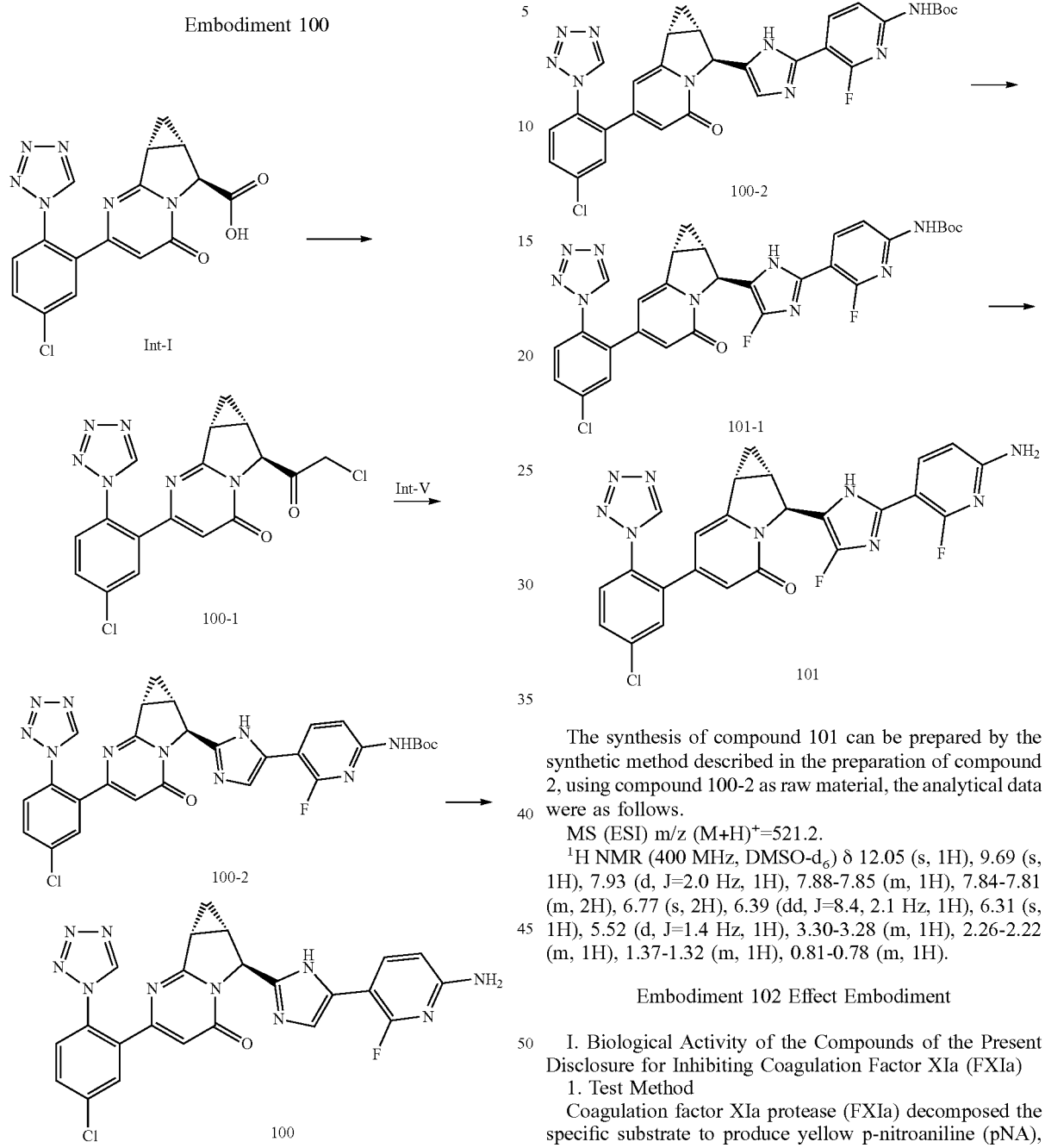

The synthesis of compound 100 can be prepared by the synthetic method described in the preparation of compound 35, using intermediate Int-I as raw material, the analytical data were as follows.

MS (ESI) m/z (M+H)$^+$=503.2.

$^1$H NMR (400 MHz, DMSO-d$_6$) δ 11.81 (s, 1H), 9.74 (s, 1H), 8.01-7.94 (m, 2H), 7.84-7.82 (m, 2H), 6.96 (d, J=2.2 Hz, 1H), 6.66 (s, 2H), 6.42-6.39 (m, 1H), 6.27 (s, 1H), 5.43 (d, J=1.6 Hz, 1H), 2.41-2.38 (m, 1H), 2.19-2.16 (m, 1H), 1.33-1.28 (m, 1H), 0.71-0.68 (m, 1H).

The synthesis of compound 101 can be prepared by the synthetic method described in the preparation of compound 2, using compound 100-2 as raw material, the analytical data were as follows.

MS (ESI) m/z (M+H)$^+$=521.2.

$^1$H NMR (400 MHz, DMSO-d$_6$) δ 12.05 (s, 1H), 9.69 (s, 1H), 7.93 (d, J=2.0 Hz, 1H), 7.88-7.85 (m, 1H), 7.84-7.81 (m, 2H), 6.77 (s, 2H), 6.39 (dd, J=8.4, 2.1 Hz, 1H), 6.31 (s, 1H), 5.52 (d, J=1.4 Hz, 1H), 3.30-3.28 (m, 1H), 2.26-2.22 (m, 1H), 1.37-1.32 (m, 1H), 0.81-0.78 (m, 1H).

Embodiment 102 Effect Embodiment

I. Biological Activity of the Compounds of the Present Disclosure for Inhibiting Coagulation Factor XIa (FXIa)

1. Test Method

Coagulation factor XIa protease (FXIa) decomposed the specific substrate to produce yellow p-nitroaniline (pNA), pNA had strong absorption at 405 nM. The inhibitory activity of the compounds on coagulation factor XIa was determined by assaying the absorbance of the compounds at 405 nM.

2. Reagents, Consumables and Instruments

The coagulation factor XIa protease used in the experiment was purchased from Abcam Company, Item No. ab62411; the coagulation factor XIa-specific substrate was purchased from HYPHEN BioMed, Item No. Biophen cs-21 (66); tris-HCl was purchased from Invitrogen, Item No. 15567-027; NaCl was purchased from ABCONE, Item No. S39168; Twain 20 was purchased from Amersco, Item No. 0777-1L.

Buffer: 100 mM tris-HCl, 200 mM NaCl, 0.02% Tween 20, pH=7.4.

ECHO liquid workstation was purchased from Labcyte, Item No. ECHO550; Bravo liquid workstation was purchased from Agilent, Item No. 16050-101; multi-functional enzyme standard was purchased from PerkinElmer, Item No. EnVision; 384-well compound plate was purchased from Labcyte, Item No. LP-0200; 384-well laboratory plate was purchased from PerkinElmer, Item No. 6007650.

3. Compound Preparation

The compounds were dissolved in 100% DMSO, 20 mM, and stored at room temperature in a nitrogen cabinet.

4. Test Method:

a. 20 mM of the tested compound was diluted to 2 mM using 100% DMSO, and the reference compound was diluted to 0.4 mM; the compound was continuously diluted with a 3-fold gradient at 10 concentration points using a Bravo liquid workstation.

b. The ECHO liquid workstation was used to transfer 10 nL of compound to the corresponding 384-well experimental plate with double replicate wells; the final concentrations of compound reactions were 1000, 333.3, 111.1, 37.0, 12.3, 4.1, 1.37, 0.46, 0.15, and 0.05 nM. The final concentrations of reference compounds were 200, 66.7, 22.2, 7.4, 2.47, 0.82, 0.27, 0.09, 0.03, 0.01 nM.

c. 10 nL DMSO and 10 nL 0.4 mM reference compounds were transferred to high signal control pores and low signal control pores respectively.

d. 0.1 μg/mL FXIa enzyme solution was prepared with buffer solution, and 10 μL enzyme solution was added to 384-well experimental plate, 5 mM substrate solution was prepared using buffer solution, and 10 μL substrate solution was added to a 384-well experimental plate. The final concentration of FXIa was 0.05 μg/mL and the final concentration of the substrate was 2.5 mM.

e. The 384-hole experimental plate was centrifuged and incubated at 37° C. for 15 minutes.

f. The absorbance was measured at 405 nM using EnVision.

The half inhibitory activity ($IC_{50}$) of the compounds of the present disclosure against FXa was determined in this embodiment as shown in Table 15 below, wherein:

TABLE 15

| Number | FXIa $IC_{50}$ |
|---|---|
| Embodiment 1 | 6.50 |
| Embodiment 2 | 6.70 |
| Embodiment 14 | 2.84 |
| Embodiment 15 | 0.82 |
| Embodiment 16 | 4.74 |
| Embodiment 17 | 0.83 |
| Embodiment 20 | 6.30 |
| Embodiment 24 | 8.65 |
| Embodiment 28 | 0.82 |
| Embodiment 29 | 0.50 |
| Embodiment 31 | 4.63 |
| Embodiment 32 | 2.72 |
| Embodiment 33 | 0.85 |
| Embodiment 34 | 11.85 |
| Embodiment 36 | 3.34 |
| Embodiment 41 | 3.26 |
| Embodiment 42 | 8.71 |
| Embodiment 48 | 3.93 |
| Embodiment 49 | 6.40 |
| Embodiment 50 | 7.02 |
| Embodiment 55 | 5.18 |

$IC_{50}$ values (nM) for FXIa inhibition of compounds of the present disclosure TABLE 15-continued

| Number | FXIa $IC_{50}$ |
|---|---|
| Embodiment 57 | 8.32 |
| Embodiment 58 | 3.25 |
| Embodiment 59 | 1.41 |
| Embodiment 62 | 6.76 |
| Embodiment 64 | 4.78 |
| Embodiment 68 | 3.54 |
| Embodiment 69 | 0.36 |
| Embodiment 70 | 2.16 |
| Embodiment 75 | 5.27 |
| Embodiment 76 | 0.76 |
| Embodiment 77 | 3.18 |
| Embodiment 78 | 1.41 |
| Embodiment 79 | 1.02 |
| Embodiment 80 | 6.36 |
| Embodiment 81 | 5.37 |
| Embodiment 82 | 4.84 |
| Embodiment 83 | 0.83 |
| Embodiment 86 | 0.31 |
| Embodiment 87 | 5.04 |
| Embodiment 88 | 2.85 |
| Embodiment 89 | 12.49 |
| Embodiment 90 | 6.33 |
| Embodiment 91 | 3.93 |
| Embodiment 92 | 4.24 |
| Embodiment 95 | 2.47 |
| Embodiment 96 | 5.24 |
| Embodiment 97 | 1.19 |
| Embodiment 101 | 3.58 |

$IC_{50}$ values (nM) for FXIa inhibition of compounds of the present disclosure It can be seen that the compounds of the present disclosure have better FXa enzyme inhibitory activity.

II. Test of Anticoagulant Effect of the Compounds of the Present Disclosure on Human Blood In Vitro 1. Test Method Activated partial thromboplastin time (APTT) measurement reagent was mixed with plasma and the reaction was carried out continuously resulting in a change in optical density up to the clotting point, and the clotting time (CT) was measured by optical turbidimetry using a semi-automatic coagulation analyzer. The in vitro anticoagulant activity of compounds on human blood was determined by detecting the clotting time of plasma treated with different concentrations of compounds, and the corresponding concentration of compounds prolonging clotting time was calculated.

2. Reagents, Consumables and Instruments

Human plasma used in the experiment was purchased from HD Biosciences (Shanghai) Co., Ltd.; Activated partial thromboplastin time determination kit was purchased from Taizhou Zhongqin Shidi Biotechnology Co., Ltd., Item No. SS00220005.

Semi-automatic coagulation analyzer was purchased from Shenzhen Shengxinkang Technology Co., Ltd., Item No. SK5004; measuring cup was purchased from Shenzhen Shengxinkang Technology Co., Ltd. Bravo liquid workstation was purchased from Agilent, Item No. 16050-101; 384-well compound plate was purchased from Labcyte, Item No. LP-0200.

3. Compound Preparation

The compounds were dissolved in 100% DMSO, 20 mM, and stored at room temperature in a nitrogen cabinet.

4. Test Method a. The NaCl reagent in the kit was incubated half an hour in advance, and the APTT reagent was balanced to room temperature.

b. The compound was continuously diluted at 14 concentration points using a Bravo liquid workstation with a 2-fold gradient.

c. 0.75 μL of the compound was added to the measuring cup, double-replicate wells; 50 μL of plasma was added and 50 μL of APTT reagent was added, the mixture was mixed well and put into coagulation analyzer for incubation at 37° C. for 3 minutes.

d. APTT assay was started, 50 μL of NaCl was added to start the reaction, and the clotting time was counted.

e. Control clotting time was measured using 100% DMSO instead of the compound, and the final concentration of DMSO was 0.5%.

5. Data Processing

Data were curve-fitted using Graphpad Prism to calculate CT2.0, the final concentration of compound corresponding to aPTT of the 2-fold blank control was calculated. In the embodiment, the inhibition of the compounds of the present disclosure on human blood coagulation was measured as shown in the table below, wherein:

TABLE 16

CT2.0 (μM) of the compounds of the present disclosure

| Number | CT2.0 (μM) |
| --- | --- |
| Embodiment 1 | 1.72 |
| Embodiment 2 | 0.55 |
| Embodiment 14 | 0.55 |
| Embodiment 15 | 0.47 |
| Embodiment 16 | 0.63 |
| Embodiment 17 | 0.54 |
| Embodiment 20 | 0.88 |
| Embodiment 24 | 0.90 |
| Embodiment 28 | 0.07 |
| Embodiment 29 | 0.37 |
| Embodiment 31 | 2.38 |
| Embodiment 32 | 0.26 |
| Embodiment 33 | 0.69 |
| Embodiment 34 | 0.58 |
| Embodiment 36 | 0.42 |
| Embodiment 41 | 1.20 |
| Embodiment 42 | 1.08 |
| Embodiment 48 | 3.65 |
| Embodiment 49 | 6.86 |
| Embodiment 50 | 3.16 |
| Embodiment 55 | 0.67 |
| Embodiment 57 | 0.54 |
| Embodiment 58 | 1.21 |
| Embodiment 59 | 0.84 |
| Embodiment 62 | 2.32 |
| Embodiment 64 | 1.11 |
| Embodiment 68 | 0.65 |
| Embodiment 69 | 0.86 |
| Embodiment 70 | 1.32 |
| Embodiment 75 | 1.42 |
| Embodiment 76 | 0.43 |
| Embodiment 77 | 0.82 |
| Embodiment 78 | 0.86 |
| Embodiment 79 | 0.72 |
| Embodiment 80 | 3.50 |
| Embodiment 81 | 2.28 |
| Embodiment 82 | 1.04 |
| Embodiment 83 | 0.82 |
| Embodiment 86 | 0.20 |
| Embodiment 87 | 0.67 |
| Embodiment 88 | 0.82 |
| Embodiment 89 | 1.29 |
| Embodiment 90 | 0.63 |
| Embodiment 91 | 2.27 |
| Embodiment 92 | 0.83 |
| Embodiment 95 | 3.76 |
| Embodiment 96 | 0.26 |

TABLE 16-continued

CT2.0 (μM) of the compounds of the present disclosure

| Number | CT2.0 (μM) |
| --- | --- |
| Embodiment 97 | 0.68 |
| Embodiment 101 | 0.51 |

It can be seen that the compounds of the present disclosure have obvious inhibitory activity on human blood coagulation.

Embodiment 103 Pharmacokinetic Experiment

In this experimental embodiment, in vivo pharmacokinetic evaluation was performed in rats by intravenous injection and oral administration.

Experimental methods and conditions: Male Sprague Dawley rats were given the test compound 1 mg/Kg (intravenous injection, solvent 5% DMSO/10% Solutol/85% Saline) and 2 mg/Kg (intragastric administration, solvent 0.5% MC) by respectively; 5 min, 15 min, 30 min, 1 hr, 2 hr, 4 hr, 6 hr, 8 hr, 24 hr after administration, blood was collected from submandibular vein, 0.20 mL was collected from each sample, and heparin sodium was used for anticoagulation. After collection, the sample was placed on ice, and the plasma was centrifuged to be measured within 1 hour. Plasma drug concentration in plasma was detected by liquid chromatography tandem mass spectrometry (LC/MS/MS) to calculate pharmacokinetic parameters. The results are shown in Tables 17 and 18.

TABLE 17

Pharmacokinetics of intravenous administration (1 mg/kg)

| Compound | $T_{1/2}$ (hr) | $AUC_{inf}$ (ng * hr/mL) | Vz (mL/Kg) | Cl (mL/min/kg) |
| --- | --- | --- | --- | --- |
| Embodiment 36 | 1.65 | 6528.72 | 348.72 | 2.66 |
| Embodiment 90 | 3.41 | 26929.84 | 179.84 | 0.63 |

TABLE 18

Pharmacokinetics of intragastric administration (2 mg/kg)

| Compound | $T_{1/2}$ (hr) | $C_{max}$ (ng/mL) | $AUC_{inf}$ (ng * hr/mL) | F (%) |
| --- | --- | --- | --- | --- |
| Embodiment 36 | 1.63 | 709.00 | 3305.90 | 25.32 |
| Embodiment 90 | 3.16 | 1830.00 | 17605.06 | 28.4 |

It can be seen that the compounds of the present disclosure have good pharmacokinetic absorption in rats and have pharmacokinetic advantages.

The invention claimed is:

1. A compound represented by formula (I), an optical isomer thereof or a pharmaceutically acceptable salt thereof,

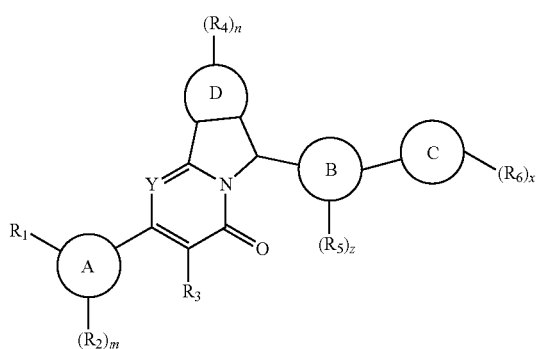

wherein, ring A is selected from phenyl and 5-6 membered heteroaryl;

ring B is selected from 5-6 membered heteroaryl;

ring C is selected from phenyl, 5-10 membered heteroaryl, benzo 5-9 membered heterocycloalkyl, pyrido 5-9 membered heterocycloalkyl and benzo 5-9 membered heterocycloalkenyl;

ring D is selected from $C_{3-5}$ cycloalkyl and 3-5 membered heterocycloalkyl;

$R_1$ is selected from H, $C_{1-6}$ alkyl, $C_{1-6}$ heteroalkyl and 5-6 membered heteroaryl, and the $C_{1-6}$ alkyl, $C_{1-6}$ heteroalkyl or 5-6 membered heteroaryl is optionally substituted by 1, 2 or 3 R;

$R_2$ is independently selected from H, halogen, OH, $NH_2$, CN, $C_{1-6}$ alkyl and $C_{1-6}$ heteroalkyl, and the $C_{1-6}$ alkyl or $C_{1-6}$ heteroalkyl is optionally substituted by 1, 2 or 3 R;

$R_3$ is selected from H, F, Cl, Br, I, OH, $NH_2$, CN and Me;

$R_4$ is selected from H, F, Cl, Br, I, OH, $NH_2$, CN, COOH, $CH_2OH$ and $C_{1-6}$ alkyl;

$R_5$ is independently selected from H, halogen, OH, $NH_2$, CN,

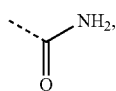

$C_{1-6}$ alkyl and $C_{1-6}$ heteroalkyl, and the $C_{1-6}$ alkyl or $C_{1-6}$ heteroalkyl is optionally substituted by 1, 2 or 3 R;

$R_6$ is independently selected from H, halogen, OH, $NH_2$, CN, COOH,

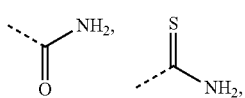

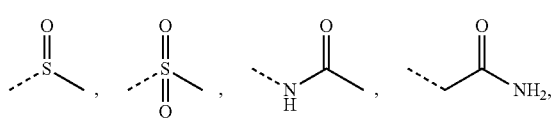

$C_{1-6}$ alkyl and $C_{1-6}$ heteroalkyl, and the $C_{1-6}$ alkyl, $C_{1-6}$ heteroalkyl or

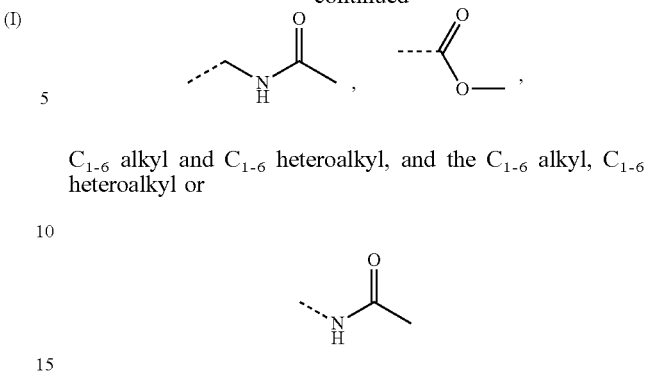

is optionally substituted by 1, 2 or 3 R;

Y is selected from N and $C(R_7)$;

$R_7$ is selected from H, F, Cl, Br, I, OH, $NH_2$, CN, $C_{1-6}$ alkyl and $C_{1-6}$ heteroalkyl, and the $C_{1-6}$ alkyl or $C_{1-6}$ heteroalkyl is optionally substituted by 1, 2 or 3 R;

m is selected from 0, 1, 2 and 3;

n is selected from 0, 1, 2 and 3;

x is selected from 0, 1, 2 and 3;

z is selected from 0, 1 and 2;

R is independently selected from H, halogen, OH, $NH_2$, CN,

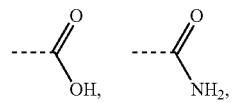

$C_{1-6}$ alkyl, $C_{1-6}$ alkoxy, $C_{1-6}$ alkylthio, $C_{1-6}$ alkylamino, $C_{3-6}$ cycloalkyl, and the $C_{1-6}$ alkyl, $C_{1-6}$ alkoxy, $C_{1-6}$ alkylthio, $C_{1-6}$ alkylamino, or $C_{3-6}$ cycloalkyl is optionally substituted by 1, 2, or 3 R';

R' is selected from H, F, Cl, Br, I, OH, $NH_2$ and $CH_3$;

the 3-5 membered heterocycloalkyl, 5-6 membered heterocycloalkyl, 5-9 membered heterocycloalkenyl, 5-9 membered heterocycloalkyl, 5-6 membered heteroaryl, 5-10 membered heteroaryl, or $C_{1-6}$ heterocycloalkyl contains 1, 2 or 3 heteroatoms or heteroatom groups independently selected from —O—, —NH—, —S—, —C(=O)—, —C(=O)O—, —S(=O)—, —S(=O)$_2$— and N.

2. The compound according to claim 1, the optical isomer thereof, or the pharmaceutically acceptable salt thereof, wherein, R is selected from H, F, Cl, Br, I, OH, $NH_2$, COOH, $CF_3$, $CF_2H$, CN, $CH_3O$, $CH_3CH_2O$,

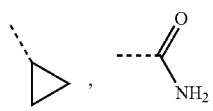

and Me.

3. The compound according to claim 1, the optical isomer thereof, or the pharmaceutically acceptable salt thereof, wherein, $R_1$ is selected from H, $C_{1-3}$ alkyl, $C_{1-3}$ heteroalkyl, tetrazolyl and 1,2,3-triazolyl, and the tetrazolyl or 1,2,3-triazolyl is optionally substituted by R, the $C_{1-3}$ alkyl or $C_{1-3}$ heteroalkyl is optionally substituted by 1, 2 or 3 R.

4. The compound according to claim 1, the optical isomer thereof, or the pharmaceutically acceptable salt thereof, wherein, $R_1$ is selected from H, $C_{1-3}$ alkyl, $C_{1-3}$ alkoxy,

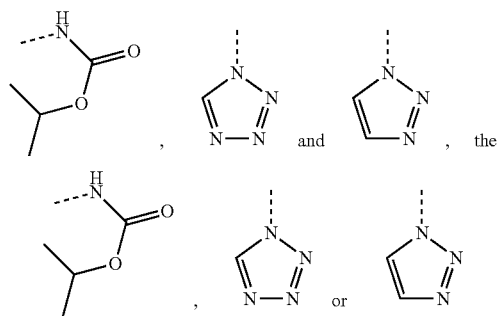, and , the

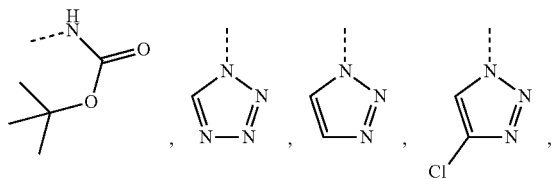, or is optionally substituted by R, the $C_{1-3}$ alkyl or $C_{1-3}$ alkoxy is optionally substituted by 1, 2 or 3 R.

5. The compound according to claim 4, the optical isomer thereof or the pharmaceutically acceptable salts thereof, wherein, $R_1$ is selected from H, —$CHF_2$, —$OCF_3$,

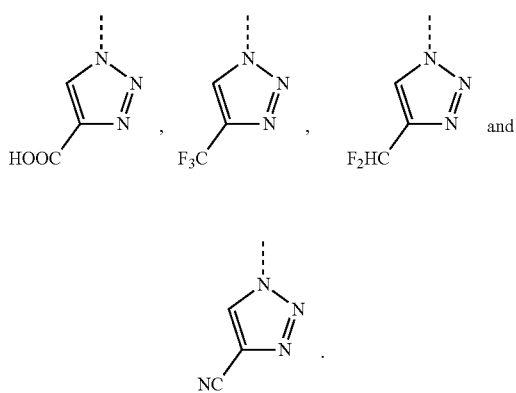

.

6. The compound according to claim 1, the optical isomer thereof, or the pharmaceutically acceptable salt thereof, wherein, $R_2$ is independently selected from H, halogen, OH, $NH_2$, CN, $C_{1-3}$ alkyl and $C_{1-3}$ alkoxy, and the $C_{1-3}$ alkyl or $C_{1-3}$ alkoxy is optionally substituted by 1, 2 or 3 R.

7. The compound according to claim 1, the optical isomer thereof, and or pharmaceutically acceptable salt thereof, wherein $R_2$ is independently selected from H, F, Cl, Br, I, OH, $NH_2$, CN, Me and 8. The compound according to claim 1, the optical isomer thereof, or the pharmaceutically acceptable salt thereof, wherein, the structural moiety

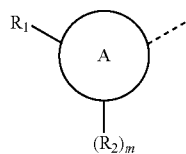

is selected from

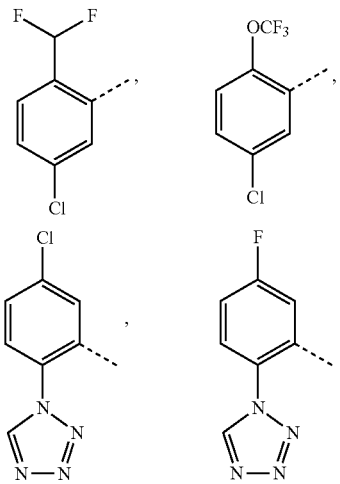

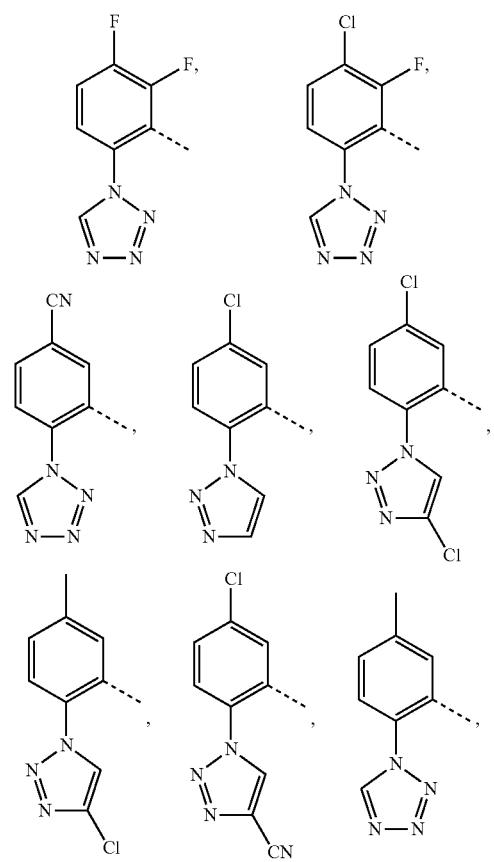

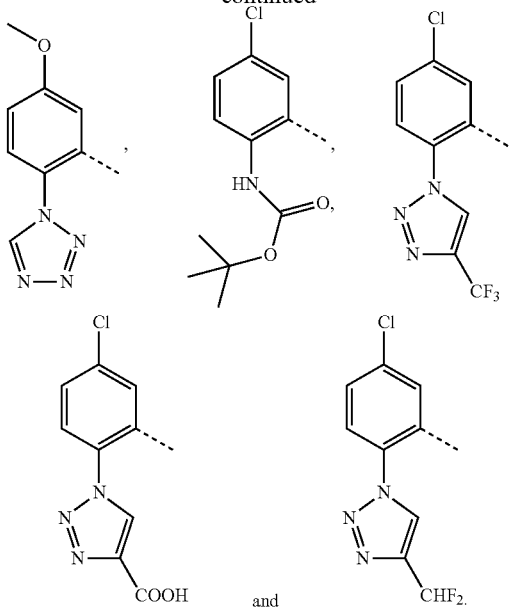

9. The compound according to claim 1, the optical isomer thereof, or the pharmaceutically acceptable salt thereof, wherein, ring B is selected from pyrrolyl, imidazolyl, 1,2,4-triazolyl and pyridyl.

10. The compound according to claim 1, the optical isomer thereof, or the pharmaceutically acceptable salt thereof, wherein, $R_5$ is independently selected from H, F, Cl, Br, OH, $NH_2$, Me, CN and

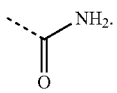

11. The compound according to claim 9, the optical isomer thereof, or the pharmaceutically acceptable salt thereof, wherein, the structural moiety

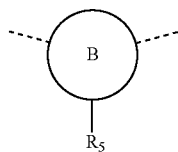

is selected from

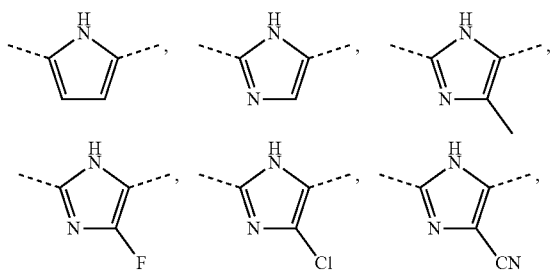

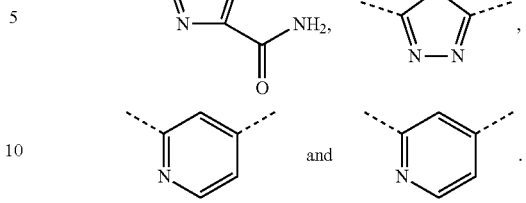

12. The compound according to claim 1, the optical isomer thereof, or the pharmaceutically acceptable salt thereof, wherein, ring C is selected from thienyl, phenyl, pyridyl, pyrimidinyl, pyridazinyl, pyrazinyl, indazolyl, isoindolin-1-one, quinolinyl, isoquinolinyl, 1,2,3,4-tetrahydroquinolinyl, quinolin-2(1H)-one, benzoisoxazolyl, 1H-benzo[d]imidazolyl, dihydroindol-2-one, dihydroindol-1-one, 3,4-dihydroquinolin-2(1H)-one, quinolin-2(1H)-one, 1H-pyrido[2,3-b][1,4]oxazin-2(3H)-one, 3,4-dihydro-2H-benzo[b][1,4]oxazinyl, 3,4-dihydro-2H-benzo[b][1,4]thiazinyl-2H-benzo[b][1,4]oxazin-3(4H)-one, 3,4-dihydro-1,8-naphthyridin-2(1H)-one, quinoxalin-2(1H)-one, spiro[benzo[b][1,4]oxazin-2,1'-cyclopropane]-3(4H)-one, 1,4-dihydro-2H-benzo[d][1,3]oxazin-2-one, 2H-benzo[b][1,4]thiazin-3(4H)-one, 3,4-dihydro-2H-benzo[b][1,4]thiazin-1,1-dioxide, 1,4-dihydrochromeno[4,3-c]pyrazolyl and 4,5-dihydro-1H-benzo[g]indazolyl.

13. The compound according to claim 1, the optical isomer thereof, or the pharmaceutically acceptable salt thereof, wherein, $R_6$ is independently selected from H, halogen, OH, $NH_2$, CN, COOH,

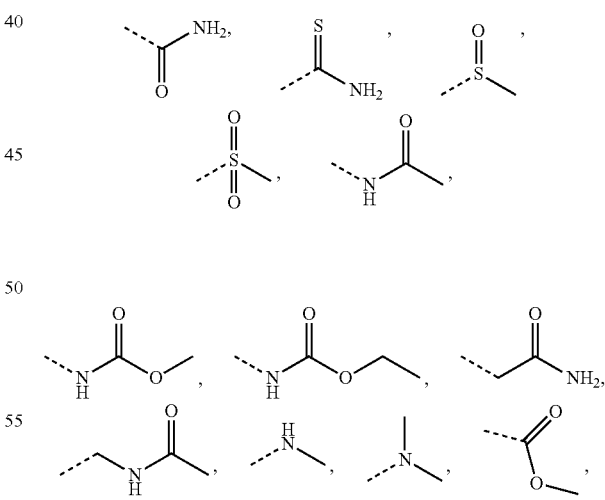

$C_{1-3}$ alkyl, $C_{1-3}$ heteroalkyl and $C_{3-6}$ cycloalkyl, and the $C_{1-3}$ alkyl, $C_{1-3}$ heteroalkyl or $C_{3-6}$ cycloalkyl is optionally substituted by 1, 2 or 3 R.

14. The compound according to claim 13, the optical isomer thereof, or the pharmaceutically acceptable salt thereof wherein, $R_6$ is independently selected from H, F, Cl, Br, I, OH, $NH_2$, CN, Me,

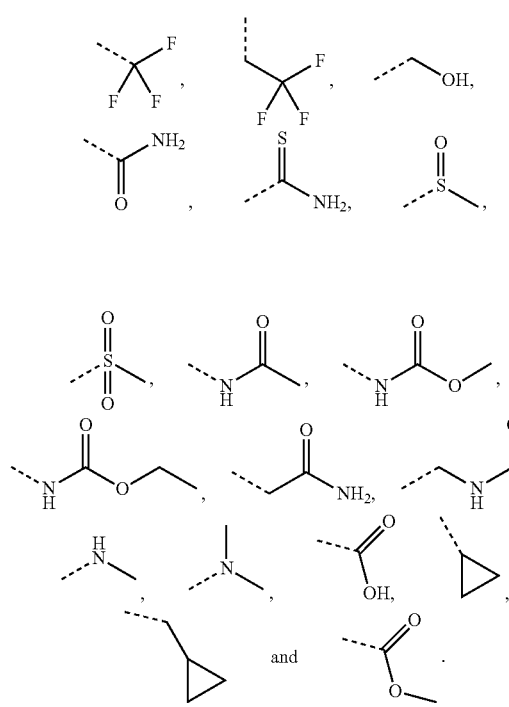
15. The compound according to claim 12, the optical isomer thereof, and the pharmaceutically acceptable salt thereof, wherein, the structural moiety
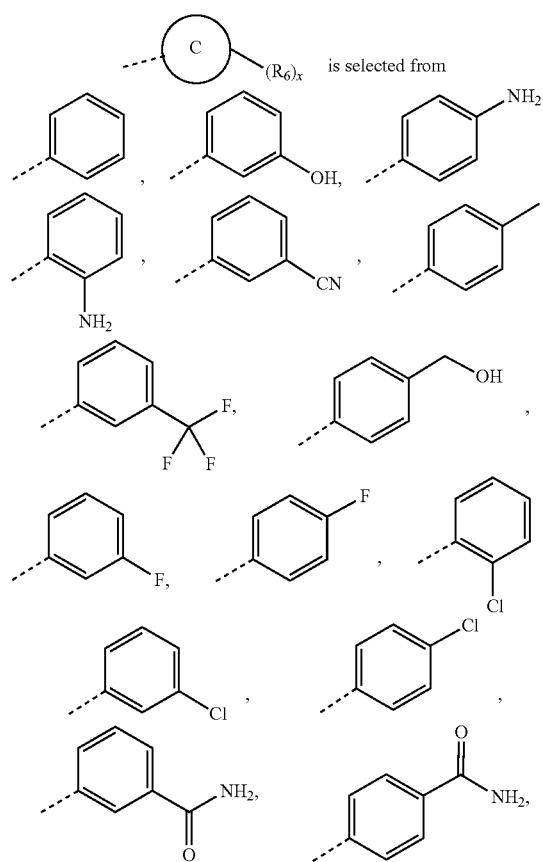
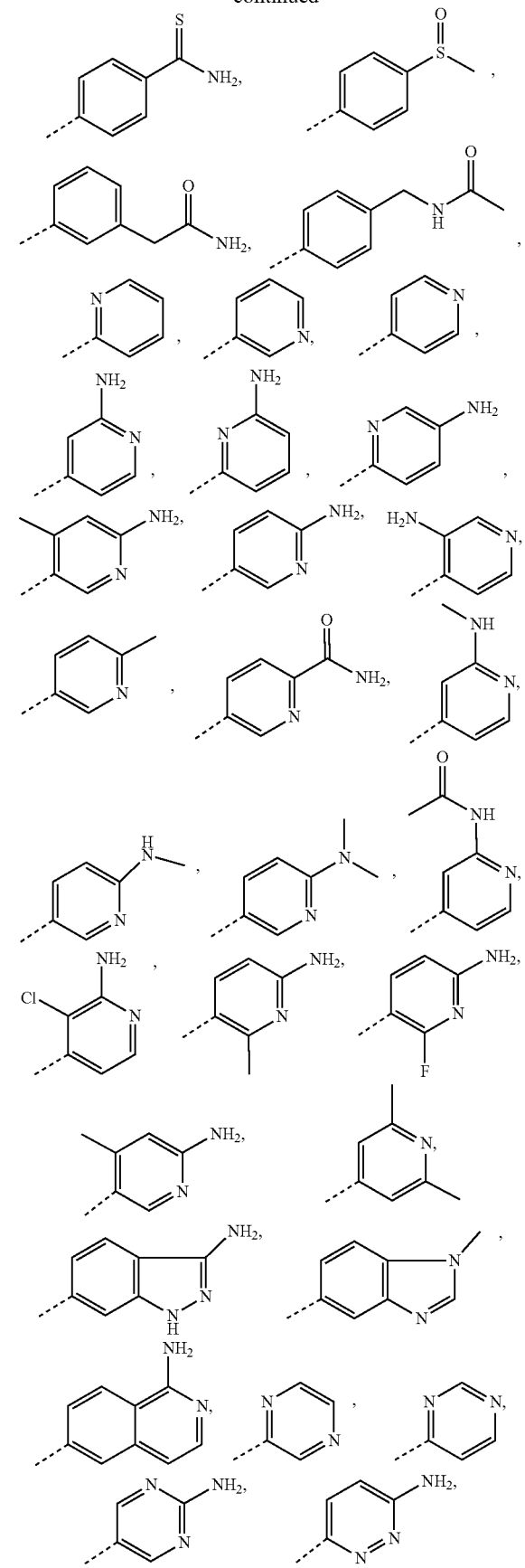

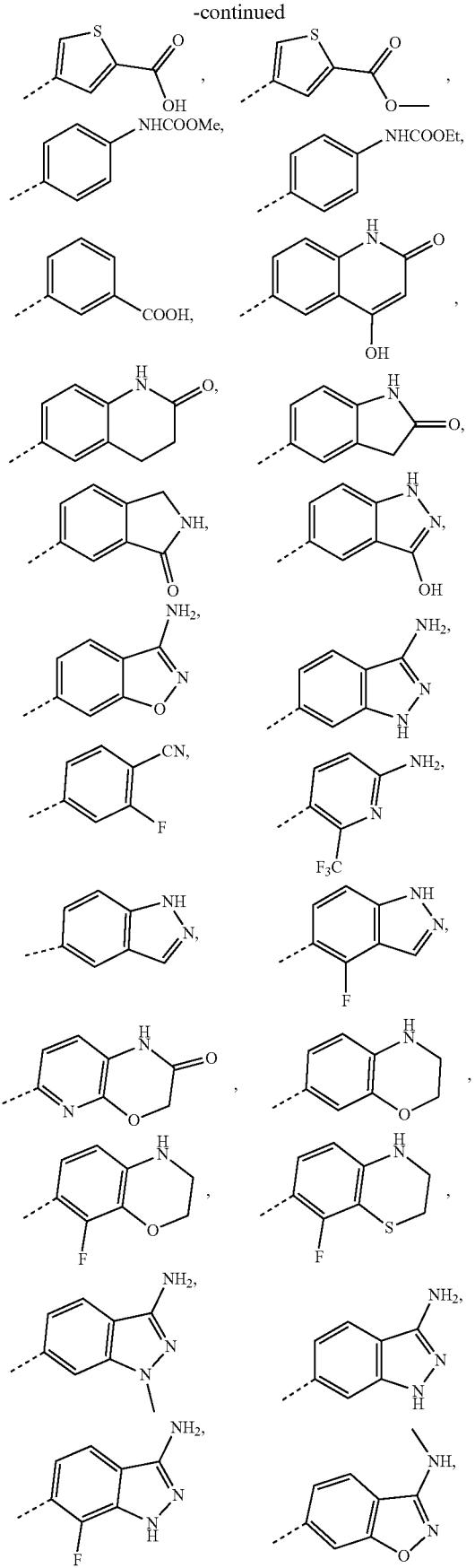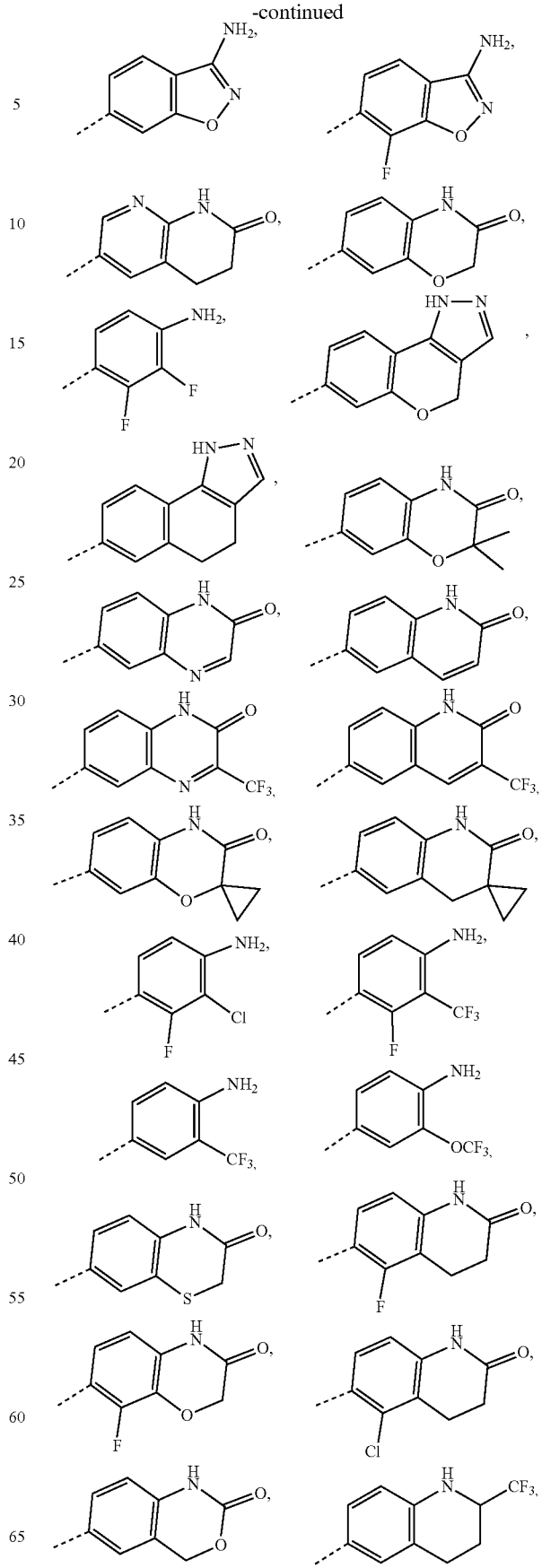

255
-continued
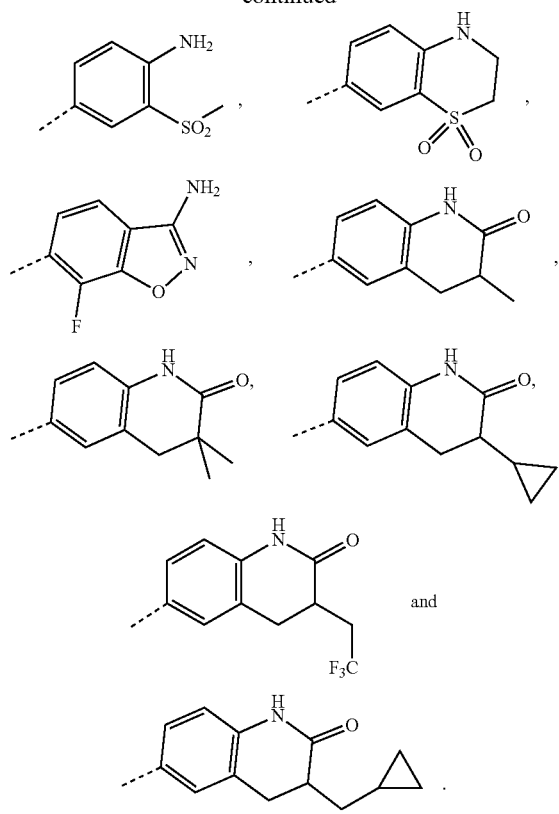
16. The compound according to claim 1, the optical isomer thereof, or the pharmaceutically acceptable salt thereof, wherein, the structural moiety
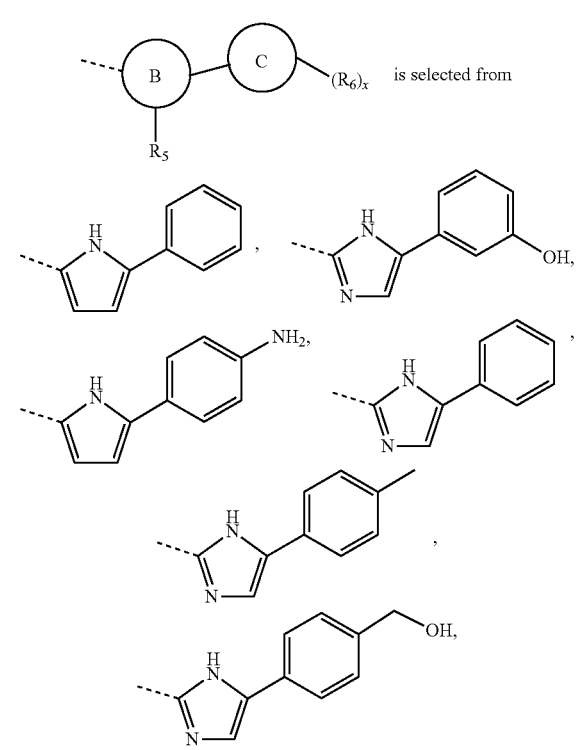
is selected from
256
-continued
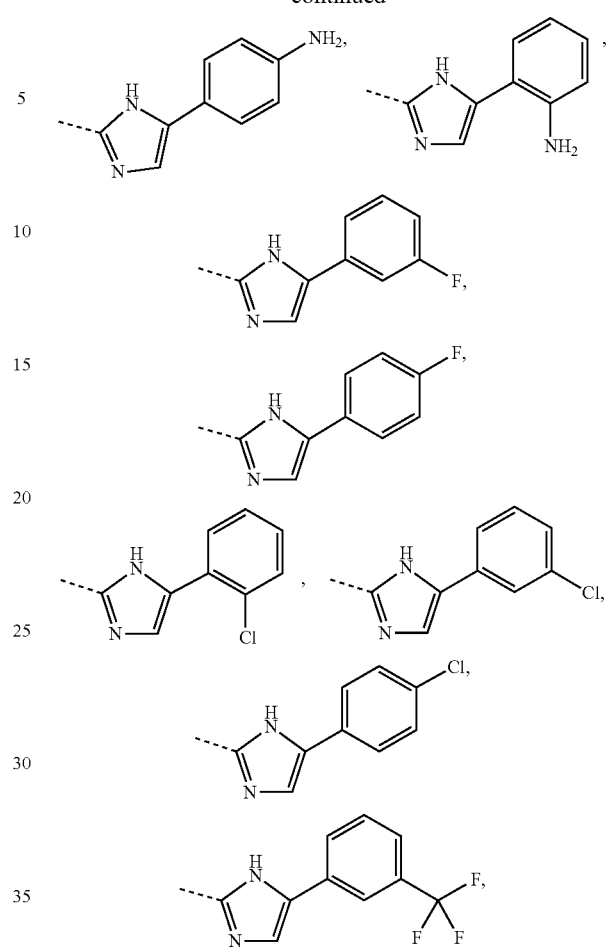
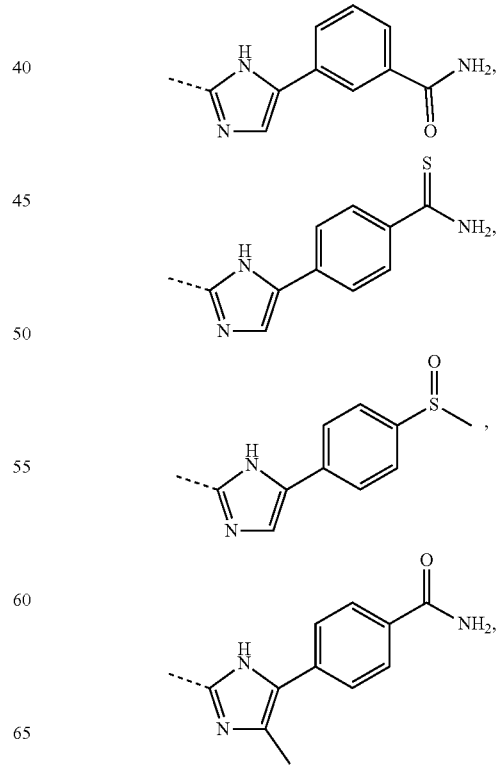

-continued
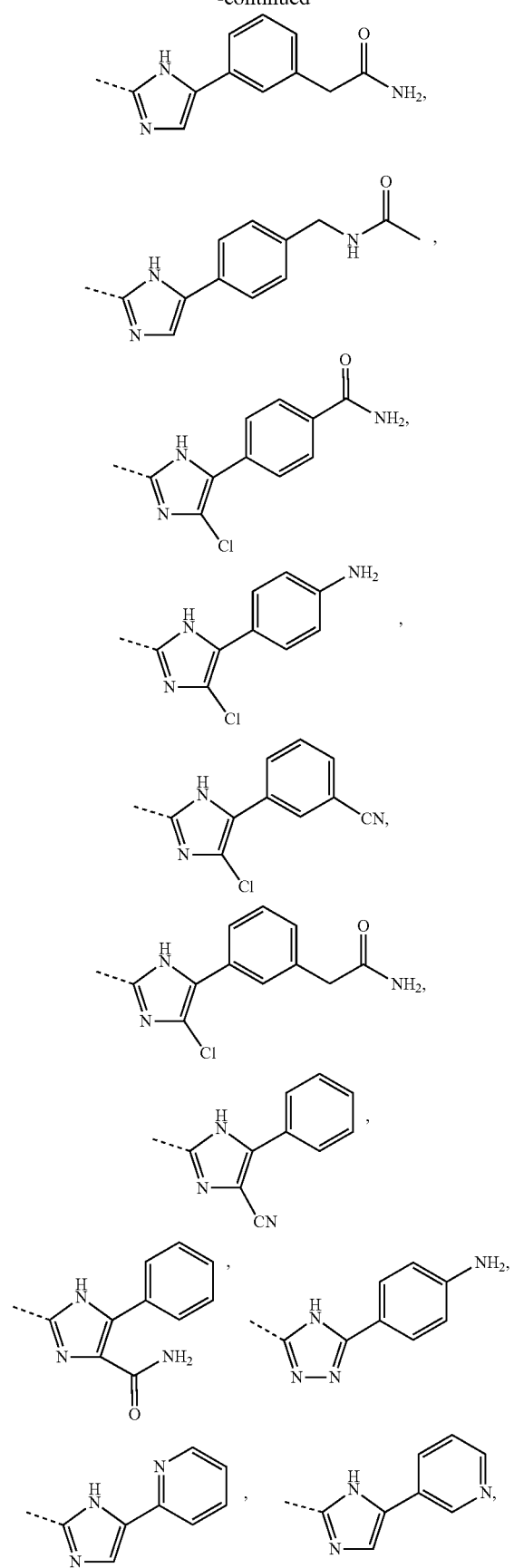
-continued
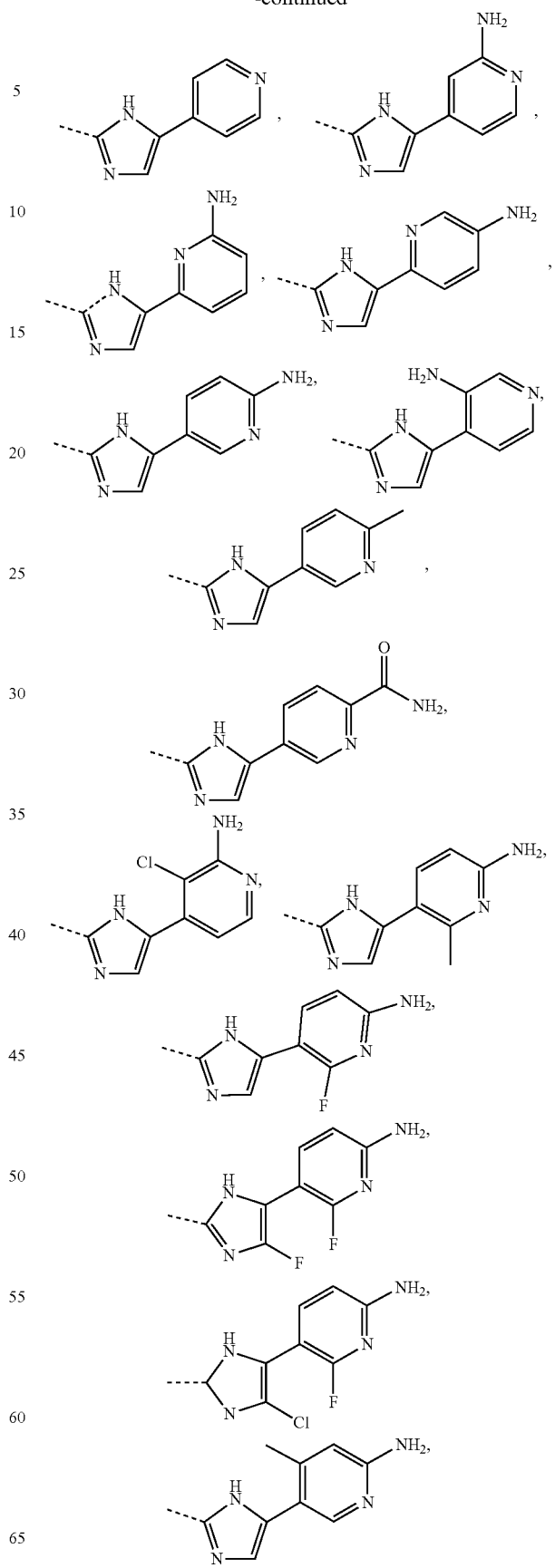

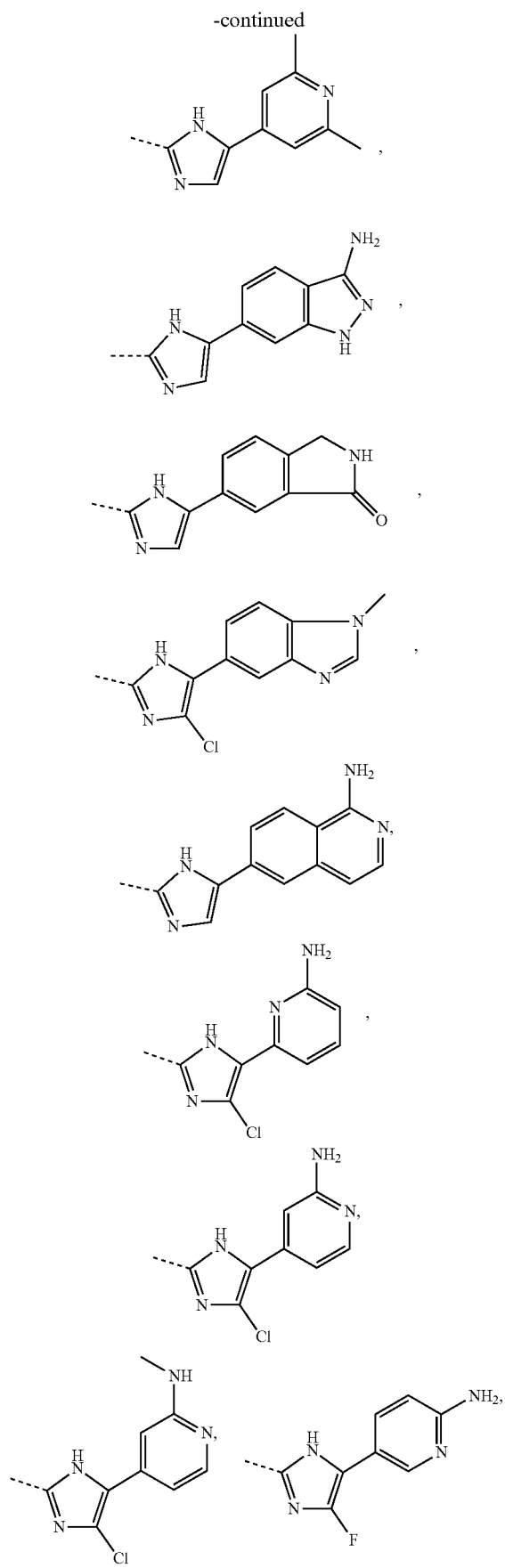
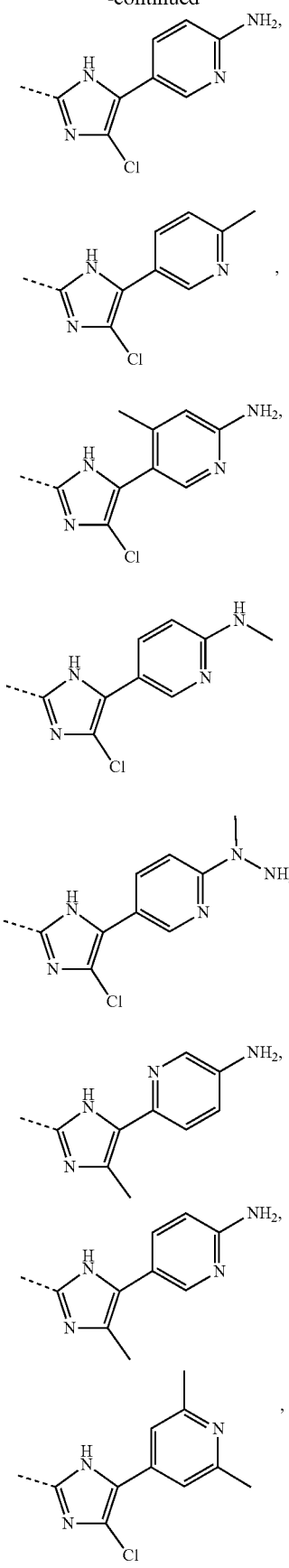

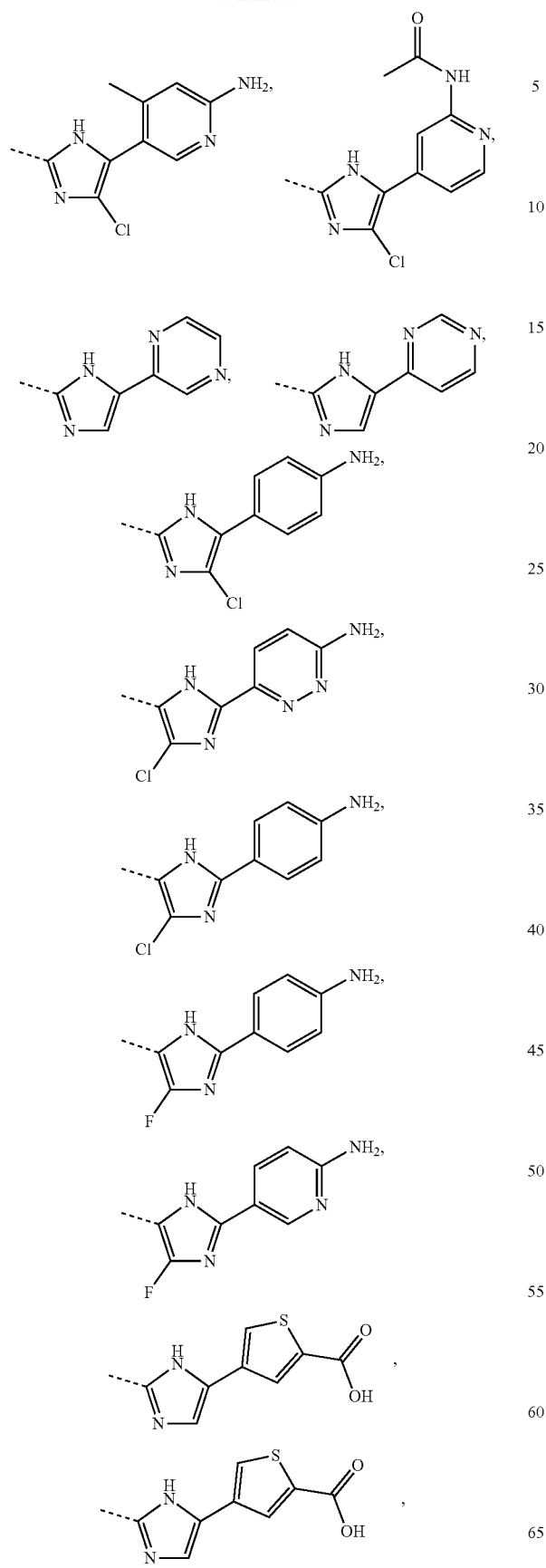
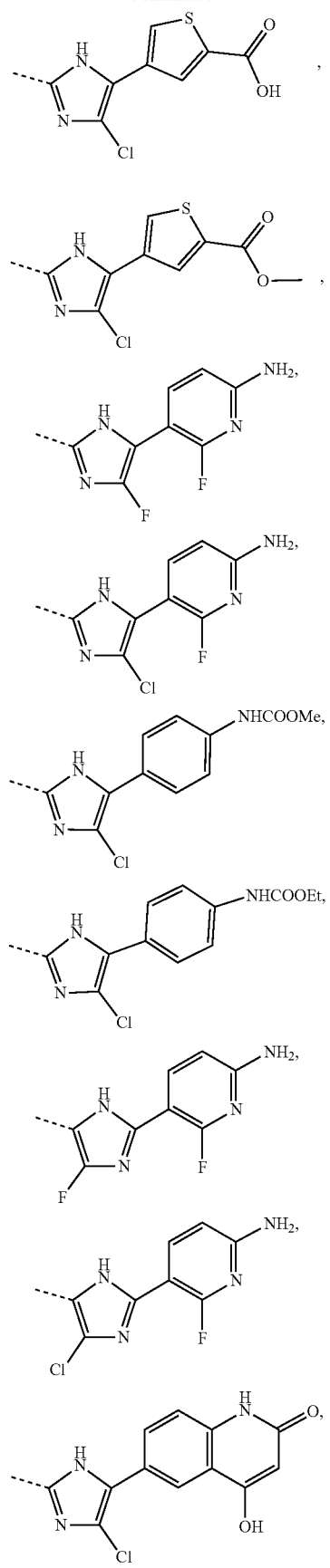

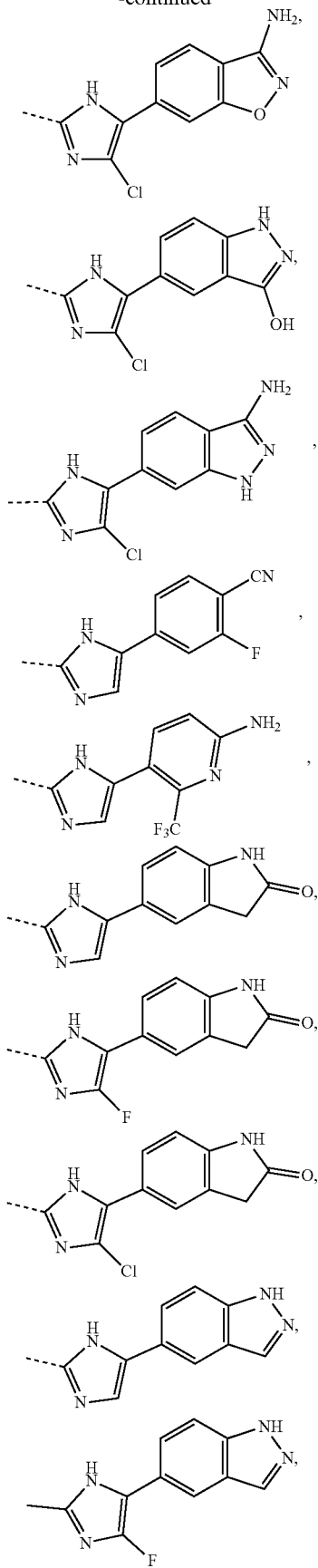
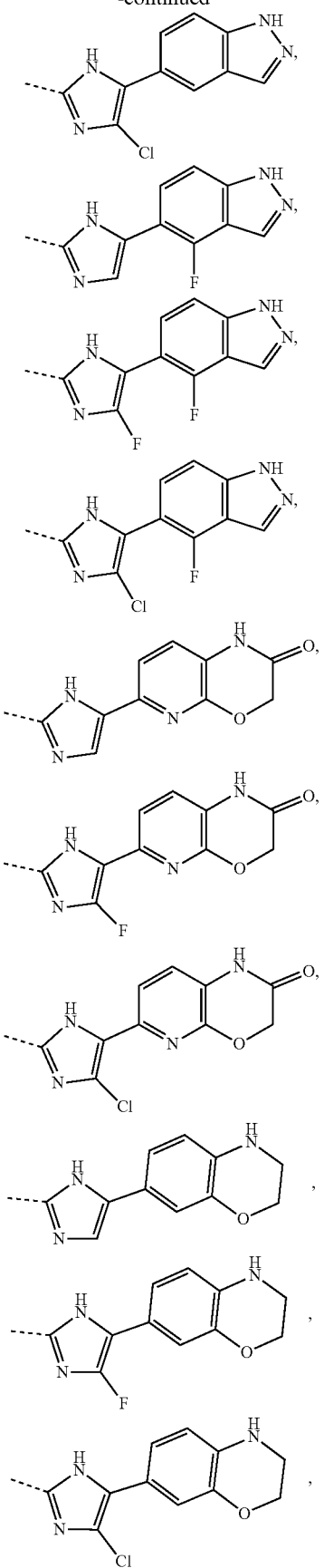

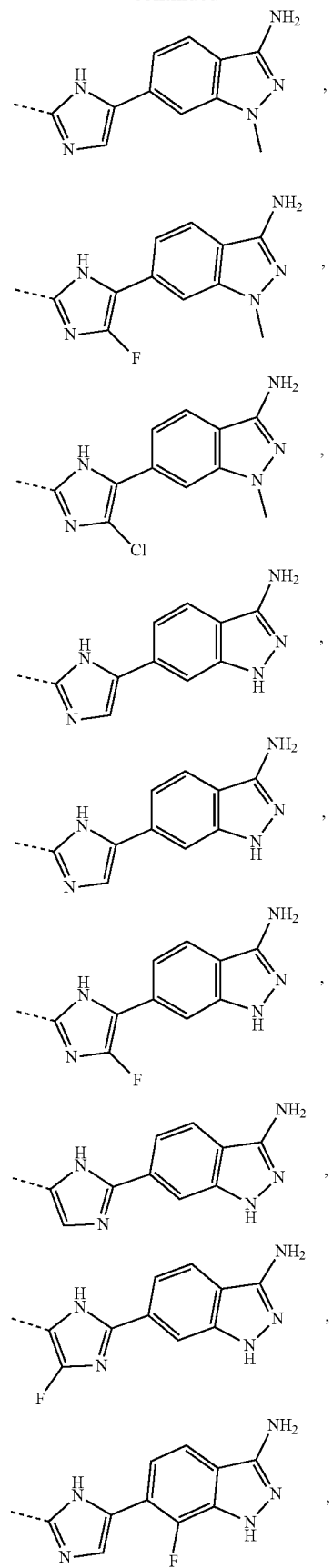
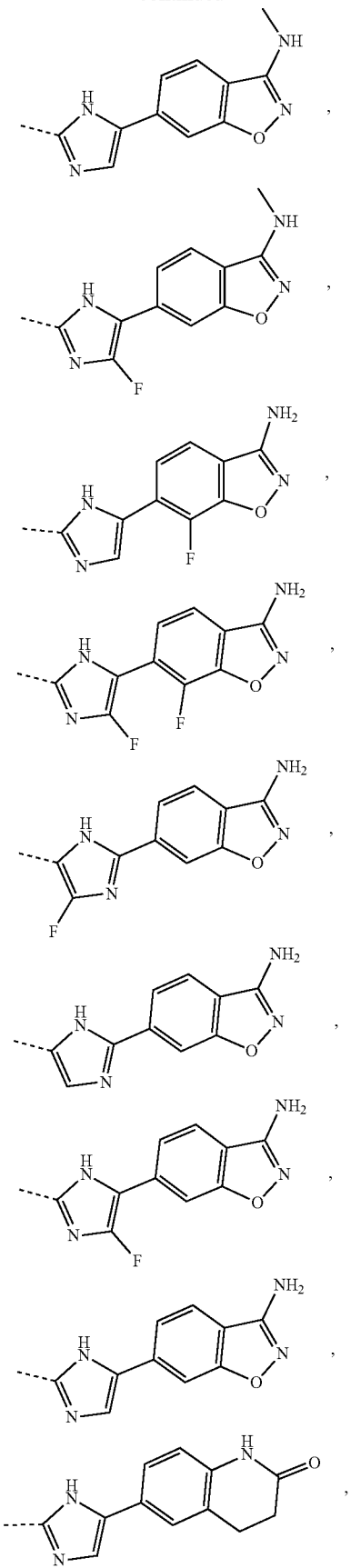

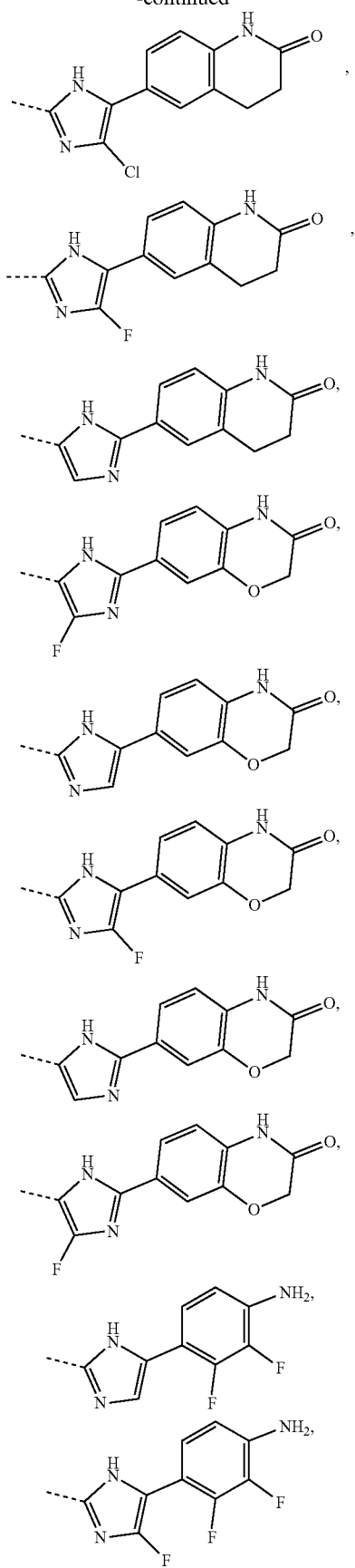
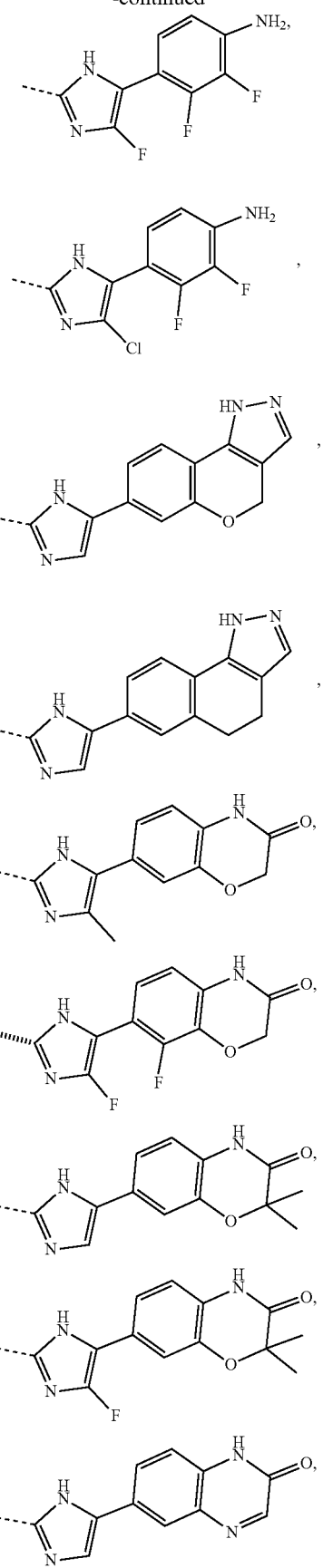

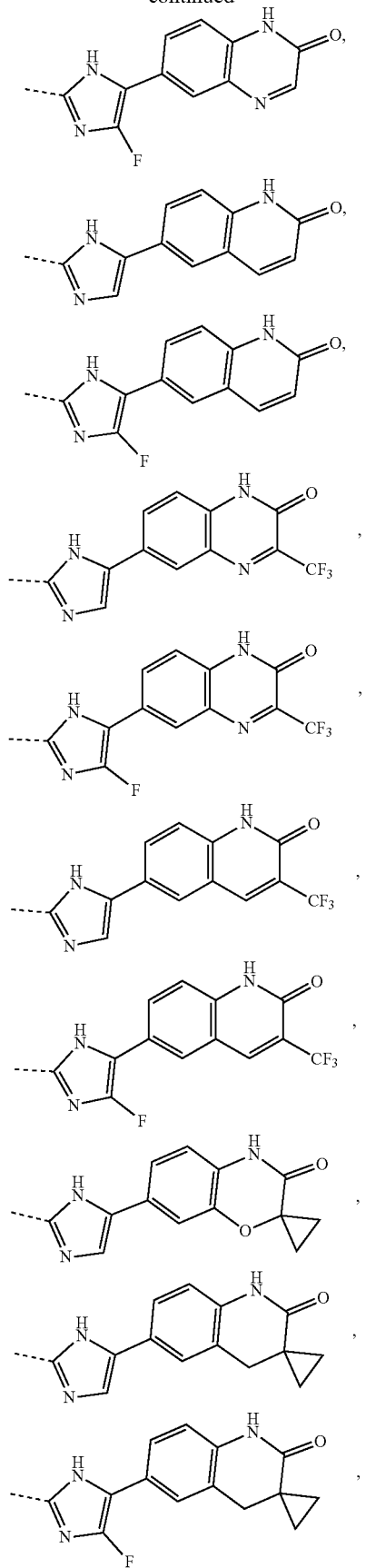
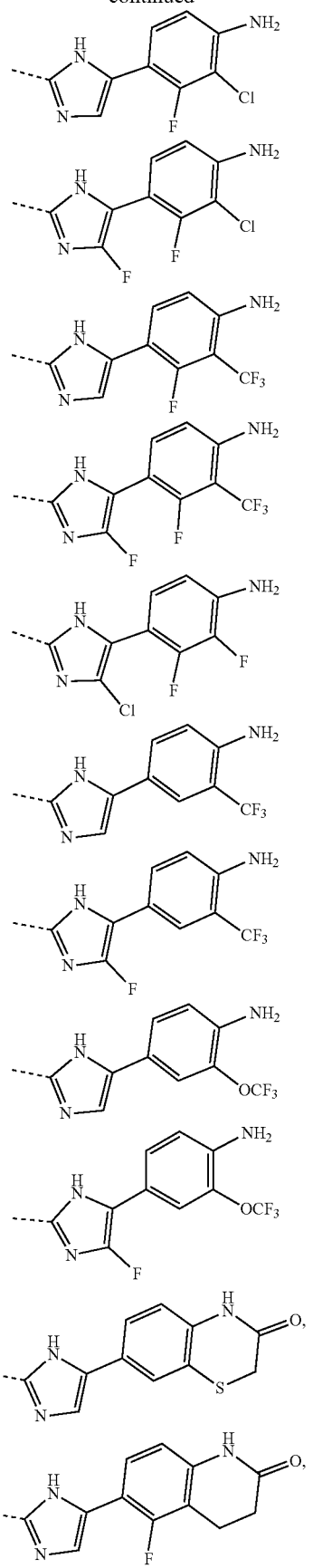

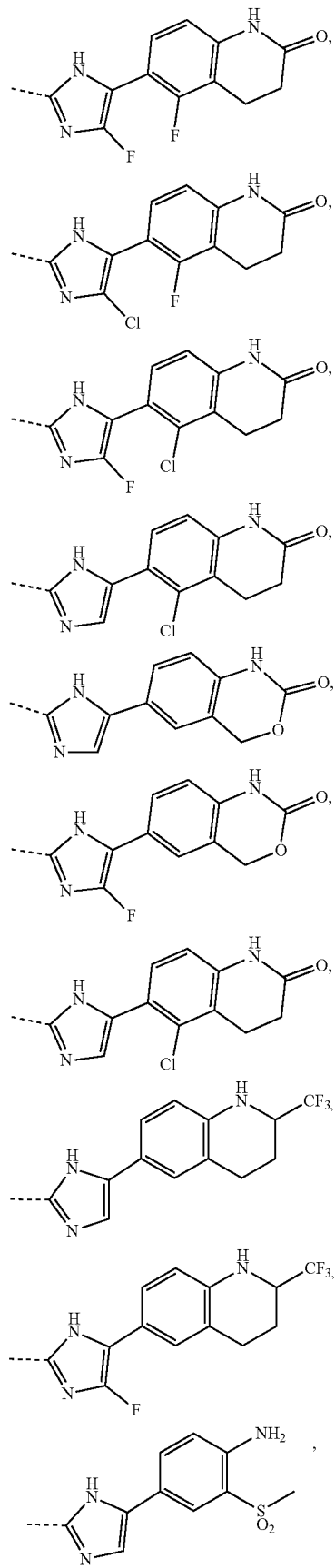
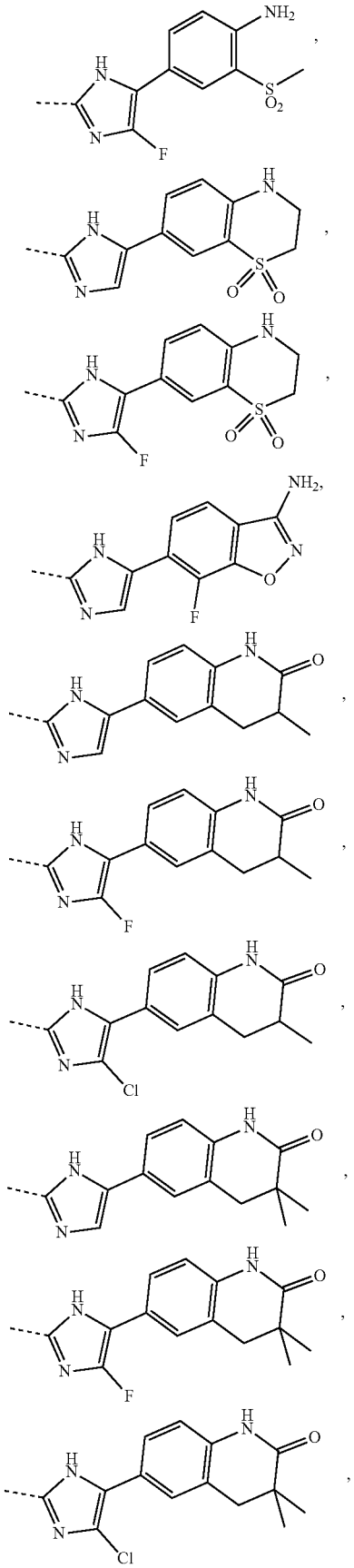

17. The compound according to claim 1, the optical isomer thereof, or the pharmaceutically acceptable salt thereof, wherein, ring D is selected from cyclopropyl, cyclobutyl, azetidinyl, oxetanyl and pyrrolidinyl.

18. The compound according to claim 17, the optical isomer thereof, or the pharmaceutically acceptable salt thereof, wherein, the structural moiety is selected from

19. The compound according to claim 18, the optical isomer thereof, or the pharmaceutically acceptable salt thereof, wherein, the structural moiety

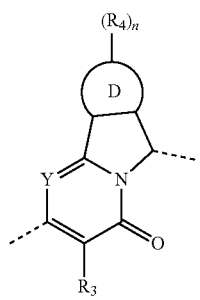
is selected from
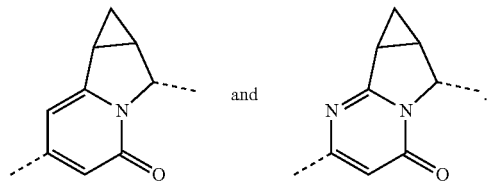
20. The compound according to claim 1, the optical isomer thereof, or the pharmaceutically acceptable salt thereof, wherein, selected from
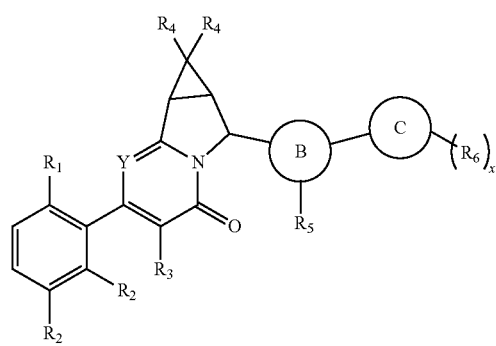
(I-1)
wherein,
$R_1$, $R_2$, $R_3$, $R_4$, $R_5$, $R_6$, x, Y, ring B and ring C are as defined in claim 1.
21. A compound of the following formula, an optical isomer thereof or a pharmaceutically acceptable salt thereof, selected from
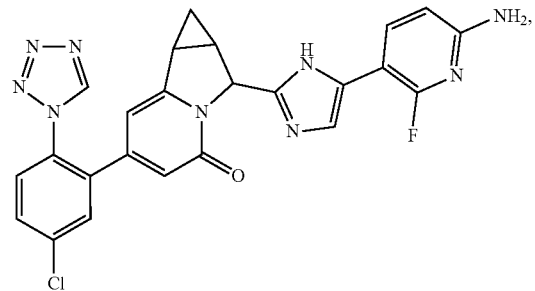
-continued
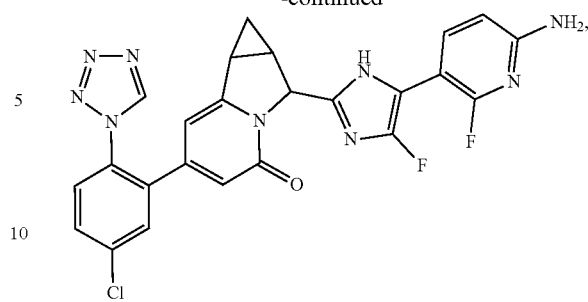
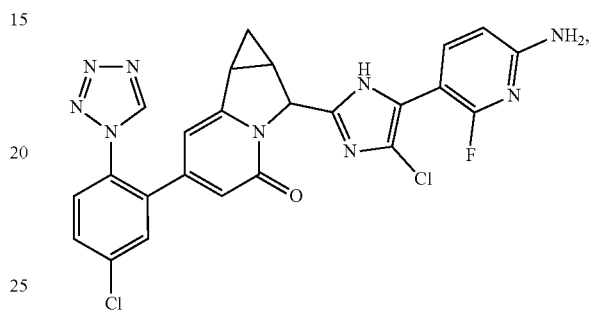
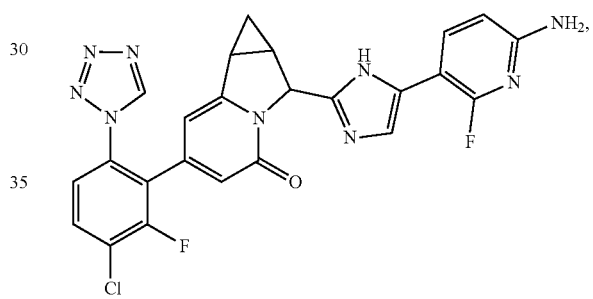
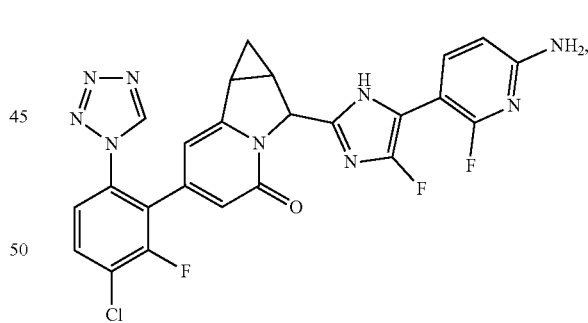
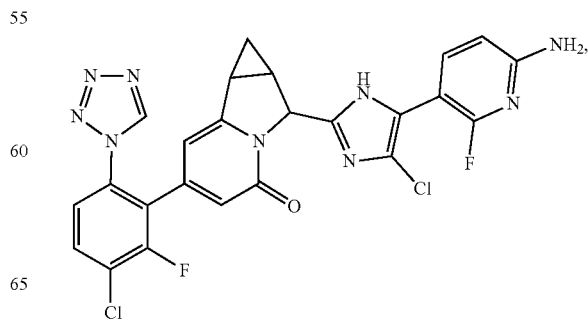

277
-continued
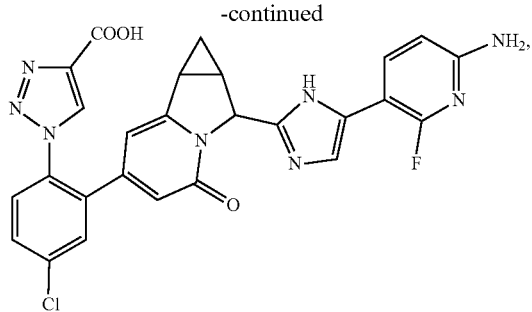
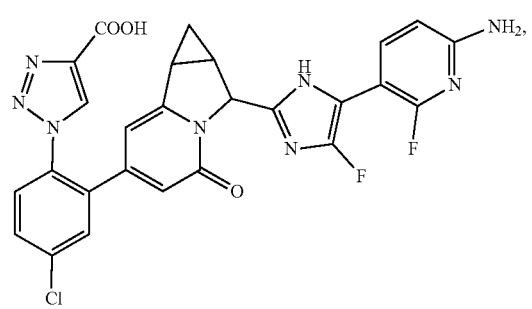
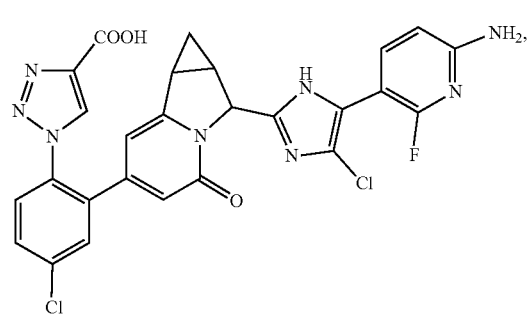
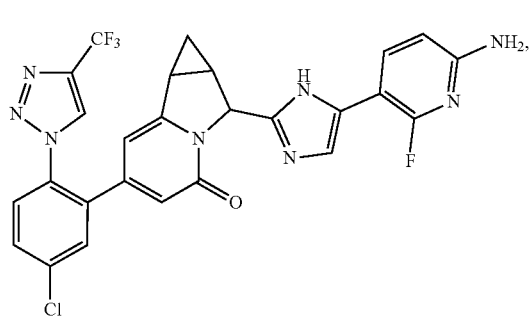
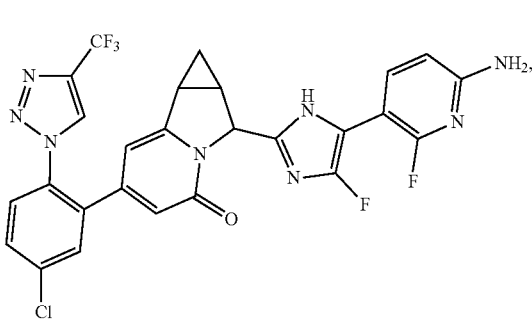
278
-continued
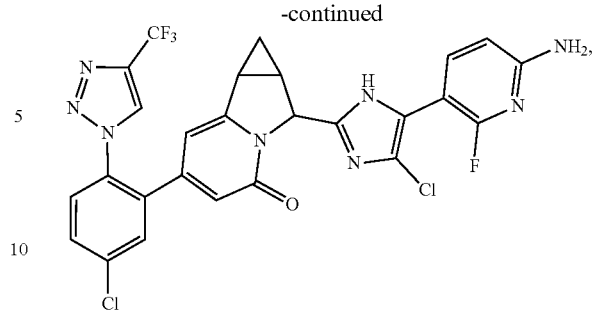
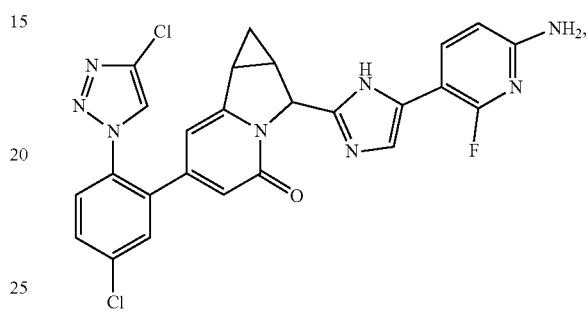
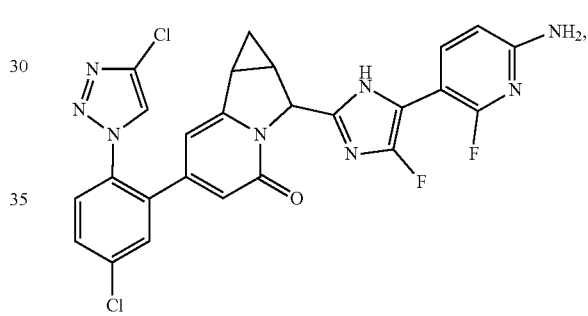
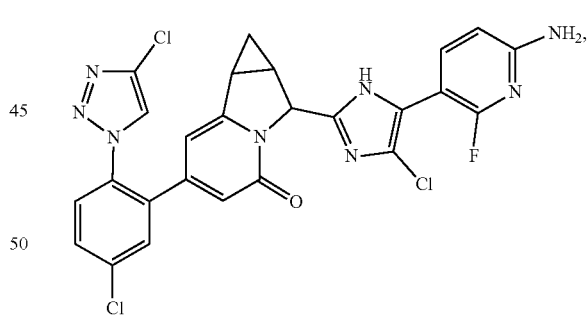
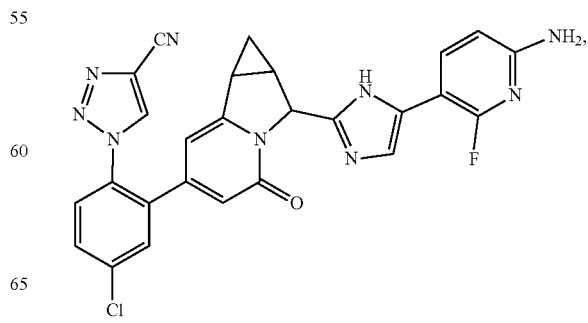

-continued
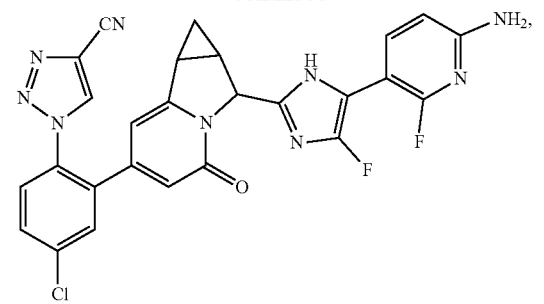
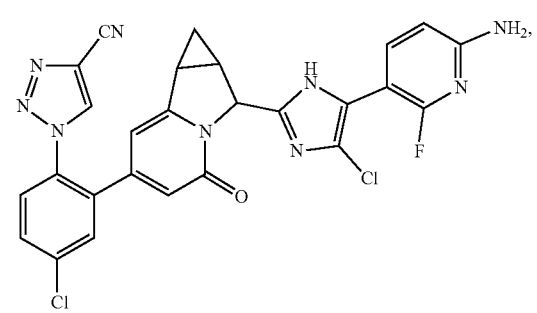
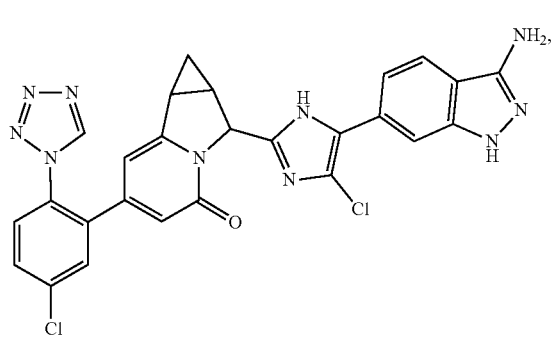
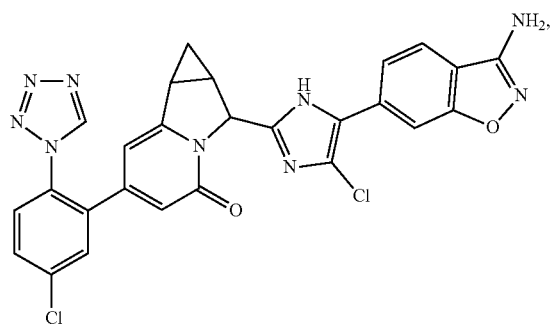
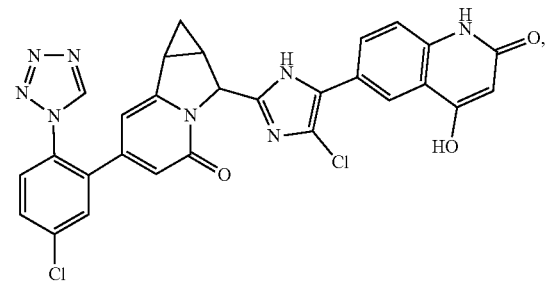
-continued
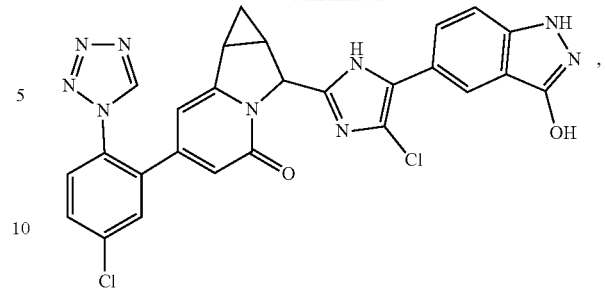
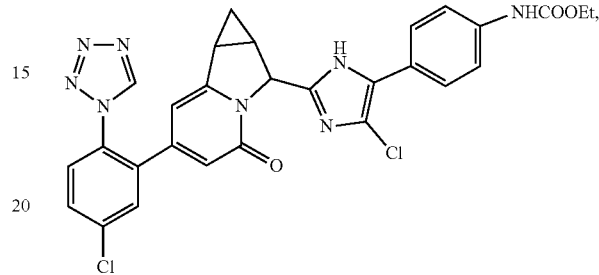
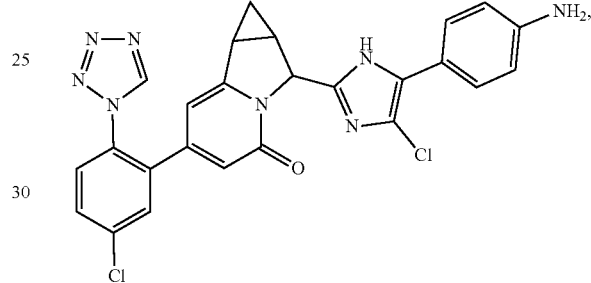
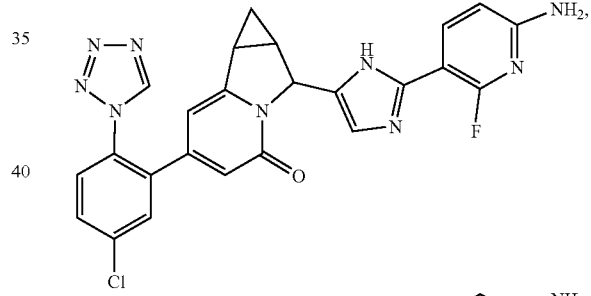
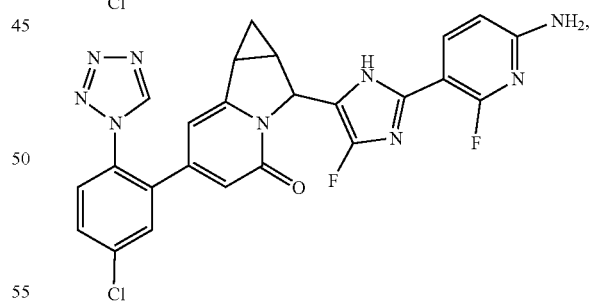
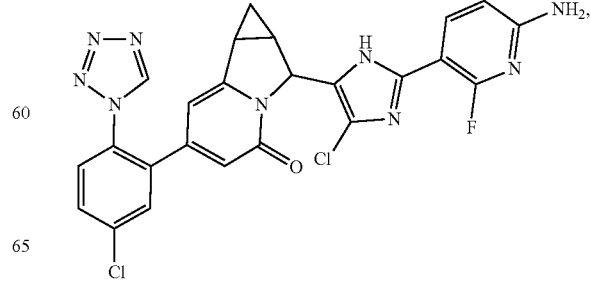

-continued
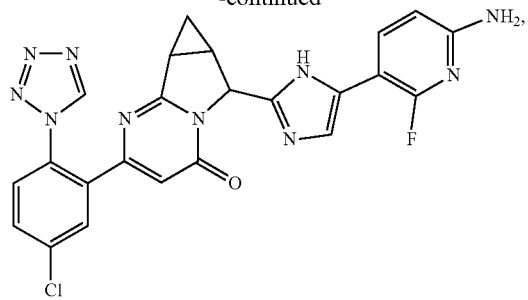
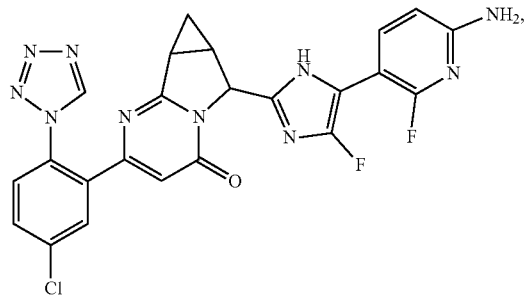
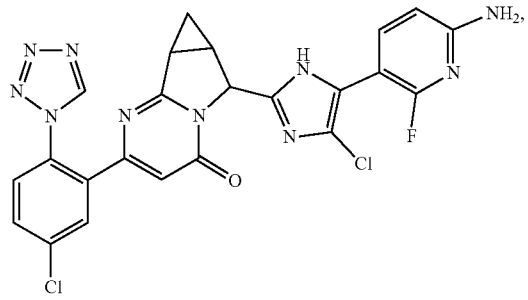
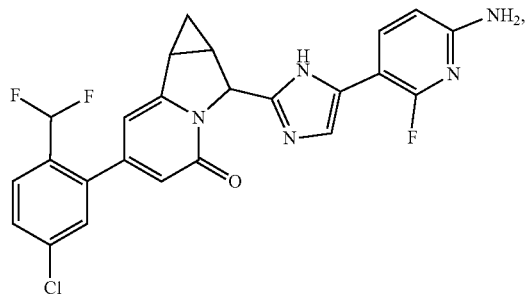
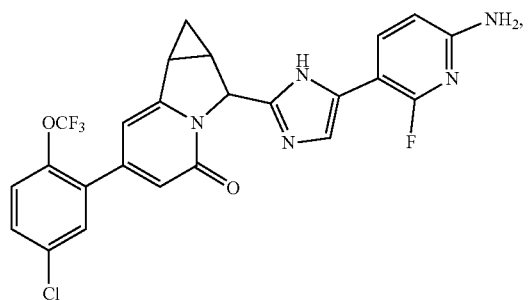
-continued
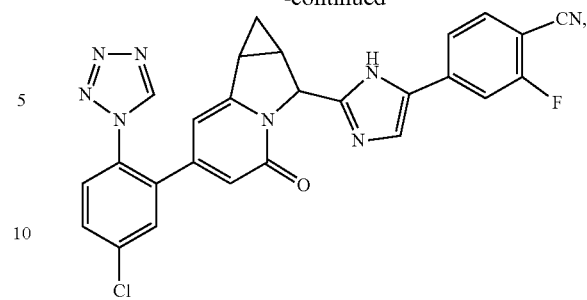
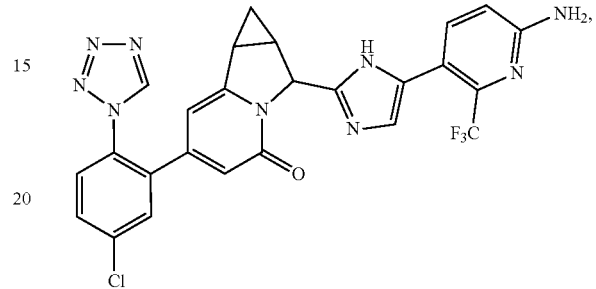
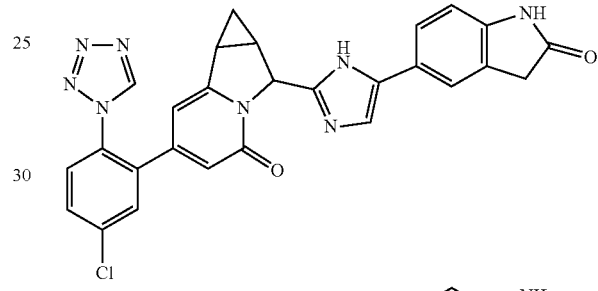
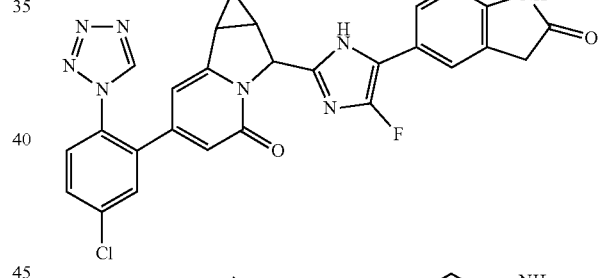
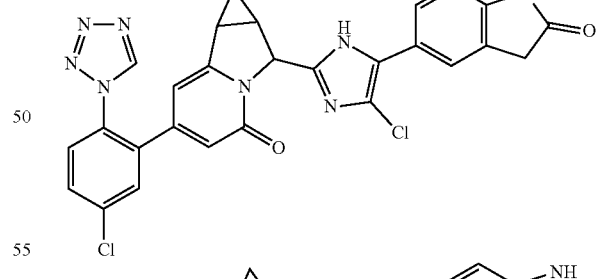
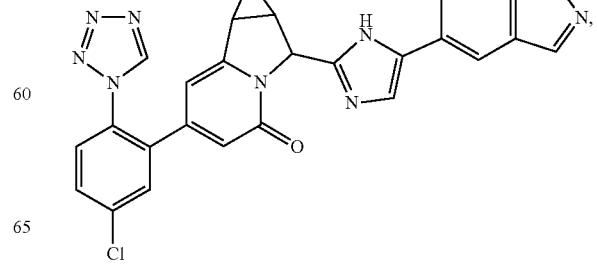

283
-continued
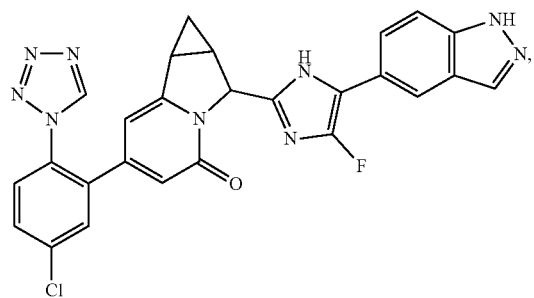
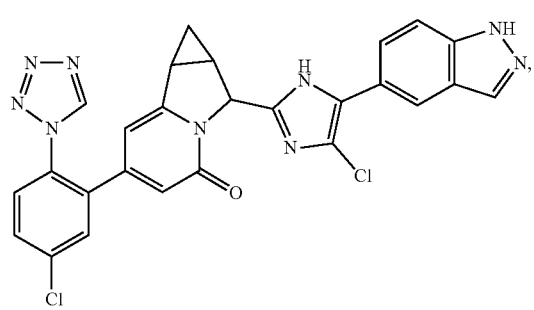
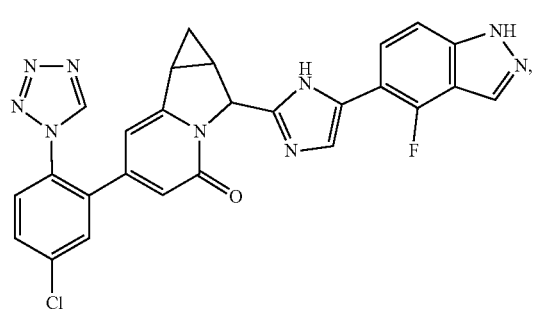
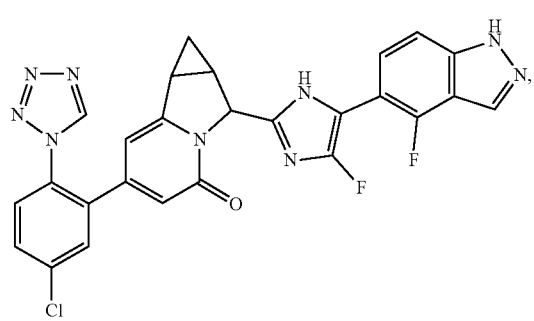
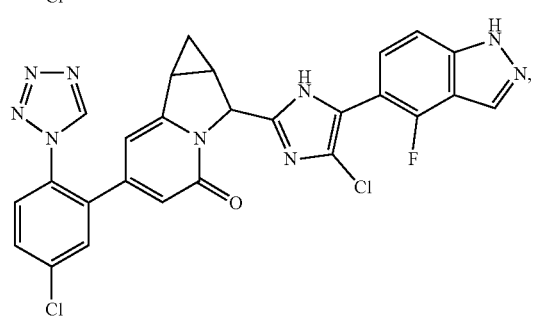
284
-continued
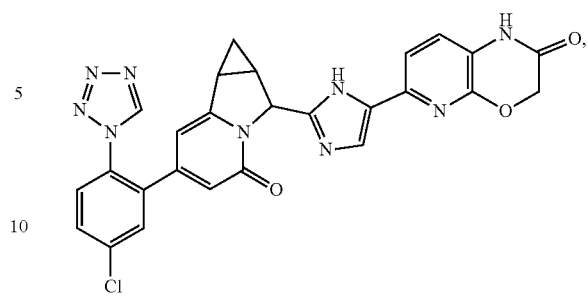
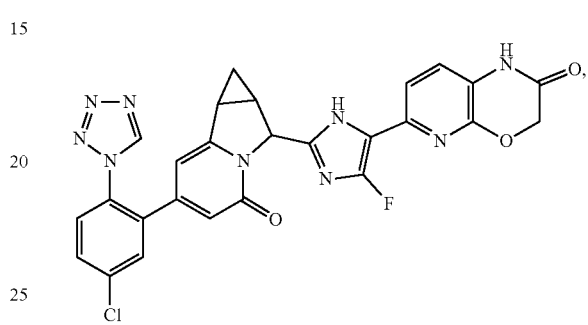
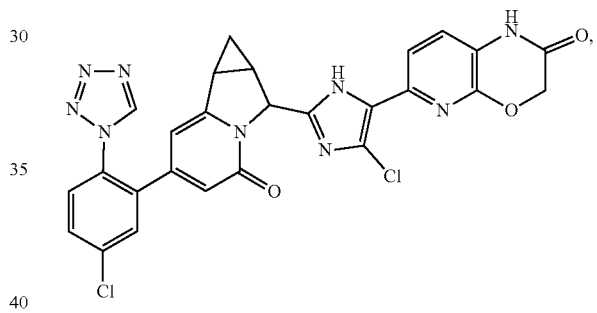
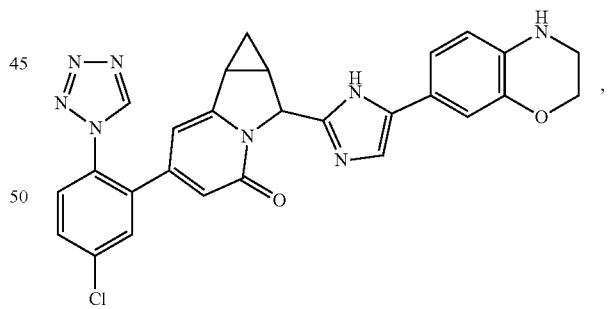
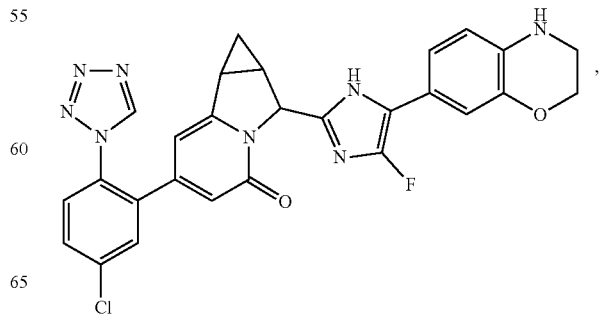

285
-continued
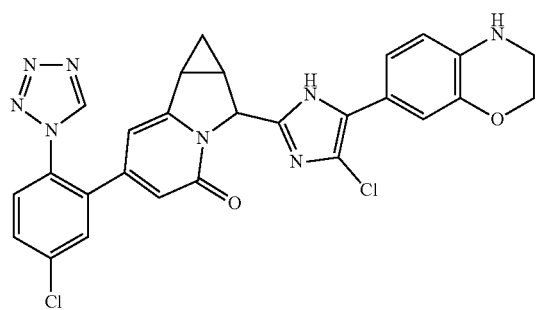
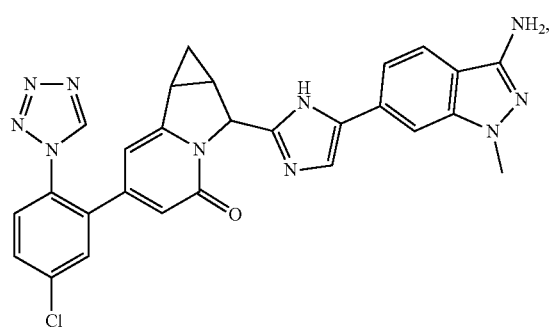
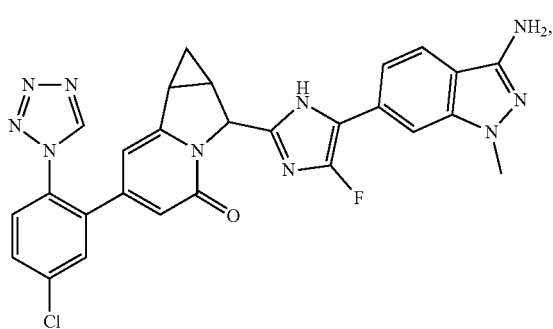
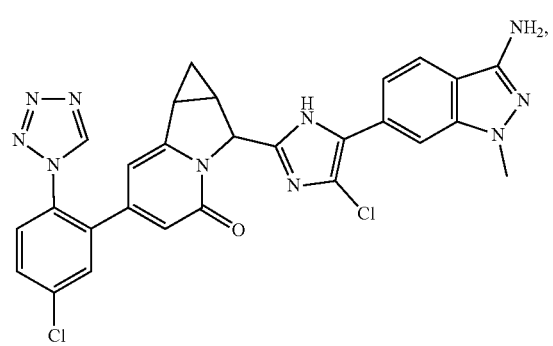
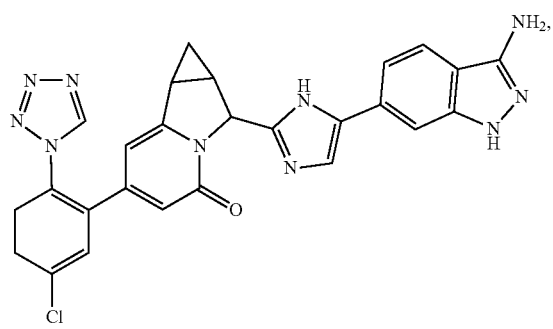
286
-continued
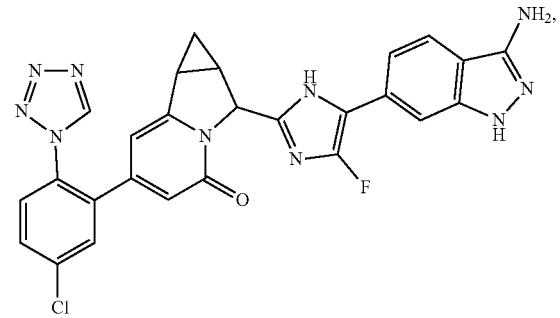
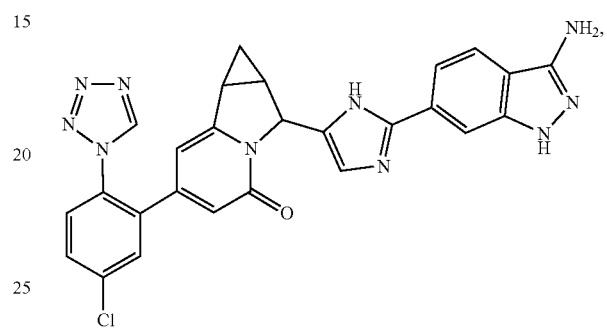
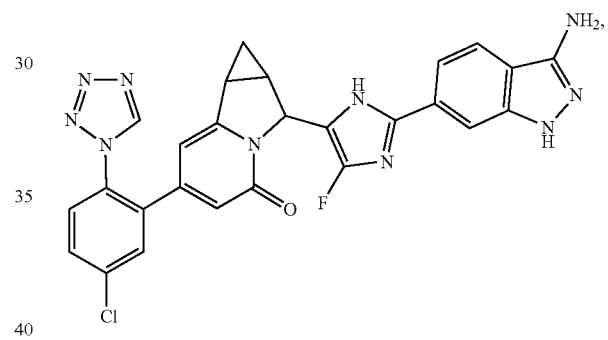
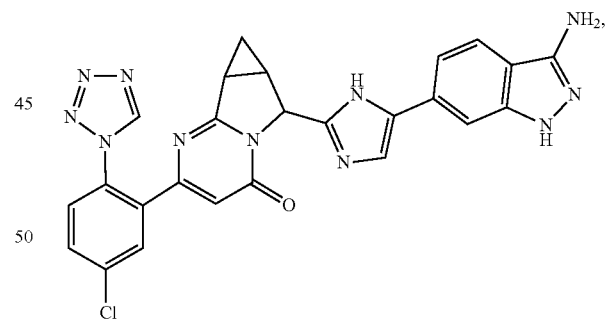
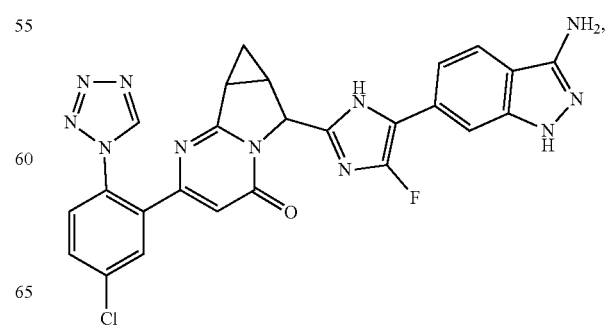

287
-continued
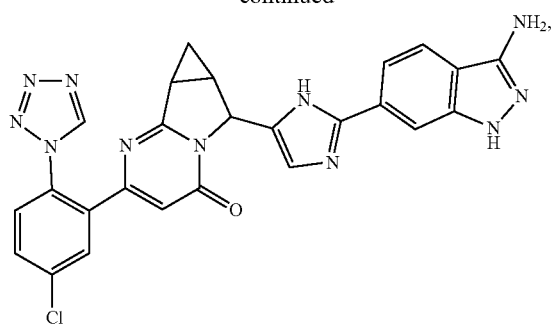
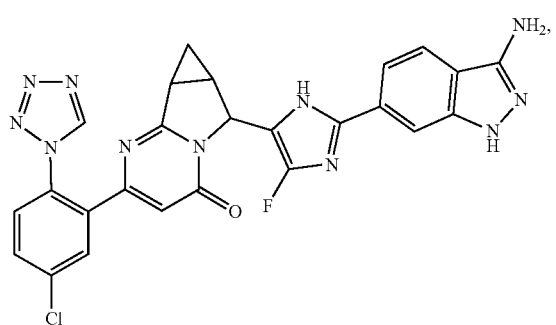
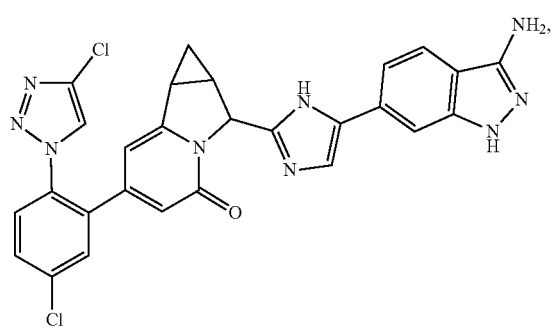
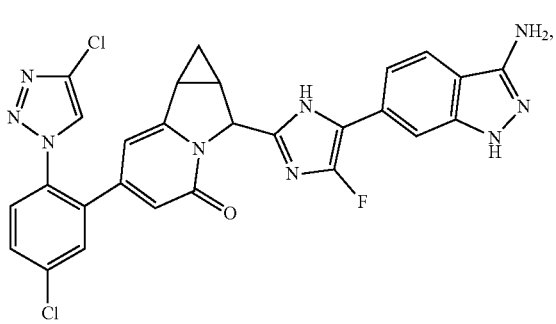
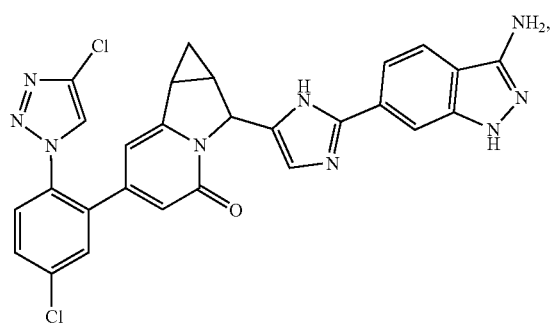
288
-continued
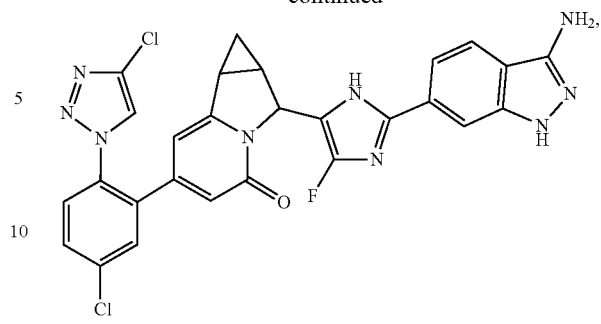
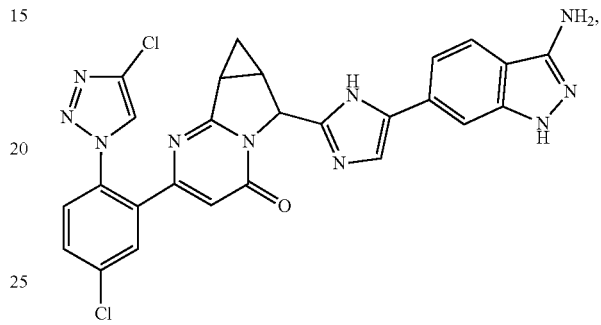
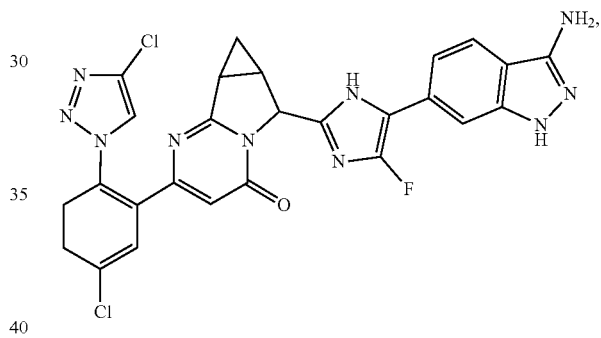
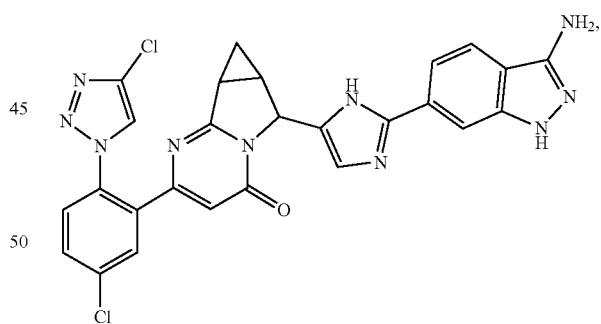
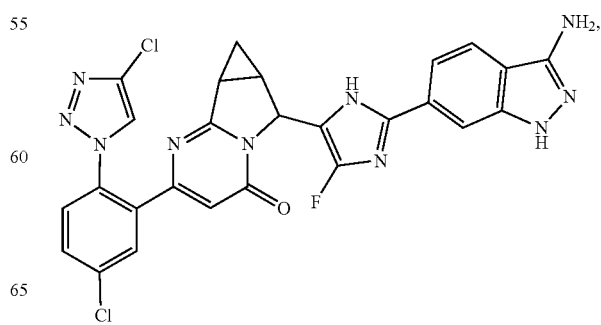

289
-continued
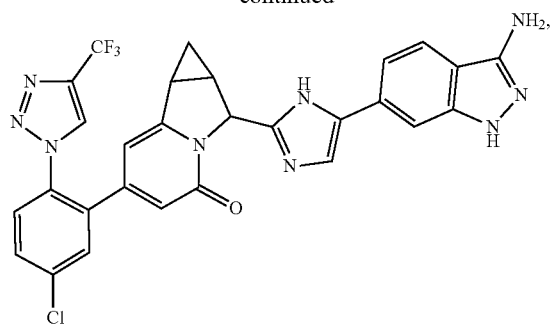
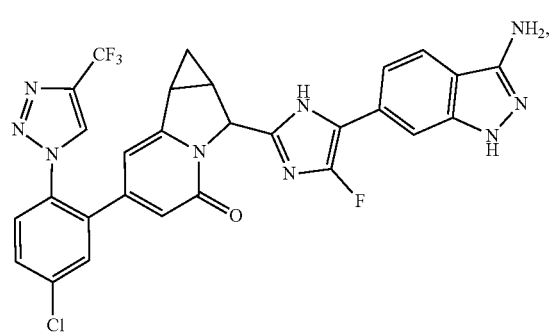
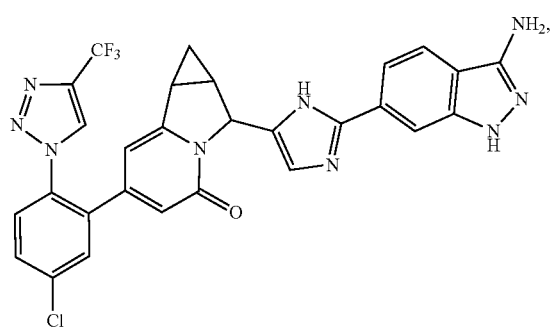
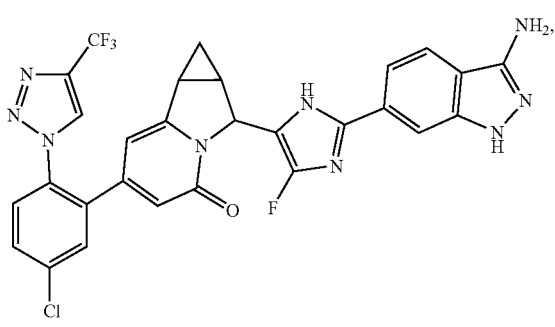
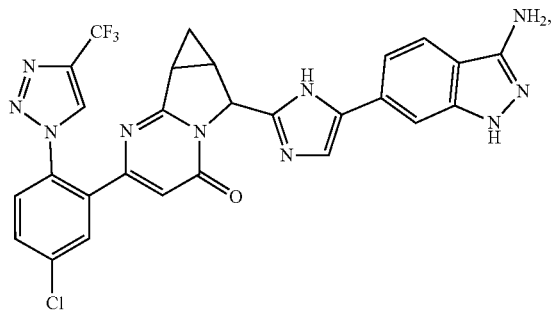
290
-continued
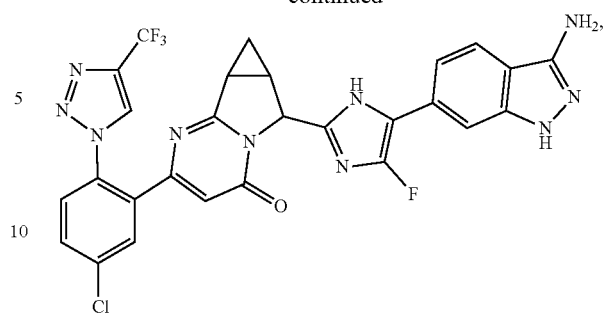
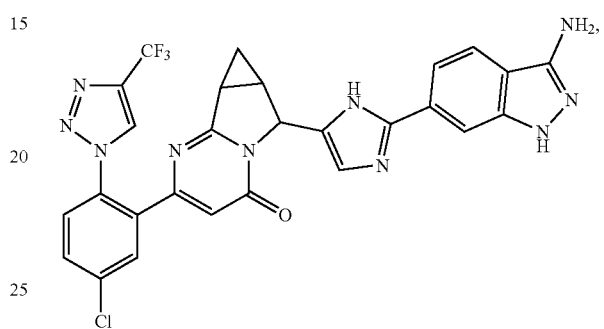
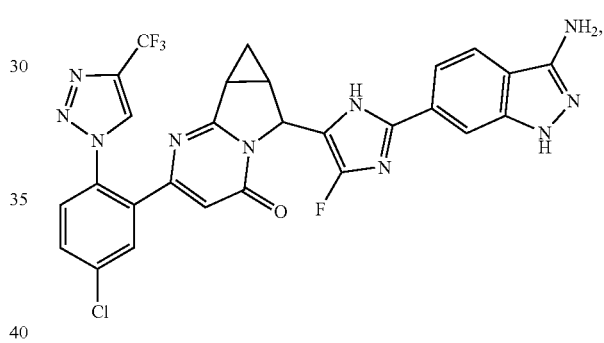
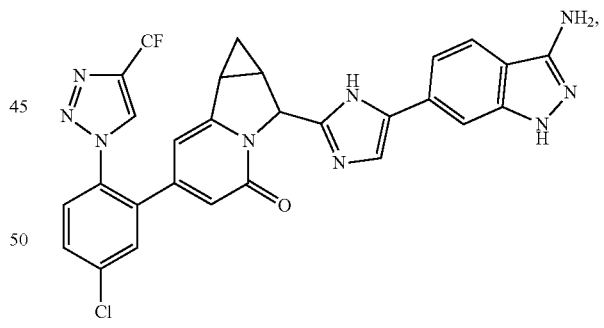
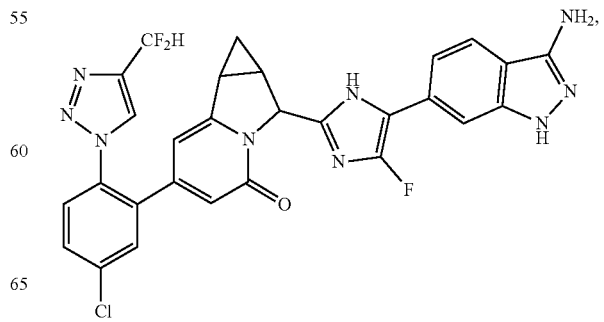

291
-continued
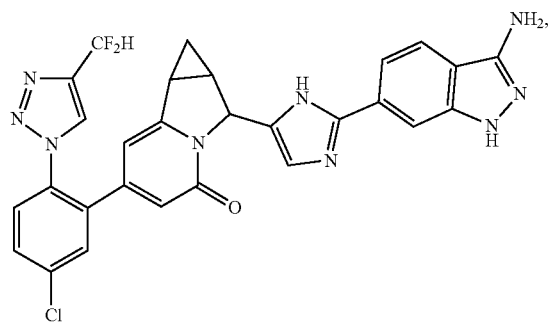
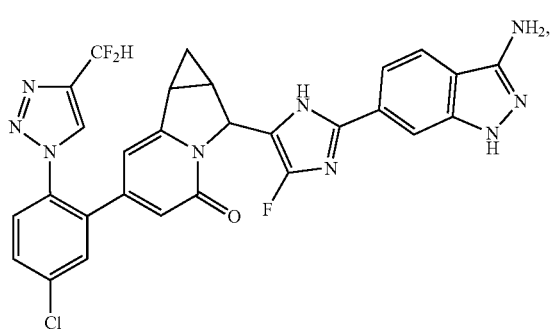
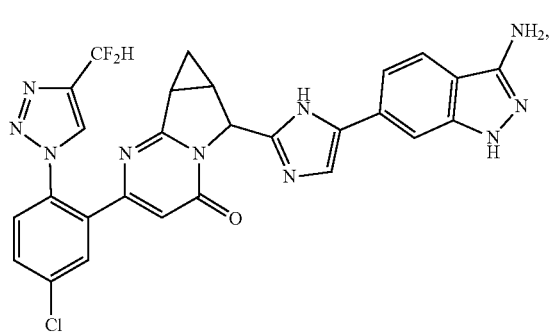
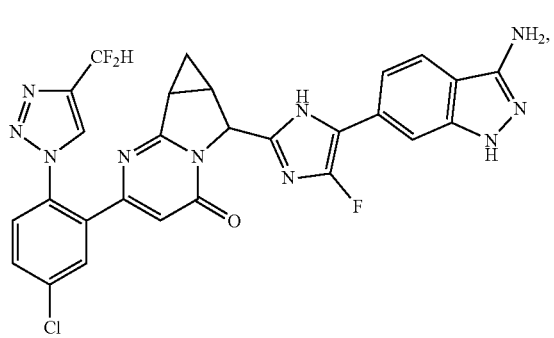
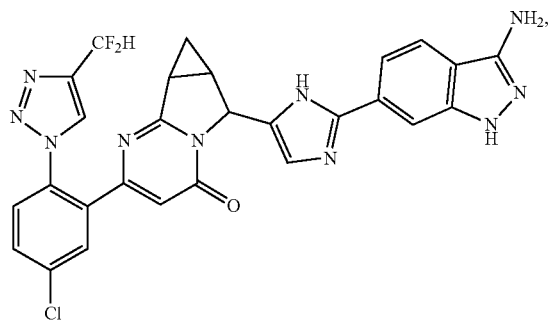
292
-continued
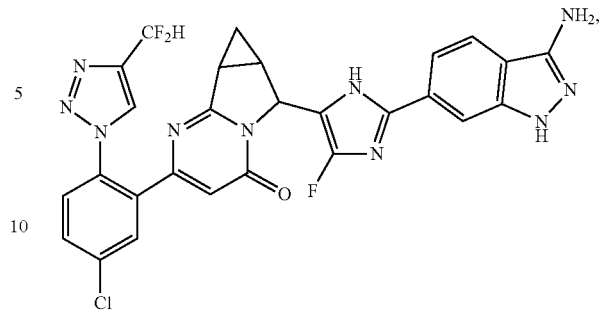
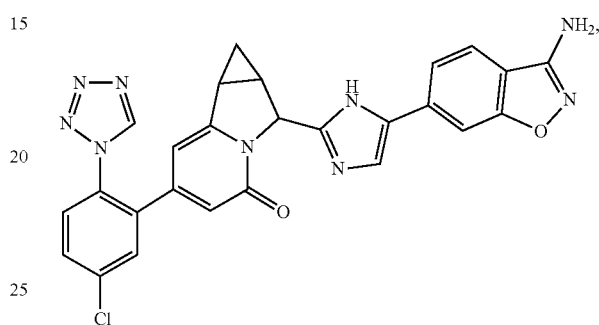
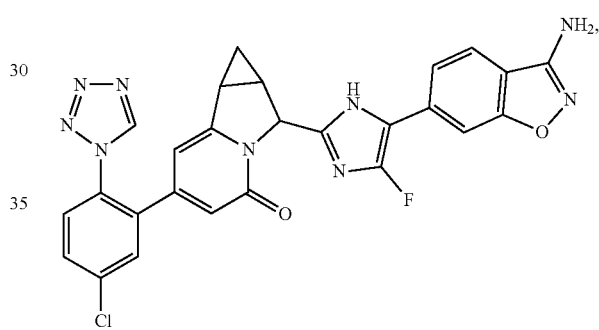
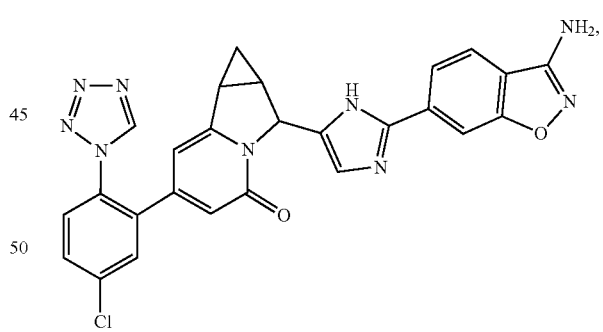
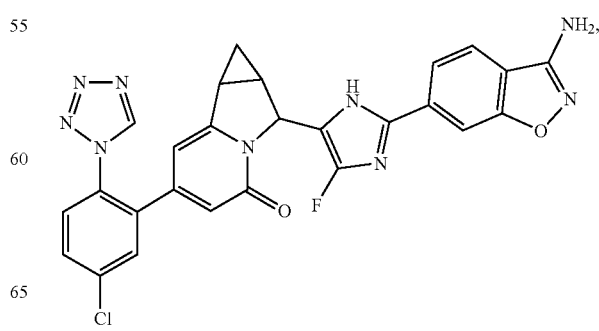

293
-continued
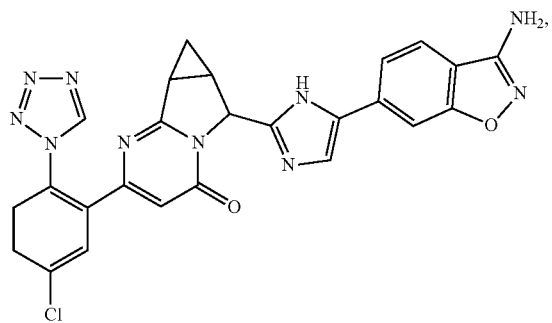
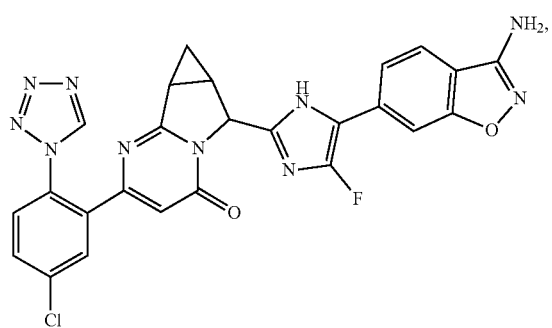
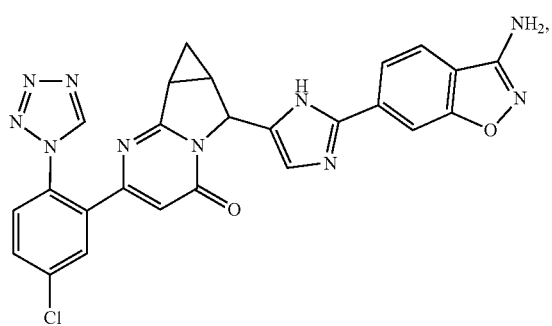
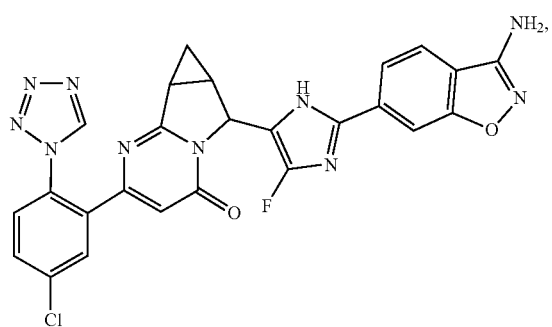
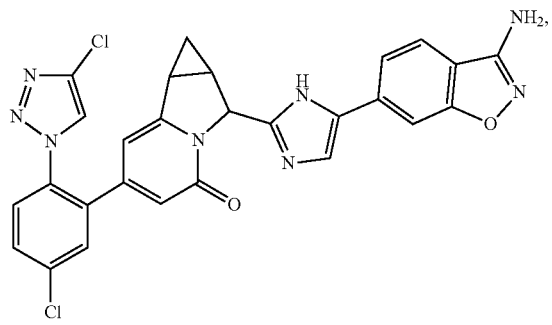
294
-continued
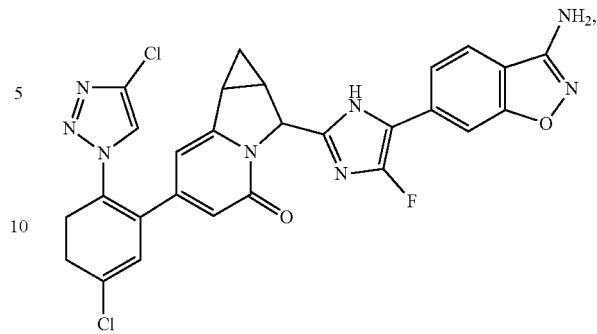
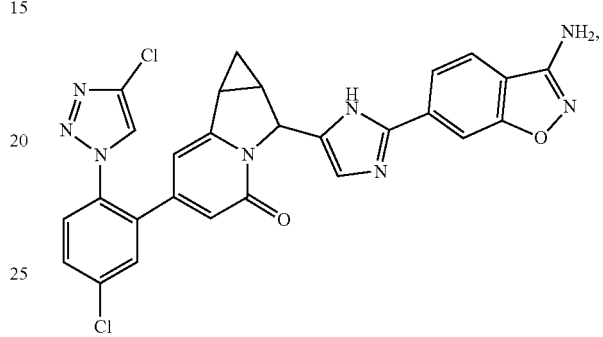
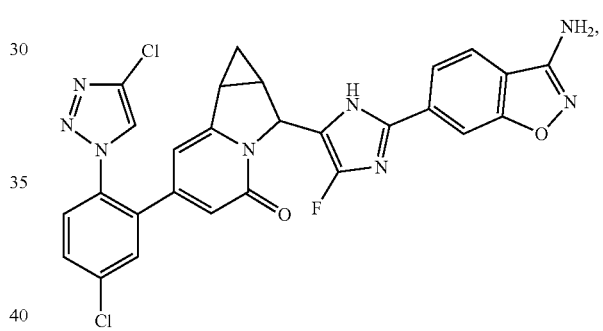
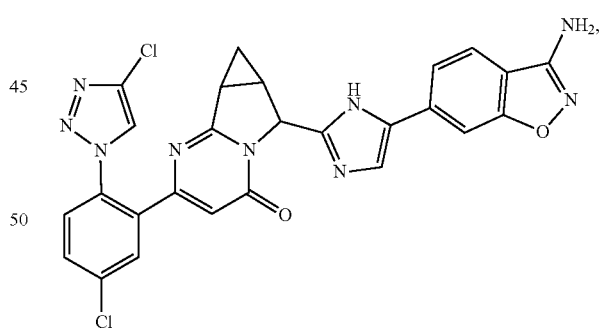
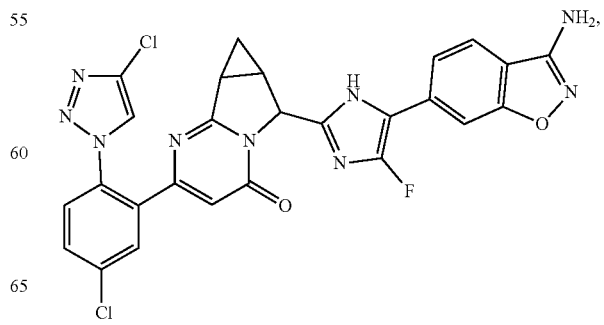

295
-continued
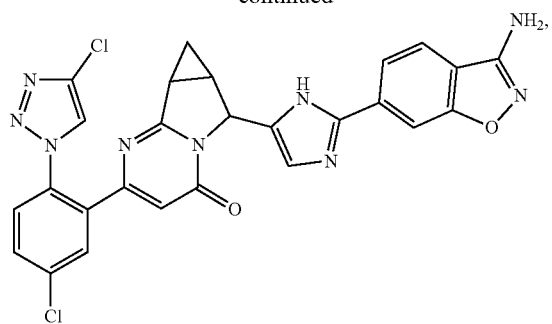
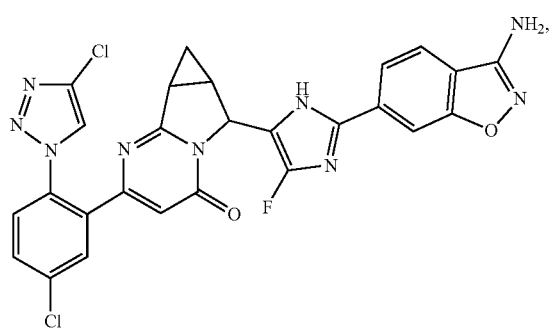
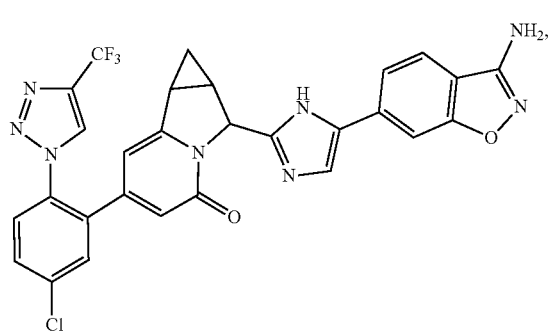
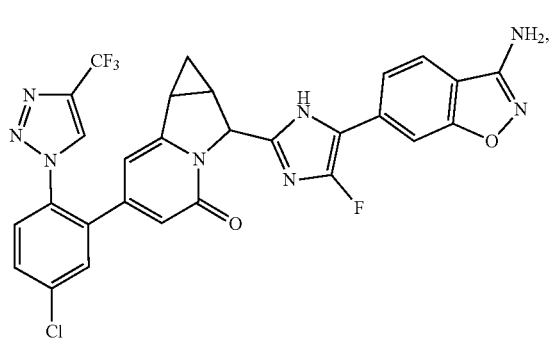
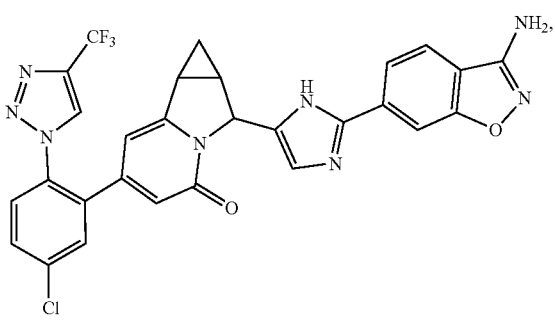
296
-continued
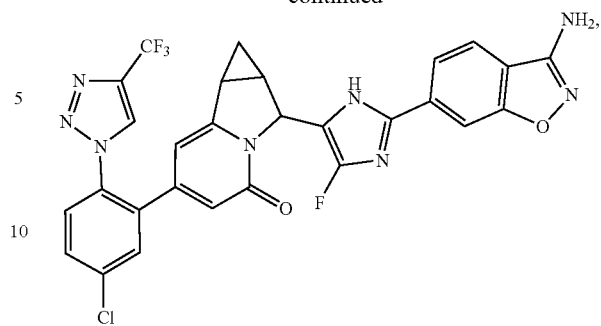
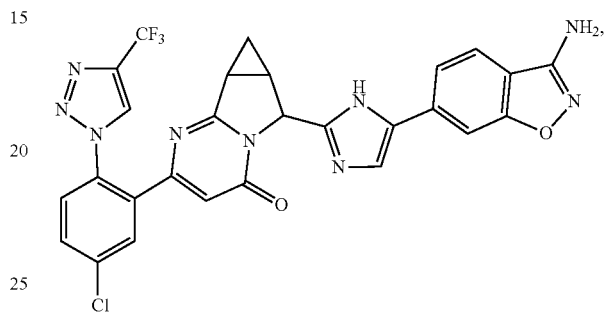
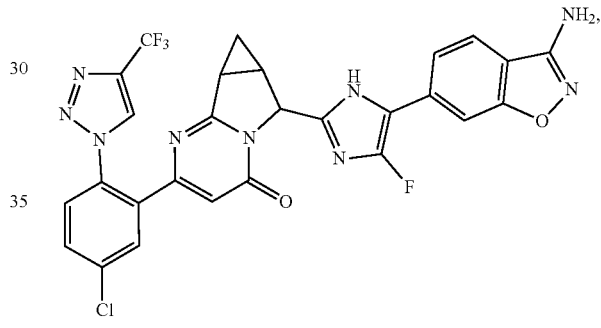
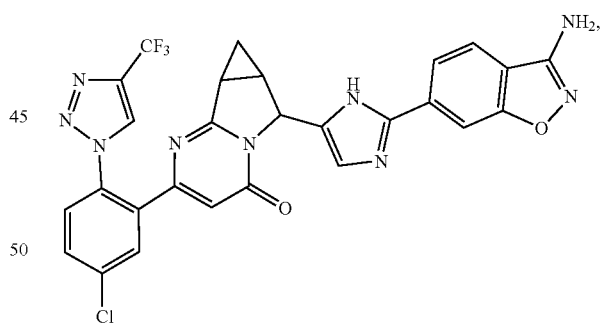
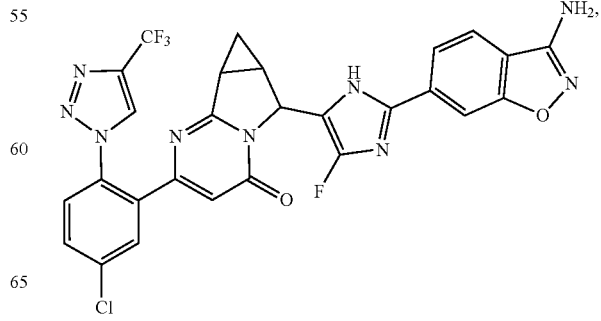

297
-continued
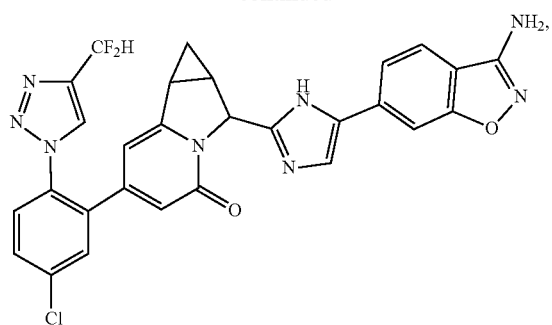
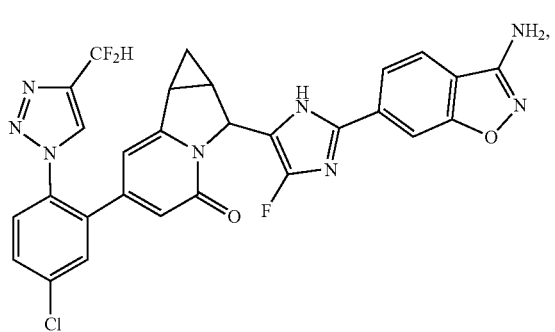
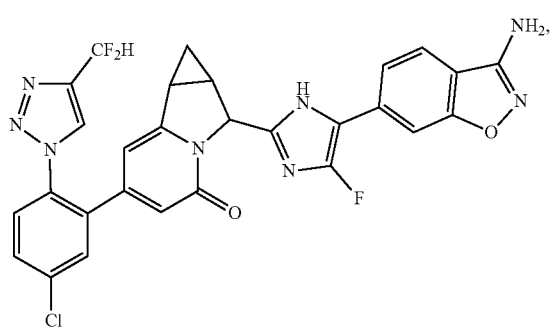
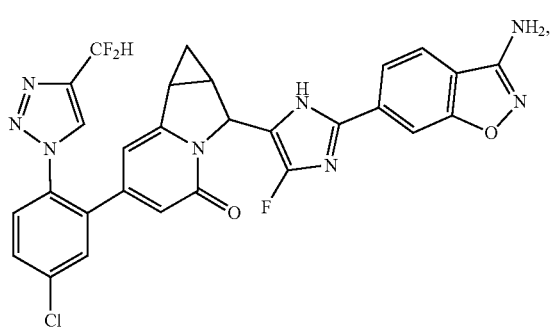
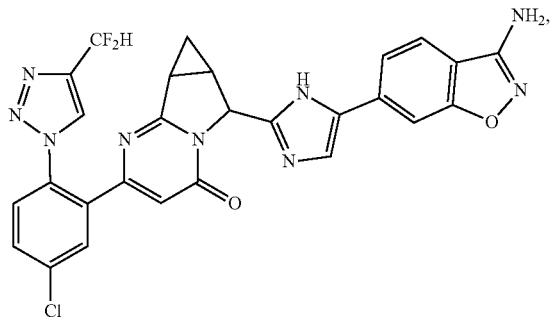
298
-continued
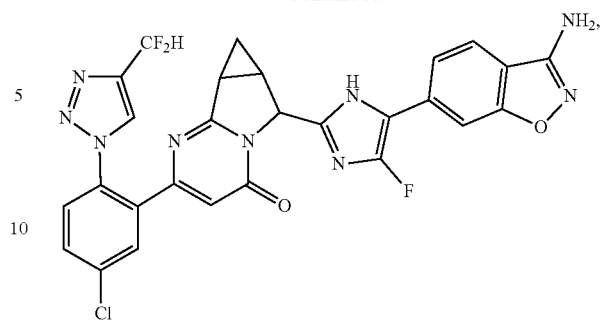
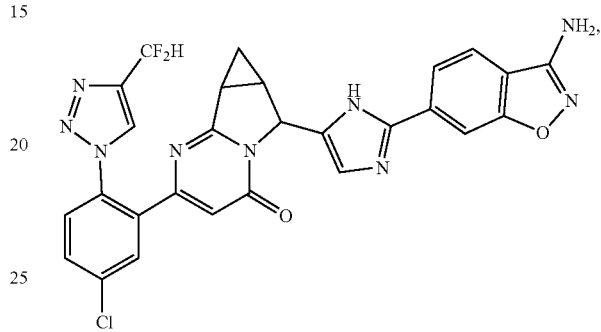
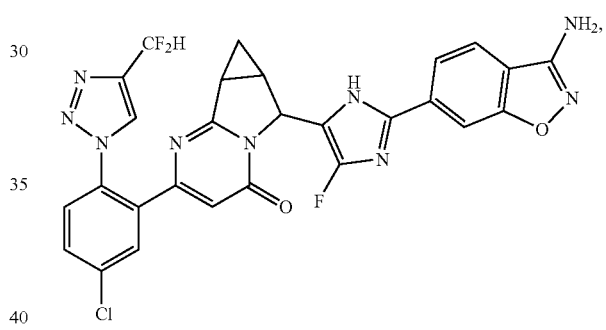
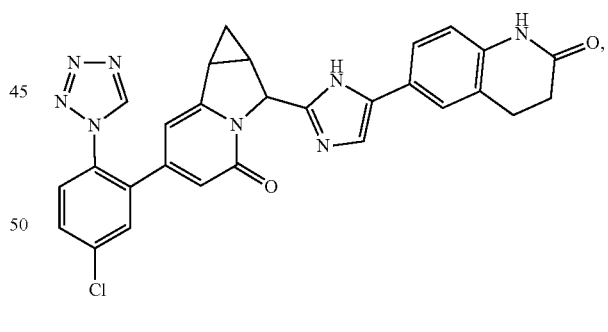
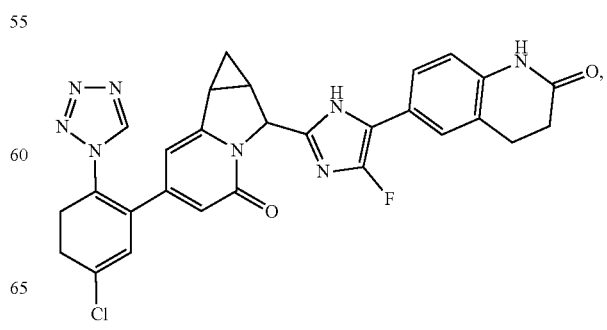

299
-continued
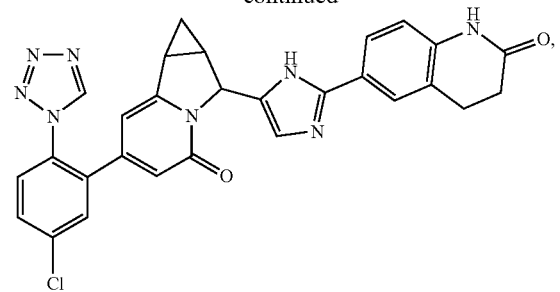
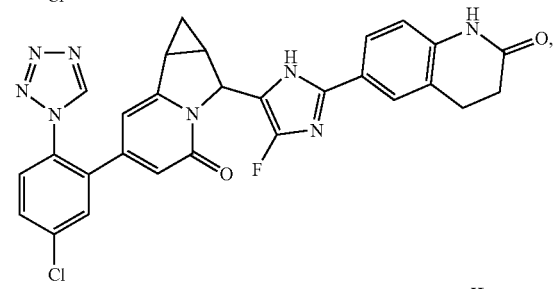
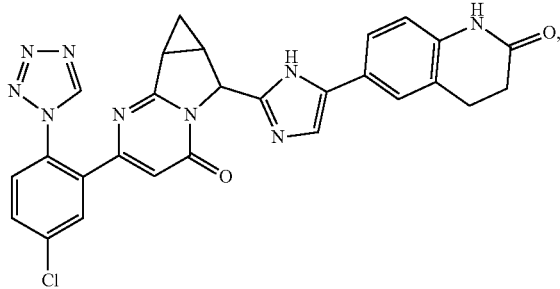
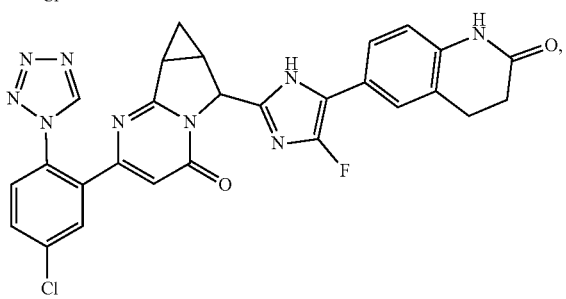
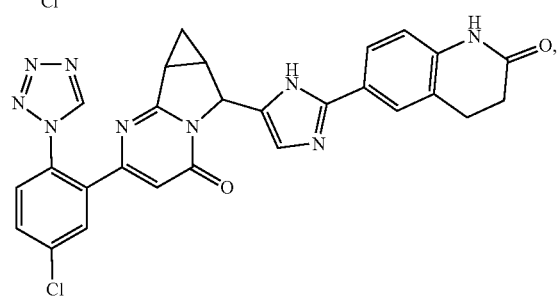
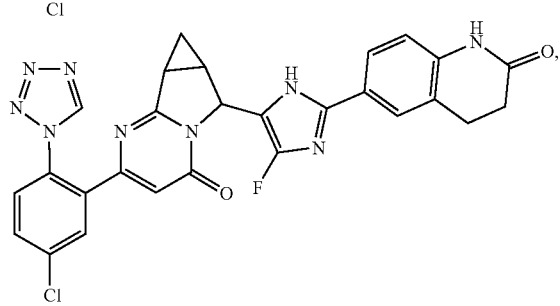
300
-continued
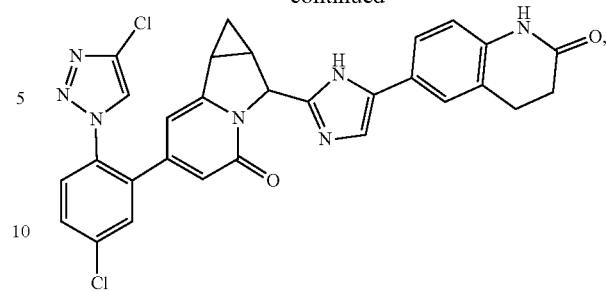
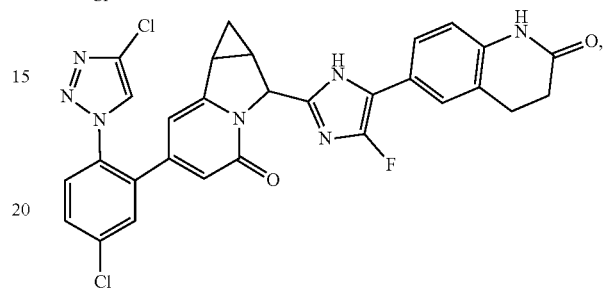
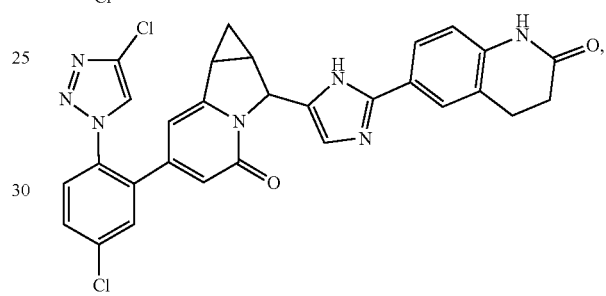
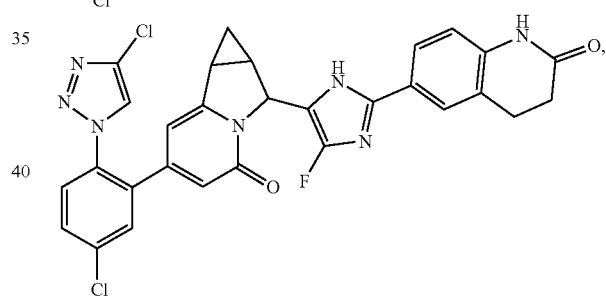
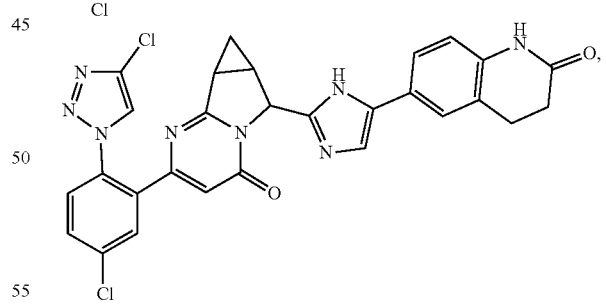
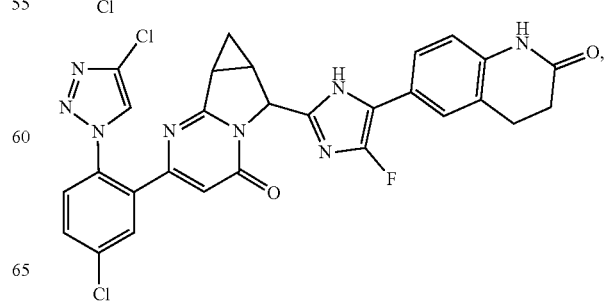

301
-continued
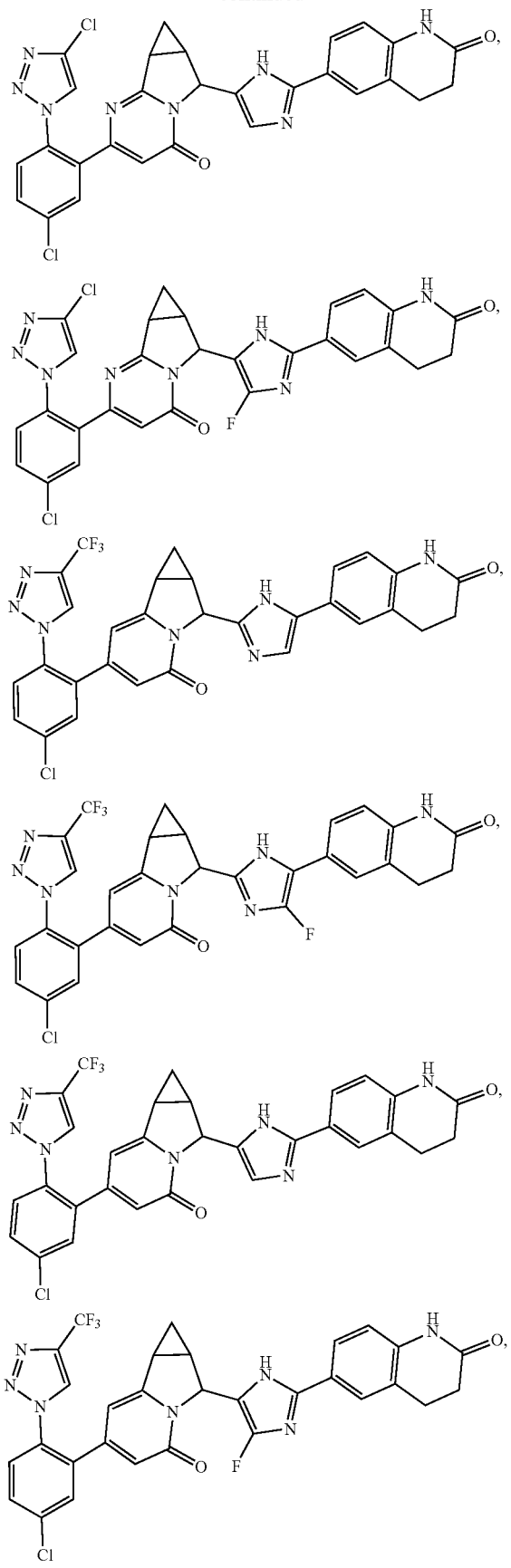
302
-continued
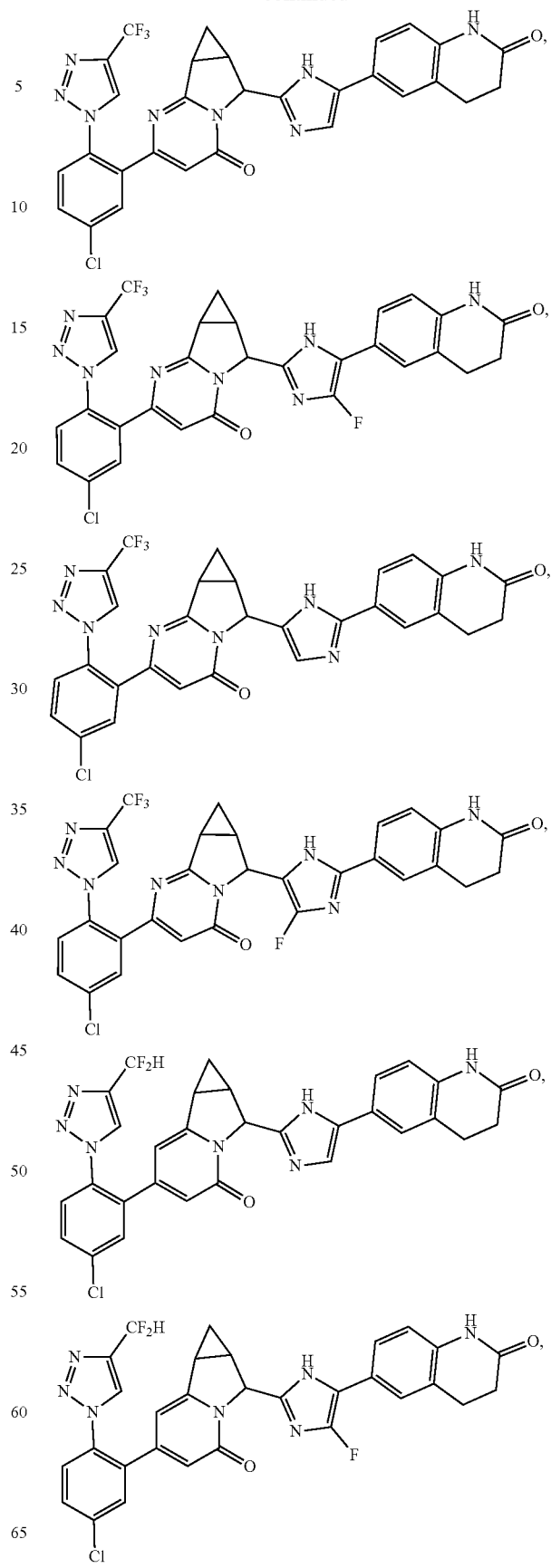

303
-continued
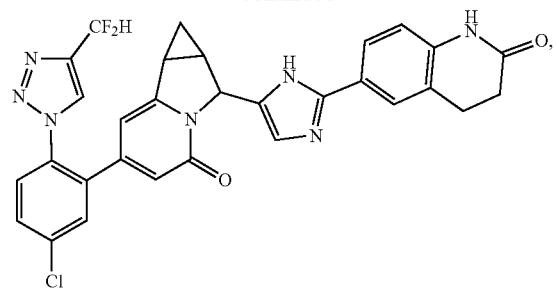
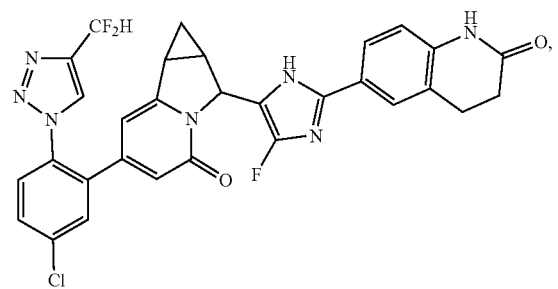
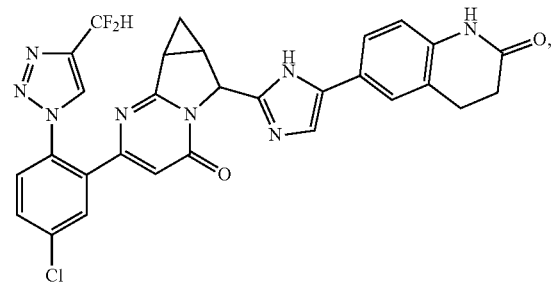
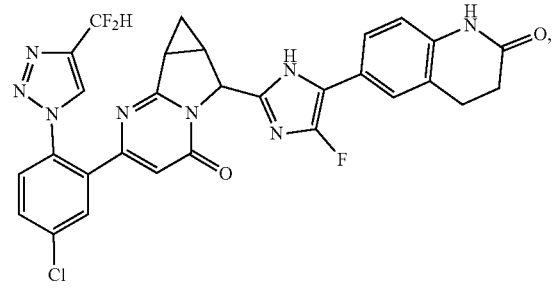
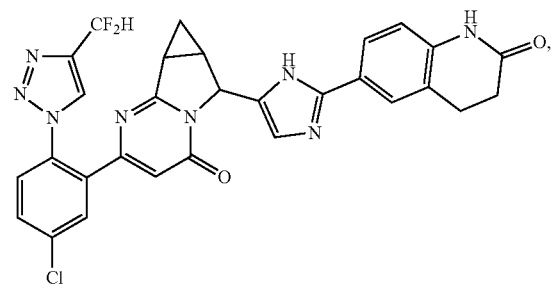
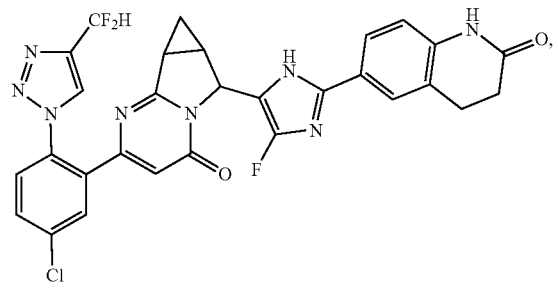
304
-continued
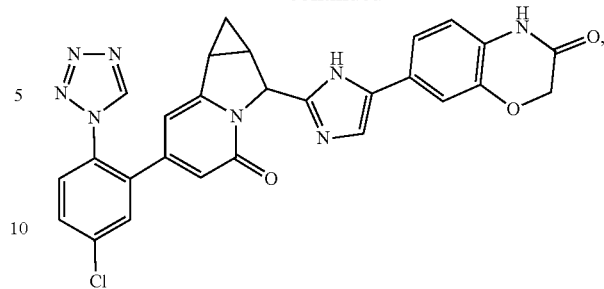
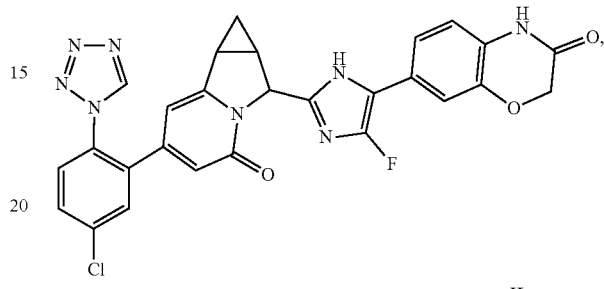
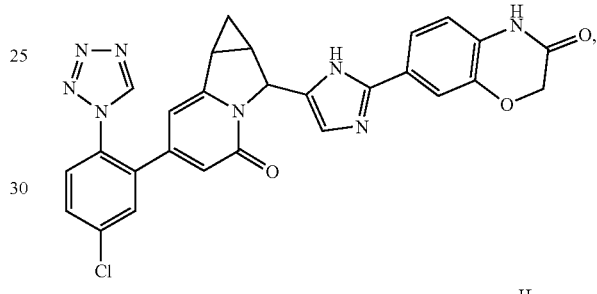
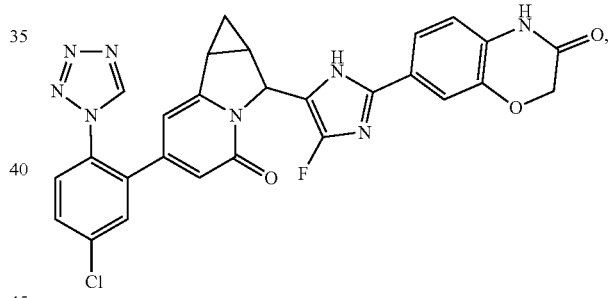
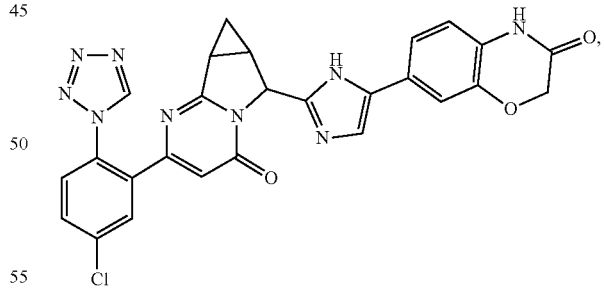
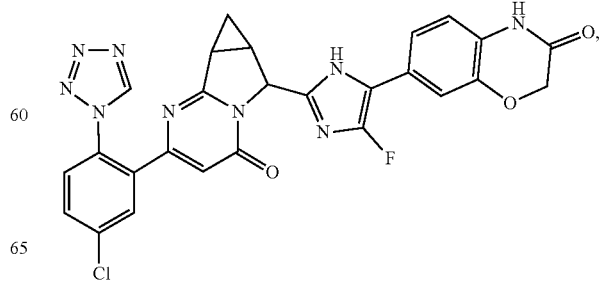

305
-continued
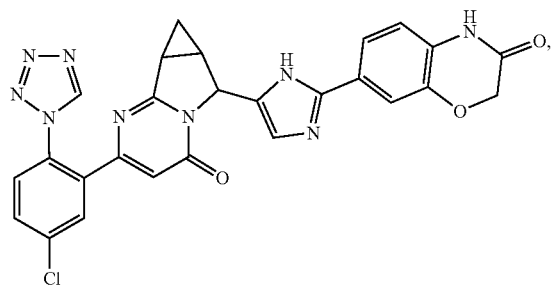
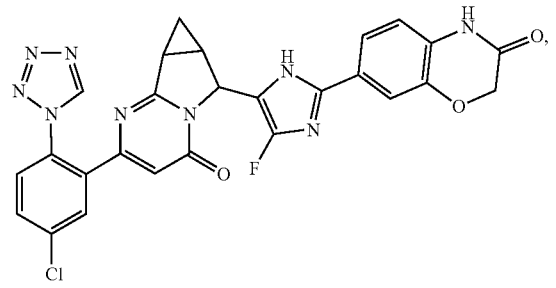
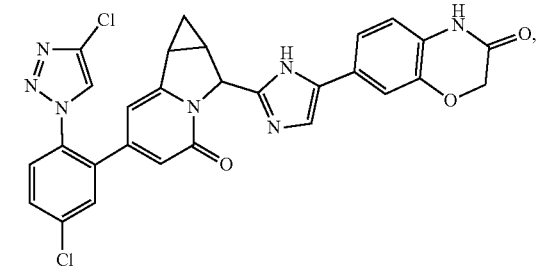
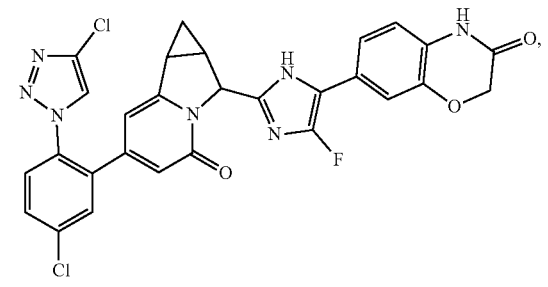
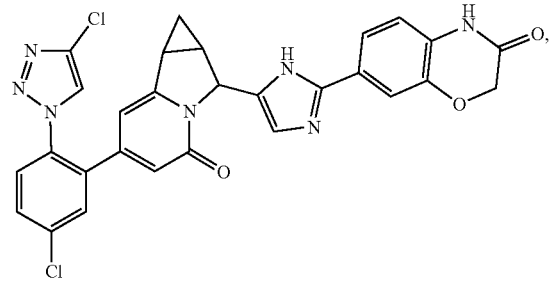
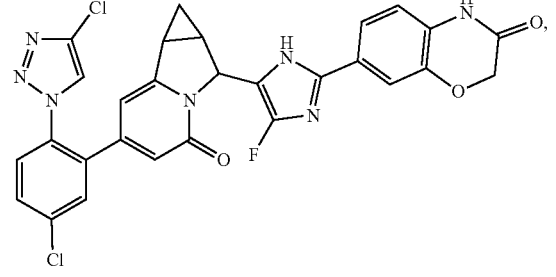
306
-continued
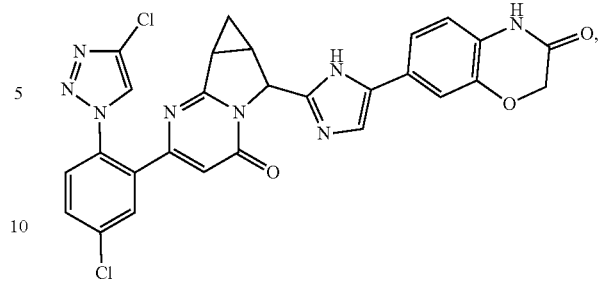
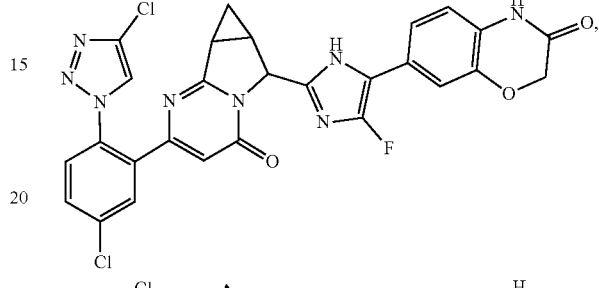
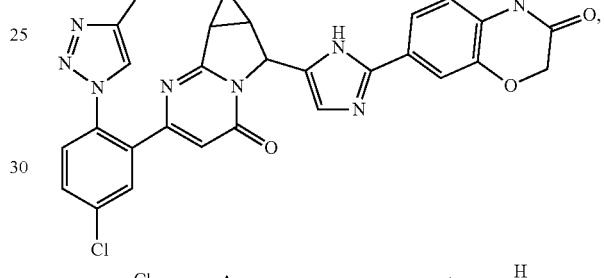
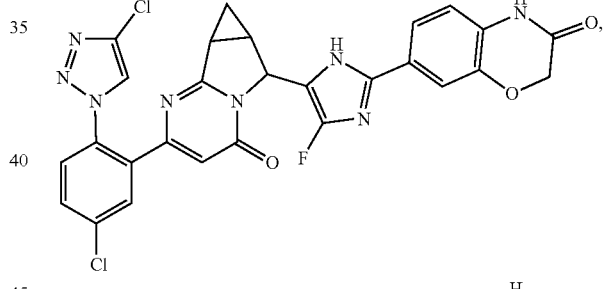
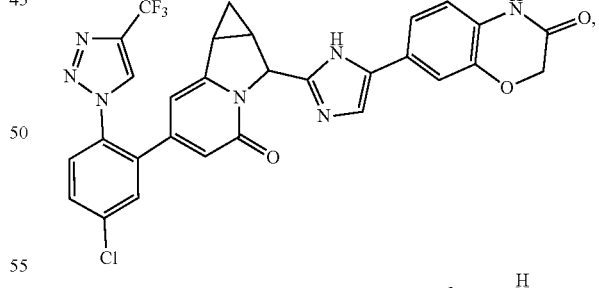
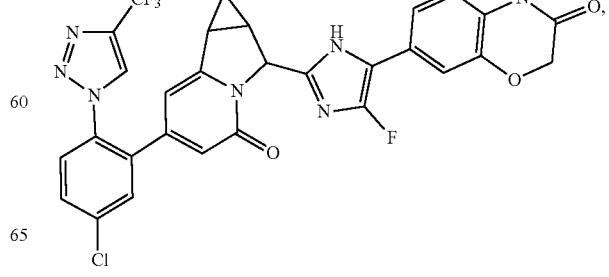

307
-continued
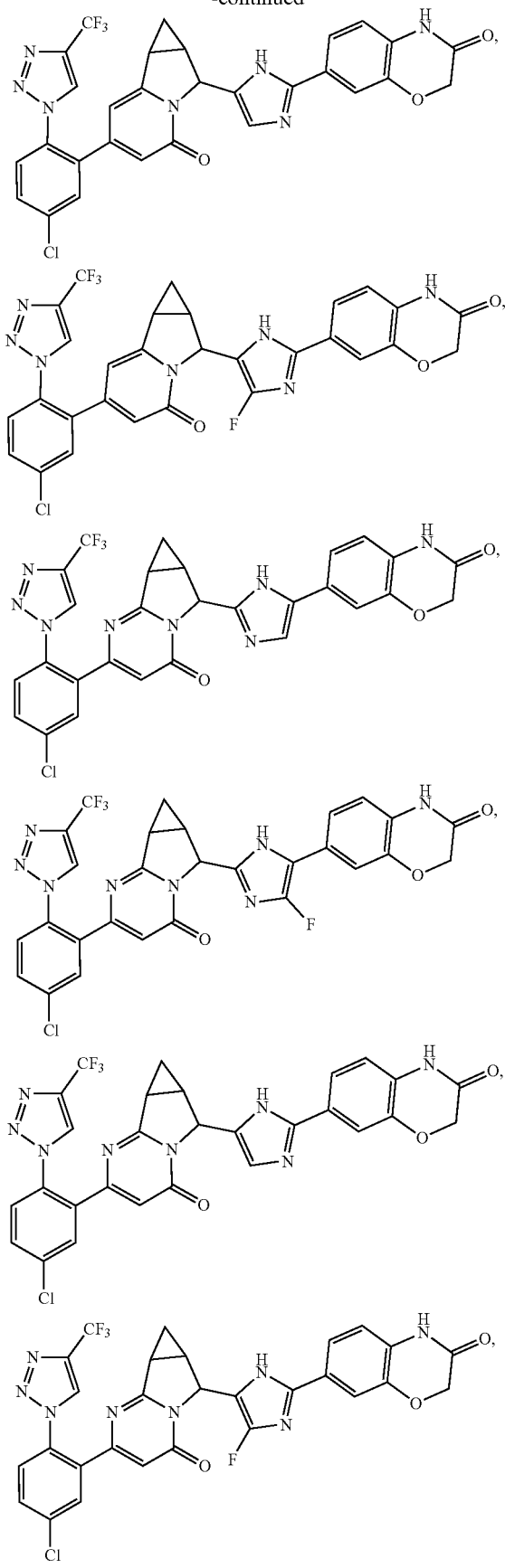
308
-continued
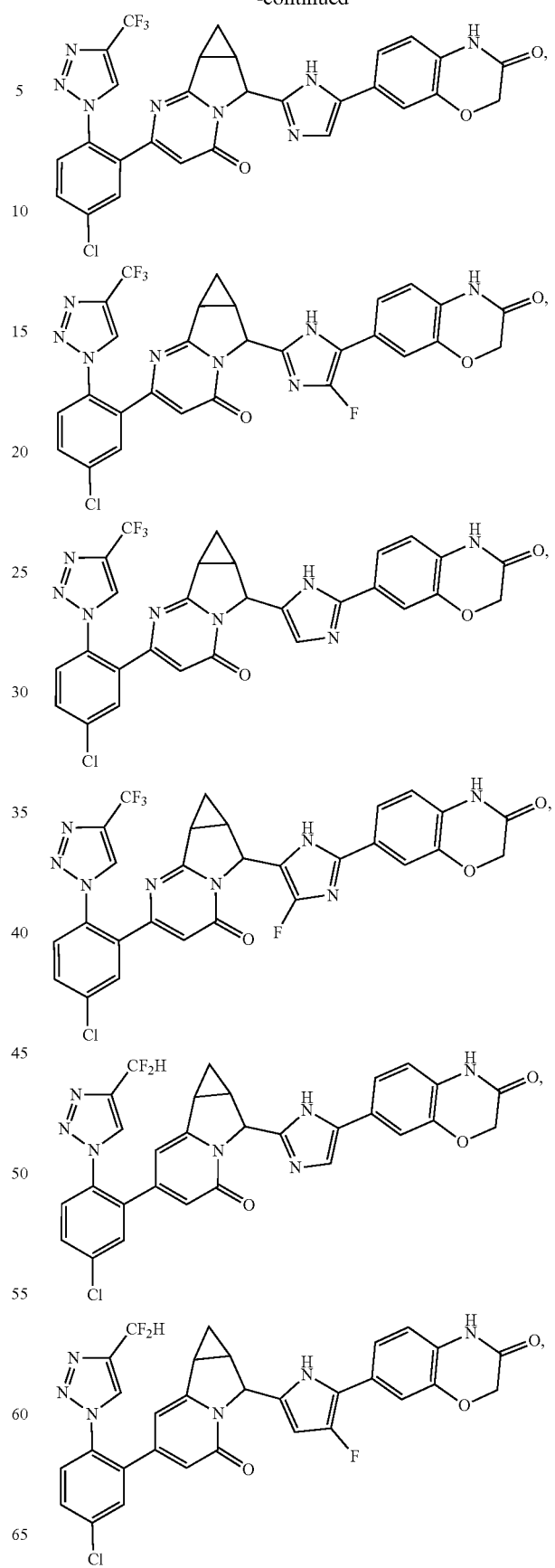

309
-continued
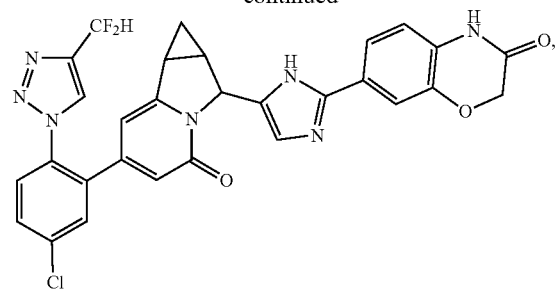
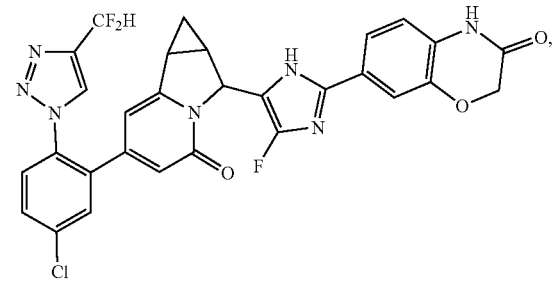
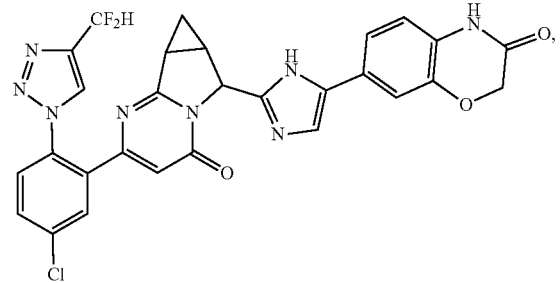
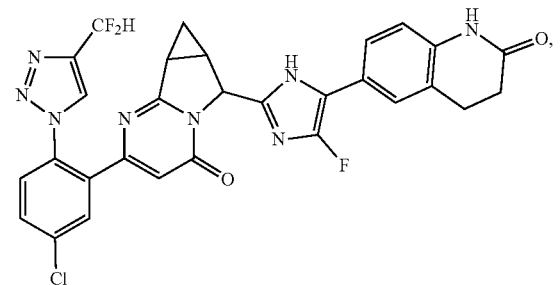
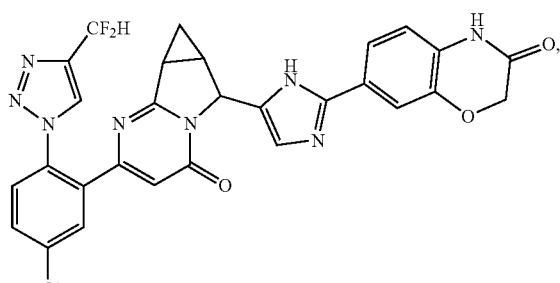
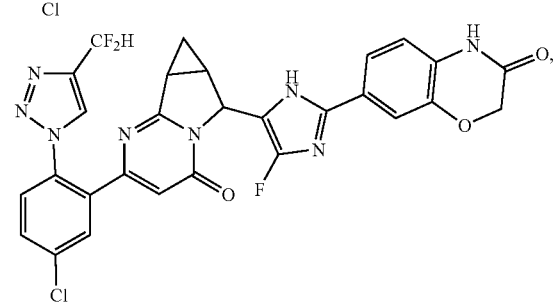
310
-continued
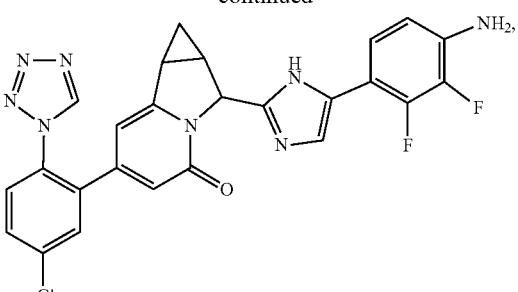
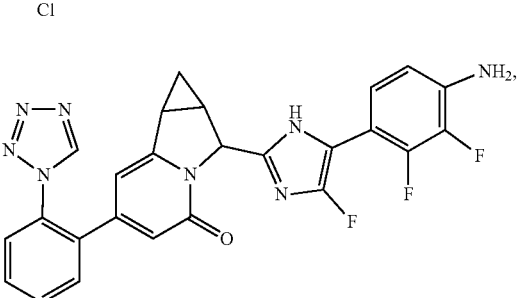
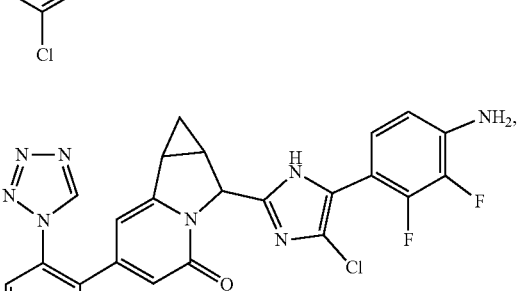
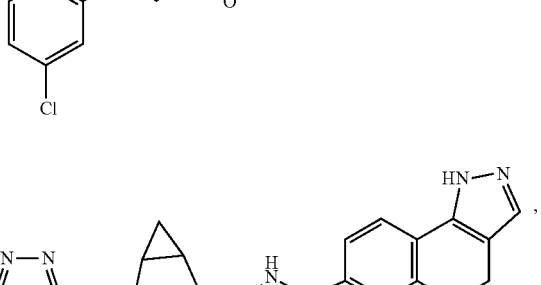
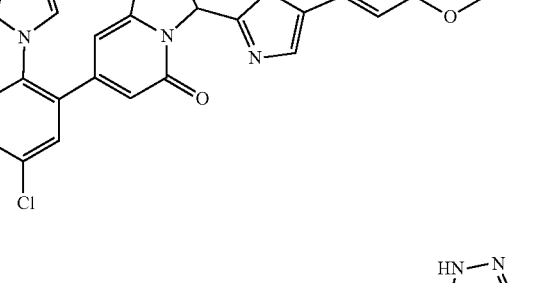
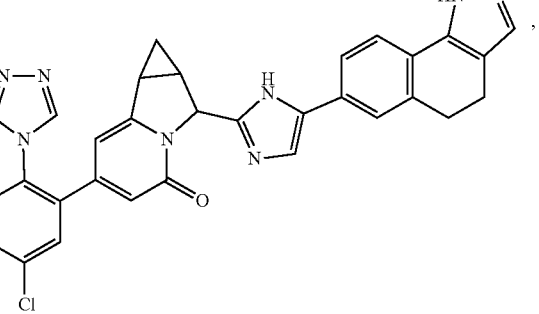

311
-continued
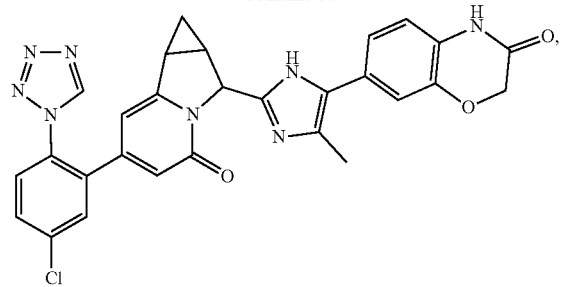
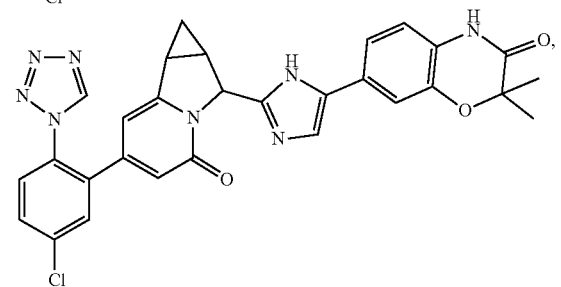
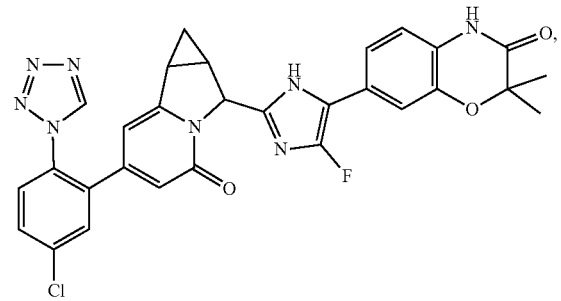
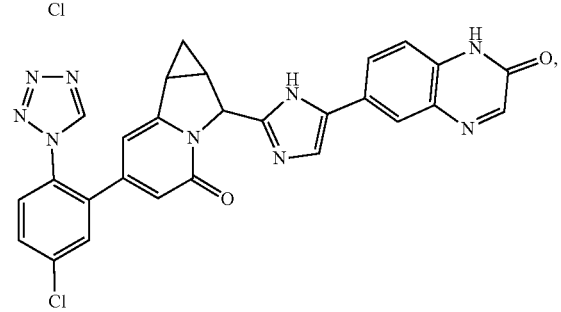
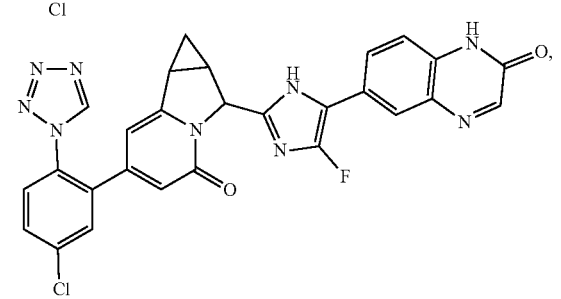
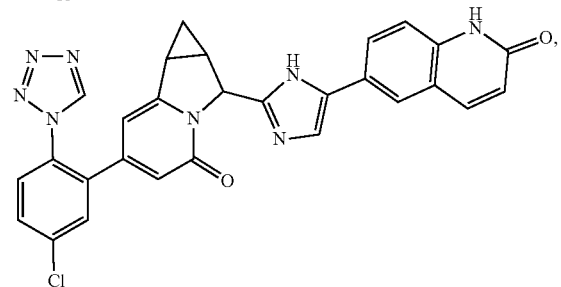
312
-continued
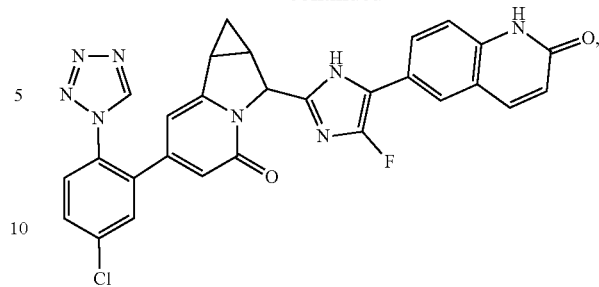
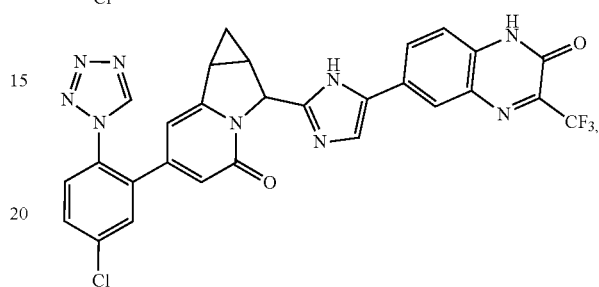
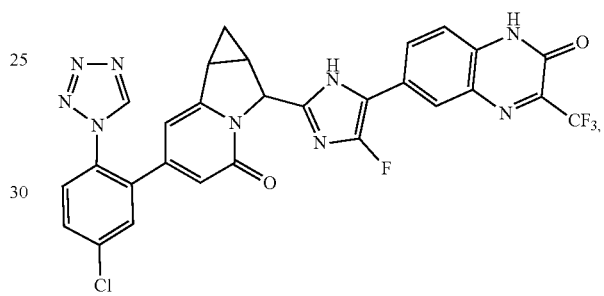
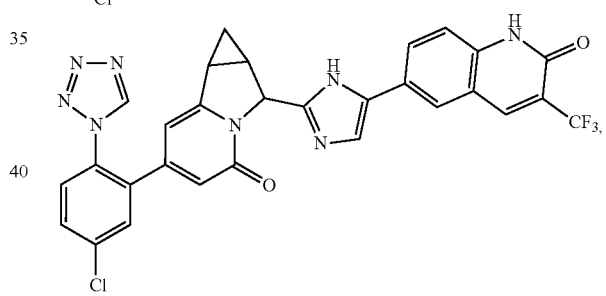
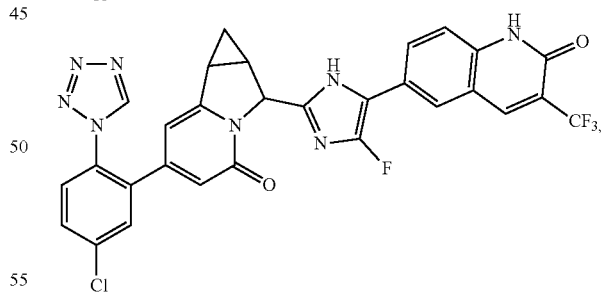
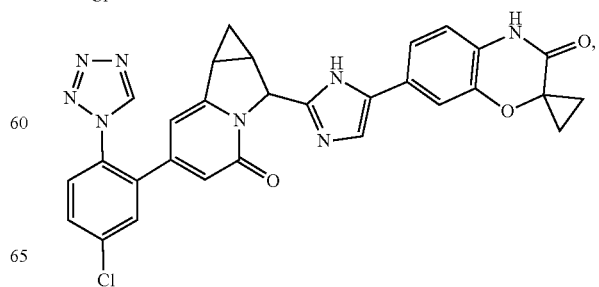

313
-continued
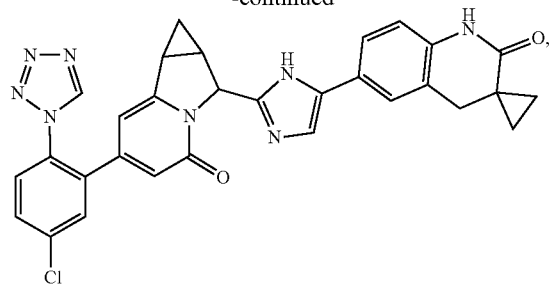
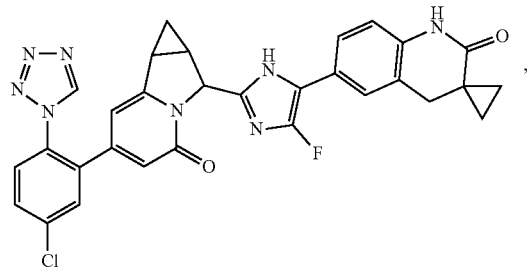
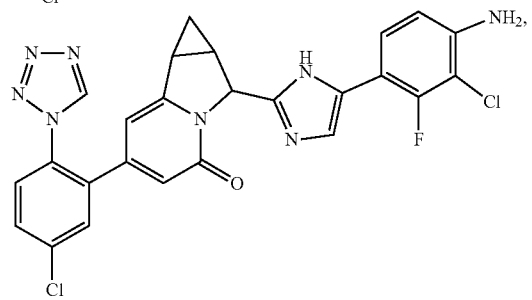
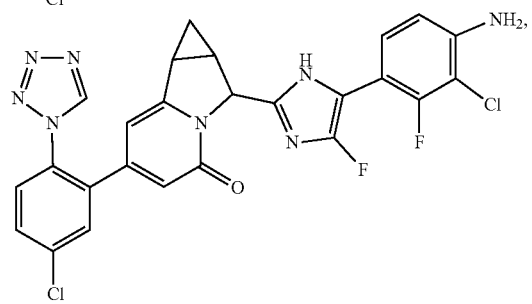
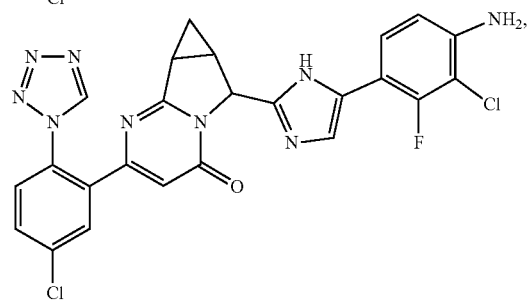
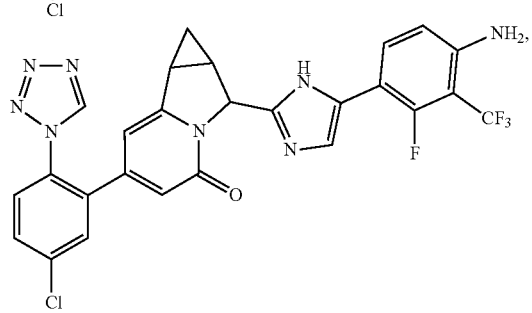
314
-continued
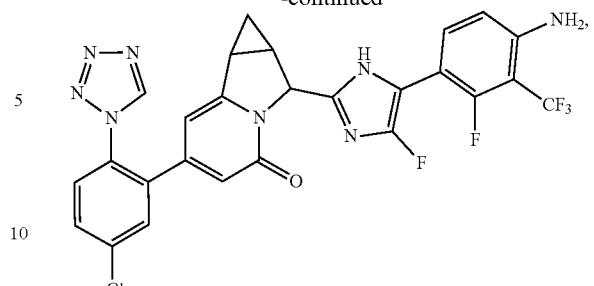
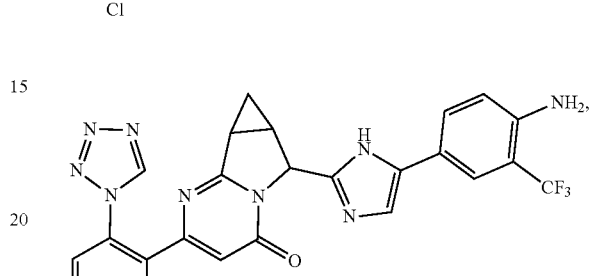
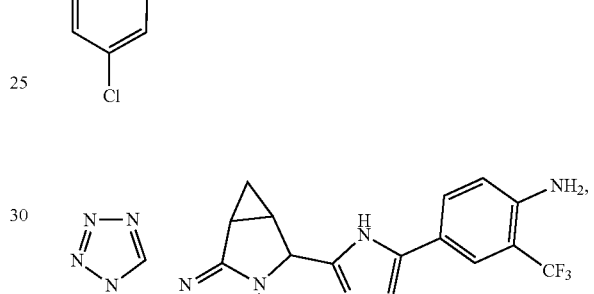
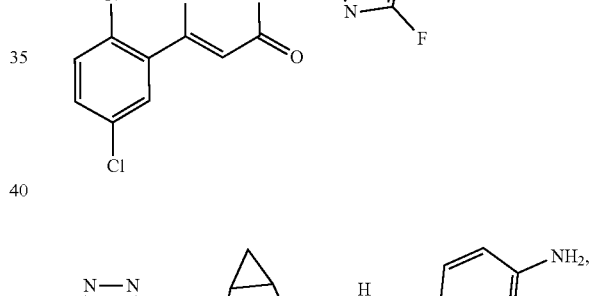
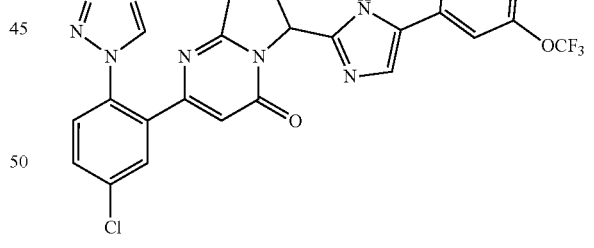
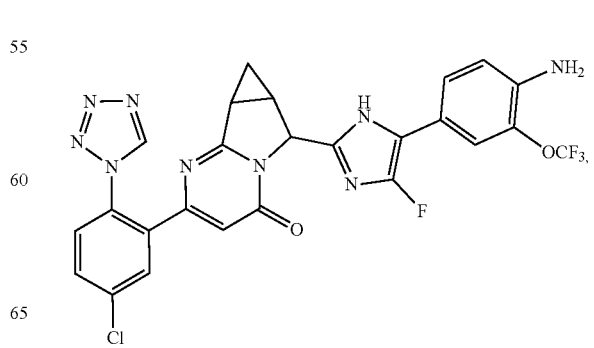

315
-continued
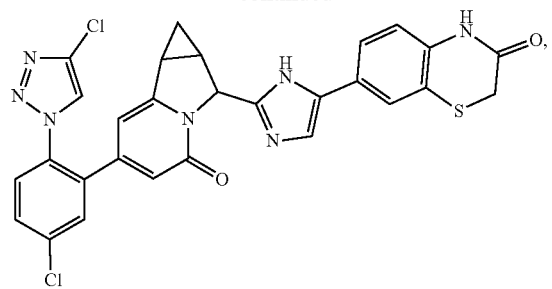
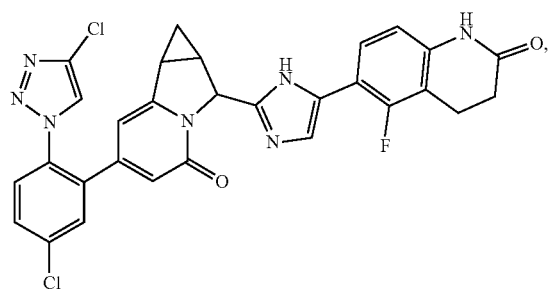
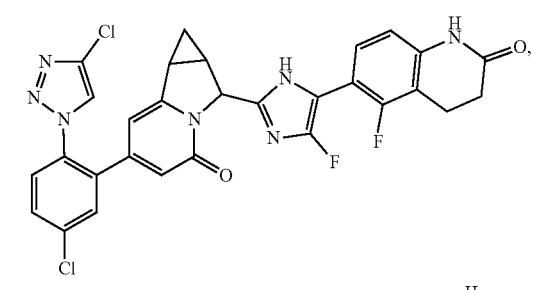
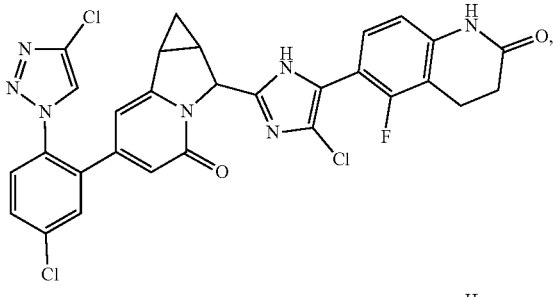
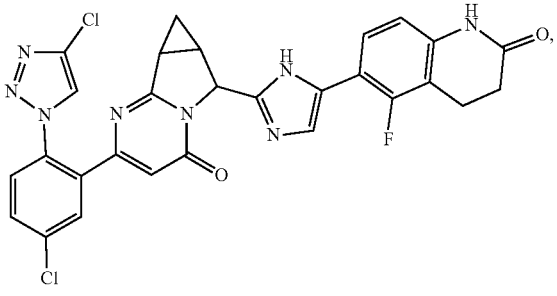
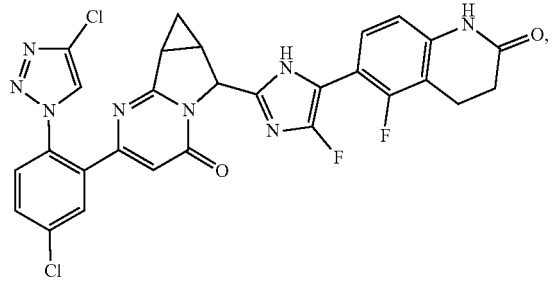
316
-continued
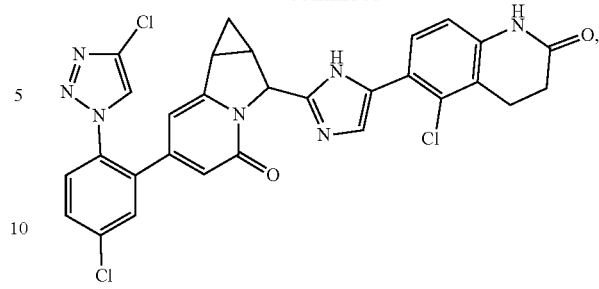
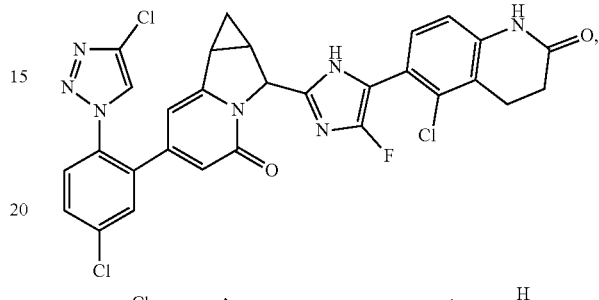
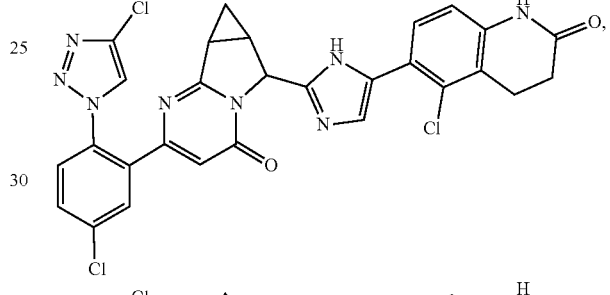
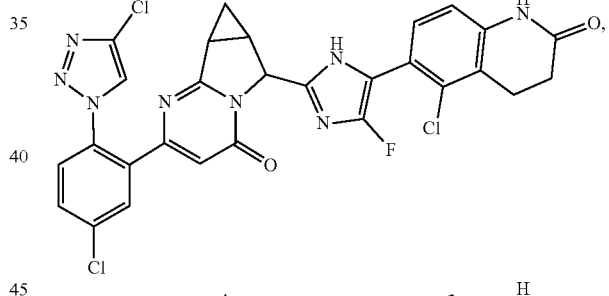
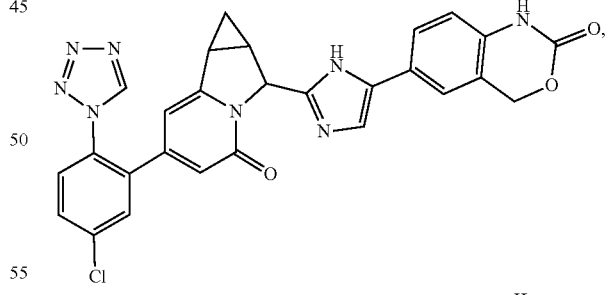
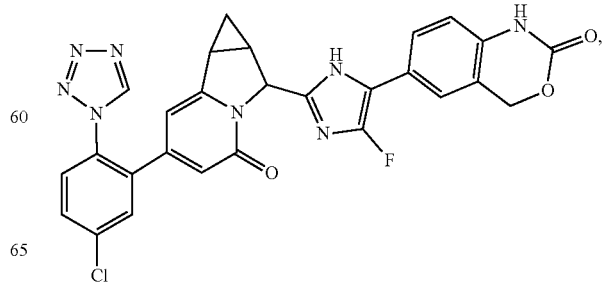

317
-continued
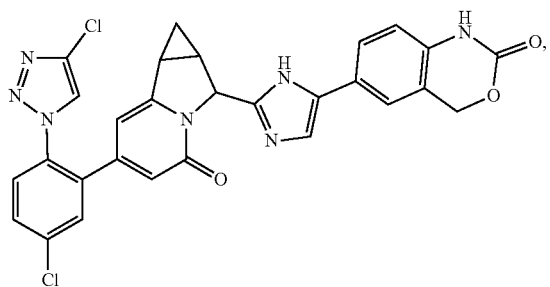
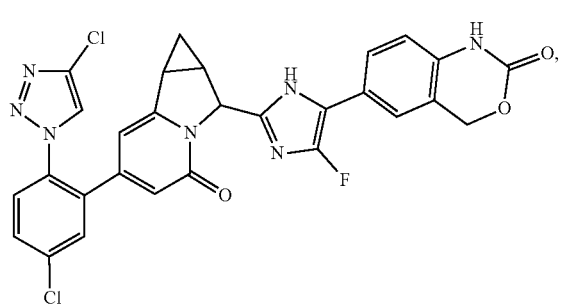
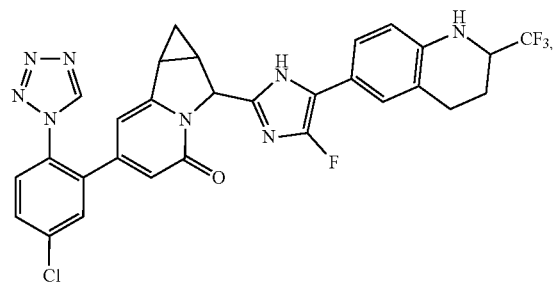
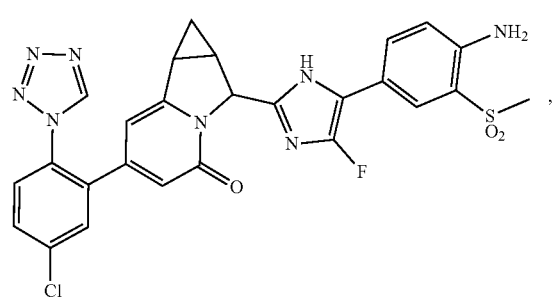
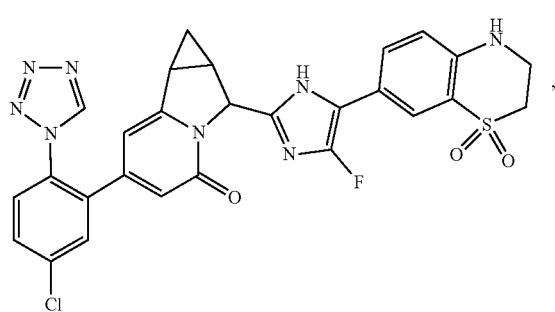
318
-continued
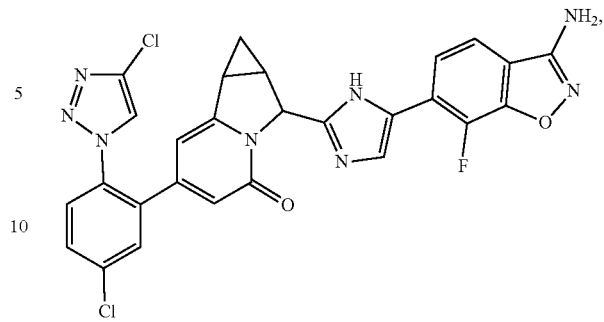
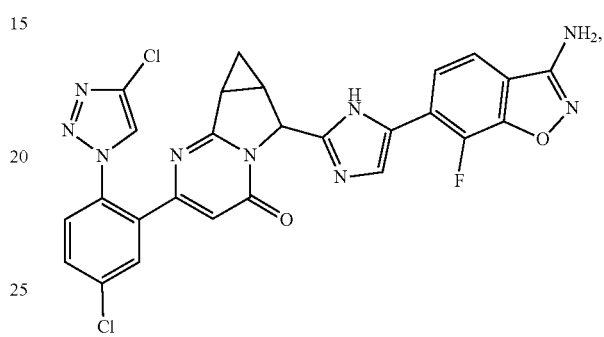
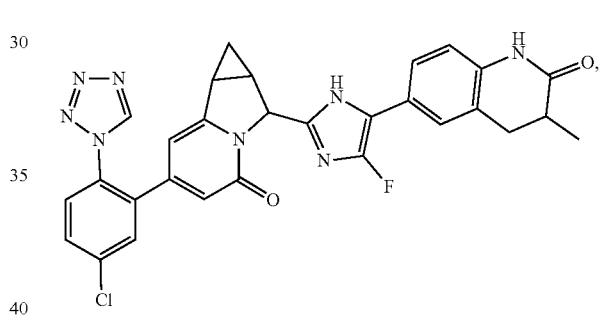
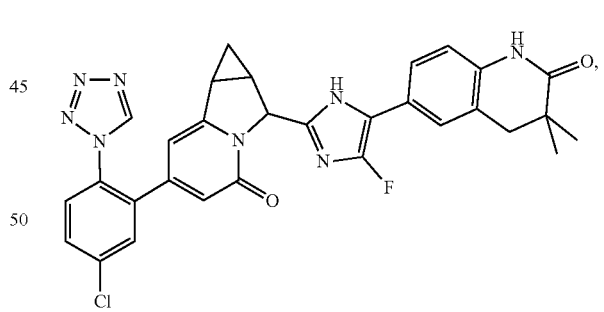
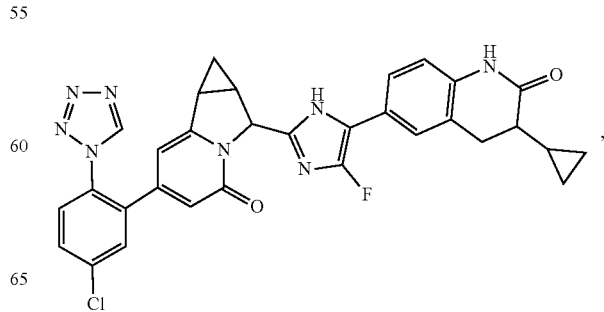

319
-continued
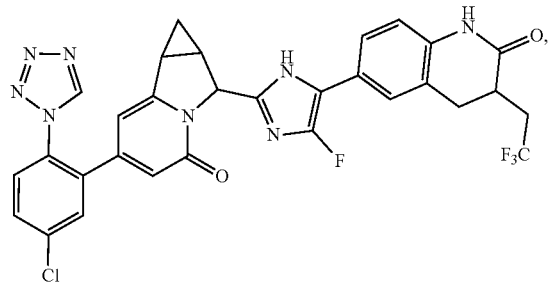
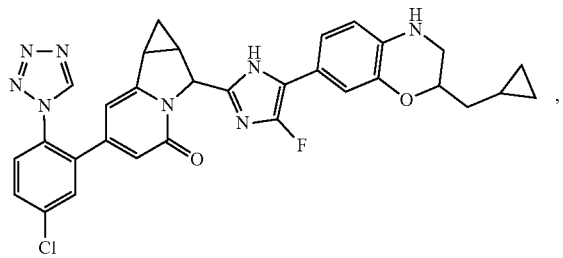
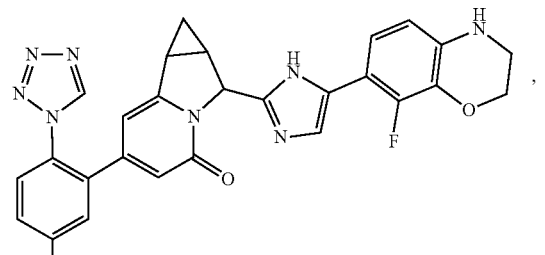
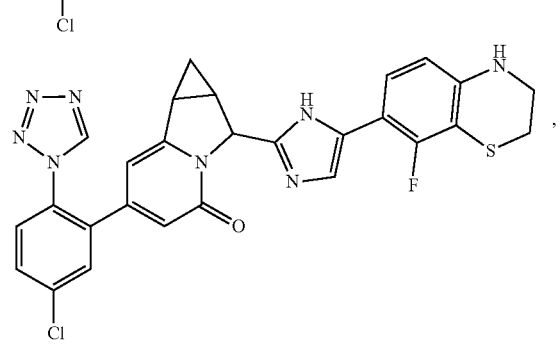
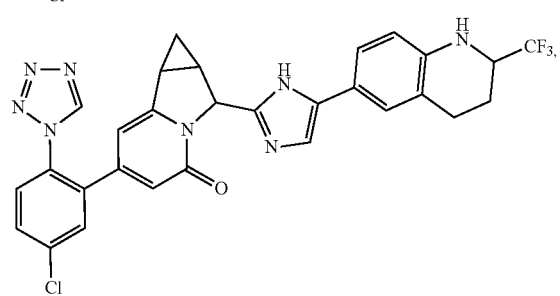
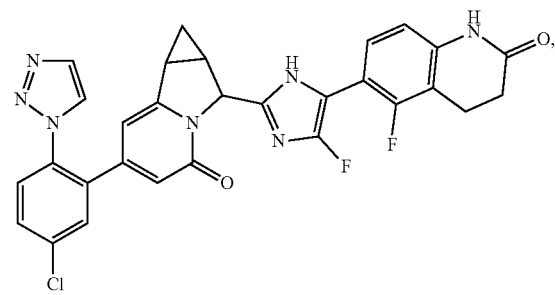
320
-continued
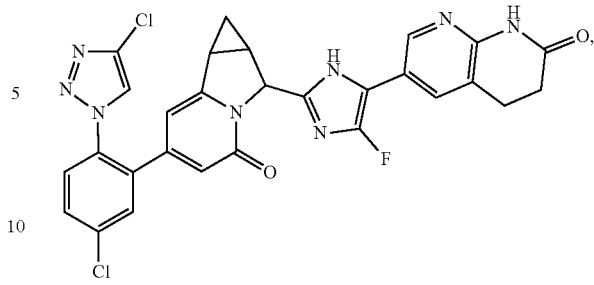
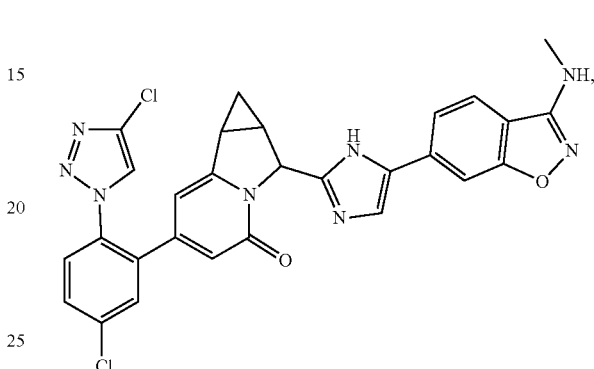
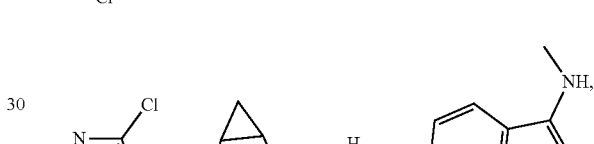
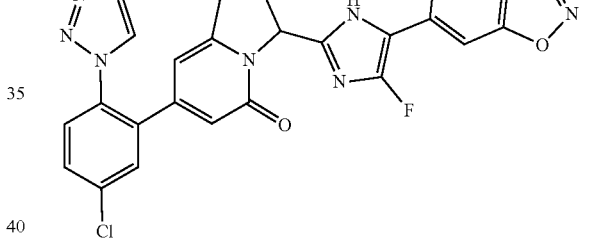
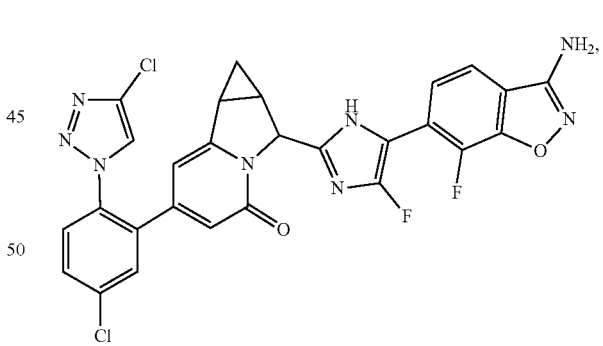
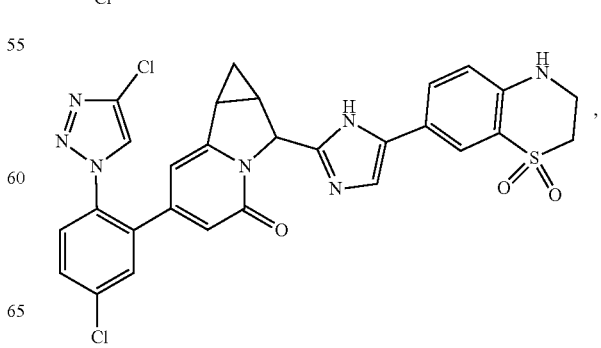

321
-continued
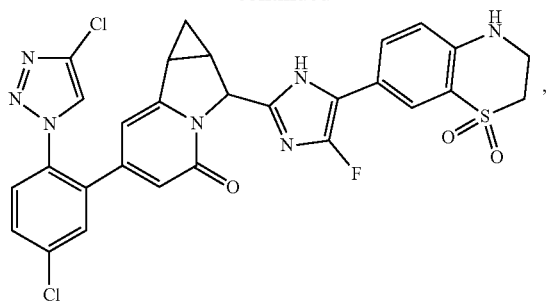
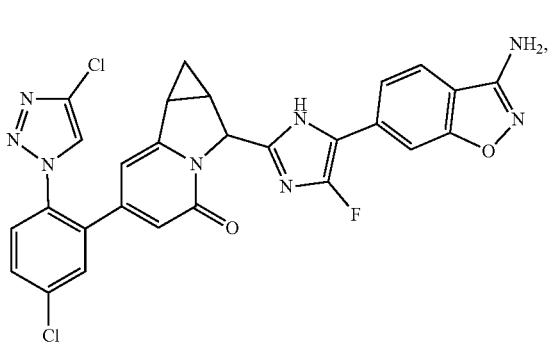
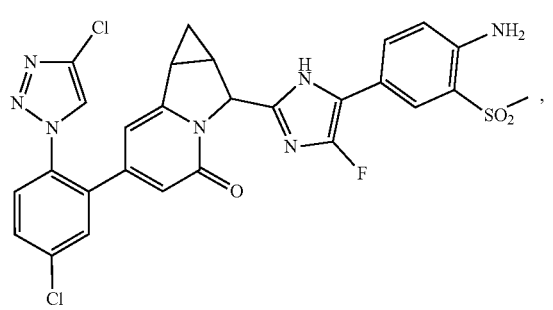
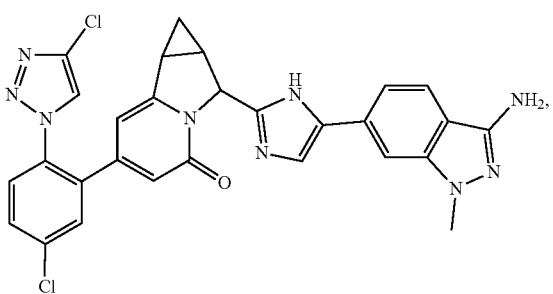
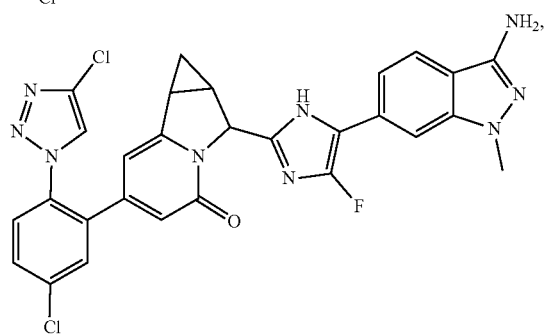
322
-continued
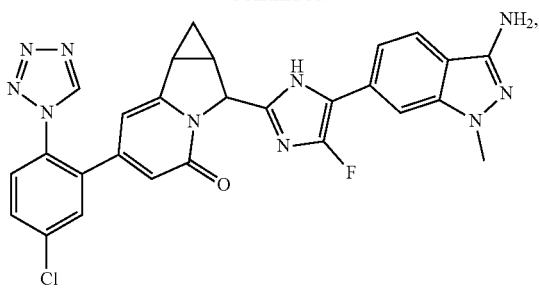
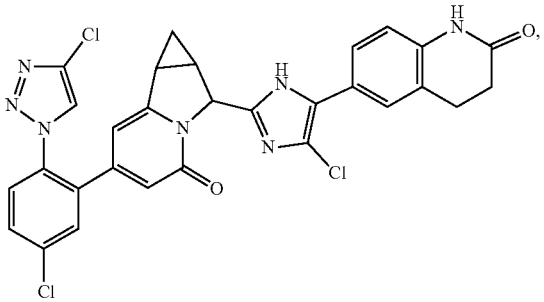
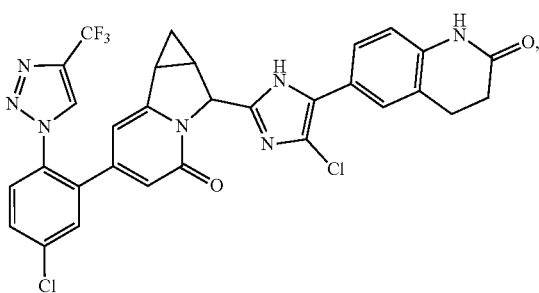
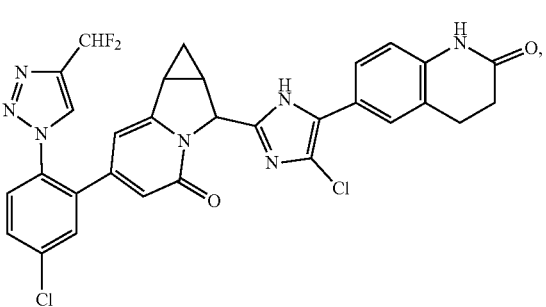
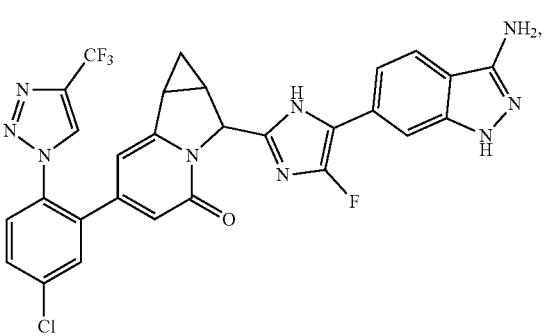

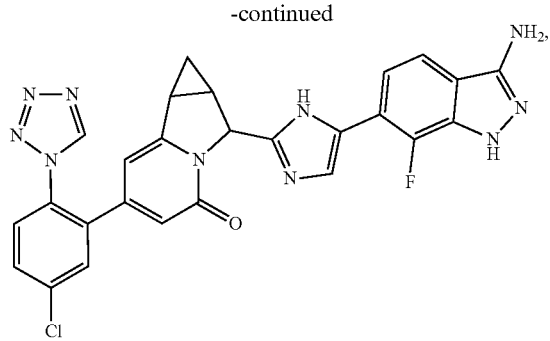

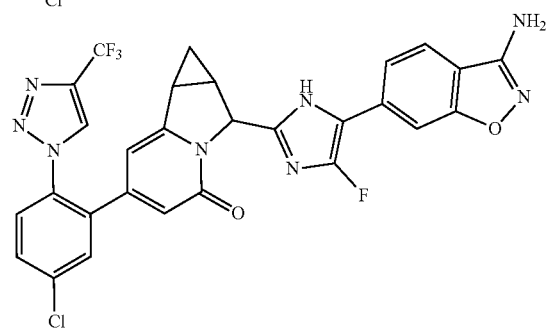

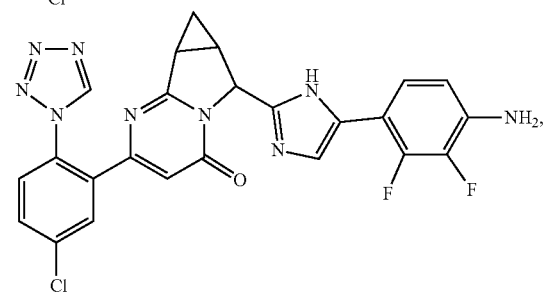

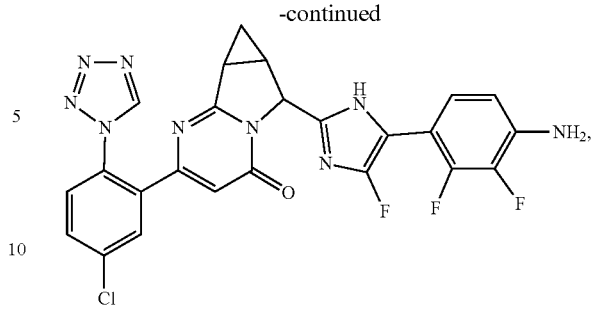

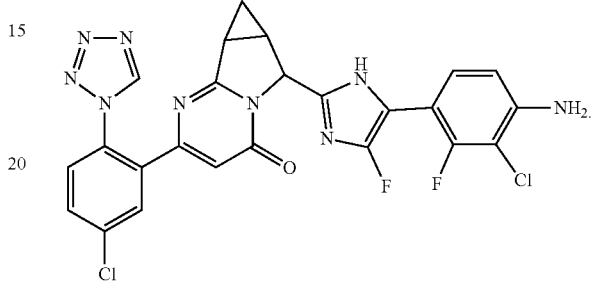

22. A pharmaceutical composition, wherein, the pharmaceutical composition comprises the compound according to claim 1 or the pharmaceutically available salt thereof.

23. A method for treating FXIa factor-mediated disease, wherein, the method comprises administering a therapeutically effective amount of the compound according to claim 1 or the pharmaceutically available salt thereof to a patient suffering from an FXIa factor-mediated disease, wherein the FXIa factor-mediated disease is selected from cardiovascular and cerebrovascular diseases.

* * * * *